US006965850B2

(12) United States Patent
Baxter et al.

(10) Patent No.: US 6,965,850 B2
(45) Date of Patent: Nov. 15, 2005

(54) METHODS FOR MODULATING NUCLEAR RECEPTOR COACTIVATOR BINDING

(75) Inventors: John D. Baxter, San Francisco, CA (US); Beatrice Darimont, San Francisco, CA (US); Weijun Feng, San Francisco, CA (US); Robert J. Fletterick, San Francisco, CA (US); Peter J. Kushner, San Francisco, CA (US); Richard L. Wagner, San Francisco, CA (US); Brian L. West, San Francisco, CA (US); Keith R. Yamamoto, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/281,717

(22) Filed: Mar. 30, 1999

(65) Prior Publication Data

US 2002/0061539 A1 May 23, 2002

Related U.S. Application Data

(60) Provisional application No. 60/079,956, filed on Mar. 30, 1998, and provisional application No. 60/113,146, filed on Dec. 16, 1998.

(51) Int. Cl.[7] .............................. G06N 7/00; G06G 7/58; G01N 33/53
(52) U.S. Cl. ................................. 703/11; 703/2; 702/27; 435/7.1
(58) Field of Search .............................. 702/27; 703/11, 703/3; 435/7.1, 7.93, 7.8, 7.2; 530/395; 434/277, 278

(56) References Cited

U.S. PATENT DOCUMENTS 5,331,573 A   7/1994   Balaji et al. ................ 364/500

| 5,500,807 A | 3/1996 | Lavin et al. ................ 364/496 |
| 6,266,622 B1 * | 7/2001 | Scanlan et al. ................ 702/22 |

FOREIGN PATENT DOCUMENTS

| WO | WO 97/21993 | * 6/1997 | |
| WO | WO 97/35195 | 9/1997 | |
| WO | WO 99/27365 | * 6/1999 | .......... G01N/33/53 |
| WO | WO 99/50658 | * 10/1999 | .......... G01N/33/48 |
| WO | WO 99/60014 | * 11/1999 | |

OTHER PUBLICATIONS

Accession P10828 GenBank Jun. 15, 2002.*

Accession CAA68539 GenBank Sep. 25, 1995.*

(Continued)

*Primary Examiner*—Marjorie Moran
(74) *Attorney, Agent, or Firm*—Morgan, Lewis & Bockius, LLP

(57) ABSTRACT

The present invention relates to methods and agonist/antagonist compounds for modulating nuclear receptor coactivator binding. The invention includes a method for identifying residues comprising a coactivator binding site for a nuclear receptor of interest. Also included is a method of identifying agonists and/or antagonists that bind to a coactivator binding site of a nuclear receptor of interest. Agonists and antagonists of coactivator binding to nuclear receptors also are provided. The invention is exemplified by identification and manipulation of the coactivator binding site of the thyroid receptor (TR), and compounds that bind to this sites. The methods can be applied to other nuclear receptors including RAR, RXR, PPAR, VDR, ER, GR, PR, MR, and AR.

40 Claims, 26 Drawing Sheets

(7 of 26 Drawing Sheet(s) Filed in Color)

OTHER PUBLICATIONS

Ribeiro et al., "Mechanisms of Thyroid Hormone Action: Insights from X-ray Crystallographic and Functional Studies", Recent Progress in Hormone Research vol. 53 1998, pp. 351–395.*

Darimont et al. Structure and specificity of nuclear receptor–coactivator interactions. Genes & Development, vol. 12, pp. 3343–3356,.Nov. 1, 1998.*

Adams et al., "Cross–validated maximum likelihood enhances crystallographic simulated annealing refinement," Proc. Natl. Acad. Sci., vol. 94, pp. 5018–5023, 1997.

Apriletti et al., "Expression of the Rat α1 Thyroid Hormone Receptor Ligand Binding Domain in *Escheria coli* and the Use of a Ligand–induced Comformation Change as a Method for its purification to Homogeneity," Protein Expr. Pruif., vol. 6, pp. 363–370, 1995.

Berry et al., "Role of the two activating domains of the oestrogen receptor in the cell–type and promoter–context dependent agonistic activity of the anti–oestrogen 4–hydroyamoxifen," EMBO J., vol. 9, No. 9, pp. 2811–2818, 1990.

Bourguet et al., "Crystal Structure of the Ligand–binding domain of the Human Nuclear Receptor RXR–α," Nature, vol. 375, pp. 377–382, 1995.

Brzozowski et al., "Molecular Basis of agonism and Antagonism in the oestrogen receptor," Nature, vol. 389, pp.753–758, 1997.

Chang et al., "A Thyroid Hormone Receptor Coactivator Negatively Regulated by the Retinoblastoma Protein," Proc. Natl. Acad. Sci. USA, vol. 94, pp. 9040–9045, 1997.

Cohen et al., "Molecular Modeling Software and Methods for Medicinal Chemistry," J. Med. Chem., vol. 33, No. 3, pp. 883–894, 1990.

Collingwood et al., "A Natural Transactivation Mutation in the Thyroid Hormone β Receptor: Impaired Interaction wiht Putative Transcriptional Mediators," Proc. Natl. Acad. Sci. USA, vol. 94, pp. 248–253, 1997.

Desjarlais et al., "Using Shape Complementarily as an Initial Screen in Designing Ligands for a Receptor Binding Site of Known Three–Dimensional Structure," J. Med. Chem., vol. 31, pp. 722–729, 1988.

Ding et al., "Nuclear Receptor–Binding Sites of Coactivators Glucocorticoid Receptor Interacting Protein 1 (GRIP1) and Steroid Receptor Coactivator 1 (SRC–1): Multiple Motifs with Different Binding Specificities," Molecular Endocrinology, vol. 12, No. 2, pp. 301–313, 1998.

Eng et al., "Probing the Structure and Function of the Estrogen Receptor Ligand Binding Domain by Analysis of Mutants with Altered Transactivation Characteristics," Molecular and Cellular Biology, vol. 17, No. 8, pp. 4644–4653, 1997.

Farmer, "Drug Design," Ariens, E.J., ed., vol. 10, pp. 119–143, Academic Press, NY, 1980.

Furey et al., "'Phases'—A Program Package for the Processing and Analysis of Diffraction Data From Macromolecules," Am. Crust. Assoc. Mtg. Abstr., PA 33, vol. 18, pp. 73, 1990.

Glass et al., "Nuclear Receptor Coactivators," Curr. Opin. Cell Bio., vol. 9, pp. 222–232, 1997.

Greene et al., "Monoclonal Antibodies to Human Estrogen Receptor," Proc. Natl. Acad. Sci. USA, vol. 77, No. 9, pp. 5115–5119, 1980.

Greene et al., "Purification of T47D Human Progesterone Receptor and Immunochemical Characterization with Monoclonal Antibodies," Molecular Endocrinology, vol. 2, No. 8, pp. 714–726, 1988.

Hegy et al., "Carboxymethylation of the Human Estrogen Receptor Ligand–Binding Domain–Estradiol Complex: HPLC/ESMS Peptide Mapping Shows That Cysteine 447 Does Not React With Iodoacetic Acid," Steroids, vol. 61:367–373 (1996).

Heery et al., "A Signature Motif in Transcriptional Co–activators Mediates Binding to Nuclear Receptors," Nature, vol. 387, pp. 733–736, 1997.

Henttu et al., "AF–2 Activity and Recruitment of Steroid Receptor Coactivator 1 to the Estrogen Receptor Depend on a Lysine Residue Conserved in Nuclear Receptors," Molecular and Cellular Biology, vol. 17, No. 4, pp. 1832–1839, 1997.

Hong et al., "GRIP1, a Novel Mouse Protein That Serves as a Transcriptional Coactivator in Yeast for the Hormone Binding Domains of Steroid Receptors," Proc. Natl. Acad. Sci. USA, vol. 93, pp. 4948–4952, 1996.

Hong et al., "GRIP1, a Transcriptional Coactivator for the AF–2 Transactivation Domain of Steroid, Thyroid, Retinoid, and Vitamin D Receptors," Molecular and Cell Biology, vol. 17, No. 5, pp. 2735–2744, 1997.

Horwitz et al., "Nuclear Receptor Coactivators and Corepressors," Molecular Endocrinology, vol. 10, pp. 1167–1177, 1996.

Janknetcht et al., "Rapid and Efficient Purification of Native Histidine–tagged Protein Expressed by Recombinant Vaccinia Virus," Proc. Natl. Acad. Sci. USA, vol. 88, pp. 8972–8976, 1991.

Jurutka et al., "Mutations in the 1,25–Dihydroxyvitamin $D_3$ Receptor Identifying C–Terminal Amino Acids Required for Transcriptional Activation That are Functionally Dissociated from Hormone Binding, Heterodimeric DNA Binding, and Interaction with Basal Transcription Factor IIB, in Vitro," J. Biol. Chem., vol. 272, No. 23, pp. 14592–14599, 1997.

Kakizawa et al., "Ligand–dependent Heterodimerization of Thyroid Hormone Receptor and Retinoid X Receptor," J. of Biol. Chem., vol. 272, No. 38, pp. 23799–23804, 1997.

Kamei et al., "A CBP Integrator Complex Mediates Transcriptional Activation and AP–1 Inhibition by Nuclear Receptors," Cell, vol. 85, pp. 403–414, 1996.

Kuiper et al., "Comparison of the Ligand Binding Specificity and Transcript Tissue Distribution of Estrogen Receptors α and β," Endocrinology, vol. 138, No. 3, pp. 863–870, 1997.

Kuntz, "Structure–Based Strategies for Drug Design and Discovery ," Science, vol. 257, pp. 1078–1082, 1992.

Kussie et al., "Structure of the MDM2 Oncoprotein Bound to the p53 Tumor Suppressor Transactivation Domain," Science, vol. 274, pp. 948–953, 1996.

Landel et al., "Estrogen Receptor Accessory Proteins Augment Receptor–DNA Interaction and DNA Bending," J. Steroid Biochem. Molec. Bio., vol. 63, pp. 59–73, 1997.

Landel et al., "The Interaction of Human Estrogen Receptor with DNA Is Modulated by Receptor–Associated Proteins," Molecular Endorinology, vol. 8, pp. 1407–1419, 1994.

Lanzennec et al., "Mechanistic Aspects of Estrogen Receptor Activation Probed with Constitutively Active Estrogen Receptors: Correlations with DNA and Coregulator Interactions and Receptor Conformational Changes," Molecular Endocrinology, vol. 11, pp. 1375–1386, 1997.

Le Douarin et al., "A Possible Involvement TIF1α and TIF1β in the Epigenetic Control of Transcription by Nuclear Receptors," EMBO J., vol. 15, No. 23, pp. 6701–6715, 1996.

Lee et al., "Thyroid Hormone Receptor Dimerization Function Maps to a Conserved Subregion of the Ligand Binding Domain," Mol. Endocrinol., vol. 6, pp. 1867–1873, 1992.

Lin et al., "A Conformation Switch in Nuclear Horone Receptors Is Involved in Coupling Hormone Binding to Corepressor Release," Mol. Cell. Biol., vol. 17, No. 10, pp. 6131–6138, 1997.

Masuyama et al., "Evidence for Ligand–Dependent Intramolecular Folding of the AF–2 Domain in Vitamin D Receptor–Activated Transcription and Coactivator Interaction," Mol. Endocrinol., vol. 11, pp. 1507–1517, 1997.

Meng et al., "Automated Docking with Grid–Based Energy Evaluation," J. Computational Chem., vol. 13, No. 4., pp. 505–524, 1992.

Mueller et al., "Complex Heterocyclic Structures—A Challenge for Computer–Assisted Molecular Modeling," Bull. Soc. Chim. Belg., vol. 97, pp. 655–667, 1988.

Murshudov et al., "Refinement of Macromolecular Structures by the Maximum–Likelihood Method," Acta Cryst., vol. D53, pp. 240–255, 1997.

Navia et al., "Use of Structural Information in Drug Design," Curr. Opin. Struct. Biol., vol. 2, pp. 202–210, 1992.

Norman et al., "The Rat Growth Hormone Gene Contains Multiple Thyroid Response Elements," J. Biol. Chem., vol. 264, No. 20, pp. 12063–12073, 1989.

Norris et al., "Enhancement of Estrogen Receptor Transcriptional Activity by the Coactivator GRIP–1 Highlights the Role of Activation Function 2 in Determining Estrogen Receptor Pharmacology," J. Biol. Chem., vol. 273, No. 12, pp. 6679–6688, 1998.

O'Donnell et al., "Thyroid Hormone Receptor Mutations that Interfere with Transcriptional Activation also Interfere with Receptor Interaction with a Nuclear Protein," Molecular Endocrinology, vol. 5, pp. 94–99, 1991.

Onate et al., "Sequence and Characterization of a Coactivator for the Steroid Hormone Receptor Superfamily," Science, vol. 270, pp. 1354–1357, 1995.

Radhakrishnan et al., "Solution Structure of the KIX Domain of CBP Bound to the Transactivation Domain of CREB: A Model for Activator: Coactivator Interactions," Cell, vol. 91, pp. 741–752, 1997.

Renaud et al., "Crystal Structure of the RAR–γ Ligand–Binding Domain Bound to All–trans Retinoic Acid," Nature, vol. 378, pp. 681–689, 1995.

Saatcioglu et al., "Mutations in the Conserved C–Terminal Sequence in Thyroid Hormone Receptor Dissociate Hormone–Dependent Activation from Interference with AP1–Activity," Mol. Cell Biol., vol. 17, No. 8, pp. 4687–4695, 1997.

Sadovsky et al., "Transcriptional Activators Differ in Their Responses to Overexpression of TATA–Box–Binding Protein," Molecular and Cellular Biology, vol. 15, pp. 1554–1563, 1995.

Seielstad et al., "Analysis of the Structural Core of the Human Estrogen Receptor Ligand Binding Domain by Selective Proteolysis/Mass Spectrometric Analysis," Biochemistry, vol. 34, pp. 12605–12615, 1995.

Seielstad et al., "Molecular Characterization by Mass Spectrometry of the Human Estrogen Receptor Ligand–Binding Domain Expressed in *Escherichia coli*," Molecular Endocrinology, vol. 9, pp. 647–658, 1995.

Shiau et al., "Activation of the Human Estrogen Receptor by Estrogenic and Antiestrogenic Compounds in *Saccharomyces cereviviae*: A Positive Selection System," Gene, vol. 179, pp. 205–210, 1996.

Shibata et al., "Role of Co–activators and Co–repressors in the Mechanism of Steroid/Thyroid Receptor Action," Recent Prog. Horm. Res., vol. 52, pp. 141–164, 1997.

Spencer et al., "Steroid Receptor Coactivator–1 is a Histone Acetyltransferase," Nature, vol. 389, pp. 194–198, 1997.

Tagami et al., "Nuclear Receptor Corepressors Activate Rather than Suppress Basal Transcription of Genes That Are Negatively Regulated by Thyroid Hormone," Molecular and Cellular Biology, vol. 17, No. 5, pp. 2642–2648, 1997.

Tanenbaum et al., "Crystallographic Comparison of the Estrogen and Progesterone Receptor's Ligand Binding Domains," Proc. Natl. Acad. Sci. USA, vol. 95, pp. 5998–6003, 1998.

Tora et al., "The Cloned Human Oestrogen Receptor Contains a Mutation which Alters Its Hormone Binding Properties ," EMBO J., vol. 8, No. 7, pp. 1981–1986, 1989.

Torchia et al., "The Transcriptional Co–activator p/CIP Binds CBP and Mediates Nuclear–Receptor Function," Nature, vol. 387, pp. 677–684, 1997.

Uesugi et al., "Induced α–Helix in the VP 16 Activation Domain upon Binding to a Human TAF," Science, vol. 277, pp. 1310–1313, 1996.

Verlinde et al., "Structure–Based Drug Design: Progress, Results and Challenges," Structure, vol. 2, pp. 577–587, 1994.

Wagner et al., "A Structural Role for Hormone in the Thyroid Hormone Receptor," Nature, vol. 378, pp. 690–697 1995.

Webb et al., "Tamoxifen Activation of the Estrogen Receptor/AP–1 Pathway: Potential Origin for the Cell–Specific Estrogen–Like Effects of Antiestrogens," Mol. Endocrinol., vol. 9, pp. 443–456, 1995.

White et al., "Ligand–Independent Activation of the Oestrogen Receptor by Mutation of a Conserved Tyrosine," EMBO J., vol. 16, No. 6, pp. 1427–1235, 1997.

Whitfield et al., "A Highly Conserved Region in the Hormone–Binding Domain of the Human Vitamin D Receptor Contains Residues Vital for Heterodimerization with Retinoid X Receptor and for Transcriptional Activation," Molecular Endocrinology, vol. 9, pp. 1166–1179, 1995.

Wurtz et al., "A Canonical Structure for the Ligand–Binding Domain of Nuclear Receptors," Nat. Struct. Biol., vol. 3, No. 1, pp. 87–94, 1996.

Zhu et al., "The Different Hormone–dependent Transcriptional Activation of Thyroid Hormone Receptor Isoforms Is Mediated by Interplay of Their Domains," J. Biol. Chem., vol. 272, No. 14, pp. 9048–9054, 1997.

Bissantz et al. Protein–based–virtual screening of chemical databses. 1. Evaluation of different docking/scoring combinations. J. Medicinal Chemistry. 2000. vol. 43, pp. 4759–4767.*

Chang et al, Dissection of the LXXLL nuclear receptor–coactivator interaction motif using cominatorial peptides librariies. Molecular and Cellular Biology. Dec. 1999. vol. 19, pp. 8226–82293*

Pope et al. Homogeneous fluorescence readouts for minitarized high–throughput screening: Theory and practice. DDT. Sep. 1999. vol. 4, No. 8, pp. 350–352.*

Schapira et al. Rotational discovery of novel nuclear hormone receptro antagonists. PNAS. Feb. 1, 2000. vol. 97, No. 3, pp. 1008–1013.*

Search report for EP 01 95 0770, completed Nov. 25, 2004.

Schmidt, S., et al. "Multiple Receptor Interaction Domains of GRIP1 Function in Synergy", *Nucleic Acids Research*, vol. 26, No. 5, pp. 1191–1197. Mar. 1, 1998.

Feng, W., et al. "Hormone–Dependent Coactivator Binding to a Hydrophobic Cleft on Nuclear Receptors", *Science*, vol. 280, Jun. 12, 1998, pp. 1747–1749.

European Patent Application No. 99944980 Supplementary Partial Research Report, Jun. 3, 2004.

* cited by examiner

|       | NR-box1<br>residues 15-21<br>SEQ ID NO: 5 | NR-box2<br>residues 15-21<br>SEQ ID NO: 6 | NR box3<br>residues 15-21<br>SEQ ID NO: 7 |
|-------|------|------|------|
| NRb 1,2,3 | KLLQLLT | ILHRLLQ | LLRYLLD |
| NRb 1,2   | KLLQLLT | ILHRLLQ | AARAAAD |
| NRb 1,3   | KLLQLLT | AAHRAAQ | LLRYLLD |
| NRb 1     | KLLQLLT | AAHRAAQ | AARAAAD |

NR-box 2 peptide
EKHKILHRLLQDS
(residues 11-23 of SEQ ID NO:6)

NR-box 3 peptide
ENALLRYLLDKDD
(residues 9-21 of SEQ ID NO:7)

NR-interaction domain:

| | |
|---|---|
| NRb 1,2 | ILHRLL |
| I689A | ALHRLL |
| L690A | IAHRLL |
| L693A | ILHRAL |
| L694A | ILHRLA |
| L690A/L694A | IAHRLA |

Residues 12-24 SEQ ID No: 6
NR-Box 2 peptide: KHK |ILLHRLL| QDSS

■ ILHRLL
□ AAHRLL
○ ILAALL
△ ILHRAA

Residues 12-24 SEQ ID No: 6

NR-Box 2 peptide: KHK |ILLHRLL| QDSS

- ■ ILHRLL
- ● FLHRLL
- □ IFHRLL
- ○ ILHRFL
- △ ILHRLF

FIGURE 19

METHODS FOR MODULATING NUCLEAR RECEPTOR COACTIVATOR BINDING

This application claims priority under Title 35, United States Code, §119(e) of U.S. provisional application No. 60/079,956 filed Mar. 30, 1998, and U.S. provisional application No. 60/113,146, filed Dec. 16, 1998.

ACKNOWLEDGEMENTS

This invention was supported in part by grants from the National Institutes of Health: Grant Nos. DK 51083, DK 51281, and P41-RR01081 and from the Army of the United States: Grant No. AIBS#562. The U.S. Government may have rights in this invention.

INTRODUCTION

Technical Field

The present invention relates to methods and compounds for modulating nuclear receptor coactivator binding.

BACKGROUND

Cells contain receptors that can elicit a biological response by binding various molecules including proteins, hormones and/or drugs. Nuclear receptors represent a super family of proteins that are hormone/ligand-activated transcription factors that enhance or repress transcription in a cell type-, ligand- and promoter-dependent manner. The nuclear receptor family includes receptors for glucocorticoids (GRs), androgens (ARs), mineralocorticoids (MRs), progestins (PRs), estrogens (ERs), thyroid hormones (TRs), vitamin D (VDRs), retinoids (RARs and RXRs), peroxisomes (XPARs and PPARs) and icosanoids (IRs). The so-called "orphan receptors" for which ligands have not been identified are also part of the nuclear receptor superfamily, as they are structurally homologous to the classic nuclear receptors, such as steroid and thyroid receptors. Although overall sequence conservation between nuclear receptors varies between different families of receptors, sequence conservation between functional regions, or modules, of the receptors is high. For example, nuclear receptors can be organized into functional modules comprising an N-terminal transcriptional activation domain, a central DNA binding domain (DBD), and a C-terminal ligand binding domain (LBD). The LBD of nuclear receptors represents a hormone/ligand-dependent molecular switch. Binding of hormone to a nuclear receptor's LBD changes its ability to modulate transcription of DNA, although they may have transcription-independent actions. Nuclear receptors also bind proteins, such as chaperone complexes, corepressors, or coactivators, that are involved in receptor function. Hormone binding by a nuclear receptor can increase or decrease binding affinity to these proteins, and can influence or mediate the multiple actions of the nuclear receptors on transcription. For example, nuclear receptors can stimulate transcription in response to hormone binding by recruiting coactivator proteins to promoters of responsive genes (Glass et al., *Curr. Opin. Cell Biol.* (1997) 9:222–32); and Horwitz et al., *Mol. Endocrinol.* (1996) 10:1167–77).

Coactivators of the p160 family mediate activity of a transcriptional activation domain, called AF2, that is part of the nuclear receptor's LBD. A few receptor mutants deficient in coactivator-dependent activation have been isolated (TR: Collingwood et al. *Proc. Natl. Acad. Sci.* (1997) 94:248–253; VDR: Jurutka et al., *J. Biol. Chem.* (1997) 227:14592–14599, Masayama et al., *Mol. Endocrinol.* (1997) 11:1507–1517; ER and RAR: Henttu et al., *Mol. Cell Biol.* (1997) 17:1832–1839). While these studies support the physiological relevance of the observed interaction, the structural and functional nature of the site to which coactivators bind has not been defined.

The medical importance of nuclear receptors is significant. They have been implicated in breast cancer, prostate cancer, cardiac arrhythmia, infertility, osteoporosis, hyperthyroidism, hypercholesterolemia, obesity and other conditions. However, limited treatments are available and current agonist/antagonist drugs used to target nuclear receptors are ligands that bind to the receptor's LBD buried deep within the receptor. Although additional targets on nuclear receptors are desired for drug development, the structural and functional basis of such sites, including the coactivator binding site, has not been described.

Accordingly, a need exists for identification and characterization of the coactivator binding sites of nuclear receptors, and molecules that affect their interaction with cellular coactivator proteins. This would provide a major new target for iterative drug design, synthesis, and selection. It also would be advantageous to devise methods and compositions for reducing the time required to discover compounds that target the coactivator binding site of nuclear receptors and administer them to organisms to modulate physiological processes regulated by nuclear receptors.

Relevant Literature

Wagner et al., (*Nature* (1995) 378:690–697) disclose the crystal structure of rat TR-alpha LBD. Various references disclose mutations in carboxyl-terminal helices of nuclear receptors (Henttu et al., supra; O'Donnell et al., *Mol. Endocrinol.* (1991) 5:94–99; Whitfield et al., *Mol. Endocrinol.* (1995) 9:1166–79; Saatcioglu et al., *Mol. Cell Biol.* (1997) 17:4687–95; Collingwood et al., supra; Kamei et al., *Cell* (1996) 85:403–14). Hong et al. (*Proc. Natl. Acad. Sci. USA* (1996) 93(10):498–49452) and Hong et al. (*Mol. Cell. Biol.* (1997) 17:2735–2744) disclose cloning and expression of GRIP1 coactivator. Torchia et al., (*Nature* (1997) 387:677–84), Le Douarin et al., (*EMBO J* (1996) 15:6701–6715) and Heery et al. (*Nature* (1997) 387:733–736) disclose sequence alignment of various coactivator proteins showing a (SEQ ID NO: 1) LxxLL motif.

SUMMARY OF THE INVENTION

The present invention relates to identification and manipulation of the coactivator binding site of nuclear receptors. Identification of this site permits design and obtention of compounds that bind to the coactivator binding site of nuclear receptors and modulate coactivator binding to the receptor. The compounds include agonists and antagonists that modulate nuclear receptor activity by promoting (agonists) or blocking (antagonists) hormone-dependent coactivator binding to the receptor, particularly antagonists. The compounds of the invention can be receptor-, cell- and/or tissue-specific.

The present invention also includes protein cocrystals of nuclear receptors with a molecule bound to the coactivator binding site and methods for making them. The cocrystals provide means to obtain atomic modeling information of the specific amino acids and their atoms forming the coactivator binding site and that interact with molecules that bind to the site, such as coactivator. The cocrystals also provide modeling information regarding the coactivator:nuclear receptor interaction, as well as the structure of coactivators bound thereto.

The present invention further provides methods for identifying and designing small molecules that bind to the coactivator binding site using atomic models of nuclear receptors. The method involves modeling test compounds that fit spatially into a nuclear receptor coactivator binding site of interest using an atomic structural model comprising a nuclear receptor coactivator binding site or portion thereof, screening the test compounds in a biological assay characterized by binding of a test compound to a nuclear receptor coactivator binding site, and identifying a test compound that modulates coactivator binding to the nuclear receptor.

The invention also includes compositions and methods for identifying coactivator binding sites of nuclear receptors. The methods involve examining the surface of a nuclear receptor of interest to identify residues that modulate coactivator binding. The residues can be identified by homology to the coactivator binding site of human TR described herein. Overlays and superpositioning with a three dimensional model of a nuclear receptor LBD, or a portion thereof that contains a coactivator binding site, also can be used for this purpose. Additionally, alignment and/or modeling can be used as a guide for the placement of mutations on the LBD surface to characterize the nature of the site in the context of a cell.

Also provided is a method of modulating the activity of a nuclear receptor. The method can be in vitro or in vivo. The method comprises administering, in vitro or in vivo, a sufficient amount of a compound that binds to the coactivator binding site. Preferred compounds bind to the site with greater affinity than coactivator proteins found in a cell of interest. Binding at this site, the compound can compete for binding of coactivator proteins, thereby inhibiting gene transcription, or in some cases promoting it, even when hormone is or is not bound.

The invention further includes a method for identifying an agonist or antagonist of coactivator binding to a nuclear receptor. The method comprises providing the atomic coordinates comprising a nuclear receptor coactivator binding site or portion thereof to a computerized modeling system; modeling compounds which fit spatially into the nuclear receptor coactivator binding site; and identifying in an assay for nuclear receptor activity a compound that increases or decreases activity of the nuclear receptor through binding the coactivator binding site.

Also provided is a machine-readable data storage medium with information for constructing and manipulating an atomic model comprising a coactivator binding site or portion thereof. The medium comprises a data storage material encoded with machine readable data which, when using a machine programmed with instructions for using said data, is capable of displaying a graphical three-dimensional representation of a molecule or molecular complex for a nuclear receptor coactivator binding site.

Also provided is a method of identifying a compound that selectively modulates the activity of one type of nuclear receptor compared to other nuclear receptors. The method is exemplified by modeling test compounds that fit spatially and preferentially into a nuclear receptor coactivator binding site of interest using an atomic structural model of a nuclear receptor coactivator binding site, selecting a compound that interacts with one or more residues of the coactivator binding site unique in the context of that site, and identifying in an assay for coactivator binding activity a compound that selectively binds to the coactivator binding site compared to other nuclear receptors. The unique features involved in receptor-selective coactivator binding can be identified by comparing atomic models of different receptors or isoforms of the same type of receptor.

The invention finds use in the selection and characterization of peptide, peptidomimetic, as well as other small molecule compounds, such as small organic molecules, identified by the methods of the invention, particularly new lead compounds useful in treating nuclear receptor-based disorders.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 19 shows alignment of amino acid sequences (single letter amino acid designations) containing residues that form the coactivator binding sites of several nuclear receptors. The boxes represent residues of alpha-helix (H3, H4, H5, H6 and H12); lower case letters "h" and "q" represent hydrophobic and polar residues, respectively.

DESCRIPTION OF SPECIFIC EMBODIMENTS

Figure 1:
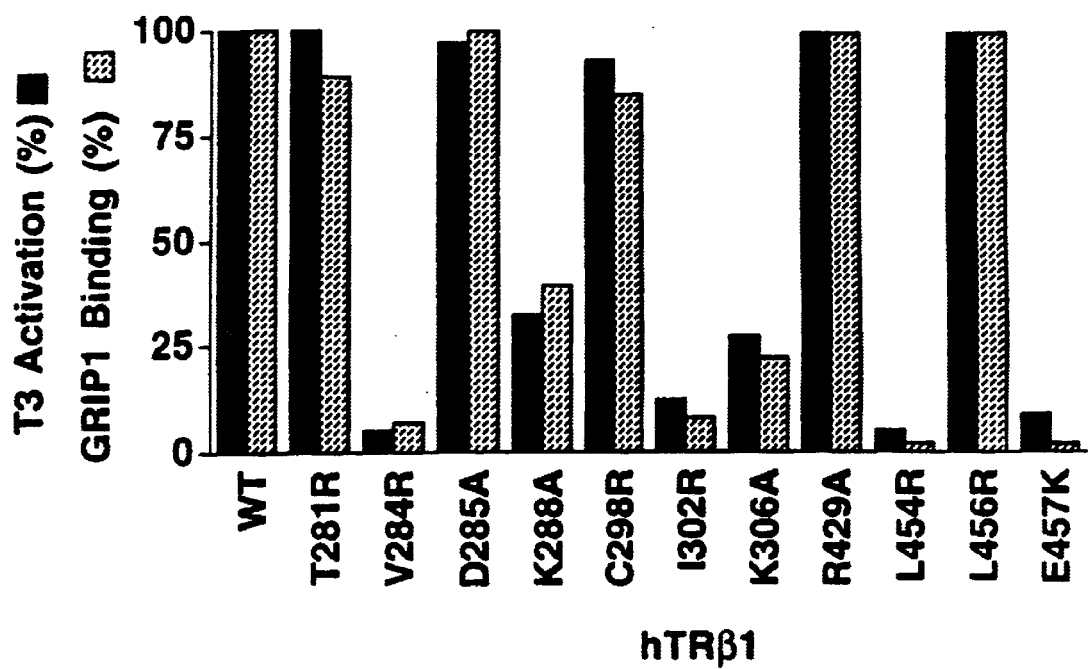
FIG. 1 shows the specific effects of mutations on hTRβ1 transcriptional activation in HeLa cells and correlation with effects on binding to GST-GRIP1. $T_3$ dependent activation of transcription of a reporter gene, expressed as the percentage of WT is plotted for each mutant. GST-GRIP1 binding, analyzed by autoradiography after separation using 10% SDS-PAGE, was also expressed as the percentage of WT and plotted for each mutant. The GST-GRIP1 used included GRIP1 amino acids 721–1121; the same results were obtained using a GST-GRIP1 construct including GRIP1 amino acids 563–1121 (data not shown).

The present invention provides methods and compositions for identifying compounds that modulate nuclear receptor activity. The compounds can be nuclear receptor agonists or antagonists that bind to the coactivator binding site (and that act as mimetics to the coactivator in this regard), and promote (agonists) or block (antagonists) binding of the coactivator to the target nuclear receptor. Compounds that bind to the coactivator binding site also are provided. The compounds can be natural or synthetic. Preferred compounds are small organic molecules, peptides and peptidomimetics (e.g., cyclic peptides, peptide analogs, or constrained peptides).

Figure 19:
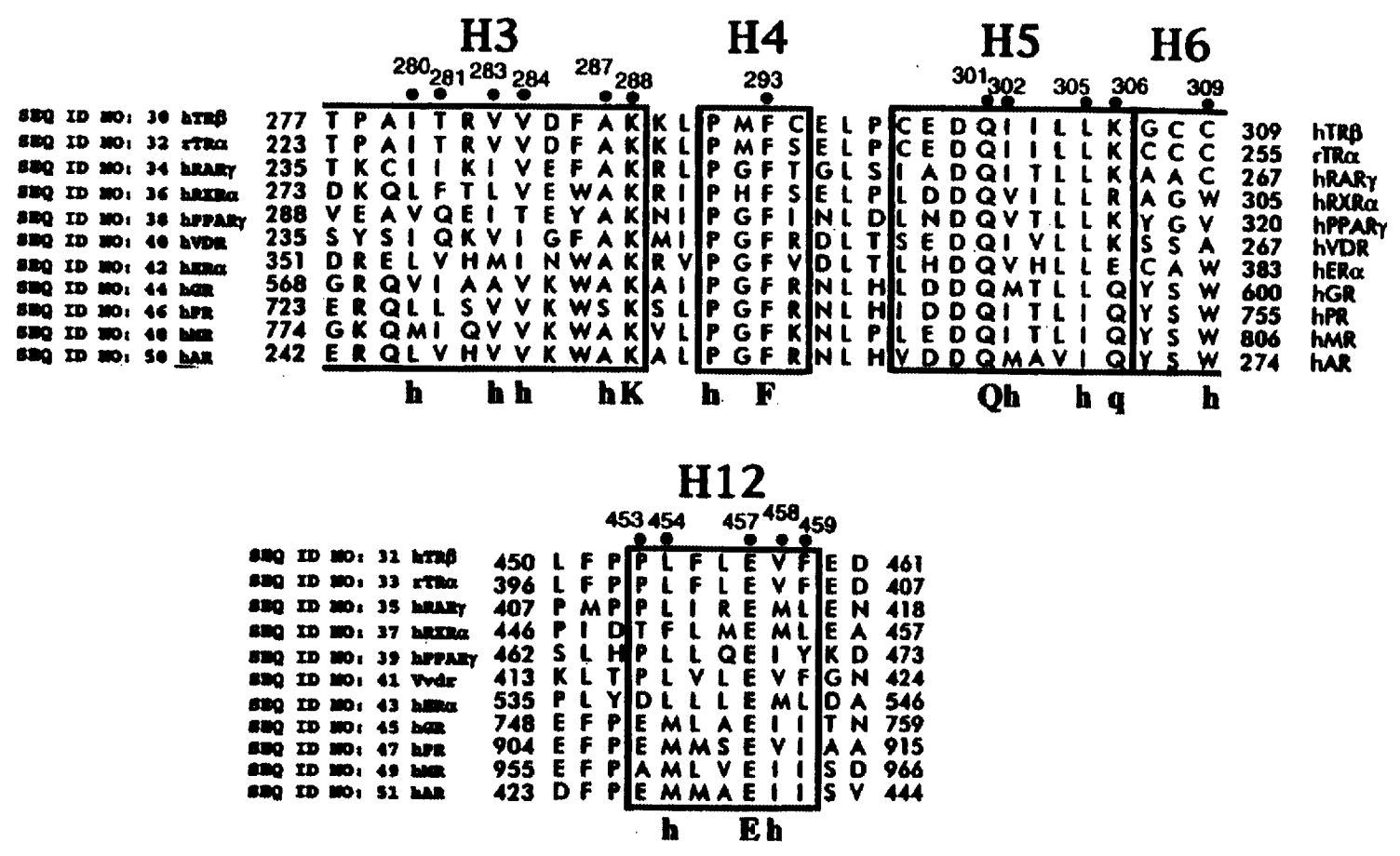

As described in the Examples, mutagenesis and coactivator binding studies, coupled with analysis of atomic models derived from cocrystals, reveals for the first time a previously unknown structure for nuclear receptors, the coactivator binding site. By "coactivator binding site" is intended a structural segment or segments of nuclear receptor polypeptide chain folded in such a way so as to give the proper geometry and amino acid residue conformation for binding a coactivator. This is the physical arrangement of protein atoms in three-dimensional space forming a coactivator binding site pocket or cavity. Residues forming the site are amino acids corresponding to (i.e., the same as or equivalent to) human TR residues of C-terminal helix 3 (Ile280, Thr281, Val283, Val284, Ala287, and Lys288), helix 4 (Phe293), helix 5 (Gln301, Ile302, Leu305, Lys306), helix 6 (Cys309), and helix 12 (Leu454, Glu457, Val458 and Phe459). The coactivator binding site is highly conserved among the nuclear receptor super family (FIG. 19). Thus, this site corresponds to a surprisingly small cluster of residues on the surface of the LBD that form a prominent hydrophobic cleft. The hydrophobic cleft is formed by hydrophobic residues corresponding to human TR residues of C-terminal helix 3 (Ile280, Val283, Val284, and Ala287), helix 4 (Phe293), helix 5 (Ile302 and Leu305), helix 6 (Cys309), and helix 12 (Leu454, Val458 and Phe459). The hydrophobic cleft of the coactivator binding site also is highly conserved among the nuclear receptor super family (FIG. 19).

The invention also includes compositions and methods for identifying coactivator binding sites of nuclear receptors. The methods involve examining the surface of a nuclear receptor of interest to identify residues that modulate coactivator binding. The residues can be identified by homology to the coactivator binding site of human TR described herein. A preferred method is alignment with the residues of any nuclear receptor corresponding to (i.e., equivalent to) human TR residues of the C-terminal helix 3 (Ile280, Thr281, Val283, Val284, Ala287, and Lys288), helix 4 (Phe293), helix 5 (Gln301, Ile302, Leu305, Lys306), helix 6 (Cys309), and helix 12 (Pro453, Leu454, Glu457, Val458 and Phe459). Overlays and superpositioning with a three-dimensional model of a nuclear receptor LBD, or a portion thereof that contains a coactivator binding site, also can be used for this purpose. For example, three-dimensional structures of TR, RAR, RXR and ER LBDs can be used for this purpose. For example, nuclear receptors identifiable by homology alignment include normal nuclear receptors or proteins structurally related to nuclear receptors found in humans, natural mutants of nuclear receptors found in humans, normal or mutant receptors found in animals, as well as non-mammalian organisms such as pests or infectious organisms, or viruses.

Alignment and/or modeling also can be used as a guide for the placement of mutations on the LBD surface to characterize the nature of the site in the context of a cell. Selected residues are mutated to preserve global receptor structure and solubility. To destroy the coactivator binding interaction, preferred mutations are to charged residues (e.g., Arg, Lys, or Glu) on the basis that bulky, surface charged residues might disrupt coactivator binding, yet preserve global receptor structure and solubility. Mutants can be tested for coactivator binding as well as the relative change in strength of the binding interaction. Ligand-dependent coactivator interaction assays also can be tested for this purpose, such as those described herein.

Compounds that bind to the coactivator binding site of nuclear receptors can be identified by computational modeling and/or screening. For example, coactivator agonists or antagonists can be identified by providing atomic coordinates comprising a nuclear receptor coactivator binding site or portion thereof to a computerized modeling system, modeling them, and identifying compounds that fit spatially into the coactivator binding site. By a "portion thereof" is intended the atomic coordinates corresponding to a sufficient number of residues or their atoms of the coactivator binding site that interact with a compound capable of binding to the site. This includes receptor residues having an atom within 4.5 Å of a bound compound or fragment thereof. For instance, human TR residues Val284, Phe293, Ile302, Leu305 and Leu454 contain side chain atoms that are within 4.5 Å, and interact with, hydrophobic residues of a (SEQ ID NO: 1) LxxLL motif of an NR-box 2 coactivator peptide. As another example, an atomic structural model utilized for computational modeling and/or screening of compounds that bind to the coactivator binding site may include a portion of atomic coordinates of amino acid residues corresponding to the site composed of residues of human thyroid receptor selected from Val284, Lys288, Ile302, Lys306, Leu454 and Glu457, or their structural and functional equivalents found in other receptors. Thus, for example, the atomic coordinates provided to the modeling system can contain atoms of the nuclear receptor LBD, part of the LBD such as atoms corresponding to the coactivator binding site or a subset of atoms useful in the modeling and design of compounds that bind to a coactivator binding site.

The atomic coordinates of a compound that fits into the coactivator binding site also can be used for modeling to identify compounds or fragments that bind the site. By "modeling" is intended quantitative and qualitative analysis of molecular structure/function based on atomic structural information and receptor-coactivator agonists/antagonists interaction models. This includes conventional numeric-based molecular dynamic and energy minimization models, interactive computer graphic models, modified molecular mechanics models, distance geometry and other structure-based constraint models. Modeling is preferably performed using a computer and may be further optimized using known methods. By "fits spatially" is intended that the three-dimensional structure of a compound is accommodated geometrically by a cavity or pocket of a nuclear receptor coactivator binding site.

Compounds of particular interest fit spatially and preferentially into the coactivator binding site. By "fits spatially and preferentially" is intended that a compound possesses a three-dimensional structure and conformation for selectively interacting with a nuclear receptor coactivator binding site. Compounds that fit spatially and preferentially into the coactivator binding site interact with amino acid residues fanning the hydrophobic cleft of this site. In particular, the hydrophobic cleft of the coactivator binding site comprises a small cluster of hydrophobic residues. The site also contains polar or charged residues at its periphery. The present invention also includes a method for identifying a compound capable of selectively modulating coactivator binding to different nuclear receptors. The method comprises the steps of modeling test compounds that fit spatially and preferentially into the coactivator binding site of a nuclear receptor of interest using an atomic structural model of a nuclear receptor, screening the test compounds in a biological assay for nuclear receptor activity characterized by preferential binding of a test compound to the coactivator binding site of a nuclear receptor, and identifying a test compound that selectively modulates the activity of a nuclear receptor. Such receptor-specific compounds are selected that exploit differences between the coactivator binding sites of one type of receptor versus a second type of receptor, such as the differences depicted in FIG. 19.

The invention also is applicable to generating new compounds that distinguish nuclear receptor isoforms. This can facilitate generation of either tissue-specific or function-specific compounds. For instance, GR subfamily members have usually one receptor encoded by a single gene, although there are exceptions. For example, there are two PR isoforms, A and B, translated from the same mRNA by alternate initiation from different AUG codons. There are two GR forms, one of which does not bind ligand. This method is especially applicable to the TR subfamily which usually has several receptors that are encoded by at least two (TR: $\alpha$, $\beta$) or three (RAR, RXR, and PPAR: $\alpha$, $\beta$, $\gamma$) genes or have alternate RNA splicing.

The receptor-specific compounds of the invention preferably interact with conformationally constrained residues of the coactivator binding site that are conserved among one type of receptor compared to a second type of receptor. "Conformationally constrained" is intended to refer to the three-dimensional structure of a chemical or moiety thereof having certain rotations about its bonds fixed by various local geometric and physical-chemical constraints. Conformationally constrained structural features of a coactivator binding site include residues that have their natural flexible conformations fixed by various geometric and physical-chemical constraints, such as local backbone, local side chain, and topological constraints. These types of constraints are exploited to restrict positioning of atoms involved in receptor-coactivator recognition and binding.

For instance, comparison of sequences of the GR and TR coactivator interaction surface shows a highly negatively charged sequence at the C-terminal end of TR helix 12 (E460 and D461) that is neutral in the equivalent positions in GR helix 12 (GR residues T788 and N759, corresponding to TR residue positions 460 and 461, as depicted in FIG. 19). As described in the Examples, the cocrystal of the hTRβ LBD complexed with the GRIP1 NR-box 2 peptide shows that TR residues E460 and D461 interact with positively charged residues of the NR-box 2 peptide. Also, when comparing the RAR LBD structure to that of the TR LBD, conformation of helix 12 differs slightly, whereas helices 3, 4, 5 and 6 are substantially the same. Thus, differences in helix 12, particularly charge differences at the C-terminal end of the helix, may modulate preferential interaction of TR for NR-box 2 containing coactivators. As further demonstrated in the Examples, TR and GR differ in their specificity for different NR-boxes containing the conserved (SEQ ID NO: 1) LxxLL motif found in members of the p160 family of coactivator proteins. As also demonstrated in the Examples, GR but not TR is able to interact with peptides containing the hydrophobic interaction motifs of p53 (SEQ ID NO: 3; FxxLW) and VP16 (SEQ ID NO: 4; FxxAL). Thus, TR exhibits preferential interaction with NR-box peptides comprising the (SEQ ID NO: 1) LxxLL motif, but GR does not discriminate and can bind peptides containing a generic amphipathic helix motif. Accordingly, these real differences among the various nuclear receptors can be exploited in the identification and design of compounds that modulate coactivator binding to one nuclear receptor compared to another.

For modeling, docking algorithms and computer programs that employ them can be used to identify compounds that fit into the coactivator binding site. For example, docking programs can be used to predict how a small molecule of interest can interact with the nuclear receptor coactivator binding site. Fragment-based docking also can be used in building molecules de novo inside the coactivator binding site, by placing chemical fragments that complement the site to optimize intermolecular interactions. The techniques can be used to optimize the geometry of the binding interactions. This design approach has been made possible by identification of the coactivator binding site structure thus, the principles of molecular recognition can now be used to design a compound which is complementary to the structure of this site. Compounds fitting the coactivator binding site serve as a starting point for an iterative design, synthesis and test cycle in which new compounds are selected and optimized for desired properties including affinity, efficacy, and selectivity. For example, the compounds can be subjected to addition modification, such as replacement and/or addition of R-group substituents of a core structure identified for a particular class of binding compounds, modeling and/or activity screening if desired, and then subjected to additional rounds of testing.

Computationally small molecule databases can be screened for chemical entities or compounds that can bind in whole, or in part, to a nuclear receptor coactivator binding site of interest. In this screening, the quality of fit of such entities or compounds to the binding site may be judged either by shape complementarity (DesJalais et al., *J. Med. Chem.* (1988) 31:722–729) or by estimated interaction energy (Meng et al., *J. Comp. Chem.* (1992) 13:505–524). The molecule databases include any virtual or physical database, such as electronic and physical compound library databases, and are preferably used in developing compounds that modulate coactivator binding.

Compounds can be designed intelligently by exploiting available structural and functional information by gaining an understanding of the quantitative structure-activity relationship (QSAR), using that understanding to design new compound libraries, particularly focused libraries having chemical diversity of one or more particular groups of a core structure, and incorporating any structural data into that iterative design process. For example, one skilled in the art may use one of several methods to screen chemical entities or fragments for their ability to associate with the coactivator binding site of a nuclear receptor of interest. This process may begin by visual inspection of, for example, the coactivator binding site on the computer screen. Selected fragments or chemical entities may then be positioned into all or part of the site. Docking may be accomplished using software such as Quanta and Sybyl, followed by energy minimization and molecular dynamics with standard molecular mechanics force-fields, such as CHARMM and AMBER.

For example, compounds and/or fragments can be designed to fill up the hydrophobic cleft, the pocket deep within the cleft, the upper end of the site, and/or the lower end of the site. Residues comprising a coactivator binding site, when defined by the user as those residues having an atom within 4.5 Å of an atom of a bound chemical entity, can be modeled to look for energetic contributions and interaction with the bound chemical entity. For example, a compound or fragment can be designed to contain hydrophobic groups that interact with hydrophobic residues of the coactivator binding site. As described in the examples, human TR residues V284, Phe293, Ile302, Leu305 and Leu454 contain side chain atoms that are within 4.5 Å, and interact with, hydrophobic residues of a (SEQ ID NO: 1) LxxLL motif of an NR-box 2 coactivator peptide. Thus, for example, peptides and/or peptide mimetics having a hxxhh motif, where "h" is a hydrophobic residue and x is any residue, can be constructed. Small organic molecules that mimic one or more of these particular interactions also can be designed, for example, by including one or more R-groups that are hydrophobic and fit into the site.

Specialized computer programs may also assist in the process of selecting chemical entity fragments or whole compounds. These include: GRID (Goodford, *J. Med. Chem.* (1985) 28:849–857; available from Oxford University, Oxford, UK); MCSS (Miranker et al., *Proteins: Structure, Function and Genetics,* (1991) 11:29–34; available from Molecular Simulations, Burlington, Mass.); AUTODOCK (Goodsell et al., *Proteins: Structure, Function and Genetics* (1990) 8:195–202; available from Scripps Research Institute, La Jolla, Calif.); and DOCK (Kuntz et al, *J. Mol. Biol.* (1982) 161:269–288; available from University of California, San Francisco, Calif.).

Additional commercially available computer databases for small molecular compounds include Cambridge Structural Database and Fine Chemical Database (Rusinko, *Chem. Des. Auto. News* (1993) 8:44–47).

Once suitable chemical entities or fragments have been selected, they can be assembled into a single compound. Assembly may be proceeded by visual inspection of the relationship of the fragments to each other on the three-dimensional image displayed on a computer screen in relation to the structure coordinates of a nuclear receptor. This can be followed by manual model building using software such as Quanta or Sybyl.

Useful programs to aid one of skill in the art in connecting the individual chemical entities or fragments include: CAVEAT (Bartlett et al., "CAVEAT: A Program to Facilitate the Structure-Derived Design of Biologically Active Molecules", In: *Molecular Recognition in Chemical and*

Biological Problems", Special Pub., *Royal Chem. Soc.* (1989) 78:182–196; CAVEAT is available from the University of California, Berkeley, Calif.); 3D Database systems such as MACCS-3D (MDL Information Systems, San Leandro, Calif.; reviewed in Martin, *J. Med. Chem.* (1992) 35:2145–2154); and HOOK (available from Molecular Simulations, Burlington, Mass.).

In addition to building a compound in a step-wise fashion, one fragment or chemical entity at a time as described above, compounds that bind to a coactivator binding site of interest also may be designed as a whole or de novo using either an empty coactivator binding site or optionally including some portion(s) of a molecule known to binds to the site, such as an NR-box type peptide. These methods include: LUDI (Bohm, *J. Comp. Aid. Molec. Design* (1992) 6:61–78; LUDI is available from Biosym Technologies, San Diego, Calif.); LEGEND (Nishibata et al., *Tetrahedron* (1991) 47:8985; LEGEND is available from Molecular Simulations, Burlington, Mass.); and LeapFrog (available from Tripos Associates, St. Louis, Mo.).

Other molecular modeling techniques may also be employed in accordance with this invention. See, for example, Cohen et al., *J. Med. Chem.* (1990) 33:883–894); Navia et al., *Curr. Opin. Struct. Biol.* (1992) 2:202–210). For example, where the structures of test compounds are known, a model of the test compound may be superimposed over the model of the structure of the invention. Numerous methods and techniques are known in the art for performing this step, any of which may be used. See, for example, Farmer, "*Drug Design,*" Ariens, E. J., ed., 10:119–143 (Academic Press, New York, 1980); U.S. Pat. No. 5,331,573; U.S. Pat. No. 5,500,807; Verlinde, *Structure,* (1994) 2:577–587); and Kuntz et al., *Science,* (1992) 257:1078–1082). The model building techniques and computer evaluation systems described herein are not a limitation on the present invention.

Using these computer modeling systems a large number of compounds may be quickly and easily examined and expensive and lengthy biochemical testing avoided. Moreover, the need for actual synthesis of many compounds can be substantially reduced and/or effectively eliminated.

Compounds identified through modeling can be screened in an assay characterized by binding of the compound to a coactivator binding site of interest for coactivator binding activity, such as a biologically based assay. Screening can be in vitro and/or in vivo. Preferred assays include cell-free competition assays and cell culture based assays. The biological screening preferably centers on activity-based response models, binding assays (which measure how well a compound binds to the receptor), and bacterial, yeast and animal cell lines (which measure the biological effect of a compound in a cell). The assays can be automated for high capacity-high throughput screening (HTS) in which large numbers of compounds can be tested to identify compounds with the desired activity.

As an example, in vitro binding assays can be performed in which compounds are tested for their ability to block the binding of a coactivator protein, fragment, fusion or peptide thereof, to a coactivator binding site of interest. For cell and tissue culture assays, they may be performed to assess a compound's ability to block function of cellular coactivators, such as members of the p160 family of coactivator proteins, such as SRC-1, AIB1, RAC3, p/CIP, and GRIP1 and its homologues TIF 2 and NcoA-2, and those that exhibit receptor and/or isoform-specific binding affinity. In a preferred embodiment, compounds of the invention bind to a nuclear receptor coactivator binding site with greater affinity than the cellular coactivator proteins. Tissue profiling and appropriate animal models also can be used to select compounds. Different cell types and tissues also can be used for these biological screening assays. Suitable assays for such screening are described herein and in Shibata et al. (*Recent Prog. Horm. Res.* 52:141–164 (1997)); Tagami et al. (*Mol. Cell Biol.* (1997) 17(5):2642–2648); Zhu et al. (*J. Biol. Chem.* (1997) 272(14):9048–9054); Lin it al. (*Mol. Cell Biol.* (1997) 17(10):6131–6138); Kakizawa et al. (*J. Biol. Chem.* (1997) 272(38):23799–23804); and Chang et al. (*Proc. Natl. Acad. Sci. USA* (1997) 94(17):9040–9045), which references are incorporated herein in their entirety by reference. For example, coactivators or binding fragments thereof can be expressed and/or assayed for binding as for GRIP1 (Hong et al., *MCB* supra; and Hong et al., *PNAS* supra) and/or SRC-1 (Spencer et al., *Nature* (1997) 389:194–198; Onate et al., *Science* (1995) 270:1354–1357), incorporated by reference.

The compounds selected can have agonist and/or antagonistic properties. The compounds also include those that exhibit new properties with varying mixtures of agonist and antagonist activities, depending on the effects of altering coactivator binding in the context of different activities of nuclear receptors, either hormone-dependent or hormone-independent, which are mediated by proteins other than coactivators, and which interact with the receptors at locations other than the coactivator binding site. The compounds also include those, which through their binding to receptor locations that are conformationally sensitive to hormone binding, have allosteric effects on the receptor by stabilizing or destabilizing the hormone-bound conformation of the receptor, or by directly inducing the same, similar, or different conformational changes induced in the receptor by the binding of hormone.

Of particular interest is use of such compounds in a method of modulating nuclear receptor activity in a mammal by administering to a mammal in need thereof a sufficient amount of a compound that fits spatially and preferentially into a coactivator binding site of a nuclear receptor of interest. By "modulating" is intended increasing or decreasing activity of a nuclear receptor. For example, pre-clinical candidate compounds can be tested in appropriate animal models in order to measure efficacy, absorption, pharmacokinetics and toxicity following standard techniques known in the art. Compounds exhibiting desired properties are then tested in clinical trials for use in treatment of various nuclear receptor-based disorders. These include ER-based disorders, such as postmenopausal symptoms and cancer resulting from loss of estrogen production, and osteoporosis and cardiovascular disease stemming from traditional estrogen replacement therapy. Others include TR-based disorders including cardiovascular disease, metabolic disorders, hyperthyroidism, glaucoma and skin disorders. GR-based disorders include Type II diabetes and inflammatory conditions such as rheumatic diseases.

The invention also provides for cocrystals made from nuclear receptor ligand binding domains with a molecule bound to the coactivator binding site. As exemplified in the Examples, TR LBDs are co-crystallized with a peptide molecule comprising a coactivator NR-box 2 peptide sequence bound to the coactivator binding site, and the hormone/ligand $T_3$.

Crystals are made from purified nuclear receptor LBDs that are usually expressed by a cell culture, such as *E. coli*. Preferably, different crystals (cocrystals) for the same nuclear receptor are separately made using different coactivators-type molecules, such as protein fragments, fusions or small peptides. The coactivator-type molecules preferably contain NR-box sequences necessary for binding to the coactivator binding site, or derivatives of NR-box sequences. Other molecules can be used in co-crystallization, such as small organics that bind to the coactivator or hormone binding site(s). Heavy atom substitutions can be included in the LBD and/or a co-crystallizing molecule.

After the three dimensional structure of the cocrystal is determined, the structural information can be used in computational methods to design synthetic compounds for the nuclear receptor, and further structure-activity relationships can be determined through routine testing using the assays described herein and known in the art.

Since nuclear receptor LBDs may crystallize in more than one crystal form, the structure coordinates of such receptors or portions thereof, as provided in Appendix 1, are particularly useful for solving the structure of those other crystal forms of nuclear receptors. They may also be used to solve the structure of mutants or co-complexes of nuclear receptors having sufficient structural similarity.

One method that may be employed for this purpose is molecular replacement. In this method, the unknown crystal structure, may be determined using the structure coordinates of this invention as provided in Appendix 1. This method will provide an accurate structural form for the unknown crystal more quickly and efficiently than attempting to determine such information ab initio.

Atomic coordinate information gleaned from the crystals of the invention can be stored. In a preferred embodiment, the information is provided in the form of a machine-readable data storage medium. This medium contains information for constructing and/or manipulating an atomic model of a coactivator binding site or portion thereof. For example, the machine readable data for the coactivator binding site comprises structure coordinates of amino acids corresponding to human TR amino acids selected from C-terminal helix 3 (Ile280, Thr281, Val283, Val284, Ala287, and Lys288), helix 4 (Phe293), helix 5 (Gln301, Ile302, Leu305, Lys306), helix 6 (Cys309), and helix 12 (Pro453, Leu454, Glu457, Val458 and Phe459), or a homologue of the molecule or molecular complex comprising the site. The homologues comprise a coactivator binding site that has a root mean square deviation from the backbone atoms of the amino acids of not more than 1.5 Å. A preferred molecule or complex represents a compound bound to the coactivator binding site.

The machine-readable data storage medium can be used for interactive drug design and molecular replacement studies. For example, a data storage material is encoded with a first set of machine-readable data that can be combined with a second set of machine-readable data. For molecular replacement, the first set of data can comprise a Fourier transform of at least a portion of the structural coordinates of the nuclear receptor or portion thereof of interest, and the second data set comprises an X-ray diffraction pattern of the molecule or molecular complex of interest. Using a machine programmed with instructions for using the first and second data sets a portion or all of the structure coordinates corresponding to the second data can be determined.

Protein for crystals and assays described herein can be produced using expression and purification techniques described herein and known in the art. For example, high level expression of nuclear receptor LBDs can be obtained in suitable expression hosts such as *E. coli*. Expression of LBDs in *E. coli*, for example, includes the TR LBD and other nuclear receptors, including members of the steroid/thyroid receptor superfamily, such as the receptors ER, AR, MR, PR, RAR, RXR and VDR. Yeast and other eukaryotic expression systems can be used with nuclear receptors that bind heat shock proteins as these nuclear receptors are generally more difficult to express in bacteria, with the exception of ER, which can be expressed in bacteria. Representative nuclear receptors or their ligand binding domains have been cloned and sequenced: human RAR-α, human RAR-γ, human RXR-α, human RXR-α, human PPAR-α, human PPAR-β, human PPAR-γ, human VDR, human ER (as described in Seielstad et al., *Molecular Endocrinol.*, (1995) 9:647–658, incorporated herein by reference), human GR, human PR, human MR, and human AR. The LBD for each of these receptors has been identified.

Coactivator proteins can be expressed using techniques known in the art, particularly members of the p160 family of coactivator proteins that have been cloned and/or expressed previously, such as SRC-1, AIB1, RAC3, p/CIP, and GRIP1 and its homologues TIF 2 and NcoA-2. A preferred method for expression of coactivator protein is to express a fragment that retains transcriptional activation activity using the "yeast 2-hybrid" method as described by Hong et al. (*PNAS* supra; and *MCB* supra), for GRIP1 expression, which reference is herein incorporated by reference.

The proteins can be expressed alone, as fragments of the mature or full-length sequence, or as fusions to heterologous sequences. For example, TR can be expressed without any portion of the DBD or amino-terminal domain. Portions of the DBD or amino-terminus can be included if further structural information with amino acids adjacent the LBD is desired. Generally, for the TR the LBD used for crystals will be less than 300 amino acids in length. Preferably, the TR LBD will be at least 150 amino acids in length, more preferably at least 200 amino acids in length, and most preferably at least 250 amino acids in length. For example the LBD used for crystallization can comprise amino acids spanning from Met 122 to Val 410 of the rat TR-α or Glu 202 to Asp 461 of the human TR-β.

Typically the LBDs are purified to homogeneity for crystallization. Purity of LBDs can be measured with sodium dodecyl sulfate polyacrylamide gel electrophoresis (SDS-PAGE), mass spectrometry (MS) and hydrophobic high performance liquid chromatography (HPLC). The purified LBD for crystallization should be at least 97.5% pure, preferably at least 99.0% pure, more preferably at least 99.5% pure.

Initially, purification of the unliganded receptor can be obtained by conventional techniques, such as hydrophobic interaction chromatography (HPLC), ion exchange chromatography (HPLC), and heparin affinity chromatography.

To achieve higher purification for improved crystals of nuclear receptors, especially the TR subfamily and TR, the receptors can be ligand-shift-purified using a column that separates the receptor according to charge, such as an ion exchange or hydrophobic interaction column, and then bind the eluted receptor with a ligand, especially an agonist. The ligand induces a change in the receptor's surface charge such that when re-chromatographed on the same column, ligand-bound receptor is separated from unliganded receptor. Usually saturating concentrations of ligand are used in the column and the protein can be preincubated with the ligand prior to passing it over the column. The structural studies detailed herein indicate the general applicability of this technique for obtaining super-pure nuclear receptor LBDs for crystallization.

Purification can also be accomplished by use of a purification handle or "tag," such as with at least one histidine amino acid engineered to reside on the end of the protein, such as on the N-terminus, and then using a nickel or cobalt chelation column for purification. (Janknecht et al., *Proc. Natl. Acad. Sci. USA,* (1991) 88:8972–8976) incorporated by reference.

Typically purified LBD, such as TR LBD, is equilibrated at a saturating concentration of ligand at a temperature that preserves the integrity of the protein. Ligand equilibration can be established between 2 and 37° C., although the receptor tends to be more stable in the 2–20° C. range. Preferably crystals are made with the hanging drop methods detailed herein. Regulated temperature control is desirable to improve crystal stability and quality. Temperatures between 4 and 25° C. are generally used and it is often preferable to test crystallization over a range of temperatures. The crystals are then subjected to vapor diffusion and bombarded with x-rays to obtain x-ray diffraction pattern following standard procedures.

For co-crystallization with a peptide that binds to the coactivator binding site, various concentrations of peptides containing a sequence that binds to a coactivator binding site of a nuclear receptor of interest can be used in microcrystallization trials, and the appropriate peptides selected for further crystallization. Any number of techniques, including those assays described herein can assay peptides for binding to the coactivator binding site of a nuclear receptor of interest. In a preferred embodiment, a NR-box 2 sequence-containing peptide is used for crystallization with TR LBD. A preferred peptide contains a NR-box (SEQ ID NO: 1) LxxLL motif, and suitable flanking sequences necessary for binding and forming complex with coactivator binding site of the nuclear receptor of interest, such as a TR LBD. The binding peptides are then tested in crystallization trials at various concentrations and ratios of concentrations with a nuclear receptor of interest, for example, as described herein and in the Examples. For crystallization trials with TR LBD, the hanging drop vapor diffusion method is preferred. Conditions of pH, solvent and solute components and concentrations and temperature can be adjusted, for instance, as described in the Examples. In the handing drop method, to obtain suitable crystals for x-ray diffraction analysis, seeding of prepared drops with microcrystals of the complex can be used. Collection of structural information can be determined by molecular replacement using the structure of TR LBD determined herein or previously by Wagner et al., supra. The structure is refined following standard techniques known in the art.

There are many uses and advantages provided by the present invention. For example, the methods and compositions described herein are useful for identifying peptides, peptidomimetics or small natural or synthetic organic molecules that modulate nuclear receptor activity. The compounds are useful in treating nuclear receptor-based disorders. Methods and compositions of the invention also find use in characterizing structure/function relationships of natural and synthetic coactivator compounds.

The following examples illustrate various aspects of this invention. These examples do not limit the scope of this invention.

EXAMPLES

Example 1

Expression and Purification of Wild-type and Mutant Nuclear Receptors and Coactivators A. Human TRβ LBD Human TRβ LBD (His6-E202-D461) was expressed and purified as described (Shiau et al., *Gene* (1996) 179(2): 205–10). Briefly, the protein was expressed from pET (e.g., pET3 and pET28) in BL21DE3 at 14° C., induced at OD(600 nm) 0.7 with 1 mM IPTG and incubation was extended for 24 hours. Cells were harvested and lysed in 50 mM sodium-phosphate buffer (pH 8.0), 0.3M NaCl, 10% glycerol, 25 mM β-merceptoethanol and 0.1 mM PMSF as described above. The lysate was cleared by ultracentrifugation (Ti45, 36000 rpm, 1 h, 4° C.), loaded on a Talon column equilibrated in the sodium phosphate buffer described above, washed with 12 mM imidazole and eluted with an imidazole gradient (12–300 mM). TRβ LBD containing fractions were loaded in 0.6M ammonium sulfate on a TSK-phenyl hydrophobic interaction column and eluted with a reverse ammonium sulfate gradient [0.6–0 M] in 50% glycerol and 10% acetonitrile. Fractions containing TRβ LBD were tested for hormone binding, pooled and incubated with a 3-fold molar excess of $T_3$ (Sigma). The hydrophobic interaction run was repeated with liganded receptor under the same conditions. Liganded receptor, which elutes earlier than unliganded receptor, was collected and buffer changed to 20 mM Hepes pH7.0, 3 mM DTT and 0.1 $\mu$M $T_3$ using NAP columns (Pharmacia). For crystallization, the protein was concentrated by ultrafiltration (Millipore UFV2BGC10 concentrators) to a final concentration of 9 mg/ml. The yield was about 9.5 mg protein per liter bacterial culture.

B. Human TR Mutants

Thirty-seven thyroid receptor mutants were created by synthesizing double-stranded oligonucleotides which encode the mutant sequence and which have ends allowing them to be ligated as a cassette using pairs of the NsiI, PstI, SstI, AlwNI, ApoI, PflMI, BstXI, BseRI, BsmFI, PvuII, NspI, SmaI, PmlI, BglII and BsmI restriction sites of the hTRβ1 cDNA sequence, or the 3' plasmid polylinker SalI, or BamHI restriction sites. The hTRβ1 sequences thus mutated were subcloned into the pCMX vector encoding the full-length 461 amino acid hTRβ1 sequence. Some of the mutations of the hTRβ1 in the CMX vector and all three mutations of the hERα in the pSG5-ER-HEGO vector (Tora et al., *EMBO* (1989) 8:1981) were created using Quick Change Site-Directed Mutagenesis Kits (Stratagene). The mutated sequences were verified by DNA sequencing using Sequenase Kits (Stratagene).

C. Human ERα LBD

The human ERα-LBD 297–554 was overexpressed as described previously (Seielstad, et al., supra) in BL21(DE3) pLysS cells transformed with a modified pET-23d-ERG vector that contained the sequence Met-Asp-Pro fused to residues 297 to 554 of the hERα (provided by Paul Sigler of Yale University). Clarified bacterial lysates were adjusted to 3 M in urea and 0.7 M in NaCl and then applied to a 10-ml column of estradiol-Sepharose (Greene, et al., *Proc. Natl. Acad. Sci. USA* (1980) 77:5115–5119; Landel, et al., *Mol. Endocrinol.* (1994) 8:1407–1419; Landel, et al., *J. Steroid Biochem. Molec. Biol.* (1997) 63:59–73).

To carboxymethylate the solvent-accessible cysteines, the bound hERα-LBD was treated with 5 mM iodoacetic acid in 10 mM Tris, pH 8.1, 250 mM NaSCN (Hegy, et al., *Steroids* (1996) 61:367–373). Protein was eluted with 3×10–5 M ligand (either DES or OHT) in 30–100 ml of 50 mM Tris, 1 mM EDTA, 1 mM DTT and 250 mM NaSCN, pH 8.5. The yield of hERα-LBD was typically close to 100% (Seielstad, et al., *Biochemistry* (1995) 34:12605–12615). The affinity-purified material was concentrated and exchanged into 20 mM Tris, 1 mM EDTA, 4 mM DTT, pH 8.1 by ultrafiltration. The protein was bound to a Resource Q column (Pharmacia) and then eluted with a linear gradient of 25–350 mM NaCl in 20 mM Tris, pH 8.1, 1 mM DTT. The hERα-LBD-ligand complexes eluted at 150–200 mM NaCl. Pooled fractions were concentrated by ultrafiltration and analyzed by SDS-PAGE, native PAGE, and electrospray ionization mass spectrometry.

D. Human ER Mutants

To test the importance of the NR box peptide/LBD interface observed in the crystal, a series of site-directed mutations were introduced into the ERα LBD. These mutations were designed either to simultaneously perturb the structural integrity and the nonpolar character of the floor of the binding groove (Ile 358->Arg, Val 376->Arg and Leu 539->Arg) or to prevent the formation of the capping interactions (Lys 362->Ala and Glu 542->Lys). Fusions of glutathione-S-transferase (GST) to the wild-type and mutant LBDs were analyzed for their ability to bind $^{35}$S-labeled GRIP1 in the absence of ligand or in the presence of DES or OHT.

$^{35}$S-labeled GRIP1 was incubated with either immobilized GST, immobilized wild type GST-hERα LBD, or immobilized mutant GST-LBDs in the absence of ligand or in the presence of DES or OHT. The bound GRIP1 was quantitated after SDS-PAGE. I358R, mutant LBD containing a Ile->Arg substitution at residue 358; K362A, mutant LBD containing a Lys->Ala substitution at residue 362; V376R, mutant LBD containing a Val->Arg substitution at residue 376; L539R, mutant LBD containing a Leu->Arg substitution at residue 539; E542K, mutant LBD containing a Glu->Lys substitution at residue 542.

In the absence of ligand or in the presence of OHT, fusions to the wild-type protein and all of the mutant LBDs showed no detectable binding to GRIP1. The Ile 358->Arg, Val 376->Arg and Leu 539->Arg mutants were all unable to interact with coactivator in the presence of agonist, confirming the importance of the packing interactions observed in the crystal. Disruption of either the N- or C-terminal capping interaction also compromised GRIP1 binding in the presence of agonist. Only the wild-type GST-LBD was able to recognize the coactivator in the presence of DES.

E. Human ER LBD-GST Fusion Protein

A fusion between glutathione-S-transferase (GST) and amino acids 282–595 of hERα was constructed by subcloning the EcoRI fragment from pSG5 ERα-LBD (Lopez et al., submitted manuscript) into pGEX-3X (Pharmacia). The Ile 358->Arg, Lys 362->Ala, and Leu 539->Arg mutations were introduced into the GST-LBD construct using the QuikChange Kit (Stratagene) according to the manufacturer's instructions. The Val 376->Arg and Glu 542->Lys mutations were created in the GST-LBD construct by subcloning the BsmI/HindIII fragments of derivatives of pSG5-ER-HEGO (Tora, et al., supra) into which these mutations had already been introduced. All constructs were verified by automated sequencing (University of Chicago Cancer Research Center DNA Sequencing Facility).

F. Radiolabeled Full-length Receptors and Coactivator Proteins

Wild-type (WT) or mutant pCMV-hTRβ1 vector and the pSG5-GRIP1 and pCMX-SRC-1a vectors were used to produce radiolabeled full-length receptors and coactivator proteins using the TNT coupled Reticulocyte Lysate System (Promega) and [$^{35}$S]-Met (DuPont). GST-GRIP1 (amino acids 721–1221), GST-GRIP1 (amino acids 563–1121), GST-SRC-1a (amino acids 381–882), GST-hTRβ1 (full-length, WT or mutants, WT provided by. C. Costa), and the GST-hRXRα (full-length provided by. C. Costa), fusion proteins were produced in *E. coli* strain HB101 as per the manufacturer's protocol (Pharmacia Biotech).

G. Coactivator GRIP1 563–767 His6 GST Fusion Protein

GRIP1 563–767 was cloned as a Bam HI-Xho I fragment derived from pGEX-2TK GRIP1 563–1121 into the corresponding sites of pGEX-4T1. A His6-tag was added by inserting a Xho I-Nae I fragment of pET23a into Xho I-Bsa AI sites of this pGEX-4T1 construct yielding pGEX GRIP1 563–767His6. Mutants of GRIP1 563–767 were generated by PCR or single stranded mutagenesis using oligonucleotides carrying the mutations and a pSG5 GRIP1 vector as template. The mutations were confirmed by sequence analysis and integrated into pGEX GRIP1 563–767His6 as NgoMI-Xho I fragments. The GRIP1 563–767 His6 GST fusion protein was expressed in HB101 at 37° C. Protein expression was induced with 1 mM IPTG at an optical density (600 nm) of 0.7 and extended for 4 hours after induction. Cells were harvested by centrifugation, resuspended in sonication buffer (20 mM TrisHCl pH 8.0, 0.1M NaCl, 10%glycerol, 0.1 mM PMSF and protease inhibitors (Complete, EDTA free, Boehringer Mannheim)). The resuspended cells were freeze-thawed once, incubated on ice with 0.1 mg/ml lysozyme for 20 minutes and lysed per sonication. The lysate was cleared by ultracentrifugation (Ti 45, 36000 rpm, 1 h 4° C.), the supernatant filtered (Costar 0.2 μm top filter) and loaded on a Talon column (Clontech). The column was washed with 10 column volumes of sonication buffer supplemented with 12 mM imidazole and eluted with an imidazole gradient [12–100 mM]. At this step the fusion proteins are about 95% pure. Imidazole was removed by gelfiltration on NAP columns (Pharmacia), and protein concentrations determined using the Biorad protein assay. Equal concentrations of the different derivatives of the fusion fragment were incubated with glutathione agarose (1 h, 4° C.) which was equilibrated in binding buffer (sonication buffer supplemented with 1 mM DTT, 1 mM EDTA and 0.01% NP-40). Beads were washed with at least 20 volumes of this buffer, diluted in binding buffer with 20% glycerol to 40%, frozen in aliqots and stored at –70° C.

H. Coactivator GRIP1 563–767 His6

GRIP1 563–767 was cloned as a Bam HI-Xho I fragment derived fron pGEX GRIP1 563–767His6 into corresponding cloning sites of pET23a yielding pETGRIP1 563–767His6. The fragment was expressed in BL21DE3. Expression, cell lysis and Talon purification was identical as described for GST GRIP1 563–767His6. The protein eluted from a Talon column in two fractions, one at 12 mM and one between 40 and 70 mM imidazole. In the earlier eluting fraction the fragment was associated with a 70 kDa protein which was removed by a MonoQ run in 50 mM TrisHCl pH7.5, 10% glycerol, 1 mM EDTA, 1 mM DTT, 0.1 mM PMSF and protease inhibitors. GRIP1 563–767His6 eluted in the flow through and was concentrated by ultrafiltration. At this step the protein was more than 95% pure.

Example 2

Peptide Synthesis

Coactivator peptides were obtained using standard techniques. All peptides were HPLC purified and analyzed by mass spectroscopy. Peptide concentrations were either determined spectroscopically using the tyrosine signal ($A_{276}$= 1450 M-1 cm-1) or by amino acid analysis following standard techniques.

Example 3

Binding Assays with Nuclear Receptors and Coactivators

A. GST-GRIP Pull-down Assays and Peptide Competition Assays

Binding experiments were performed by mixing glutathione beads containing 10 μg of GST fusion proteins (Coomassie Plus Protein Assay Reagent, Pierce) with 1–2 μl of the [$^{35}$S]-labeled wild-type or mutant hTRβ1 (25 fmoles, 4000 cpm of receptor), or coactivators in 150 μl of binding buffer (20 mM HEPES, 150 mM KCl, 25 mM MgCl$_2$, 10% glycerol, 1 mM dithiothreitol, 0.2 mM phenylmethylsulfonyl fluoride, and protease inhibitors) containing 2 mg/ml BSA for 1.5 hrs in the presence or absence of 1 μM T$_3$. Beads were washed 3 times with 1 ml of binding buffer and the bound proteins were separated using 10% SDS-PAGE and visualized by autoradiography. Binding was quantitated by phosphorimaging using ImageQuant (Molecular Dynamics).

For in vitro binding studies GR, TR and their derivatives were translated in the presence of [$^{35}$S]methionine using the TNT Coupled Reticulocyte System (Promega). Separate translations were performed in the presence and absence of 10 μM dexamethasone or 1 μM RU486 for GR and 10 μM triiodothyronine for TR. Expression was quantified by phosphoimager analysis (BAS2000, Fuji). For all binding assays 50 μl of a 20% bead suspension containing either 1.6 or 4.0 μM bound purified GST GRIP1 fragment (either 568–767 or 563–1121) was incubated with 0.2 μl or 1.4 μl in vitro transcribed and translated TR or GR, respectively. Binding was performed in the binding buffer described above supplemented with 20 μg/ml BSA and appropriate hormone. The chosen GST GRIP1 fragment concentrations were sufficient to bind either 70 or 100% of the TR derivatives. The reaction was incubated at 4° C. under rotation for 2 hours. In case of competition experiments, the appropriate concentration of peptides were added to the reaction before addition of receptors. However, no differences in the results were noted by adding the peptides after half of the incubation of the GST GRIP1 fragment with nuclear receptors. This demonstrates that equilibrium is reached under the chosen conditions. Beads were washed five times with 200 μl binding buffer+BSA at 4° C. before elution of the bound proteins in 20 μl SDS loading buffer. Eluted beads and input labeled protein were subjected to SDS-PAGE. The fraction of bound nuclear receptors was determined by phosphoimager analysis.

B. GST-hTRβ1 Pull-down Assays

Assay and analysis was performed as for Example 3A. In vitro binding of [$^{35}$S]-labeled full-length GRIP1, [$^{35}$S]-labeled full-length SRC-1a, and [$^{35}$S]-labeled full-length hRXRα, to GST-hTRβ1 wild-type (WT) and mutants was performed. Mutants V284R, K288A, I302R, L454R, and E457K all bound to hRXRα with an affinity equivalent to wild type hTR. All of these mutants showed decreased ability to bind GRIP1 and SRC-1a, as expected from the results of Example 3A. The same results were obtained when a GST-SRC1 construct including SRC-1a amino acids 381–882 was tested for binding of [$^{35}$S]-Met-labeled full-length hTRβ1 WT and mutants (data not shown).

C. GST-hERα LBD Pull-down Assays

The wild-type and mutant GST-hERα LBDs were expressed in BL21(DE3) cells. Total ligand binding activity was determined by a controlled pore glass bead assay (Greene, et al., *Mol. Endocrinol.* (1988) 2:714–726) and protein levels were monitored by western blotting with a monoclonal antibody to hERα (H222). Cleared extracts containing the GST-hERα LBDs were incubated in buffer alone (50 mM Tris, pH 7.4, 150 mM NaCl, 2 mM EDTA, 1 mM DTT, 0.5% NP-40 and a protease inhibitor cocktail) or with 1 μM of either DES or OHT for 1 hour at 4° C. Extract samples containing thirty pmol of GST-LBD were then incubated with 10 μl glutathione-Sepharose-4B beads (Pharmacia) for 1 hour at 4° C. Beads were washed five times with 20 mM HEPES, pH 7.4, 400 mM NaCl, and 0.05% NP-40. $^{35}$S-labeled GRIP1 was synthesized by in vitro transcription and translation using the TNT Coupled Reticulocyte Lysate System (Promega) according to the manufacturer's instructions and pSG5-GRIP1 as the template. Immobilized GST-hERα LBDs were incubated for 2.5 hours with 2.5 μl aliquots of crude translation reaction mixture diluted in 300 μl of Tris-buffered saline (TBS). After five washes in TBS containing 0.05% NP-40, proteins were eluted by boiling the beads for 10 minutes in sample buffer. Bound $^{35}$S-GRIP1 was quantitated by fluorography following SDS-PAGE.

D. Electrophoretic Mobility Shift Assays

GRIP1, a mouse p160 coactivator, recognizes the ERα LBD in a ligand-dependent manner. The binding of agonists to the ERαLBD promotes recruitment of GRIP1, whereas binding of antagonists prevents this interaction (Norris, et al., *J. Biol. Chem.* (1998) 273:6679–88). While agonist-bound receptor will bind to all three of the NR boxes from GRIP1, ERα strongly prefers NR-box 2 (Ding, et al., *Mol. Endocrinol.* (1998) 12:302–13).

An electrophoretic mobility shift assay was used to directly assess the ability of the NR-box 2 peptide to bind the purified ERα LBD in the presence of either DES or OHT. Eight microgram samples of purified hERα-LBD bound to either DES or OHT were incubated in the absence of the peptide, i.e., buffer alone, or in the presence of either a 2-fold or 10-fold molar excess of the GRIP1 NR-box 2 peptide. The binding reactions were performed on ice for 45 minutes in 10 μl of buffer containing 20 mM Tris, pH 8.1, 1 mM DTT, and 200 mM NaCl and then subjected to 6% native PAGE. Gels were stained with GELCODE Blue Stain reagent (Pierce).

In the presence of the NR-box 2 peptide, the migration of the DES-hERα-LBD complex was retarded. In contrast, peptide addition had no effect on the mobility of the OHT-hERα-LBD complex. Hence, this peptide fragment of GRIP1 possesses the ligand-dependent receptor binding activity characteristic of the full-length protein.

Example: 4

Transfection Assays with TR and hERα

HeLa cell transfection and assay conditions are described (Webb et al., *Mol Endocrinol* (1995) 9:443). For TR assays, 5 μg of the reporter p(DR-4)$_2$-TK-LUC consisting of two copies of the DR-4 element (a direct repeat of the consensus TR response element (TRE) spaced by 4 base pairs) placed upstream of a minimal (−32/+45) thymidine kinase gene promoter linked to luciferase (LUC) coding sequences were used. A reporter containing palindromic TREs gave the same results (data not shown). Also, 2 μg of the hTRβ1 expression vector, pCMX-TR (WT or mutant), and 0.5 μg transfection control vector, pJ3LacZ, which contains the SV40 promoter linked to the β-galactosidase gene, were used. Other cells co-transfected with vector or receptor constructs can be used for same purpose. Alternative cells expressing sufficient levels of an endogenous receptor(s), or cells selected that express a single reporter, can be used for transfection assays, including MCF-7 cells expressing ER (Webb et al., supra), and GC cells expressing TR (Norman et al., *J. Biol. Chem.* (1989) 264:12063–12073).

For hERα assays, 5 µg of estrogen responsive reporter plasmid encoding chloramphenicol acetyltransferase (CAT), pERE-collTATA (Sadovsky, et al., *Mol Cell Biol.* (1995) 15:1554), 0.5 µg expression vector encoding full-length hERα, pSG5-er HEGO (WT or mutants), and 2 µg of pj3lacz, were used. For the experiments of FIGS. 2 and 4, 0.5 µg of a full-length GRIP1 expression vector, pSG5-GRIP1, was also included in the transfection. Transfected cells were treated with or without 1 µM $T_3$ or $E_2$, as indicated. After culturing for 24 hrs, the LUC or CAT activities were assayed and the β-galactosidase activities were also assayed to correct for differences in transfection efficiencies. The triplicate points were averaged and standard deviations were less than 10%.

Example 5

Hormone Binding Assays for Wild-type and Mutant TRs

The $T_3$ binding affinity constants (Kd) for in vitro-translated WT and mutant TRs were measured using [$^{125}$I] 3,5,3' triiodo-L-thyronine ([$^{125}$I]$T_3$) in gel filtration binding assays as described (Apriletti et al., *Protein Expr. Purif.* (1995) 6:363). Both the Kd and standard error (S.E.) values were calculated using the Prism computer program (GraphPad Software, Inc.). Mutations are indicated by the single-letter amino acid abbreviations, with the native residue name, followed by the primary sequence position number, and then the mutated residue name. The affinity of the WT TR is 81±12 pM. The relative affinity was determined by dividing the WT Kd by each mutant Kd. The 37 mutants tested with their relative affinities are: E217R (123%), E227R (109%), K242E (92%), E267R (117%), H271R (123%), T277R (7%), T281R (145%), V284R (105%), D285A (89%), K288A (98%), C294K (94%), E295R (118%), C298A (87%), C298R (141%), E299A (171%), I302A (86%), I302R (99%), K306A (6%), K306E (6%), P384R (164%), A387R (107%), E390R (151%), E393R (146%), L400OR (95%), H413R (109%), H416R (153%), M423R (156%), R429A (48%), S437R (170%), L440R (174%), V444R (89%), T448R (234%), E499R (36%), P453E (32%), L454R (26%), L456R (46%), E457K (71%).

Example 6

Coactivator Binding Assays for Wild-type and Mutant TRs

Wild type (WT) TR and most of the TR mutants liganded to 3,5,3'-triiodo-L-thyronine ($T_3$) bind equally well to the coactivator, GRIP1. In all cases, GRIP1 binding was hormone-dependent (data not shown). Mutations L454R and E457K in surface residues of helix 12 abolish GRIP1 binding (FIG. 1). Mutations in two residues of helix 3, V284R and K288A, and two residues of helix 5, I302R and K306A, also impair binding (FIG. 1). Five mutations with diminished GRIP1 binding (V284R, K288A, I302R, L454R, and E457K) also show decreased binding to another coactivator, SRC-1a (data not shown). Thus, these results show that two different coactivators recognize the same TR surface residues.

Example 7

Figure 2:
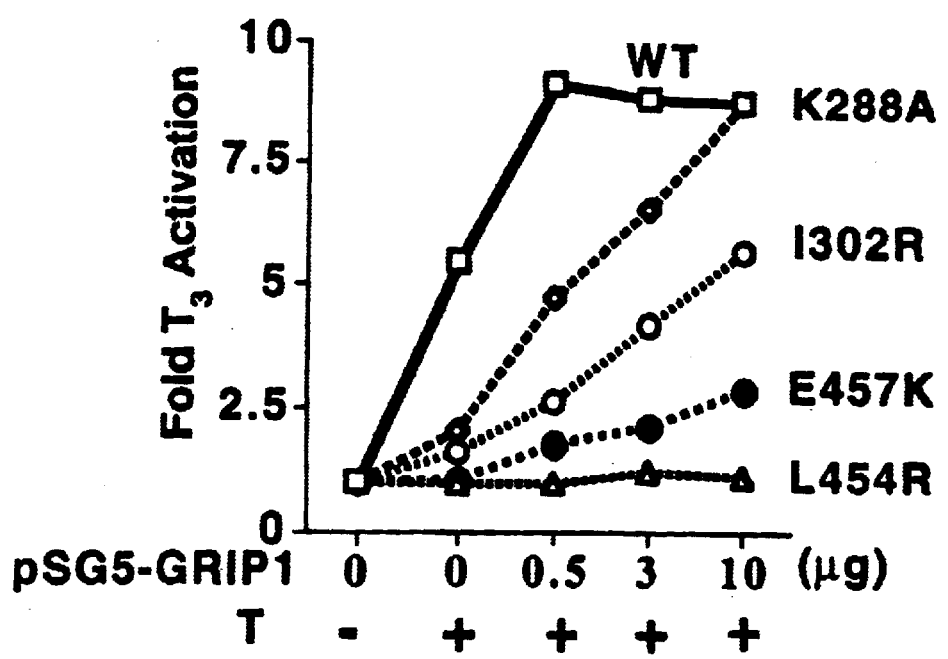
FIG. 2 shows that overexpression of full-length GRIP1 rescues loss of transcriptional activation by hTRβ1 mutants. Indicated amounts of the expression vector for full-length GRIP1, pSG5-GRIP1, is included in the cotransfections, which otherwise are performed as in FIG. 1. The WT or different representative hTRβ1 mutants are indicated.

TR Residues Involved in Ligand-dependent Transcription Activation in Context of a Cell Residues involved in ligand-mediated transcription activation were identified by testing the TR mutants of Example 8 in HeLa cells. $T_3$ increased reporter gene activity 5-fold in cells expressing either WT TR or mutated TRs showing normal GRIP1 binding (representative mutants are shown in FIG. 1. By contrast, TR mutants with diminished or absent GRIP1 binding (V284R, K288A, I302R, K306A, L454R, and E457K) show a diminished or absent response to $T_3$ which correlates with the GRIP1 binding defect. Overexpression of GRIP1 increases activation by the WT TR and rescues activation by TR mutants roughly in proportion to the severity of the defect of GRIP1 binding and activation (FIG. 2). These results suggest that the same residues are required for coactivator binding, function of the endogenous coactivator(s) in HeLa cells, and responsiveness of TRs to GRIP1.

Example 8

Effect of TR Mutations on Other Receptor Functions

The effects of the mutations on other receptor functions also were examined. All of the mutants bound radiolabeled thyroid hormone (Kd values, 6%–234% that for native receptor); occasional lower values were expected because some residues have partially buried side chains. None of the residues that decrease GRIP1 binding affected TR binding to a GST-RXR fusion protein or to DNA using three different DNA half-site arrangements and testing with or without added RXR (data not shown). Some mutations that affect GRIP1 binding occur in a region spanning helices 3–5, which has been suggested as important for TR/RXR heterodimerization (O'Donnell et al., supra; Lee et al., *Mol. Endocrinol.* (1992) 6:1867–1873). In contrast, however, the above results indicate that these residues do not contribute to TR/RXR heterodimerization. Further, TRs mutated in the CBS residues retain the ability of WT TR of $T_3$-dependent inhibition of the activity of the Jun and Fos transcription factors at an AP-1 site (Saatcioglu et al., supra), suggesting that the CBS residues do not participate in TR actions mediated through these proteins. These data indicate that the mutational effects are specific, the amount of input labeled TR in the different reactions is comparable, and the levels of expression of the mutant TRs are comparable to those of WT receptors.

Example 9

Coactivator Binding Site in ER

Figure 3:
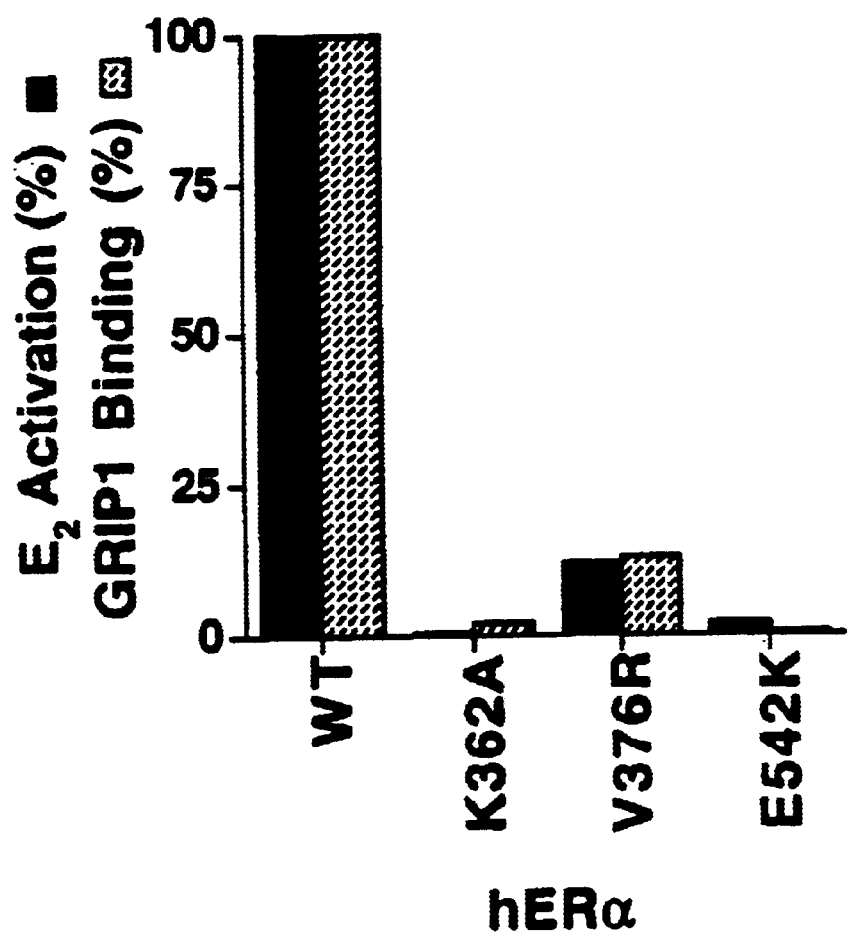
FIG. 3 shows specific hERα surface mutants cause loss of transcriptional activation in HeLa cells in parallel with their loss of in vitro GRIP1 binding. The fold $E_2$ activation, expressed as the percentage of WT, and the phosphorimager quantitation of in vitro binding of [$^{35}$S]-labeled hERα WT and mutants to GST-GRIP1 (GRIP1 amino acids 721–1121) also expressed as the percentage of WT is plotted for each mutant.
Figure 4:
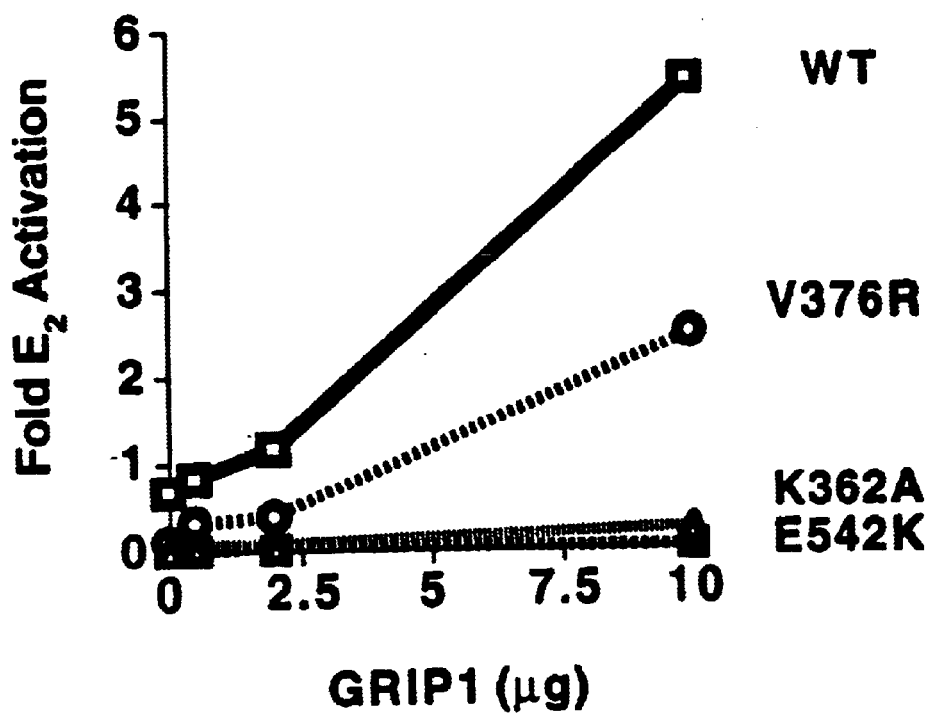
FIG. 4 shows a plot of the fold $E_2$ activation observed when the indicated amounts of the full-length GRIP1 expression vector, pSG5-GRIP1, are added to the co-transfection experiment, which otherwise is performed as for FIG. 3. The WT or different hERα mutants are indicated. The data represent the averages of three independent experiments, with standard deviations less than 10%.

Three separate mutations (K362A, V376R, and E542K) were created in human estrogen receptor-α (hERα) which align to three of the effective positions in hTRβ1 (K288A, I302R, and E457K). All three mutations diminish GRIP1 binding and abolish transcriptional activation (FIG. 3), and mutant V376R, with 10% residual GRIP1 binding, was rescued partially by overexpression of GRIP1 (FIG. 4). As a control, the ER mutants demonstrated a normal hormone-dependent ability to activate a vitellogenin-LUC hybrid reporter gene, GL45, which responds to the ER amino-terminal activation function (Berry et al., *EMBO J* (1990) 9:2811–2818) (data not shown). The finding that similar residues are required for GRIP1 binding and transcription activation activity in the TR and ER suggests that the coactivator binding site residues are similar in different nuclear receptors.

Example 10

Coactivator NR-box Binding Affinity for TR

Figure 6:
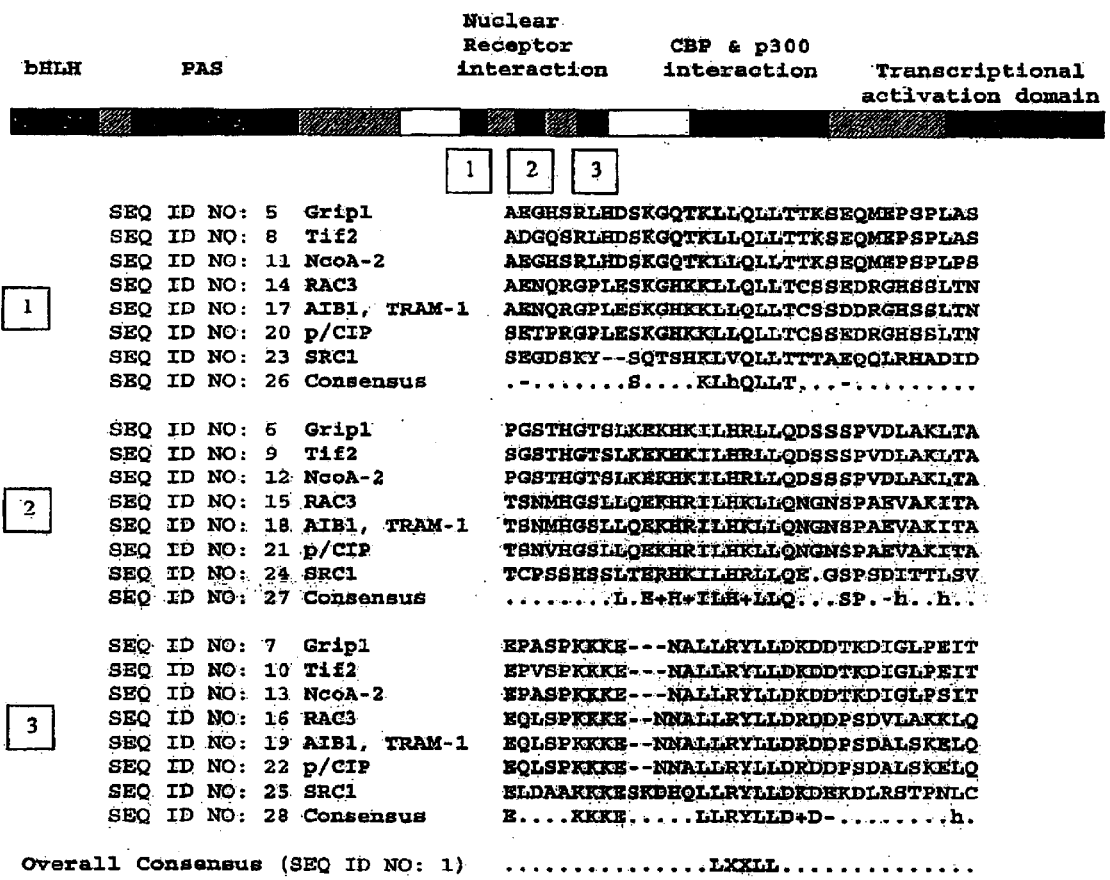
FIG. 6 shows sequence alignment of amino acid residues of members of the p160 coactivator family. Single amino acid designations are used. Members of the p160 coactivator family interact with the nuclear receptors through conserved (SEQ ID NO: 1) LxxLL motifs.
Figure 7A:
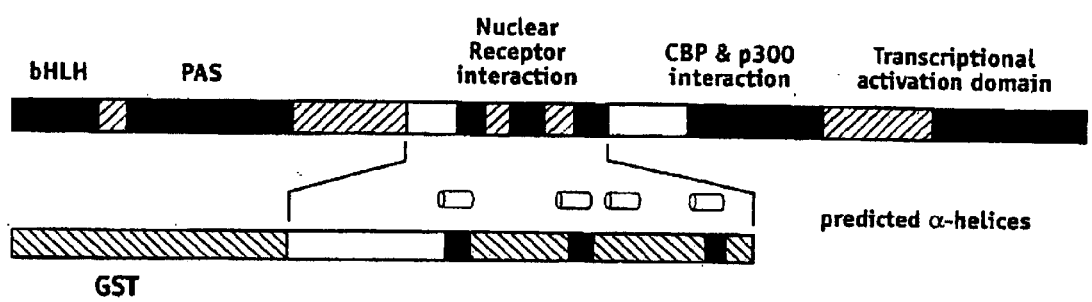
FIG. 7 (comprising FIGS. 7a and 7b) shows binding affinity assays of GST-GRIP1 constructs with NR-boxes 1, 2, and/or 3 and their interaction with TR LBD (FIG. 7b). GRIP-1 NR boxes 1,2 and 3 interact differently with TRβ LBD. Single letter designations are used for the amino acids (FIG. 7a).

To study the interaction between nuclear receptors and GRIP1 in vitro, a fragment of GRIP1 (563–767) was purified that contains all three NR-boxes (FIGS. 6 and 7). The fragment was found to be highly soluble and, in agreement with a secondary structure prediction using PhD, displays a mainly alpha-helical far UV-CD spectrum (data not shown). Three of the four helices predicted for the fragment include the NR-boxes at their C-terminus, suggesting that these boxes are part of amphipathic alpha-helices. These results show that the NR-boxes of GRIP1 are contained in a soluble, alpha-helical 24 kD fragment.

Figure 7B:
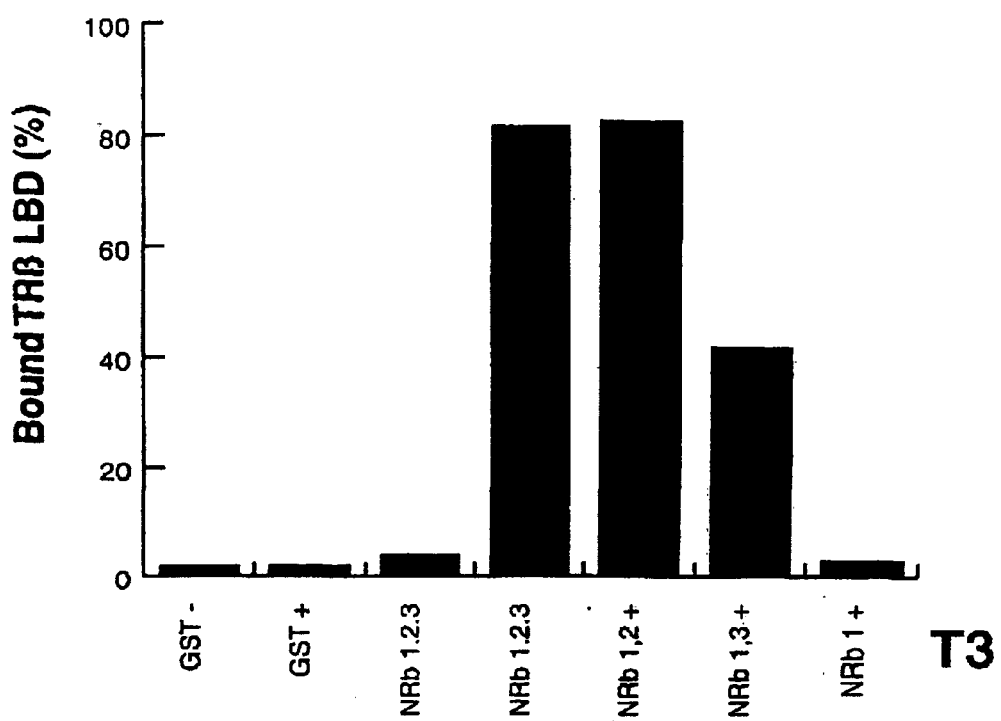

Binding assays show that GRIP1 NR-boxes 1, 2 and 3, interact differentially with hTRβ LBD (FIG. 7b). A GST-fusion of the GRIP1 (563–767) fragment strongly binds TR (kD or EC50) in a ligand dependent fashion. Replacement of the hydrophobic residues of NR-box 3 with alanine does not reduce binding of TR significantly, whereas similar replacement of NR-box 2 results in loss of TR binding of about 50%. By titrating the amount of GRIP1 fragment, about a 4-fold stronger binding of TR for NR-box 2 (EC50=1.0 μM) over NR-box 3 (EC50=4.0 μM) was estimated. In the absence of functional NR-boxes 2 and 3, almost no binding to TR was detected suggesting that under these experimental conditions NR-box 1 is not a cognate binding site for TR. Full length TR or TR-LBD bound GRIP1 equally. These results show that TR recognizes GRIP1 NR-box 2 and 3, with preference for NR-box 2.

Example 11

Coactivator NR-box Binding Affinity for GR

Figure 8A:
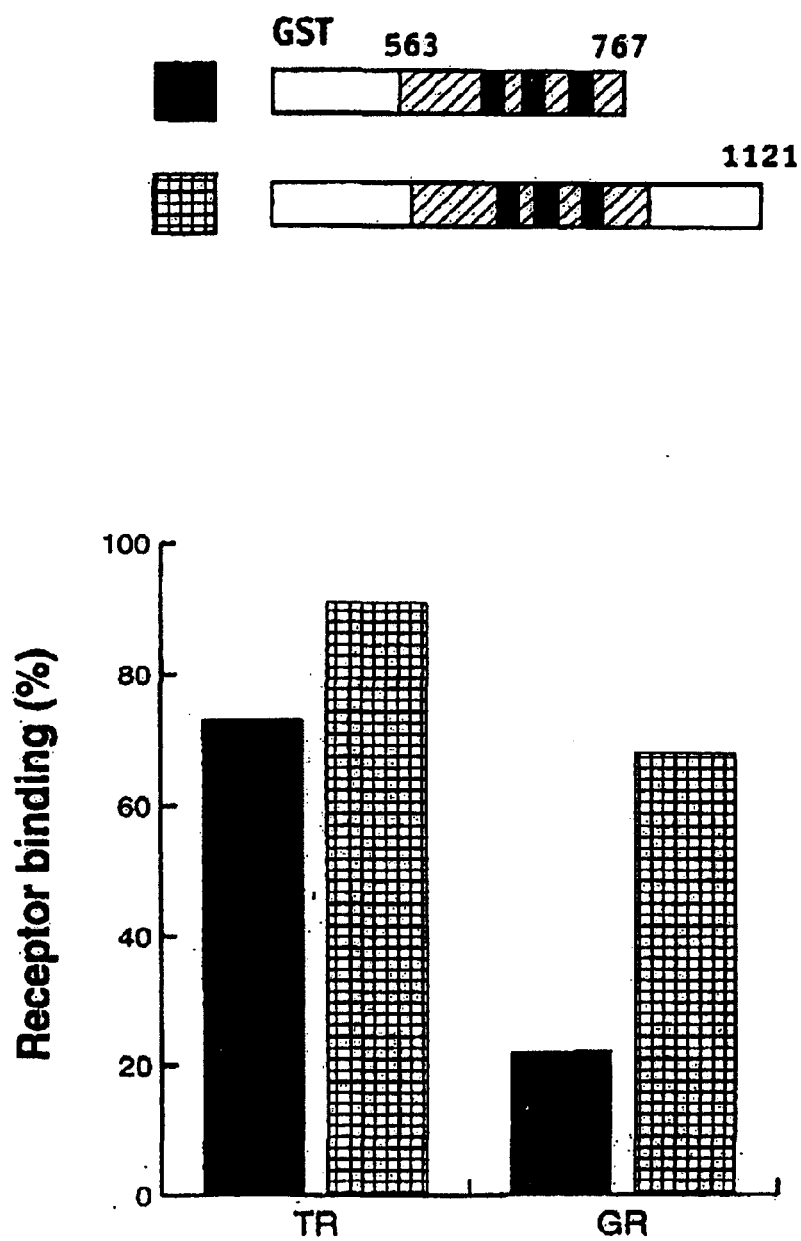
FIG. 8 (comprising FIGS. 8a and 8b) shows binding affinity assays of GST-GRIP1 constructs with NR-boxes 1, 2, and/or 3 and their interaction with TR and GR LBDs. TR and GR differ in their interactions with GRIP-1.
Figure 8B:
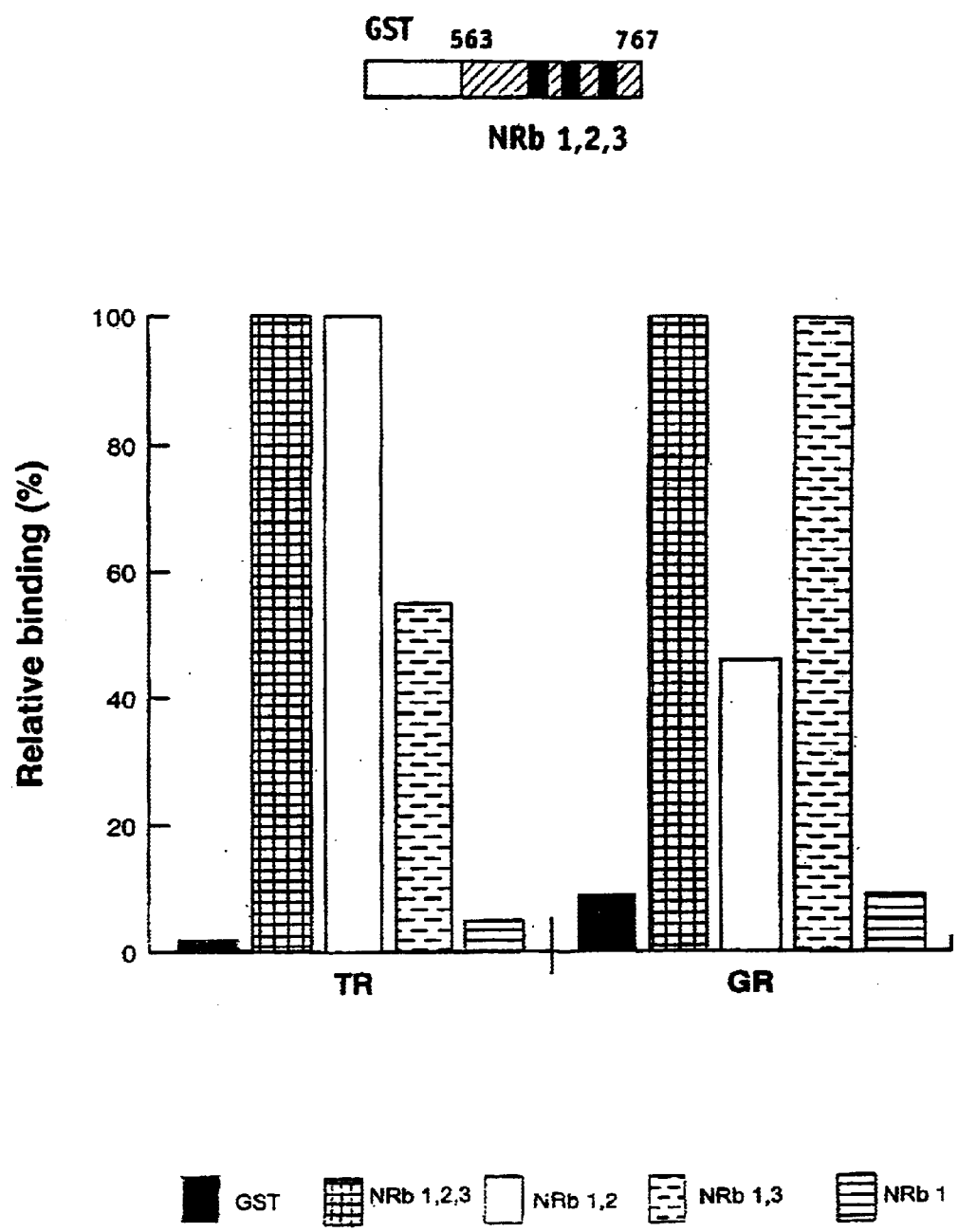

GR also was found to bind GRIP1 (563–767) in a ligand-dependent manner. However, in contrast to TR, extension of GRIP1 (563–767) to residue 1121 increases binding to GR about 3-fold suggesting an additional binding site on GRIP1 for GR FIG. 8a. Binding of the larger fragment remains ligand-dependent; no interaction can be observed in the presence of the GR partial antagonist RU486. These results are in agreement with in vivo 2-hybrid GR GRIP1 interaction studies. In the presence of ligand no difference was detected in the binding of GRIP1 by full length GR or a deletion mutant of GR that lacks the N-terminal activation domain AF-1. However in the absence of ligand, binding of GR to GRIP1 (563–1121) increased by about 10-fold indicating that sequences in the GR N-terminus are able to suppress binding of unliganded GR to this additional binding site in GRIP1. Additionally, (FIG. 8b) GR did not bind to a GRIP1 (563–767) mutant in which both NR-box 2 and 3 are replaced by alanines, and binds most strongly to a fragment that lacks a functional NR-box 2. As with TR, GR does not recognize NR-box 1. In contrast to TR, the GR prefers NR-box 3 to NR-box 2. These results demonstrate that GR prefers binding to NR-box 3 and interacts with an additional GRIP1 site within the CREB (cAMP—response—element binding protein)—binding protein (CBP) binding site.

Example 12

Coactivator Peptide Binding Affinity for TR

Figure 9A:
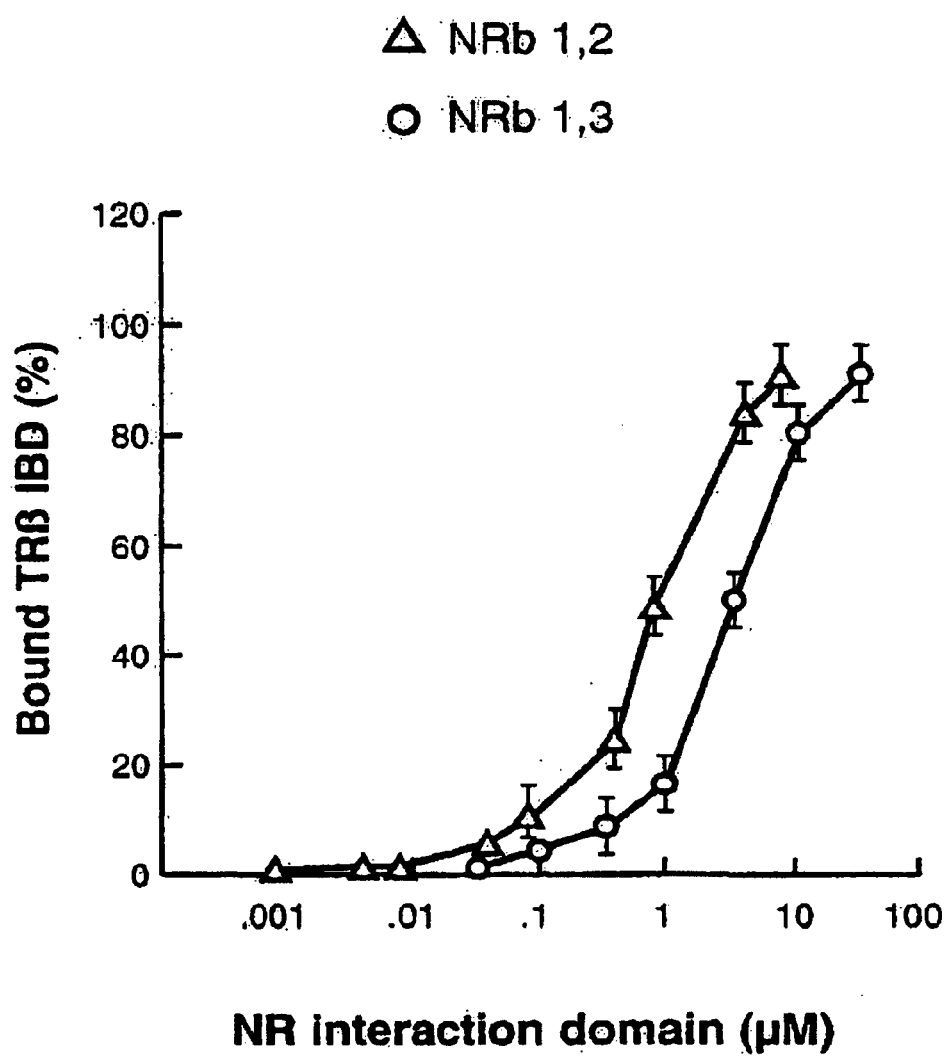
FIG. 9 (comprising FIGS. 9a and 9b) shows binding affinity assays for NR-box 2- and 3-peptides and GRIP1 and their interaction with TR LBD. NR box 2- and 3-containing peptides (FIG. 9b) reproduce the affinity and specificity of the NR interaction domain (FIG. 9a).
Figure 9B:
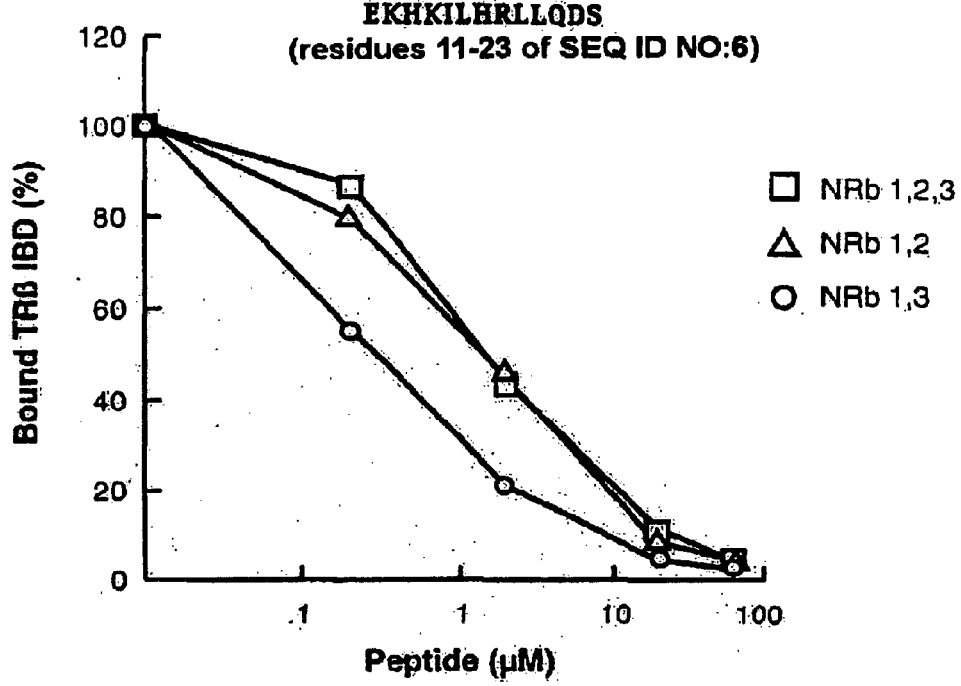
Figure 9B:
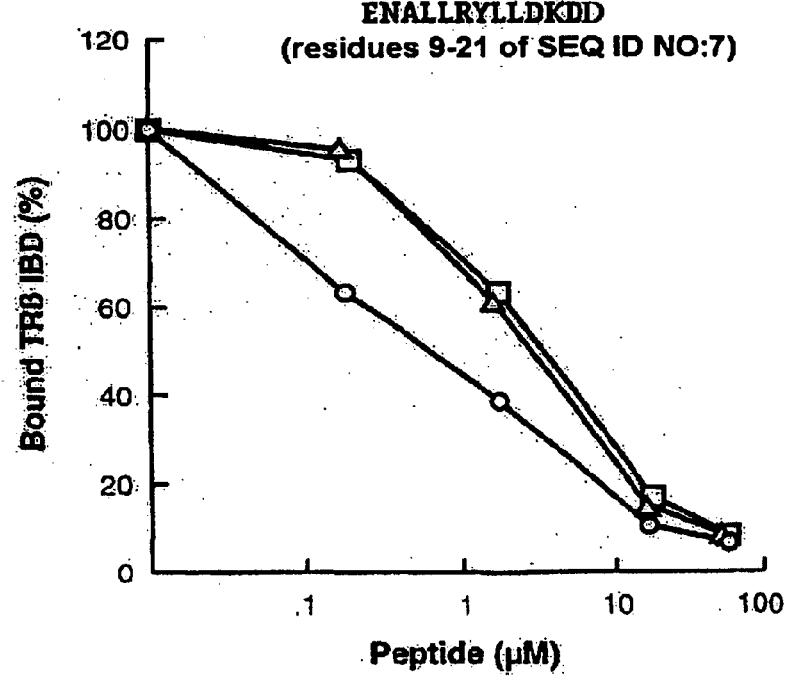

To investigate whether the preference of TR for NR-box 2 is dependent on the sequence or structural context of the NR-boxes, competition studies on the interaction of GRIP1 with hTRβ LBD were performed using coactivator peptides containing different NR-boxes (NR-box 2 peptide (residues 11–23 of SEQ ID NO: 6) EKHKILHRLLQDS, and NR-box 3 peptide (residues 9–21 of SEQ ID NO: 7) ENALLRYLLDKDD) (FIG. 9b). Consistent with the interaction of hTR LBDβ with GRIP1 (563–767) NR-box mutants, a peptide containing NR-box 1 competes with the interaction of GRIP1 with hTRβ LBD only at very high concentrations (EC50=130 μM). Peptides containing either NR-box 2 or 3 compete with GRIP1 (563–767) efficiently and display the preference of hTRβ LBD for NR-box 2 (EC50 (NR-box 2)=1.5 μM, EC50 (NR-box 3)=4 μM). The apparent affinities (EC50) for peptides of NR-box 2 and 3 are comparable with the analogous GRIP1 (563–767) NR-box mutants suggesting that the preference of TR for NR-boxes is solely dependent on the sequence and independent of the structural context of the NR-boxes.

Peptides of NR-box 2 or 3 compete with GRIP1 (563–767) containing functional NR-boxes 2 and 3 or a mutant of this fragment that contains only a functional NR-box 2 with comparable affinity. Thus, while TR can bind both NR-box 2 and 3, in a GRIP1 coactivator peptide fragment containing both boxes, TR preferentially binds NR-box 2.

These results show the preference of TR for NR-box 2 is sequence dependent.

The same types of assays for TR competition are performed to assess coactivator peptide binding affinity for GR. The peptide concentrations are normalized relative to TR for obtaining comparable dose response curves.

Example 13

Binding Affinity of TR for Extended Coactivator Peptides

Figure 10A:
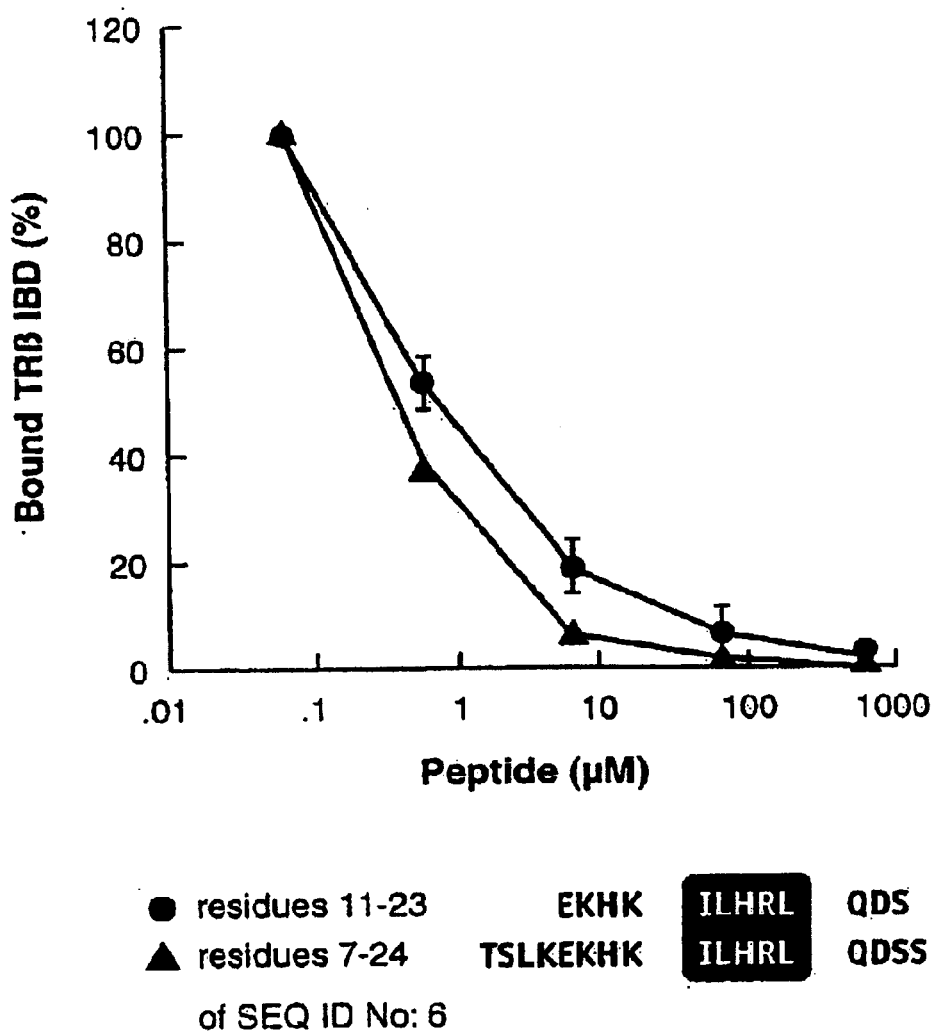
FIG. 10 (comprising FIGS. 10a, 10b and 10c) shows binding affinity assays for NR-box 2- and 3-peptides and their interaction with TR LBD. Sequences adjacent to the (SEQ ID NO: 1) LxxLL motif modulate the affinity of NR-box-TRβ LBD interactions.
Figure 10B:
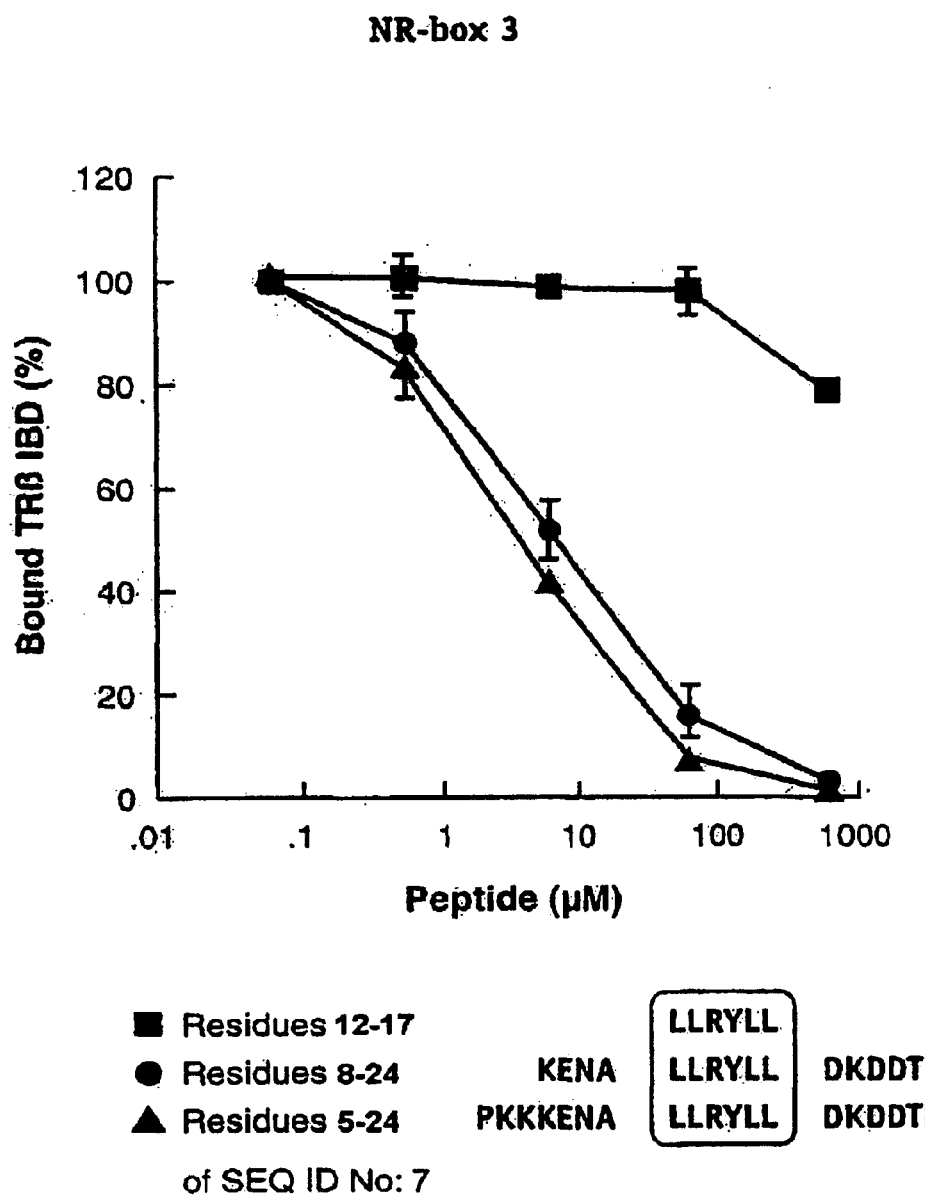
Figure 10C:
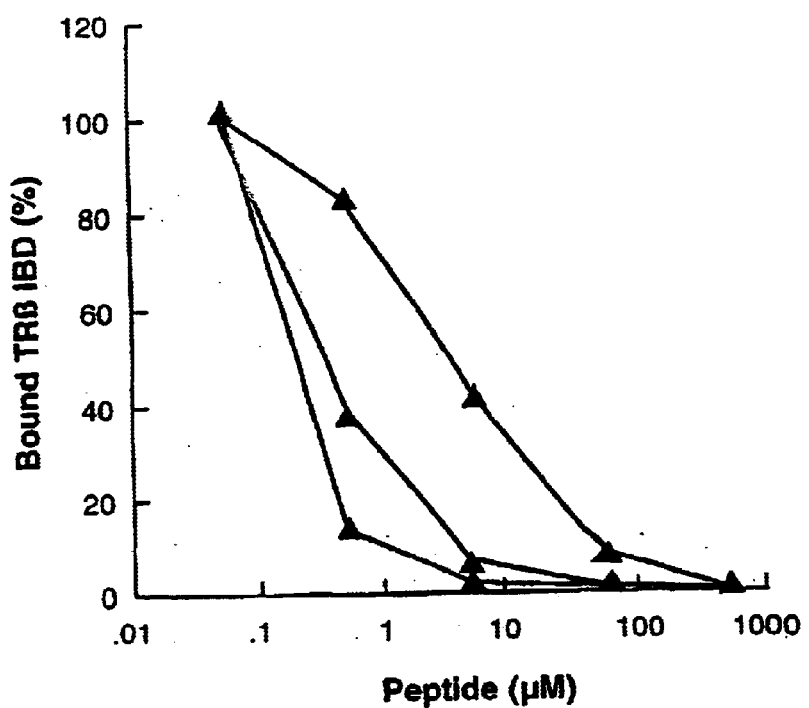

Sequence identity between all three central NR-boxes of the p160 coactivator family is limited to the conserved leucine residues of the (SEQ ID NO: 1) LxxLL motif (FIG. 6). However, the sequence conservation of a particular NR-box can extend into neighboring residues. To investigate the contribution of these neighboring residues to affinity and specificity of the different NR-boxes for TR, the ability of peptides containing individual NR-boxes with different lengths of adjacent sequences to compete with the interaction of GRIP1 (563–767) with hTRβ LBD were compared (FIGS. 10a, 10b, and 10c).

A peptide (FIG. 10b) consisting of the minimal motif of NR-box 3 (residues 12–17 of SEQ ID NO: 7; LLRYLL) does not compete with the TR LBD interaction with GRIP1 (563–767). A peptide consisting of the NR-box 2 (residues 15–20 of SEQ ID NO: 6; ILHRLL) also does not sufficiently compete with the interaction (data not shown). Extending peptides containing a (SEQ ID NO: 1) LxxLL motif to include adjacent residues increased affinity for both NR-box motifs and magnified the preference of TR for NR-box 2 (NR-box 2 peptides in FIG. 10a: (residues 11–23 SEQ ID NO: 6) EKHKILHRLLQDS and (residues 7–23 of SEQ ID NO: 6) TSLKEKHKILHRLLQDS; and NR-box 3 peptides in FIG. 10b: (residues 8–24 of SEQ ID NO: 7) KENALLRYLLDKDDTKD and (residues 5–24 of SEQ ID NO: 7) PKKKENALLRYLLDKDDTKD). A chimeric peptide containing the NR-box 3 motif in the context of the NR-box 2 flanking sequences (SEQ ID NO: 29; TSLKEKHKLLRYLLQDSS) binds like a NR-box 2 peptide (FIG. 10c).

These results demonstrates that preference of TR for NR-box 2 is at least partially due to features of the bound peptide (residues 15–20 of SEQ ID NO: 6; ILHRLL), but that their affinity and specificity is modulated by adjacent sequences.

Example 14

Binding Affinity of TR and GR for Mutant Coactivator

A. TR Affinity for ILxxLL Motif Residues

Figure 11A:
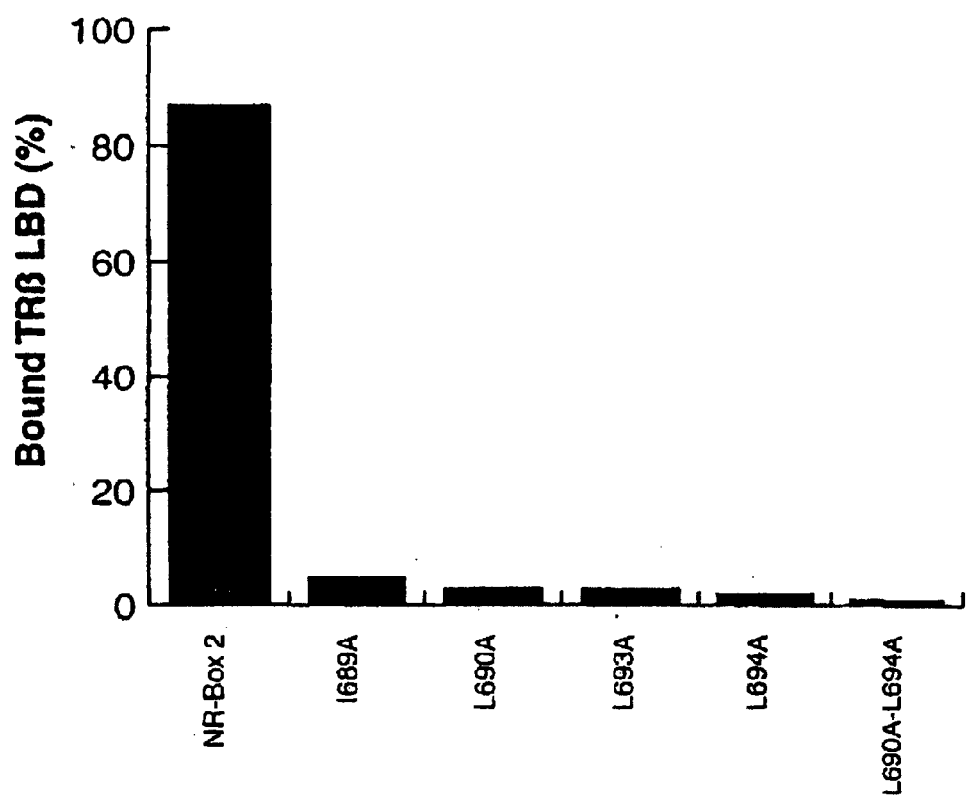
FIG. 11 (comprising FIGS. 11a, 11b and 11c) shows binding affinity assays for mutant GRIP1 and NR-box 2- and 3-peptides and their interaction with TR LBD. The individual leucine residues of the (SEQ ID NO: 1) LxxLL motif are crucial for binding of the GRIP-1 NR interaction domain to TRβ LBD.

To investigate the role of the hydrophobic residues in NR-box 2, individual residues of the (residues 15–20 of SEQ ID NO: 6) ILHRLL motif were replaced by alanine in the background of GRIP1 (563–767) containing a non-functional NR-box 3 (FIG. 11a). Surprisingly, replacement of any of the conserved leucines prevents binding to TR almost completely. Only replacement of the nonconserved isoleucine exhibited a lessened but still severe impact on the affinity of NR-box 2 for TR. As replacement of a single leucine by alanine is sufficient to overcome the interaction of both the remaining hydrophobic residues and adjacent sequences with hTRβ LBD, it appears that their contribution to the affinity of NR-box 2 for hTRβ LBD is cooperative rather than additive.

Figure 11B:
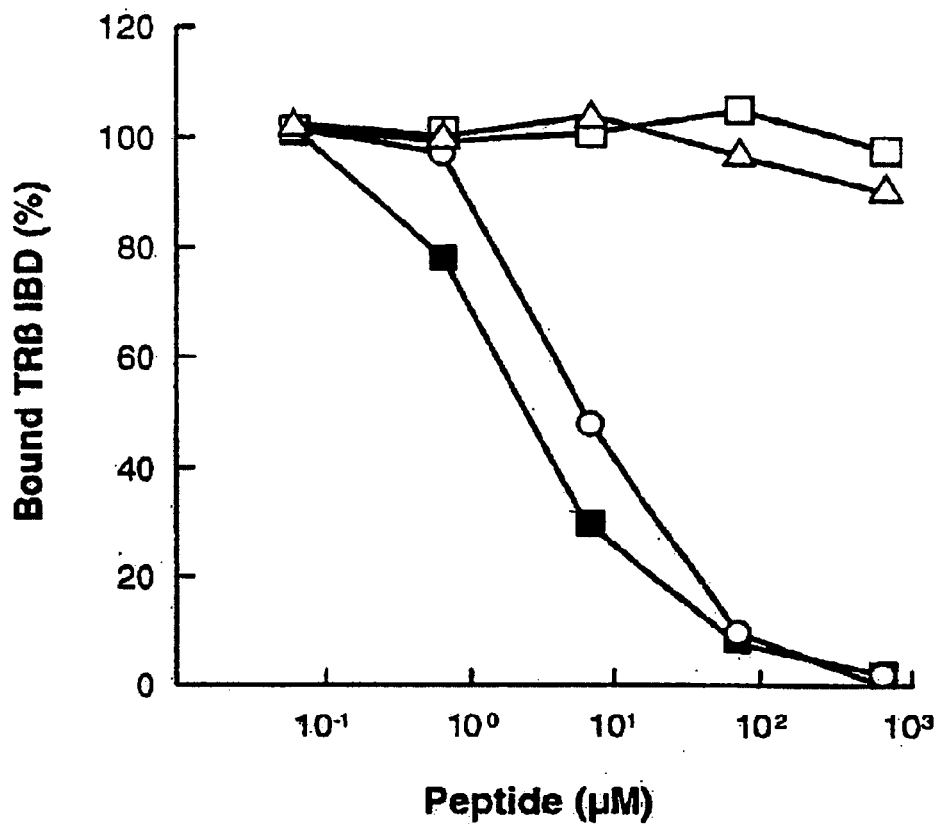

Similar results were obtained by competing the interaction of hTRβ LBD with the GRIP1 (563–767) NR-box 3 mutant using peptides in which either IL, HR or LL of the NR-box 2 motif are replaced by alanines (FIG. 11b). Whereas the peptides containing the IL or LL replacement failed to interact with the hTRβ LBD even at very high concentrations, in agreement with a proposed alpha-helical structure of the motif, replacement of the "HR spacer" by alanines showed a marginal effect on the affinity of the peptide for TR-LBD.

Figure 11C:
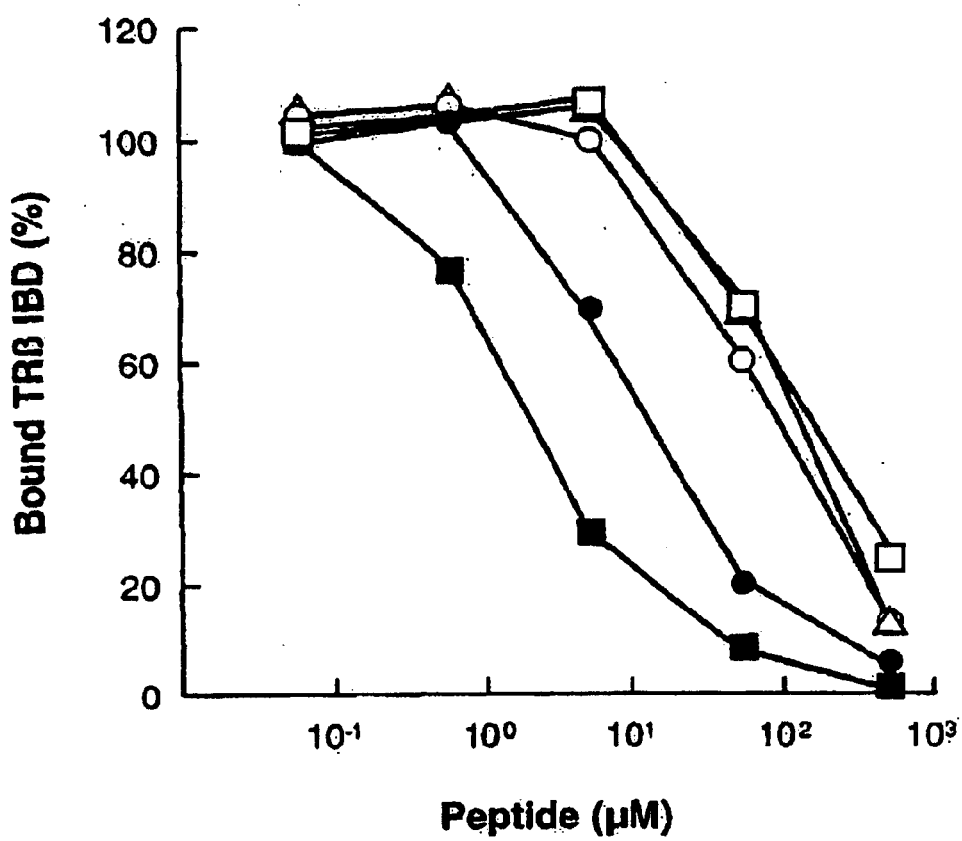

Replacement of single leucine residues of NR-box 2 by phenylalanine reduced the affinity of NR-box 2 peptides for TR LBD about 100-fold, replacement of the isoleucine about 10-fold (FIG. 11c). Therefore, the interaction of TR with GRIP1 relies not simply on the hydrophobicity of the (SEQ ID NO: 1) LxxLL motif, but also on positive contributions by the leucine residues themselves.

These results demonstrate that single mutations of the conserved leucines in the (SEQ ID NO: 1) LxxLL motif strongly reduce affinity of GRIP1 for hTRβ LBD.

Collectively, the above examples demonstrate that peptides containing NR-boxes, particularly NR-box 2, reproduce the affinity and specificity of the interaction of GRIP1 (563–767) with hTRβ LBD.

B. TR Affinity of FxxLW and FxxAL Motif Residues

Figure 16:
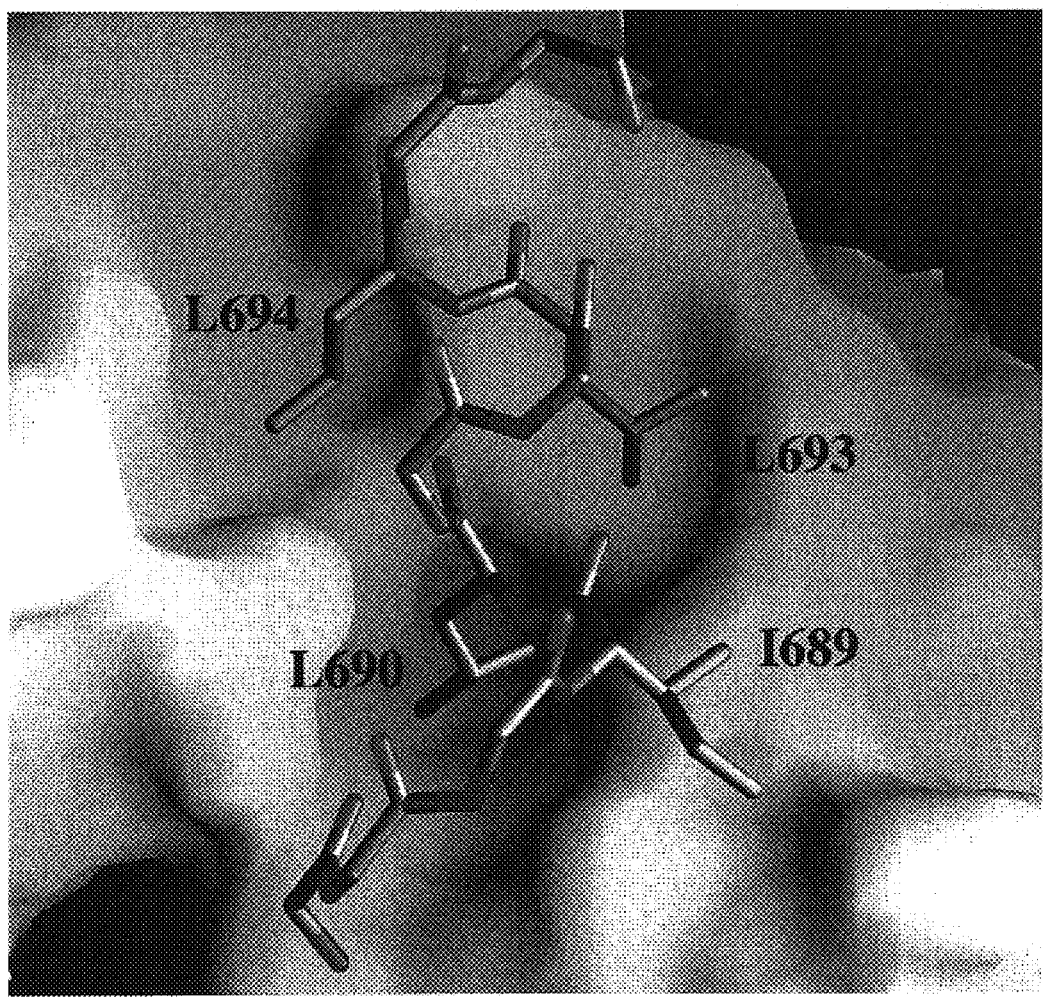
FIG. 16 shows molecular surface of the hTR LBD. The side chains of the leucines resides fit within a hydrophobic groove formed from helices H3, H5, and H12, while the side chain of the non-conserved isoleucine residue packs against the outside edge of the groove. The remainder of the peptide is shown as main chain.
Figure 17:
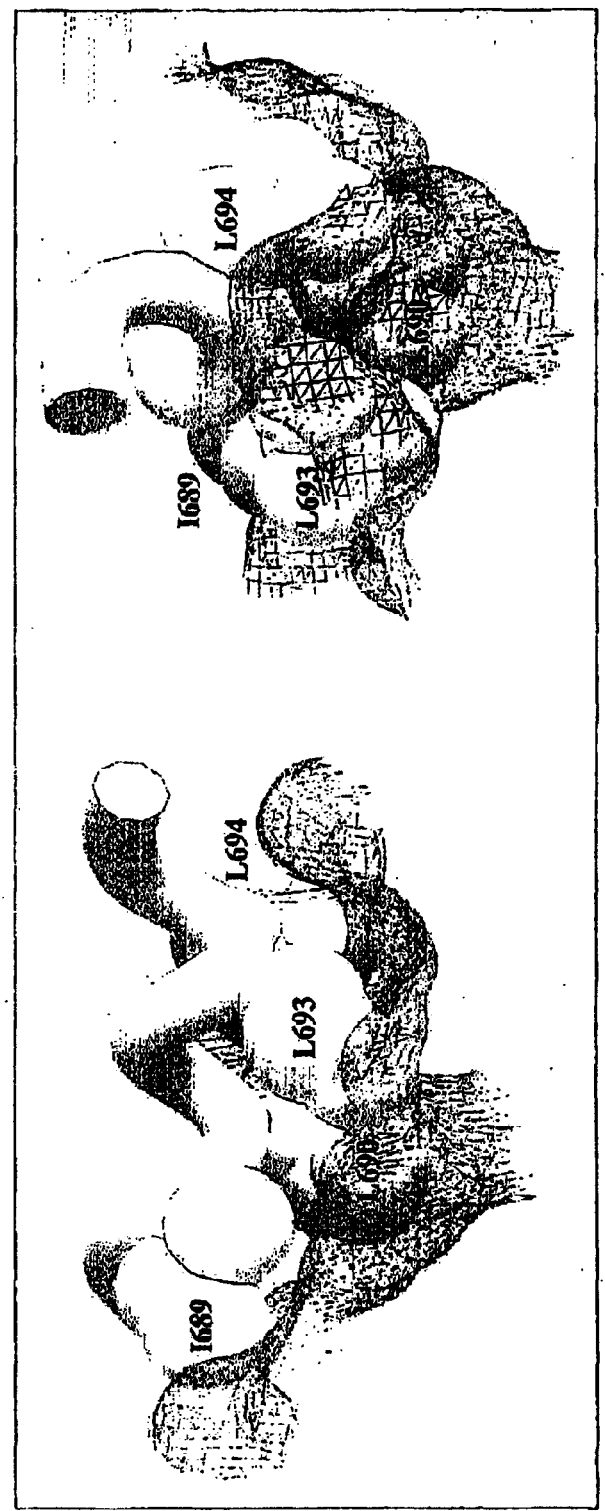
FIG. 17 shows complementarity between the (SEQ ID NO: 1) LxxLL motif and the surface of the hTR LBD. The side chains of the (SEQ ID NO: 2) ILxxLL motif are shown in a CPK representation, with the main chain of the peptide drawn as a C-alpha trace. The three leucine residues fit into pockets of the coactivator binding site of the hTRβ LBD, depicted as mesh, while the isoleucine residue rests on the edge of the site's cleft.

The three conserved leucines of the NR-box 2 (SEQ ID NO: 2) ILxxLL motif are embedded in the hydrophobic cleft of the hTRβ LBD:NR-box 2 interaction surface, whereas the non conserved isoleucine is located on the rim of this cleft where structural changes can be more easily accommodated (See Example 18). In agreement with this structure, replacement of this residue by alanine or phenylalanine reduced binding to hTRβ LBD to a less extent than the comparable mutations of the conserved leucine residues. The surface generated by the three conserved leucines (L690, L693, L694) of the NR-box 2 peptide (residues 12–24 of SEQ ID NO: 6) 686-KHKILHRLLQDSS-698 is highly complementary to the corresponding binding site in the hTRβ LBD (FIGS. 16 and 17). Comparison of this binding site to other nuclear receptors shows that it contains a structural motif that is unique, highly conserved and present in all known structures of nuclear receptor LBDs (Wurtz et al., *Nat Struct Biol.* (1996) 3:87–94; Wagner et al., supra; Renaud et al., *Nature* (1995) 378:681–689; Bourguet et al., *Nature* (1995) 375:377–382; and Brzozowski et al., *Nature* (1997) 389:753–758).

Interaction of highly conserved hydrophobic motifs, which are part of amphipathic alpha-helices, with complementary hydrophobic surfaces resembles a feature observed for the interaction of several other transcriptional activators with their target proteins (p53:MDM2, VP16:TAFII31 or CREB:KIX-CBP). However, the motifs of p53 (FxxLW), VP16 (FxxAL) and CREB (YxxIL) differ from the (SEQ ID NO: 1) LxxLL motif of nuclear receptor coactivators. A Fxxxh motif may be generally involved in interaction with TAFII31, where "h" represents any hydrophobic residue. Though with respect to the known structures, complementarity of the interacting hydrophobic surfaces identified here seem to be a common feature of these interactions, cross-reactions between different motifs are possible. For instance, VP16, p53, and p65 (FxxFL) are able to functionally interact with TAFII31, or p53 and E2F1-DP1 (FxxLL) both interact with MDM2. These interactions are sensitive to mutations in the Fxxxh motif. Therefore it appears that either complementarity of the hydrophobic surfaces is not an absolute requirement or that induced fitting of the interacting surfaces is possible.

Based on these observations, studies were performed to determine whether GRIP1 interacts with TAFII31 or MDM2. However, no interaction was detected. GRIP1 mutants changing NR-box 2 (SEQ ID NO: 1; LxxLL) to VP16 (SEQ ID NO: 4; FxxAL) or p53 (SEQ ID NO: 3; FxxLW) like binding sites also failed to bind TAFII31 or MDM2 demonstrating that the presence of the correct binding site is not sufficient to create binding (data not shown). Moreover, peptides containing the VP16 or p53 binding sites are not able to compete the interaction of GRIP1 with TR, even in very high concentration, but do compete the interaction with GR (data not shown). The affinity of this interaction is weak, but comparable to affinity of a peptide of NR-box 2 that, in the context of a GRIP1 mutant lacking NR-box 3, binds GR in vivo (Ding et al., sura). This binding is only about ten times less than a peptide containing NR-box 3, GR's primary binding site.

As shown above, GR binds GRIP1 (563–767) with about one-fifth the affinity than a comparable amount of TR. Thus, the high concentration of NR-box 3 peptide required to compete the interaction of GR with GRIP1 (563–767) may rather reflect a weak affinity of GR for the peptide rather than a particular strong interaction of GR with GRIP1 (563–767).

These results suggest that at least on the peptide level, other hydrophobic motifs besides (SEQ ID NO: 1) LxxLL can interact with the coactivator binding site, but that it is receptor dependent.

C. TR Affinity for Residues Adjacent to ILxxLL Motif

Peptides containing a FxxLL motif bind TR but with two orders of magnitude lower affinity than a (SEQ ID NO: 1) LxxLL motif (FIG. 11). To test whether the additional changes in the hydrophobic motif or adjacent sequences of the VP16 peptide prevent its binding to TR, a chimeric peptide containing the NR box-2 motif (SEQ ID NO: 1) LxxLL in the context of the VP16 sequence was constructed. This peptide binds to TR but with an about 100-fold lower affinity than the original NR-box 2 peptide. Thus, the inability to bind the VP16 peptide appears to be due to the combination of an imperfect hydrophobic motif and the incompatibility of TR to adjacent sequences of the VP16 motif.

As the interaction of the chimeric peptide with GR was comparable to the original NR-box 2 and VP16 peptides, this incompatibility appears due to TR-specific features in the NR-box interaction surface. These results show sequences adjacent the NR-box motif LxxLL can reduce binding of NR-box 2 to TR, but not GR.

Example 15

Crystallization and Structure Determination of NR LBD Complexes

A. Crystallization of hTRβ LBD With T$_3$ and GRIP1 NR-box 2 Peptide

Several peptides containing GRIP1 NR-box 2 were tested in crystallization trials with the hTRβ LBD. The complex of the hTRβ LBD with the GRIP1 NR-box 2 peptide 686-KHKILHRLLQDSS-698 (residues 12–24 of SEQ ID NO: 6) produced crystals that were dependent on both the presence and the concentration of the peptide. Without the peptide, the hTRβ LBD precipitated immediately. However, nucleation was erratic, but could be overcome through seeding of repared drops with microcrystals of the hTRβ LBD:GRIP1 NR-box 2 peptide complex. Structure of the hTRβ LBD-:GRIP1 NR-box 2 peptide complex was determined by molecular replacement using the structure of the hTRβ LBD determined previously (Wagner et al., supra), and refined to a resolution of 3.6 Å (Table 1). The refined model consists of residues K211–P254 and V264–D461 of monomer 1 of the hTRβ LBD, residues K211–P254 and G261–D461 of monomer 2 of the hTRβ LBD, and the GRIP1 NR-box 2 peptides (residues 14–24 of SEQ ID NO: 6) 688-KILHRLLQDSS-698, and (residues 14–22 of SEQ ID NO: 6) 688-KILHRLLQD-696 (Appendix 1). The structure in Appendix 1 consists of: a portion of each of two molecules of hTRβ, chain A (SEQ ID NO: 52) and chain B (SEQ ID NO: 53); two molecules of T$_3$, chain J and chain K; and two molecules of GRIP-1 peptide, chain X (SEQ ID NO: 54) and chain Y (SEQ ID NO: 55).

Briefly, the complex between the hTRβ LBD and the GRIP1 NR-box 2 peptide 686-KHKILHRLLQDSS-698 (residues 12–24 of SEQ ID NO: 6) was prepared by mixing (equal) volumes of a solution of 9 mg/ml hTRβ LBD in 20 mM HEPES pH 7.4 with a solution of 14 mM GRIP1 in 0.4 mM ammonium acetate pH 4.72, and incubating the mixture on ice for 1 hour. Crystals were obtained after 2 days at 4° C. using hanging drop vapor diffusion from a drop containing 1.5 μl of hTRβ LBD:GRIP1 complex, prepared as described, and 0.5 μl 15%PEG 4K, 0.2M sodium citrate pH 4.9, suspended above a reservoir containing 10% PEG 4K, 0.1M ammonium acetate, and 0.05 M sodium citrate (pH 5.6). After allowing the drop to equilibrate for 1 hour, 0.2 μl of 10-3 to 10-5 dilutions of microcrystals in reservoir buffer were introduced to provide nucleation. Crystals are of space group P3121 (a=95.2, b=95.2, c=137.6) and contain two molecules of the hTRβ LBD and two molecules of the GRIP1 NR-box 2 peptide 686-KHKILHRLLQDSS-698 (residues 12–24 of SEQ ID NO: 6).

TABLE 1

Data collection, phasing, and refinement statistics

Data collection

| Data set | Resolution (Å) | Reflections measured | unique | Coverage (%) | R$_{sym}$ |
|---|---|---|---|---|---|
| Native | 3.6 | 35565 | 8490 | 96.3 | 0.007 |

TABLE 1-continued

Data collection, phasing, and refinement statistics

Rotation search

| | | Euler angles (°) | | | Correlation coefficient | |
|---|---|---|---|---|---|---|
| Search model | | Θ$_1$ | Θ$_2$ | Θ$_3$ | Highest peak | Highest false peak |
| hTR β LBD | M1 | 60.12 | 80.68 | 241.90 | 16.3 | |
| | M2 | 9.93 | 87.70 | 180.6 | 15.9 | 14.2 |

Translation search

| | Fractional coordinates | | | Translation function | |
|---|---|---|---|---|---|
| | x | y | z | Highest peak (o) | Highest false peak (o) |
| M1 | 0.522 | 0.428 | 0.250 | 19.52 | 10.02 |
| M2 | 0.200 | 0.932 | 0.119 | 26.11 | 5.77 |

Refinement

| | Resolution (Å) | Reflection | R | R$_{free}$ |
|---|---|---|---|---|
| F > 2( | 25 – 3.7 | 7614 | 0.2990 | 0.3219 |
| All data | 25 – 3.7 | 7851 | 0.3010 | 0.317 |

R$_{sym}$ = Σ$_h$ Σ$_i$ | I$_{h,i}$ û(I$_h$(|/ Σ I$_h$ for the intensity (I) of i observations of reflection h.
Correlation coefficient = Σ$_h$Eo$^2$Ec$^2$ – Eo$^2$Ec$^2$/[Σ$_h$(Eo$_2$ – Eo$^2$)$^2$ Σ$_h$ (Ec$^2$ – Ec$^2$)$^2$]$^{½}$
Translation function (t$_a$, t$_b$, ...) = Σ$_h$ (|Eo$_{(h)}$|$^2$ – Σ$_h$ <|Eo$_{(h)}$|$^2$>) (Ec$_{(h, t_a, t_b,...)}$|$^2$ – <|Ec$_{(h)}$|$^2$) where E$_o$ represents the normalized observed structure factor amplitudes, and E$_c$ represents the normalized structure factors for the search model in a triclinic unit cell with dimensions identical to that of the crystal. The reported peak height represents the value of the function for the translation (t$_a$, t$_b$) of the NCS monomers, divided by the rms value of the translation function density.
R factor = Σ | F$_{obs}$ – F$_{calc}$ | / Σ | F$_{obs}$ |.
R$_{free}$ is calculated the same as R factor, except only for 10% of the reflections that were set aside for cross validation and not used in refinement.

B. Crystallization of hERα LBD With DES and GRIP1 NR-box 2 Peptide

Crystals of a DES-hERα LBD-GRIP1 NR-box 2 peptide complex were obtained by hanging drop vapor diffusion. Prior to crystallization, the DES-hERα LBD (residues 297–554) complex was incubated with a 2–4 fold molar excess of the GRIP1 NR-box 2 peptide 686-KHKILHRLLQDSS-698 (residues 12–24 of SEQ ID NO: 6) for 7–16 hr. Two μL samples of this solution were mixed with equal volume samples of reservoir buffer consisting of 25–27% (w/v) PEG 4000, 90 mM Tris (pH 8.75–9.0) and 180 mM Na Acetate and suspended over wells containing 800 μL of the reservoir buffer. After 4–7 days at 19–21° C., rod-like crystals were obtained. The coactivator complex crystals lie in the spacegroup P2$_1$ with cell dimensions a=54.09, b=82.22, c=58.04 and β=111.34. Two molecules each of the DES-LBD and the coactivator peptide form the asymmetric unit. A 200 μm×40 μm×40 μm crystal was transferred to a cryosolvent solution containing 25% (w/v) PEG 4000, 10% (w/v) ethylene glycol, 100 mM Tris (pH 8.5), 200 mM Na Acetate and 10 μM peptide and frozen in an N$_2$ stream at −170° C. in a rayon loop. Diffraction data from this crystal were measured at −170° C. using a 300 mm MAR image plate at the Stanford Synchrotron Radiation Laboratory (SSRL) at beamline 7-1 at a wavelength of 1.08 Å. The diffraction images were processed with DENZO and scaled with SCALEPACK (Otwinowski, et al., *Methods Enzymol.* (1997) 276:307–326) using the default −3σ cutoff.

C. Crystallization of hERα LBD With OHT

Crystals of the hERα LBD (residues 297–554) complexed to OHT were obtained by the hanging drop vapor diffusion method. Equal volume aliquots (2 μL) of a solution containing 3.9 mg/mL protein-ligand complex and the reservoir solution containing 9% (w/v) PEG 8000, 6% (w/v) ethylene glycol, 50 mM HEPES (pH 6.7) and 200 mM NaCl were mixed and suspended over 800 μL of the reservoir solution. Hexagonal plate-like crystals formed after 4–7 days at 21–23° C. Both crystal size and quality were improved through microseeding techniques. These crystals belong to the space group P6$_5$22 with cell parameters a=b=58.24 Å and c=277.47 Å. The asymmetric unit consists of a single hERα LBD monomer; the dimer axis lies along a crystallographic two-fold. A single crystal (400 μm×250 μm×40 μm) was briefly incubated in a cryoprotectant solution consisting of 10% (w/v) PEG 8000, 25% (w/v) ethylene glycol, 50 mM HEPES (pH 7.0) and 200 mM NaCl and then flash frozen in liquid N$_2$ suspended in a rayon loop. Diffraction data were measured at −170° C. using a 345 mm MAR image plate at SSRL at beamline 9-1 and at a wavelength of 0.98 Å. The diffraction images were processed with DENZO and scaled with SCALEPACK (Otwinowski, et al., supra) using the default −3σ cutoff.

Example 16

Structure Determination and Refinement of NR LBD Complexes

A. Structure of hTRβ LBD With T$_3$ and GRIP1 NR-box 2 Peptide

Data were measured using Cu Kα radiation from an R-axis generator at 50 kV and 300 mA with a 0.3 mM collimator and a Ni filter. Reflections were measured using an R-Axis II detector and integrated with Denzo, and equivalent reflections scaled using Scalepack (Otwinowski and Minor, "Processing of x-ray diffraction data collected in oscillation mode." In *Macromolecular Crystallography*, Part A (ed. C. W. Carter, Jr. and R. M. Sweet), pp. 307–326. Academic Press, New York, N.Y.). Possible rotation function solutions were calculated using normalized amplitudes in AMORE from a model of hTRβ LBD with the ligand, T$_3$, omitted; translation function solutions were subsequently determined using TFFC for the two rotation solutions with the highest correlation coefficients. For two hTRβ LBD molecules in the asymmetric unit, the calculated solvent content is 52%. After rigid body refinement of the two hTRβ LBD molecules, electron density maps were calculated. Strong positive density present in both the anomalous and conventional difference Fourier maps for the iodine atoms of the T$_3$ ligand confirmed the correctness of the solution. The iodine atoms for both T$_3$ ligands were modeled as a rigid body, and the structure refined with strict NCS symmetry using CNS. Both 2FoFc and FoFc electron density maps showed interpretable density, related by the NCS operator, near H12 of both molecules of the hTRβ LBD. The electron density could be modeled as a short α-helix, and the observed side chain density was used to tentatively assign the sequence and direction to the chain. The refined model consists of residues of the hTRβ LBD, and peptide residues of the GRIP1 NR-box 2 peptide 686-KHKILHRLLQDSS-698 (residues 12–24 of SEQ ID NO: 6).

Atomic coordinates of the hTRβ LBD:GRP1 site 2 peptide complex are attached as Appendix 1.

B. Structure of hERα LBD With DES and GRIP1 NR-box 2 Peptide

Initial efforts to determine the structure of the DES-hERα LBD-NR box 2 peptide 686-KHKILHRLLQDSS-698 (residues 12–24 of SEQ ID NO: 6) complex utilized a low resolution (3.1 Å) data set (data not shown). A self-rotation search implemented with POLARRFN ("The CCP4 suite: programs for protein crystallography", *Acta Crystallogr.* (1994) D50:760–763) indicated the presence of a noncrystallographic dyad. The two LBDs in the asymmetric were located by molecular replacement in AMoRe (CCP4, 1994) using a partial polyalanine model of the human RARγ LBD (Renaud, et al., supra) as the search probe (R=58.2%, CC=35.6% after placement of both monomers). Given that the model at this point was both inaccurate (r.m.s.d. 1.7 Å between this model and the final model based on Cα positions) and incomplete (accounting for only ~45% of the total scattering matter in the asymmetric unit), an aggressive density modification protocol was undertaken. Iterative cycles of two-fold NCS averaging in DM (CCP4, 1994) interspersed with model building in MOLOC (Muller, et al., *Bull. Soc. Chim. Belg.* (1988) 97:655–667) and model refinement in REFMAC (Murshudov, et al., *Acta Crystallogr.* (1997) D53:240–255) (using tight NCS restraints) were used to quickly build a model of the LBD alone. For this procedure, MAMA (Kleywegt, et al., "Halloween . . . masks and bones. In From First Map to Final Model", Bailey, et al, eds., Warrington, England, SERC Daresbury Laboratory, 1994) was used for all mask manipulations and PHASES (Furey, et al., PA33 *Am. Cyst. Assoc. Mtg. Abstr.* (1990) 18:73) and the CCP4 suite (CCP4, 1994) were used for the generation of structure factors and the calculation of weights.

However, although the DES-hERα LBD-NR complex model accounted for ~90% of the scattering matter in the asymmetric unit, refinement was being hampered by severe model bias. The high-resolution data set of the DES-hERα LBD-NR-box 2 peptide complex became available when the $R_{free}$ of the OHT-hERα LBD model was ~31%. Both monomers in the asymmetric unit of the DES complex crystal were relocated using AMoRe and the incompletely refined OHT-hERα LBD model (with helix 12 and the loop between helices 11 and 12 removed) as the search model. The missing parts of the model were built and the rest of the model was corrected using MOLOC and two-fold averaged maps generated in DM. Initially, refinement was carried out with REFMAC using tight NCS restraints. At later stages, the model was refined without NCS restraints using the simulated annealing, minimization and B-factor refinement protocols in X-PLOR and a maximum-likelihood target. All B-factors were refined isotropically and anisotropic scaling and a bulk solvent correction were used. The $R_{free}$ set contained a random sample of 6.5% of all data. In refinement, all data between 27 and 2.03 Å (with no σ cutoff) were used. The final model was composed of residues 305–549 of monomer A, residues 305–461 and 470–554 of monomer B, residues 687–697 of peptide A, residues 686–696 of peptide B, 164 waters, two carboxymethyl groups and a chloride ion. According to PROCHECK, 93.7% of all residues in the model were in the core regions of the Ramachandran plot and none were in the disallowed regions. Thus, the structure of the DES-hERα LBD-NR-box 2 peptide complex has been refined to a crystallographic R-factor of 19.9% ($R_{free}$=25.0%) using data to 2.03 Å resolution.

Ile 689 from the peptide interacts with three receptor residues (Asp 538, Glu 542 and Leu 539). The γ-carboxylate of Glu 542 forms hydrogen bonds to the amides of residues 689 and 690 of the peptide. A water-mediated hydrogen bond network is formed between the imidazole ring of His 377, the γ-carboxylate of Glu 380, and the amide of Tyr 537. Three residues (Glu 380, Leu 536 and Tyr 537) interact with each other through van der Waals contacts and/or hydrogen bonds. Intriguingly, mutations in each these three residues dramatically increase the transcription activity of unliganded ERα LBD (Eng, et al., *Mol. Cell. Biol.* (1997) 17:4644–4653); Lazennec, et al., *Mol. Endocrinol.* (1997) 11:1375–86; White, et al., *EMBO J.* (1997) 16:1427–35). Atomic coordinates of DES-LBD-peptide complex are attached as Appendix 2. The structure in Appendix 2 comprises: human ERα residues 305–549 of chain A (SEQ ID NO: 56), human ERα residues 305–549 of chain B (SEQ ID NO: 57); peptide chain C (SEQ ID NO: 58); and peptide chain D (SEQ ID NO: 60).

TABLE 2

Summary of Crystallographic Statistics

| | Ligand | |
|---|---|---|
| | DES | OHT |
| Data Collection | | |
| Space group | P2$_1$ | P6$_5$22 |
| Resolution | 2.03 | 1.90 |
| Observations | 104189 | 269253 |
| Unique | 30265 | 23064 |
| Completeness (%) | 98.4 | 99.1 |
| R$_{sym}$(%)[a] | 7.8 | 7.0 |
| Average I/σI | 9.8 | 16.1 |
| Refinement | | |
| Number of non-hydrogen atoms | 4180 | 2070 |
| R$_{cryst}$ (%)[b]/R$_{free}$ (%) | 19.9/25.0 | 23.0/26.1 |
| Bond r.m.s. deviation (Å) | 0.006 | 0.006 |
| Angle r.m.s. deviation (°) | 1.05 | 1.05 |
| Average B factor (Å$^2$) | 34.0 | 40.4 |

[a]$R_{sym} = \Sigma_i |I_i - \langle I_i \rangle| / \Sigma_i I_i$ where $\langle I_i \rangle$ is the average intensity over symmetry equivalents
[b]$R_{cryst} = \Sigma |F_o - F_c| / \Sigma |F_o|$ C. Structure of hERα LBD-OHT Complex The OHT complex data set was then collected. Starting with one of the monomers of the preliminary low-resolution DES-hERα LBD-NR-box 2 peptide model as the search probe, molecular replacement in AMoRe was used to search for the location of LBD in this crystal form in both P6$_1$22 and P6$_5$22. A translation search in P6$_5$22 yielded the correct solution (R=53.8%, CC=38.2%). In order to reduce model bias, DMMULTI (CCP4, 1994) was then used to project averaged density from the DES complex cell into the OHT complex cell. Using MOLOC, a model of the hERα LBD was built into the resulting density. The model was refined initially in REFMAC and later with the simulated annealing, positional and R-factor refinement protocols in X-PLOR (Brunger, X-PLOR. Version 3.843, New Haven, Conn.: Yale University, 1996) using a maximum-likelihood target (Adams, et al., *Proc. Natl. Acad. Sci. USA* (1997) 94:5018–23). Anisotropic scaling and a bulk solvent correction were used and all B-factors were refined isotropically. Except for the R$_{free}$ set (a random sampling consisting of 8% of the data set), all data between 41 and 1.9 Å (with no σ cutoff) were included. The final model consisted of residues 306–551, the ligand and 78 waters. According to PROCHECK (CCP4, 1994), 91.6% of all residues in the model were in the core regions of the Ramachandran plot and none were in the disallowed regions. Thus, the structure of the OHT-hERα LBD complex has been refined against data of comparable resolution (1.90 Å) to a crystallographic B-factor of 23.0% (R$_{free}$=26.2%). Atomic coordinates of OHT-hERα LBD complex are attached as Appendix 3. The structure in Appendix 3 consists of: atomic coordinates for a portion of human ERα, (SEQ ID NO: 59) complexed with OHT.

Example 17

Structural Analysis of hTRβ LBD:GRIP 1 NR-box 2 Peptide Complex

A. Structure of Cocrystal Complex (Contents of Asu)

Figure 12:
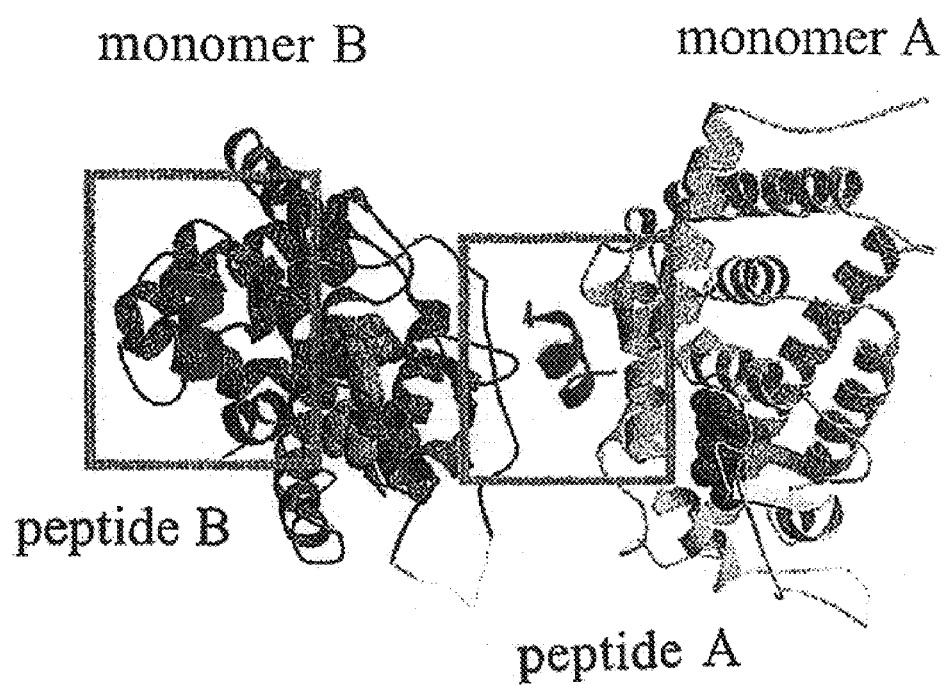
FIG. 12 shows the contents of the asymmetric unit of the crystallized hTRβ LBD:GRIP1 NR-box 2 peptide complex. The crystal lattice consists of a repeating unit containing a 2:2 complex of hTR LBD and GRIP1 site 2 peptide. Positions of the two GRIP1 site 2 peptides are boxed, in green (site1), and red (site 2), with the peptides drawn as a C-alpha trace. The two NCS related monomers of the hTR LBD are shown as a secondary structure ribbon drawing, with monomer 1 in light grey, and monomer 2 in dark grey. The side chains of the hydrophobic residues I689, L690, L693, L694 of the GRIP1 NR-box 2 peptides are drawn to emphasize those interactions observed in both bound peptides.
Figure 13:
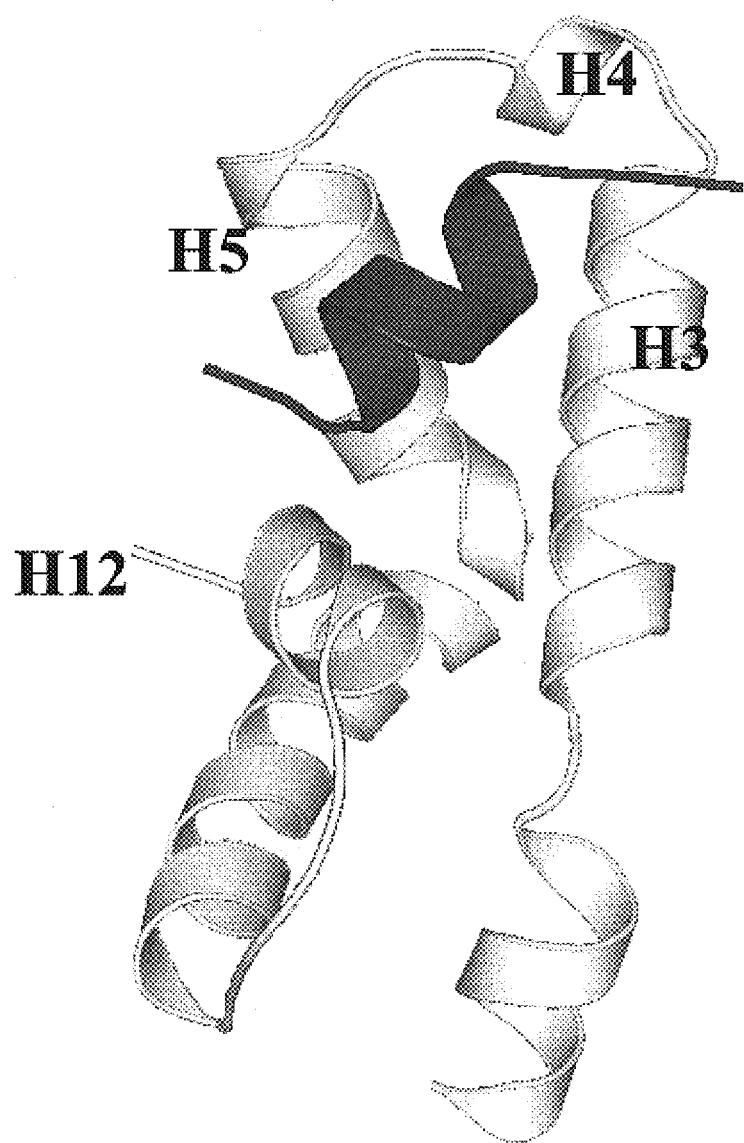
FIG. 13 shows a ribbon diagram depicting the interaction of the GRIP1 NR-box 2 peptide with the hTRβ LBD. The GRIP1 NR-box 2 peptide (dark grey) forms three turns of α-helix, and binds the hTR LBD (light gray) in a hydrophobic cleft defined by helices H3, H4, H5, and H12. Portions of the hTRβ LBD, and the neighboring monomer, are omitted for clarity.

The asymmetric unit (asu) of the crystal contains two monomers of the hTRβ LBD and two molecules of the GRIP1 NR-box 2 peptide 686-KHKILHRLLQDSS-698 (residues 12–24 of SEQ ID NO: 6), which observes the NCS relation of the two TR monomers (FIG. 12). The structure of the hTRβ LBD, which closely resembles that of the rTRα LBD (Wagner et al., supra), consists of twelve alpha-helices and two β-strands organized in three layers, resembling an alpha-helical sandwich. The only significant difference between the hTRβ LBD and the rTRα LBD is disorder in the loop between helices H1 and H3. The GRIP1 NR-box 2 peptide forms an amphipathic α-helix of about 3 turns, preceded by 2 residues and followed by 3 residues in extended coil conformation.

The relation of the two monomers of the hTRβ LBD is primarily translational, and does not resemble the homodimer structures reported for the hRXR, or the hER (Bourguet et al., supra; Brzozowski et al., supra). Furthermore, the interface between the two monomers does not involve residues necessary for formation of the physiological TR dimer. Instead, one of the cocrystal peptides appears to bridge the interaction between the two monomers. The hydrophobic face of the alpha-helix of the cocrystal peptide contacts monomer 1 of the hTRβ LBD at H3, H5, and H12, while the hydrophilic face contacts monomer 2 at the hairpin turn preceding strand S3. The second cocrystal peptide also contacts monomer 2 at H3, H5, and H12, and the two cocrystal peptides observe the same NCS relation as TR LBD monomers.

The common interface between both cocrystal peptides and the hTRβ LBD buries the hydrophobic residues that define the cocrystal peptide (SEQ ID NO: 1) LxxLL sequence motif, residues Ile689, Leu690, Leu693, and Leu694; against the surface of the receptor LBD (FIGS. 16 and 17). The presence of the second peptide in the crystal, duplicating the interactions of the hydrophobic residues, suggests those interactions are specific and drive the interaction of the peptide with the hTRβ LBD, while the hydrophilic interactions provide a fortuitous crystal contact and account for the dependence of crystallization on the presence and concentration of the peptide.

B. Structure of the GRIP1 NR-box 2 Peptide

The GRIP1 NR-box 2 peptide used in the crystallization is 13 amino acids long (residues 12–24 of SEQ ID NO: 6; 686-KHKILHRLLQDSS-698). For the NR-box 2 peptide in monomer 1 (peptide 1), 12 amino acids are ordered in the crystal. Residues K688–Q694 form an amphipathic helix, with residues K686–H687 and D695–S698 on either end in extended coil conformations. For the NR-box 2 peptide in monomer 2 (peptide 2), residues K688–Q694 again form an amphipathic helix, but the ends of the peptide are disordered. While the resolution of the current data prevents absolute assignment of hydrogen bonds, it is evident from the periodicity of the side chain density that the central residues form an alpha-helix. In the absence of TR the far UV-CD spectrum of the GRIP1 NR-box 2 peptide 686-KHKILHRLLQDSS-698 (residues 12–24 of SEQ ID NO: 6) appears to be random coil (data not shown). Stable helix formation may thus be induced by the interaction of the hydrophobic amino acids with the receptor LBD as it has been proposed in other protein:protein interactions, such as p53:MDM2 (Kussie et al., *Science* (1996) 274:948–953), VP16:TAF31 (Uesugi et al., *Science* (1996) 277:1310–1313), and CREB:KIX-CBP (Radhakrishnan et al., *Cell* (1997) 91:741–752).

C. Structure of the hTRβ LBD:GRIP1 NR-box 2 Peptide Interface

The hTRβ LBD of the cocrystal contributes residues from three helices, H3, H5, and H12 to the interface, which pack against one another to create a hydrophobic cleft. The residues lining the cleft are I280, T281, V283, V284, A287, and K288 from H3; Q301, I302, L305, and K306 from H5; and L454, E457, V458, and F459 from H12. A cysteine residue (C309) from H6 appears to provide a partial surface that is buried deep within the bottom of the cleft.

The GRIP1 NR-box 2 peptide 686-KHKILHRLLQDSS-698 (residues 12–24 of SEQ ID NO: 6) binds at the junction of H3 and H12. Leu690 of the bound peptide inserts into a shallow but defined depression at the base of the cleft, making van der Waals contact with L454 and V458 of H12, while peptide residue Ile689 packs against L454 of H12 outside the edge of the cleft; L454, then, interdigitates between the two residues. One further turn C-terminal along the alpha-helix, L693 and L694 of the bound peptide pack into complementary pockets within the hydrophobic cleft. Peptide residue L693 forms van der Waals contact with V284 of H3, while peptide residue L694, bound more deeply in the cleft, makes contact with F298 and L305 of H4 and H5. The hydrophobic interactions of the GRIP1 NR-box 2 peptide with the hTRβ LBD are observed for both cocrystal peptides 1 and 2 in their respective monomers of the crystal dimer complex, suggesting that the interactions are specific to the peptide, and not induced by crystallization.

Example 18

Overall Structure of the DES-hERα-LBD-NR-box 2 Peptide Complex

The asymmetric unit of the DES-hERα LBD-NR-box 2 peptide 686-KHKILHRLLQDSS-698 (residues 12–24 of SEQ ID NO: 6) complex crystals contains the same non-crystallographic dimer of LBDs that has been observed in the previously determined structures of the LBD bound to both $E_2$ and RAL (Brzozowski, et al., supra and Tanenbaum, et al., supra). Beyond the flexible loops between helices 2 and 3 and helices 9 and 10, the two LBDs of the dimer adopt similar structures (r.m.s.d. 0.47 Å based on Cα positions). The conformation of each LBD complexed with DES closely resembles that of the LBD bound to $E_2$ (Brzozowski, et al., supra); each monomer is a wedge shaped molecule consisting of three layers of eleven to twelve helices and a single beta hairpin. In each LBD, the hydrophobic face of helix 12 is packed against helices 3, 5/6 and 11 covering the ligand binding pocket. One NR-box 2 peptide is bound to each LBD in a hydrophobic cleft composed of residues from helices 3, 4, 5 and 12 and the turn between 3 and 4. The density for both peptides in the asymmetric unit is continuous and unambiguous. Residues 687 to 697 from peptide A and residues 686 to 696 from peptide B have been modeled; the remaining residues are disordered. Given that each peptide lies within a different environment within the crystal, it is striking that from residues Ile 689 to Gln 695 each peptide forms a two turn, amphipathic α helix. Flanking this region of common secondary structure, the peptides adopt dissimilar random coil conformations.

Example 19

Structure of the OHT-hERα LBD Complex

The binding of OHT induces a conformation of the hERα LBD that differs in both secondary and tertiary structural organization from that driven by DES binding. In the DES complex, the main chain from residues 339 to 341, 421 to 423, and 527 to 530 form parts of helices 3, 8 and 11 respectively. In contrast, these regions adopt an extended conformation in the OHT complex. In addition, the composition and orientation of helix 12 are different in the two structures. Helix 12 in the DES complex consists of residues 538 to 546 whereas helix 12 in the OHT complex consists of residues 536 to 544. Most dramatically, rather than covering the ligand binding pocket as it does in the DES complex, helix 12 in the OHT complex occupies the part of the coactivator binding groove formed by residues from helices 3, 4, and 5, and the turn connecting helices 3 and 4. This alternative conformation of helix 12 appears to be similar to that observed in the RAL complex (Brzozowski, et al., supra).

Example 20

Coactivator Binding Site Structure and Function

A. TR Coactivator Binding Site

The above examples demonstrate that nuclear receptors, exemplified by TR, GR and ER, are recognized by specific coactivators that bind thereto through a coupling surface comprising a hydrophobic cleft and a charged hydrophobic perimeter. Identification and characterization of this coupling surface and the coactivator binding site of nuclear receptors offers a new target for the design and selection of compounds that modulate binding of coactivator to nuclear receptors.

Figure 5:
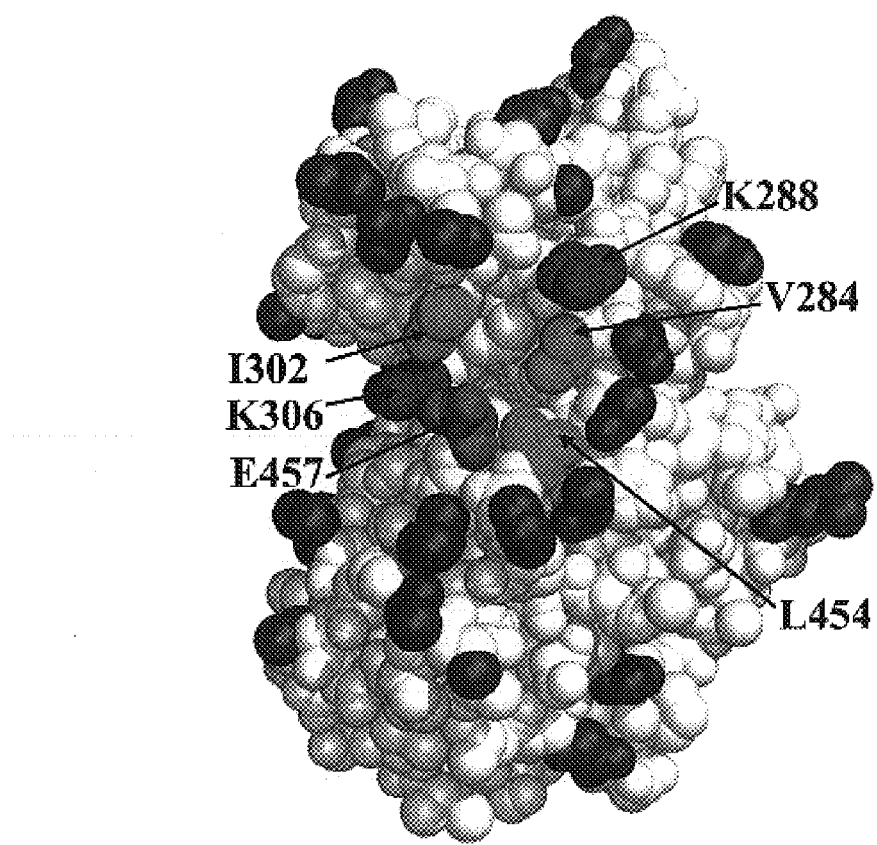
FIG. 5 shows a CPK model of the TRα-LBD, indicating the LBD surface locations of mutations made in the full-length hTRβ1. Mutated residues having no effect on GRIP1 binding or effect on activation in HeLa cells are shaded gray. Mutated residues with diminished GRIP1 and SRC-1a binding and diminished activation in HeLa cells are colored to reflect chemical properties of the residues: red, blue (purple), and green indicate acidic, basic, and hydrophobic residues, respectively. The main chain structures of the TRα- and TRβ-LBDs are the same (data not shown).
Figure 14:
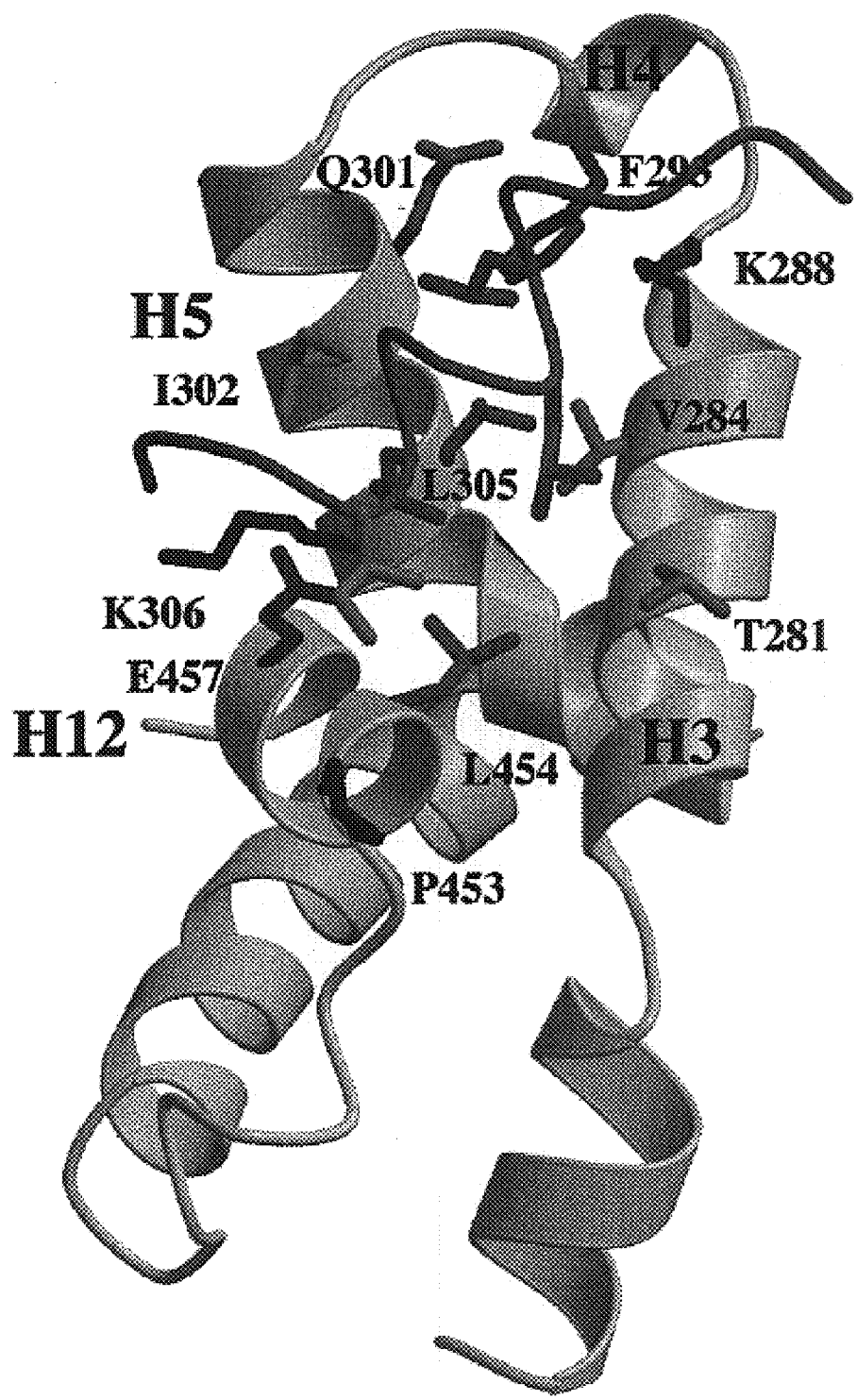
FIG. 14 shows interface between the GRIP1 NR-box 2 peptide and the hTRβ LBD. Side chains of residues of the hTRβ LBD within 4.5 Å of the GRIP-1 NR-box 2 peptide are labeled. The color of the individual side chains reflects the chemical nature of the residue: acidic residues are red, basic residue are blue, aliphatic residues are green, aromatic residues are brown, and polar residues are orange. The peptide is depicted as a C-alpha trace with the side chains of (SEQ ID NO: 2) ILxxLL motif shown explicitly.
Figure 15:
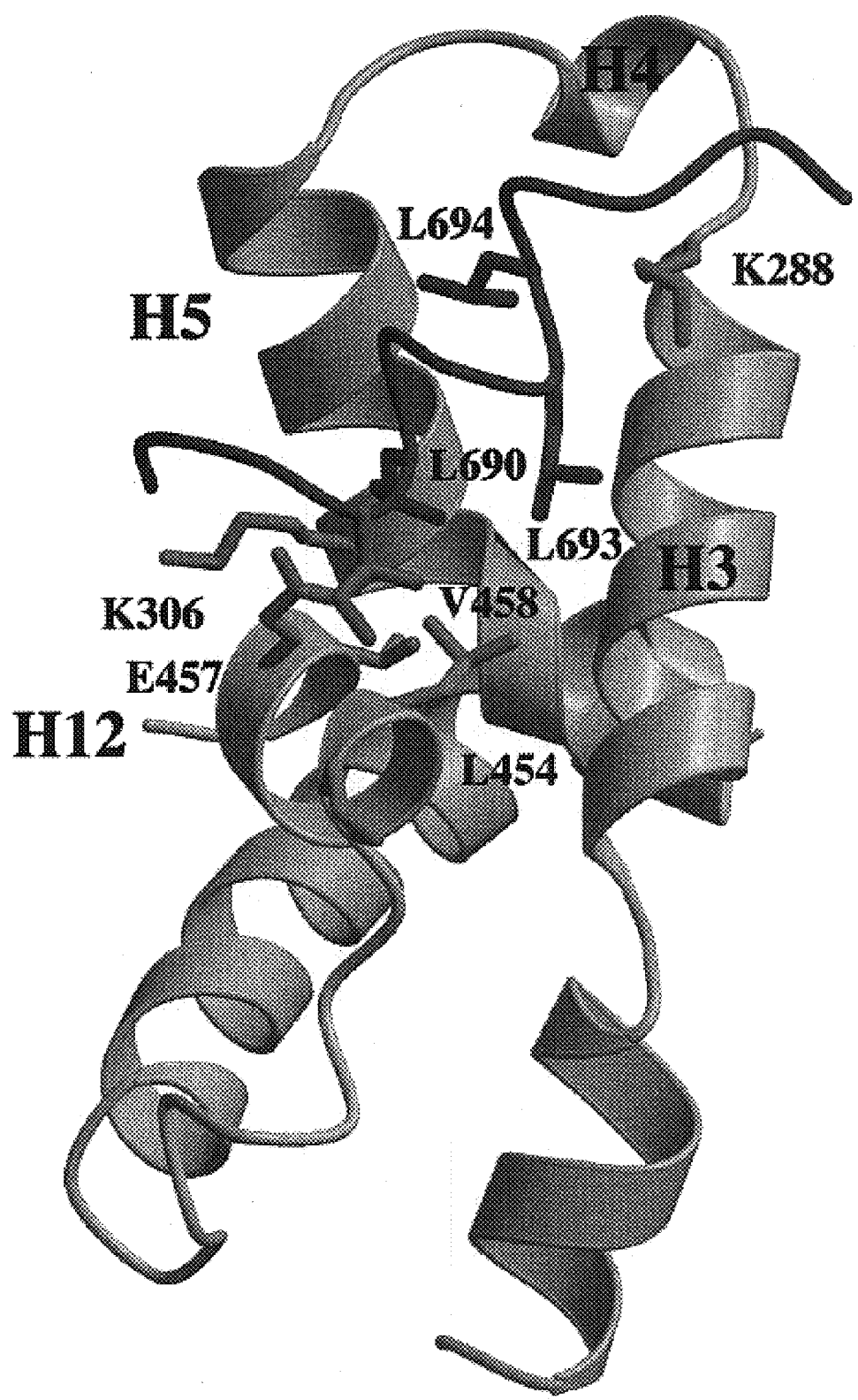
FIG. 15 shows residues in the hTRβ LBD that are necessary for transactivation. The transactivation mutations are mapped onto the interface between the GRIP1 NR-box 2 peptide and the hTRβ LBD.

Residues forming the coactivator binding site were found to cluster within a surprisingly small area with well-defined borders (see, e.g., FIGS. 5, 14, and 15). As is shown in above Examples, mutated residues nearby this area do not affect coactivator binding or transcriptional activation. Additionally, the coactivator binding assays and structural analyses demonstrated that NR-box containing proteins and peptides bind to this site. These results also showed that the GRIP1 coactivator protein binds to the site through a highly (SEQ ID NO: 1) LxxLL.

The structural analyses showed that residues contacting a conserved leucine residue of the (SEQ ID NO: 1) LxxLL motif included V284, F293, I302, L305 and L454. Residues within 4.5 Å of an atom of the bound peptide included T281, V284, K288, F293, Q301, I302, L305, K306, P453, L454 and E457. Structural analyses also revealed two other features of the site: a hydrophobic residue from helix 12 (Phe459) that contributes to local packing, and a cysteine residue contributed by helix 6 (Cys309) that provides a partial surface buried deep within the site. Mutational analyses showed that residues which block GRIP1 and SRC-1 coactivator binding when mutated are residues V284, K288, I302, K306, L454, and V458. Mutated residues likely to undergo a conformational change upon hormone binding included Leu454 and Glu457. Thus, the site identified by mutational, binding assays and crystallography corresponds to a surprisingly small cluster of residues on the surface of the LBD that define a prominent hydrophobic cleft formed by hydrophobic residues corresponding to human TR residues of C-terminal helix 3 (Ile280, Val283, Val284, and Ala287), helix 4 (Phe293), helix 5 (Ile302 and Leu305), helix 6 (Cys309), and helix 12 (Leu454, Val458 and Phe459). Collectively, the Examples indicate that residues forming the site are amino acids corresponding to human TR residues of C-terminal helix 3 (Ile280, Thr281, Val283, Val284, Ala287, and Lys288), helix 4 (Phe293), helix 5 (Gln301, Ile302, Leu305, Lys306), helix 6 (Cys309), and helix 12 (Pro453, Leu454, Glu457, Val458 and Phe459). The coactivator binding site is highly conserved among the nuclear receptor super family (FIG. 19).

Figure 18:
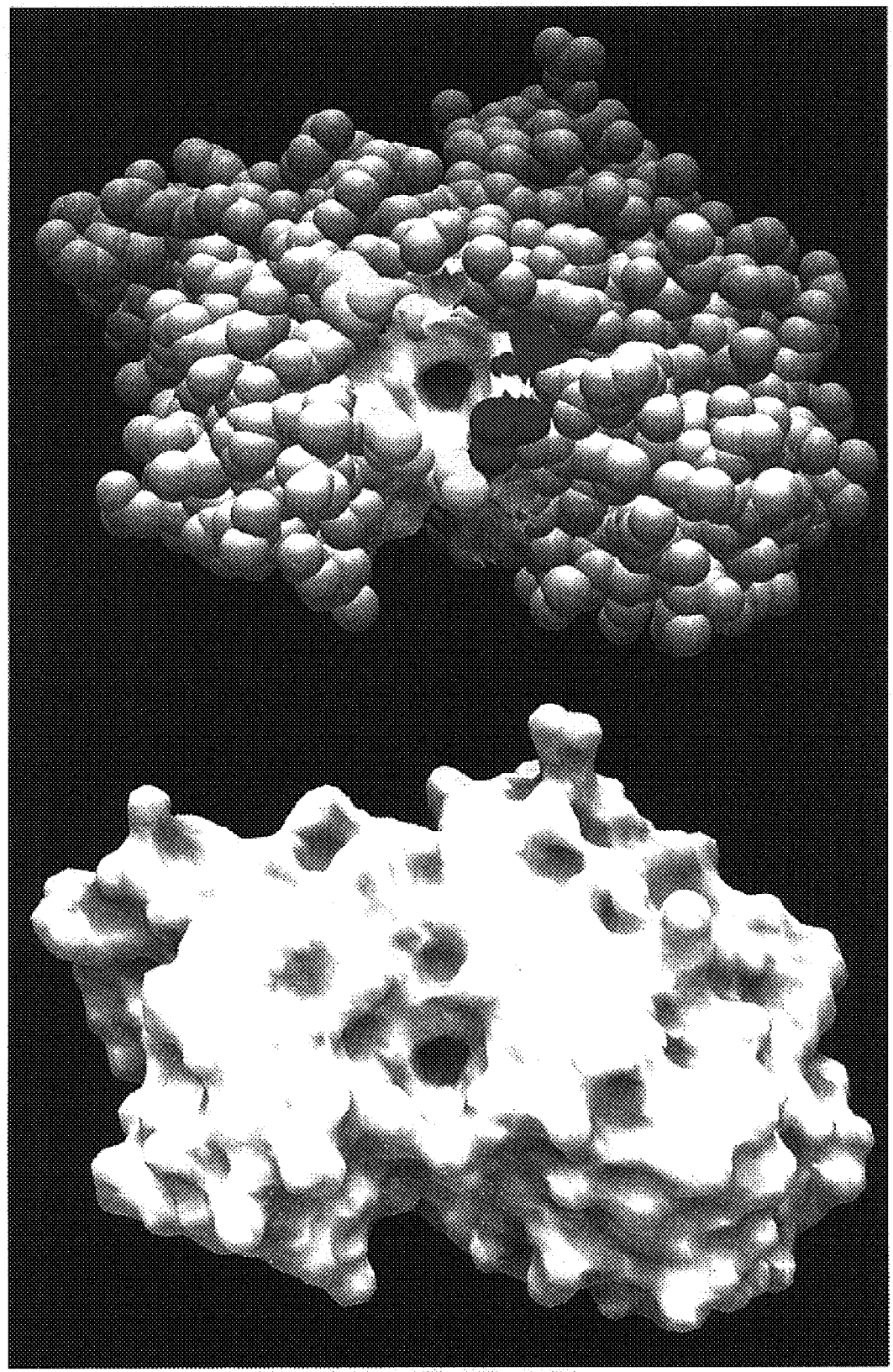
FIG. 18 shows the coactivator binding site cleft, one side of which is formed by conformationally hormone-responsive residues. On the left is a view of the TR-LBD molecular surface showing the concave surfaces in gray. The cavity is shown at the center of the figure. On the right is shown a CPK model of the TR-LBD, overlaid with a molecular surface view, which is restricted to a 12 Å radius of the hydrophobic cavity. Mutated residues of the coactivator binding site that are hormone-insensitive (V284, K288, I302 and K306) are located on one side of the cleft and are colored yellow. Mutated CBS residues likely undergo a conformational change upon hormone binding (L454 and E457) are located on the opposite side of the cleft and are colored red.

The coactivator binding site of TR contains charged and hydrophobic residues at its periphery, but only hydrophobic residues at its center (see, e.g., FIGS. 5 and 18). The hydrophobic cleft at the center of the site may play a significant role in driving the coactivator binding reaction. The site is comprised of two parts (FIG. 18), right). Residues contained in helices 3, 5 and 6 (FIG. 18, yellow residues) likely form a constitutive part, since their positions are identical in all nuclear receptor structures reported, including the liganded, activated states of the TR, RAR, and ER, the unliganded RXR, and the inhibitor-liganded ER. By contrast, the residues of helix 12 (FIG. 18, red residues) are differently positioned in the active and inactive states reported. Thus the coactivator binding site for the nuclear receptors is likely to be formed in response to an active hormone by positioning helix 12 against a scaffold formed by helices 3–6. Because the coactivator binding site is so small, it is easy to understand how even slight changes in the position of helix 12, which may, for example, be induced by an antagonist ligand, could impair coactivator binding, and thus receptor activation.

B. ER Coactivator Binding Site

Binding of the NR-box 2 peptide 686-KHKILHRLLQDSS-698 (residues 12–24 of SEQ ID NO: 6) to the ERα LBD buries 1000 Å$^2$ of predominantly hydrophobic surface area from both molecules. The NR-box 2 peptide binding site is a shallow groove composed of residues Leu 354, Val 355, Ile 358, Ala 361 and Lys 362 from helix 3; Phe 367 and Val 368 from helix 4; Leu 372 from the turn between helices 3 and 4; Gln 375, Val 376, Leu 379 and Glu 380 from helix 5; and Asp 538, Leu 539, Glu 542 and Met 543 from helix 12. The floor and sides of this groove are completely nonpolar, but the ends of this groove are charged. Therefore, structural characterization of the binding site of the NR-box 2 peptide 686-KHKILHRLLQDSS-698 (residues 12–24 of SEQ ID NO: 6) to the ERα LBD, which is the same NR-box 2 peptide utilized to crystallize the T$_3$-TR LBD, supports the findings for TR that residues forming the coactivator binding site of nuclear receptors is composed of a well defined hydrophobic cleft and a charged hydrophobic perimeter. These residues are highly conserved among the nuclear receptor super family (FIG. 19). Structural characterization of the coactivator peptide-bound ER LBD also supports the concept of exploiting the slight differences among the coactivator binding sites of nuclear receptors in designing and identifying compounds that target specific nuclear receptors.

The ERα LBD interacts primarily with the hydrophobic face of the NR-box 2 peptide 686-KHKILHRLLQDSS-698 (residues 12–24 of SEQ ID NO: 6) α helix formed by the side chains of Ile 689 and the three (SEQ ID NO: 1) LxxLL motif leucines (Leu 690, Leu 693 and Leu 694). The side chain of Leu 690 is deeply embedded within the groove and forms van der Waals contacts with the side chains of Ile 358, Val 376, Leu 379, Glu 380 and Met 543. The side chain of Leu 694 is similarly isolated within the groove and makes van der Waals contacts with the side chains of Ile 358, Lys 362, Leu 372, Gln 375, Val 376 and Leu 379. In contrast, the side chains of both Ile 689 and the second NR box leucine, Leu 693, rest against the rim of the groove. The side chain of Ile 689 lies in a shallow depression formed by the side chains of Asp 538, Leu 539 and Glu 542. The side chain of Leu 693 makes nonpolar contacts with the side chains of Ile 358 and Leu 539.

The charged and polar side chains which form the hydrophilic face of the peptide helix project away from the ERα receptor and either interact predominantly with solvent or form symmetry contacts. None of the side chains of the polar and charged residues outside the helical region of either peptide in the asymmetric unit, with the exception of Lys 688 of peptide B, is involved in hydrogen bonds or salt bridges with its associated ERα LBD monomer. The ε-amino group of Lys 688 of peptide B hydrogen bonds to the side chain carboxylate of Glu 380 of monomer B. This interaction is presumably a crystal artifact; the main chain atoms of the N-terminal three residues of peptide B are displaced from monomer B and interact extensively with a symmetry-related ERα LBD.

In addition to interacting with the hydrophobic face of the peptide helix, the ERα LBD stabilizes the main chain conformation of the NR box peptide by forming capping interactions with both ends of the peptide helix. Glu 542 and Lys 362 are positioned at opposite ends of the peptide binding site. The side chains of Glu 542 and Lys 362 form van der Waals contacts with main chain and side chain atoms at the N- and C-terminal turns of the peptide helix respectively. These interactions position the stabilizing charges of the γ-carboxylate of Glu 542 and ε-amino group of Lys 362 near the ends of the NR box peptide helix. The side chain carboxylate of Glu 542 hydrogen bonds to the amides of the residues of N-terminal turn of the peptide helix (residues 688 and 689 of peptide A; residues 689 and 690 of peptide B). Similarly, the ε-amino group of Lys 362 hydrogen bonds to the carbonyls of the residues of the C-terminal turn of the peptide helix (residue 693 of peptide A; residues 693 and 694 of peptide B).

Except for the orientation of helix 12, the structure of the peptide binding groove of the ERα LBD is almost identical in the DES and OHT complexes. The region of this groove outside of helix 12 is referred to herein as the "static region" of the NR box binding site. Helix 12 in the OHT complex and the NR box peptide helix in the DES complex interact with the static region of the coactivator recognition groove in strikingly similar ways.

Helix 12 mimics the hydrophobic interactions of the NR box peptide with the static region of the groove with a stretch of residues (residues 540 to 544) that resembles an NR box ((residues 6–10 of SEQ ID NO: 43) LLEML instead of (SEQ ID NO: 1) LxxLL). The side chains of Leu 540 and Met 543 lie in approximately the same locations as those of the first and second motif leucines (Leu 690 and Leu 693) in the peptide complex. Leu 540 is inserted into the groove and makes van der Waals contacts with Leu 354, Val 376 and Glu 380. Met 543 lies along the edge of the groove and forms van der Waals contacts with the side chains of Leu 354, Val 355 and Ile 358. The side chain position of Leu 544 almost exactly overlaps that of the third NR box leucine, Leu 694. Deep within the groove, the Leu 544 side chain makes van der Waals contacts with the side chains of Ile 358, Lys 362, Leu 372, Gln 375, Val 376 and Leu 379.

Helix 12 in the OHT complex is also stabilized by N- and C-terminal capping interactions. Lys 362 interacts with the C-terminal turn of helix 12 much as it does with the equivalent turn of the peptide helix. The Lys 362 side chain packs against the C-terminal turn of the helix 12 with its ε-amino group hydrogen bonding to the carbonyls of residues 543 and 544. Given that the capping interaction at the N-terminal turn coactivator helix is formed by a helix 12 residue (Glu 542), the N-terminal turn of helix 12 in the antagonist complex is forced to interact with another residue, Glu 380. The Glu 380 γ-carboxylate forms van der Waals contacts with Tyr 537 and interacts with the amide of Tyr 537 through a series of water-mediated hydrogen bonds.

In addition to forming these "NR box-like" interactions, helix 12 also forms van der Waals contacts with areas of the ERα LBD outside of the coactivator recognition groove. The side chain of Leu 536 forms van der Waals contacts with Glu 380 and Trp 383 and that of Tyr 537 forms van der Waals contacts with His 373, Val 376 and Glu 380. As a result of these contacts, helix 12 in the OHT complex buries more solvent accessible surface area (~1200 Å$^2$) than the NR box peptide in the DES-ERα LBD-peptide complex.

Identification and characterization of the coactivator binding site for TR, and extension of this information to other nuclear receptors shows that this site is common for all nuclear receptors identified to date. Additionally, sequence and structural comparison, coupled with the Examples showing differential specificity for coactivator binding to TR, GR and ER, reveal that minor differences between the receptors, such as found in helix 12, are likely to influence specificity of a coactivator for different types of nuclear receptors. Thus, the Examples presented herein demonstrate that information derived from the structure and function of the TR coactivator binding site can be applied in design and selection of compounds that modulate binding of coactivator proteins to nuclear receptors for all members of the nuclear receptor super family.

References

1. U.S. Pat. No. 5,331,573
2. U.S. Pat. No. 5,500,807
3. Adams, P. D., Pannu, N. S., Read, R. J., and Brunger, A. T. (1997). Proc. Natl. Acad. Sci. USA 94, 5018–23.
4. Apriletti et al., *Protein Expr. Purif.* (1995) 6:363
5. Bartlett et al., In: *Molecular Recognition in Chemical and Biological Problems"*, Special Pub., *Royal Chem. Soc.* (1989) 78:182–196
6. Berry, M., Metzger, D., and Chambon, P. (1990). EMBO J 9, 2811–8.
7. Bohm, *J. Comp. Aid. Molec. Design* (1992) 6:61–78
8. Bourguet, W., Ruff, M., Chambon, P., Gronemeyer, H., and Moras, D. (1995). Nature 375, 377–82.
9. Brzozowski, A., Pike, A., Dauter, Z., Hubbard, R., Bonn, T., Engstrom, O., Ohman, L., Greene, G., Gustafsson, J., and Carlquist, M. (1997). Nature 389, 753–758.
10. Chang et al., *Proc. Natl. Acad. Sci. USA* (1997) 94(17):9040–9045
11. Cohen et al., *J Med. Chem.* (1990)33:883–894)
12. Collingwood et al. *Proc. Natl. Acad Sci.* (1997) 94:248–253
13. DesJalais et al., *J. Med. Chem.* (1988) 31:722–729
14. Ding, S., Anderson, C., Ma, H., Hong, H., Uht, R., Kushner, P., and Stallcup, M. (1998). Mol. Endocrinol. 12, 302–313.
15. Eng, F. C. S., Lee, H. S., Ferrara, J., Willson, T. M., and White, J. H. (1997). Mol. Cell. Biol. 17, 4644–4653.
16. Farmer, "*Drug Design,*" Ariens, E. J., ed., 10:119–143 (Academic Press, New York, 1980)
17. Furey, et al., PA33 *Am. Cryst. Assoc. Mtg. Abstr.* (1990) 18:73
18. Glass, C. K., Rose, D. W., and Rosenfeld, M. G. (1997). Nuclear receptor coactivators. Curr. Opin. Cell Biol. 9, 222–32.
19. Goodford, *J. Med. Chem.* (1985) 28:849–857
20. Goodsell et al., *Proteins: Structure, Function and Genetics* (1990) 8:195–202
21. Greene, G., Harris, K., Bova, R., Kinders, R., Moore, B., and Nolan, C. (1988). Mol. Endocrinol. 2, 714–726.
22. Greene, G., Nolan, C., Engler, J., and Jensen, E. (1980). Proc. Natl. Acad. Sci. USA 77, 5115–5119.
23. Heery, D., Kalkhoven, E., Hoare, S., and Parker, M. (1997). Nature 387, 733–736.
24. Hegy, G., Shackleton, C., Carlquist, M., Bonn, T., Engstrom, O., Sjoholm, P., and Witkowska, H. (1996). Steroids 61, 367–373.
25. Henttu, P. M., Kalkhoven, E., and Parker, M. G. (1997). Mol. Cell. Biol. 17, 1832–9.
26. Hong et al., *Mol. Cell Biol.* (1997) 17:2735–44
27. Hong, H., Kohli, K., Trivedi, A., Johnson, D. L., and Stallcup, M. R. (1996). Proc. Natl. Acad. Sci. USA 93, 4948–4952.
28. Horwitz et al., *Mol. Endocrinol.* (1996) 10:1167–77
29. Janknecht et al., *Proc. Natl. Acad. Sci. USA,* (1991) 88:8972–8976
30. Jurutka et al., *J. Biol. Chem.* (1997) 227:14592–14599
31. Kakizawa et al., *J. Biol. Chem.* (1997) 272(38):23799–23804
32. Kamei, Y., Xu, L., Heinzel, T., Torchia, J., Kurokawa, R., Gloss, B., Lin, S. C., Heyman, R. A., Rose, D. W., Glass, C. K., and Rosenfeld, M. G. (1996). Cell 85, 403–14.
33. Kuiper, G. G., Carlsson, B., Grandien, K., Enmark, E., Haggblad, J., Nilsson, S., and Gustafsson, J. A. (1997). Endocrinology 138, 863–70.
34. Kuntz et al, *J. Mol. Biol.* (1982) 161:269–288
35. Kuntz et al., *Science,* (1992) 257:1078–1082
36. Kussie et al., *Science* (1996) 274:948–953
37. Landel, C., Kushner, P., and Greene, G. (1994). Mol. Endocrinol. 8, 1407–1419.
38. Landel, C., Potthoff, S., Nardulli, A., Kushner, J., and Greene, G. (1997). J. Steroid Biochem. Molec. Biol. 63, 59–73.
39. Lazennec, G., Ediger, T. R., Petz, L. N., Nardulli, A. M., and Katzenellenbogen, B. S. (1997). Mol. Endocrinol. 11, 1375–86.
40. Le Douarin, B., Nielsen, A. L., Garnier, J. M., Ichinose, H., Jeanmougin, F., Losson, R., and Chambon, P. (1996). EMBO J 15, 6701–15.
41. Lee et al., *Mol. Endocrinol.* (1992) 6:1867–1873
42. Lin et al., *Mol. Cell Biol.* (1997) 17(10):6131–6138
43. Masayama et al., *Mol. Endocrinol.* (1997) 11:1507–1517
44. Meng et al., *J. Comp. Chem.* (1992) 13:505–524
45. Miranker et al., *Proteins: Structure, Function and Genetics,* (1991) 11:29–34
46. Muller, K., Amman, H. J., Doran, D. M., Gerber, P. R., Gubemator, K., and Schrepfer, G. (1988). Bull. Soc. Chim. Belg. 97, 655–667.
47. Murshudov, G. N., Vagin, A. A., and Dodson, E. J. (1997). Acta Crystallogr. D 53, 240–255.
48. Navia et al., *Curr. Opin. Struct. Biol.* (1992) 2:202–210
49. Nishibata et al., *Tetrahedron* (1991) 47:8985;
50. Norman et al., *J. Biol. Chem.* (1989) 264:12063–12073

51. Norris, J. D., Fan, D., Stallcup, M. R., and McDonnell, D. P. (1998). J Biol Chem 273, 6679–88.
52. O'Donnell et al., *Mol. Endocrinol.* (1991) 5:94–99
53. Onate et al., *Science* (1995) 270:1354–1357
54. Radhakrishnan et al., *Cell* (1997) 91:741–752
55. Renaud, J., Rochel, N., Ruff, M., Vivat, V., Chambon, P., Gronemeyer, H., and Moras, D. (1995). Nature 378, 681–689.
56. Saatcioglu et al., *Mol. Cell Biol.* (1997) 17:4687–4695
57. Sadovsky, et al., *Mol Cell Biol.* (1995) 15:1554
58. Seielstad, D., Carlson, K., Katzenellenbogen, J., Kushner, P., and Greene, G. (1995a). Mol. Endocrinol. 9, 647–658.
59. Seielstad, et al., *Biochemistry* (1995) 34:12605–12615
60. Shiau et al. *Gene* (1996) 179(2):205–10
61. Shibata et al., *Recent Prog. Horm. Res.* 52:141–164 (1997)
62. Spencer, T. E., Jenster, G., Burcin, M. M., Allis, C. D., Zhou, J., Mizzen, C. A., McKenna, N. J., Onate, S. A., Tsai, S. Y., Tsai, M. J., and O'Malley, B. W. (1997). Nature 389, 194–8.
63. Tagami et al., *Mol. Cell Biol.* (1997) 17(5):2642–2648
64. Tanenbaum, D. M., Wang, Y., Williams, S. P., and Sigler, P. B. (1998). Proc. Natl. Acad. Sci. U S A 95, 5998–6003.
65. Tora, L., Mullick, A., Metzger, D., Ponglikitmongkol, M., Park, I., and Chambon, P. (1989). EMBO J 8,1981–6.
66. Torchia, J., Rose, D., Inostroza, J., Kamel, Y., Westin, S., Glass, C., and Rosenfeld, M. (1997). Nature 387, 677–684.
67. Uesugi et al., *Science* (1996) 277:1310–1313
68. Verlinde, *Structure,* (1994) 2:577–587)
69. Wagner, R., Apriletti, J., McGrath, M., West, B., Baxter, J., and Fletterick, R. (1995). Nature 378, 690–697.
70. Webb et al., *Mol Endocrinol* (1995) 9:443
71. White, R., Sjoberg, M., Kalkhoven, E., and Parker, M. G. (1997). EMBO J 16, 1427–35.
72. Whitfield et al., *Mol Endocrinol.* (1995) 9:1166–79
73. Wurtz, J. M., Bourguet, W., Renaud, J. P., Vivat, V., Chambon, P., Moras, D., and Gronemeyer, H. (1996). Nat. Struct. Biol. 3, 87–94.
74. Zhu et al., *J. Biol. Chem.* (1997) 272(14):9048–9054

All publications and Patent applications mentioned in this specification are herein incorporated by reference to the same extent as if each individual publication or Patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of identifying a compound that binds to a nuclear receptor coactivator binding site, said method comprising:

modeling a test compound that fits spatially into the nuclear receptor coactivator binding site using an atomic structural model of the nuclear receptor coactivator binding site or portion thereof; and screening said test compound in an assay that measures binding of the test compound to the nuclear receptor coactivator binding site, thereby identifying a test compound that binds to the nuclear receptor coactivator binding site.

2. The method of claim 1, wherein said nuclear receptor is selected from the group consisting of receptors for thyroid hormones, retinoids, peroxisomes, vitamin D, estrogens, glucocorticoids, progestins, mineralocorticoids and androgens.

3. The method of claim 1, wherein said atomic structural model is a model of human thyroid beta receptor and comprises atomic coordinates of amino acid residues selected from the group consisting of Val284, Phe293, Ile302, Leu305, and Lue454 as shown in FIG. 19.

4. The method of claim 1, wherein said atomic structural model is a model of human thyroid beta receptor and comprises atomic coordinates of amino acid residues selected from the group consisting of Val284, Lys288, Ile302, Lys306, Leu454 and Glu457, as shown in FIG. 19.

5. The method of claim 1, wherein said atomic structural model is a model of human thryoid beta receptor and comprises atomic coordinates of amino acid residues selected from the group consisting of helix 3 residues Ile280, Thr281, Val283, Val284, Ala287, Lys288, helix 4 residue Phe293, helix 5 residues Gln301, Ile302, Leu305, Lys306, helix 6 residue Cys309, helix 12 residues Pro453, Leu454, Glu457, Val458, and Phe459, as shown in FIG. 19.

6. The method of claim 1, wherein said nuclear receptor coactivator binding site is a coactivator binding site of human thyroid beta receptor and comprises amino acid residues selected from the group consisting of helix 3 residues Ile280, Thr281, Val283, Val284, Ala287, and Lys288, helix 4 residue Phe293, helix 5 residues Gln301, Ile302, Leu305, Lys306, helix 6 residue Cys309, and helix 12 residues Pro453, Leu454, Glu457, Val458 and Phe459, as shown in FIG. 19.

7. The method of claim 1, wherein said nuclear receptor coactivator binding site is a coactivator binding site of human throid beta receptor and comprises amino acid residues selected from the group consisting of Val284, Phe293, Ile302, Leu305, and Leu454, as shown in FIG. 19.

8. The method of claim 1, wherein said nuclear receptor coactivator binding site is a coactivator binding site of human thyroid beta receptor and comprises amino acid residues selected from the group consisting of Val284, Lys288, Ile302, Lys306, Leu454 and Glu457, as shown is FIG. 19.

9. The method of claim 1, wherein said nuclear receptor coactivator binding site is a coactivator binding site of human thyroid beta receptor and comprises amino acid residues selected from the group consisting of Ile280, Val283, Val284, Ala287, helix 4 residue Phe293, helix 5 residues Ile302, Leu305, helix 6 residue Cys309, and helix 12 residues Leu454, Val458 and Phe459, as shown in FIG. 19.

10. The method of any one of claims 3–9 wherein the test compound interacts with amino acid residues that form a hydrophobic cleft in the coactivator binding site.

11. The method of any one of claims 3–9 wherein the test compound interacts with the amino acid residues.

12. The method of claim 1, wherein said atomic structural model is a model of human estrogen alpha receptor and comprises atomic coordinates of amino acid residues selected from the group consisting of helix 3 residues Leu354, Val355, Met357, Ile358, Ala361, and Lys362, helix 4 residue Phe367, helix 5 residues Gln375, Val376, Leu379, Glu380, helix 6 residue Trp383, and helix 12 residues Asp538, Leu539, Glu542, Met543 and Leu544, as shown in FIG. 19.

13. The method of claim 1, wherein said nuclear receptor coactivator binding site is a coactivator binding site of human estrogen alpha receptor and comprises amino acid residues selected from the group consisting of helix 3 residues Leu354, Val355, Met357, Ile358, Ala361, and Lys362, helix 4 residue Phe367, helix 5 residues Gln375, Val376, Leu379, Glu380, helix 6 residue Trp383, and helix 12 residues Asp538, Leu539, Glu542, Met543, and Leu544, as shown in FIG. 19.

14. The method of claim 1, wherein said nuclear receptor coactivator binding site is a coactivator binding site of human retinoid receptor hRARγ and comprises amino acid redisues selected from the group consisting of helix 3 residues Ile238, Ile239, Ile241, Val242, Ala245, and Lys246, helix 4 residue Phe251, helix 5 residues Gln259, Ile260, Leu263, Lys264, helix 6 residue Cys267, and helix 12 residues Pro410, Leu411, Glu414, Met415 and Leu416, as shown in FIG. 19.

15. The method of claim 1, wherein said nuclear receptor coactivator binding site is a coactivator binding site of human retinoid receptor hRXRα and comprises amino acid residues selected from the group consisting of helix 3 residues Leu276, Phe277, Leu279, Val280, Ala283, and Lys284, helix 4 residue Phe289, helix 5 residues Gln297, Val298, Leu301, Arg302, helix 6 residue Trp305, and helix 12 residues Thr449, Phe450, Glu453, Met454 and Leu455, as shown in FIG. 19.

16. The method of claim 1, wherein said nuclear receptor coactivator binding site is a coactivator binding site of human peroxisome receptor hPPARγ and comprises amino acid residues selected from the group consisting of helix 3 residues Val291, Glu292, Ile294, Thr295, Ala298, and Lys299, helix 4 residue Phe304, helix 5 residues Gln312, Val313, Leu316, Lys317, helix 6 residue Val320, and helix 12 residues Pro465, Leu466, Glu469, Ile470 and Tyr471, as shown in FIG. 19.

17. The method of claim 1, wherein said nuclear receptor coactivator binding site is a coactivator binding site of human vitamin D receptor hVDR and comprises amino acid residues selected from the group consisting of helix 3 residues Ile238, Glu239, Val241, Ile242, Ala245, and Lys246, helix 4 residue Phe251, helix 5 residue Gln259, Val260, Leu263, Lys264, helix 6 residue Ala267, and helix 12 residues Pro416, Leu417, Glu420, Val421 and Phe422, as shown in FIG. 19.

18. The method of claim 1, wherein said nuclear receptor coactivator binding site is a coactivator binding site of human glucocorticoid receptor hGR and comprises amino acid residues selected from the group consisting of helix 3 residues Val571, Ile572, Ala574, Val575, Ala578, and Lys579, helix 4 residue Phe584, helix 5 residues Gln592, Met593, Leu596, Gln597, helix 6 residue Trp600, and helix 12 residues Glu751, Met752, Glu755, Ile756, and Ile757, as shown in FIG. 19.

19. The method of claim 1, wherein said nuclear receptor coactivator binding site is a coactivator binding site of human progestin receptor hPR and comprises amino acid residues selected from the gorup consisting of helix 3 residues Val726, Ile727, Ala729, Val730, Ala733, and Lys734, helix 4 residue Phe739, helix 5 residue Gln747, Met748, Leu751, Gln752, helix 6 residue Trp755, and helix 12 residues Glu907, Met908, Glu911, Ile912 and Ile913, as shown in FIG. 19.

20. The method of claim 1, wherein said nuclear receptor coactivator binding site is a coactivator binding site of human mileralocorticoid receptor hMR and comprises amino acid residues selected from the group consisting of helix 3 residues Met777, Ile778, Val780, Val781, Ala784, and Lys785, helix 4 residue Phe790, helix 5 residues Gln798, Ile799, Ile802, Gln803, helix 6 residue Trp806, and helix 12 residues Ala958, Met959, Glu962, Ile963 and Ile964, as shown in FIG. 19.

21. The method of claim 1, wherein said nuclear receptor coactivator binding site is a coactivator binding site of human androgen receptor hAR and comprises amino acid residues selected from the group consisting of helix 3 residues Leu245, Val246, Val248, Val249, Ala252, and Lys253, helix 4 residue Phe258, helix 5 residues Gln266, Met267, Ile270, Gln271, helix 6 residue Trp274, and helix 12 residues Glu426, Met427, Glu430, Ile431 and Ile432, as shown in FIG. 19.

22. The method of claim 1, wherein said atomic structural model additionally comprises atomic coordinates of a molecule bound to the coactivator binding site.

23. The method of claim 22 wherein the molecule is a peptide.

24. The method of claim 23 wherein the peptide comprises a nuclear receptor box sequence.

25. The method of claim 23 wherein the peptide consists of a portion of GRIP1 comprising a nuclear receptor box 2 sequence.

26. The method of claim 23 wherein the peptide consists of a portion of GRIP1 comprising a nuclear receptor box 3 sequence.

27. The method of claim 1, wherein said atomic structural model comprises atomic coordinates of amino acid residues that form a hydrophobic cleft of the coactivator binding site.

28. The method of claim 27 wherein the test compound interacts with the amino acid residues.

29. The method of claim 27 wherein the test compound interacts with at least one of the amino acid residues.

30. The method of claim 1 wherein the atomic structural model comprises data which is experimentally derived.

31. The method of claim 1 wherein the atomic structural model of the nuclear receptor coactivator binding site is provided to a computerized modeling system.

32. The method of claim 1, wherein said screening is in vitro.

33. The method of claim 32, wherein said screening is high throughput screening.

34. The method of claim 1, wherein said assay is an in vivo assay.

35. The method of claim 1, wherein said test compound is from a library of compounds.

36. The method of claim 1, wherein said test compound is an agonist or antagonist of coactivator binding.

37. The method of claim 36 wherein the agonist promotes hormone-dependent coactivator binding to the receptor.

38. The method of claim 36 wherein the antagonist blocks hormone-dependent coactivator binding to the receptor.

39. The method of claim 36, wherein said test compound is a small organic molecule, a peptide, or a peptidomimetic.

40. The method of claim 39, wherein the test compound is a peptide comprising a nuclear receptor box amino acid sequence or derivative thereof.

* * * * *

UNITED STATES PATENT AND TRADEMARK OFFICE
CERTIFICATE OF CORRECTION

PATENT NO.         : 6,965,850 B2
APPLICATION NO. : 09/281717
DATED              : November 15, 2005
INVENTOR(S)        : John D. Baxter et al.

It is certified that error appears in the above-identified patent and that said Letters Patent is hereby corrected as shown below:

Please insert Appendix 1, Appendix 2, and Appendix 3 as attached hereto, at Col. 40, after "The invention now being fully described, it will be apparent to one of ordinary skill in the art that many changes and modifications can be made thereto without departing from the spirit or scope of the appended claims" and before "SEQUENCE LISTING".

Signed and Sealed this

Tenth Day of February, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 6,965,850 B2 | Page 2 of 186 |
| APPLICATION NO. | : 09/281717 | |
| DATED | : November 15, 2005 | |
| INVENTOR(S) | : John D. Baxter et al. | |

It is certified that error appears in the above-identified patent and that said Letters Patent is hereby corrected as shown below:

Appendix 1

Atomic Coordinates for Human TR-β Complexed With $T_3$, and a GRIP1 NR-box 2 Peptide

```
REMARK full length numbering
REMARK all residue names correct
REMARK peptide sequence
REMARK two molecules of TRB - CHAIN A and CHAIN B
REMARK two molecules of T3 - CHAIN J and CHAIN K
REMARK two molecules of GRIP-1 peptide - CHAIN X and CHAIN Y
REMARK chain X lies between A and B
REMARK chain Y interacts with B only
REMARK residues differing between A and B include:
REMARK A 217 Glu, A 252 Gln, A 263 Lys (missing side chains)
REMARK B 237 Ser, B239 His, B 394 Lys (missing side chains)
REMARK additionally Gly 261, Gly 262 are not visible in chain A
REMARK residues differing between X and Y include:
REMARK A 692 Arg
REMARK additionally, residues Lys 688, Lys 689; Ser 697, Ser 698
REMARK are not visible in chain Y
ATOM      1  N    LYS A 211      52.546  23.912  35.239  1.00 45.76      7
ATOM      2  CA   LYS A 211      52.944  24.345  36.586  1.00 43.42      6
ATOM      3  C    LYS A 211      52.035  23.665  37.836  1.00 35.68      6
ATOM      4  O    LYS A 211      51.511  22.556  37.763  1.00 33.58      8
ATOM      5  CB   LYS A 211      52.610  25.825  36.779  1.00 46.72      6
ATOM      6  N    PRO A 212      51.678  24.182  39.199  1.00 35.64      7
ATOM      7  CD   PRO A 212      52.082  25.474  39.842  1.00 38.60      6
ATOM      8  CA   PRO A 212      50.809  23.379  40.166  1.00 38.35      6
ATOM      9  CB   PRO A 212      50.670  24.194  41.440  1.00 38.95      6
ATOM     10  CG   PRO A 212      51.455  25.469  41.255  1.00 42.00      6
ATOM     11  C    PRO A 212      49.433  23.097  39.594  1.00 38.78      6
ATOM     12  O    PRO A 212      48.920  23.949  38.802  1.00 34.64      8
ATOM     13  N    GLU A 213      48.901  21.948  40.014  1.00 40.31      7
ATOM     14  CA   GLU A 213      47.609  21.419  39.529  1.00 43.87      6
ATOM     15  CB   GLU A 213      47.943  20.307  38.520  1.00 45.16      6
ATOM     16  CG   GLU A 213      49.125  20.708  37.601  1.00 47.60      6
ATOM     17  CD   GLU A 213      49.284  19.828  36.353  1.00 50.68      6
ATOM     18  OE1  GLU A 213      49.355  18.547  36.474  1.00 59.18      8
ATOM     19  OE2  GLU A 213      49.356  20.368  35.180  1.00 49.06      8
ATOM     20  C    GLU A 213      46.711  20.988  40.747  1.00 45.96      6
ATOM     21  O    GLU A 213      47.111  21.136  41.910  1.00 43.13      8
ATOM     22  N    PRO A 214      45.463  20.460  40.515  1.00 46.52      7
ATOM     23  CD   PRO A 214      44.985  20.184  39.148  1.00 46.44      6
ATOM     24  CA   PRO A 214      44.447  20.124  41.596  1.00 47.52      6
ATOM     25  CB   PRO A 214      43.249  19.629  40.816  1.00 45.40      6
ATOM     26  CG   PRO A 214      43.588  19.674  39.327  1.00 49.89      6
ATOM     27  C    PRO A 214      44.787  19.082  42.625  1.00 45.70      6
ATOM     28  O    PRO A 214      45.816  18.466  42.535  1.00 44.49      8
ATOM     29  N    THR A 215      43.915  18.876  43.606  1.00 45.24      7
ATOM     30  CA   THR A 215      44.161  17.890  44.686  1.00 49.36      6
ATOM     31  CB   THR A 215      44.163  18.586  46.093  1.00 44.86      6
ATOM     32  OG1  THR A 215      42.878  18.447  46.728  1.00 52.26      8
ATOM     33  CG2  THR A 215      44.514  20.031  45.974  1.00 39.43      6
ATOM     34  C    THR A 215      42.934  16.995  44.667  1.00 52.51      6
```

UNITED STATES PATENT AND TRADEMARK OFFICE
CERTIFICATE OF CORRECTION

PATENT NO. : 6,965,850 B2  Page 3 of 186
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM     35  O    THR A 215    41.816  17.501  44.691  1.00  53.48   8
ATOM     36  N    ASP A 216    43.118  15.683  44.607  1.00  58.81   7
ATOM     37  CA   ASP A 216    41.973  14.740  44.615  1.00  61.51   6
ATOM     38  CB   ASP A 216    42.386  13.451  45.343  1.00  70.57   6
ATOM     39  CG   ASP A 216    42.399  12.283  44.475  1.00  78.07   6
ATOM     40  OD1  ASP A 216    41.532  12.161  43.586  1.00  82.31   8
ATOM     41  OD2  ASP A 216    43.293  11.436  44.684  1.00  86.55   8
ATOM     42  C    ASP A 216    40.640  15.311  45.268  1.00  58.42   6
ATOM     43  O    ASP A 216    39.598  14.840  44.924  1.00  56.85   8
ATOM     44  N    GLU A 217    40.673  16.270  46.217  1.00  54.92   7
ATOM     45  CA   GLU A 217    39.502  16.937  46.856  1.00  53.37   6
ATOM     46  CB   GLU A 217    39.943  17.459  48.216  1.00  51.02   6
ATOM     47  C    GLU A 217    39.113  18.144  45.956  1.00  53.55   6
ATOM     48  O    GLU A 217    37.905  18.394  45.695  1.00  54.33   8
ATOM     49  N    GLU A 218    40.162  18.895  45.511  1.00  49.20   7
ATOM     50  CA   GLU A 218    39.933  20.073  44.661  1.00  45.94   6
ATOM     51  CB   GLU A 218    41.232  20.855  44.304  1.00  43.43   6
ATOM     52  CG   GLU A 218    41.907  21.579  45.479  1.00  40.86   6
ATOM     53  CD   GLU A 218    43.061  22.446  45.074  1.00  39.88   6
ATOM     54  OE1  GLU A 218    43.895  22.019  44.232  1.00  37.61   8
ATOM     55  OE2  GLU A 218    43.183  23.583  45.599  1.00  34.01   8
ATOM     56  C    GLU A 218    39.249  19.647  43.390  1.00  44.71   6
ATOM     57  O    GLU A 218    38.302  20.291  42.964  1.00  45.31   8
ATOM     58  N    TRP A 219    39.720  18.553  42.797  1.00  44.02   7
ATOM     59  CA   TRP A 219    39.109  18.061  41.574  1.00  46.97   6
ATOM     60  CB   TRP A 219    39.799  16.793  41.074  1.00  48.42   6
ATOM     61  CG   TRP A 219    40.879  17.029  40.141  1.00  54.61   6
ATOM     62  CD2  TRP A 219    40.755  17.256  38.733  1.00  55.24   6
ATOM     63  CE2  TRP A 219    42.067  17.523  38.245  1.00  53.67   6
ATOM     64  CE3  TRP A 219    39.691  17.234  37.828  1.00  54.55   6
ATOM     65  CD1  TRP A 219    42.159  17.159  40.447  1.00  55.75   6
ATOM     66  NE1  TRP A 219    42.895  17.485  39.339  1.00  54.43   7
ATOM     67  CZ2  TRP A 219    42.330  17.851  36.895  1.00  52.54   6
ATOM     68  CZ3  TRP A 219    39.943  17.535  36.509  1.00  55.17   6
ATOM     69  CH2  TRP A 219    41.239  17.820  36.029  1.00  55.59   6
ATOM     70  C    TRP A 219    37.646  17.743  41.812  1.00  47.32   6
ATOM     71  O    TRP A 219    36.788  18.028  40.978  1.00  43.56   8
ATOM     72  N    GLU A 220    37.376  17.142  42.965  1.00  49.91   7
ATOM     73  CA   GLU A 220    36.021  16.769  43.316  1.00  53.57   6
ATOM     74  CB   GLU A 220    36.052  16.055  44.649  1.00  58.18   6
ATOM     75  CG   GLU A 220    35.149  14.930  44.672  1.00  73.13   6
ATOM     76  CD   GLU A 220    35.735  13.935  45.442  1.00  80.06   6
ATOM     77  OE1  GLU A 220    36.886  13.575  45.173  1.00  82.12   8
ATOM     78  OE2  GLU A 220    35.078  13.478  46.378  1.00  82.78   8
ATOM     79  C    GLU A 220    35.161  18.026  43.381  1.00  50.51   6
ATOM     80  O    GLU A 220    33.991  18.010  42.995  1.00  49.94   8
ATOM     81  N    LEU A 221    35.761  19.120  43.865  1.00  43.71   7
ATOM     82  CA   LEU A 221    35.047  20.398  43.951  1.00  42.81   6
ATOM     83  CB   LEU A 221    35.935  21.510  44.510  1.00  39.21   6
ATOM     84  CG   LEU A 221    35.375  22.908  44.353  1.00  36.34   6
ATOM     85  CD1  LEU A 221    33.941  22.929  44.836  1.00  36.93   6
ATOM     86  CD2  LEU A 221    36.226  23.910  45.122  1.00  24.18   6
ATOM     87  C    LEU A 221    34.563  20.815  42.575  1.00  43.46   6
ATOM     88  O    LEU A 221    33.392  21.104  42.395  1.00  45.25   8
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM     89   N    ILE A 222      35.498  20.871  41.628  1.00 39.09    7
ATOM     90   CA   ILE A 222      35.192  21.226  40.254  1.00 35.47    6
ATOM     91   CB   ILE A 222      36.379  20.997  39.343  1.00 33.74    6
ATOM     92   CG2  ILE A 222      35.970  21.182  37.893  1.00 28.86    6
ATOM     93   CG1  ILE A 222      37.532  21.922  39.707  1.00 33.33    6
ATOM     94   CD1  ILE A 222      38.804  21.586  39.004  1.00 34.85    6
ATOM     95   C    ILE A 222      34.067  20.365  39.735  1.00 34.26    6
ATOM     96   O    ILE A 222      33.033  20.873  39.319  1.00 31.90    8
ATOM     97   N    LYS A 223      34.301  19.058  39.750  1.00 39.49    7
ATOM     98   CA   LYS A 223      33.316  18.100  39.276  1.00 44.43    6
ATOM     99   CB   LYS A 223      33.603  16.713  39.852  1.00 50.81    6
ATOM    100   CG   LYS A 223      32.741  15.631  39.227  1.00 62.51    6
ATOM    101   CD   LYS A 223      32.859  14.291  39.943  1.00 72.22    6
ATOM    102   CE   LYS A 223      31.798  13.318  39.430  1.00 74.55    6
ATOM    103   NZ   LYS A 223      31.900  11.985  40.106  1.00 75.78    7
ATOM    104   C    LYS A 223      31.913  18.565  39.681  1.00 42.81    6
ATOM    105   O    LYS A 223      30.936  18.323  38.984  1.00 40.36    8
ATOM    106   N    THR A 224      31.849  19.236  40.833  1.00 39.89    7
ATOM    107   CA   THR A 224      30.602  19.792  41.378  1.00 39.93    6
ATOM    108   CB   THR A 224      30.805  20.206  42.851  1.00 40.57    6
ATOM    109   OG1  THR A 224      31.330  19.113  43.616  1.00 39.27    8
ATOM    110   CG2  THR A 224      29.500  20.684  43.461  1.00 38.11    6
ATOM    111   C    THR A 224      30.167  21.011  40.533  1.00 39.96    6
ATOM    112   O    THR A 224      29.313  20.899  39.655  1.00 36.67    8
ATOM    113   N    VAL A 225      30.777  22.160  40.832  1.00 38.02    7
ATOM    114   CA   VAL A 225      30.532  23.426  40.137  1.00 38.12    6
ATOM    115   CB   VAL A 225      31.797  24.292  40.122  1.00 38.19    6
ATOM    116   CG1  VAL A 225      31.512  25.636  39.491  1.00 36.77    6
ATOM    117   CG2  VAL A 225      32.343  24.464  41.505  1.00 41.76    6
ATOM    118   C    VAL A 225      30.070  23.195  38.706  1.00 37.52    6
ATOM    119   O    VAL A 225      29.119  23.803  38.239  1.00 36.77    8
ATOM    120   N    THR A 226      30.783  22.316  38.018  1.00 34.02    7
ATOM    121   CA   THR A 226      30.489  21.971  36.636  1.00 34.67    6
ATOM    122   CB   THR A 226      31.565  20.999  36.083  1.00 30.56    6
ATOM    123   OG1  THR A 226      32.805  21.696  35.889  1.00 32.20    8
ATOM    124   CG2  THR A 226      31.108  20.346  34.783  1.00 20.99    6
ATOM    125   C    THR A 226      29.100  21.361  36.510  1.00 36.41    6
ATOM    126   O    THR A 226      28.255  21.877  35.785  1.00 39.64    8
ATOM    127   N    ALA A 227      28.880  20.260  37.222  1.00 39.20    7
ATOM    128   CA   ALA A 227      27.602  19.562  37.204  1.00 36.93    6
ATOM    129   CB   ALA A 227      27.526  18.600  38.381  1.00 38.06    6
ATOM    130   C    ALA A 227      26.507  20.604  37.318  1.00 37.69    6
ATOM    131   O    ALA A 227      25.444  20.489  36.718  1.00 40.94    8
ATOM    132   N    ALA A 228      26.811  21.630  38.107  1.00 32.86    7
ATOM    133   CA   ALA A 228      25.903  22.734  38.356  1.00 32.48    6
ATOM    134   CB   ALA A 228      26.448  23.587  39.486  1.00 28.25    6
ATOM    135   C    ALA A 228      25.732  23.570  37.101  1.00 36.12    6
ATOM    136   O    ALA A 228      24.673  23.560  36.473  1.00 37.86    8
ATOM    137   N    HIS A 229      26.782  24.306  36.752  1.00 33.58    7
ATOM    138   CA   HIS A 229      26.762  25.158  35.585  1.00 32.97    6
ATOM    139   CB   HIS A 229      28.155  25.691  35.266  1.00 33.69    6
ATOM    140   CG   HIS A 229      28.250  26.333  33.929  1.00 28.39    6
ATOM    141   CD2  HIS A 229      29.025  26.081  32.838  1.00 28.83    6
ATOM    142   ND1  HIS A 229      27.386  27.368  33.542  1.00 30.47    7
```

UNITED STATES PATENT AND TRADEMARK OFFICE
CERTIFICATE OF CORRECTION

PATENT NO. : 6,965,850 B2  Page 5 of 186
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    143  CE1  HIS A 229    27.654  27.692  32.280  1.00  26.95  6
ATOM    144  NE2  HIS A 229    28.635  26.934  31.840  1.00  31.27  7
ATOM    145  C    HIS A 229    26.225  24.541  34.312  1.00  38.40  6
ATOM    146  O    HIS A 229    25.591  25.227  33.528  1.00  41.49  8
ATOM    147  N    VAL A 230    26.519  23.256  34.113  1.00  38.55  7
ATOM    148  CA   VAL A 230    26.088  22.554  32.916  1.00  40.40  6
ATOM    149  CB   VAL A 230    26.890  21.256  32.701  1.00  44.68  6
ATOM    150  CG1  VAL A 230    26.557  20.656  31.345  1.00  39.39  6
ATOM    151  CG2  VAL A 230    28.381  21.509  32.817  1.00  42.18  6
ATOM    152  C    VAL A 230    24.603  22.239  32.900  1.00  44.28  6
ATOM    153  O    VAL A 230    23.959  22.316  31.847  1.00  45.94  8
ATOM    154  N    ALA A 231    24.072  21.862  34.059  1.00  45.59  7
ATOM    155  CA   ALA A 231    22.669  21.500  34.175  1.00  47.84  6
ATOM    156  CB   ALA A 231    22.482  20.582  35.374  1.00  45.08  6
ATOM    157  C    ALA A 231    21.792  22.734  34.314  1.00  48.04  6
ATOM    158  O    ALA A 231    20.565  22.647  34.324  1.00  49.95  8
ATOM    159  N    THR A 232    22.436  23.894  34.384  1.00  47.26  7
ATOM    160  CA   THR A 232    21.722  25.161  34.528  1.00  43.64  6
ATOM    161  CB   THR A 232    22.112  25.832  35.850  1.00  41.93  6
ATOM    162  OG1  THR A 232    23.467  26.283  35.791  1.00  39.10  8
ATOM    163  CG2  THR A 232    21.990  24.846  37.008  1.00  29.80  6
ATOM    164  C    THR A 232    22.055  26.114  33.387  1.00  43.97  6
ATOM    165  O    THR A 232    21.679  27.279  33.436  1.00  40.55  8
ATOM    166  N    ASN A 233    22.783  25.625  32.381  1.00  48.62  7
ATOM    167  CA   ASN A 233    23.134  26.468  31.231  1.00  58.62  6
ATOM    168  CB   ASN A 233    24.626  26.283  30.880  1.00  62.44  6
ATOM    169  CG   ASN A 233    25.141  27.355  29.927  1.00  68.35  6
ATOM    170  OD1  ASN A 233    24.822  28.544  30.096  1.00  65.50  8
ATOM    171  ND2  ASN A 233    25.951  26.951  28.959  1.00  74.29  7
ATOM    172  C    ASN A 233    22.241  26.035  30.073  1.00  65.06  6
ATOM    173  O    ASN A 233    22.312  24.900  29.604  1.00  69.47  8
ATOM    174  N    ALA A 234    21.381  26.954  29.646  1.00  68.80  7
ATOM    175  CA   ALA A 234    20.423  26.708  28.564  1.00  70.98  6
ATOM    176  CB   ALA A 234    19.748  28.015  28.186  1.00  71.43  6
ATOM    177  C    ALA A 234    20.988  26.062  27.308  1.00  73.83  6
ATOM    178  O    ALA A 234    22.041  26.419  26.822  1.00  74.33  8
ATOM    179  N    GLN A 235    20.227  25.096  26.819  1.00  75.07  7
ATOM    180  CA   GLN A 235    20.562  24.363  25.629  1.00  76.32  6
ATOM    181  CB   GLN A 235    20.328  25.239  24.391  1.00  76.98  6
ATOM    182  CG   GLN A 235    18.887  25.292  23.908  1.00  77.07  6
ATOM    183  CD   GLN A 235    17.896  25.420  25.019  1.00  80.85  6
ATOM    184  OE1  GLN A 235    17.668  24.448  25.768  1.00  82.01  8
ATOM    185  NE2  GLN A 235    17.313  26.596  25.149  1.00  78.80  7
ATOM    186  C    GLN A 235    21.960  23.840  25.573  1.00  77.15  6
ATOM    187  O    GLN A 235    22.386  23.458  24.508  1.00  76.06  8
ATOM    188  N    GLY A 236    22.676  23.766  26.687  1.00  77.46  7
ATOM    189  CA   GLY A 236    24.053  23.245  26.627  1.00  78.37  6
ATOM    190  C    GLY A 236    24.923  23.491  25.390  1.00  79.43  6
ATOM    191  O    GLY A 236    24.917  24.565  24.844  1.00  79.47  8
ATOM    192  N    SER A 237    25.739  22.526  24.991  1.00  77.98  7
ATOM    193  CA   SER A 237    26.566  22.760  23.801  1.00  76.49  6
ATOM    194  CB   SER A 237    27.981  22.206  24.015  1.00  76.46  6
ATOM    195  OG   SER A 237    28.821  23.145  24.669  1.00  40.00  8
ATOM    196  C    SER A 237    25.938  22.127  22.542  1.00  75.35  6
```

UNITED STATES PATENT AND TRADEMARK OFFICE
CERTIFICATE OF CORRECTION

PATENT NO. : 6,965,850 B2  Page 6 of 186
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    197  O    SER A 237    26.605  21.418  21.797  1.00  75.47   8
ATOM    198  N    HIS A 238    24.648  22.410  22.353  1.00  75.56   7
ATOM    199  CA   HIS A 238    23.842  21.981  21.236  1.00  75.46   6
ATOM    200  CB   HIS A 238    22.990  20.732  21.661  1.00  75.85   6
ATOM    201  CG   HIS A 238    22.408  19.933  20.542  1.00  40.00   6
ATOM    202  CD2  HIS A 238    22.790  18.757  19.957  1.00  40.00   6
ATOM    203  ND1  HIS A 238    21.223  20.303  19.875  1.00  40.00   7
ATOM    204  CE1  HIS A 238    20.951  19.365  18.953  1.00  40.00   6
ATOM    205  NE2  HIS A 238    21.874  18.444  18.994  1.00  40.00   7
ATOM    206  C    HIS A 238    22.971  23.284  20.964  1.00  74.10   6
ATOM    207  O    HIS A 238    21.863  23.137  20.441  1.00  75.34   8
ATOM    208  N    TRP A 239    23.487  24.510  21.368  1.00  73.39   7
ATOM    209  CA   TRP A 239    22.872  25.894  21.195  1.00  74.02   6
ATOM    210  CB   TRP A 239    23.563  27.026  22.005  1.00  81.77   6
ATOM    211  CG   TRP A 239    25.022  27.366  21.688  1.00  89.67   6
ATOM    212  CD2  TRP A 239    25.532  28.662  21.240  1.00  93.19   6
ATOM    213  CE2  TRP A 239    26.961  28.522  21.136  1.00  95.46   6
ATOM    214  CE3  TRP A 239    24.936  29.911  20.969  1.00  95.35   6
ATOM    215  CD1  TRP A 239    26.102  26.548  21.781  1.00  94.16   6
ATOM    216  NE1  TRP A 239    27.268  27.241  21.475  1.00  97.48   7
ATOM    217  CZ2  TRP A 239    27.798  29.598  20.764  1.00  96.23   6
ATOM    218  CZ3  TRP A 239    25.763  30.967  20.569  1.00  96.75   6
ATOM    219  CH2  TRP A 239    27.171  30.825  20.482  1.00  97.32   6
ATOM    220  C    TRP A 239    22.799  26.407  19.774  1.00  70.77   6
ATOM    221  O    TRP A 239    21.706  26.562  19.263  1.00  71.70   8
ATOM    222  N    LYS A 240    23.946  26.701  19.157  1.00  67.10   7
ATOM    223  CA   LYS A 240    23.978  27.180  17.783  1.00  65.63   6
ATOM    224  CB   LYS A 240    25.314  26.780  17.153  1.00  66.65   6
ATOM    225  CG   LYS A 240    26.529  27.342  17.872  1.00  69.83   6
ATOM    226  CD   LYS A 240    27.805  27.037  17.108  1.00  71.49   6
ATOM    227  CE   LYS A 240    28.980  27.720  17.776  1.00  71.31   6
ATOM    228  NZ   LYS A 240    30.238  27.438  17.034  1.00  72.23   7
ATOM    229  C    LYS A 240    22.808  26.699  16.895  1.00  66.19   6
ATOM    230  O    LYS A 240    22.550  27.298  15.851  1.00  65.20   8
ATOM    231  N    ASN A 241    22.113  25.640  17.325  1.00  66.69   7
ATOM    232  CA   ASN A 241    20.976  25.078  16.599  1.00  67.53   6
ATOM    233  CB   ASN A 241    21.122  23.562  16.550  1.00  67.98   6
ATOM    234  CG   ASN A 241    22.304  23.121  15.693  1.00  70.19   6
ATOM    235  OD1  ASN A 241    22.404  23.506  14.503  1.00  71.37   8
ATOM    236  ND2  ASN A 241    23.176  22.310  16.271  1.00  71.48   7
ATOM    237  C    ASN A 241    19.570  25.421  17.152  1.00  66.62   6
ATOM    238  O    ASN A 241    18.581  24.822  16.731  1.00  64.76   8
ATOM    239  N    LYS A 242    19.475  26.380  18.069  1.00  66.86   7
ATOM    240  CA   LYS A 242    18.191  26.786  18.642  1.00  67.46   6
ATOM    241  CB   LYS A 242    18.164  26.396  20.119  1.00  67.93   6
ATOM    242  CG   LYS A 242    18.250  24.896  20.337  1.00  71.52   6
ATOM    243  CD   LYS A 242    17.004  24.149  19.821  1.00  74.32   6
ATOM    244  CE   LYS A 242    15.755  24.491  20.643  1.00  74.41   6
ATOM    245  NZ   LYS A 242    15.927  24.161  22.109  1.00  74.44   7
ATOM    246  C    LYS A 242    18.143  28.291  18.483  1.00  66.28   6
ATOM    247  O    LYS A 242    17.102  28.923  18.592  1.00  67.61   8
ATOM    248  N    ARG A 243    19.334  28.813  18.204  1.00  64.19   7
ATOM    249  CA   ARG A 243    19.617  30.219  17.975  1.00  62.43   6
ATOM    250  CB   ARG A 243    21.070  30.274  17.463  1.00  60.12   6
```

UNITED STATES PATENT AND TRADEMARK OFFICE
CERTIFICATE OF CORRECTION

| | |
|---|---|
| PATENT NO. | : 6,965,850 B2 |
| APPLICATION NO. | : 09/281717 |
| DATED | : November 15, 2005 |
| INVENTOR(S) | : John D. Baxter et al. |

It is certified that error appears in the above-identified patent and that said Letters Patent is hereby corrected as shown below:

```
ATOM    251  CG   ARG A 243    21.665  31.636  17.305  1.00 40.00  6
ATOM    252  CD   ARG A 243    23.213  31.599  17.267  1.00 40.00  6
ATOM    253  NE   ARG A 243    23.826  31.217  15.996  1.00 40.00  7
ATOM    254  CZ   ARG A 243    25.113  31.439  15.714  1.00 40.00  6
ATOM    255  NH1  ARG A 243    25.905  32.041  16.616  1.00 40.00  7
ATOM    256  NH2  ARG A 243    25.592  31.097  14.520  1.00 40.00  7
ATOM    257  C    ARG A 243    18.639  30.789  16.950  1.00 62.97  6
ATOM    258  O    ARG A 243    18.662  30.390  15.784  1.00 63.96  8
ATOM    259  N    LYS A 244    17.771  31.692  17.393  1.00 62.41  7
ATOM    260  CA   LYS A 244    16.790  32.309  16.498  1.00 61.57  6
ATOM    261  CB   LYS A 244    15.368  31.974  16.962  1.00 63.68  6
ATOM    262  CG   LYS A 244    15.102  30.471  17.104  1.00 71.29  6
ATOM    263  CD   LYS A 244    13.641  30.167  17.468  1.00 73.83  6
ATOM    264  CE   LYS A 244    13.182  30.908  18.737  1.00 74.71  6
ATOM    265  NZ   LYS A 244    13.951  30.536  19.970  1.00 73.32  7
ATOM    266  C    LYS A 244    17.009  33.806  16.501  1.00 59.30  6
ATOM    267  O    LYS A 244    16.562  34.514  17.399  1.00 56.34  8
ATOM    268  N    PHE A 245    17.705  34.264  15.468  1.00 57.06  7
ATOM    269  CA   PHE A 245    18.045  35.692  15.333  1.00 59.01  6
ATOM    270  CB   PHE A 245    18.825  35.947  14.049  1.00 59.62  6
ATOM    271  CG   PHE A 245    19.908  34.979  13.834  1.00 66.60  6
ATOM    272  CD1  PHE A 245    19.618  33.714  13.399  1.00 67.17  6
ATOM    273  CD2  PHE A 245    21.198  35.309  14.139  1.00 69.25  6
ATOM    274  CE1  PHE A 245    20.614  32.794  13.255  1.00 69.92  6
ATOM    275  CE2  PHE A 245    22.189  34.385  13.994  1.00 70.50  6
ATOM    276  CZ   PHE A 245    21.897  33.126  13.552  1.00 70.89  6
ATOM    277  C    PHE A 245    16.856  36.620  15.340  1.00 60.68  6
ATOM    278  O    PHE A 245    15.946  36.516  14.528  1.00 62.37  8
ATOM    279  N    LEU A 246    16.919  37.558  16.272  1.00 60.10  7
ATOM    280  CA   LEU A 246    15.884  38.554  16.437  1.00 59.44  6
ATOM    281  CB   LEU A 246    16.227  39.510  17.585  1.00 57.43  6
ATOM    282  CG   LEU A 246    15.100  40.384  18.086  1.00 54.41  6
ATOM    283  CD1  LEU A 246    14.010  39.474  18.640  1.00 52.43  6
ATOM    284  CD2  LEU A 246    15.575  41.325  19.151  1.00 51.69  6
ATOM    285  C    LEU A 246    15.717  39.330  15.135  1.00 62.05  6
ATOM    286  O    LEU A 246    16.706  39.609  14.430  1.00 59.85  8
ATOM    287  N    PRO A 247    14.473  39.668  14.784  1.00 63.33  7
ATOM    288  CD   PRO A 247    13.263  39.314  15.534  1.00 64.44  6
ATOM    289  CA   PRO A 247    14.198  40.421  13.558  1.00 63.56  6
ATOM    290  CB   PRO A 247    12.687  40.671  13.600  1.00 64.42  6
ATOM    291  CG   PRO A 247    12.161  39.922  14.729  1.00 64.90  6
ATOM    292  C    PRO A 247    14.996  41.733  13.496  1.00 61.94  6
ATOM    293  O    PRO A 247    15.159  42.455  14.486  1.00 61.60  8
ATOM    294  N    GLU A 248    15.506  42.006  12.299  1.00 61.33  7
ATOM    295  CA   GLU A 248    16.280  43.197  11.976  1.00 63.50  6
ATOM    296  CB   GLU A 248    16.481  43.273  10.437  1.00 66.94  6
ATOM    297  CG   GLU A 248    17.012  44.671   9.966  1.00 68.70  6
ATOM    298  CD   GLU A 248    16.981  44.939   8.471  1.00 40.00  6
ATOM    299  OE1  GLU A 248    16.432  44.144   7.644  1.00 40.00  8
ATOM    300  OE2  GLU A 248    17.509  46.015   8.086  1.00 40.00  8
ATOM    301  C    GLU A 248    15.624  44.489  12.458  1.00 64.19  6
ATOM    302  O    GLU A 248    16.298  45.395  12.918  1.00 65.56  8
ATOM    303  N    ASP A 249    14.300  44.545  12.323  1.00 64.36  7
ATOM    304  CA   ASP A 249    13.493  45.703  12.673  1.00 63.33  6
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    305  CB   ASP A 249    12.088  45.531  12.116  1.00  62.97  6
ATOM    306  CG   ASP A 249    11.277  44.527  12.870  1.00  64.63  6
ATOM    307  OD1  ASP A 249    11.687  43.352  12.963  1.00  64.84  8
ATOM    308  OD2  ASP A 249    10.183  44.880  13.395  1.00  66.52  8
ATOM    309  C    ASP A 249    13.371  46.062  14.130  1.00  64.31  6
ATOM    310  O    ASP A 249    13.310  47.250  14.468  1.00  64.73  8
ATOM    311  N    ILE A 250    13.274  45.049  14.997  1.00  63.09  7
ATOM    312  CA   ILE A 250    13.133  45.318  16.418  1.00  64.39  6
ATOM    313  CB   ILE A 250    13.035  44.034  17.214  1.00  65.79  6
ATOM    314  CG2  ILE A 250    12.001  44.104  18.336  1.00  64.78  6
ATOM    315  CG1  ILE A 250    12.611  42.860  16.341  1.00  65.28  6
ATOM    316  CD1  ILE A 250    11.753  41.852  17.088  1.00  65.08  6
ATOM    317  C    ILE A 250    14.404  46.104  17.276  1.00  65.21  6
ATOM    318  O    ILE A 250    15.155  45.506  18.047  1.00  64.05  8
ATOM    319  N    GLY A 251    14.670  47.529  17.299  1.00  65.48  7
ATOM    320  CA   GLY A 251    15.871  48.326  18.042  1.00  67.32  6
ATOM    321  C    GLY A 251    16.595  49.110  16.895  1.00  68.52  6
ATOM    322  O    GLY A 251    17.528  48.616  16.266  1.00  65.49  8
ATOM    323  N    GLN A 252    16.162  50.356  16.557  1.00  72.26  7
ATOM    324  CA   GLN A 252    16.541  50.930  15.207  1.00  74.10  6
ATOM    325  CB   GLN A 252    15.316  50.844  14.295  1.00  75.82  6
ATOM    326  C    GLN A 252    16.995  52.403  15.084  1.00  77.17  6
ATOM    327  O    GLN A 252    17.572  52.955  15.986  1.00  76.50  8
ATOM    328  N    ALA A 253    16.374  53.372  13.908  1.00  80.78  7
ATOM    329  CA   ALA A 253    16.687  54.725  13.567  1.00  83.70  6
ATOM    330  CB   ALA A 253    16.381  54.956  12.093  1.00  83.23  6
ATOM    331  C    ALA A 253    16.159  55.960  14.345  1.00  85.59  6
ATOM    332  O    ALA A 253    15.317  56.721  13.798  1.00  85.69  8
ATOM    333  N    PRO A 254    16.384  56.155  15.264  1.00  35.05  7
ATOM    334  CD   PRO A 254    17.102  55.053  15.908  1.00  33.97  6
ATOM    335  CA   PRO A 254    16.002  57.231  17.219  1.00  35.89  6
ATOM    336  CB   PRO A 254    16.534  56.756  18.563  1.00  33.94  6
ATOM    337  CG   PRO A 254    17.146  55.441  18.349  1.00  33.31  6
ATOM    338  C    PRO A 254    16.717  58.498  16.731  1.00  37.75  6
ATOM    339  O    PRO A 254    17.838  58.804  17.100  1.00  38.78  8
TER
ATOM      1  N    LYS A 263    18.045  57.462  23.875  1.00  61.71  7
ATOM      2  CA   LYS A 263    16.824  56.712  24.215  1.00  64.36  6
ATOM      3  CB   LYS A 263    15.758  57.004  23.141  1.00  63.50  6
ATOM      4  C    LYS A 263    16.841  55.180  24.429  1.00  63.41  6
ATOM      5  O    LYS A 263    17.877  54.542  24.409  1.00  61.93  8
ATOM      6  N    VAL A 264    15.615  54.664  24.654  1.00  61.15  7
ATOM      7  CA   VAL A 264    15.292  53.229  24.856  1.00  59.46  6
ATOM      8  CB   VAL A 264    14.251  52.974  25.978  1.00  59.03  6
ATOM      9  CG1  VAL A 264    14.229  51.494  26.368  1.00  53.79  6
ATOM     10  CG2  VAL A 264    14.449  53.818  27.142  1.00  55.32  6
ATOM     11  C    VAL A 264    14.590  52.820  23.554  1.00  60.96  6
ATOM     12  O    VAL A 264    14.734  53.468  22.508  1.00  62.13  8
ATOM     13  N    ASP A 265    13.802  51.755  23.634  1.00  62.59  7
ATOM     14  CA   ASP A 265    12.995  51.263  22.526  1.00  64.95  6
ATOM     15  CB   ASP A 265    13.825  51.077  21.271  1.00  64.32  6
ATOM     16  CG   ASP A 265    13.282  50.048  20.485  1.00  67.70  6
ATOM     17  OD1  ASP A 265    12.795  50.011  19.446  1.00  72.59  8
ATOM     18  OD2  ASP A 265    13.354  48.867  20.294  1.00  68.84  8
```

UNITED STATES PATENT AND TRADEMARK OFFICE
CERTIFICATE OF CORRECTION

PATENT NO. : 6,965,850 B2 Page 9 of 186
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM     19  C    ASP A 265     12.326  49.943  22.952  1.00  65.64  6
ATOM     20  O    ASP A 265     12.771  48.850  22.655  1.00  68.81  8
ATOM     21  N    LEU A 266     11.256  50.152  23.702  1.00  65.12  7
ATOM     22  CA   LEU A 266     10.368  49.169  24.288  1.00  63.40  6
ATOM     23  CB   LEU A 266      9.115  49.938  24.708  1.00  67.34  6
ATOM     24  CG   LEU A 266      9.399  51.124  25.618  1.00  69.35  6
ATOM     25  CD1  LEU A 266      8.304  52.148  25.533  1.00  68.24  6
ATOM     26  CD2  LEU A 266      9.581  50.631  27.021  1.00  70.47  6
ATOM     27  C    LEU A 266      9.940  47.888  23.559  1.00  59.67  6
ATOM     28  O    LEU A 266      9.694  46.879  24.220  1.00  53.35  8
ATOM     29  N    GLU A 267      9.815  47.904  22.235  1.00  58.01  7
ATOM     30  CA   GLU A 267      9.417  46.682  21.572  1.00  58.34  6
ATOM     31  CB   GLU A 267      9.311  46.855  20.048  1.00  59.21  6
ATOM     32  CG   GLU A 267      9.129  45.494  19.322  1.00  62.89  6
ATOM     33  CD   GLU A 267      8.736  45.592  17.883  1.00  67.66  6
ATOM     34  OE1  GLU A 267      9.433  46.263  17.080  1.00  69.95  8
ATOM     35  OE2  GLU A 267      7.710  44.974  17.503  1.00  69.40  8
ATOM     36  C    GLU A 267     10.504  45.683  21.895  1.00  57.67  6
ATOM     37  O    GLU A 267     10.255  44.485  21.988  1.00  58.34  8
ATOM     38  N    ALA A 268     11.712  46.222  22.054  1.00  53.43  7
ATOM     39  CA   ALA A 268     12.903  45.454  22.374  1.00  49.00  6
ATOM     40  CB   ALA A 268     14.137  46.241  21.983  1.00  45.72  6
ATOM     41  C    ALA A 268     12.908  45.196  23.873  1.00  45.76  6
ATOM     42  O    ALA A 268     12.887  44.042  24.307  1.00  41.50  8
ATOM     43  N    PHE A 269     12.918  46.277  24.663  1.00  41.43  7
ATOM     44  CA   PHE A 269     12.920  46.158  26.118  1.00  43.96  6
ATOM     45  CB   PHE A 269     12.395  47.426  26.777  1.00  40.10  6
ATOM     46  CG   PHE A 269     12.332  47.345  28.271  1.00  40.44  6
ATOM     47  CD1  PHE A 269     13.457  47.595  29.043  1.00  38.98  6
ATOM     48  CD2  PHE A 269     11.165  46.946  28.903  1.00  37.15  6
ATOM     49  CE1  PHE A 269     13.409  47.469  30.436  1.00  32.12  6
ATOM     50  CE2  PHE A 269     11.105  46.815  30.303  1.00  38.41  6
ATOM     51  CZ   PHE A 269     12.228  47.070  31.071  1.00  40.55  6
ATOM     52  C    PHE A 269     12.017  45.012  26.520  1.00  49.76  6
ATOM     53  O    PHE A 269     12.277  44.324  27.484  1.00  52.15  8
ATOM     54  N    SER A 270     10.934  44.835  25.768  1.00  53.15  7
ATOM     55  CA   SER A 270      9.988  43.768  26.043  1.00  52.29  6
ATOM     56  CB   SER A 270      8.727  43.943  25.215  1.00  51.85  6
ATOM     57  OG   SER A 270      7.785  42.918  25.497  1.00  53.42  8
ATOM     58  C    SER A 270     10.637  42.464  25.685  1.00  49.38  6
ATOM     59  O    SER A 270     11.068  41.741  26.562  1.00  48.74  8
ATOM     60  N    HIS A 271     10.683  42.173  24.383  1.00  50.15  7
ATOM     61  CA   HIS A 271     11.276  40.932  23.877  1.00  51.67  6
ATOM     62  CB   HIS A 271     11.797  41.118  22.455  1.00  58.52  6
ATOM     63  CG   HIS A 271     10.775  40.885  21.399  1.00  68.97  6
ATOM     64  CD2  HIS A 271     10.633  39.891  20.485  1.00  70.88  6
ATOM     65  ND1  HIS A 271      9.673  41.732  21.199  1.00  71.98  7
ATOM     66  CE1  HIS A 271      8.936  41.242  20.209  1.00  73.91  6
ATOM     67  NE2  HIS A 271      9.495  40.132  19.764  1.00  73.59  7
ATOM     68  C    HIS A 271     12.402  40.416  24.745  1.00  48.33  6
ATOM     69  O    HIS A 271     12.707  39.225  24.728  1.00  48.39  8
ATOM     70  N    PHE A 272     13.029  41.334  25.487  1.00  41.34  7
ATOM     71  CA   PHE A 272     14.130  41.001  26.384  1.00  39.44  6
ATOM     72  CB   PHE A 272     15.077  42.194  26.512  1.00  36.67  6
```

UNITED STATES PATENT AND TRADEMARK OFFICE
CERTIFICATE OF CORRECTION

| | |
|---|---|
| PATENT NO. | : 6,965,850 B2 |
| APPLICATION NO. | : 09/281717 |
| DATED | : November 15, 2005 |
| INVENTOR(S) | : John D. Baxter et al. |

It is certified that error appears in the above-identified patent and that said Letters Patent is hereby corrected as shown below:

```
ATOM      73  CG   PHE A 272      15.953  42.413  25.282  1.00  33.39      6
ATOM      74  CD1  PHE A 272      16.619  43.615  25.093  1.00  33.14      6
ATOM      75  CD2  PHE A 272      16.138  41.394  24.346  1.00  38.28      6
ATOM      76  CE1  PHE A 272      17.454  43.807  23.988  1.00  38.26      6
ATOM      77  CE2  PHE A 272      16.973  41.585  23.244  1.00  43.28      6
ATOM      78  CZ   PHE A 272      17.634  42.786  23.068  1.00  39.74      6
ATOM      79  C    PHE A 272      13.650  40.528  27.764  1.00  40.75      6
ATOM      80  O    PHE A 272      14.081  39.476  28.227  1.00  35.51      8
ATOM      81  N    THR A 273      12.756  41.266  28.428  1.00  41.64      7
ATOM      82  CA   THR A 273      12.290  40.854  29.757  1.00  45.97      6
ATOM      83  CB   THR A 273      11.651  42.025  30.506  1.00  51.52      6
ATOM      84  OG1  THR A 273      10.442  42.422  29.859  1.00  45.74      8
ATOM      85  CG2  THR A 273      12.601  43.211  30.565  1.00  49.73      6
ATOM      86  C    THR A 273      11.267  39.731  29.664  1.00  46.23      6
ATOM      87  O    THR A 273      10.854  39.183  30.680  1.00  41.21      8
ATOM      88  N    LYS A 274      10.849  39.412  28.440  1.00  46.21      7
ATOM      89  CA   LYS A 274       9.871  38.362  28.211  1.00  54.53      6
ATOM      90  CB   LYS A 274       9.414  38.405  26.773  1.00  54.36      6
ATOM      91  C    LYS A 274      10.498  37.015  28.515  1.00  56.88      6
ATOM      92  O    LYS A 274       9.789  36.044  28.759  1.00  57.98      8
ATOM      93  N    ILE A 275      11.836  36.973  28.491  1.00  56.48      7
ATOM      94  CA   ILE A 275      12.609  35.746  28.767  1.00  52.64      6
ATOM      95  CB   ILE A 275      13.444  35.346  27.543  1.00  49.15      6
ATOM      96  CG2  ILE A 275      12.568  34.829  26.429  1.00  47.42      6
ATOM      97  CG1  ILE A 275      14.238  36.532  27.026  1.00  45.31      6
ATOM      98  CD1  ILE A 275      15.001  36.242  25.771  1.00  37.22      6
ATOM      99  C    ILE A 275      13.541  35.870  29.982  1.00  51.78      6
ATOM     100  O    ILE A 275      14.014  34.873  30.503  1.00  49.80      8
ATOM     101  N    ILE A 276      13.790  37.107  30.415  1.00  51.76      7
ATOM     102  CA   ILE A 276      14.681  37.389  31.537  1.00  52.58      6
ATOM     103  CB   ILE A 276      14.691  38.877  31.844  1.00  55.04      6
ATOM     104  CG2  ILE A 276      13.311  39.340  32.261  1.00  53.28      6
ATOM     105  CG1  ILE A 276      15.675  39.206  32.976  1.00  57.31      6
ATOM     106  CD1  ILE A 276      17.096  38.942  32.655  1.00  60.32      6
ATOM     107  C    ILE A 276      14.323  36.644  32.828  1.00  50.70      6
ATOM     108  O    ILE A 276      15.177  36.458  33.691  1.00  55.55      8
ATOM     109  N    THR A 277      13.072  36.209  32.963  1.00  47.33      7
ATOM     110  CA   THR A 277      12.631  35.523  34.158  1.00  42.59      6
ATOM     111  CB   THR A 277      11.098  35.456  34.217  1.00  44.97      6
ATOM     112  OG1  THR A 277      10.545  36.777  34.102  1.00  46.38      8
ATOM     113  CG2  THR A 277      10.657  34.838  35.539  1.00  37.17      6
ATOM     114  C    THR A 277      13.211  34.118  34.304  1.00  39.84      6
ATOM     115  O    THR A 277      13.796  33.796  35.365  1.00  40.55      8
ATOM     116  N    PRO A 278      13.055  33.261  33.288  1.00  38.20      7
ATOM     117  CD   PRO A 278      12.370  33.534  32.023  1.00  36.34      6
ATOM     118  CA   PRO A 278      13.595  31.894  33.363  1.00  36.63      6
ATOM     119  CB   PRO A 278      13.153  31.244  32.064  1.00  32.95      6
ATOM     120  CG   PRO A 278      12.573  32.291  31.239  1.00  35.75      6
ATOM     121  C    PRO A 278      15.101  31.932  33.476  1.00  38.60      6
ATOM     122  O    PRO A 278      15.746  30.981  33.898  1.00  37.67      8
ATOM     123  N    ALA A 279      15.656  33.051  33.035  1.00  37.05      7
ATOM     124  CA   ALA A 279      17.087  33.277  33.041  1.00  33.18      6
ATOM     125  CB   ALA A 279      17.376  34.599  32.348  1.00  30.56      6
ATOM     126  C    ALA A 279      17.624  33.312  34.452  1.00  33.47      6
```

UNITED STATES PATENT AND TRADEMARK OFFICE
CERTIFICATE OF CORRECTION

| | | |
|---|---|---|
| PATENT NO. | : 6,965,850 B2 | |
| APPLICATION NO. | : 09/281717 | |
| DATED | : November 15, 2005 | |
| INVENTOR(S) | : John D. Baxter et al. | |

It is certified that error appears in the above-identified patent and that said Letters Patent is hereby corrected as shown below:

```
ATOM    127  O    ALA A 279     18.523  32.555  34.789  1.00  33.74  8
ATOM    128  N    ILE A 280     17.060  34.215  35.260  1.00  29.96  7
ATOM    129  CA   ILE A 280     17.459  34.362  36.646  1.00  25.94  6
ATOM    130  CB   ILE A 280     16.686  35.484  37.315  1.00  26.95  6
ATOM    131  CG2  ILE A 280     17.109  35.632  38.733  1.00  15.40  6
ATOM    132  CG1  ILE A 280     16.931  36.808  36.595  1.00  26.73  6
ATOM    133  CD1  ILE A 280     16.292  38.002  37.272  1.00  34.31  6
ATOM    134  C    ILE A 280     17.263  33.066  37.412  1.00  31.39  6
ATOM    135  O    ILE A 280     18.116  32.679  38.207  1.00  35.69  8
ATOM    136  N    THR A 281     16.145  32.386  37.165  1.00  30.90  7
ATOM    137  CA   THR A 281     15.854  31.118  37.851  1.00  33.49  6
ATOM    138  CB   THR A 281     14.598  30.413  37.277  1.00  37.18  6
ATOM    139  OG1  THR A 281     14.795  30.099  35.898  1.00  46.48  8
ATOM    140  CG2  THR A 281     13.352  31.281  37.444  1.00  32.85  6
ATOM    141  C    THR A 281     17.045  30.176  37.713  1.00  29.94  6
ATOM    142  O    THR A 281     17.478  29.546  38.684  1.00  25.55  8
ATOM    143  N    ARG A 282     17.561  30.076  36.489  1.00  32.70  7
ATOM    144  CA   ARG A 282     18.692  29.198  36.218  1.00  34.27  6
ATOM    145  CB   ARG A 282     19.136  29.374  34.780  1.00  33.78  6
ATOM    146  CG   ARG A 282     19.272  28.086  34.013  1.00  45.15  6
ATOM    147  CD   ARG A 282     18.179  27.921  32.977  1.00  58.24  6
ATOM    148  NE   ARG A 282     18.041  29.077  32.117  1.00  68.41  7
ATOM    149  CZ   ARG A 282     19.018  29.529  31.352  1.00  72.31  6
ATOM    150  NH1  ARG A 282     20.190  28.886  31.327  1.00  77.89  7
ATOM    151  NH2  ARG A 282     18.802  30.593  30.595  1.00  69.25  7
ATOM    152  C    ARG A 282     19.823  29.582  37.170  1.00  34.81  6
ATOM    153  O    ARG A 282     20.380  28.735  37.855  1.00  36.03  8
ATOM    154  N    VAL A 283     20.135  30.882  37.190  1.00  31.71  7
ATOM    155  CA   VAL A 283     21.171  31.434  38.057  1.00  30.16  6
ATOM    156  CB   VAL A 283     21.198  32.965  37.981  1.00  29.00  6
ATOM    157  CG1  VAL A 283     22.208  33.533  38.952  1.00  28.64  6
ATOM    158  CG2  VAL A 283     21.525  33.415  36.578  1.00  28.28  6
ATOM    159  C    VAL A 283     20.942  30.992  39.498  1.00  32.50  6
ATOM    160  O    VAL A 283     21.879  30.717  40.229  1.00  33.48  8
ATOM    161  N    VAL A 284     19.671  30.941  39.892  1.00  30.96  7
ATOM    162  CA   VAL A 284     19.289  30.527  41.239  1.00  29.14  6
ATOM    163  CB   VAL A 284     17.822  30.865  41.548  1.00  31.27  6
ATOM    164  CG1  VAL A 284     17.472  30.461  42.945  1.00  24.21  6
ATOM    165  CG2  VAL A 284     17.555  32.334  41.360  1.00  30.51  6
ATOM    166  C    VAL A 284     19.529  29.037  41.353  1.00  28.89  6
ATOM    167  O    VAL A 284     20.073  28.568  42.345  1.00  27.29  8
ATOM    168  N    ASP A 285     19.121  28.296  40.327  1.00  28.76  7
ATOM    169  CA   ASP A 285     19.277  26.842  40.306  1.00  35.32  6
ATOM    170  CB   ASP A 285     18.586  26.234  39.072  1.00  33.29  6
ATOM    171  CG   ASP A 285     17.083  26.277  39.149  1.00  38.15  6
ATOM    172  OD1  ASP A 285     16.484  25.743  40.110  1.00  34.70  8
ATOM    173  OD2  ASP A 285     16.431  26.828  38.231  1.00  34.43  8
ATOM    174  C    ASP A 285     20.751  26.449  40.305  1.00  36.70  6
ATOM    175  O    ASP A 285     21.106  25.389  40.808  1.00  37.96  8
ATOM    176  N    PHE A 286     21.604  27.300  39.737  1.00  35.96  7
ATOM    177  CA   PHE A 286     23.029  27.022  39.704  1.00  37.10  6
ATOM    178  CB   PHE A 286     23.754  28.009  38.793  1.00  37.97  6
ATOM    179  CG   PHE A 286     25.252  28.027  38.987  1.00  36.50  6
ATOM    180  CD1  PHE A 286     25.963  26.849  38.974  1.00  36.75  6
```

UNITED STATES PATENT AND TRADEMARK OFFICE
CERTIFICATE OF CORRECTION

PATENT NO.         : 6,965,850 B2
APPLICATION NO.    : 09/281717
DATED              : November 15, 2005
INVENTOR(S)        : John D. Baxter et al.

It is certified that error appears in the above-identified patent and that said Letters Patent is hereby corrected as shown below:

```
ATOM    181  CD2  PHE A 286    25.931  29.218  39.199  1.00 33.83    6
ATOM    182  CE1  PHE A 286    27.331  26.860  39.161  1.00 39.55    6
ATOM    183  CE2  PHE A 286    27.307  29.233  39.387  1.00 38.08    6
ATOM    184  CZ   PHE A 286    28.008  28.052  39.371  1.00 34.44    6
ATOM    185  C    PHE A 286    23.631  27.105  41.083  1.00 36.83    6
ATOM    186  O    PHE A 286    24.317  26.192  41.504  1.00 35.61    8
ATOM    187  N    ALA A 287    23.393  28.228  41.752  1.00 37.33    7
ATOM    188  CA   ALA A 287    23.917  28.448  43.087  1.00 36.34    6
ATOM    189  CB   ALA A 287    23.523  29.828  43.555  1.00 36.40    6
ATOM    190  C    ALA A 287    23.346  27.393  44.027  1.00 38.76    6
ATOM    191  O    ALA A 287    23.994  26.973  44.981  1.00 41.98    8
ATOM    192  N    LYS A 288    22.114  26.979  43.735  1.00 38.28    7
ATOM    193  CA   LYS A 288    21.429  25.971  44.538  1.00 45.26    6
ATOM    194  CB   LYS A 288    19.994  25.746  44.054  1.00 48.35    6
ATOM    195  CG   LYS A 288    19.025  26.819  44.464  1.00 51.43    6
ATOM    196  CD   LYS A 288    17.628  26.246  44.682  1.00 60.23    6
ATOM    197  CE   LYS A 288    17.135  25.478  43.485  1.00 62.81    6
ATOM    198  NZ   LYS A 288    17.196  26.327  42.268  1.00 64.69    7
ATOM    199  C    LYS A 288    22.120  24.632  44.536  1.00 43.31    6
ATOM    200  O    LYS A 288    21.967  23.857  45.462  1.00 45.66    8
ATOM    201  N    LYS A 289    22.865  24.366  43.467  1.00 41.70    7
ATOM    202  CA   LYS A 289    23.571  23.120  43.351  1.00 40.67    6
ATOM    203  CB   LYS A 289    23.655  22.708  41.877  1.00 42.25    6
ATOM    204  CG   LYS A 289    22.271  22.492  41.247  1.00 39.53    6
ATOM    205  CD   LYS A 289    22.331  21.606  40.012  1.00 43.19    6
ATOM    206  CE   LYS A 289    20.941  21.362  39.447  1.00 45.74    6
ATOM    207  NZ   LYS A 289    20.273  20.165  40.006  1.00 52.49    7
ATOM    208  C    LYS A 289    24.948  23.185  44.003  1.00 41.50    6
ATOM    209  O    LYS A 289    25.642  22.184  44.080  1.00 39.77    8
ATOM    210  N    LEU A 290    25.312  24.370  44.490  1.00 40.68    7
ATOM    211  CA   LEU A 290    26.594  24.583  45.149  1.00 39.33    6
ATOM    212  CB   LEU A 290    27.153  25.972  44.829  1.00 36.14    6
ATOM    213  CG   LEU A 290    27.358  26.290  43.365  1.00 34.81    6
ATOM    214  CD1  LEU A 290    27.945  27.675  43.208  1.00 29.07    6
ATOM    215  CD2  LEU A 290    28.267  25.242  42.757  1.00 33.45    6
ATOM    216  C    LEU A 290    26.434  24.405  46.652  1.00 40.08    6
ATOM    217  O    LEU A 290    25.803  25.235  47.333  1.00 42.00    8
ATOM    218  N    PRO A 291    27.028  23.333  47.210  1.00 40.27    7
ATOM    219  CD   PRO A 291    27.851  22.330  46.519  1.00 39.65    6
ATOM    220  CA   PRO A 291    26.905  23.096  48.659  1.00 38.28    6
ATOM    221  CB   PRO A 291    27.755  21.860  48.911  1.00 35.88    6
ATOM    222  CG   PRO A 291    28.202  21.355  47.585  1.00 34.19    6
ATOM    223  C    PRO A 291    27.327  24.298  49.522  1.00 40.05    6
ATOM    224  O    PRO A 291    26.571  24.739  50.391  1.00 41.33    8
ATOM    225  N    MET A 292    28.522  24.843  49.299  1.00 40.59    7
ATOM    226  CA   MET A 292    29.021  25.957  50.097  1.00 42.86    6
ATOM    227  CB   MET A 292    30.313  26.475  49.477  1.00 43.28    6
ATOM    228  CG   MET A 292    31.269  25.378  49.050  1.00 50.35    6
ATOM    229  SD   MET A 292    32.895  26.096  48.757  1.00 51.17   16
ATOM    230  CE   MET A 292    33.812  24.647  48.074  1.00 54.63    6
ATOM    231  C    MET A 292    27.984  27.066  50.149  1.00 41.05    6
ATOM    232  O    MET A 292    27.986  27.886  51.057  1.00 39.66    8
ATOM    233  N    PHE A 293    27.080  27.078  49.172  1.00 39.30    7
ATOM    234  CA   PHE A 293    26.030  28.091  49.114  1.00 40.92    6
```

UNITED STATES PATENT AND TRADEMARK OFFICE
CERTIFICATE OF CORRECTION

PATENT NO. : 6,965,850 B2 Page 13 of 186
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    235  CB   PHE A 293    25.398  28.107  47.715  1.00 40.98   6
ATOM    236  CG   PHE A 293    24.348  29.168  47.524  1.00 42.78   6
ATOM    237  CD1  PHE A 293    24.654  30.493  47.747  1.00 44.40   6
ATOM    238  CD2  PHE A 293    23.071  28.833  47.116  1.00 43.66   6
ATOM    239  CE1  PHE A 293    23.701  31.478  47.564  1.00 39.83   6
ATOM    240  CE2  PHE A 293    22.112  29.819  46.930  1.00 46.21   6
ATOM    241  CZ   PHE A 293    22.430  31.146  47.153  1.00 45.18   6
ATOM    242  C    PHE A 293    24.979  27.772  50.164  1.00 45.54   6
ATOM    243  O    PHE A 293    24.686  28.576  51.034  1.00 42.01   8
ATOM    244  N    CYS A 294    24.426  26.572  50.062  1.00 47.05   7
ATOM    245  CA   CYS A 294    23.386  26.125  50.962  1.00 50.15   6
ATOM    246  CB   CYS A 294    22.944  24.733  50.524  1.00 45.90   6
ATOM    247  SG   CYS A 294    22.303  24.663  48.829  1.00 51.50  16
ATOM    248  C    CYS A 294    23.825  26.125  52.423  1.00 51.38   6
ATOM    249  O    CYS A 294    23.008  25.954  53.322  1.00 53.83   8
ATOM    250  N    GLU A 295    25.119  26.327  52.645  1.00 49.72   7
ATOM    251  CA   GLU A 295    25.666  26.384  53.996  1.00 52.53   6
ATOM    252  CB   GLU A 295    27.103  25.830  54.015  1.00 57.40   6
ATOM    253  CG   GLU A 295    27.182  24.309  54.061  1.00 69.63   6
ATOM    254  CD   GLU A 295    26.660  23.747  55.342  1.00 78.49   6
ATOM    255  OE1  GLU A 295    27.291  23.946  56.412  1.00 82.82   8
ATOM    256  OE2  GLU A 295    25.590  23.086  55.335  1.00 85.30   8
ATOM    257  C    GLU A 295    25.653  27.831  54.488  1.00 48.54   6
ATOM    258  O    GLU A 295    26.365  28.184  55.426  1.00 49.82   8
ATOM    259  N    LEU A 296    24.804  28.631  53.846  1.00 43.79   7
ATOM    260  CA   LEU A 296    24.670  30.034  54.159  1.00 45.42   6
ATOM    261  CB   LEU A 296    25.062  30.864  52.923  1.00 41.04   6
ATOM    262  CG   LEU A 296    26.438  30.658  52.315  1.00 42.74   6
ATOM    263  CD1  LEU A 296    26.447  31.030  50.861  1.00 40.99   6
ATOM    264  CD2  LEU A 296    27.437  31.454  53.086  1.00 39.44   6
ATOM    265  C    LEU A 296    23.239  30.366  54.548  1.00 45.56   6
ATOM    266  O    LEU A 296    22.301  29.660  54.148  1.00 43.07   8
ATOM    267  N    PRO A 297    23.050  31.405  55.365  1.00 46.99   7
ATOM    268  CD   PRO A 297    24.121  32.241  55.930  1.00 47.12   6
ATOM    269  CA   PRO A 297    21.700  31.811  55.787  1.00 49.61   6
ATOM    270  CB   PRO A 297    21.937  32.990  56.738  1.00 49.91   6
ATOM    271  CG   PRO A 297    23.401  33.155  56.872  1.00 51.28   6
ATOM    272  C    PRO A 297    20.864  32.212  54.558  1.00 49.39   6
ATOM    273  O    PRO A 297    21.402  32.684  53.556  1.00 51.66   8
ATOM    274  N    CYS A 298    19.545  32.035  54.655  1.00 51.02   7
ATOM    275  CA   CYS A 298    18.618  32.369  53.567  1.00 52.86   6
ATOM    276  CB   CYS A 298    17.201  31.877  53.915  1.00 54.57   6
ATOM    277  SG   CYS A 298    16.040  33.162  54.440  1.00 67.87  16
ATOM    278  C    CYS A 298    18.583  33.863  53.291  1.00 48.51   6
ATOM    279  O    CYS A 298    18.039  34.288  52.282  1.00 49.58   8
ATOM    280  N    GLU A 299    19.144  34.654  54.202  1.00 44.17   7
ATOM    281  CA   GLU A 299    19.179  36.096  54.016  1.00 47.57   6
ATOM    282  CB   GLU A 299    19.265  36.833  55.360  1.00 49.92   6
ATOM    283  CG   GLU A 299    17.931  36.996  56.125  1.00 59.30   6
ATOM    284  CD   GLU A 299    17.613  35.904  57.095  1.00 63.80   6
ATOM    285  OE1  GLU A 299    16.512  35.952  57.706  1.00 69.03   8
ATOM    286  OE2  GLU A 299    18.436  34.976  57.292  1.00 67.10   8
ATOM    287  C    GLU A 299    20.359  36.492  53.152  1.00 46.57   6
ATOM    288  O    GLU A 299    20.265  37.441  52.379  1.00 44.65   8
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    289  N    ASP A 300     21.467  35.765  53.294  1.00  45.17   7
ATOM    290  CA   ASP A 300     22.661  36.042  52.509  1.00  43.32   6
ATOM    291  CB   ASP A 300     23.919  35.513  53.213  1.00  37.38   6
ATOM    292  CG   ASP A 300     24.223  36.239  54.473  1.00  36.23   6
ATOM    293  OD1  ASP A 300     24.153  37.488  54.493  1.00  35.87   8
ATOM    294  OD2  ASP A 300     24.572  35.575  55.483  1.00  40.14   8
ATOM    295  C    ASP A 300     22.514  35.390  51.138  1.00  42.81   6
ATOM    296  O    ASP A 300     22.775  36.021  50.113  1.00  46.02   8
ATOM    297  N    GLN A 301     22.095  34.124  51.137  1.00  38.60   7
ATOM    298  CA   GLN A 301     21.896  33.390  49.902  1.00  40.00   6
ATOM    299  CB   GLN A 301     20.991  32.179  50.137  1.00  38.59   6
ATOM    300  CG   GLN A 301     21.644  31.003  50.808  1.00  40.26   6
ATOM    301  CD   GLN A 301     20.690  29.824  50.988  1.00  44.15   6
ATOM    302  OE1  GLN A 301     19.658  29.957  51.675  1.00  45.73   8
ATOM    303  NE2  GLN A 301     21.027  28.685  50.394  1.00  46.13   7
ATOM    304  C    GLN A 301     21.242  34.305  48.877  1.00  41.64   6
ATOM    305  O    GLN A 301     21.482  34.185  47.686  1.00  45.02   8
ATOM    306  N    ILE A 302     20.413  35.228  49.372  1.00  41.01   7
ATOM    307  CA   ILE A 302     19.726  36.179  48.511  1.00  40.23   6
ATOM    308  CB   ILE A 302     18.502  36.774  49.217  1.00  39.52   6
ATOM    309  CG2  ILE A 302     17.818  37.788  48.342  1.00  31.98   6
ATOM    310  CG1  ILE A 302     17.502  35.673  49.581  1.00  40.77   6
ATOM    311  CD1  ILE A 302     17.003  34.897  48.385  1.00  45.43   6
ATOM    312  C    ILE A 302     20.698  37.268  48.096  1.00  38.58   6
ATOM    313  O    ILE A 302     20.960  37.453  46.906  1.00  40.81   8
ATOM    314  N    ILE A 303     21.228  37.972  49.097  1.00  37.50   7
ATOM    315  CA   ILE A 303     22.179  39.060  48.874  1.00  39.33   6
ATOM    316  CB   ILE A 303     23.023  39.338  50.109  1.00  39.06   6
ATOM    317  CG2  ILE A 303     23.946  40.522  49.861  1.00  36.19   6
ATOM    318  CG1  ILE A 303     22.141  39.653  51.313  1.00  40.15   6
ATOM    319  CD1  ILE A 303     22.916  39.806  52.589  1.00  36.93   6
ATOM    320  C    ILE A 303     23.093  38.705  47.722  1.00  36.49   6
ATOM    321  O    ILE A 303     23.354  39.509  46.835  1.00  36.58   8
ATOM    322  N    LEU A 304     23.580  37.477  47.762  1.00  32.91   7
ATOM    323  CA   LEU A 304     24.465  36.964  46.734  1.00  27.55   6
ATOM    324  CB   LEU A 304     24.935  35.554  47.123  1.00  22.35   6
ATOM    325  CG   LEU A 304     26.150  35.480  48.029  1.00  26.88   6
ATOM    326  CD1  LEU A 304     26.267  36.731  48.876  1.00  24.82   6
ATOM    327  CD2  LEU A 304     26.084  34.226  48.861  1.00  23.69   6
ATOM    328  C    LEU A 304     23.764  36.968  45.389  1.00  28.05   6
ATOM    329  O    LEU A 304     24.212  37.623  44.443  1.00  24.68   8
ATOM    330  N    LEU A 305     22.657  36.236  45.318  1.00  26.34   7
ATOM    331  CA   LEU A 305     21.892  36.147  44.089  1.00  30.91   6
ATOM    332  CB   LEU A 305     20.565  35.434  44.359  1.00  32.50   6
ATOM    333  CG   LEU A 305     20.637  33.950  44.635  1.00  33.36   6
ATOM    334  CD1  LEU A 305     19.247  33.370  44.779  1.00  33.87   6
ATOM    335  CD2  LEU A 305     21.340  33.280  43.466  1.00  31.72   6
ATOM    336  C    LEU A 305     21.665  37.524  43.477  1.00  29.76   6
ATOM    337  O    LEU A 305     21.954  37.747  42.301  1.00  29.33   8
ATOM    338  N    LYS A 306     21.157  38.439  44.298  1.00  29.72   7
ATOM    339  CA   LYS A 306     20.868  39.800  43.864  1.00  34.28   6
ATOM    340  CB   LYS A 306     20.293  40.615  45.026  1.00  35.98   6
ATOM    341  CG   LYS A 306     18.919  40.163  45.511  1.00  43.35   6
ATOM    342  CD   LYS A 306     18.397  41.127  46.559  1.00  51.50   6
```

UNITED STATES PATENT AND TRADEMARK OFFICE
CERTIFICATE OF CORRECTION

| | |
|---|---|
| PATENT NO. | : 6,965,850 B2 |
| APPLICATION NO. | : 09/281717 |
| DATED | : November 15, 2005 |
| INVENTOR(S) | : John D. Baxter et al. |

It is certified that error appears in the above-identified patent and that said Letters Patent is hereby corrected as shown below:

```
ATOM    343  CE   LYS A 306     18.271  42.515  45.971  1.00  53.26     6
ATOM    344  NZ   LYS A 306     18.325  43.548  47.038  1.00  59.61     7
ATOM    345  C    LYS A 306     22.075  40.527  43.302  1.00  35.25     6
ATOM    346  O    LYS A 306     21.972  41.286  42.334  1.00  33.95     8
ATOM    347  N    GLY A 307     23.228  40.306  43.928  1.00  35.79     7
ATOM    348  CA   GLY A 307     24.445  40.962  43.482  1.00  34.59     6
ATOM    349  C    GLY A 307     25.109  40.353  42.259  1.00  33.80     6
ATOM    350  O    GLY A 307     25.489  41.087  41.344  1.00  31.59     8
ATOM    351  N    CYS A 308     25.248  39.024  42.256  1.00  31.15     7
ATOM    352  CA   CYS A 308     25.899  38.326  41.174  1.00  29.04     6
ATOM    353  CB   CYS A 308     26.604  37.089  41.704  1.00  27.59     6
ATOM    354  SG   CYS A 308     25.472  35.770  42.071  1.00  30.50    16
ATOM    355  C    CYS A 308     24.974  37.870  40.062  1.00  30.59     6
ATOM    356  O    CYS A 308     25.458  37.319  39.077  1.00  33.77     8
ATOM    357  N    CYS A 309     23.664  38.084  40.195  1.00  28.46     7
ATOM    358  CA   CYS A 309     22.739  37.623  39.168  1.00  30.10     6
ATOM    359  CB   CYS A 309     21.311  38.004  39.490  1.00  33.43     6
ATOM    360  SG   CYS A 309     20.198  37.299  38.307  1.00  35.20    16
ATOM    361  C    CYS A 309     23.065  38.123  37.788  1.00  27.72     6
ATOM    362  O    CYS A 309     23.212  37.334  36.865  1.00  27.69     8
ATOM    363  N    MET A 310     23.157  39.439  37.639  1.00  26.15     7
ATOM    364  CA   MET A 310     23.476  40.016  36.342  1.00  26.06     6
ATOM    365  CB   MET A 310     23.482  41.547  36.419  1.00  25.32     6
ATOM    366  CG   MET A 310     23.913  42.230  35.109  1.00  24.08     6
ATOM    367  SD   MET A 310     22.765  41.751  33.762  1.00  27.71    16
ATOM    368  CE   MET A 310     23.650  42.321  32.270  1.00  28.50     6
ATOM    369  C    MET A 310     24.842  39.527  35.908  1.00  25.94     6
ATOM    370  O    MET A 310     25.020  39.076  34.788  1.00  28.09     8
ATOM    371  N    GLU A 311     25.800  39.638  36.826  1.00  25.39     7
ATOM    372  CA   GLU A 311     27.176  39.234  36.589  1.00  27.03     6
ATOM    373  CB   GLU A 311     27.973  39.303  37.900  1.00  24.39     6
ATOM    374  CG   GLU A 311     27.842  40.628  38.668  1.00  26.00     6
ATOM    375  CD   GLU A 311     28.726  40.720  39.870  1.00  23.95     6
ATOM    376  OE1  GLU A 311     28.891  39.706  40.588  1.00  19.72     8
ATOM    377  OE2  GLU A 311     29.270  41.818  40.159  1.00  26.51     8
ATOM    378  C    GLU A 311     27.266  37.827  35.997  1.00  27.51     6
ATOM    379  O    GLU A 311     27.956  37.620  35.014  1.00  29.67     8
ATOM    380  N    ILE A 312     26.569  36.866  36.602  1.00  26.82     7
ATOM    381  CA   ILE A 312     26.593  35.497  36.112  1.00  25.71     6
ATOM    382  CB   ILE A 312     25.991  34.518  37.123  1.00  23.35     6
ATOM    383  CG2  ILE A 312     25.917  33.123  36.533  1.00  20.27     6
ATOM    384  CG1  ILE A 312     26.837  34.471  38.398  1.00  20.88     6
ATOM    385  CD1  ILE A 312     26.462  33.342  39.341  1.00  18.15     6
ATOM    386  C    ILE A 312     25.871  35.371  34.791  1.00  27.91     6
ATOM    387  O    ILE A 312     26.274  34.593  33.934  1.00  28.96     8
ATOM    388  N    MET A 313     24.788  36.130  34.633  1.00  27.66     7
ATOM    389  CA   MET A 313     24.013  36.081  33.395  1.00  30.18     6
ATOM    390  CB   MET A 313     22.716  36.888  33.508  1.00  36.89     6
ATOM    391  CG   MET A 313     21.608  36.198  34.305  1.00  37.95     6
ATOM    392  SD   MET A 313     19.892  36.817  34.055  1.00  42.38    16
ATOM    393  CE   MET A 313     20.034  38.503  34.740  1.00  40.68     6
ATOM    394  C    MET A 313     24.834  36.579  32.222  1.00  27.43     6
ATOM    395  O    MET A 313     25.116  35.814  31.308  1.00  28.61     8
ATOM    396  N    SER A 314     25.209  37.859  32.253  1.00  24.88     7
```

UNITED STATES PATENT AND TRADEMARK OFFICE
CERTIFICATE OF CORRECTION

| | |
|---|---|
| PATENT NO. | : 6,965,850 B2 |
| APPLICATION NO. | : 09/281717 |
| DATED | : November 15, 2005 |
| INVENTOR(S) | : John D. Baxter et al. |

It is certified that error appears in the above-identified patent and that said Letters Patent is hereby corrected as shown below:

```
ATOM    397  CA    SER A 314      26.005  38.472  31.197  1.00 27.98     6
ATOM    398  CB    SER A 314      26.354  39.914  31.581  1.00 29.64     6
ATOM    399  OG    SER A 314      26.956  39.972  32.858  1.00 43.44     8
ATOM    400  C     SER A 314      27.275  37.679  30.851  1.00 22.30     6
ATOM    401  O     SER A 314      27.675  37.629  29.690  1.00 24.18     8
ATOM    402  N     LEU A 315      27.905  37.048  31.845  1.00 23.99     7
ATOM    403  CA    LEU A 315      29.099  36.261  31.563  1.00 25.07     6
ATOM    404  CB    LEU A 315      29.685  35.593  32.816  1.00 19.11     6
ATOM    405  CG    LEU A 315      30.675  34.479  32.505  1.00 20.39     6
ATOM    406  CD1   LEU A 315      31.866  35.040  31.756  1.00 18.92     6
ATOM    407  CD2   LEU A 315      31.125  33.789  33.765  1.00 12.93     6
ATOM    408  C     LEU A 315      28.700  35.180  30.597  1.00 24.53     6
ATOM    409  O     LEU A 315      29.304  35.036  29.556  1.00 26.32     8
ATOM    410  N     ARG A 316      27.678  34.426  30.982  1.00 28.18     7
ATOM    411  CA    ARG A 316      27.151  33.312  30.216  1.00 27.54     6
ATOM    412  CB    ARG A 316      25.915  32.752  30.928  1.00 27.39     6
ATOM    413  CG    ARG A 316      26.188  32.190  32.336  1.00 22.00     6
ATOM    414  CD    ARG A 316      24.934  31.526  32.901  1.00 18.78     6
ATOM    415  NE    ARG A 316      25.245  30.376  33.721  1.00 26.57     7
ATOM    416  CZ    ARG A 316      24.341  29.468  34.054  1.00 30.81     6
ATOM    417  NH1   ARG A 316      23.084  29.614  33.639  1.00 33.71     7
ATOM    418  NH2   ARG A 316      24.701  28.416  34.776  1.00 33.13     7
ATOM    419  C     ARG A 316      26.774  33.660  28.794  1.00 28.09     6
ATOM    420  O     ARG A 316      26.737  32.792  27.931  1.00 32.41     8
ATOM    421  N     ALA A 317      26.484  34.936  28.571  1.00 28.36     7
ATOM    422  CA    ALA A 317      26.094  35.411  27.264  1.00 26.64     6
ATOM    423  CB    ALA A 317      25.232  36.666  27.418  1.00 22.93     6
ATOM    424  C     ALA A 317      27.323  35.714  26.417  1.00 28.35     6
ATOM    425  O     ALA A 317      27.398  35.342  25.252  1.00 32.10     8
ATOM    426  N     ALA A 318      28.286  36.396  27.026  1.00 29.12     7
ATOM    427  CA    ALA A 318      29.515  36.760  26.350  1.00 27.50     6
ATOM    428  CB    ALA A 318      30.434  37.452  27.333  1.00 28.39     6
ATOM    429  C     ALA A 318      30.181  35.502  25.825  1.00 28.10     6
ATOM    430  O     ALA A 318      30.600  35.447  24.678  1.00 28.18     8
ATOM    431  N     VAL A 319      30.255  34.491  26.700  1.00 29.16     7
ATOM    432  CA    VAL A 319      30.880  33.198  26.393  1.00 35.24     6
ATOM    433  CB    VAL A 319      30.703  32.210  27.547  1.00 27.34     6
ATOM    434  CG1   VAL A 319      30.895  32.891  28.858  1.00 29.96     6
ATOM    435  CG2   VAL A 319      29.353  31.552  27.482  1.00 31.70     6
ATOM    436  C     VAL A 319      30.215  32.608  25.165  1.00 40.01     6
ATOM    437  O     VAL A 319      30.640  31.575  24.680  1.00 42.70     8
ATOM    438  N     ARG A 320      29.176  33.284  24.683  1.00 38.64     7
ATOM    439  CA    ARG A 320      28.415  32.822  23.545  1.00 38.61     6
ATOM    440  CB    ARG A 320      27.031  32.458  24.043  1.00 37.26     6
ATOM    441  CG    ARG A 320      26.863  30.991  24.192  1.00 43.12     6
ATOM    442  CD    ARG A 320      25.637  30.642  25.014  1.00 50.79     6
ATOM    443  NE    ARG A 320      25.258  29.256  24.770  1.00 54.71     7
ATOM    444  CZ    ARG A 320      24.331  28.625  25.501  1.00 57.89     6
ATOM    445  NH1   ARG A 320      23.667  29.291  26.440  1.00 49.08     7
ATOM    446  NH2   ARG A 320      23.964  27.385  25.242  1.00 59.59     7
ATOM    447  C     ARG A 320      28.292  33.825  22.405  1.00 42.14     6
ATOM    448  O     ARG A 320      27.251  33.909  21.748  1.00 46.30     8
ATOM    449  N     TYR A 321      29.352  34.583  22.173  1.00 42.04     7
ATOM    450  CA    TYR A 321      29.366  35.555  21.098  1.00 42.70     6
```

UNITED STATES PATENT AND TRADEMARK OFFICE
CERTIFICATE OF CORRECTION

| | |
|---|---|
| PATENT NO. | : 6,965,850 B2 |
| APPLICATION NO. | : 09/281717 |
| DATED | : November 15, 2005 |
| INVENTOR(S) | : John D. Baxter et al. |

It is certified that error appears in the above-identified patent and that said Letters Patent is hereby corrected as shown below:

```
ATOM    451  CB   TYR A 321    30.083  36.810  21.575  1.00 38.01   6
ATOM    452  CG   TYR A 321    30.601  37.650  20.448  1.00 37.94   6
ATOM    453  CD1  TYR A 321    29.733  38.296  19.574  1.00 33.85   6
ATOM    454  CE1  TYR A 321    30.235  39.037  18.494  1.00 34.49   6
ATOM    455  CD2  TYR A 321    31.966  37.743  20.224  1.00 28.03   6
ATOM    456  CE2  TYR A 321    32.473  38.475  19.153  1.00 32.69   6
ATOM    457  CZ   TYR A 321    31.612  39.125  18.276  1.00 35.18   6
ATOM    458  OH   TYR A 321    32.107  39.866  17.223  1.00 39.48   8
ATOM    459  C    TYR A 321    30.086  35.005  19.877  1.00 45.51   6
ATOM    460  O    TYR A 321    31.261  34.697  19.951  1.00 48.02   8
ATOM    461  N    ASP A 322    29.354  34.879  18.773  1.00 44.56   7
ATOM    462  CA   ASP A 322    29.912  34.400  17.502  1.00 45.86   6
ATOM    463  CB   ASP A 322    28.804  33.670  16.736  1.00 46.64   6
ATOM    464  CG   ASP A 322    29.050  33.608  15.255  1.00 40.00   6
ATOM    465  OD1  ASP A 322    30.010  34.256  14.768  1.00 40.00   8
ATOM    466  OD2  ASP A 322    28.262  32.929  14.536  1.00 40.00   8
ATOM    467  C    ASP A 322    30.460  35.629  16.755  1.00 45.82   6
ATOM    468  O    ASP A 322    29.678  36.464  16.271  1.00 45.38   8
ATOM    469  N    PRO A 323    31.800  35.735  16.584  1.00 46.53   7
ATOM    470  CD   PRO A 323    32.774  34.719  16.991  1.00 47.16   6
ATOM    471  CA   PRO A 323    32.424  36.889  15.890  1.00 46.63   6
ATOM    472  CB   PRO A 323    33.921  36.603  15.936  1.00 43.95   6
ATOM    473  CG   PRO A 323    34.099  35.303  16.582  1.00 43.93   6
ATOM    474  C    PRO A 323    31.953  37.087  14.453  1.00 48.34   6
ATOM    475  O    PRO A 323    31.797  38.210  13.960  1.00 50.84   8
ATOM    476  N    GLU A 324    31.778  35.970  13.752  1.00 52.39   7
ATOM    477  CA   GLU A 324    31.339  35.968  12.370  1.00 55.85   6
ATOM    478  CB   GLU A 324    31.035  34.528  11.965  1.00 55.54   6
ATOM    479  CG   GLU A 324    32.224  33.584  12.104  1.00 40.00   6
ATOM    480  CD   GLU A 324    33.432  34.023  11.310  1.00 40.00   6
ATOM    481  OE1  GLU A 324    33.350  35.040  10.555  1.00 40.00   8
ATOM    482  OE2  GLU A 324    34.506  33.356  11.415  1.00 40.00   8
ATOM    483  C    GLU A 324    30.077  36.798  12.277  1.00 54.94   6
ATOM    484  O    GLU A 324    30.070  37.892  11.730  1.00 59.81   8
ATOM    485  N    SER A 325    29.009  36.212  12.810  1.00 52.95   7
ATOM    486  CA   SER A 325    27.695  36.812  12.839  1.00 50.10   6
ATOM    487  CB   SER A 325    26.701  35.797  13.402  1.00 48.23   6
ATOM    488  OG   SER A 325    27.183  35.239  14.615  1.00 48.71   8
ATOM    489  C    SER A 325    27.651  38.093  13.659  1.00 50.61   6
ATOM    490  O    SER A 325    26.885  38.992  13.354  1.00 52.19   8
ATOM    491  N    GLU A 326    28.495  38.168  14.687  1.00 45.64   7
ATOM    492  CA   GLU A 326    28.567  39.341  15.546  1.00 43.35   6
ATOM    493  CB   GLU A 326    28.830  40.608  14.711  1.00 42.74   6
ATOM    494  CG   GLU A 326    30.148  40.606  13.945  1.00 50.32   6
ATOM    495  CD   GLU A 326    30.451  41.925  13.313  1.00 56.34   6
ATOM    496  OE1  GLU A 326    31.509  42.046  12.649  1.00 59.31   8
ATOM    497  OE2  GLU A 326    29.656  42.890  13.452  1.00 55.74   8
ATOM    498  C    GLU A 326    27.288  39.526  16.340  1.00 40.23   6
ATOM    499  O    GLU A 326    26.695  40.603  16.340  1.00 40.44   8
ATOM    500  N    THR A 327    26.888  38.474  17.051  1.00 35.90   7
ATOM    501  CA   THR A 327    25.663  38.506  17.860  1.00 37.29   6
ATOM    502  CB   THR A 327    24.466  38.057  17.024  1.00 37.63   6
ATOM    503  OG1  THR A 327    24.661  36.709  16.580  1.00 38.12   8
ATOM    504  CG2  THR A 327    24.269  38.965  15.810  1.00 39.90   6
```

UNITED STATES PATENT AND TRADEMARK OFFICE
CERTIFICATE OF CORRECTION

| | |
|---|---|
| PATENT NO. | : 6,965,850 B2 |
| APPLICATION NO. | : 09/281717 |
| DATED | : November 15, 2005 |
| INVENTOR(S) | : John D. Baxter et al. |

It is certified that error appears in the above-identified patent and that said Letters Patent is hereby corrected as shown below:

```
ATOM    505  C    THR A 327    25.767  37.562  19.038  1.00  39.49   6
ATOM    506  O    THR A 327    26.284  36.438  18.903  1.00  40.50   8
ATOM    507  N    LEU A 328    25.250  37.987  20.184  1.00  36.64   7
ATOM    508  CA   LEU A 328    25.264  37.141  21.381  1.00  37.73   6
ATOM    509  CB   LEU A 328    25.148  37.999  22.650  1.00  37.78   6
ATOM    510  CG   LEU A 328    26.102  39.150  22.843  1.00  36.26   6
ATOM    511  CD1  LEU A 328    26.066  39.623  24.272  1.00  36.56   6
ATOM    512  CD2  LEU A 328    27.481  38.688  22.500  1.00  39.85   6
ATOM    513  C    LEU A 328    24.063  36.220  21.244  1.00  37.27   6
ATOM    514  O    LEU A 328    23.306  36.337  20.279  1.00  34.96   8
ATOM    515  N    THR A 329    23.891  35.317  22.205  1.00  39.73   7
ATOM    516  CA   THR A 329    22.785  34.376  22.180  1.00  40.81   6
ATOM    517  CB   THR A 329    23.241  32.991  21.699  1.00  42.67   6
ATOM    518  OG1  THR A 329    23.879  33.103  20.421  1.00  42.52   8
ATOM    519  CG2  THR A 329    22.026  32.057  21.589  1.00  43.52   6
ATOM    520  C    THR A 329    22.168  34.245  23.548  1.00  44.31   6
ATOM    521  O    THR A 329    22.526  33.370  24.320  1.00  43.72   8
ATOM    522  N    LEU A 330    21.237  35.149  23.830  1.00  44.62   7
ATOM    523  CA   LEU A 330    20.532  35.170  25.111  1.00  45.09   6
ATOM    524  CB   LEU A 330    19.677  36.444  25.195  1.00  44.66   6
ATOM    525  CG   LEU A 330    20.436  37.750  25.259  1.00  51.06   6
ATOM    526  CD1  LEU A 330    21.405  37.831  24.104  1.00  48.58   6
ATOM    527  CD2  LEU A 330    19.466  38.909  25.238  1.00  45.18   6
ATOM    528  C    LEU A 330    19.656  33.919  25.301  1.00  48.06   6
ATOM    529  O    LEU A 330    19.049  33.422  24.359  1.00  49.33   8
ATOM    530  N    ASN A 331    19.618  33.431  26.540  1.00  52.20   7
ATOM    531  CA   ASN A 331    18.842  32.256  26.913  1.00  54.41   6
ATOM    532  CB   ASN A 331    17.361  32.628  27.009  1.00  54.94   6
ATOM    533  CG   ASN A 331    16.724  32.112  28.269  1.00  60.35   6
ATOM    534  OD1  ASN A 331    17.124  32.505  29.383  1.00  61.84   8
ATOM    535  ND2  ASN A 331    15.750  31.238  28.117  1.00  65.92   7
ATOM    536  C    ASN A 331    19.016  31.108  25.934  1.00  58.00   6
ATOM    537  O    ASN A 331    18.243  30.157  25.941  1.00  60.17   8
ATOM    538  N    GLY A 332    20.063  31.196  25.114  1.00  58.45   7
ATOM    539  CA   GLY A 332    20.341  30.161  24.131  1.00  58.55   6
ATOM    540  C    GLY A 332    19.316  30.016  23.021  1.00  59.79   6
ATOM    541  O    GLY A 332    19.413  29.094  22.213  1.00  61.32   8
ATOM    542  N    GLU A 333    18.346  30.929  22.983  1.00  60.28   7
ATOM    543  CA   GLU A 333    17.294  30.883  21.985  1.00  59.13   6
ATOM    544  CB   GLU A 333    15.919  30.875  22.662  1.00  62.40   6
ATOM    545  CG   GLU A 333    15.667  29.750  23.658  1.00  75.69   6
ATOM    546  CD   GLU A 333    14.341  29.865  24.346  1.00  80.41   6
ATOM    547  OE1  GLU A 333    14.052  30.932  24.945  1.00  79.98   8
ATOM    548  OE2  GLU A 333    13.549  28.884  24.329  1.00  83.81   8
ATOM    549  C    GLU A 333    17.356  32.090  21.073  1.00  57.18   6
ATOM    550  O    GLU A 333    17.239  31.969  19.852  1.00  57.50   8
ATOM    551  N    MET A 334    17.512  33.258  21.696  1.00  55.20   7
ATOM    552  CA   MET A 334    17.561  34.529  20.980  1.00  50.85   6
ATOM    553  CB   MET A 334    16.751  35.556  21.763  1.00  48.70   6
ATOM    554  CG   MET A 334    16.859  36.947  21.212  1.00  45.39   6
ATOM    555  SD   MET A 334    15.881  38.186  22.127  1.00  44.56  16
ATOM    556  CE   MET A 334    14.229  37.371  22.113  1.00  45.25   6
ATOM    557  C    MET A 334    18.956  35.087  20.713  1.00  51.59   6
ATOM    558  O    MET A 334    19.739  35.268  21.633  1.00  52.52   8
```

UNITED STATES PATENT AND TRADEMARK OFFICE
CERTIFICATE OF CORRECTION

| | |
|---|---|
| PATENT NO. | : 6,965,850 B2 |
| APPLICATION NO. | : 09/281717 |
| DATED | : November 15, 2005 |
| INVENTOR(S) | : John D. Baxter et al. |

It is certified that error appears in the above-identified patent and that said Letters Patent is hereby corrected as shown below:

```
ATOM    559  N    ALA A 335      19.234  35.371  19.444  1.00 51.00      7
ATOM    560  CA   ALA A 335      20.520  35.932  19.039  1.00 48.98      6
ATOM    561  CB   ALA A 335      20.997  35.254  17.768  1.00 47.86      6
ATOM    562  C    ALA A 335      20.342  37.420  18.805  1.00 51.01      6
ATOM    563  O    ALA A 335      19.594  37.830  17.919  1.00 51.61      8
ATOM    564  N    VAL A 336      21.024  38.232  19.612  1.00 46.62      7
ATOM    565  CA   VAL A 336      20.910  39.699  19.502  1.00 42.35      6
ATOM    566  CB   VAL A 336      20.517  40.325  20.840  1.00 42.41      6
ATOM    567  CG1  VAL A 336      19.242  39.691  21.361  1.00 42.00      6
ATOM    568  CG2  VAL A 336      21.639  40.211  21.852  1.00 40.32      6
ATOM    569  C    VAL A 336      22.204  40.321  19.036  1.00 45.33      6
ATOM    570  O    VAL A 336      23.263  39.691  19.025  1.00 47.42      8
ATOM    571  N    THR A 337      22.090  41.590  18.668  1.00 41.60      7
ATOM    572  CA   THR A 337      23.230  42.377  18.175  1.00 39.69      6
ATOM    573  CB   THR A 337      22.882  43.061  16.852  1.00 41.35      6
ATOM    574  OG1  THR A 337      21.987  44.157  17.080  1.00 49.35      8
ATOM    575  CG2  THR A 337      22.216  42.067  15.904  1.00 40.38      6
ATOM    576  C    THR A 337      23.588  43.481  19.159  1.00 37.88      6
ATOM    577  O    THR A 337      22.734  43.989  19.892  1.00 34.06      8
ATOM    578  N    ARG A 338      24.865  43.849  19.138  1.00 37.61      7
ATOM    579  CA   ARG A 338      25.388  44.919  19.984  1.00 38.68      6
ATOM    580  CB   ARG A 338      26.669  45.479  19.351  1.00 35.95      6
ATOM    581  CG   ARG A 338      27.250  46.713  20.038  1.00 38.83      6
ATOM    582  CD   ARG A 338      28.443  47.254  19.247  1.00 35.88      6
ATOM    583  NE   ARG A 338      29.559  46.320  19.175  1.00 37.42      7
ATOM    584  CZ   ARG A 338      30.449  46.122  20.145  1.00 30.20      6
ATOM    585  NH1  ARG A 338      30.338  46.791  21.295  1.00 27.98      7
ATOM    586  NH2  ARG A 338      31.433  45.240  19.954  1.00 27.40      7
ATOM    587  C    ARG A 338      24.333  46.010  20.085  1.00 38.09      6
ATOM    588  O    ARG A 338      23.894  46.397  21.169  1.00 34.12      8
ATOM    589  N    GLY A 339      23.915  46.496  18.922  1.00 41.25      7
ATOM    590  CA   GLY A 339      22.918  47.547  18.890  1.00 41.35      6
ATOM    591  C    GLY A 339      21.692  47.140  19.672  1.00 41.23      6
ATOM    592  O    GLY A 339      21.445  47.671  20.750  1.00 38.30      8
ATOM    593  N    GLN A 340      20.924  46.203  19.105  1.00 38.58      7
ATOM    594  CA   GLN A 340      19.701  45.700  19.729  1.00 40.79      6
ATOM    595  CB   GLN A 340      19.436  44.260  19.253  1.00 40.82      6
ATOM    596  CG   GLN A 340      19.087  44.146  17.767  1.00 41.10      6
ATOM    597  CD   GLN A 340      18.876  42.705  17.305  1.00 48.84      6
ATOM    598  OE1  GLN A 340      19.826  41.888  17.309  1.00 50.53      8
ATOM    599  NE2  GLN A 340      17.650  42.393  16.907  1.00 54.25      7
ATOM    600  C    GLN A 340      19.779  45.750  21.263  1.00 41.50      6
ATOM    601  O    GLN A 340      18.998  46.444  21.923  1.00 42.72      8
ATOM    602  N    LEU A 341      20.758  45.026  21.806  1.00 42.00      7
ATOM    603  CA   LEU A 341      20.952  44.947  23.243  1.00 38.10      6
ATOM    604  CB   LEU A 341      22.209  44.145  23.575  1.00 36.66      6
ATOM    605  CG   LEU A 341      22.361  43.804  25.029  1.00 39.94      6
ATOM    606  CD1  LEU A 341      21.219  42.884  25.410  1.00 34.98      6
ATOM    607  CD2  LEU A 341      23.685  43.128  25.284  1.00 40.95      6
ATOM    608  C    LEU A 341      21.072  46.321  23.860  1.00 36.37      6
ATOM    609  O    LEU A 341      20.484  46.588  24.892  1.00 37.89      8
ATOM    610  N    LYS A 342      21.848  47.184  23.209  1.00 33.29      7
ATOM    611  CA   LYS A 342      22.089  48.546  23.679  1.00 35.17      6
ATOM    612  CB   LYS A 342      23.057  49.242  22.721  1.00 34.97      6
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    613  CG   LYS A 342     23.655  50.536  23.240  1.00 40.00    6
ATOM    614  CD   LYS A 342     24.673  51.109  22.245  1.00 34.48    6
ATOM    615  CE   LYS A 342     25.514  52.229  22.873  1.00 37.54    6
ATOM    616  NZ   LYS A 342     26.655  52.634  21.987  1.00 42.32    7
ATOM    617  C    LYS A 342     20.796  49.349  23.774  1.00 38.29    8
ATOM    618  O    LYS A 342     20.345  49.711  24.861  1.00 36.23    8
ATOM    619  N    ASN A 343     20.223  49.622  22.603  1.00 39.25    7
ATOM    620  CA   ASN A 343     18.993  50.385  22.485  1.00 40.19    6
ATOM    621  CB   ASN A 343     18.521  50.373  21.033  1.00 37.96    6
ATOM    622  CG   ASN A 343     19.664  50.550  20.052  1.00 39.22    6
ATOM    623  OD1  ASN A 343     20.428  51.537  20.125  1.00 42.37    8
ATOM    624  ND2  ASN A 343     19.773  49.612  19.125  1.00 42.19    7
ATOM    625  C    ASN A 343     17.928  49.748  23.375  1.00 40.12    6
ATOM    626  O    ASN A 343     17.010  50.417  23.859  1.00 36.01    8
ATOM    627  N    GLY A 344     18.073  48.433  23.568  1.00 40.95    7
ATOM    628  CA   GLY A 344     17.152  47.670  24.394  1.00 39.25    6
ATOM    629  C    GLY A 344     17.039  48.092  25.842  1.00 38.26    6
ATOM    630  O    GLY A 344     16.072  47.724  26.512  1.00 35.69    8
ATOM    631  N    GLY A 345     18.017  48.857  26.329  1.00 35.89    7
ATOM    632  CA   GLY A 345     17.964  49.301  27.706  1.00 34.00    6
ATOM    633  C    GLY A 345     19.273  49.199  28.443  1.00 38.64    6
ATOM    634  O    GLY A 345     19.469  49.888  29.441  1.00 38.14    8
ATOM    635  N    LEU A 346     20.170  48.337  27.973  1.00 39.52    7
ATOM    636  CA   LEU A 346     21.444  48.180  28.649  1.00 36.05    6
ATOM    637  CB   LEU A 346     22.124  46.876  28.209  1.00 35.72    6
ATOM    638  CG   LEU A 346     21.355  45.617  28.501  1.00 34.89    6
ATOM    639  CD1  LEU A 346     22.295  44.413  28.422  1.00 44.09    6
ATOM    640  CD2  LEU A 346     20.786  45.721  29.902  1.00 34.84    6
ATOM    641  C    LEU A 346     22.358  49.361  28.396  1.00 33.52    6
ATOM    642  O    LEU A 346     23.267  49.653  29.178  1.00 35.58    8
ATOM    643  N    GLY A 347     22.087  50.056  27.295  1.00 30.47    7
ATOM    644  CA   GLY A 347     22.909  51.192  26.931  1.00 33.01    6
ATOM    645  C    GLY A 347     24.360  50.768  26.747  1.00 30.72    6
ATOM    646  O    GLY A 347     24.669  49.775  26.082  1.00 30.89    8
ATOM    647  N    VAL A 348     25.244  51.556  27.355  1.00 31.30    7
ATOM    648  CA   VAL A 348     26.671  51.325  27.286  1.00 31.27    6
ATOM    649  CB   VAL A 348     27.441  52.294  28.184  1.00 31.66    6
ATOM    650  CG1  VAL A 348     27.067  52.107  29.631  1.00 20.19    6
ATOM    651  CG2  VAL A 348     28.931  52.138  27.986  1.00 24.77    6
ATOM    652  C    VAL A 348     27.063  49.892  27.678  1.00 33.84    6
ATOM    653  O    VAL A 348     28.095  49.392  27.229  1.00 29.99    8
ATOM    654  N    VAL A 349     26.253  49.227  28.514  1.00 33.31    7
ATOM    655  CA   VAL A 349     26.568  47.881  28.906  1.00 32.23    6
ATOM    656  CB   VAL A 349     25.581  47.259  29.858  1.00 32.59    6
ATOM    657  CG1  VAL A 349     25.865  45.795  29.985  1.00 33.68    6
ATOM    658  CG2  VAL A 349     25.687  47.899  31.213  1.00 32.30    6
ATOM    659  C    VAL A 349     26.706  46.985  27.726  1.00 34.91    6
ATOM    660  O    VAL A 349     27.583  46.136  27.735  1.00 33.73    8
ATOM    661  N    SER A 350     25.875  47.134  26.702  1.00 32.81    7
ATOM    662  CA   SER A 350     26.001  46.252  25.556  1.00 30.10    6
ATOM    663  CB   SER A 350     25.119  46.665  24.411  1.00 24.95    6
ATOM    664  OG   SER A 350     25.209  45.675  23.394  1.00 23.16    8
ATOM    665  C    SER A 350     27.445  46.257  25.129  1.00 31.59    6
ATOM    666  O    SER A 350     28.116  45.244  25.284  1.00 37.62    8
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    667  N    ASP A 351    27.945  47.367  24.591  1.00 28.60   7
ATOM    668  CA   ASP A 351    29.351  47.437  24.183  1.00 29.82   6
ATOM    669  CB   ASP A 351    29.808  48.891  24.105  1.00 27.49   6
ATOM    670  CG   ASP A 351    28.875  49.744  23.303  1.00 30.22   6
ATOM    671  OD1  ASP A 351    28.055  50.483  23.909  1.00 32.61   8
ATOM    672  OD2  ASP A 351    28.942  49.714  22.044  1.00 30.02   8
ATOM    673  C    ASP A 351    30.173  46.653  25.231  1.00 30.63   6
ATOM    674  O    ASP A 351    30.981  45.792  24.903  1.00 29.54   8
ATOM    675  N    ALA A 352    29.939  46.949  26.503  1.00 25.33   7
ATOM    676  CA   ALA A 352    30.623  46.280  27.602  1.00 28.59   6
ATOM    677  CB   ALA A 352    30.072  46.799  28.922  1.00 20.95   6
ATOM    678  C    ALA A 352    30.492  44.756  27.527  1.00 29.69   6
ATOM    679  O    ALA A 352    31.481  44.054  27.587  1.00 30.36   8
ATOM    680  N    ILE A 353    29.260  44.260  27.413  1.00 27.63   7
ATOM    681  CA   ILE A 353    29.003  42.832  27.326  1.00 27.55   6
ATOM    682  CB   ILE A 353    27.512  42.528  27.429  1.00 28.04   6
ATOM    683  CG2  ILE A 353    27.269  41.042  27.289  1.00 23.68   6
ATOM    684  CG1  ILE A 353    26.955  42.965  28.789  1.00 27.33   6
ATOM    685  CD1  ILE A 353    25.452  42.688  28.944  1.00 26.23   6
ATOM    686  C    ILE A 353    29.534  42.207  26.054  1.00 30.88   6
ATOM    687  O    ILE A 353    30.007  41.076  26.068  1.00 31.22   8
ATOM    688  N    PHE A 354    29.426  42.917  24.939  1.00 29.86   7
ATOM    689  CA   PHE A 354    29.922  42.369  23.686  1.00 31.08   6
ATOM    690  CB   PHE A 354    29.371  43.146  22.487  1.00 28.80   6
ATOM    691  CG   PHE A 354    28.029  42.643  21.988  1.00 28.80   6
ATOM    692  CD1  PHE A 354    26.872  42.842  22.724  1.00 30.96   6
ATOM    693  CD2  PHE A 354    27.950  41.953  20.783  1.00 29.45   6
ATOM    694  CE1  PHE A 354    25.657  42.360  22.250  1.00 27.12   6
ATOM    695  CE2  PHE A 354    26.738  41.470  20.305  1.00 25.19   6
ATOM    696  CZ   PHE A 354    25.590  41.672  21.038  1.00 28.09   6
ATOM    697  C    PHE A 354    31.444  42.399  23.682  1.00 29.17   6
ATOM    698  O    PHE A 354    32.087  41.389  23.398  1.00 32.62   8
ATOM    699  N    ASP A 355    32.013  43.569  23.980  1.00 23.86   7
ATOM    700  CA   ASP A 355    33.466  43.739  24.030  1.00 25.34   6
ATOM    701  CB   ASP A 355    33.820  45.053  24.737  1.00 21.41   6
ATOM    702  CG   ASP A 355    33.841  46.226  23.809  1.00 32.08   6
ATOM    703  OD1  ASP A 355    32.979  46.322  22.902  1.00 33.58   8
ATOM    704  OD2  ASP A 355    34.711  47.117  23.968  1.00 33.20   8
ATOM    705  C    ASP A 355    34.074  42.559  24.781  1.00 27.86   6
ATOM    706  O    ASP A 355    35.131  42.053  24.410  1.00 32.42   8
ATOM    707  N    LEU A 356    33.387  42.128  25.843  1.00 26.84   7
ATOM    708  CA   LEU A 356    33.845  40.993  26.642  1.00 28.66   6
ATOM    709  CB   LEU A 356    32.893  40.747  27.825  1.00 25.37   6
ATOM    710  CG   LEU A 356    33.235  39.608  28.755  1.00 27.61   6
ATOM    711  CD1  LEU A 356    34.538  39.917  29.451  1.00 25.43   6
ATOM    712  CD2  LEU A 356    32.149  39.414  29.765  1.00 27.49   6
ATOM    713  C    LEU A 356    33.849  39.779  25.723  1.00 30.44   6
ATOM    714  O    LEU A 356    34.884  39.160  25.470  1.00 31.55   8
ATOM    715  N    GLY A 357    32.661  39.451  25.218  1.00 32.69   7
ATOM    716  CA   GLY A 357    32.511  38.304  24.338  1.00 29.87   6
ATOM    717  C    GLY A 357    33.653  38.157  23.359  1.00 33.12   6
ATOM    718  O    GLY A 357    34.302  37.110  23.323  1.00 29.41   8
ATOM    719  N    MET A 358    33.876  39.206  22.564  1.00 33.31   7
ATOM    720  CA   MET A 358    34.949  39.206  21.580  1.00 35.87   6
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    721  CB   MET A 358    35.143  40.606  21.009  1.00  34.56   6
ATOM    722  CG   MET A 358    33.949  41.145  20.290  1.00  46.43   6
ATOM    723  SD   MET A 358    34.207  42.776  19.514  1.00  42.13  16
ATOM    724  CE   MET A 358    34.507  43.855  20.994  1.00  44.29   6
ATOM    725  C    MET A 358    36.256  38.762  22.230  1.00  33.26   6
ATOM    726  O    MET A 358    36.894  37.807  21.795  1.00  36.39   8
ATOM    727  N    SER A 359    36.637  39.491  23.281  1.00  33.31   7
ATOM    728  CA   SER A 359    37.860  39.226  24.019  1.00  34.39   6
ATOM    729  CB   SER A 359    37.869  40.067  25.295  1.00  30.84   6
ATOM    730  OG   SER A 359    39.135  40.008  25.930  1.00  47.14   8
ATOM    731  C    SER A 359    37.984  37.748  24.357  1.00  36.43   6
ATOM    732  O    SER A 359    38.900  37.078  23.896  1.00  35.46   8
ATOM    733  N    LEU A 360    37.046  37.264  25.166  1.00  36.74   7
ATOM    734  CA   LEU A 360    37.017  35.875  25.604  1.00  35.44   6
ATOM    735  CB   LEU A 360    35.708  35.579  26.336  1.00  34.16   6
ATOM    736  CG   LEU A 360    35.471  36.290  27.644  1.00  34.59   6
ATOM    737  CD1  LEU A 360    34.225  35.765  28.312  1.00  33.53   6
ATOM    738  CD2  LEU A 360    36.658  36.052  28.541  1.00  31.69   6
ATOM    739  C    LEU A 360    37.203  34.862  24.500  1.00  38.72   6
ATOM    740  O    LEU A 360    37.820  33.828  24.728  1.00  38.29   8
ATOM    741  N    SER A 361    36.635  35.147  23.328  1.00  40.96   7
ATOM    742  CA   SER A 361    36.777  34.262  22.186  1.00  45.67   6
ATOM    743  CB   SER A 361    36.518  35.045  20.904  1.00  46.45   6
ATOM    744  OG   SER A 361    35.210  35.598  20.906  1.00  51.81   8
ATOM    745  C    SER A 361    38.166  33.627  22.145  1.00  44.49   6
ATOM    746  O    SER A 361    38.347  32.538  21.625  1.00  46.67   8
ATOM    747  N    SER A 362    39.134  34.348  22.703  1.00  41.44   7
ATOM    748  CA   SER A 362    40.525  33.918  22.790  1.00  42.13   6
ATOM    749  CB   SER A 362    41.408  35.131  23.066  1.00  42.61   6
ATOM    750  OG   SER A 362    41.219  36.136  22.076  1.00  51.87   8
ATOM    751  C    SER A 362    40.798  32.870  23.876  1.00  38.41   6
ATOM    752  O    SER A 362    41.553  31.938  23.641  1.00  38.01   8
ATOM    753  N    PHE A 363    40.198  33.039  25.058  1.00  34.55   7
ATOM    754  CA   PHE A 363    40.417  32.126  26.174  1.00  32.96   6
ATOM    755  CB   PHE A 363    39.832  32.718  27.447  1.00  31.99   6
ATOM    756  CG   PHE A 363    40.448  34.036  27.840  1.00  29.97   6
ATOM    757  CD1  PHE A 363    40.102  34.650  29.020  1.00  30.61   6
ATOM    758  CD2  PHE A 363    41.379  34.646  27.014  1.00  32.02   6
ATOM    759  CE1  PHE A 363    40.685  35.856  29.391  1.00  33.67   6
ATOM    760  CE2  PHE A 363    41.959  35.843  27.377  1.00  30.91   6
ATOM    761  CZ   PHE A 363    41.615  36.456  28.558  1.00  29.33   6
ATOM    762  C    PHE A 363    39.883  30.716  25.967  1.00  30.52   6
ATOM    763  O    PHE A 363    40.436  29.766  26.526  1.00  32.19   8
ATOM    764  N    ASN A 364    38.817  30.570  25.175  1.00  33.51   7
ATOM    765  CA   ASN A 364    38.239  29.264  24.918  1.00  38.03   6
ATOM    766  CB   ASN A 364    39.240  28.404  24.139  1.00  42.32   6
ATOM    767  CG   ASN A 364    39.696  29.065  22.861  1.00  53.11   6
ATOM    768  OD1  ASN A 364    38.874  29.330  21.954  1.00  59.51   8
ATOM    769  ND2  ASN A 364    40.986  29.330  22.772  1.00  55.95   7
ATOM    770  C    ASN A 364    37.916  28.572  26.235  1.00  31.89   6
ATOM    771  O    ASN A 364    38.324  27.428  26.457  1.00  30.28   8
ATOM    772  N    LEU A 365    37.176  29.271  27.094  1.00  27.62   7
ATOM    773  CA   LEU A 365    36.806  28.743  28.406  1.00  29.36   6
ATOM    774  CB   LEU A 365    36.195  29.866  29.237  1.00  27.54   6
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    775  CG   LEU A 365    36.990  31.150  29.185  1.00 38.91   6
ATOM    776  CD1  LEU A 365    36.316  32.216  30.036  1.00 34.47   6
ATOM    777  CD2  LEU A 365    38.406  30.883  29.663  1.00 34.24   6
ATOM    778  C    LEU A 365    35.830  27.590  28.262  1.00 26.23   6
ATOM    779  O    LEU A 365    34.890  27.649  27.472  1.00 27.06   8
ATOM    780  N    ASP A 366    36.083  26.528  29.021  1.00 25.23   7
ATOM    781  CA   ASP A 366    35.213  25.358  28.988  1.00 26.07   6
ATOM    782  CB   ASP A 366    36.027  24.049  29.033  1.00 29.68   6
ATOM    783  CG   ASP A 366    36.799  23.874  30.303  1.00 35.74   6
ATOM    784  OD1  ASP A 366    36.285  24.177  31.402  1.00 36.78   8
ATOM    785  OD2  ASP A 366    37.959  23.386  30.240  1.00 41.23   8
ATOM    786  C    ASP A 366    34.278  25.434  30.181  1.00 27.70   6
ATOM    787  O    ASP A 366    34.587  26.097  31.173  1.00 31.94   8
ATOM    788  N    ASP A 367    33.141  24.743  30.066  1.00 29.18   7
ATOM    789  CA   ASP A 367    32.120  24.679  31.120  1.00 32.72   6
ATOM    790  CB   ASP A 367    31.472  23.284  31.147  1.00 38.04   6
ATOM    791  CG   ASP A 367    30.806  22.924  29.854  1.00 42.43   6
ATOM    792  OD1  ASP A 367    29.877  23.650  29.409  1.00 35.95   8
ATOM    793  OD2  ASP A 367    31.186  21.884  29.250  1.00 51.42   8
ATOM    794  C    ASP A 367    32.754  24.969  32.482  1.00 33.71   6
ATOM    795  O    ASP A 367    32.484  26.000  33.098  1.00 38.30   8
ATOM    796  N    THR A 368    33.602  24.032  32.919  1.00 31.06   7
ATOM    797  CA   THR A 368    34.329  24.124  34.181  1.00 26.28   6
ATOM    798  CB   THR A 368    35.559  23.222  34.141  1.00 27.30   6
ATOM    799  OG1  THR A 368    35.161  21.871  33.885  1.00 33.42   8
ATOM    800  CG2  THR A 368    36.323  23.303  35.454  1.00 25.16   6
ATOM    801  C    THR A 368    34.764  25.557  34.479  1.00 21.13   6
ATOM    802  O    THR A 368    34.408  26.153  35.503  1.00 23.17   8
ATOM    803  N    GLU A 369    35.545  26.092  33.551  1.00 21.32   7
ATOM    804  CA   GLU A 369    36.065  27.435  33.661  1.00 28.00   6
ATOM    805  CB   GLU A 369    36.960  27.707  32.453  1.00 32.79   6
ATOM    806  CG   GLU A 369    38.089  26.663  32.346  1.00 36.29   6
ATOM    807  CD   GLU A 369    38.906  26.747  31.110  1.00 41.03   6
ATOM    808  OE1  GLU A 369    38.337  26.744  29.994  1.00 42.05   8
ATOM    809  OE2  GLU A 369    40.158  26.795  31.218  1.00 42.03   8
ATOM    810  C    GLU A 369    34.953  28.471  33.821  1.00 25.57   6
ATOM    811  O    GLU A 369    34.987  29.256  34.760  1.00 20.56   8
ATOM    812  N    VAL A 370    33.967  28.463  32.921  1.00 25.39   7
ATOM    813  CA   VAL A 370    32.849  29.396  33.029  1.00 25.99   6
ATOM    814  CB   VAL A 370    31.763  29.131  31.987  1.00 26.15   6
ATOM    815  CG1  VAL A 370    30.609  30.093  32.183  1.00 27.65   6
ATOM    816  CG2  VAL A 370    32.306  29.251  30.592  1.00 17.70   6
ATOM    817  C    VAL A 370    32.245  29.209  34.412  1.00 26.49   6
ATOM    818  O    VAL A 370    32.012  30.170  35.147  1.00 28.16   8
ATOM    819  N    ALA A 371    31.988  27.947  34.739  1.00 21.01   7
ATOM    820  CA   ALA A 371    31.393  27.554  36.011  1.00 19.57   6
ATOM    821  CB   ALA A 371    31.441  26.039  36.145  1.00 18.62   6
ATOM    822  C    ALA A 371    32.116  28.211  37.177  1.00 23.48   6
ATOM    823  O    ALA A 371    31.531  28.989  37.931  1.00 32.67   8
ATOM    824  N    LEU A 372    33.401  27.893  37.305  1.00 22.89   7
ATOM    825  CA   LEU A 372    34.217  28.447  38.369  1.00 23.28   6
ATOM    826  CB   LEU A 372    35.675  27.996  38.178  1.00 27.76   6
ATOM    827  CG   LEU A 372    35.943  26.524  38.415  1.00 21.18   6
ATOM    828  CD1  LEU A 372    37.356  26.171  38.049  1.00 27.64   6
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    829  CD2  LEU A 372    35.675  26.204  39.880  1.00  20.90   6
ATOM    830  C    LEU A 372    34.098  29.966  38.396  1.00  21.34   6
ATOM    831  O    LEU A 372    33.828  30.572  39.439  1.00  23.16   8
ATOM    832  N    LEU A 373    34.288  30.561  37.223  1.00  24.42   7
ATOM    833  CA   LEU A 373    34.214  32.007  37.074  1.00  23.78   6
ATOM    834  CB   LEU A 373    34.296  32.360  35.575  1.00  22.18   6
ATOM    835  CG   LEU A 373    34.784  33.726  35.165  1.00  31.52   6
ATOM    836  CD1  LEU A 373    36.000  34.084  35.962  1.00  31.93   6
ATOM    837  CD2  LEU A 373    35.103  33.720  33.693  1.00  30.24   6
ATOM    838  C    LEU A 373    32.904  32.480  37.720  1.00  25.69   6
ATOM    839  O    LEU A 373    32.895  33.410  38.532  1.00  30.13   8
ATOM    840  N    GLN A 374    31.814  31.800  37.368  1.00  26.24   7
ATOM    841  CA   GLN A 374    30.487  32.104  37.896  1.00  21.60   6
ATOM    842  CB   GLN A 374    29.454  31.121  37.335  1.00  24.57   6
ATOM    843  CG   GLN A 374    29.310  31.145  35.821  1.00  21.02   6
ATOM    844  CD   GLN A 374    28.224  30.201  35.331  1.00  22.86   6
ATOM    845  OE1  GLN A 374    28.037  30.042  34.123  1.00  24.07   8
ATOM    846  NE2  GLN A 374    27.515  29.590  36.249  1.00  25.59   7
ATOM    847  C    GLN A 374    30.421  32.039  39.422  1.00  20.66   6
ATOM    848  O    GLN A 374    29.717  32.832  40.04   1.00  24.47   8
ATOM    849  N    ALA A 375    31.136  31.074  40.004  1.00  16.26   7
ATOM    850  CA   ALA A 375    31.155  30.889  41.445  1.00  17.16   6
ATOM    851  CB   ALA A 375    31.805  29.568  41.780  1.00  19.53   6
ATOM    852  C    ALA A 375    31.907  32.025  42.108  1.00  25.13   6
ATOM    853  O    ALA A 375    31.397  32.646  43.034  1.00  23.81   8
ATOM    854  N    VAL A 376    33.122  32.277  41.611  1.00  24.57   7
ATOM    855  CA   VAL A 376    33.959  33.354  42.118  1.00  25.80   6
ATOM    856  CB   VAL A 376    35.101  33.658  41.164  1.00  26.48   6
ATOM    857  CG1  VAL A 376    35.926  34.812  41.697  1.00  23.20   6
ATOM    858  CG2  VAL A 376    35.959  32.429  40.952  1.00  19.08   6
ATOM    859  C    VAL A 376    33.107  34.599  42.312  1.00  25.69   6
ATOM    860  O    VAL A 376    33.297  35.364  43.251  1.00  27.87   8
ATOM    861  N    LEU A 377    32.159  34.781  41.399  1.00  23.09   7
ATOM    862  CA   LEU A 377    31.242  35.915  41.423  1.00  22.86   6
ATOM    863  CB   LEU A 377    30.540  36.031  40.061  1.00  18.50   6
ATOM    864  CG   LEU A 377    31.424  36.368  38.885  1.00  22.65   6
ATOM    865  CD1  LEU A 377    30.689  36.227  37.601  1.00  16.70   6
ATOM    866  CD2  LEU A 377    31.916  37.776  39.051  1.00  19.58   6
ATOM    867  C    LEU A 377    30.228  35.719  42.543  1.00  26.14   6
ATOM    868  O    LEU A 377    30.131  36.532  43.452  1.00  20.62   8
ATOM    869  N    LEU A 378    29.483  34.614  42.468  1.00  28.99   7
ATOM    870  CA   LEU A 378    28.469  34.303  43.475  1.00  28.87   6
ATOM    871  CB   LEU A 378    28.053  32.826  43.397  1.00  26.89   6
ATOM    872  CG   LEU A 378    27.110  32.344  44.472  1.00  28.83   6
ATOM    873  CD1  LEU A 378    25.915  33.252  44.525  1.00  27.97   6
ATOM    874  CD2  LEU A 378    26.693  30.928  44.205  1.00  27.69   6
ATOM    875  C    LEU A 378    28.992  34.617  44.853  1.00  31.09   6
ATOM    876  O    LEU A 378    28.399  35.421  45.573  1.00  31.77   8
ATOM    877  N    MET A 379    30.118  33.991  45.189  1.00  31.44   7
ATOM    878  CA   MET A 379    30.736  34.141  46.494  1.00  32.62   6
ATOM    879  CB   MET A 379    31.690  32.960  46.744  1.00  31.45   6
ATOM    880  CG   MET A 379    30.984  31.595  46.792  1.00  38.75   6
ATOM    881  SD   MET A 379    29.741  31.626  48.107  1.00  41.27  16
ATOM    882  CE   MET A 379    28.896  30.036  47.851  1.00  35.68   6
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    883   C    MET A 379    31.485   35.448   46.727   1.00   33.72   6
ATOM    884   O    MET A 379    32.567   35.450   47.305   1.00   36.29   8
ATOM    885   N    SER A 380    30.889   36.555   46.315   1.00   34.49   7
ATOM    886   CA   SER A 380    31.498   37.853   46.550   1.00   33.97   6
ATOM    887   CB   SER A 380    30.921   38.890   45.576   1.00   31.24   6
ATOM    888   OG   SER A 380    31.205   38.543   44.230   1.00   39.42   8
ATOM    889   C    SER A 380    31.179   38.239   47.992   1.00   39.69   6
ATOM    890   O    SER A 380    30.029   38.446   48.357   1.00   44.64   8
ATOM    891   N    SER A 381    32.214   38.313   48.812   1.00   41.04   7
ATOM    892   CA   SER A 381    32.060   38.640   50.216   1.00   44.91   6
ATOM    893   CB   SER A 381    33.324   38.234   50.951   1.00   44.50   6
ATOM    894   OG   SER A 381    34.431   39.002   50.510   1.00   45.42   8
ATOM    895   C    SER A 381    31.795   40.106   50.499   1.00   44.59   6
ATOM    896   O    SER A 381    31.476   40.470   51.618   1.00   49.32   8
ATOM    897   N    ASP A 382    31.939   40.942   49.486   1.00   43.75   7
ATOM    898   CA   ASP A 382    31.744   42.362   49.641   1.00   43.93   6
ATOM    899   CB   ASP A 382    32.673   43.111   48.677   1.00   48.39   6
ATOM    900   CG   ASP A 382    32.572   42.624   47.263   1.00   53.23   6
ATOM    901   OD1  ASP A 382    32.705   41.400   47.034   1.00   56.97   8
ATOM    902   OD2  ASP A 382    32.358   43.454   46.333   1.00   58.91   8
ATOM    903   C    ASP A 382    30.314   42.885   49.507   1.00   41.09   6
ATOM    904   O    ASP A 382    30.048   44.036   49.845   1.00   40.93   8
ATOM    905   N    ARG A 383    29.397   42.049   49.034   1.00   42.63   7
ATOM    906   CA   ARG A 383    28.036   42.485   48.876   1.00   43.32   6
ATOM    907   CB   ARG A 383    27.138   41.332   48.443   1.00   42.31   6
ATOM    908   CG   ARG A 383    27.651   40.399   47.352   1.00   40.83   6
ATOM    909   CD   ARG A 383    27.586   40.954   45.925   1.00   38.09   6
ATOM    910   NE   ARG A 383    27.768   39.878   44.975   1.00   37.33   7
ATOM    911   CZ   ARG A 383    28.037   40.058   43.693   1.00   38.35   6
ATOM    912   NH1  ARG A 383    28.142   41.292   43.198   1.00   33.70   7
ATOM    913   NH2  ARG A 383    28.194   38.992   42.918   1.00   35.46   7
ATOM    914   C    ARG A 383    27.523   42.989   50.216   1.00   44.96   6
ATOM    915   O    ARG A 383    27.744   42.344   51.260   1.00   45.60   8
ATOM    916   N    PRO A 384    26.852   44.144   50.223   1.00   45.33   7
ATOM    917   CD   PRO A 384    26.625   44.964   49.027   1.00   46.85   6
ATOM    918   CA   PRO A 384    26.298   44.738   51.446   1.00   47.37   6
ATOM    919   CB   PRO A 384    25.841   46.130   51.012   1.00   46.90   6
ATOM    920   CG   PRO A 384    26.075   46.229   49.567   1.00   46.41   6
ATOM    921   C    PRO A 384    25.158   43.919   52.049   1.00   48.29   6
ATOM    922   O    PRO A 384    24.404   43.264   51.329   1.00   48.34   8
ATOM    923   N    GLY A 385    25.039   43.983   53.383   1.00   49.88   7
ATOM    924   CA   GLY A 385    23.991   43.270   54.113   1.00   50.35   6
ATOM    925   C    GLY A 385    24.347   41.852   54.495   1.00   50.70   6
ATOM    926   O    GLY A 385    23.614   41.204   55.244   1.00   53.48   8
ATOM    927   N    LEU A 386    25.466   41.371   53.955   1.00   49.04   7
ATOM    928   CA   LEU A 386    25.901   40.017   54.215   1.00   50.53   6
ATOM    929   CB   LEU A 386    27.224   39.751   53.492   1.00   45.17   6
ATOM    930   CG   LEU A 386    27.152   39.592   51.993   1.00   48.26   6
ATOM    931   CD1  LEU A 386    28.542   39.439   51.404   1.00   41.68   6
ATOM    932   CD2  LEU A 386    26.302   38.374   51.682   1.00   38.40   6
ATOM    933   C    LEU A 386    26.045   39.776   55.691   1.00   52.13   6
ATOM    934   O    LEU A 386    26.296   40.692   56.459   1.00   53.67   8
ATOM    935   N    ALA A 387    25.861   38.522   56.077   1.00   53.42   7
ATOM    936   CA   ALA A 387    25.976   38.129   57.470   1.00   56.01   6
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    937  CB   ALA A 387      24.802  37.234  57.854  1.00 56.47    6
ATOM    938  C    ALA A 387      27.289  37.385  57.659  1.00 55.52    6
ATOM    939  O    ALA A 387      28.275  37.940  58.134  1.00 53.75    8
ATOM    940  N    CYS A 388      27.273  36.120  57.253  1.00 56.03    7
ATOM    941  CA   CYS A 388      28.412  35.236  57.370  1.00 59.57    6
ATOM    942  CB   CYS A 388      27.923  33.803  57.172  1.00 59.23    6
ATOM    943  SG   CYS A 388      26.397  33.431  58.009  1.00 58.64   16
ATOM    944  C    CYS A 388      29.482  35.581  56.328  1.00 62.18    6
ATOM    945  O    CYS A 388      29.720  34.821  55.400  1.00 67.88    8
ATOM    946  N    VAL A 389      30.110  36.747  56.495  1.00 60.78    7
ATOM    947  CA   VAL A 389      31.173  37.212  55.590  1.00 57.70    6
ATOM    948  CB   VAL A 389      31.740  38.567  56.024  1.00 57.09    6
ATOM    949  CG1  VAL A 389      32.795  39.037  55.041  1.00 59.03    6
ATOM    950  CG2  VAL A 389      30.640  39.598  56.171  1.00 53.98    6
ATOM    951  C    VAL A 389      32.297  36.182  55.550  1.00 57.77    6
ATOM    952  O    VAL A 389      32.358  35.336  54.662  1.00 60.94    8
ATOM    953  N    ALA A 390      33.182  36.292  56.528  1.00 52.68    7
ATOM    954  CA   ALA A 390      34.347  35.431  56.684  1.00 48.41    6
ATOM    955  CB   ALA A 390      34.703  35.321  58.185  1.00 45.19    6
ATOM    956  C    ALA A 390      34.224  34.040  56.082  1.00 47.63    6
ATOM    957  O    ALA A 390      35.107  33.597  55.348  1.00 51.95    8
ATOM    958  N    ARG A 391      33.117  33.366  56.391  1.00 47.11    7
ATOM    959  CA   ARG A 391      32.879  32.018  55.885  1.00 51.64    6
ATOM    960  CB   ARG A 391      31.520  31.498  56.383  1.00 54.22    6
ATOM    961  CG   ARG A 391      31.267  30.012  56.059  1.00 64.20    6
ATOM    962  CD   ARG A 391      29.930  29.489  56.602  1.00 73.80    6
ATOM    963  NE   ARG A 391      29.787  28.044  56.454  1.00 79.76    7
ATOM    964  CZ   ARG A 391      30.573  27.140  57.043  1.00 84.27    6
ATOM    965  NH1  ARG A 391      31.598  27.535  57.806  1.00 85.28    7
ATOM    966  NH2  ARG A 391      30.340  25.840  56.849  1.00 86.84    7
ATOM    967  C    ARG A 391      32.922  31.986  54.358  1.00 48.18    6
ATOM    968  O    ARG A 391      33.494  31.080  53.756  1.00 49.57    8
ATOM    969  N    ILE A 392      32.281  32.993  53.762  1.00 45.01    7
ATOM    970  CA   ILE A 392      32.196  33.148  52.319  1.00 48.77    6
ATOM    971  CB   ILE A 392      31.224  34.297  51.963  1.00 46.45    6
ATOM    972  CG2  ILE A 392      31.241  34.582  50.479  1.00 42.35    6
ATOM    973  CG1  ILE A 392      29.791  33.953  52.402  1.00 49.69    6
ATOM    974  CD1  ILE A 392      28.792  35.039  52.113  1.00 51.09    6
ATOM    975  C    ILE A 392      33.554  33.356  51.641  1.00 50.90    6
ATOM    976  O    ILE A 392      33.914  32.605  50.732  1.00 52.21    8
ATOM    977  N    GLU A 393      34.298  34.374  52.071  1.00 50.43    7
ATOM    978  CA   GLU A 393      35.592  34.684  51.471  1.00 50.30    6
ATOM    979  CB   GLU A 393      36.437  35.561  52.387  1.00 53.97    6
ATOM    980  CG   GLU A 393      36.550  36.966  51.844  1.00 62.18    6
ATOM    981  CD   GLU A 393      37.546  37.777  52.564  1.00 67.69    6
ATOM    982  OE1  GLU A 393      38.149  38.741  52.119  1.00 66.42    8
ATOM    983  OE2  GLU A 393      37.856  37.640  53.729  1.00 70.64    8
ATOM    984  C    GLU A 393      36.341  33.429  51.230  1.00 49.31    6
ATOM    985  O    GLU A 393      36.755  33.089  50.125  1.00 49.53    8
ATOM    986  N    LYS A 394      36.552  32.730  52.303  1.00 46.07    7
ATOM    987  CA   LYS A 394      37.265  31.543  52.078  1.00 45.76    6
ATOM    988  CB   LYS A 394      37.396  30.800  53.373  1.00 43.85    6
ATOM    989  CG   LYS A 394      38.207  31.617  54.394  1.00 40.00    6
ATOM    990  CD   LYS A 394      39.372  32.374  53.705  1.00 40.00    6
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    991  CE   LYS A 394      40.136  33.265  54.681  1.00 40.00  6
ATOM    992  NZ   LYS A 394      41.516  33.602  54.162  1.00 40.00  7
ATOM    993  C    LYS A 394      36.568  30.778  50.966  1.00 46.69  6
ATOM    994  O    LYS A 394      37.215  30.427  49.988  1.00 49.13  8
ATOM    995  N    TYR A 395      35.269  30.514  51.095  1.00 46.57  7
ATOM    996  CA   TYR A 395      34.553  29.823  50.022  1.00 43.33  6
ATOM    997  CB   TYR A 395      33.059  30.123  50.076  1.00 48.44  6
ATOM    998  CG   TYR A 395      32.275  29.236  50.994  1.00 53.83  6
ATOM    999  CD1  TYR A 395      31.010  29.598  51.415  1.00 56.43  6
ATOM   1000  CE1  TYR A 395      30.266  28.769  52.252  1.00 59.73  6
ATOM   1001  CD2  TYR A 395      32.790  28.033  51.428  1.00 56.47  6
ATOM   1002  CE2  TYR A 395      32.054  27.198  52.265  1.00 62.60  6
ATOM   1003  CZ   TYR A 395      30.787  27.565  52.687  1.00 63.18  6
ATOM   1004  OH   TYR A 395      30.059  26.753  53.528  1.00 64.46  8
ATOM   1005  C    TYR A 395      35.120  30.356  48.716  1.00 37.30  6
ATOM   1006  O    TYR A 395      35.643  29.601  47.908  1.00 34.10  8
ATOM   1007  N    GLN A 396      35.029  31.670  48.522  1.00 31.92  7
ATOM   1008  CA   GLN A 396      35.563  32.273  47.305  1.00 34.81  6
ATOM   1009  CB   GLN A 396      35.403  33.801  47.329  1.00 32.64  6
ATOM   1010  CG   GLN A 396      36.088  34.485  46.162  1.00 29.57  6
ATOM   1011  CD   GLN A 396      35.616  35.891  45.927  1.00 29.46  6
ATOM   1012  OE1  GLN A 396      35.599  36.726  46.862  1.00 34.65  8
ATOM   1013  NE2  GLN A 396      35.245  36.173  44.689  1.00 27.21  7
ATOM   1014  C    GLN A 396      37.035  31.909  47.167  1.00 37.13  6
ATOM   1015  O    GLN A 396      37.511  31.590  46.080  1.00 37.36  8
ATOM   1016  N    ASP A 397      37.751  31.970  48.285  1.00 38.61  7
ATOM   1017  CA   ASP A 397      39.164  31.642  48.298  1.00 40.37  6
ATOM   1018  CB   ASP A 397      39.757  31.869  49.704  1.00 40.51  6
ATOM   1019  CG   ASP A 397      39.813  33.319  50.095  1.00 43.77  6
ATOM   1020  OD1  ASP A 397      40.397  34.123  49.334  1.00 46.50  8
ATOM   1021  OD2  ASP A 397      39.299  33.702  51.184  1.00 51.34  8
ATOM   1022  C    ASP A 397      39.302  30.176  47.898  1.00 38.62  6
ATOM   1023  O    ASP A 397      40.230  29.809  47.199  1.00 39.20  8
ATOM   1024  N    SER A 398      38.350  29.359  48.344  1.00 37.84  7
ATOM   1025  CA   SER A 398      38.348  27.929  48.063  1.00 37.80  6
ATOM   1026  CB   SER A 398      37.240  27.240  48.878  1.00 34.28  6
ATOM   1027  OG   SER A 398      37.297  25.826  48.755  1.00 46.60  8
ATOM   1028  C    SER A 398      38.164  27.639  46.581  1.00 38.41  6
ATOM   1029  O    SER A 398      38.677  26.642  46.075  1.00 39.98  8
ATOM   1030  N    PHE A 399      37.419  28.507  45.893  1.00 34.82  7
ATOM   1031  CA   PHE A 399      37.181  28.325  44.462  1.00 35.96  6
ATOM   1032  CB   PHE A 399      35.873  28.983  44.015  1.00 35.75  6
ATOM   1033  CG   PHE A 399      34.632  28.216  44.403  1.00 39.30  6
ATOM   1034  CD1  PHE A 399      34.107  28.294  45.677  1.00 39.86  6
ATOM   1035  CD2  PHE A 399      34.018  27.393  43.488  1.00 36.81  6
ATOM   1036  CE1  PHE A 399      32.961  27.557  46.013  1.00 41.25  6
ATOM   1037  CE2  PHE A 399      32.880  26.661  43.825  1.00 43.61  6
ATOM   1038  CZ   PHE A 399      32.354  26.740  45.087  1.00 40.34  6
ATOM   1039  C    PHE A 399      38.328  28.890  43.630  1.00 33.48  6
ATOM   1040  O    PHE A 399      38.867  28.200  42.756  1.00 26.86  8
ATOM   1041  N    LEU A 400      38.680  30.156  43.877  1.00 31.47  7
ATOM   1042  CA   LEU A 400      39.754  30.796  43.132  1.00 37.41  6
ATOM   1043  CB   LEU A 400      40.179  32.100  43.814  1.00 34.24  6
ATOM   1044  CG   LEU A 400      39.239  33.265  43.628  1.00 35.10  6
```

UNITED STATES PATENT AND TRADEMARK OFFICE
CERTIFICATE OF CORRECTION

PATENT NO.        : 6,965,850 B2
APPLICATION NO.   : 09/281717
DATED             : November 15, 2005
INVENTOR(S)       : John D. Baxter et al.

It is certified that error appears in the above-identified patent and that said Letters Patent is hereby corrected as shown below:

```
ATOM   1045  CD1  LEU A 400    39.803  34.531  44.256  1.00  26.60  6
ATOM   1046  CD2  LEU A 400    39.065  33.479  42.137  1.00  29.44  6
ATOM   1047  C    LEU A 400    40.941  29.872  42.947  1.00  38.84  6
ATOM   1048  O    LEU A 400    41.367  29.632  41.821  1.00  40.38  8
ATOM   1049  N    LEU A 401    41.464  29.350  44.055  1.00  42.79  7
ATOM   1050  CA   LEU A 401    42.605  28.449  43.988  1.00  43.48  6
ATOM   1051  CB   LEU A 401    42.900  27.821  45.355  1.00  44.73  6
ATOM   1052  CG   LEU A 401    44.105  26.899  45.354  1.00  51.39  6
ATOM   1053  CD1  LEU A 401    45.374  27.749  45.143  1.00  50.11  6
ATOM   1054  CD2  LEU A 401    44.205  26.122  46.662  1.00  49.30  6
ATOM   1055  C    LEU A 401    42.324  27.340  42.981  1.00  41.62  6
ATOM   1056  O    LEU A 401    43.052  27.180  42.004  1.00  45.14  8
ATOM   1057  N    ALA A 402    41.269  26.574  43.245  1.00  37.92  7
ATOM   1058  CA   ALA A 402    40.873  25.469  42.386  1.00  29.90  6
ATOM   1059  CB   ALA A 402    39.522  24.928  42.834  1.00  30.70  6
ATOM   1060  C    ALA A 402    40.798  25.909  40.929  1.00  28.88  6
ATOM   1061  O    ALA A 402    41.277  25.203  40.034  1.00  32.14  8
ATOM   1062  N    PHE A 403    40.200  27.086  40.707  1.00  31.07  7
ATOM   1063  CA   PHE A 403    40.052  27.642  39.363  1.00  29.90  6
ATOM   1064  CB   PHE A 403    39.379  29.019  39.438  1.00  27.03  6
ATOM   1065  CG   PHE A 403    38.943  29.574  38.100  1.00  26.97  6
ATOM   1066  CD1  PHE A 403    38.228  30.758  38.033  1.00  25.55  6
ATOM   1067  CD2  PHE A 403    39.224  28.905  36.925  1.00  19.75  6
ATOM   1068  CE1  PHE A 403    37.784  31.266  36.808  1.00  27.90  6
ATOM   1069  CE2  PHE A 403    38.780  29.416  35.694  1.00  22.56  6
ATOM   1070  CZ   PHE A 403    38.063  30.596  35.640  1.00  22.24  6
ATOM   1071  C    PHE A 403    41.429  27.756  38.719  1.00  28.82  6
ATOM   1072  O    PHE A 403    41.666  27.210  37.646  1.00  26.00  8
ATOM   1073  N    GLU A 404    42.329  28.463  39.402  1.00  30.25  7
ATOM   1074  CA   GLU A 404    43.695  28.665  38.922  1.00  34.03  6
ATOM   1075  CB   GLU A 404    44.513  29.416  39.983  1.00  39.45  6
ATOM   1076  CG   GLU A 404    45.867  29.935  39.489  1.00  47.68  6
ATOM   1077  CD   GLU A 404    46.734  30.507  40.571  1.00  54.02  6
ATOM   1078  OE1  GLU A 404    46.236  31.298  41.408  1.00  57.27  8
ATOM   1079  OE2  GLU A 404    47.956  30.202  40.606  1.00  63.85  8
ATOM   1080  C    GLU A 404    44.352  27.322  38.534  1.00  36.01  6
ATOM   1081  O    GLU A 404    44.936  27.112  37.574  1.00  38.64  8
ATOM   1082  N    HIS A 405    44.259  26.420  39.610  1.00  29.56  7
ATOM   1083  CA   HIS A 405    44.840  25.093  39.468  1.00  31.69  6
ATOM   1084  CB   HIS A 405    44.540  24.228  40.694  1.00  33.75  6
ATOM   1085  CG   HIS A 405    45.292  24.657  41.908  1.00  34.75  6
ATOM   1086  CD2  HIS A 405    46.198  25.640  42.130  1.00  34.58  6
ATOM   1087  ND1  HIS A 405    45.161  23.984  43.130  1.00  32.43  7
ATOM   1088  CE1  HIS A 405    45.975  24.568  44.018  1.00  36.15  6
ATOM   1089  NE2  HIS A 405    46.601  25.561  43.430  1.00  39.84  7
ATOM   1090  C    HIS A 405    44.274  24.445  38.225  1.00  34.21  6
ATOM   1091  O    HIS A 405    45.029  23.949  37.386  1.00  37.06  8
ATOM   1092  N    TYR A 406    42.947  24.453  38.100  1.00  30.83  7
ATOM   1093  CA   TYR A 406    42.313  23.859  36.930  1.00  28.85  6
ATOM   1094  CB   TYR A 406    40.805  24.080  36.934  1.00  31.48  6
ATOM   1095  CG   TYR A 406    40.139  23.494  35.709  1.00  23.49  6
ATOM   1096  CD1  TYR A 406    40.073  22.123  35.532  1.00  19.42  6
ATOM   1097  CE1  TYR A 406    39.517  21.577  34.382  1.00  23.80  6
ATOM   1098  CD2  TYR A 406    39.646  24.313  34.704  1.00  21.81  6
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1099  CE2  TYR A 406    39.090  23.769  33.551  1.00  24.64   6
ATOM   1100  CZ   TYR A 406    39.029  22.395  33.380  1.00  21.56   6
ATOM   1101  OH   TYR A 406    38.489  21.850  32.236  1.00  24.96   8
ATOM   1102  C    TYR A 406    42.882  24.504  35.672  1.00  24.24   6
ATOM   1103  O    TYR A 406    42.958  23.872  34.621  1.00  27.08   8
ATOM   1104  N    ILE A 407    43.253  25.784  35.807  1.00  25.76   7
ATOM   1105  CA   ILE A 407    43.824  26.548  34.705  1.00  33.75   6
ATOM   1106  CB   ILE A 407    43.986  28.033  35.070  1.00  34.23   6
ATOM   1107  CG2  ILE A 407    44.967  28.712  34.139  1.00  32.46   6
ATOM   1108  CG1  ILE A 407    42.615  28.728  35.042  1.00  43.30   6
ATOM   1109  CD1  ILE A 407    41.896  28.602  33.694  1.00  40.40   6
ATOM   1110  C    ILE A 407    45.143  25.973  34.256  1.00  39.03   6
ATOM   1111  O    ILE A 407    45.383  25.771  33.063  1.00  35.18   8
ATOM   1112  N    ASN A 408    46.003  25.721  35.227  1.00  37.25   7
ATOM   1113  CA   ASN A 408    47.307  25.194  34.926  1.00  37.01   6
ATOM   1114  CB   ASN A 408    48.107  25.017  36.213  1.00  32.27   6
ATOM   1115  CG   ASN A 408    48.346  26.362  36.936  1.00  33.56   6
ATOM   1116  OD1  ASN A 408    48.827  27.335  36.320  1.00  31.99   8
ATOM   1117  ND2  ASN A 408    48.038  26.403  38.231  1.00  31.23   7
ATOM   1118  C    ASN A 408    47.205  23.892  34.136  1.00  38.14   6
ATOM   1119  O    ASN A 408    47.900  23.734  33.124  1.00  42.16   8
ATOM   1120  N    TYR A 409    46.334  22.981  34.568  1.00  35.62   7
ATOM   1121  CA   TYR A 409    46.159  21.710  33.866  1.00  35.91   6
ATOM   1122  CB   TYR A 409    45.051  20.859  34.507  1.00  34.41   6
ATOM   1123  CG   TYR A 409    44.624  19.687  33.619  1.00  38.73   6
ATOM   1124  CD1  TYR A 409    45.563  18.765  33.155  1.00  41.34   6
ATOM   1125  CE1  TYR A 409    45.186  17.709  32.321  1.00  47.16   6
ATOM   1126  CD2  TYR A 409    43.292  19.515  33.232  1.00  46.20   6
ATOM   1127  CE2  TYR A 409    42.913  18.455  32.397  1.00  50.74   6
ATOM   1128  CZ   TYR A 409    43.863  17.551  31.946  1.00  50.88   6
ATOM   1129  OH   TYR A 409    43.498  16.514  31.130  1.00  53.14   8
ATOM   1130  C    TYR A 409    45.760  21.966  32.424  1.00  38.16   6
ATOM   1131  O    TYR A 409    46.202  21.281  31.502  1.00  41.83   8
ATOM   1132  N    ARG A 410    44.872  22.943  32.272  1.00  42.25   7
ATOM   1133  CA   ARG A 410    44.345  23.332  30.984  1.00  42.83   6
ATOM   1134  CB   ARG A 410    43.311  24.427  31.195  1.00  36.83   6
ATOM   1135  CG   ARG A 410    41.994  23.979  31.795  1.00  34.32   6
ATOM   1136  CD   ARG A 410    41.073  23.504  30.675  1.00  36.62   6
ATOM   1137  NE   ARG A 410    40.888  24.550  29.685  1.00  38.64   7
ATOM   1138  CZ   ARG A 410    40.177  24.397  28.576  1.00  35.73   6
ATOM   1139  NH1  ARG A 410    39.572  23.230  28.348  1.00  33.17   7
ATOM   1140  NH2  ARG A 410    40.077  25.407  27.708  1.00  32.70   7
ATOM   1141  C    ARG A 410    45.442  23.850  30.083  1.00  46.67   6
ATOM   1142  O    ARG A 410    45.467  23.591  28.882  1.00  41.78   8
ATOM   1143  N    LYS A 411    46.360  24.577  30.710  1.00  52.99   7
ATOM   1144  CA   LYS A 411    47.467  25.194  30.017  1.00  58.32   6
ATOM   1145  CB   LYS A 411    48.645  24.216  29.876  1.00  64.99   6
ATOM   1146  CG   LYS A 411    48.349  22.835  29.367  1.00  70.48   6
ATOM   1147  CD   LYS A 411    49.608  21.974  29.494  1.00  77.18   6
ATOM   1148  CE   LYS A 411    49.461  20.621  28.795  1.00  84.30   6
ATOM   1149  NZ   LYS A 411    50.740  19.828  28.857  1.00  86.48   7
ATOM   1150  C    LYS A 411    47.032  25.756  28.686  1.00  56.66   6
ATOM   1151  O    LYS A 411    47.160  25.153  27.633  1.00  55.47   8
ATOM   1152  N    HIS A 412    46.458  26.943  28.823  1.00  54.67   7
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1153  CA   HIS A 412      45.984  27.722  27.705  1.00 48.67      6
ATOM   1154  CB   HIS A 412      45.124  28.884  28.201  1.00 43.14      6
ATOM   1155  CG   HIS A 412      43.812  28.480  28.755  1.00 41.36      6
ATOM   1156  CD2  HIS A 412      43.429  28.064  29.987  1.00 35.44      6
ATOM   1157  ND1  HIS A 412      42.651  28.440  27.966  1.00 38.19      7
ATOM   1158  CE1  HIS A 412      41.648  28.014  28.723  1.00 34.75      6
ATOM   1159  NE2  HIS A 412      42.094  27.780  29.942  1.00 35.52      7
ATOM   1160  C    HIS A 412      47.231  28.303  27.101  1.00 46.35      6
ATOM   1161  O    HIS A 412      48.269  28.452  27.775  1.00 42.73      8
ATOM   1162  N    HIS A 413      47.116  28.696  25.839  1.00 48.92      7
ATOM   1163  CA   HIS A 413      48.234  29.290  25.146  1.00 53.15      6
ATOM   1164  CB   HIS A 413      48.404  28.666  23.755  1.00 55.27      6
ATOM   1165  CG   HIS A 413      49.326  29.446  22.886  1.00 58.77      6
ATOM   1166  CD2  HIS A 413      49.213  30.660  22.304  1.00 61.65      6
ATOM   1167  ND1  HIS A 413      50.617  28.997  22.564  1.00 60.31      7
ATOM   1168  CE1  HIS A 413      51.214  29.924  21.828  1.00 63.01      6
ATOM   1169  NE2  HIS A 413      50.386  30.941  21.658  1.00 62.93      7
ATOM   1170  C    HIS A 413      47.932  30.768  24.998  1.00 53.19      6
ATOM   1171  O    HIS A 413      47.639  31.301  23.934  1.00 54.93      8
ATOM   1172  N    VAL A 414      47.964  31.413  26.139  1.00 53.77      7
ATOM   1173  CA   VAL A 414      47.735  32.811  26.146  1.00 51.06      6
ATOM   1174  CB   VAL A 414      46.291  33.183  26.417  1.00 51.49      6
ATOM   1175  CG1  VAL A 414      46.186  34.715  26.603  1.00 45.22      6
ATOM   1176  CG2  VAL A 414      45.419  32.732  25.263  1.00 52.67      6
ATOM   1177  C    VAL A 414      48.623  33.283  27.226  1.00 54.28      6
ATOM   1178  O    VAL A 414      48.427  33.029  28.409  1.00 55.49      8
ATOM   1179  N    THR A 415      49.706  33.863  26.733  1.00 56.28      7
ATOM   1180  CA   THR A 415      50.721  34.484  27.357  1.00 57.83      6
ATOM   1181  CB   THR A 415      51.268  35.675  26.758  1.00 59.64      6
ATOM   1182  OG1  THR A 415      51.605  36.754  27.636  1.00 66.69      8
ATOM   1183  CG2  THR A 415      50.197  36.158  25.745  1.00 59.42      6
ATOM   1184  C    THR A 415      50.146  35.049  28.879  1.00 56.98      6
ATOM   1185  O    THR A 415      48.933  35.146  29.051  1.00 55.70      8
ATOM   1186  N    HIS A 416      51.068  35.330  29.795  1.00 57.44      7
ATOM   1187  CA   HIS A 416      50.808  36.011  31.047  1.00 57.34      6
ATOM   1188  CB   HIS A 416      51.346  37.422  30.708  1.00 61.35      6
ATOM   1189  CG   HIS A 416      51.872  38.237  31.821  1.00 69.78      6
ATOM   1190  CD2  HIS A 416      53.114  38.297  32.390  1.00 71.42      6
ATOM   1191  ND1  HIS A 416      51.135  39.263  32.416  1.00 72.49      7
ATOM   1192  CE1  HIS A 416      51.914  39.884  33.290  1.00 75.50      6
ATOM   1193  NE2  HIS A 416      53.099  39.323  33.291  1.00 73.91      7
ATOM   1194  C    HIS A 416      49.261  35.892  31.297  1.00 53.79      6
ATOM   1195  O    HIS A 416      48.499  36.779  30.902  1.00 52.81      8
ATOM   1196  N    PHE A 417      48.806  34.779  31.911  1.00 48.05      7
ATOM   1197  CA   PHE A 417      47.355  34.428  32.061  1.00 47.99      6
ATOM   1198  CB   PHE A 417      47.165  32.954  31.996  1.00 46.11      6
ATOM   1199  CG   PHE A 417      45.835  32.590  31.399  1.00 44.27      6
ATOM   1200  CD1  PHE A 417      45.680  32.720  30.046  1.00 41.79      6
ATOM   1201  CD2  PHE A 417      44.758  32.135  32.164  1.00 40.23      6
ATOM   1202  CE1  PHE A 417      44.498  32.397  29.422  1.00 44.30      6
ATOM   1203  CE2  PHE A 417      43.540  31.802  31.529  1.00 36.80      6
ATOM   1204  CZ   PHE A 417      43.427  31.928  30.144  1.00 40.69      6
ATOM   1205  C    PHE A 417      46.427  34.836  33.196  1.00 46.69      6
ATOM   1206  O    PHE A 417      46.147  36.004  33.331  1.00 43.35      8
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1207  N    TRP A 418    45.906  33.801  33.909  1.00  45.14   7
ATOM   1208  CA   TRP A 418    44.982  33.867  35.065  1.00  44.89   6
ATOM   1209  CB   TRP A 418    45.545  33.099  36.255  1.00  42.24   6
ATOM   1210  CG   TRP A 418    44.959  33.452  37.598  1.00  47.11   6
ATOM   1211  CD2  TRP A 418    43.724  32.924  38.149  1.00  46.98   6
ATOM   1212  CE2  TRP A 418    43.534  33.565  39.413  1.00  48.94   6
ATOM   1213  CE3  TRP A 418    42.777  31.986  37.688  1.00  45.23   6
ATOM   1214  CD1  TRP A 418    45.434  34.390  38.512  1.00  46.24   6
ATOM   1215  NE1  TRP A 418    44.588  34.407  39.608  1.00  50.63   7
ATOM   1216  CZ2  TRP A 418    42.441  33.270  40.238  1.00  45.46   6
ATOM   1217  CZ3  TRP A 418    41.686  31.706  38.300  1.00  44.50   6
ATOM   1218  CH2  TRP A 418    41.511  32.335  39.753  1.00  47.55   6
ATOM   1219  C    TRP A 418    44.308  35.324  35.398  1.00  43.88   6
ATOM   1220  O    TRP A 418    43.797  35.839  35.702  1.00  43.17   8
ATOM   1221  N    PRO A 419    46.084  35.976  35.461  1.00  43.55   7
ATOM   1222  CD   PRO A 419    47.467  35.482  35.400  1.00  41.52   6
ATOM   1223  CA   PRO A 419    46.003  37.396  35.758  1.00  41.48   6
ATOM   1224  CB   PRO A 419    47.436  37.884  35.535  1.00  39.21   6
ATOM   1225  CG   PRO A 419    48.261  36.696  35.223  1.00  39.25   6
ATOM   1226  C    PRO A 419    44.960  38.090  34.817  1.00  36.28   6
ATOM   1227  O    PRO A 419    44.208  38.978  35.237  1.00  37.08   8
ATOM   1228  N    LYS A 420    44.915  37.701  33.540  1.00  35.96   7
ATOM   1229  CA   LYS A 420    43.977  38.287  32.575  1.00  40.82   6
ATOM   1230  CB   LYS A 420    44.314  37.805  31.155  1.00  40.78   6
ATOM   1231  CG   LYS A 420    45.684  38.244  30.641  1.00  48.62   6
ATOM   1232  CD   LYS A 420    45.904  37.781  29.206  1.00  55.12   6
ATOM   1233  CE   LYS A 420    47.248  38.261  28.673  1.00  53.26   6
ATOM   1234  NZ   LYS A 420    47.448  37.884  27.222  1.00  52.69   7
ATOM   1235  C    LYS A 420    42.580  37.832  32.948  1.00  40.29   6
ATOM   1236  O    LYS A 420    41.656  38.626  32.982  1.00  39.66   8
ATOM   1237  N    LEU A 421    42.461  36.537  33.245  1.00  38.33   7
ATOM   1238  CA   LEU A 421    41.186  35.931  33.613  1.00  37.60   6
ATOM   1239  CB   LEU A 421    41.397  34.433  33.915  1.00  43.66   6
ATOM   1240  CG   LEU A 421    40.204  33.518  33.828  1.00  46.50   6
ATOM   1241  CD1  LEU A 421    39.643  33.624  32.426  1.00  45.15   6
ATOM   1242  CD2  LEU A 421    40.595  32.094  34.131  1.00  51.31   6
ATOM   1243  C    LEU A 421    40.575  36.664  34.808  1.00  39.59   6
ATOM   1244  O    LEU A 421    39.371  36.910  34.837  1.00  40.66   8
ATOM   1245  N    LEU A 422    41.412  37.017  35.782  1.00  39.57   7
ATOM   1246  CA   LEU A 422    40.946  37.726  36.961  1.00  38.63   6
ATOM   1247  CB   LEU A 422    42.085  37.890  37.971  1.00  41.79   6
ATOM   1248  CG   LEU A 422    42.424  36.671  38.798  1.00  42.74   6
ATOM   1249  CD1  LEU A 422    43.490  37.010  39.820  1.00  42.89   6
ATOM   1250  CD2  LEU A 422    41.168  36.216  39.523  1.00  39.27   6
ATOM   1251  C    LEU A 422    40.381  39.073  36.589  1.00  40.47   6
ATOM   1252  O    LEU A 422    39.428  39.525  37.210  1.00  47.83   8
ATOM   1253  N    MET A 423    40.969  39.698  35.569  1.00  34.27   7
ATOM   1254  CA   MET A 423    40.511  41.001  35.117  1.00  35.25   6
ATOM   1255  CB   MET A 423    41.427  41.553  34.028  1.00  32.56   6
ATOM   1256  CG   MET A 423    42.856  41.732  34.456  1.00  40.70   6
ATOM   1257  SD   MET A 423    43.707  43.101  33.619  1.00  47.65  16
ATOM   1258  CE   MET A 423    43.348  42.776  31.848  1.00  47.16   6
ATOM   1259  C    MET A 423    39.100  40.899  34.574  1.00  35.13   6
ATOM   1260  O    MET A 423    38.315  41.829  34.696  1.00  29.85   8
```

UNITED STATES PATENT AND TRADEMARK OFFICE
CERTIFICATE OF CORRECTION

| | |
|---|---|
| PATENT NO. | : 6,965,850 B2 |
| APPLICATION NO. | : 09/281717 |
| DATED | : November 15, 2005 |
| INVENTOR(S) | : John D. Baxter et al. |

It is certified that error appears in the above-identified patent and that said Letters Patent is hereby corrected as shown below:

```
ATOM   1261  N    LYS A 424     38.791  39.752  33.975  1.00  31.56   7
ATOM   1262  CA   LYS A 424     37.470  39.529  33.423  1.00  32.29   6
ATOM   1263  CB   LYS A 424     37.446  38.205  32.658  1.00  30.56   6
ATOM   1264  CG   LYS A 424     38.394  38.192  31.455  1.00  30.07   6
ATOM   1265  CD   LYS A 424     38.050  39.326  30.488  1.00  33.22   6
ATOM   1266  CE   LYS A 424     39.032  39.433  29.322  1.00  28.75   6
ATOM   1267  NZ   LYS A 424     40.394  39.942  29.707  1.00  31.01   7
ATOM   1268  C    LYS A 424     36.418  39.558  34.524  1.00  29.26   6
ATOM   1269  O    LYS A 424     35.307  39.998  34.289  1.00  30.22   8
ATOM   1270  N    VAL A 425     36.796  39.098  35.719  1.00  23.53   7
ATOM   1271  CA   VAL A 425     35.897  39.107  36.866  1.00  28.91   6
ATOM   1272  CB   VAL A 425     36.541  38.460  38.094  1.00  29.44   6
ATOM   1273  CG1  VAL A 425     35.673  38.642  39.320  1.00  28.81   6
ATOM   1274  CG2  VAL A 425     36.764  36.985  37.849  1.00  31.22   6
ATOM   1275  C    VAL A 425     35.512  40.548  37.161  1.00  32.03   6
ATOM   1276  O    VAL A 425     34.350  40.839  37.429  1.00  31.95   8
ATOM   1277  N    THR A 426     36.496  41.444  37.124  1.00  33.61   7
ATOM   1278  CA   THR A 426     36.248  42.866  37.356  1.00  30.76   6
ATOM   1279  CB   THR A 426     37.559  43.670  37.360  1.00  32.34   6
ATOM   1280  OG1  THR A 426     38.209  43.565  38.630  1.00  33.07   8
ATOM   1281  CG2  THR A 426     37.302  45.131  37.015  1.00  25.40   6
ATOM   1282  C    THR A 426     35.363  43.324  36.211  1.00  32.53   6
ATOM   1283  O    THR A 426     34.357  44.006  36.405  1.00  35.19   8
ATOM   1284  N    ASP A 427     35.763  42.929  35.006  1.00  28.83   7
ATOM   1285  CA   ASP A 427     35.011  43.272  33.810  1.00  35.12   6
ATOM   1286  CB   ASP A 427     35.556  42.524  32.578  1.00  39.14   6
ATOM   1287  CG   ASP A 427     36.837  43.103  32.057  1.00  45.80   6
ATOM   1288  OD1  ASP A 427     36.982  44.346  32.024  1.00  41.97   8
ATOM   1289  OD2  ASP A 427     37.735  42.333  31.616  1.00  50.06   8
ATOM   1290  C    ASP A 427     33.537  42.925  34.028  1.00  33.94   6
ATOM   1291  O    ASP A 427     32.659  43.712  33.702  1.00  38.02   8
ATOM   1292  N    LEU A 428     33.283  41.745  34.584  1.00  27.15   7
ATOM   1293  CA   LEU A 428     31.925  41.293  34.850  1.00  29.99   6
ATOM   1294  CB   LEU A 428     31.924  39.786  35.133  1.00  22.49   6
ATOM   1295  CG   LEU A 428     32.104  38.873  33.939  1.00  25.54   6
ATOM   1296  CD1  LEU A 428     32.202  37.421  34.353  1.00  20.60   6
ATOM   1297  CD2  LEU A 428     30.920  39.083  33.029  1.00  17.24   6
ATOM   1298  C    LEU A 428     31.276  42.057  35.991  1.00  28.94   6
ATOM   1299  O    LEU A 428     30.082  42.306  35.939  1.00  31.26   8
ATOM   1300  N    ARG A 429     32.059  42.423  37.011  1.00  27.64   7
ATOM   1301  CA   ARG A 429     31.527  43.162  38.147  1.00  28.13   6
ATOM   1302  CB   ARG A 429     32.564  43.298  39.264  1.00  29.59   6
ATOM   1303  CG   ARG A 429     32.818  42.040  40.080  1.00  34.85   6
ATOM   1304  CD   ARG A 429     33.588  42.360  41.367  1.00  47.18   6
ATOM   1305  NE   ARG A 429     34.093  41.175  42.049  1.00  57.93   7
ATOM   1306  CZ   ARG A 429     33.327  40.210  42.547  1.00  63.62   6
ATOM   1307  NH1  ARG A 429     31.998  40.270  42.396  1.00  60.71   7
ATOM   1308  NH2  ARG A 429     33.900  39.165  43.150  1.00  62.38   7
ATOM   1309  C    ARG A 429     31.099  44.536  37.707  1.00  29.81   6
ATOM   1310  O    ARG A 429     30.044  45.009  38.101  1.00  30.81   8
ATOM   1311  N    MET A 430     31.941  45.176  36.901  1.00  29.64   7
ATOM   1312  CA   MET A 430     31.644  46.502  36.383  1.00  34.72   6
ATOM   1313  CB   MET A 430     32.745  46.955  35.434  1.00  34.97   6
ATOM   1314  CG   MET A 430     33.937  47.597  36.080  1.00  45.34   6
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1315  SD   MET A 430    33.520  49.120  36.937  1.00  52.55  16
ATOM   1316  CE   MET A 430    32.942  50.174  35.585  1.00  55.96   6
ATOM   1317  C    MET A 430    30.315  46.455  35.634  1.00  34.01   6
ATOM   1318  O    MET A 430    29.455  47.295  35.854  1.00  37.29   8
ATOM   1319  N    ILE A 431    30.180  45.468  34.740  1.00  29.99   7
ATOM   1320  CA   ILE A 431    28.954  45.269  33.969  1.00  28.82   6
ATOM   1321  CB   ILE A 431    28.962  43.936  33.211  1.00  27.39   6
ATOM   1322  CG2  ILE A 431    27.622  43.671  32.572  1.00  23.87   6
ATOM   1323  CG1  ILE A 431    30.044  43.920  32.138  1.00  25.56   6
ATOM   1324  CD1  ILE A 431    29.989  42.703  31.244  1.00  17.29   6
ATOM   1325  C    ILE A 431    27.769  45.269  34.907  1.00  29.49   6
ATOM   1326  O    ILE A 431    26.810  45.993  34.712  1.00  24.19   8
ATOM   1327  N    GLY A 432    27.839  44.435  35.936  1.00  25.25   7
ATOM   1328  CA   GLY A 432    26.748  44.343  36.890  1.00  30.38   6
ATOM   1329  C    GLY A 432    26.494  45.671  37.554  1.00  32.75   6
ATOM   1330  O    GLY A 432    25.411  46.206  37.469  1.00  36.38   8
ATOM   1331  N    ALA A 433    27.514  46.189  38.221  1.00  26.77   7
ATOM   1332  CA   ALA A 433    27.428  47.459  38.910  1.00  26.48   6
ATOM   1333  CB   ALA A 433    28.836  47.970  39.203  1.00  19.90   6
ATOM   1334  C    ALA A 433    26.663  48.502  38.114  1.00  30.73   6
ATOM   1335  O    ALA A 433    25.773  49.164  38.635  1.00  31.60   8
ATOM   1336  N    CYS A 434    27.027  48.654  36.854  1.00  33.22   7
ATOM   1337  CA   CYS A 434    26.371  49.616  35.996  1.00  34.34   6
ATOM   1338  CB   CYS A 434    27.047  49.612  34.711  1.00  35.20   6
ATOM   1339  SG   CYS A 434    27.789  50.811  34.285  1.00  54.48  16
ATOM   1340  C    CYS A 434    24.974  49.198  35.612  1.00  34.09   6
ATOM   1341  O    CYS A 434    24.107  50.040  35.415  1.00  34.89   8
ATOM   1342  N    HIS A 435    24.756  47.898  35.447  1.00  34.30   7
ATOM   1343  CA   HIS A 435    23.453  47.423  35.042  1.00  35.44   6
ATOM   1344  CB   HIS A 435    23.404  45.904  35.104  1.00  31.76   6
ATOM   1345  CG   HIS A 435    22.099  45.351  34.675  1.00  32.03   6
ATOM   1346  CD2  HIS A 435    21.697  44.790  33.519  1.00  28.61   6
ATOM   1347  ND1  HIS A 435    20.941  45.482  35.452  1.00  28.48   7
ATOM   1348  CE1  HIS A 435    19.912  45.025  34.759  1.00  33.27   6
ATOM   1349  NE2  HIS A 435    20.345  44.597  33.583  1.00  31.57   7
ATOM   1350  C    HIS A 435    22.400  47.974  35.972  1.00  32.74   6
ATOM   1351  O    HIS A 435    21.304  48.284  35.565  1.00  32.87   8
ATOM   1352  N    ALA A 436    22.777  48.046  37.241  1.00  31.01   7
ATOM   1353  CA   ALA A 436    21.910  48.563  38.266  1.00  29.91   6
ATOM   1354  CB   ALA A 436    22.661  48.595  39.580  1.00  21.23   6
ATOM   1355  C    ALA A 436    21.475  49.969  37.884  1.00  33.86   6
ATOM   1356  O    ALA A 436    20.296  50.298  37.910  1.00  36.10   8
ATOM   1357  N    SER A 437    22.453  50.795  37.532  1.00  35.19   7
ATOM   1358  CA   SER A 437    22.172  52.167  37.140  1.00  33.03   6
ATOM   1359  CB   SER A 437    23.441  52.815  36.603  1.00  35.31   6
ATOM   1360  OG   SER A 437    23.203  54.151  36.193  1.00  44.99   8
ATOM   1361  C    SER A 437    21.110  52.158  36.055  1.00  38.39   6
ATOM   1362  O    SER A 437    20.049  52.745  36.204  1.00  37.54   8
ATOM   1363  N    ARG A 438    21.432  51.483  34.956  1.00  37.32   7
ATOM   1364  CA   ARG A 438    20.534  51.379  33.821  1.00  39.30   6
ATOM   1365  CB   ARG A 438    21.114  50.402  32.786  1.00  42.97   6
ATOM   1366  CG   ARG A 438    22.343  50.911  32.051  1.00  41.72   6
ATOM   1367  CD   ARG A 438    21.955  52.134  31.251  1.00  45.23   6
ATOM   1368  NE   ARG A 438    20.964  51.839  30.237  1.00  45.66   7
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1369  CZ    ARG A 438    20.063  52.718  29.809  1.00  49.71   6
ATOM   1370  NH1   ARG A 438    20.046  53.958  30.318  1.00  50.91   7
ATOM   1371  NH2   ARG A 438    19.198  52.354  28.865  1.00  46.86   7
ATOM   1372  C     ARG A 438    19.147  50.922  34.240  1.00  42.37   6
ATOM   1373  O     ARG A 438    18.147  51.297  33.625  1.00  40.58   8
ATOM   1374  N     PHE A 439    19.080  50.120  35.298  1.00  42.25   7
ATOM   1375  CA    PHE A 439    17.803  49.624  35.763  1.00  42.81   6
ATOM   1376  CB    PHE A 439    17.975  48.794  37.013  1.00  42.18   6
ATOM   1377  CG    PHE A 439    16.739  48.053  37.413  1.00  42.48   6
ATOM   1378  CD1   PHE A 439    16.198  47.111  36.562  1.00  47.09   6
ATOM   1379  CD2   PHE A 439    16.105  48.320  38.613  1.00  39.76   6
ATOM   1380  CE1   PHE A 439    15.047  46.427  36.905  1.00  49.17   6
ATOM   1381  CE2   PHE A 439    14.940  47.630  38.963  1.00  45.10   6
ATOM   1382  CZ    PHE A 439    14.411  46.683  38.098  1.00  46.36   6
ATOM   1383  C     PHE A 439    16.921  50.803  36.075  1.00  44.79   6
ATOM   1384  O     PHE A 439    15.830  50.903  35.554  1.00  40.26   8
ATOM   1385  N     LEU A 440    17.410  51.681  36.951  1.00  42.77   7
ATOM   1386  CA    LEU A 440    16.660  52.871  37.344  1.00  42.96   6
ATOM   1387  CB    LEU A 440    17.546  53.824  38.150  1.00  37.19   6
ATOM   1388  CG    LEU A 440    17.943  53.297  39.500  1.00  36.97   6
ATOM   1389  CD1   LEU A 440    18.620  54.389  40.316  1.00  33.65   6
ATOM   1390  CD2   LEU A 440    16.679  52.837  40.216  1.00  35.42   6
ATOM   1391  C     LEU A 440    16.025  53.596  36.168  1.00  45.47   6
ATOM   1392  O     LEU A 440    14.809  53.750  36.126  1.00  52.48   8
ATOM   1393  N     HIS A 441    16.836  54.060  35.223  1.00  49.15   7
ATOM   1394  CA    HIS A 441    16.277  54.725  34.063  1.00  54.76   6
ATOM   1395  CB    HIS A 441    17.329  54.955  33.031  1.00  56.68   6
ATOM   1396  CG    HIS A 441    18.134  56.161  33.282  1.00  62.73   6
ATOM   1397  CD2   HIS A 441    18.468  57.216  32.499  1.00  65.73   6
ATOM   1398  ND1   HIS A 441    18.701  56.431  34.538  1.00  66.01   7
ATOM   1399  CE1   HIS A 441    19.332  57.594  34.473  1.00  65.55   6
ATOM   1400  NE2   HIS A 441    19.205  58.085  33.255  1.00  60.09   7
ATOM   1401  C     HIS A 441    15.244  53.822  33.481  1.00  55.93   6
ATOM   1402  O     HIS A 441    14.149  54.263  33.170  1.00  57.33   8
ATOM   1403  N     MET A 442    15.605  52.549  33.313  1.00  57.81   7
ATOM   1404  CA    MET A 442    14.661  51.583  32.778  1.00  59.11   6
ATOM   1405  CB    MET A 442    15.191  50.154  32.922  1.00  55.93   6
ATOM   1406  CG    MET A 442    16.336  49.813  32.022  1.00  58.52   6
ATOM   1407  SD    MET A 442    16.681  48.008  31.851  1.00  60.99  16
ATOM   1408  CE    MET A 442    17.085  47.602  33.581  1.00  52.61   6
ATOM   1409  C     MET A 442    13.339  51.727  33.534  1.00  60.31   6
ATOM   1410  O     MET A 442    12.266  51.560  32.968  1.00  58.18   8
ATOM   1411  N     LYS A 443    13.425  52.054  34.818  1.00  61.45   7
ATOM   1412  CA    LYS A 443    12.236  52.202  35.626  1.00  64.90   6
ATOM   1413  CB    LYS A 443    12.608  52.141  37.090  1.00  64.40   6
ATOM   1414  CG    LYS A 443    11.461  51.748  37.959  1.00  69.12   6
ATOM   1415  CD    LYS A 443    12.068  51.551  39.257  1.00  71.14   6
ATOM   1416  CE    LYS A 443    11.368  51.897  40.091  1.00  73.43   6
ATOM   1417  NZ    LYS A 443    11.883  51.712  41.415  1.00  67.97   7
ATOM   1418  C     LYS A 443    11.513  53.514  35.348  1.00  67.29   6
ATOM   1419  O     LYS A 443    10.390  53.700  35.780  1.00  67.90   8
ATOM   1420  N     VAL A 444    12.171  54.429  34.629  1.00  66.57   7
ATOM   1421  CA    VAL A 444    11.575  55.719  34.297  1.00  64.76   6
ATOM   1422  CB    VAL A 444    12.569  56.869  34.560  1.00  62.76   6
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1423  CG1  VAL A 444    11.952  58.195  34.174  1.00  64.00   6
ATOM   1424  CG2  VAL A 444    12.999  56.891  36.035  1.00  59.27   6
ATOM   1425  C    VAL A 444    11.043  55.730  32.861  1.00  68.61   6
ATOM   1426  O    VAL A 444     9.937  56.210  32.612  1.00  70.60   8
ATOM   1427  N    GLU A 445    11.814  55.173  31.935  1.00  70.71   7
ATOM   1428  CA   GLU A 445    11.457  55.152  30.514  1.00  71.45   6
ATOM   1429  CB   GLU A 445    12.725  55.255  29.664  1.00  72.36   6
ATOM   1430  CG   GLU A 445    13.598  56.429  30.022  1.00  40.00   6
ATOM   1431  CD   GLU A 445    14.875  56.472  29.239  1.00  40.00   6
ATOM   1432  OE1  GLU A 445    15.155  55.565  28.414  1.00  40.00   8
ATOM   1433  OE2  GLU A 445    15.663  57.430  29.430  1.00  40.00   8
ATOM   1434  C    GLU A 445    10.724  53.912  30.049  1.00  71.46   6
ATOM   1435  O    GLU A 445    10.536  53.701  28.844  1.00  73.02   8
ATOM   1436  N    CYS A 446    10.301  53.099  30.999  1.00  71.12   7
ATOM   1437  CA   CYS A 446     9.628  51.899  30.634  1.00  70.83   6
ATOM   1438  CB   CYS A 446    10.595  50.719  30.687  1.00  71.05   6
ATOM   1439  SG   CYS A 446    12.009  50.842  29.573  1.00  72.83  16
ATOM   1440  C    CYS A 446     8.454  51.671  31.535  1.00  71.91   6
ATOM   1441  O    CYS A 446     8.495  52.014  32.728  1.00  72.06   8
ATOM   1442  N    PRO A 447     7.372  51.133  30.978  1.00  73.12   7
ATOM   1443  CD   PRO A 447     7.267  50.764  29.560  1.00  72.88   6
ATOM   1444  CA   PRO A 447     6.150  50.853  31.740  1.00  74.22   6
ATOM   1445  CB   PRO A 447     5.187  50.281  30.714  1.00  72.98   6
ATOM   1446  CG   PRO A 447     5.875  50.271  29.437  1.00  74.77   6
ATOM   1447  C    PRO A 447     6.435  49.843  32.831  1.00  75.94   6
ATOM   1448  O    PRO A 447     7.181  48.908  32.612  1.00  76.67   8
ATOM   1449  N    THR A 448     5.820  50.002  33.997  1.00  76.91   7
ATOM   1450  CA   THR A 448     6.024  49.066  35.113  1.00  78.24   6
ATOM   1451  CB   THR A 448     5.528  49.734  36.401  1.00  81.33   6
ATOM   1452  OG1  THR A 448     4.105  49.917  36.328  1.00  84.46   8
ATOM   1453  CG2  THR A 448     6.192  51.081  36.585  1.00  83.51   6
ATOM   1454  C    THR A 448     5.113  47.912  34.755  1.00  77.42   6
ATOM   1455  O    THR A 448     4.915  46.995  35.519  1.00  77.65   8
ATOM   1456  N    GLU A 449     4.539  48.021  33.565  1.00  76.29   7
ATOM   1457  CA   GLU A 449     3.630  47.023  33.024  1.00  75.03   6
ATOM   1458  CB   GLU A 449     2.600  47.773  32.191  1.00  74.62   6
ATOM   1459  CG   GLU A 449     2.145  47.051  31.001  1.00  40.00   6
ATOM   1460  CD   GLU A 449     1.297  47.889  30.178  1.00  40.00   6
ATOM   1461  OE1  GLU A 449     1.479  49.137  30.146  1.00  40.00   8
ATOM   1462  OE2  GLU A 449     0.424  47.322  29.497  1.00  40.00   8
ATOM   1463  C    GLU A 449     4.434  46.036  32.179  1.00  73.49   6
ATOM   1464  O    GLU A 449     3.882  45.142  31.559  1.00  70.24   8
ATOM   1465  N    LEU A 450     5.747  46.224  32.161  1.00  70.80   7
ATOM   1466  CA   LEU A 450     6.608  45.347  31.378  1.00  68.82   6
ATOM   1467  CB   LEU A 450     7.301  46.154  30.277  1.00  71.91   6
ATOM   1468  CG   LEU A 450     6.464  46.819  29.217  1.00  76.62   6
ATOM   1469  CD1  LEU A 450     7.337  47.662  28.328  1.00  77.95   6
ATOM   1470  CD2  LEU A 450     5.786  45.750  28.415  1.00  76.46   6
ATOM   1471  C    LEU A 450     7.669  44.673  32.243  1.00  66.22   6
ATOM   1472  O    LEU A 450     8.427  43.841  31.752  1.00  66.01   8
ATOM   1473  N    PHE A 451     7.705  45.039  33.530  1.00  61.96   7
ATOM   1474  CA   PHE A 451     8.681  44.506  34.480  1.00  58.44   6
ATOM   1475  CB   PHE A 451     9.041  45.562  35.540  1.00  61.34   6
ATOM   1476  CG   PHE A 451     9.873  46.717  35.008  1.00  63.02   6
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    1477  CD1  PHE  A  451      9.426   47.507   33.963  1.00  62.92   6
ATOM    1478  CD2  PHE  A  451     11.089   47.017   35.593  1.00  63.07   6
ATOM    1479  CE1  PHE  A  451     10.199   48.598   33.521  1.00  65.12   6
ATOM    1480  CE2  PHE  A  451     11.860   48.102   35.156  1.00  64.66   6
ATOM    1481  CZ   PHE  A  451     11.410   48.897   34.118  1.00  67.12   6
ATOM    1482  C    PHE  A  451      8.259   43.264   35.260  1.00  56.41   6
ATOM    1483  O    PHE  A  451      7.641   43.392   36.331  1.00  56.56   8
ATOM    1484  N    PRO  A  452      8.555   42.045   34.755  1.00  53.28   7
ATOM    1485  CD   PRO  A  452      9.177   41.689   33.481  1.00  50.46   6
ATOM    1486  CA   PRO  A  452      8.153   40.859   35.843  1.00  50.26   6
ATOM    1487  CB   PRO  A  452      8.739   39.680   34.780  1.00  49.19   6
ATOM    1488  CG   PRO  A  452      9.178   40.206   33.482  1.00  45.89   6
ATOM    1489  C    PRO  A  452      8.770   40.999   36.935  1.00  49.62   6
ATOM    1490  O    PRO  A  452      9.867   41.529   37.094  1.00  52.35   8
ATOM    1491  N    PRO  A  453      8.139   40.425   37.947  1.00  51.50   7
ATOM    1492  CD   PRO  A  453      7.001   39.542   37.797  1.00  49.66   6
ATOM    1493  CA   PRO  A  453      8.610   40.528   39.323  1.00  50.89   6
ATOM    1494  CB   PRO  A  453      7.675   39.659   40.109  1.00  51.49   6
ATOM    1495  CG   PRO  A  453      6.703   39.141   39.185  1.00  50.82   6
ATOM    1496  C    PRO  A  453     10.015   40.084   39.532  1.00  50.99   6
ATOM    1497  O    PRO  A  453     10.876   40.900   39.838  1.00  54.17   8
ATOM    1498  N    LEU  A  454     10.255   38.781   39.423  1.00  51.21   7
ATOM    1499  CA   LEU  A  454     11.585   38.298   39.674  1.00  47.17   6
ATOM    1500  CB   LEU  A  454     11.813   36.962   38.975  1.00  44.44   6
ATOM    1501  CG   LEU  A  454     13.167   36.375   39.289  1.00  41.33   6
ATOM    1502  CD1  LEU  A  454     13.524   36.638   40.720  1.00  35.93   6
ATOM    1503  CD2  LEU  A  454     13.169   34.907   38.992  1.00  34.79   6
ATOM    1504  C    LEU  A  454     12.541   39.375   39.182  1.00  42.25   6
ATOM    1505  O    LEU  A  454     13.477   39.718   39.886  1.00  40.82   8
ATOM    1506  N    PHE  A  455     12.270   39.957   38.011  1.00  39.29   7
ATOM    1507  CA   PHE  A  455     13.133   41.005   37.473  1.00  41.81   6
ATOM    1508  CB   PHE  A  455     12.527   41.592   36.192  1.00  47.22   6
ATOM    1509  CG   PHE  A  455     13.433   42.565   35.467  1.00  56.97   6
ATOM    1510  CD1  PHE  A  455     14.715   42.189   35.135  1.00  57.23   6
ATOM    1511  CD2  PHE  A  455     12.999   43.840   35.126  1.00  59.40   6
ATOM    1512  CE1  PHE  A  455     15.557   43.059   34.466  1.00  56.58   6
ATOM    1513  CE2  PHE  A  455     13.848   44.716   34.452  1.00  61.80   6
ATOM    1514  CZ   PHE  A  455     15.129   44.322   34.126  1.00  59.94   6
ATOM    1515  C    PHE  A  455     13.273   42.085   38.534  1.00  45.12   6
ATOM    1516  O    PHE  A  455     14.361   42.323   39.034  1.00  39.95   8
ATOM    1517  N    LEU  A  456     12.155   42.735   38.849  1.00  43.92   7
ATOM    1518  CA   LEU  A  456     12.122   43.803   39.840  1.00  44.08   6
ATOM    1519  CB   LEU  A  456     10.680   44.251   40.093  1.00  50.20   6
ATOM    1520  CG   LEU  A  456     10.062   45.242   39.144  1.00  55.79   6
ATOM    1521  CD1  LEU  A  456      8.598   45.432   39.450  1.00  54.70   6
ATOM    1522  CD2  LEU  A  456     10.807   46.548   39.295  1.00  53.01   6
ATOM    1523  C    LEU  A  456     12.739   43.355   41.136  1.00  44.65   6
ATOM    1524  O    LEU  A  456     13.597   44.022   41.685  1.00  45.93   8
ATOM    1525  N    GLU  A  457     11.973   41.761   41.831  1.00  44.56   7
ATOM    1526  CA   GLU  A  457     12.475   41.179   43.105  1.00  46.37   6
ATOM    1527  C    GLU  A  457     14.005   41.236   43.132  1.00  43.60   6
ATOM    1528  O    GLU  A  457     14.583   41.724   44.117  1.00  42.69   8
ATOM    1529  CB   GLU  A  457     12.024   39.723   43.223  1.00  50.16   6
ATOM    1530  CG   GLU  A  457     11.114   39.476   44.427  1.00  20.00   6
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    1531  CD   GLU A 457      10.807  37.994  44.648  1.00  20.00     6
ATOM    1532  OE1  GLU A 457      11.673  37.099  44.311  1.00  20.00     8
ATOM    1533  OE2  GLU A 457       9.683  37.639  45.172  1.00  20.00     8
ATOM    1534  N    VAL A 458      14.928  41.078  41.903  1.00  43.21     7
ATOM    1535  CA   VAL A 458      16.412  41.094  41.868  1.00  44.98     6
ATOM    1536  CB   VAL A 458      16.881  40.306  40.642  1.00  44.83     6
ATOM    1537  CG1  VAL A 458      18.365  40.106  40.698  1.00  49.72     6
ATOM    1538  CG2  VAL A 458      16.185  38.979  40.558  1.00  40.89     6
ATOM    1539  C    VAL A 458      17.130  42.420  41.877  1.00  42.72     6
ATOM    1540  O    VAL A 458      18.061  42.617  42.658  1.00  42.88     8
ATOM    1541  N    PHE A 459      16.713  43.325  41.010  1.00  44.53     7
ATOM    1542  CA   PHE A 459      17.385  44.606  40.892  1.00  48.18     6
ATOM    1543  CB   PHE A 459      17.281  45.104  39.494  1.00  43.60     6
ATOM    1544  CG   PHE A 459      17.915  44.190  38.547  1.00  40.79     6
ATOM    1545  CD1  PHE A 459      17.325  42.983  38.244  1.00  41.01     6
ATOM    1546  CD2  PHE A 459      19.153  44.483  38.054  1.00  39.48     6
ATOM    1547  CE1  PHE A 459      17.988  42.081  37.441  1.00  40.62     6
ATOM    1548  CE2  PHE A 459      19.814  43.589  37.257  1.00  36.87     6
ATOM    1549  CZ   PHE A 459      19.233  42.385  36.940  1.00  36.39     6
ATOM    1550  C    PHE A 459      16.837  45.648  41.744  1.00  52.71     6
ATOM    1551  O    PHE A 459      17.492  46.682  42.017  1.00  51.34     8
ATOM    1552  N    GLU A 460      15.606  45.422  42.161  1.00  62.92     7
ATOM    1553  CA   GLU A 460      15.066  46.428  42.965  1.00  69.33     6
ATOM    1554  CB   GLU A 460      13.552  46.352  43.094  1.00  72.95     6
ATOM    1555  CG   GLU A 460      12.978  47.767  42.957  1.00  78.35     6
ATOM    1556  CD   GLU A 460      12.246  48.261  44.157  1.00  82.97     6
ATOM    1557  OE1  GLU A 460      12.471  47.759  45.281  1.00  88.28     8
ATOM    1558  OE2  GLU A 460      11.422  49.200  44.017  1.00  84.80     8
ATOM    1559  C    GLU A 460      15.736  46.245  44.272  1.00  71.87     6
ATOM    1560  O    GLU A 460      16.187  45.170  44.691  1.00  74.51     8
ATOM    1561  N    ASP A 461      15.790  47.373  44.917  1.00  78.50     7
ATOM    1562  CA   ASP A 461      16.415  47.505  46.173  1.00  84.19     6
ATOM    1563  CB   ASP A 461      16.394  48.981  46.471  1.00  85.82     6
ATOM    1564  CG   ASP A 461      16.801  49.786  45.276  1.00  89.62     6
ATOM    1565  OD1  ASP A 461      16.692  49.344  44.086  1.00  93.00     8
ATOM    1566  OD2  ASP A 461      17.239  50.923  45.482  1.00  93.04     8
ATOM    1567  C    ASP A 461      15.639  46.703  47.214  1.00  86.80     6
ATOM    1568  O    ASP A 461      16.245  45.748  47.731  1.00  88.70     8
ATOM    1569  OXT  ASP A 461      14.457  47.026  47.451  1.00  88.70     8
TER
ATOM       1  CB   LYS B 211     -20.802  66.251  39.780  1.00  46.72     6
ATOM       2  CG   LYS B 211     -19.566  65.345  39.922  1.00  56.48     6
ATOM       3  CD   LYS B 211     -18.264  66.114  40.045  1.00  60.93     6
ATOM       4  CE   LYS B 211     -18.043  67.067  38.886  1.00  61.95     6
ATOM       5  NZ   LYS B 211     -19.008  68.224  38.903  1.00  69.93     7
ATOM       6  C    LYS B 211     -22.418  67.861  40.818  1.00  35.68     6
ATOM       7  O    LYS B 211     -23.356  67.113  40.454  1.00  33.58     8
ATOM       8  N    LYS B 211     -20.742  66.675  42.239  1.00  45.76     7
ATOM       9  CA   LYS B 211     -20.998  67.285  40.894  1.00  43.42     6
ATOM      10  N    PRO B 212     -22.610  69.205  41.068  1.00  35.64     7
ATOM      11  CD   PRO B 212     -21.526  70.177  41.287  1.00  38.60     6
ATOM      12  CA   PRO B 212     -23.943  69.861  41.036  1.00  38.35     6
ATOM      13  CB   PRO B 212     -23.657  71.320  41.420  1.00  38.95     6
ATOM      14  CG   PRO B 212     -22.226  71.474  41.551  1.00  42.00     6
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM     15   C    PRO B 212    -24.798   69.772   39.807   1.00   38.78    6
ATOM     16   O    PRO B 212    -24.350   70.045   38.696   1.00   34.64    8
ATOM     17   N    GLU B 213    -26.058   69.424   40.032   1.00   40.31    7
ATOM     18   CA   GLU B 213    -27.081   69.290   39.003   1.00   43.87    6
ATOM     19   CB   GLU B 213    -27.895   68.004   39.265   1.00   45.16    6
ATOM     20   CG   GLU B 213    -27.032   66.709   39.286   1.00   47.60    6
ATOM     21   CD   GLU B 213    -27.807   65.421   39.199   1.00   50.68    6
ATOM     22   OE1  GLU B 213    -28.847   65.244   39.886   1.00   59.18    8
ATOM     23   OE2  GLU B 213    -27.382   64.516   38.442   1.00   49.06    8
ATOM     24   C    GLU B 213    -27.924   70.576   39.080   1.00   45.96    6
ATOM     25   O    GLU B 213    -27.624   71.467   39.859   1.00   43.13    8
ATOM     26   N    PRO B 214    -28.987   70.698   38.308   1.00   46.52    7
ATOM     27   CD   PRO B 214    -29.484   69.635   37.446   1.00   46.44    6
ATOM     28   CA   PRO B 214    -29.843   71.907   38.302   1.00   47.52    6
ATOM     29   CB   PRO B 214    -30.799   71.639   37.210   1.00   45.40    6
ATOM     30   CG   PRO B 214    -30.530   70.257   36.805   1.00   49.89    6
ATOM     31   C    PRO B 214    -30.574   72.330   39.535   1.00   45.70    6
ATOM     32   O    PRO B 214    -30.597   71.595   40.483   1.00   44.49    8
ATOM     33   N    THR B 215    -31.180   73.515   39.506   1.00   45.24    7
ATOM     34   CA   THR B 215    -31.965   74.036   40.652   1.00   49.36    6
ATOM     35   CB   THR B 215    -31.443   75.420   41.091   1.00   44.86    6
ATOM     36   OG1  THR B 215    -32.249   76.464   40.534   1.00   52.26    8
ATOM     37   CG2  THR B 215    -30.011   75.617   40.659   1.00   39.43    6
ATOM     38   C    THR B 215    -33.386   74.239   40.114   1.00   52.51    6
ATOM     39   O    THR B 215    -33.562   74.868   39.078   1.00   53.48    8
ATOM     40   N    ASP B 216    -34.387   73.741   40.829   1.00   58.81    7
ATOM     41   CA   ASP B 216    -35.795   73.865   40.435   1.00   61.51    6
ATOM     42   CB   ASP B 216    -36.674   74.005   41.650   1.00   70.57    6
ATOM     43   CG   ASP B 216    -37.675   72.981   41.710   1.00   78.07    6
ATOM     44   OD1  ASP B 216    -38.228   72.588   40.652   1.00   82.31    8
ATOM     45   OD2  ASP B 216    -37.983   72.567   42.830   1.00   86.55    8
ATOM     46   C    ASP B 216    -35.920   75.123   39.648   1.00   58.42    6
ATOM     47   O    ASP B 216    -36.847   75.317   38.827   1.00   56.85    8
ATOM     48   N    GLU B 217    -34.954   75.979   39.984   1.00   54.92    7
ATOM     49   CA   GLU B 217    -34.851   77.259   39.353   1.00   53.37    6
ATOM     50   CB   GLU B 217    -34.104   78.264   40.251   1.00   51.02    6
ATOM     51   CG   GLU B 217    -34.151   79.689   39.679   1.00   40.00    6
ATOM     52   CD   GLU B 217    -34.301   80.745   40.739   1.00   40.00    6
ATOM     53   OE1  GLU B 217    -34.089   80.443   41.945   1.00   40.00    8
ATOM     54   OE2  GLU B 217    -34.625   81.921   40.411   1.00   40.00    8
ATOM     55   C    GLU B 217    -34.232   77.163   37.957   1.00   53.55    6
ATOM     56   O    GLU B 217    -34.815   77.612   37.018   1.00   54.33    8
ATOM     57   N    GLU B 218    -33.063   76.572   37.839   1.00   49.20    7
ATOM     58   CA   GLU B 218    -32.318   76.385   36.608   1.00   45.94    6
ATOM     59   CB   GLU B 218    -30.965   75.793   36.981   1.00   43.43    6
ATOM     60   CG   GLU B 218    -30.065   76.728   37.801   1.00   40.86    6
ATOM     61   CD   GLU B 218    -28.713   76.159   38.072   1.00   39.88    6
ATOM     62   OE1  GLU B 218    -28.606   74.967   38.449   1.00   37.61    8
ATOM     63   OE2  GLU B 218    -27.707   76.901   37.945   1.00   34.01    8
ATOM     64   C    GLU B 218    -33.014   75.475   35.610   1.00   44.71    6
ATOM     65   O    GLU B 218    -32.935   75.686   34.405   1.00   45.31    8
ATOM     66   N    TRP B 219    -33.669   74.439   36.131   1.00   44.02    7
ATOM     67   CA   TRP B 219    -34.368   73.490   35.290   1.00   46.97    6
ATOM     68   CB   TRP B 219    -35.046   72.408   36.119   1.00   48.42    6
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM     69  CG   TRP B 219     -34.195  71.230  36.374  1.00  54.61   6
ATOM     70  CD2  TRP B 219     -34.048  70.120  35.478  1.00  55.24   6
ATOM     71  CE2  TRP B 219     -33.076  69.248  36.063  1.00  53.67   6
ATOM     72  CE3  TRP B 219     -34.615  69.771  34.252  1.00  54.55   6
ATOM     73  CD1  TRP B 219     -33.399  71.019  37.415  1.00  55.75   6
ATOM     74  NE1  TRP B 219     -32.697  69.838  37.236  1.00  54.43   7
ATOM     75  CZ2  TRP B 219     -32.635  68.075  35.431  1.00  52.54   6
ATOM     76  CZ3  TRP B 219     -34.214  68.603  33.643  1.00  55.17   6
ATOM     77  CH2  TRP B 219     -33.234  67.758  34.214  1.00  55.59   6
ATOM     78  C    TRP B 219     -35.409  74.199  34.459  1.00  47.32   6
ATOM     79  O    TRP B 219     -35.561  73.914  33.277  1.00  43.56   8
ATOM     80  N    GLU B 220     -36.126  75.130  35.084  1.00  49.91   7
ATOM     81  CA   GLU B 220     -37.158  75.874  34.402  1.00  53.57   6
ATOM     82  CB   GLU B 220     -37.811  76.820  35.373  1.00  58.18   6
ATOM     83  CG   GLU B 220     -39.251  76.812  35.221  1.00  73.13   6
ATOM     84  CD   GLU B 220     -39.824  76.858  36.489  1.00  80.06   6
ATOM     85  OE1  GLU B 220     -39.485  75.995  37.324  1.00  82.12   8
ATOM     86  OE2  GLU B 220     -40.635  77.740  36.718  1.00  82.78   8
ATOM     87  C    GLU B 220     -36.539  76.645  33.250  1.00  50.51   6
ATOM     88  O    GLU B 220     -37.160  76.793  32.195  1.00  49.94   8
ATOM     89  N    LEU B 221     -35.312  77.135  33.455  1.00  43.71   7
ATOM     90  CA   LEU B 221     -34.604  77.884  32.411  1.00  42.81   6
ATOM     91  CB   LEU B 221     -33.214  78.324  32.865  1.00  39.21   6
ATOM     92  CG   LEU B 221     -32.321  78.833  31.754  1.00  36.34   6
ATOM     93  CD1  LEU B 221     -33.073  79.843  30.927  1.00  36.93   6
ATOM     94  CD2  LEU B 221     -31.058  79.446  32.331  1.00  24.18   6
ATOM     95  C    LEU B 221     -34.454  77.011  31.192  1.00  43.46   6
ATOM     96  O    LEU B 221     -34.819  77.406  30.104  1.00  45.25   8
ATOM     97  N    ILE B 222     -33.878  75.829  31.398  1.00  39.09   7
ATOM     98  CA   ILE B 222     -33.687  74.857  30.330  1.00  35.47   6
ATOM     99  CB   ILE B 222     -33.224  73.516  30.871  1.00  33.74   6
ATOM    100  CG2  ILE B 222     -33.204  72.488  29.776  1.00  28.86   6
ATOM    101  CG1  ILE B 222     -31.840  73.631  31.493  1.00  33.33   6
ATOM    102  CD1  ILE B 222     -31.435  72.419  32.264  1.00  34.85   6
ATOM    103  C    ILE B 222     -34.991  74.627  29.598  1.00  34.26   6
ATOM    104  O    ILE B 222     -35.082  74.832  28.392  1.00  31.90   8
ATOM    105  N    LYS B 223     -35.992  74.183  30.346  1.00  39.49   7
ATOM    106  CA   LYS B 223     -37.300  73.892  29.785  1.00  44.43   6
ATOM    107  CB   LYS B 223     -38.351  73.876  30.882  1.00  50.81   6
ATOM    108  CG   LYS B 223     -39.693  73.358  30.411  1.00  62.51   6
ATOM    109  CD   LYS B 223     -40.795  73.532  31.449  1.00  72.22   6
ATOM    110  CE   LYS B 223     -42.163  73.249  30.827  1.00  74.55   6
ATOM    111  NZ   LYS B 223     -43.268  73.378  31.837  1.00  75.78   7
ATOM    112  C    LYS B 223     -37.648  74.942  28.755  1.00  42.81   6
ATOM    113  O    LYS B 223     -38.337  74.661  27.796  1.00  40.36   8
ATOM    114  N    THR B 224     -37.146  76.156  28.979  1.00  39.89   7
ATOM    115  CA   THR B 224     -37.353  77.293  28.074  1.00  39.93   6
ATOM    116  CB   THR B 224     -36.956  78.609  28.776  1.00  40.57   6
ATOM    117  OG1  THR B 224     -37.646  78.740  30.028  1.00  39.27   8
ATOM    118  CG2  THR B 224     -37.273  79.805  27.893  1.00  38.11   6
ATOM    119  C    THR B 224     -36.521  77.094  26.789  1.00  39.96   6
ATOM    120  O    THR B 224     -37.043  76.677  25.756  1.00  36.67   8
ATOM    121  N    VAL B 225     -35.231  77.421  26.888  1.00  38.02   7
ATOM    122  CA   VAL B 225     -34.263  77.295  25.801  1.00  38.12   6
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    123   CB   VAL B 225    -32.869   77.015   26.348   1.00 38.19   6
ATOM    124   CG1  VAL B 225    -31.863   76.983   25.226   1.00 36.77   6
ATOM    125   CG2  VAL B 225    -32.483   78.050   27.353   1.00 41.76   6
ATOM    126   C    VAL B 225    -34.656   76.191   24.843   1.00 37.52   6
ATOM    127   O    VAL B 225    -34.621   76.364   23.638   1.00 36.77   8
ATOM    128   N    THR B 226    -35.005   75.046   25.410   1.00 34.02   7
ATOM    129   CA   THR B 226    -35.423   73.887   24.638   1.00 34.67   6
ATOM    130   CB   THR B 226    -35.677   72.707   25.574   1.00 30.56   6
ATOM    131   OG1  THR B 226    -34.432   72.225   26.084   1.00 32.20   8
ATOM    132   CG2  THR B 226    -36.413   71.595   24.874   1.00 20.99   6
ATOM    133   C    THR B 226    -36.664   74.170   23.803   1.00 36.41   6
ATOM    134   O    THR B 226    -36.633   74.054   22.578   1.00 39.64   8
ATOM    135   N    ALA B 227    -37.746   74.542   24.480   1.00 39.20   7
ATOM    136   CA   ALA B 227    -39.008   74.861   23.822   1.00 36.93   6
ATOM    137   CB   ALA B 227    -39.914   75.631   24.785   1.00 38.06   6
ATOM    138   C    ALA B 227    -38.686   75.719   22.608   1.00 37.69   6
ATOM    139   O    ALA B 227    -39.317   75.616   21.566   1.00 40.94   8
ATOM    140   N    ALA B 228    -37.677   76.572   22.785   1.00 32.86   7
ATOM    141   CA   ALA B 228    -37.216   77.483   21.753   1.00 32.48   6
ATOM    142   CB   ALA B 228    -36.252   78.458   22.358   1.00 28.25   6
ATOM    143   C    ALA B 228    -36.545   76.704   20.638   1.00 36.12   6
ATOM    144   O    ALA B 228    -37.078   76.586   19.544   1.00 37.86   8
ATOM    145   N    HIS B 229    -35.364   76.175   20.924   1.00 33.58   7
ATOM    146   CA   HIS B 229    -34.611   75.409   19.956   1.00 32.97   6
ATOM    147   CB   HIS B 229    -33.418   74.721   20.597   1.00 33.69   6
ATOM    148   CG   HIS B 229    -32.776   73.714   19.715   1.00 28.39   6
ATOM    149   CD2  HIS B 229    -32.535   72.384   19.863   1.00 28.83   6
ATOM    150   ND1  HIS B 229    -32.336   74.030   18.426   1.00 30.47   7
ATOM    151   CE1  HIS B 229    -31.867   72.929   17.855   1.00 26.95   6
ATOM    152   NE2  HIS B 229    -31.976   71.927   18.700   1.00 31.27   7
ATOM    153   C    HIS B 229    -35.362   74.352   19.202   1.00 38.40   6
ATOM    154   O    HIS B 229    -35.069   74.131   18.045   1.00 41.49   8
ATOM    155   N    VAL B 230    -36.296   73.688   19.882   1.00 38.55   7
ATOM    156   CA   VAL B 230    -37.077   72.634   19.263   1.00 40.40   6
ATOM    157   CB   VAL B 230    -37.744   71.747   20.310   1.00 44.68   6
ATOM    158   CG1  VAL B 230    -38.381   70.537   19.637   1.00 39.39   6
ATOM    159   CG2  VAL B 230    -36.742   71.311   21.356   1.00 42.18   6
ATOM    160   C    VAL B 230    -38.133   73.130   18.284   1.00 44.28   6
ATOM    161   O    VAL B 230    -38.375   72.505   17.248   1.00 45.94   8
ATOM    162   N    ALA B 231    -38.774   74.240   18.623   1.00 45.59   7
ATOM    163   CA   ALA B 231    -39.820   74.804   17.792   1.00 47.84   6
ATOM    164   CB   ALA B 231    -40.736   75.661   18.647   1.00 45.08   6
ATOM    165   C    ALA B 231    -39.235   75.636   16.673   1.00 48.04   6
ATOM    166   O    ALA B 231    -39.959   76.128   15.816   1.00 49.95   8
ATOM    167   N    THR B 232    -37.914   75.773   16.669   1.00 47.26   7
ATOM    168   CA   THR B 232    -37.220   76.563   15.654   1.00 43.64   6
ATOM    169   CB   THR B 232    -36.482   77.746   16.315   1.00 41.93   6
ATOM    170   OG1  THR B 232    -35.385   77.270   17.098   1.00 39.10   8
ATOM    171   CG2  THR B 232    -37.423   78.523   17.232   1.00 29.80   6
ATOM    172   C    THR B 232    -36.194   75.719   14.914   1.00 43.97   6
ATOM    173   O    THR B 232    -35.401   76.252   14.155   1.00 40.55   8
ATOM    174   N    ASN B 233    -36.195   74.407   15.157   1.00 48.62   7
ATOM    175   CA   ASN B 233    -35.247   73.511   14.483   1.00 58.62   6
ATOM    176   CB   ASN B 233    -34.621   72.537   15.500   1.00 62.44   6
```

UNITED STATES PATENT AND TRADEMARK OFFICE
CERTIFICATE OF CORRECTION

| | | |
|---|---|---|
| PATENT NO. | : 6,965,850 B2 | Page 41 of 186 |
| APPLICATION NO. | : 09/281717 | |
| DATED | : November 15, 2005 | |
| INVENTOR(S) | : John D. Baxter et al. | |

It is certified that error appears in the above-identified patent and that said Letters Patent is hereby corrected as shown below:

```
ATOM    177  CG   ASN B 233    -33.407  71.812  14.946  1.00  68.35   6
ATOM    178  OD1  ASN B 233    -32.569  72.427  14.256  1.00  65.50   8
ATOM    179  ND2  ASN B 233    -33.288  70.529  15.265  1.00  74.29   7
ATOM    180  C    ASN B 233    -36.033  72.755  13.437  1.00  65.06   6
ATOM    181  O    ASN B 233    -36.950  72.005  13.754  1.00  69.47   8
ATOM    182  N    ALA B 234    -35.674  72.986  12.182  1.00  68.80   7
ATOM    183  CA   ALA B 234    -36.352  72.376  11.036  1.00  70.98   6
ATOM    184  CB   ALA B 234    -35.585  72.701   9.769  1.00  71.43   6
ATOM    185  C    ALA B 234    -36.556  70.880  11.111  1.00  73.83   6
ATOM    186  O    ALA B 234    -35.677  70.142  11.801  1.00  74.33   8
ATOM    187  N    GLN B 235    -37.754  70.479  10.717  1.00  75.07   7
ATOM    188  CA   GLN B 235    -38.149  69.095  10.690  1.00  76.32   6
ATOM    189  CB   GLN B 235    -37.468  68.365   9.533  1.00  76.98   6
ATOM    190  CG   GLN B 235    -38.120  68.540   8.170  1.00  77.07   6
ATOM    191  CD   GLN B 235    -38.572  69.940   7.909  1.00  80.85   6
ATOM    192  OE1  GLN B 235    -39.575  70.401   8.491  1.00  82.01   8
ATOM    193  NE2  GLN B 235    -37.862  70.620   7.040  1.00  78.80   7
ATOM    194  C    GLN B 235    -37.904  68.331  11.953  1.00  77.15   6
ATOM    195  O    GLN B 235    -38.087  67.137  11.947  1.00  76.06   8
ATOM    196  N    GLY B 236    -37.511  68.985  13.039  1.00  77.46   7
ATOM    197  CA   GLY B 236    -37.304  68.263  14.288  1.00  78.37   6
ATOM    198  C    GLY B 236    -36.717  66.882  14.217  1.00  79.43   6
ATOM    199  O    GLY B 236    -35.717  66.650  13.542  1.00  79.47   8
ATOM    200  N    SER B 237    -37.420  66.007  14.943  1.00  77.98   7
ATOM    201  CA   SER B 237    -37.117  64.600  15.092  1.00  76.49   6
ATOM    202  CB   SER B 237    -38.118  63.953  16.066  1.00  76.46   6
ATOM    203  C    SER B 237    -37.181  63.895  13.737  1.00  75.35   6
ATOM    204  O    SER B 237    -36.493  62.911  13.524  1.00  75.47   8
ATOM    205  N    HIS B 238    -38.004  64.443  12.845  1.00  75.36   7
ATOM    206  CA   HIS B 238    -38.293  63.926  11.519  1.00  75.46   6
ATOM    207  CB   HIS B 238    -39.663  64.397  11.096  1.00  75.85   6
ATOM    208  C    HIS B 238    -37.369  64.216  10.380  1.00  74.10   6
ATOM    209  O    HIS B 238    -37.747  64.135   9.222  1.00  75.34   8
ATOM    210  N    TRP B 239    -36.127  64.427  10.651  1.00  73.39   7
ATOM    211  CA   TRP B 239    -35.345  64.786   9.519  1.00  74.02   6
ATOM    212  CB   TRP B 239    -34.121  65.542   9.934  1.00  81.77   6
ATOM    213  CG   TRP B 239    -33.085  64.786  10.737  1.00  89.67   6
ATOM    214  CD2  TRP B 239    -31.727  64.530  10.302  1.00  93.19   6
ATOM    215  CE2  TRP B 239    -31.069  63.848  11.393  1.00  95.46   6
ATOM    216  CE3  TRP B 239    -30.949  64.941   9.196  1.00  95.35   6
ATOM    217  CD1  TRP B 239    -33.237  64.180  11.926  1.00  94.16   6
ATOM    218  NE1  TRP B 239    -32.022  63.631  12.347  1.00  97.48   7
ATOM    219  CZ2  TRP B 239    -29.706  63.475  11.348  1.00  96.23   6
ATOM    220  CZ3  TRP B 239    -29.613  64.533   9.128  1.00  96.75   6
ATOM    221  CH2  TRP B 239    -28.978  63.870  10.215  1.00  97.32   6
ATOM    222  C    TRP B 239    -34.994  63.722   8.539  1.00  70.77   6
ATOM    223  O    TRP B 239    -35.423  63.772   7.388  1.00  71.70   8
ATOM    224  N    LYS B 240    -34.165  62.791   8.955  1.00  67.10   7
ATOM    225  CA   LYS B 240    -33.724  61.744   8.077  1.00  65.63   6
ATOM    226  CB   LYS B 240    -33.321  60.539   8.906  1.00  66.65   6
ATOM    227  CG   LYS B 240    -32.210  60.824   9.905  1.00  69.83   6
ATOM    228  CD   LYS B 240    -31.759  59.553  10.602  1.00  71.49   6
ATOM    229  CE   LYS B 240    -30.576  59.843  11.493  1.00  71.31   6
ATOM    230  NZ   LYS B 240    -30.106  58.604  12.157  1.00  72.23   7
```

UNITED STATES PATENT AND TRADEMARK OFFICE
CERTIFICATE OF CORRECTION

| | |
|---|---|
| PATENT NO. | : 6,965,850 B2 |
| APPLICATION NO. | : 09/281717 |
| DATED | : November 15, 2005 |
| INVENTOR(S) | : John D. Baxter et al. |

It is certified that error appears in the above-identified patent and that said Letters Patent is hereby corrected as shown below:

```
ATOM    231  C    LYS B 240    -34.719  61.331   6.996  1.00  66.19   6
ATOM    232  O    LYS B 240    -34.321  60.673   6.031  1.00  65.20   8
ATOM    233  N    ASN B 241    -35.986  61.727   7.139  1.00  66.69   7
ATOM    234  CA   ASN B 241    -37.031  61.393   6.171  1.00  67.53   6
ATOM    235  CB   ASN B 241    -38.240  60.846   6.915  1.00  67.98   6
ATOM    236  CG   ASN B 241    -37.966  59.479   7.544  1.00  70.19   6
ATOM    237  OD1  ASN B 241    -37.561  58.526   6.845  1.00  71.37   8
ATOM    238  ND2  ASN B 241    -38.205  59.370   8.836  1.00  71.48   7
ATOM    239  C    ASN B 241    -37.496  62.532   5.255  1.00  66.62   6
ATOM    240  O    ASN B 241    -38.504  62.395   4.578  1.00  64.76   8
ATOM    241  N    LYS B 242    -36.753  63.633   5.209  1.00  66.86   7
ATOM    242  CA   LYS B 242    -37.096  64.772   4.362  1.00  67.46   6
ATOM    243  CB   LYS B 242    -37.501  65.948   5.258  1.00  67.93   6
ATOM    244  CG   LYS B 242    -38.746  65.694   6.076  1.00  71.52   6
ATOM    245  CD   LYS B 242    -40.007  65.528   5.215  1.00  74.32   6
ATOM    246  CE   LYS B 242    -40.416  66.852   4.564  1.00  74.41   6
ATOM    247  NZ   LYS B 242    -40.657  67.941   5.575  1.00  74.44   7
ATOM    248  C    LYS B 242    -35.826  65.081   3.592  1.00  66.28   6
ATOM    249  O    LYS B 242    -35.814  65.799   2.601  1.00  67.61   8
ATOM    250  N    ARG B 243    -34.763  64.485   4.112  1.00  64.19   7
ATOM    251  CA   ARG B 243    -33.410  64.577   3.591  1.00  62.43   6
ATOM    252  CB   ARG B 243    -32.599  63.547   4.390  1.00  60.12   6
ATOM    253  CG   ARG B 243    -31.128  63.558   4.171  1.00  40.00   6
ATOM    254  CD   ARG B 243    -30.335  62.888   5.319  1.00  40.00   6
ATOM    255  NE   ARG B 243    -30.269  61.428   5.296  1.00  40.00   7
ATOM    256  CZ   ARG B 243    -29.364  60.724   6.009  1.00  40.00   6
ATOM    257  NH1  ARG B 243    -28.510  61.357   6.798  1.00  40.00   7
ATOM    258  NH2  ARG B 243    -29.355  59.401   5.908  1.00  40.00   7
ATOM    259  C    ARG B 243    -33.408  64.252   2.100  1.00  62.97   6
ATOM    260  O    ARG B 243    -33.690  63.122   1.722  1.00  63.96   8
ATOM    261  N    LYS B 244    -33.105  65.245   1.270  1.00  62.41   7
ATOM    262  CA   LYS B 244    -33.054  65.053  -0.179  1.00  61.57   6
ATOM    263  CB   LYS B 244    -34.104  65.941  -0.866  1.00  63.68   6
ATOM    264  CG   LYS B 244    -35.527  65.731  -0.337  1.00  71.29   6
ATOM    265  CD   LYS B 244    -36.566  66.549  -1.107  1.00  73.83   6
ATOM    266  CE   LYS B 244    -36.219  68.045  -1.138  1.00  74.71   6
ATOM    267  NZ   LYS B 244    -36.169  68.689   0.219  1.00  73.32   7
ATOM    268  C    LYS B 244    -31.659  65.402  -0.670  1.00  59.30   6
ATOM    269  O    LYS B 244    -31.317  66.570  -0.852  1.00  56.34   8
ATOM    270  N    PHE B 245    -30.859  64.359  -0.875  1.00  57.06   7
ATOM    271  CA   PHE B 245    -29.462  64.525  -1.305  1.00  59.01   6
ATOM    272  CB   PHE B 245    -28.786  63.179  -1.478  1.00  59.62   6
ATOM    273  CG   PHE B 245    -28.991  62.288  -0.339  1.00  66.60   6
ATOM    274  CD1  PHE B 245    -30.200  61.669  -0.172  1.00  67.17   6
ATOM    275  CD2  PHE B 245    -28.012  62.117   0.593  1.00  69.25   6
ATOM    276  CE1  PHE B 245    -30.404  60.882   0.911  1.00  69.92   6
ATOM    277  CE2  PHE B 245    -28.229  61.329   1.669  1.00  70.50   6
ATOM    278  CZ   PHE B 245    -29.418  60.714   1.830  1.00  70.89   6
ATOM    279  C    PHE B 245    -29.301  65.282  -2.592  1.00  60.68   6
ATOM    280  O    PHE B 245    -29.859  64.911  -3.619  1.00  62.37   8
ATOM    281  N    LEU B 246    -28.495  66.336  -2.505  1.00  60.10   7
ATOM    282  CA   LEU B 246    -28.201  67.199  -3.631  1.00  59.44   6
ATOM    283  CB   LEU B 246    -27.248  68.332  -3.231  1.00  57.43   6
ATOM    284  CG   LEU B 246    -27.118  69.474  -4.207  1.00  54.41   6
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    285  CD1  LEU  B  246    -28.481  70.137   -4.349  1.00  52.43  6
ATOM    286  CD2  LEU  B  246    -26.112  70.470   -3.719  1.00  51.69  6
ATOM    287  C    LEU  B  246    -27.585  66.379   -4.740  1.00  62.05  6
ATOM    288  O    LEU  B  246    -26.789  65.446   -4.486  1.00  59.85  8
ATOM    289  N    PRO  B  247    -27.930  66.693   -5.984  1.00  63.33  7
ATOM    290  CD   PRO  B  247    -28.839  67.781   -6.363  1.00  64.44  6
ATOM    291  CA   PRO  B  247    -27.391  65.958   -7.130  1.00  63.56  6
ATOM    292  CB   PRO  B  247    -27.976  66.675   -8.340  1.00  64.42  6
ATOM    293  CG   PRO  B  247    -28.873  67.714   -7.841  1.00  64.90  6
ATOM    294  C    PRO  B  247    -25.866  65.947   -7.143  1.00  61.94  6
ATOM    295  O    PRO  B  247    -25.223  66.944   -6.856  1.00  61.60  8
ATOM    296  N    GLU  B  248    -25.333  64.771   -7.478  1.00  61.33  7
ATOM    297  CA   GLU  B  248    -23.896  64.516   -7.590  1.00  63.50  6
ATOM    298  CB   GLU  B  248    -23.630  63.154   -8.248  1.00  66.94  6
ATOM    299  CG   GLU  B  248    -22.168  62.953   -8.713  1.00  68.70  6
ATOM    300  CD   GLU  B  248    -21.898  61.745   -9.580  1.00  40.00  6
ATOM    301  OE1  GLU  B  248    -22.863  61.007  -10.035  1.00  40.00  8
ATOM    302  OE2  GLU  B  248    -20.709  61.460   -9.838  1.00  40.00  8
ATOM    303  C    GLU  B  248    -23.158  65.571   -8.415  1.00  64.19  6
ATOM    304  O    GLU  B  248    -22.056  65.975   -8.066  1.00  65.56  8
ATOM    305  N    ASP  B  249    -23.796  66.019   -9.498  1.00  64.36  7
ATOM    306  CA   ASP  B  249    -23.254  66.994  -10.436  1.00  63.33  6
ATOM    307  CB   ASP  B  249    -24.122  67.031  -11.698  1.00  62.97  6
ATOM    308  CG   ASP  B  249    -25.437  67.715  -11.489  1.00  64.63  6
ATOM    309  OD1  ASP  B  249    -26.235  67.285  -10.629  1.00  64.84  8
ATOM    310  OD2  ASP  B  249    -25.726  68.718  -12.189  1.00  66.52  8
ATOM    311  C    ASP  B  249    -23.068  68.413   -9.960  1.00  64.31  6
ATOM    312  O    ASP  B  249    -22.117  69.084  -10.355  1.00  64.73  8
ATOM    313  N    ILE  B  250    -23.987  68.892   -9.136  1.00  63.09  7
ATOM    314  CA   ILE  B  250    -23.921  70.281   -8.660  1.00  64.39  6
ATOM    315  CB   ILE  B  250    -25.124  70.575   -7.798  1.00  65.79  6
ATOM    316  CG2  ILE  B  250    -25.559  72.041   -7.858  1.00  64.78  6
ATOM    317  CG1  ILE  B  250    -26.348  69.752   -8.206  1.00  65.28  6
ATOM    318  CD1  ILE  B  250    -27.671  70.444   -7.887  1.00  65.08  6
ATOM    319  C    ILE  B  250    -22.815  70.488   -7.714  1.00  65.21  6
ATOM    320  O    ILE  B  250    -22.754  69.847   -6.656  1.00  64.05  8
ATOM    321  N    GLY  B  251    -22.024  71.392   -8.103  1.00  65.48  7
ATOM    322  CA   GLY  B  251    -20.873  71.721   -7.342  1.00  67.32  6
ATOM    323  C    GLY  B  251    -19.808  70.806   -7.800  1.00  68.52  6
ATOM    324  O    GLY  B  251    -19.791  70.548   -9.025  1.00  65.49  8
ATOM    325  N    GLN  B  252    -19.074  70.440   -6.799  1.00  72.26  7
ATOM    326  CA   GLN  B  252    -17.949  69.540   -6.883  1.00  74.10  6
ATOM    327  CB   GLN  B  252    -18.460  68.098   -6.723  1.00  75.82  6
ATOM    328  CG   GLN  B  252    -17.367  67.088   -6.356  1.00  77.81  6
ATOM    329  CD   GLN  B  252    -17.924  65.759   -5.824  1.00  79.38  6
ATOM    330  OE1  GLN  B  252    -18.615  65.042   -6.549  1.00  80.55  8
ATOM    331  NE2  GLN  B  252    -17.661  65.380   -4.586  1.00  78.12  7
ATOM    332  C    GLN  B  252    -17.258  69.727   -8.258  1.00  77.17  6
ATOM    333  O    GLN  B  252    -17.977  70.009   -9.227  1.00  76.50  8
ATOM    334  N    ALA  B  253    -15.718  69.795   -8.279  1.00  80.78  7
ATOM    335  CA   ALA  B  253    -14.615  70.766   -8.544  1.00  83.70  6
ATOM    336  CB   ALA  B  253    -13.794  70.914   -7.255  1.00  83.23  6
ATOM    337  C    ALA  B  253    -13.605  70.732   -9.731  1.00  85.59  6
ATOM    338  O    ALA  B  253    -13.186  69.691  -10.171  1.00  85.69  8
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    339  N    PRO B 254     -13.223  71.944 -10.246  1.00 35.05     7
ATOM    340  CD   PRO B 254     -13.798  73.217  -9.792  1.00 33.97     6
ATOM    341  CA   PRO B 254     -12.266  72.177 -11.351  1.00 35.89     6
ATOM    342  CB   PRO B 254     -12.275  73.710 -11.596  1.00 33.94     6
ATOM    343  CG   PRO B 254     -13.222  74.277 -10.688  1.00 33.31     6
ATOM    344  C    PRO B 254     -10.827  71.665 -11.121  1.00 37.75     6
ATOM    345  O    PRO B 254     -10.379  71.426 -10.009  1.00 38.78     8
TER
ATOM      1  N    GLY B 261      -8.238  79.356  -2.979  1.00 40.00     7
ATOM      2  CA   GLY B 261      -9.314  78.411  -3.005  1.00 40.00     6
ATOM      3  C    GLY B 261     -10.206  78.717  -4.355  1.00 40.00     6
ATOM      4  O    GLY B 261     -11.372  79.141  -4.256  1.00 40.00     8
ATOM      5  N    GLY B 262      -9.565  78.527  -5.597  1.00 40.00     7
ATOM      6  CA   GLY B 262     -10.136  78.609  -7.087  1.00 40.00     6
ATOM      7  C    GLY B 262     -10.849  79.966  -7.577  1.00 40.00     6
ATOM      8  O    GLY B 262     -10.200  81.044  -7.543  1.00 40.00     8
ATOM      9  N    LYS B 263     -12.086  79.687  -8.124  1.00 61.71     7
ATOM     10  CA   LYS B 263     -13.323  80.536  -8.428  1.00 64.36     6
ATOM     11  C    LYS B 263     -14.367  79.750  -7.614  1.00 63.41     6
ATOM     12  O    LYS B 263     -14.102  78.579  -7.280  1.00 61.93     8
ATOM     13  CB   LYS B 263     -13.901  80.405  -9.876  1.00 63.50     6
ATOM     14  CG   LYS B 263     -13.487  81.474 -10.881  1.00 20.00     6
ATOM     15  CD   LYS B 263     -14.016  82.897 -10.612  1.00 20.00     6
ATOM     16  CE   LYS B 263     -13.641  83.874 -11.742  1.00 20.00     6
ATOM     17  NZ   LYS B 263     -13.680  85.287 -11.341  1.00 20.00     7
ATOM     18  N    VAL B 264     -15.489  80.335  -7.307  1.00 61.15     7
ATOM     19  CA   VAL B 264     -16.616  79.632  -6.619  1.00 59.46     6
ATOM     20  CB   VAL B 264     -17.574  80.703  -6.099  1.00 59.03     6
ATOM     21  CG1  VAL B 264     -18.479  80.215  -4.979  1.00 53.79     6
ATOM     22  CG2  VAL B 264     -16.847  81.938  -5.562  1.00 55.32     6
ATOM     23  C    VAL B 264     -17.330  78.824  -7.700  1.00 60.96     6
ATOM     24  O    VAL B 264     -16.940  78.873  -8.873  1.00 62.13     8
ATOM     25  N    ASP B 265     -18.378  78.098  -7.340  1.00 62.59     7
ATOM     26  CA   ASP B 265     -19.175  77.339  -8.312  1.00 64.95     6
ATOM     27  CB   ASP B 265     -18.796  75.851  -8.270  1.00 64.32     6
ATOM     28  CG   ASP B 265     -19.928  75.022  -8.584  1.00 67.70     6
ATOM     29  OD1  ASP B 265     -20.856  75.062  -9.295  1.00 72.59     8
ATOM     30  OD2  ASP B 265     -20.370  73.959  -8.310  1.00 68.84     8
ATOM     31  C    ASP B 265     -20.658  77.614  -8.016  1.00 65.64     6
ATOM     32  O    ASP B 265     -21.342  76.895  -7.313  1.00 68.81     8
ATOM     33  N    LEU B 266     -21.066  78.737  -8.588  1.00 65.12     7
ATOM     34  CA   LEU B 266     -22.385  79.330  -8.499  1.00 63.40     6
ATOM     35  CB   LEU B 266     -22.429  80.448  -9.542  1.00 67.34     6
ATOM     36  CG   LEU B 266     -21.295  81.459  -9.399  1.00 69.35     6
ATOM     37  CD1  LEU B 266     -20.983  82.127 -10.712  1.00 68.24     6
ATOM     38  CD2  LEU B 266     -21.663  82.461  -8.344  1.00 70.47     6
ATOM     39  C    LEU B 266     -23.673  78.507  -8.602  1.00 59.67     6
ATOM     40  O    LEU B 266     -24.684  78.890  -7.988  1.00 53.35     8
ATOM     41  N    GLU B 267     -23.677  77.416  -9.371  1.00 58.01     7
ATOM     42  CA   GLU B 267     -24.901  76.640  -9.449  1.00 58.34     6
ATOM     43  CB   GLU B 267     -24.752  75.410 -10.368  1.00 59.21     6
ATOM     44  CG   GLU B 267     -25.979  74.464 -10.268  1.00 62.89     6
ATOM     45  CD   GLU B 267     -26.048  73.419 -11.328  1.00 67.66     6
ATOM     46  OE1  GLU B 267     -25.076  72.645 -11.512  1.00 69.95     8
```

UNITED STATES PATENT AND TRADEMARK OFFICE
CERTIFICATE OF CORRECTION

| | |
|---|---|
| PATENT NO. | : 6,965,850 B2 |
| APPLICATION NO. | : 09/281717 |
| DATED | : November 15, 2005 |
| INVENTOR(S) | : John D. Baxter et al. |

Page 45 of 186

It is certified that error appears in the above-identified patent and that said Letters Patent is hereby corrected as shown below:

```
ATOM      47   OE2  GLU  B  267      -27.098   73.328  -12.008   1.00  69.40   8
ATOM      48   C    GLU  B  267      -25.200   76.184   -8.032   1.00  57.67   6
ATOM      49   O    GLU  B  267      -26.354   76.009   -7.643   1.00  58.34   8
ATOM      50   N    ALA  B  268      -24.114   75.996   -7.285   1.00  53.43   7
ATOM      51   CA   ALA  B  268      -24.151   75.560   -5.905   1.00  49.00   6
ATOM      52   CB   ALA  B  268      -22.818   74.956   -5.526   1.00  45.72   6
ATOM      53   C    ALA  B  268      -24.421   76.775   -5.056   1.00  45.76   6
ATOM      54   O    ALA  B  268      -25.419   76.823   -4.351   1.00  41.50   8
ATOM      55   N    PHE  B  269      -23.533   77.766   -5.142   1.00  41.43   7
ATOM      56   CA   PHE  B  269      -23.688   78.989   -4.358   1.00  43.96   6
ATOM      57   CB   PHE  B  269      -22.903   80.150   -4.971   1.00  40.10   6
ATOM      58   CG   PHE  B  269      -23.057   81.458   -4.224   1.00  40.44   6
ATOM      59   CD1  PHE  B  269      -22.284   81.727   -3.105   1.00  38.98   6
ATOM      60   CD2  PHE  B  269      -24.033   82.372   -4.603   1.00  37.15   6
ATOM      61   CE1  PHE  B  269      -22.472   82.921   -2.388   1.00  32.12   6
ATOM      62   CE2  PHE  B  269      -24.228   83.567   -3.890   1.00  38.41   6
ATOM      63   CZ   PHE  B  269      -23.457   83.838   -2.780   1.00  40.55   6
ATOM      64   C    PHE  B  269      -25.154   79.374   -4.320   1.00  49.76   6
ATOM      65   O    PHE  B  269      -25.645   79.905   -3.336   1.00  52.15   8
ATOM      66   N    SER  B  270      -25.840   79.112   -5.425   1.00  53.15   7
ATOM      67   CA   SER  B  270      -27.253   79.431   -5.520   1.00  52.29   6
ATOM      68   CB   SER  B  270      -27.742   79.274   -6.948   1.00  51.85   6
ATOM      69   OG   SER  B  270      -29.118   79.606   -7.048   1.00  53.42   8
ATOM      70   C    SER  B  270      -28.012   78.486   -4.630   1.00  49.38   6
ATOM      71   O    SER  B  270      -28.438   78.864   -3.548   1.00  48.74   8
ATOM      72   N    HIS  B  271      -28.185   77.253   -5.115   1.00  50.15   7
ATOM      73   CA   HIS  B  271      -28.904   76.203   -4.382   1.00  51.67   6
ATOM      74   CB   HIS  B  271      -28.409   74.812   -4.782   1.00  58.52   6
ATOM      75   CG   HIS  B  271      -29.096   74.248   -5.976   1.00  68.97   6
ATOM      76   CD2  HIS  B  271      -29.987   73.233   -6.102   1.00  70.88   6
ATOM      77   ND1  HIS  B  271      -28.943   74.770   -7.270   1.00  71.98   7
ATOM      78   CE1  HIS  B  271      -29.716   74.080   -8.100   1.00  73.91   6
ATOM      79   NE2  HIS  B  271      -30.354   73.149   -7.419   1.00  73.59   7
ATOM      80   C    HIS  B  271      -28.785   76.347   -2.886   1.00  49.33   6
ATOM      81   O    HIS  B  271      -29.641   75.874   -2.156   1.00  48.39   8
ATOM      82   N    PHE  B  272      -27.702   76.992   -2.444   1.00  41.34   7
ATOM      83   CA   PHE  B  272      -27.440   77.224   -1.033   1.00  39.44   6
ATOM      84   CB   PHE  B  272      -25.936   77.302   -0.801   1.00  36.67   6
ATOM      85   CG   PHE  B  272      -25.241   75.945   -0.861   1.00  33.39   6
ATOM      86   CD1  PHE  B  272      -23.856   75.857   -0.976   1.00  33.14   6
ATOM      87   CD2  PHE  B  272      -25.973   74.767   -0.732   1.00  38.28   6
ATOM      88   CE1  PHE  B  272      -23.200   74.606   -0.989   1.00  38.26   6
ATOM      89   CE2  PHE  B  272      -25.321   73.518   -0.743   1.00  43.28   6
ATOM      90   CZ   PHE  B  272      -23.937   73.441   -0.856   1.00  39.74   6
ATOM      91   C    PHE  B  272      -28.144   78.472   -0.477   1.00  40.75   6
ATOM      92   O    PHE  B  272      -28.803   78.393    0.558   1.00  35.51   8
ATOM      93   N    THR  B  273      -28.027   79.621   -1.144   1.00  41.64   7
ATOM      94   CA   THR  B  273      -28.658   80.850   -0.652   1.00  45.97   6
ATOM      95   CB   THR  B  273      -28.023   82.105   -1.283   1.00  51.52   6
ATOM      96   OG1  THR  B  273      -28.292   82.151   -2.688   1.00  45.74   8
ATOM      97   CG2  THR  B  273      -26.511   82.123   -1.048   1.00  49.73   6
ATOM      98   C    THR  B  273      -30.142   80.859   -0.971   1.00  46.23   6
ATOM      99   O    THR  B  273      -30.862   81.751   -0.535   1.00  41.21   8
ATOM     100   N    LYS  B  274      -30.583   79.876   -1.758   1.00  46.21   7
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    101  CA   LYS B 274    -31.983  79.774  -2.147  1.00 54.53     6
ATOM    102  CB   LYS B 274    -32.133  78.724  -3.232  1.00 54.36     6
ATOM    103  C    LYS B 274    -32.819  79.396  -0.931  1.00 56.88     6
ATOM    104  O    LYS B 274    -34.025  79.624  -0.906  1.00 57.98     8
ATOM    105  N    ILE B 275    -32.151  78.820   0.076  1.00 56.48     7
ATOM    106  CA   ILE B 275    -32.791  78.381   1.332  1.00 52.64     6
ATOM    107  CB   ILE B 275    -32.638  76.863   1.519  1.00 49.15     6
ATOM    108  CG2  ILE B 275    -33.505  76.105   0.529  1.00 47.42     6
ATOM    109  CG1  ILE B 275    -31.188  76.441   1.343  1.00 45.31     6
ATOM    110  CD1  ILE B 275    -30.990  74.952   1.391  1.00 37.22     6
ATOM    111  C    ILE B 275    -32.241  79.086   2.574  1.00 51.78     6
ATOM    112  O    ILE B 275    -32.858  79.049   3.622  1.00 49.80     8
ATOM    113  N    ILE B 276    -31.071  79.709   2.435  1.00 51.76     7
ATOM    114  CA   ILE B 276    -30.410  80.409   3.533  1.00 52.58     6
ATOM    115  CB   ILE B 276    -29.145  81.110   3.042  1.00 55.04     6
ATOM    116  CG2  ILE B 276    -29.486  82.172   2.017  1.00 53.28     6
ATOM    117  CG1  ILE B 276    -28.396  81.786   4.203  1.00 57.31     6
ATOM    118  CD1  ILE B 276    -27.862  80.854   5.231  1.00 60.32     6
ATOM    119  C    ILE B 276    -31.282  81.461   4.237  1.00 50.70     6
ATOM    120  O    ILE B 276    -31.015  81.817   5.385  1.00 55.55     8
ATOM    121  N    THR B 277    -32.322  81.953   3.568  1.00 47.33     7
ATOM    122  CA   THR B 277    -33.174  82.968   4.141  1.00 42.59     6
ATOM    123  CB   THR B 277    -34.042  83.632   3.048  1.00 44.97     6
ATOM    124  OG1  THR B 277    -33.202  84.145   2.001  1.00 46.38     8
ATOM    125  CG2  THR B 277    -34.856  84.781   3.653  1.00 37.17     6
ATOM    126  C    THR B 277    -34.069  82.447   5.267  1.00 39.84     6
ATOM    127  O    THR B 277    -34.083  83.026   6.375  1.00 40.55     8
ATOM    128  N    PRO B 278    -34.832  81.385   5.017  1.00 38.20     7
ATOM    129  CD   PRO B 278    -34.925  80.666   3.747  1.00 36.34     6
ATOM    130  CA   PRO B 278    -35.711  80.834   6.059  1.00 36.63     6
ATOM    131  CB   PRO B 278    -36.475  79.715   5.357  1.00 32.95     6
ATOM    132  CG   PRO B 278    -35.833  79.516   4.056  1.00 35.75     6
ATOM    133  C    PRO B 278    -34.892  80.324   7.220  1.00 38.60     6
ATOM    134  O    PRO B 278    -35.372  80.157   8.331  1.00 37.67     8
ATOM    135  N    ALA B 279    -33.636  80.040   6.927  1.00 37.05     7
ATOM    136  CA   ALA B 279    -32.696  79.525   7.903  1.00 33.18     6
ATOM    137  CB   ALA B 279    -31.391  79.195   7.205  1.00 30.56     6
ATOM    138  C    ALA B 279    -32.447  80.536   8.991  1.00 33.47     6
ATOM    139  O    ALA B 279    -32.623  80.238  10.158  1.00 33.74     8
ATOM    140  N    ILE B 280    -32.010  81.728   8.577  1.00 29.96     7
ATOM    141  CA   ILE B 280    -31.728  82.809   9.501  1.00 25.94     6
ATOM    142  CB   ILE B 280    -31.190  84.040   8.754  1.00 26.95     6
ATOM    143  CG2  ILE B 280    -30.881  85.149   9.715  1.00 15.40     6
ATOM    144  CG1  ILE B 280    -29.904  83.696   8.007  1.00 26.73     6
ATOM    145  CD1  ILE B 280    -29.255  84.878   7.362  1.00 34.31     6
ATOM    146  C    ILE B 280    -32.964  83.172  10.310  1.00 31.39     6
ATOM    147  O    ILE B 280    -32.882  83.378  11.522  1.00 35.69     8
ATOM    148  N    THR B 281    -34.113  83.233   9.647  1.00 30.90     7
ATOM    149  CA   THR B 281    -35.361  83.586  10.328  1.00 33.49     6
ATOM    150  CB   THR B 281    -36.598  83.396   9.419  1.00 37.18     6
ATOM    151  OG1  THR B 281    -36.703  82.034   9.005  1.00 46.48     8
ATOM    152  CG2  THR B 281    -36.525  84.289   8.198  1.00 32.85     6
ATOM    153  C    THR B 281    -35.523  82.706  11.556  1.00 29.94     6
ATOM    154  O    THR B 281    -35.855  83.186  12.634  1.00 25.55     8
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    155  N    ARG B 282    -35.296  81.405  11.378  1.00  32.70   7
ATOM    156  CA   ARG B 282    -35.439  80.449  12.475  1.00  34.27   6
ATOM    157  CB   ARG B 282    -34.999  79.060  12.020  1.00  33.78   6
ATOM    158  CG   ARG B 282    -35.986  77.944  12.280  1.00  45.15   6
ATOM    159  CD   ARG B 282    -36.701  77.514  11.015  1.00  58.24   6
ATOM    160  NE   ARG B 282    -35.771  77.153   9.969  1.00  68.41   7
ATOM    161  CZ   ARG B 282    -34.862  76.200  10.098  1.00  72.31   6
ATOM    162  NH1  ARG B 282    -34.779  75.502  11.232  1.00  77.89   7
ATOM    163  NH2  ARG B 282    -34.022  75.963   9.096  1.00  69.25   7
ATOM    164  C    ARG B 282    -34.556  80.919  13.622  1.00  34.81   6
ATOM    165  O    ARG B 282    -35.008  81.034  14.753  1.00  36.03   8
ATOM    166  N    VAL B 283    -33.288  81.183  13.289  1.00  31.71   7
ATOM    167  CA   VAL B 283    -32.304  81.567  14.249  1.00  30.16   6
ATOM    168  CB   VAL B 283    -30.993  82.029  13.559  1.00  29.00   6
ATOM    169  CG1  VAL B 283    -30.015  82.617  14.557  1.00  28.64   6
ATOM    170  CG2  VAL B 283    -30.385  80.816  12.915  1.00  28.28   6
ATOM    171  C    VAL B 283    -32.848  82.884  14.994  1.00  32.50   6
ATOM    172  O    VAL B 283    -32.619  83.057  16.185  1.00  33.48   8
ATOM    173  N    VAL B 284    -33.573  83.728  14.265  1.00  30.96   7
ATOM    174  CA   VAL B 284    -34.177  84.925  14.844  1.00  29.14   6
ATOM    175  CB   VAL B 284    -34.672  85.892  13.751  1.00  31.27   6
ATOM    176  CG1  VAL B 284    -35.278  87.129  14.371  1.00  24.21   6
ATOM    177  CG2  VAL B 284    -33.554  86.270  12.812  1.00  30.51   6
ATOM    178  C    VAL B 284    -35.336  84.498  15.747  1.00  28.89   6
ATOM    179  O    VAL B 284    -35.491  84.994  16.860  1.00  27.29   8
ATOM    180  N    ASP B 285    -36.143  83.564  15.250  1.00  28.76   7
ATOM    181  CA   ASP B 285    -37.299  83.057  15.983  1.00  35.32   6
ATOM    182  CB   ASP B 285    -38.129  82.098  15.111  1.00  33.29   6
ATOM    183  CG   ASP B 285    -38.881  82.795  14.013  1.00  38.15   6
ATOM    184  OD1  ASP B 285    -39.660  83.729  14.305  1.00  34.70   8
ATOM    185  OD2  ASP B 285    -38.741  82.406  12.821  1.00  34.43   8
ATOM    186  C    ASP B 285    -36.863  82.339  17.257  1.00  36.70   6
ATOM    187  O    ASP B 285    -37.606  82.304  18.237  1.00  37.96   8
ATOM    188  N    PHE B 286    -35.663  81.755  17.235  1.00  35.96   7
ATOM    189  CA   PHE B 286    -35.134  81.053  18.401  1.00  37.10   6
ATOM    190  CB   PHE B 286    -33.870  80.262  18.052  1.00  37.97   6
ATOM    191  CG   PHE B 286    -33.079  79.818  19.258  1.00  36.50   6
ATOM    192  CD1  PHE B 286    -33.704  79.168  20.294  1.00  36.75   6
ATOM    193  CD2  PHE B 286    -31.721  80.063  19.343  1.00  33.83   6
ATOM    194  CE1  PHE B 286    -32.987  78.769  21.401  1.00  39.55   6
ATOM    195  CE2  PHE B 286    -30.997  79.662  20.456  1.00  38.08   6
ATOM    196  CZ   PHE B 286    -31.632  79.013  21.486  1.00  34.44   6
ATOM    197  C    PHE B 286    -34.808  82.023  19.504  1.00  36.83   6
ATOM    198  O    PHE B 286    -35.246  81.845  20.631  1.00  35.61   8
ATOM    199  N    ALA B 287    -34.005  83.027  19.169  1.00  37.33   7
ATOM    200  CA   ALA B 287    -33.599  84.035  20.132  1.00  36.34   6
ATOM    201  CB   ALA B 287    -32.644  85.008  19.469  1.00  36.40   6
ATOM    202  C    ALA B 287    -34.831  84.769  20.657  1.00  38.76   6
ATOM    203  O    ALA B 287    -34.882  85.193  21.814  1.00  41.98   8
ATOM    204  N    LYS B 288    -35.820  84.912  19.779  1.00  38.28   7
ATOM    205  CA   LYS B 288    -37.066  85.584  20.112  1.00  45.26   6
ATOM    206  CB   LYS B 288    -37.983  85.690  18.898  1.00  48.35   6
ATOM    207  CG   LYS B 288    -37.577  86.756  17.916  1.00  51.43   6
ATOM    208  CD   LYS B 288    -38.806  87.359  17.226  1.00  60.23   6
```

UNITED STATES PATENT AND TRADEMARK OFFICE
CERTIFICATE OF CORRECTION

PATENT NO. : 6,965,850 B2  Page 48 of 186
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   209  CE   LYS B 288    -39.680  86.308  16.864  1.00 62.81   6
ATOM   210  NZ   LYS B 288    -38.897  85.460  15.614  1.00 64.69   7
ATOM   211  C    LYS B 288    -37.846  84.901  21.191  1.00 43.31   6
ATOM   212  O    LYS B 288    -38.650  85.532  21.857  1.00 45.66   8
ATOM   213  N    LYS B 289    -37.618  83.604  21.345  1.00 41.70   7
ATOM   214  CA   LYS B 289    -38.313  82.849  22.351  1.00 40.67   6
ATOM   215  CB   LYS B 289    -38.554  81.418  21.845  1.00 42.25   6
ATOM   216  CG   LYS B 289    -39.438  81.368  20.589  1.00 39.53   6
ATOM   217  CD   LYS B 289    -40.093  80.010  20.422  1.00 43.19   6
ATOM   218  CE   LYS B 289    -41.025  79.987  19.223  1.00 45.74   6
ATOM   219  NZ   LYS B 289    -42.391  80.476  19.512  1.00 52.49   7
ATOM   220  C    LYS B 289    -37.555  82.871  23.668  1.00 41.50   6
ATOM   221  O    LYS B 289    -38.057  82.366  24.657  1.00 39.77   8
ATOM   222  N    LEU B 290    -36.365  83.482  23.661  1.00 40.68   7
ATOM   223  CA   LEU B 290    -35.539  83.599  24.834  1.00 39.33   6
ATOM   224  CB   LEU B 290    -34.053  83.499  24.491  1.00 36.14   6
ATOM   225  CG   LEU B 290    -33.640  82.240  23.767  1.00 34.81   6
ATOM   226  CD1  LEU B 290    -32.147  82.255  23.523  1.00 29.07   6
ATOM   227  CD2  LEU B 290    -34.013  81.040  24.607  1.00 33.45   6
ATOM   228  C    LEU B 290    -35.832  84.915  25.577  1.00 40.08   6
ATOM   229  O    LEU B 290    -35.479  86.006  25.088  1.00 42.00   8
ATOM   230  N    PRO B 291    -36.462  84.840  26.765  1.00 40.27   7
ATOM   231  CD   PRO B 291    -36.819  83.613  27.494  1.00 39.65   6
ATOM   232  CA   PRO B 291    -36.782  86.069  27.501  1.00 38.28   6
ATOM   233  CB   PRO B 291    -37.376  85.574  28.811  1.00 35.88   6
ATOM   234  CG   PRO B 291    -37.549  84.110  28.695  1.00 34.19   6
ATOM   235  C    PRO B 291    -35.570  87.002  27.714  1.00 40.05   6
ATOM   236  O    PRO B 291    -35.625  88.197  27.403  1.00 41.33   8
ATOM   237  N    MET B 292    -34.474  86.476  28.258  1.00 40.59   7
ATOM   238  CA   MET B 292    -33.296  87.286  28.545  1.00 42.86   6
ATOM   239  CB   MET B 292    -32.149  86.376  28.975  1.00 43.28   6
ATOM   240  CG   MET B 292    -32.553  85.302  29.970  1.00 50.35   6
ATOM   241  SD   MET B 292    -31.070  84.609  30.755  1.00 51.17  16
ATOM   242  CE   MET B 292    -31.797  83.212  31.701  1.00 54.63   6
ATOM   243  C    MET B 292    -32.895  88.077  27.315  1.00 41.05   6
ATOM   244  O    MET B 292    -32.228  89.098  27.420  1.00 39.66   8
ATOM   245  N    PHE B 293    -33.322  87.604  26.143  1.00 39.30   7
ATOM   246  CA   PHE B 293    -33.017  88.271  24.878  1.00 40.92   6
ATOM   247  CB   PHE B 293    -33.296  87.329  23.707  1.00 40.98   6
ATOM   248  CG   PHE B 293    -32.937  87.909  22.365  1.00 42.78   6
ATOM   249  CD1  PHE B 293    -31.653  88.354  22.120  1.00 44.40   6
ATOM   250  CD2  PHE B 293    -33.872  87.972  21.350  1.00 43.66   6
ATOM   251  CE1  PHE B 293    -31.306  88.869  20.872  1.00 39.83   6
ATOM   252  CE2  PHE B 293    -33.525  88.486  20.100  1.00 46.21   6
ATOM   253  CZ   PHE B 293    -32.239  88.926  19.859  1.00 45.18   6
ATOM   254  C    PHE B 293    -33.873  89.518  24.744  1.00 45.84   6
ATOM   255  O    PHE B 293    -33.369  90.626  24.579  1.00 42.01   8
ATOM   256  N    CYS B 294    -35.181  89.305  24.808  1.00 47.05   7
ATOM   257  CA   CYS B 294    -36.146  90.382  24.689  1.00 50.15   6
ATOM   258  CB   CYS B 294    -37.553  89.793  24.756  1.00 45.90   6
ATOM   259  SG   CYS B 294    -37.899  88.607  23.449  1.00 51.50  16
ATOM   260  C    CYS B 294    -35.974  91.474  25.751  1.00 51.38   6
ATOM   261  O    CYS B 294    -36.585  92.536  25.656  1.00 53.83   8
ATOM   262  N    GLU B 295    -35.137  91.200  26.753  1.00 49.72   7
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    263  CA   GLU B 295    -34.839   92.159   27.816  1.00 52.53   6
ATOM    264  CB   GLU B 295    -34.553   91.412   29.131  1.00 57.40   6
ATOM    265  CG   GLU B 295    -35.811   90.978   29.874  1.00 69.63   6
ATOM    266  CD   GLU B 295    -36.610   92.144   30.375  1.00 78.49   6
ATOM    267  OE1  GLU B 295    -36.153   92.869   31.297  1.00 82.82   8
ATOM    268  OE2  GLU B 295    -37.730   92.385   29.860  1.00 85.30   8
ATOM    269  C    GLU B 295    -33.629   93.009   27.415  1.00 48.54   6
ATOM    270  O    GLU B 295    -32.981   93.627   28.260  1.00 49.82   8
ATOM    271  N    LEU B 296    -33.374   93.030   26.109  1.00 43.79   7
ATOM    272  CA   LEU B 296    -32.268   93.761   25.540  1.00 45.42   6
ATOM    273  CB   LEU B 296    -31.319   92.769   24.838  1.00 41.04   6
ATOM    274  CG   LEU B 296    -30.735   91.631   25.662  1.00 42.74   6
ATOM    275  CD1  LEU B 296    -30.354   90.478   24.764  1.00 40.99   6
ATOM    276  CD2  LEU B 296    -29.559   92.119   26.468  1.00 39.44   6
ATOM    277  C    LEU B 296    -32.760   94.779   24.522  1.00 45.56   6
ATOM    278  O    LEU B 296    -33.845   94.600   23.924  1.00 43.07   8
ATOM    279  N    PRO B 297    -32.004   95.875   24.338  1.00 46.99   7
ATOM    280  CD   PRO B 297    -30.740   96.123   25.046  1.00 47.12   6
ATOM    281  CA   PRO B 297    -32.388   96.912   23.363  1.00 49.61   6
ATOM    282  CB   PRO B 297    -31.294   97.973   23.494  1.00 49.91   6
ATOM    283  CG   PRO B 297    -30.302   97.477   24.545  1.00 51.28   6
ATOM    284  C    PRO B 297    -32.263   96.273   21.913  1.00 49.59   6
ATOM    285  O    PRO B 297    -31.441   95.340   21.685  1.00 51.66   8
ATOM    286  N    CYS B 298    -33.035   96.667   20.854  1.00 51.02   7
ATOM    287  CA   CYS B 298    -32.761   96.150   19.456  1.00 52.86   6
ATOM    288  CB   CYS B 298    -33.140   97.165   18.356  1.00 54.57   6
ATOM    289  SG   CYS B 298    -34.884   97.085   17.836  1.00 67.87  16
ATOM    290  C    CYS B 298    -31.385   96.330   19.127  1.00 48.51   6
ATOM    291  O    CYS B 298    -30.579   95.506   18.744  1.00 49.58   8
ATOM    292  N    GLU B 299    -31.107   97.447   19.230  1.00 44.17   7
ATOM    293  CA   GLU B 299    -29.989   97.645   18.718  1.00 47.57   6
ATOM    294  CB   GLU B 299    -29.402   98.973   19.208  1.00 49.92   6
ATOM    295  CG   GLU B 299    -29.944  100.187   18.433  1.00 59.30   6
ATOM    296  CD   GLU B 299    -31.090  100.887   19.164  1.00 63.80   6
ATOM    297  OE1  GLU B 299    -31.673  101.904   18.629  1.00 69.03   8
ATOM    298  OE2  GLU B 299    -31.473  100.458   20.319  1.00 67.10   8
ATOM    299  C    GLU B 299    -28.993   96.533   18.987  1.00 46.57   6
ATOM    300  O    GLU B 299    -28.200   96.179   18.111  1.00 44.65   8
ATOM    301  N    ASP B 300    -29.045   95.989   20.203  1.00 45.17   7
ATOM    302  CA   ASP B 300    -28.152   94.908   20.584  1.00 43.32   6
ATOM    303  CB   ASP B 300    -27.985   94.849   22.105  1.00 37.38   6
ATOM    304  CG   ASP B 300    -27.239   96.016   22.650  1.00 36.23   6
ATOM    305  OD1  ASP B 300    -26.208   96.421   22.052  1.00 35.87   8
ATOM    306  OD2  ASP B 300    -27.661   96.543   23.716  1.00 40.14   8
ATOM    307  C    ASP B 300    -28.721   93.591   20.071  1.00 42.81   6
ATOM    308  O    ASP B 300    -28.001   92.775   19.489  1.00 46.02   8
ATOM    309  N    GLN B 301    -30.019   93.399   20.306  1.00 38.60   7
ATOM    310  CA   GLN B 301    -30.712   92.197   19.858  1.00 40.00   6
ATOM    311  CB   GLN B 301    -32.234   92.418   19.836  1.00 38.59   6
ATOM    312  CG   GLN B 301    -32.908   92.380   21.187  1.00 40.26   6
ATOM    313  CD   GLN B 301    -34.401   92.583   21.083  1.00 44.15   6
ATOM    314  OE1  GLN B 301    -34.859   93.637   20.589  1.00 45.73   8
ATOM    315  NE2  GLN B 301    -35.165   91.602   21.544  1.00 46.13   7
ATOM    316  C    GLN B 301    -30.237   91.830   18.455  1.00 41.64   6
```

UNITED STATES PATENT AND TRADEMARK OFFICE
CERTIFICATE OF CORRECTION

PATENT NO.       : 6,965,850 B2
APPLICATION NO.  : 09/281717
DATED            : November 15, 2005
INVENTOR(S)      : John D. Baxter et al.

It is certified that error appears in the above-identified patent and that said Letters Patent is hereby corrected as shown below:

```
ATOM    317  O    GLN B 301    -30.162  90.662  18.100  1.00  45.02   8
ATOM    318  N    ILE B 302    -29.916  92.864  17.674  1.00  41.01   7
ATOM    319  CA   ILE B 302    -29.424  92.692  16.311  1.00  40.23   6
ATOM    320  CB   ILE B 302    -29.584  93.978  15.498  1.00  39.52   6
ATOM    321  CG2  ILE B 302    -29.034  93.792  14.100  1.00  31.98   6
ATOM    322  CG1  ILE B 302    -31.059  94.385  15.416  1.00  40.77   6
ATOM    323  CD1  ILE B 302    -31.939  93.317  14.775  1.00  45.43   6
ATOM    324  C    ILE B 302    -27.966  92.260  16.342  1.00  38.58   6
ATOM    325  O    ILE B 302    -27.613  91.197  15.830  1.00  40.81   8
ATOM    326  N    ILE B 303    -27.128  93.111  16.933  1.00  37.50   7
ATOM    327  CA   ILE B 303    -25.692  92.846  17.062  1.00  39.33   6
ATOM    328  CB   ILE B 303    -25.066  93.648  18.203  1.00  39.06   6
ATOM    329  CG2  ILE B 303    -23.566  93.405  18.257  1.00  36.19   6
ATOM    330  CG1  ILE B 303    -25.309  95.143  18.020  1.00  40.15   6
ATOM    331  CD1  ILE B 303    -24.816  95.966  19.173  1.00  36.93   6
ATOM    332  C    ILE B 303    -25.470  91.385  17.323  1.00  36.49   6
ATOM    333  O    ILE B 303    -24.619  90.725  16.712  1.00  36.58   8
ATOM    334  N    LEU B 304    -26.244  90.843  18.266  1.00  32.91   7
ATOM    335  CA   LEU B 304    -26.194  89.433  18.633  1.00  27.55   6
ATOM    336  CB   LEU B 304    -27.172  89.182  19.793  1.00  22.35   6
ATOM    337  CG   LEU B 304    -26.623  89.449  21.187  1.00  26.88   6
ATOM    338  CD1  LEU B 304    -25.540  90.495  21.136  1.00  24.82   6
ATOM    339  CD2  LEU B 304    -27.747  89.840  22.121  1.00  23.69   6
ATOM    340  C    LEU B 304    -26.505  88.547  17.425  1.00  28.05   6
ATOM    341  O    LEU B 304    -25.668  87.751  16.983  1.00  24.68   8
ATOM    342  N    LEU B 305    -27.716  88.700  16.897  1.00  26.34   7
ATOM    343  CA   LEU B 305    -28.145  87.939  15.741  1.00  30.91   6
ATOM    344  CB   LEU B 305    -29.460  88.514  15.199  1.00  32.50   6
ATOM    345  CG   LEU B 305    -30.699  88.305  16.050  1.00  33.36   6
ATOM    346  CD1  LEU B 305    -31.938  88.839  15.342  1.00  33.87   6
ATOM    347  CD2  LEU B 305    -30.863  86.812  16.298  1.00  31.72   6
ATOM    348  C    LEU B 305    -27.072  87.922  14.666  1.00  29.76   6
ATOM    349  O    LEU B 305    -26.687  86.860  14.202  1.00  29.33   8
ATOM    350  N    LYS B 306    -26.597  89.107  14.291  1.00  29.72   7
ATOM    351  CA   LYS B 306    -25.576  89.254  13.264  1.00  34.28   6
ATOM    352  CB   LYS B 306    -25.224  90.732  13.077  1.00  35.98   6
ATOM    353  CG   LYS B 306    -26.350  91.581  12.494  1.00  43.35   6
ATOM    354  CD   LYS B 306    -25.852  92.987  12.182  1.00  51.50   6
ATOM    355  CE   LYS B 306    -24.706  92.932  11.190  1.00  53.26   6
ATOM    356  NZ   LYS B 306    -23.883  94.161  11.251  1.00  59.61   7
ATOM    357  C    LYS B 306    -24.308  88.484  13.556  1.00  35.25   6
ATOM    358  O    LYS B 306    -23.681  87.917  12.653  1.00  33.95   8
ATOM    359  N    GLY B 307    -23.918  88.478  14.829  1.00  35.79   7
ATOM    360  CA   GLY B 307    -22.702  87.793  15.227  1.00  34.59   6
ATOM    361  C    GLY B 307    -22.811  86.291  15.383  1.00  33.80   6
ATOM    362  O    GLY B 307    -21.944  85.564  14.895  1.00  31.59   8
ATOM    363  N    CYS B 308    -23.861  85.843  16.071  1.00  31.15   7
ATOM    364  CA   CYS B 308    -24.069  84.434  16.320  1.00  29.04   6
ATOM    365  CB   CYS B 308    -24.761  84.240  17.663  1.00  27.59   6
ATOM    366  SG   CYS B 308    -26.496  84.629  17.608  1.00  30.50  16
ATOM    367  C    CYS B 308    -24.911  83.712  15.266  1.00  30.59   6
ATOM    368  O    CYS B 308    -25.088  82.499  15.365  1.00  33.77   8
ATOM    369  N    CYS B 309    -25.432  84.429  14.266  1.00  28.46   7
ATOM    370  CA   CYS B 309    -26.270  83.787  13.265  1.00  30.10   6
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    371  CB   CYS B 309     -26.706  84.761  12.194  1.00 33.43   6
ATOM    372  SG   CYS B 309     -27.875  84.011  11.089  1.00 35.28  16
ATOM    373  C    CYS B 309     -25.617  82.608  12.603  1.00 27.72   6
ATOM    374  O    CYS B 309     -26.170  81.518  12.610  1.00 27.69   8
ATOM    375  N    MET B 310     -24.447  82.829  12.011  1.00 26.15   7
ATOM    376  CA   MET B 310     -23.737  81.748  11.352  1.00 26.06   6
ATOM    377  CB   MET B 310     -22.439  82.263  10.712  1.00 25.32   6
ATOM    378  CG   MET B 310     -21.584  81.157  10.080  1.00 24.08   6
ATOM    379  SD   MET B 310     -22.555  80.324   8.758  1.00 27.71  16
ATOM    380  CE   MET B 310     -21.549  78.826   8.427  1.00 28.50   6
ATOM    381  C    MET B 310     -23.416  80.673  12.374  1.00 25.94   6
ATOM    382  O    MET B 310     -23.659  79.489  12.151  1.00 28.09   8
ATOM    383  N    GLU B 311     -22.865  81.117  13.500  1.00 25.39   7
ATOM    384  CA   GLU B 311     -22.466  80.231  14.576  1.00 27.03   6
ATOM    385  CB   GLU B 311     -22.036  81.048  15.797  1.00 24.39   6
ATOM    386  CG   GLU B 311     -21.019  82.141  15.509  1.00 26.00   6
ATOM    387  CD   GLU B 311     -20.524  82.835  16.740  1.00 23.95   6
ATOM    388  OE1  GLU B 311     -21.321  83.108  17.668  1.00 19.72   8
ATOM    389  OE2  GLU B 311     -19.313  83.163  16.815  1.00 26.51   8
ATOM    390  C    GLU B 311     -23.582  79.264  14.964  1.00 27.51   6
ATOM    391  O    GLU B 311     -23.347  78.068  15.093  1.00 29.67   8
ATOM    392  N    ILE B 312     -24.794  79.792  15.145  1.00 26.82   7
ATOM    393  CA   ILE B 312     -25.933  78.967  15.527  1.00 25.71   6
ATOM    394  CB   ILE B 312     -27.125  79.814  16.021  1.00 23.35   6
ATOM    395  CG2  ILE B 312     -28.327  78.933  16.276  1.00 20.27   6
ATOM    396  CG1  ILE B 312     -26.771  80.541  17.325  1.00 20.88   6
ATOM    397  CD1  ILE B 312     -27.952  81.163  18.028  1.00 18.15   6
ATOM    398  C    ILE B 312     -26.370  78.072  14.392  1.00 27.91   6
ATOM    399  O    ILE B 312     -26.769  76.926  14.605  1.00 28.96   8
ATOM    400  N    MET B 313     -26.303  78.603  13.174  1.00 27.66   7
ATOM    401  CA   MET B 313     -26.696  77.832  11.999  1.00 30.18   6
ATOM    402  CB   MET B 313     -26.696  78.691  10.734  1.00 36.89   6
ATOM    403  CG   MET B 313     -27.882  79.634  10.607  1.00 37.95   6
ATOM    404  SD   MET B 313     -28.238  80.275   8.907  1.00 42.38  16
ATOM    405  CE   MET B 313     -26.787  81.316   8.639  1.00 40.68   6
ATOM    406  C    MET B 313     -25.791  76.632  11.808  1.00 27.43   6
ATOM    407  O    MET B 313     -26.258  75.501  11.893  1.00 28.61   8
ATOM    408  N    SER B 314     -24.508  76.882  11.549  1.00 24.88   7
ATOM    409  CA   SER B 314     -23.533  75.824  11.346  1.00 27.98   6
ATOM    410  CB   SER B 314     -22.150  76.441  11.165  1.00 29.64   6
ATOM    411  OG   SER B 314     -21.844  77.316  12.227  1.00 43.44   8
ATOM    412  C    SER B 314     -23.514  74.774  12.465  1.00 22.30   6
ATOM    413  O    SER B 314     -23.279  73.592  12.199  1.00 24.18   8
ATOM    414  N    LEU B 315     -23.760  75.187  13.714  1.00 23.99   7
ATOM    415  CA   LEU B 315     -23.792  74.219  14.811  1.00 25.07   6
ATOM    416  CB   LEU B 315     -24.095  74.869  16.169  1.00 19.11   6
ATOM    417  CG   LEU B 315     -24.507  73.860  17.234  1.00 20.39   6
ATOM    418  CD1  LEU B 315     -23.390  72.878  17.493  1.00 18.92   6
ATOM    419  CD2  LEU B 315     -24.895  74.560  18.514  1.00 12.93   6
ATOM    420  C    LEU B 315     -24.892  73.219  14.517  1.00 24.53   6
ATOM    421  O    LEU B 315     -24.672  72.014  14.550  1.00 26.32   8
ATOM    422  N    ARG B 316     -26.079  73.762  14.254  1.00 28.18   7
ATOM    423  CA   ARG B 316     -27.278  72.996  13.971  1.00 27.54   6
ATOM    424  CB   ARG B 316     -28.432  73.941  13.651  1.00 27.39   6
```

UNITED STATES PATENT AND TRADEMARK OFFICE
CERTIFICATE OF CORRECTION

PATENT NO. : 6,965,850 B2  Page 52 of 186
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   425  CG   ARG B 316    -28.823  74.857  14.809  1.00  22.00   6
ATOM   426  CD   ARG B 316    -30.074  75.657  14.451  1.00  18.78   6
ATOM   427  NE   ARG B 316    -30.905  75.944  15.598  1.00  26.57   7
ATOM   428  CZ   ARG B 316    -32.166  76.337  15.489  1.00  30.81   6
ATOM   429  NH1  ARG B 316    -32.686  76.535  14.280  1.00  33.71   7
ATOM   430  NH2  ARG B 316    -32.900  76.542  16.581  1.00  33.13   7
ATOM   431  C    ARG B 316    -27.128  72.028  12.830  1.00  28.09   6
ATOM   432  O    ARG B 316    -27.852  71.053  12.760  1.00  32.41   8
ATOM   433  N    ALA B 317    -26.187  72.309  11.941  1.00  28.36   7
ATOM   434  CA   ALA B 317    -25.938  71.466  10.794  1.00  26.64   6
ATOM   435  CB   ALA B 317    -25.337  72.300   9.675  1.00  22.93   6
ATOM   436  C    ALA B 317    -24.998  70.327  11.150  1.00  28.35   6
ATOM   437  O    ALA B 317    -25.223  69.187  10.773  1.00  32.10   8
ATOM   438  N    ALA B 318    -23.941  70.659  11.882  1.00  29.12   7
ATOM   439  CA   ALA B 318    -22.957  69.682  12.299  1.00  27.50   6
ATOM   440  CB   ALA B 318    -21.915  70.355  13.160  1.00  28.39   6
ATOM   441  C    ALA B 318    -23.645  68.591  13.084  1.00  28.10   6
ATOM   442  O    ALA B 318    -23.415  67.415  12.854  1.00  28.18   8
ATOM   443  N    VAL B 319    -24.502  69.012  14.016  1.00  29.16   7
ATOM   444  CA   VAL B 319    -25.259  68.107  14.889  1.00  35.24   6
ATOM   445  CB   VAL B 319    -26.228  68.897  15.765  1.00  27.34   6
ATOM   446  CG1  VAL B 319    -25.576  70.149  16.246  1.00  29.96   6
ATOM   447  CG2  VAL B 319    -27.505  69.212  15.022  1.00  31.70   6
ATOM   448  C    VAL B 319    -26.066  67.146  14.043  1.00  40.01   6
ATOM   449  O    VAL B 319    -26.701  66.250  14.578  1.00  42.70   8
ATOM   450  N    ARG B 320    -26.025  67.353  12.723  1.00  38.64   7
ATOM   451  CA   ARG B 320    -26.770  66.541  11.762  1.00  38.61   6
ATOM   452  CB   ARG B 320    -27.838  67.409  11.123  1.00  37.26   6
ATOM   453  CG   ARG B 320    -29.152  67.280  11.822  1.00  43.12   6
ATOM   454  CD   ARG B 320    -30.145  68.340  11.387  1.00  50.79   6
ATOM   455  NE   ARG B 320    -31.500  67.911  11.705  1.00  54.71   7
ATOM   456  CZ   ARG B 320    -32.555  68.723  11.597  1.00  57.89   6
ATOM   457  NH1  ARG B 320    -32.398  69.957  11.130  1.00  49.08   7
ATOM   458  NH2  ARG B 320    -33.773  68.302  11.844  1.00  59.59   7
ATOM   459  C    ARG B 320    -25.937  65.910  10.670  1.00  42.14   6
ATOM   460  O    ARG B 320    -26.381  65.802   9.532  1.00  46.30   8
ATOM   461  N    TYR B 321    -24.734  65.488  11.022  1.00  42.04   7
ATOM   462  CA   TYR B 321    -23.858  64.848  10.063  1.00  42.70   6
ATOM   463  CB   TYR B 321    -22.433  65.332  10.297  1.00  38.01   6
ATOM   464  CG   TYR B 321    -21.393  64.396   9.756  1.00  37.94   6
ATOM   465  CD1  TYR B 321    -21.265  64.176   8.397  1.00  33.85   6
ATOM   466  CE1  TYR B 321    -20.333  63.258   7.912  1.00  34.49   6
ATOM   467  CD2  TYR B 321    -20.583  63.683  10.613  1.00  28.03   6
ATOM   468  CE2  TYR B 321    -19.658  62.769  10.134  1.00  32.69   6
ATOM   469  CZ   TYR B 321    -19.532  62.551   8.781  1.00  35.18   6
ATOM   470  OH   TYR B 321    -18.616  61.661   8.292  1.00  39.48   8
ATOM   471  C    TYR B 321    -23.897  63.347  10.234  1.00  45.51   6
ATOM   472  O    TYR B 321    -23.560  62.857  11.292  1.00  48.02   8
ATOM   473  N    ASP B 322    -24.317  62.642   9.188  1.00  44.56   7
ATOM   474  CA   ASP B 322    -24.391  61.170   9.182  1.00  45.86   6
ATOM   475  CB   ASP B 322    -25.570  60.749   8.294  1.00  46.64   6
ATOM   476  CG   ASP B 322    -25.449  59.359   7.775  1.00  40.00   6
ATOM   477  OD1  ASP B 322    -24.388  58.737   7.986  1.00  40.00   8
ATOM   478  OD2  ASP B 322    -26.414  58.862   7.117  1.00  40.00   8
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    479  C    ASP B 322    -23.044  60.659   8.682  1.00  45.82  6
ATOM    480  O    ASP B 322    -22.738  60.783   7.495  1.00  45.38  8
ATOM    481  N    PRO B 323    -22.242  60.005   9.549  1.00  46.53  7
ATOM    482  CD   PRO B 323    -22.594  59.676  10.934  1.00  47.16  6
ATOM    483  CA   PRO B 323    -20.910  59.487   9.162  1.00  46.63  6
ATOM    484  CB   PRO B 323    -20.367  58.847  10.433  1.00  43.95  6
ATOM    485  CG   PRO B 323    -21.398  58.958  11.454  1.00  43.93  6
ATOM    486  C    PRO B 323    -20.933  58.489   8.017  1.00  48.34  6
ATOM    487  O    PRO B 323    -20.040  58.457   7.171  1.00  50.84  8
ATOM    488  N    GLU B 324    -21.951  57.631   8.022  1.00  52.39  7
ATOM    489  CA   GLU B 324    -22.126  56.615   7.008  1.00  55.85  6
ATOM    490  CB   GLU B 324    -23.491  55.960   7.216  1.00  55.34  6
ATOM    491  CG   GLU B 324    -23.678  55.332   8.581  1.00  40.00  6
ATOM    492  CD   GLU B 324    -22.642  54.294   8.888  1.00  40.00  6
ATOM    493  OE1  GLU B 324    -21.796  53.979   8.000  1.00  40.00  8
ATOM    494  OE2  GLU B 324    -22.645  53.751  10.029  1.00  40.00  8
ATOM    495  C    GLU B 324    -22.087  57.292   5.655  1.00  54.94  6
ATOM    496  O    GLU B 324    -21.144  57.149   4.896  1.00  59.81  8
ATOM    497  N    SER B 325    -23.165  58.022   5.389  1.00  52.95  7
ATOM    498  CA   SER B 325    -23.388  58.762   4.163  1.00  50.10  6
ATOM    499  CB   SER B 325    -24.768  59.357   4.163  1.00  48.23  6
ATOM    500  OG   SER B 325    -25.051  59.976   5.403  1.00  48.71  8
ATOM    501  C    SER B 325    -22.324  59.861   3.964  1.00  50.61  6
ATOM    502  O    SER B 325    -21.956  60.176   2.848  1.00  52.19  8
ATOM    503  N    GLU B 326    -21.851  60.422   5.070  1.00  45.64  7
ATOM    504  CA   GLU B 326    -20.854  61.476   5.050  1.00  43.35  6
ATOM    505  CB   GLU B 326    -19.602  61.022   4.277  1.00  42.74  6
ATOM    506  CG   GLU B 326    -18.880  59.814   4.876  1.00  50.32  6
ATOM    507  CD   GLU B 326    -17.576  59.524   4.207  1.00  56.34  6
ATOM    508  OE1  GLU B 326    -16.898  58.545   4.608  1.00  59.31  8
ATOM    509  OE2  GLU B 326    -17.177  60.255   3.266  1.00  55.74  8
ATOM    510  C    GLU B 326    -21.401  62.731   4.418  1.00  40.23  6
ATOM    511  O    GLU B 326    -20.793  63.285   3.514  1.00  40.44  8
ATOM    512  N    THR B 327    -22.528  63.208   4.934  1.00  35.90  7
ATOM    513  CA   THR B 327    -23.163  64.418   4.401  1.00  37.29  6
ATOM    514  CB   THR B 327    -24.146  64.052   3.285  1.00  37.63  6
ATOM    515  OG1  THR B 327    -25.172  63.199   3.803  1.00  38.12  8
ATOM    516  CG2  THR B 327    -23.445  63.342   2.130  1.00  39.90  6
ATOM    517  C    THR B 327    -23.961  65.125   5.473  1.00  39.49  6
ATOM    518  O    THR B 327    -24.645  64.473   6.264  1.00  40.50  8
ATOM    519  N    LEU B 328    -23.909  66.454   5.473  1.00  36.64  7
ATOM    520  CA   LEU B 328    -24.675  67.239   6.447  1.00  37.73  6
ATOM    521  CB   LEU B 328    -24.061  68.637   6.620  1.00  37.78  6
ATOM    522  CG   LEU B 328    -22.586  68.750   6.931  1.00  36.26  6
ATOM    523  CD1  LEU B 328    -22.260  70.145   7.411  1.00  36.56  6
ATOM    524  CD2  LEU B 328    -22.231  67.751   8.000  1.00  39.85  6
ATOM    525  C    LEU B 328    -26.090  67.344   5.897  1.00  37.27  6
ATOM    526  O    LEU B 328    -26.358  66.855   4.805  1.00  34.96  8
ATOM    527  N    THR B 329    -26.989  67.975   6.647  1.00  39.73  7
ATOM    528  CA   THR B 329    -28.369  68.132   6.215  1.00  40.81  6
ATOM    529  CB   THR B 329    -29.279  67.135   6.918  1.00  42.67  6
ATOM    530  OG1  THR B 329    -28.799  65.809   6.686  1.00  42.52  8
ATOM    531  CG2  THR B 329    -30.702  67.255   6.375  1.00  43.52  6
ATOM    532  C    THR B 329    -28.853  69.529   6.498  1.00  44.31  6
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    533  O    THR  B  329    -29.432   69.801    7.535   1.00  43.72    8
ATOM    534  N    LEU  B  330    -28.389   70.413    5.546   1.00  44.62    7
ATOM    535  CA   LEU  B  330    -28.983   71.812    5.698   1.00  45.09    6
ATOM    536  CB   LEU  B  330    -28.354   72.608    4.510   1.00  44.66    6
ATOM    537  CG   LEU  B  330    -26.847   72.735    4.539   1.00  51.06    6
ATOM    538  CD1  LEU  B  330    -26.226   71.367    4.840   1.00  48.58    6
ATOM    539  CD2  LEU  B  330    -26.364   73.450    3.299   1.00  45.18    6
ATOM    540  C    LEU  B  330    -30.508   71.965    5.652   1.00  48.06    6
ATOM    541  O    LEU  B  330    -31.211   71.244    4.959   1.00  49.33    8
ATOM    542  N    ASN  B  331    -30.988   72.911    6.458   1.00  52.20    7
ATOM    543  CA   ASN  B  331    -32.407   73.214    6.588   1.00  54.41    6
ATOM    544  CB   ASN  B  331    -32.870   74.013    5.370   1.00  54.94    6
ATOM    545  CG   ASN  B  331    -33.687   75.220    5.749   1.00  60.35    6
ATOM    546  OD1  ASN  B  331    -33.182   76.130    6.430   1.00  61.84    8
ATOM    547  ND2  ASN  B  331    -34.935   75.242    5.324   1.00  65.92    7
ATOM    548  C    ASN  B  331    -33.251   71.959    6.731   1.00  58.00    6
ATOM    549  O    ASN  B  331    -34.464   72.000    6.579   1.00  60.17    8
ATOM    550  N    GLY  B  332    -32.596   70.846    7.054   1.00  58.45    7
ATOM    551  CA   GLY  B  332    -33.295   69.587    7.235   1.00  58.55    6
ATOM    552  C    GLY  B  332    -33.909   69.004    5.984   1.00  59.79    6
ATOM    553  O    GLY  B  332    -34.609   68.000    6.065   1.00  61.32    8
ATOM    554  N    GLU  B  333    -33.639   69.628    4.838   1.00  60.28    7
ATOM    555  CA   GLU  B  333    -34.196   69.182    3.571   1.00  59.13    6
ATOM    556  CB   GLU  B  333    -34.966   70.323    2.885   1.00  62.40    6
ATOM    557  CG   GLU  B  333    -36.099   70.963    3.690   1.00  75.69    6
ATOM    558  CD   GLU  B  333    -36.720   72.135    2.998   1.00  80.41    6
ATOM    559  OE1  GLU  B  333    -35.984   73.081    2.618   1.00  79.98    8
ATOM    560  OE2  GLU  B  333    -37.966   72.158    2.830   1.00  83.81    8
ATOM    561  C    GLU  B  333    -33.110   68.722    2.624   1.00  57.18    6
ATOM    562  O    GLU  B  333    -33.236   67.689    1.974   1.00  57.50    8
ATOM    563  N    MET  B  334    -32.054   69.528    2.539   1.00  55.20    7
ATOM    564  CA   MET  B  334    -30.926   69.259    1.653   1.00  50.85    6
ATOM    565  CB   MET  B  334    -30.514   70.563    0.984   1.00  48.70    6
ATOM    566  CG   MET  B  334    -29.244   70.460    0.194   1.00  45.39    6
ATOM    567  SD   MET  B  334    -28.743   72.008   -0.624   1.00  44.56   16
ATOM    568  CE   MET  B  334    -30.307   72.445   -1.503   1.00  45.25    6
ATOM    569  C    MET  B  334    -29.711   68.634    2.319   1.00  51.59    6
ATOM    570  O    MET  B  334    -29.185   69.161    3.291   1.00  52.52    8
ATOM    571  N    ALA  B  335    -29.270   67.515    1.758   1.00  51.00    7
ATOM    572  CA   ALA  B  335    -28.106   66.802    2.267   1.00  48.98    6
ATOM    573  CB   ALA  B  335    -28.377   65.304    2.274   1.00  47.86    6
ATOM    574  C    ALA  B  335    -26.931   67.108    1.371   1.00  51.01    6
ATOM    575  O    ALA  B  335    -26.936   66.760    0.190   1.00  51.61    8
ATOM    576  N    VAL  B  336    -25.921   67.770    1.930   1.00  46.62    7
ATOM    577  CA   VAL  B  336    -24.730   68.142    1.152   1.00  42.35    6
ATOM    578  CB   VAL  B  336    -24.466   69.635    1.258   1.00  42.41    6
ATOM    579  CG1  VAL  B  336    -25.695   70.418    0.860   1.00  42.00    6
ATOM    580  CG2  VAL  B  336    -24.018   70.004    2.642   1.00  40.32    6
ATOM    581  C    VAL  B  336    -23.493   67.390    1.611   1.00  45.33    6
ATOM    582  O    VAL  B  336    -23.464   66.775    2.681   1.00  47.42    8
ATOM    583  N    THR  B  337    -22.461   67.478    0.781   1.00  41.60    7
ATOM    584  CA   THR  B  337    -21.172   66.818    1.041   1.00  39.69    6
ATOM    585  CB   THR  B  337    -20.720   66.011   -0.173   1.00  41.35    6
ATOM    586  OG1  THR  B  337    -20.273   66.887   -1.213   1.00  49.35    8
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    587  CG2  THR B 337     -21.869  65.175  -0.702  1.00  40.38  6
ATOM    588  C    THR B 337     -20.087  67.846   1.318  1.00  37.88  6
ATOM    589  O    THR B 337     -20.141  68.975   0.832  1.00  34.06  8
ATOM    590  N    ARG B 338     -19.097  67.417   2.095  1.00  37.61  7
ATOM    591  CA   ARG B 338     -17.942  68.241   2.442  1.00  36.68  6
ATOM    592  CB   ARG B 338     -16.770  67.333   2.823  1.00  35.95  6
ATOM    593  CG   ARG B 338     -15.455  68.042   3.064  1.00  38.83  6
ATOM    594  CD   ARG B 338     -14.348  67.029   3.319  1.00  35.88  6
ATOM    595  NE   ARG B 338     -14.520  66.239   4.530  1.00  37.42  7
ATOM    596  CZ   ARG B 338     -14.274  66.669   5.766  1.00  30.20  6
ATOM    597  NH1  ARG B 338     -13.794  67.892   5.973  1.00  27.98  7
ATOM    598  NH2  ARG B 338     -14.481  65.847   6.788  1.00  27.40  7
ATOM    599  C    ARG B 338     -17.581  69.075   1.229  1.00  38.09  6
ATOM    600  O    ARG B 338     -17.537  70.299   1.284  1.00  34.12  8
ATOM    601  N    GLY B 339     -17.345  68.383   0.117  1.00  41.25  7
ATOM    602  CA   GLY B 339     -16.981  69.054  -1.119  1.00  41.35  6
ATOM    603  C    GLY B 339     -18.004  70.109  -1.460  1.00  41.23  6
ATOM    604  O    GLY B 339     -17.736  71.291  -1.330  1.00  38.30  8
ATOM    605  N    GLN B 340     -19.174  69.665  -1.909  1.00  38.58  7
ATOM    606  CA   GLN B 340     -20.258  70.564  -2.276  1.00  40.79  6
ATOM    607  CB   GLN B 340     -21.596  69.843  -2.079  1.00  40.82  6
ATOM    608  CG   GLN B 340     -21.830  68.657  -3.029  1.00  41.10  6
ATOM    609  CD   GLN B 340     -23.154  67.937  -2.783  1.00  48.84  6
ATOM    610  OE1  GLN B 340     -23.353  67.313  -1.715  1.00  50.53  8
ATOM    611  NE2  GLN B 340     -24.050  68.015  -3.753  1.00  54.25  7
ATOM    612  C    GLN B 340     -20.239  71.872  -1.475  1.00  41.50  6
ATOM    613  O    GLN B 340     -20.114  72.958  -2.032  1.00  42.72  8
ATOM    614  N    LEU B 341     -20.352  71.736  -0.156  1.00  42.00  7
ATOM    615  CA   LEU B 341     -20.375  72.879   0.746  1.00  38.10  6
ATOM    616  CB   LEU B 341     -20.401  72.419   2.201  1.00  36.66  6
ATOM    617  CG   LEU B 341     -20.678  73.514   3.194  1.00  39.94  6
ATOM    618  CD1  LEU B 341     -22.088  74.038   2.936  1.00  34.98  6
ATOM    619  CD2  LEU B 341     -20.870  72.990   4.609  1.00  40.95  6
ATOM    620  C    LEU B 341     -19.170  73.763   0.543  1.00  36.37  6
ATOM    621  O    LEU B 341     -19.293  74.974   0.497  1.00  37.89  8
ATOM    622  N    LYS B 342     -18.003  73.136   0.433  1.00  33.29  7
ATOM    623  CA   LYS B 342     -16.737  73.843   0.239  1.00  35.17  6
ATOM    624  CB   LYS B 342     -15.603  72.821   0.176  1.00  34.97  6
ATOM    625  CG   LYS B 342     -14.210  73.401   0.306  1.00  40.00  6
ATOM    626  CD   LYS B 342     -13.155  72.288   0.316  1.00  34.48  6
ATOM    627  CE   LYS B 342     -11.775  72.809   0.755  1.00  37.54  6
ATOM    628  NZ   LYS B 342     -10.790  71.680   0.981  1.00  42.32  7
ATOM    629  C    LYS B 342     -16.744  74.685  -1.038  1.00  38.29  6
ATOM    630  O    LYS B 342     -16.725  75.911  -0.993  1.00  36.23  8
ATOM    631  N    ASN B 343     -16.760  73.990  -2.172  1.00  39.25  7
ATOM    632  CA   ASN B 343     -16.762  74.609  -3.481  1.00  40.19  6
ATOM    633  CB   ASN B 343     -16.977  73.539  -4.551  1.00  37.96  6
ATOM    634  CG   ASN B 343     -16.178  72.272  -4.277  1.00  39.22  6
ATOM    635  OD1  ASN B 343     -14.938  72.313  -4.106  1.00  42.37  8
ATOM    636  ND2  ASN B 343     -16.877  71.144  -4.259  1.00  42.19  7
ATOM    637  C    ASN B 343     -17.894  75.624  -3.547  1.00  40.12  6
ATOM    638  O    ASN B 343     -17.835  76.600  -4.284  1.00  36.01  8
ATOM    639  N    GLY B 344     -18.934  75.361  -2.756  1.00  40.95  7
ATOM    640  CA   GLY B 344     -20.101  76.222  -2.709  1.00  39.25  6
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    641  C    GLY B 344     -19.867  77.636  -2.258  1.00  38.26  6
ATOM    642  O    GLY B 344     -20.715  78.501  -2.484  1.00  35.69  8
ATOM    643  N    GLY B 345     -18.724  77.871  -1.619  1.00  35.89  7
ATOM    644  CA   GLY B 345     -18.426  79.209  -1.159  1.00  34.00  6
ATOM    645  C    GLY B 345     -17.848  79.298   0.230  1.00  38.64  6
ATOM    646  O    GLY B 345     -17.216  80.303   0.573  1.00  38.14  8
ATOM    647  N    LEU B 346     -18.071  78.266   1.041  1.00  39.52  7
ATOM    648  CA   LEU B 346     -17.563  78.279   2.403  1.00  36.05  6
ATOM    649  CB   LEU B 346     -18.311  77.256   3.269  1.00  35.72  6
ATOM    650  CG   LEU B 346     -19.800  77.473   3.378  1.00  34.89  6
ATOM    651  CD1  LEU B 346     -20.322  76.678   4.554  1.00  44.09  6
ATOM    652  CD2  LEU B 346     -20.086  78.937   3.612  1.00  34.84  6
ATOM    653  C    LEU B 346     -16.079  78.018   2.445  1.00  33.52  6
ATOM    654  O    LEU B 346     -15.392  78.387   3.394  1.00  35.58  8
ATOM    655  N    GLY B 347     -15.586  77.388   1.385  1.00  30.47  7
ATOM    656  CA   GLY B 347     -14.174  77.078   1.305  1.00  33.01  6
ATOM    657  C    GLY B 347     -13.768  76.214   2.477  1.00  30.72  6
ATOM    658  O    GLY B 347     -14.433  75.243   2.808  1.00  30.89  8
ATOM    659  N    VAL B 348     -12.647  76.585   3.087  1.00  31.30  7
ATOM    660  CA   VAL B 348     -12.097  75.867   4.227  1.00  31.27  6
ATOM    661  CB   VAL B 348     -10.889  76.609   4.817  1.00  31.66  6
ATOM    662  CG1  VAL B 348     -11.292  77.974   5.360  1.00  20.19  6
ATOM    663  CG2  VAL B 348     -10.250  75.786   5.905  1.00  24.77  6
ATOM    664  C    VAL B 348     -13.136  75.651   5.360  1.00  33.84  6
ATOM    665  O    VAL B 348     -13.002  74.707   6.153  1.00  29.99  8
ATOM    666  N    VAL B 349     -14.157  76.518   5.449  1.00  33.31  7
ATOM    667  CA   VAL B 349     -15.147  76.339   6.483  1.00  32.23  6
ATOM    668  CB   VAL B 349     -16.226  77.393   6.476  1.00  32.59  6
ATOM    669  CG1  VAL B 349     -17.342  76.979   7.399  1.00  33.68  6
ATOM    670  CG2  VAL B 349     -15.667  78.703   6.959  1.00  32.30  6
ATOM    671  C    VAL B 349     -15.792  74.987   6.380  1.00  34.91  6
ATOM    672  O    VAL B 349     -16.055  74.359   7.394  1.00  33.73  8
ATOM    673  N    SER B 350     -16.054  74.507   5.176  1.00  32.81  7
ATOM    674  CA   SER B 350     -16.695  73.215   5.100  1.00  30.10  6
ATOM    675  CB   SER B 350     -16.772  72.697   3.684  1.00  24.95  6
ATOM    676  OG   SER B 350     -17.538  71.502   3.644  1.00  23.16  8
ATOM    677  C    SER B 350     -15.910  72.254   5.942  1.00  31.59  6
ATOM    678  O    SER B 350     -16.417  71.807   6.950  1.00  37.62  8
ATOM    679  N    ASP B 351     -14.675  71.942   5.565  1.00  28.60  7
ATOM    680  CA   ASP B 351     -13.905  71.010   6.378  1.00  29.82  6
ATOM    681  CB   ASP B 351     -12.419  71.139   6.050  1.00  27.49  6
ATOM    682  CG   ASP B 351     -12.151  71.094   4.585  1.00  30.22  6
ATOM    683  OD1  ASP B 351     -12.013  72.174   3.954  1.00  32.61  8
ATOM    684  OD2  ASP B 351     -12.064  69.980   4.017  1.00  30.02  8
ATOM    685  C    ASP B 351     -14.176  71.343   7.861  1.00  30.63  6
ATOM    686  O    ASP B 351     -14.458  70.474   8.681  1.00  29.54  8
ATOM    687  N    ALA B 352     -14.111  72.629   8.177  1.00  25.33  7
ATOM    688  CA   ALA B 352     -14.346  73.092   9.533  1.00  28.59  6
ATOM    689  CB   ALA B 352     -14.252  74.606   9.572  1.00  20.95  6
ATOM    690  C    ALA B 352     -15.690  72.630  10.086  1.00  29.69  6
ATOM    691  O    ALA B 352     -15.757  72.068  11.164  1.00  30.36  8
ATOM    692  N    ILE B 353     -16.754  72.884   9.330  1.00  27.63  7
ATOM    693  CA   ILE B 353     -18.096  72.506   9.729  1.00  27.55  6
ATOM    694  CB   ILE B 353     -19.144  73.129   8.800  1.00  28.04  6
```

UNITED STATES PATENT AND TRADEMARK OFFICE
CERTIFICATE OF CORRECTION

| | | |
|---|---|---|
| PATENT NO. | : 6,965,850 B2 | |
| APPLICATION NO. | : 09/281717 | |
| DATED | : November 15, 2005 | |
| INVENTOR(S) | : John D. Baxter et al. | |

It is certified that error appears in the above-identified patent and that said Letters Patent is hereby corrected as shown below:

```
ATOM    695  CG2 ILE B 353     -20.529  72.673   9.195  1.00 23.68   6
ATOM    696  CG1 ILE B 353     -19.108  74.657   8.869  1.00 27.33   6
ATOM    697  CD1 ILE B 353     -20.141  75.313   7.964  1.00 26.23   6
ATOM    698  C   ILE B 353     -18.309  71.002   9.775  1.00 30.88   6
ATOM    699  O   ILE B 353     -19.021  70.499  10.639  1.00 31.22   8
ATOM    700  N   PHE B 354     -17.728  70.279   8.822  1.00 29.86   7
ATOM    701  CA  PHE B 354     -17.881  68.831   8.797  1.00 31.08   6
ATOM    702  CB  PHE B 354     -17.461  68.249   7.439  1.00 28.80   6
ATOM    703  CG  PHE B 354     -18.568  68.233   6.405  1.00 28.80   6
ATOM    704  CD1 PHE B 354     -19.031  69.403   5.833  1.00 30.96   6
ATOM    705  CD2 PHE B 354     -19.150  67.027   6.034  1.00 29.45   6
ATOM    706  CE1 PHE B 354     -20.066  69.362   4.902  1.00 27.12   6
ATOM    707  CE2 PHE B 354     -20.186  66.978   5.104  1.00 25.19   6
ATOM    708  CZ  PHE B 354     -20.644  68.146   4.535  1.00 28.09   6
ATOM    709  C   PHE B 354     -17.041  68.223   9.913  1.00 29.17   6
ATOM    710  O   PHE B 354     -17.544  67.429  10.700  1.00 32.62   8
ATOM    711  N   ASP B 355     -15.761  68.593   9.972  1.00 23.86   7
ATOM    712  CA  ASP B 355     -14.864  68.090  11.005  1.00 25.34   6
ATOM    713  CB  ASP B 355     -13.582  68.929  11.045  1.00 21.41   6
ATOM    714  CG  ASP B 355     -12.548  68.456  10.086  1.00 32.08   6
ATOM    715  OD1 ASP B 355     -12.899  68.069   8.944  1.00 33.58   8
ATOM    716  OD2 ASP B 355     -11.345  68.477  10.450  1.00 33.20   8
ATOM    717  C   ASP B 355     -15.570  68.153  12.357  1.00 27.86   6
ATOM    718  O   ASP B 355     -15.430  67.257  13.182  1.00 32.42   8
ATOM    719  N   LEU B 356     -16.339  69.223  12.561  1.00 26.84   7
ATOM    720  CA  LEU B 356     -17.085  69.400  13.803  1.00 28.66   6
ATOM    721  CB  LEU B 356     -17.832  70.742  13.800  1.00 25.37   6
ATOM    722  CG  LEU B 356     -18.655  71.091  15.023  1.00 27.61   6
ATOM    723  CD1 LEU B 356     -17.729  71.248  16.191  1.00 25.43   6
ATOM    724  CD2 LEU B 356     -19.430  72.363  14.808  1.00 27.49   6
ATOM    725  C   LEU B 356     -18.084  68.260  13.883  1.00 30.44   6
ATOM    726  O   LEU B 356     -18.054  67.445  14.804  1.00 31.55   8
ATOM    727  N   GLY B 357     -18.972  68.214  12.891  1.00 32.69   7
ATOM    728  CA  GLY B 357     -20.001  67.186  12.846  1.00 29.87   6
ATOM    729  C   GLY B 357     -19.486  65.832  13.279  1.00 33.12   6
ATOM    730  O   GLY B 357     -20.032  65.246  14.207  1.00 29.41   8
ATOM    731  N   MET B 358     -18.444  65.351  12.593  1.00 33.31   7
ATOM    732  CA  MET B 358     -17.834  64.066  12.902  1.00 35.87   6
ATOM    733  CB  MET B 358     -16.513  63.903  12.151  1.00 34.56   6
ATOM    734  CG  MET B 358     -16.649  63.908  10.657  1.00 46.43   6
ATOM    735  SD  MET B 358     -15.094  63.597   9.751  1.00 42.13  16
ATOM    736  CE  MET B 358     -14.121  65.063  10.228  1.00 44.29   6
ATOM    737  C   MET B 358     -17.552  63.976  14.392  1.00 33.26   6
ATOM    738  O   MET B 358     -18.019  63.075  15.075  1.00 36.39   8
ATOM    739  N   SER B 359     -16.766  64.933  14.875  1.00 33.31   7
ATOM    740  CA  SER B 359     -16.380  64.998  16.270  1.00 34.39   6
ATOM    741  CB  SER B 359     -15.724  66.339  16.541  1.00 30.84   6
ATOM    742  OG  SER B 359     -15.130  66.355  17.825  1.00 47.14   8
ATOM    743  C   SER B 359     -17.579  64.813  17.169  1.00 36.43   6
ATOM    744  O   SER B 359     -17.635  63.853  17.922  1.00 35.46   8
ATOM    745  N   LEU B 360     -18.525  65.744  17.079  1.00 36.74   7
ATOM    746  CA  LEU B 360     -19.741  65.729  17.889  1.00 35.44   6
ATOM    747  CB  LEU B 360     -20.706  66.817  17.405  1.00 34.16   6
ATOM    748  CG  LEU B 360     -20.263  68.255  17.575  1.00 34.59   6
```

UNITED STATES PATENT AND TRADEMARK OFFICE
CERTIFICATE OF CORRECTION

PATENT NO. : 6,965,850 B2  
APPLICATION NO. : 09/281717  
DATED : November 15, 2005  
INVENTOR(S) : John D. Baxter et al.

Page 58 of 186

It is certified that error appears in the above-identified patent and that said Letters Patent is hereby corrected as shown below:

```
ATOM    749  CD1  LEU B 360     -21.394  69.181  17.212  1.00 33.53  6
ATOM    750  CD2  LEU B 360     -19.869  68.486  19.010  1.00 31.89  6
ATOM    751  C    LEU B 360     -20.464  64.397  17.924  1.00 38.72  6
ATOM    752  O    LEU B 360     -21.021  64.011  18.958  1.00 38.29  8
ATOM    753  N    SER B 361     -20.466  63.708  16.791  1.00 40.96  7
ATOM    754  CA   SER B 361     -21.106  62.416  16.721  1.00 45.67  6
ATOM    755  CB   SER B 361     -20.532  61.630  15.551  1.00 46.45  6
ATOM    756  OG   SER B 361     -20.750  62.314  14.322  1.00 51.81  8
ATOM    757  C    SER B 361     -20.895  61.638  18.018  1.00 44.49  6
ATOM    758  O    SER B 361     -21.696  60.793  18.362  1.00 46.67  8
ATOM    759  N    SER B 362     -19.811  61.953  18.726  1.00 41.44  7
ATOM    760  CA   SER B 362     -19.453  61.309  19.972  1.00 42.13  6
ATOM    761  CB   SER B 362     -17.962  61.510  20.234  1.00 42.61  6
ATOM    762  OG   SER B 362     -17.164  61.025  19.158  1.00 51.87  8
ATOM    763  C    SER B 362     -20.228  61.812  21.174  1.00 38.41  6
ATOM    764  O    SER B 362     -20.602  61.025  22.035  1.00 38.01  8
ATOM    765  N    PHE B 363     -20.455  63.123  21.228  1.00 34.55  7
ATOM    766  CA   PHE B 363     -21.150  63.735  22.346  1.00 32.96  6
ATOM    767  CB   PHE B 363     -21.006  65.245  22.285  1.00 31.99  6
ATOM    768  CG   PHE B 363     -19.578  65.719  22.378  1.00 29.97  6
ATOM    769  CD1  PHE B 363     -19.286  67.058  22.447  1.00 30.61  6
ATOM    770  CD2  PHE B 363     -18.536  64.800  22.391  1.00 32.02  6
ATOM    771  CE1  PHE B 363     -17.966  67.489  22.543  1.00 33.67  6
ATOM    772  CE2  PHE B 363     -17.221  65.222  22.484  1.00 30.91  6
ATOM    773  CZ   PHE B 363     -16.927  66.557  22.554  1.00 29.33  6
ATOM    774  C    PHE B 363     -22.617  63.361  22.482  1.00 30.52  6
ATOM    775  O    PHE B 363     -23.142  63.331  23.596  1.00 32.19  8
ATOM    776  N    ASN B 364     -23.279  63.075  21.361  1.00 33.51  7
ATOM    777  CA   ASN B 364     -24.683  62.701  21.377  1.00 38.03  6
ATOM    778  CB   ASN B 364     -24.855  61.369  22.111  1.00 42.32  6
ATOM    779  CG   ASN B 364     -24.008  60.271  21.524  1.00 53.11  6
ATOM    780  OD1  ASN B 364     -24.183  59.895  20.344  1.00 59.51  8
ATOM    781  ND2  ASN B 364     -23.102  59.746  22.325  1.00 55.95  7
ATOM    782  C    ASN B 364     -25.494  63.771  22.091  1.00 31.89  6
ATOM    783  O    ASN B 364     -26.279  63.471  22.990  1.00 30.28  8
ATOM    784  N    LEU B 365     -25.306  65.018  21.673  1.00 27.62  7
ATOM    785  CA   LEU B 365     -26.005  66.144  22.280  1.00 29.36  6
ATOM    786  CB   LEU B 365     -25.402  67.443  21.743  1.00 27.54  6
ATOM    787  CG   LEU B 365     -23.897  67.453  21.738  1.00 38.91  6
ATOM    788  CD1  LEU B 365     -23.391  68.766  21.190  1.00 34.47  6
ATOM    789  CD2  LEU B 365     -23.393  67.214  23.143  1.00 34.24  6
ATOM    790  C    LEU B 365     -27.496  66.074  21.987  1.00 26.23  6
ATOM    791  O    LEU B 365     -27.911  65.790  20.863  1.00 27.06  8
ATOM    792  N    ASP B 366     -28.296  66.321  23.022  1.00 25.23  7
ATOM    793  CA   ASP B 366     -29.752  66.320  22.878  1.00 26.07  6
ATOM    794  CB   ASP B 366     -30.441  65.651  24.076  1.00 29.68  6
ATOM    795  CG   ASP B 366     -30.221  66.374  25.360  1.00 35.74  6
ATOM    796  OD1  ASP B 366     -30.277  67.617  25.387  1.00 36.78  8
ATOM    797  OD2  ASP B 366     -30.017  65.711  26.410  1.00 41.23  8
ATOM    798  C    ASP B 366     -30.230  67.752  22.740  1.00 27.70  6
ATOM    799  O    ASP B 366     -29.552  68.678  23.171  1.00 31.94  8
ATOM    800  N    ASP B 367     -31.409  67.913  22.142  1.00 29.18  7
ATOM    801  CA   ASP B 367     -32.031  69.225  21.930  1.00 32.72  6
ATOM    802  CB   ASP B 367     -33.558  69.106  22.071  1.00 38.04  6
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    803  CG   ASP B 367    -34.172  68.166  21.081  1.00  42.43  6
ATOM    804  OD1  ASP B 367    -34.051  68.373  19.894  1.00  35.95  8
ATOM    805  OD2  ASP B 367    -34.829  67.188  21.504  1.00  51.42  8
ATOM    806  C    ASP B 367    -31.496  70.238  22.959  1.00  33.71  6
ATOM    807  O    ASP B 367    -30.791  71.188  22.624  1.00  38.30  8
ATOM    808  N    THR B 368    -31.858  69.997  24.218  1.00  31.06  7
ATOM    809  CA   THR B 368    -31.453  70.822  25.344  1.00  26.28  6
ATOM    810  CB   THR B 368    -31.567  70.020  26.643  1.00  27.30  6
ATOM    811  OG1  THR B 368    -32.916  69.578  26.824  1.00  33.42  8
ATOM    812  CG2  THR B 368    -31.143  70.855  27.824  1.00  25.16  6
ATOM    813  C    THR B 368    -30.025  71.315  25.181  1.00  21.13  6
ATOM    814  O    THR B 368    -29.746  72.508  25.150  1.00  23.17  8
ATOM    815  N    GLU B 369    -29.123  70.354  25.072  1.00  21.32  7
ATOM    816  CA   GLU B 369    -27.711  70.634  24.932  1.00  28.00  6
ATOM    817  CB   GLU B 369    -26.947  69.306  24.878  1.00  32.79  6
ATOM    818  CG   GLU B 369    -27.229  68.433  26.130  1.00  36.29  6
ATOM    819  CD   GLU B 369    -26.689  67.051  26.083  1.00  41.03  6
ATOM    820  OE1  GLU B 369    -26.960  66.318  25.102  1.00  42.05  8
ATOM    821  OE2  GLU B 369    -25.992  66.645  27.048  1.00  42.03  8
ATOM    822  C    GLU B 369    -27.428  71.527  23.731  1.00  25.57  6
ATOM    823  O    GLU B. 369   -26.780  72.549  23.886  1.00  20.56  8
ATOM    824  N    VAL B 370    -27.922  71.154  22.548  1.00  25.39  7
ATOM    825  CA   VAL B 370    -27.710  71.968  21.355  1.00  25.99  6
ATOM    826  CB   VAL B 370    -28.457  71.429  20.130  1.00  26.15  6
ATOM    827  CG1  VAL B 370    -28.255  72.358  18.953  1.00  27.65  6
ATOM    828  CG2  VAL B 370    -28.014  70.021  19.788  1.00  17.70  6
ATOM    829  C    VAL B 370    -28.238  73.346  21.676  1.00  26.49  6
ATOM    830  O    VAL B 370    -27.580  74.351  21.445  1.00  28.16  8
ATOM    831  N    ALA B 371    -29.450  73.362  22.213  1.00  21.01  7
ATOM    832  CA   ALA B 371    -30.145  74.589  22.573  1.00  19.57  6
ATOM    833  CB   ALA B 371    -31.414  74.246  23.335  1.00  18.62  6
ATOM    834  C    ALA B 371    -29.256  75.501  23.401  1.00  23.48  6
ATOM    835  O    ALA B 371    -28.936  76.613  22.989  1.00  32.67  8
ATOM    836  N    LEU B 372    -28.860  75.008  24.571  1.00  22.89  7
ATOM    837  CA   LEU B 372    -27.999  75.758  25.472  1.00  23.28  6
ATOM    838  CB   LEU B 372    -27.606  74.860  26.658  1.00  27.76  6
ATOM    839  CG   LEU B 372    -28.728  74.524  27.619  1.00  21.18  6
ATOM    840  CD1  LEU B 372    -28.272  73.529  28.648  1.00  27.64  6
ATOM    841  CD2  LEU B 372    -29.198  75.801  28.284  1.00  20.90  6
ATOM    842  C    LEU B 372    -26.769  76.268  24.722  1.00  21.34  6
ATOM    843  O    LEU B 372    -26.439  77.454  24.762  1.00  23.16  8
ATOM    844  N    LEU B 373    -26.111  75.349  24.023  1.00  24.42  7
ATOM    845  CA   LEU B 373    -24.916  75.669  23.254  1.00  23.78  6
ATOM    846  CB   LEU B 373    -24.525  74.446  22.396  1.00  22.18  6
ATOM    847  CG   LEU B 373    -23.098  74.283  21.942  1.00  31.52  6
ATOM    848  CD1  LEU B 373    -22.196  74.576  23.100  1.00  31.93  6
ATOM    849  CD2  LEU B 373    -22.873  72.889  21.457  1.00  30.24  6
ATOM    850  C    LEU B 373    -25.235  76.902  22.405  1.00  25.69  6
ATOM    851  O    LEU B 373    -24.491  77.880  22.416  1.00  30.13  8
ATOM    852  N    GLN B 374    -26.368  76.842  21.707  1.00  26.24  7
ATOM    853  CA   GLN B 374    -26.836  77.922  20.839  1.00  21.60  6
ATOM    854  CB   GLN B 374    -28.196  77.571  20.221  1.00  24.57  6
ATOM    855  CG   GLN B 374    -28.188  76.330  19.348  1.00  21.02  6
ATOM    856  CD   GLN B 374    -29.538  76.071  18.698  1.00  22.86  6
```

UNITED STATES PATENT AND TRADEMARK OFFICE
CERTIFICATE OF CORRECTION

| | | |
|---|---|---|
| PATENT NO. | : 6,965,850 B2 | |
| APPLICATION NO. | : 09/281717 | |
| DATED | : November 15, 2005 | |
| INVENTOR(S) | : John D. Baxter et al. | |

It is certified that error appears in the above-identified patent and that said Letters Patent is hereby corrected as shown below:

```
ATOM    857  OE1  GLN  B  374     -29.720   75.049   18.009   1.00  24.07   8
ATOM    858  NE2  GLN  B  374     -30.473   76.980   18.901   1.00  25.59   7
ATOM    859  C    GLN  B  374     -26.988   79.249   21.569   1.00  20.66   6
ATOM    860  O    GLN  B  374     -26.733   80.307   20.994   1.00  24.47   8
ATOM    861  N    ALA  B  375     -27.429   79.182   22.825   1.00  16.26   7
ATOM    862  CA   ALA  B  375     -27.639   80.374   23.831   1.00  17.16   6
ATOM    863  CB   ALA  B  375     -28.435   80.025   24.865   1.00  19.53   6
ATOM    864  C    ALA  B  375     -26.304   80.966   24.025   1.00  25.13   6
ATOM    865  O    ALA  B  375     -26.074   82.154   23.833   1.00  23.81   8
ATOM    866  N    VAL  B  376     -25.433   80.111   24.568   1.00  24.57   7
ATOM    867  CA   VAL  B  376     -24.102   80.526   24.986   1.00  25.80   6
ATOM    868  CB   VAL  B  376     -23.192   79.321   25.234   1.00  26.48   6
ATOM    869  CG1  VAL  B  376     -21.806   79.780   25.620   1.00  23.20   6
ATOM    870  CG2  VAL  B  376     -23.771   78.433   26.310   1.00  19.08   6
ATOM    871  C    VAL  B  376     -23.510   81.403   23.898   1.00  25.69   6
ATOM    872  O    VAL  B  376     -22.796   82.364   24.166   1.00  27.07   8
ATOM    873  N    LEU  B  377     -23.827   81.049   22.659   1.00  23.09   7
ATOM    874  CA   LEU  B  377     -23.340   81.774   21.492   1.00  22.86   6
ATOM    875  CB   LEU  B  377     -23.552   80.920   20.230   1.00  18.50   6
ATOM    876  CG   LEU  B  377     -22.756   79.638   20.146   1.00  22.65   6
ATOM    877  CD1  LEU  B  377     -23.221   78.786   19.000   1.00  16.70   6
ATOM    878  CD2  LEU  B  377     -21.300   79.995   20.000   1.00  19.58   6
ATOM    879  C    LEU  B  377     -24.073   83.102   21.384   1.00  26.14   6
ATOM    880  O    LEU  B  377     -23.464   84.164   21.419   1.00  20.62   8
ATOM    881  N    LEU  B  378     -25.396   83.023   21.265   1.00  28.99   7
ATOM    882  CA   LEU  B  378     -26.228   84.217   21.147   1.00  28.87   6
ATOM    883  CB   LEU  B  378     -27.696   83.894   21.450   1.00  26.89   6
ATOM    884  CG   LEU  B  378     -28.648   85.068   21.500   1.00  28.83   6
ATOM    885  CD1  LEU  B  378     -28.507   85.854   20.225   1.00  27.97   6
ATOM    886  CD2  LEU  B  378     -30.072   84.605   21.692   1.00  27.69   6
ATOM    887  C    LEU  B  378     -25.738   85.280   22.090   1.00  31.09   6
ATOM    888  O    LEU  B  378     -25.398   86.379   21.651   1.00  31.77   8
ATOM    889  N    MET  B  379     -25.695   84.931   23.376   1.00  31.44   7
ATOM    890  CA   MET  B  379     -25.291   85.851   24.434   1.00  32.62   6
ATOM    891  CB   MET  B  379     -25.797   85.335   25.793   1.00  31.45   6
ATOM    892  CG   MET  B  379     -27.332   85.262   25.883   1.00  38.75   6
ATOM    893  SD   MET  B  379     -28.020   86.915   25.550   1.00  41.27  16
ATOM    894  CE   MET  B  379     -29.814   86.586   25.513   1.00  35.68   6
ATOM    895  C    MET  B  379     -23.796   86.129   24.538   1.00  33.72   6
ATOM    896  O    MET  B  379     -23.246   86.190   25.633   1.00  36.29   8
ATOM    897  N    SER  B  380     -23.152   86.335   23.399   1.00  34.49   7
ATOM    898  CA   SER  B  380     -21.738   86.659   23.391   1.00  33.97   6
ATOM    899  CB   SER  B  380     -21.132   86.360   22.010   1.00  31.24   6
ATOM    900  OG   SER  B  380     -21.224   84.978   21.696   1.00  39.42   8
ATOM    901  C    SER  B  380     -21.635   88.145   23.705   1.00  39.69   6
ATOM    902  O    SER  B  380     -22.084   88.989   22.933   1.00  44.64   8
ATOM    903  N    SER  B  381     -21.053   88.451   24.857   1.00  41.04   7
ATOM    904  CA   SER  B  381     -20.907   89.826   25.308   1.00  44.91   6
ATOM    905  CB   SER  B  381     -20.610   89.832   26.797   1.00  44.50   6
ATOM    906  OG   SER  B  381     -19.351   89.229   27.037   1.00  45.42   8
ATOM    907  C    SER  B  381     -19.815   90.614   24.602   1.00  44.59   6
ATOM    908  O    SER  B  381     -19.725   91.825   24.751   1.00  49.32   8
ATOM    909  N    ASP  B  382     -18.977   89.922   23.840   1.00  43.75   7
ATOM    910  CA   ASP  B  382     -17.886   90.556   23.144   1.00  43.93   6
```

UNITED STATES PATENT AND TRADEMARK OFFICE
CERTIFICATE OF CORRECTION

PATENT NO. : 6,965,850 B2  
APPLICATION NO. : 09/281717  
DATED : November 15, 2005  
INVENTOR(S) : John D. Baxter et al.

Page 61 of 186

It is certified that error appears in the above-identified patent and that said Letters Patent is hereby corrected as shown below:

```
ATOM    911  CB   ASP B 382     -16.727  89.562  23.028  1.00 48.39   6
ATOM    912  CG   ASP B 382     -17.142  88.232  22.471  1.00 53.23   6
ATOM    913  OD1  ASP B 382     -18.102  87.621  23.002  1.00 56.97   8
ATOM    914  OD2  ASP B 382     -16.513  87.753  21.480  1.00 58.81   8
ATOM    915  C    ASP B 382     -18.191  91.172  21.772  1.00 41.09   6
ATOM    916  O    ASP B 382     -17.366  91.899  21.229  1.00 40.93   8
ATOM    917  N    ARG B 383     -19.369  90.908  21.224  1.00 42.63   7
ATOM    918  CA   ARG B 383     -19.698  91.445  19.934  1.00 43.32   6
ATOM    919  CB   ARG B 383     -21.131  91.101  19.537  1.00 42.31   6
ATOM    920  CG   ARG B 383     -21.619  89.672  19.811  1.00 40.83   6
ATOM    921  CD   ARG B 383     -21.144  88.627  18.804  1.00 38.09   6
ATOM    922  NE   ARG B 383     -21.922  87.415  18.943  1.00 37.33   7
ATOM    923  CZ   ARG B 383     -21.584  86.250  18.411  1.00 38.35   6
ATOM    924  NH1  ARG B 383     -20.465  86.143  17.700  1.00 33.70   7
ATOM    925  NH2  ARG B 383     -22.369  85.196  18.604  1.00 35.46   7
ATOM    926  C    ARG B 383     -19.591  92.958  20.007  1.00 44.96   6
ATOM    927  O    ARG B 383     -20.050  93.577  20.980  1.00 45.60   8
ATOM    928  N    PRO B 384     -18.975  93.579  19.005  1.00 45.33   7
ATOM    929  CD   PRO B 384     -18.395  92.881  17.854  1.00 46.85   6
ATOM    930  CA   PRO B 384     -18.808  95.035  18.947  1.00 47.37   6
ATOM    931  CB   PRO B 384     -17.868  95.255  17.764  1.00 46.90   6
ATOM    932  CG   PRO B 384     -17.575  93.934  17.187  1.00 46.41   6
ATOM    933  C    PRO B 384     -20.125  95.778  18.762  1.00 48.29   6
ATOM    934  O    PRO B 384     -21.048  95.277  18.120  1.00 48.34   8
ATOM    935  N    GLY B 385     -20.185  96.994  19.314  1.00 49.88   7
ATOM    936  CA   GLY B 385     -21.371  97.838  19.192  1.00 50.35   6
ATOM    937  C    GLY B 385     -22.410  97.615  20.265  1.00 50.70   6
ATOM    938  O    GLY B 385     -23.382  98.363  20.374  1.00 53.48   8
ATOM    939  N    LEU B 386     -22.205  96.557  21.044  1.00 49.04   7
ATOM    940  CA   LEU B 386     -23.136  96.211  22.101  1.00 50.53   6
ATOM    941  CB   LEU B 386     -22.640  94.972  22.853  1.00 45.17   6
ATOM    942  CG   LEU B 386     -22.744  93.653  22.121  1.00 48.26   6
ATOM    943  CD1  LEU B 386     -22.122  92.525  22.938  1.00 41.68   6
ATOM    944  CD2  LEU B 386     -24.215  93.376  21.852  1.00 38.40   6
ATOM    945  C    LEU B 386     -23.322  97.357  23.058  1.00 52.13   6
ATOM    946  O    LEU B 386     -22.438  98.182  23.234  1.00 53.67   8
ATOM    947  N    ALA B 387     -24.499  97.398  23.666  1.00 53.42   7
ATOM    948  CA   ALA B 387     -24.830  98.441  24.624  1.00 56.01   6
ATOM    949  CB   ALA B 387     -26.223  98.993  24.339  1.00 56.47   6
ATOM    950  C    ALA B 387     -24.775  97.853  26.024  1.00 55.52   6
ATOM    951  O    ALA B 387     -23.798  98.027  26.753  1.00 53.75   8
ATOM    952  N    CYS B 388     -25.843  97.145  26.371  1.00 56.03   7
ATOM    953  CA   CYS B 388     -26.000  96.525  27.673  1.00 59.57   6
ATOM    954  CB   CYS B 388     -27.469  96.134  27.839  1.00 59.23   6
ATOM    955  SG   CYS B 388     -28.620  97.392  27.264  1.00 58.64  16
ATOM    956  C    CYS B 388     -25.105  95.283  27.798  1.00 62.18   6
ATOM    957  O    CYS B 388     -25.590  94.164  27.868  1.00 67.88   8
ATOM    958  N    VAL B 389     -23.789  95.510  27.824  1.00 60.78   7
ATOM    959  CA   VAL B 389     -22.797  94.434  27.959  1.00 57.70   6
ATOM    960  CB   VAL B 389     -21.355  94.976  27.998  1.00 57.09   6
ATOM    961  CG1  VAL B 389     -20.361  93.832  28.085  1.00 59.03   6
ATOM    962  CG2  VAL B 389     -21.065  95.845  26.791  1.00 53.98   6
ATOM    963  C    VAL B 389     -23.078  93.642  29.230  1.00 57.77   6
ATOM    964  O    VAL B 389     -23.727  92.602  29.203  1.00 60.94   8
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    965  N    ALA B 390    -22.561  94.159  30.332  1.00  52.68  7
ATOM    966  CA   ALA B 390    -22.684  93.570  31.659  1.00  48.41  6
ATOM    967  CB   ALA B 390    -22.650  94.681  32.716  1.00  45.19  6
ATOM    968  C    ALA B 390    -23.905  92.697  31.877  1.00  47.63  6
ATOM    969  O    ALA B 390    -23.784  91.576  32.369  1.00  51.95  8
ATOM    970  N    ARG B 391    -25.075  93.216  31.498  1.00  47.11  7
ATOM    971  CA   ARG B 391    -26.330  92.481  31.656  1.00  51.64  6
ATOM    972  CB   ARG B 391    -27.502  93.318  31.122  1.00  54.22  6
ATOM    973  CG   ARG B 391    -28.887  92.713  31.430  1.00  64.20  6
ATOM    974  CD   ARG B 391    -30.059  93.582  30.929  1.00  73.80  6
ATOM    975  NE   ARG B 391    -31.361  93.097  31.378  1.00  79.76  7
ATOM    976  CZ   ARG B 391    -31.736  93.015  32.656  1.00  84.27  6
ATOM    977  NH1  ARG B 391    -30.887  93.372  33.625  1.00  85.28  7
ATOM    978  NH2  ARG B 391    -32.957  92.566  32.955  1.00  86.84  7
ATOM    979  C    ARG B 391    -26.277  91.133  30.940  1.00  48.18  6
ATOM    980  O    ARG B 391    -26.724  90.119  31.465  1.00  49.57  8
ATOM    981  N    ILE B 392    -25.743  91.167  29.718  1.00  45.01  7
ATOM    982  CA   ILE B 392    -25.592  89.999  28.867  1.00  48.77  6
ATOM    983  CB   ILE B 392    -25.112  90.424  27.469  1.00  46.45  6
ATOM    984  CG2  ILE B 392    -24.805  89.221  26.614  1.00  42.35  6
ATOM    985  CG1  ILE B 392    -26.178  91.283  26.768  1.00  49.69  6
ATOM    986  CD1  ILE B 392    -25.762  91.768  25.386  1.00  51.09  6
ATOM    987  C    ILE B 392    -24.671  88.935  29.462  1.00  50.90  6
ATOM    988  O    ILE B 392    -25.086  87.780  29.605  1.00  52.21  8
ATOM    989  N    GLU B 393    -23.431  89.298  29.790  1.00  50.43  7
ATOM    990  CA   GLU B 393    -22.504  88.328  30.378  1.00  50.30  6
ATOM    991  CB   GLU B 393    -21.314  89.022  31.044  1.00  53.97  6
ATOM    992  CG   GLU B 393    -20.063  89.005  30.209  1.00  62.18  6
ATOM    993  CD   GLU B 393    -18.877  89.415  30.976  1.00  67.69  6
ATOM    994  OE1  GLU B 393    -17.709  89.264  30.656  1.00  66.42  8
ATOM    995  OE2  GLU B 393    -18.897  89.976  32.052  1.00  70.64  8
ATOM    996  C    GLU B 393    -23.251  87.477  31.416  1.00  49.31  6
ATOM    997  O    GLU B 393    -23.226  86.260  31.303  1.00  49.53  8
ATOM    998  N    LYS B 394    -23.898  88.153  32.409  1.00  46.07  7
ATOM    999  CA   LYS B 394    -24.721  87.579  33.506  1.00  45.76  6
ATOM   1000  CB   LYS B 394    -25.594  88.693  34.161  1.00  43.85  6
ATOM   1001  C    LYS B 394    -25.626  86.548  32.851  1.00  46.69  6
ATOM   1002  O    LYS B 394    -25.772  85.430  33.329  1.00  49.13  8
ATOM   1003  N    TYR B 395    -26.203  86.948  31.719  1.00  46.57  7
ATOM   1004  CA   TYR B 395    -27.076  86.078  30.938  1.00  43.33  6
ATOM   1005  CB   TYR B 395    -27.621  86.821  29.716  1.00  48.44  6
ATOM   1006  CG   TYR B 395    -28.827  87.688  29.980  1.00  53.83  6
ATOM   1007  CD1  TYR B 395    -29.204  88.680  29.080  1.00  56.43  6
ATOM   1008  CE1  TYR B 395    -30.331  89.469  29.309  1.00  59.73  6
ATOM   1009  CD2  TYR B 395    -29.596  87.509  31.113  1.00  56.47  6
ATOM   1010  CE2  TYR B 395    -30.723  88.295  31.346  1.00  62.60  6
ATOM   1011  CZ   TYR B 395    -31.090  89.281  30.446  1.00  63.18  6
ATOM   1012  OH   TYR B 395    -32.189  90.068  30.671  1.00  64.46  8
ATOM   1013  C    TYR B 395    -26.276  84.867  30.485  1.00  37.30  6
ATOM   1014  O    TYR B 395    -26.611  83.737  30.825  1.00  34.10  8
ATOM   1015  N    GLN B 396    -25.213  85.108  29.718  1.00  31.92  7
ATOM   1016  CA   GLN B 396    -24.380  84.018  29.244  1.00  34.81  6
ATOM   1017  CB   GLN B 396    -23.176  84.550  28.464  1.00  32.64  6
ATOM   1018  CG   GLN B 396    -22.184  83.470  28.103  1.00  29.57  6
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1019  CD   GLN B 396     -21.214  83.871  27.016  1.00  29.46   6
ATOM   1020  OE1  GLN B 396     -20.547  84.930  27.109  1.00  34.65   8
ATOM   1021  NE2  GLN B 396     -21.112  83.032  25.992  1.00  27.21   7
ATOM   1022  C    GLN B 396     -23.908  83.207  30.434  1.00  37.13   6
ATOM   1023  O    GLN B 396     -23.876  81.986  30.384  1.00  37.36   8
ATOM   1024  N    ASP B 397     -23.544  83.903  31.508  1.00  38.61   7
ATOM   1025  CA   ASP B 397     -23.069  83.250  32.717  1.00  40.37   6
ATOM   1026  CB   ASP B 397     -22.617  84.297  33.754  1.00  40.51   6
ATOM   1027  CG   ASP B 397     -21.360  85.025  33.352  1.00  43.77   6
ATOM   1028  OD1  ASP B 397     -20.337  84.366  33.054  1.00  46.50   8
ATOM   1029  OD2  ASP B 397     -21.343  86.287  33.350  1.00  51.34   8
ATOM   1030  C    ASP B 397     -24.223  82.422  33.267  1.00  38.62   6
ATOM   1031  O    ASP B 397     -24.023  81.327  33.778  1.00  39.20   8
ATOM   1032  N    SER B 398     -25.432  82.962  33.138  1.00  37.84   7
ATOM   1033  CA   SER B 398     -26.633  82.293  33.622  1.00  37.80   6
ATOM   1034  CB   SER B 398     -27.830  83.246  33.501  1.00  34.28   6
ATOM   1035  OG   SER B 398     -28.995  82.715  34.114  1.00  46.60   8
ATOM   1036  C    SER B 398     -26.911  80.997  32.867  1.00  38.41   6
ATOM   1037  O    SER B 398     -27.454  80.047  33.433  1.00  39.98   8
ATOM   1038  N    PHE B 399     -26.546  80.963  31.587  1.00  34.82   7
ATOM   1039  CA   PHE B 399     -26.772  79.768  30.781  1.00  35.96   6
ATOM   1040  CB   PHE B 399     -26.892  80.100  29.293  1.00  35.75   6
ATOM   1041  CG   PHE B 399     -28.211  80.717  28.906  1.00  39.30   6
ATOM   1042  CD1  PHE B 399     -28.466  82.056  29.109  1.00  39.86   6
ATOM   1043  CD2  PHE B 399     -29.194  79.938  28.355  1.00  36.81   6
ATOM   1044  CE1  PHE B 399     -29.700  82.602  28.739  1.00  41.25   6
ATOM   1045  CE2  PHE B 399     -30.424  80.483  27.987  1.00  43.61   6
ATOM   1046  CZ   PHE B 399     -30.677  81.813  28.181  1.00  40.34   6
ATOM   1047  C    PHE B 399     -25.658  78.754  30.976  1.00  33.48   6
ATOM   1048  O    PHE B 399     -25.927  77.589  31.256  1.00  26.86   8
ATOM   1049  N    LEU B 400     -24.408  79.187  30.796  1.00  31.47   7
ATOM   1050  CA   LEU B 400     -23.275  78.291  30.945  1.00  37.41   6
ATOM   1051  CB   LEU B 400     -21.976  79.091  31.030  1.00  34.24   6
ATOM   1052  CG   LEU B 400     -21.470  79.642  29.726  1.00  35.10   6
ATOM   1053  CD1  LEU B 400     -20.121  80.304  29.917  1.00  26.60   6
ATOM   1054  CD2  LEU B 400     -21.326  78.488  28.759  1.00  29.44   6
ATOM   1055  C    LEU B 400     -23.430  77.376  32.145  1.00  38.84   6
ATOM   1056  O    LEU B 400     -23.366  76.157  32.007  1.00  40.38   8
ATOM   1057  N    LEU B 401     -23.639  77.968  33.321  1.00  42.79   7
ATOM   1058  CA   LEU B 401     -23.801  77.181  34.537  1.00  43.48   6
ATOM   1059  CB   LEU B 401     -24.226  78.067  35.712  1.00  44.73   6
ATOM   1060  CG   LEU B 401     -24.378  77.303  37.012  1.00  51.39   6
ATOM   1061  CD1  LEU B 401     -22.990  76.844  37.484  1.00  50.11   6
ATOM   1062  CD2  LEU B 401     -25.027  78.163  38.083  1.00  49.30   6
ATOM   1063  C    LEU B 401     -24.854  76.095  34.311  1.00  41.62   6
ATOM   1064  O    LEU B 401     -24.576  74.900  34.427  1.00  45.14   8
ATOM   1065  N    ALA B 402     -26.068  76.532  33.997  1.00  37.92   7
ATOM   1066  CA   ALA B 402     -27.177  75.631  33.752  1.00  29.90   6
ATOM   1067  CB   ALA B 402     -28.361  76.433  33.200  1.00  30.70   6
ATOM   1068  C    ALA B 402     -26.779  74.521  32.773  1.00  28.88   6
ATOM   1069  O    ALA B 402     -27.078  73.347  32.996  1.00  32.14   8
ATOM   1070  N    PHE B 403     -26.091  74.908  31.698  1.00  31.07   7
ATOM   1071  CA   PHE B 403     -25.655  73.970  30.673  1.00  29.90   6
ATOM   1072  CB   PHE B 403     -24.847  74.715  29.607  1.00  27.03   6
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1073  CG   PHE B 403     -24.557  73.908  28.359  1.00  26.97    6
ATOM   1074  CD1  PHE B 403     -23.916  74.494  27.272  1.00  25.55    6
ATOM   1075  CD2  PHE B 403     -24.939  72.583  28.271  1.00  19.75    6
ATOM   1076  CE1  PHE B 403     -23.670  73.765  26.104  1.00  27.90    6
ATOM   1077  CE2  PHE B 403     -24.693  71.848  27.102  1.00  22.56    6
ATOM   1078  CZ   PHE B 403     -24.057  72.439  26.020  1.00  22.24    6
ATOM   1079  C    PHE B 403     -24.810  72.902  31.329  1.00  28.82    6
ATOM   1080  O    PHE B 403     -25.092  71.726  31.205  1.00  26.00    8
ATOM   1081  N    GLU B 404     -23.776  73.335  32.037  1.00  30.25    7
ATOM   1082  CA   GLU B 404     -22.865  72.419  32.712  1.00  34.03    6
ATOM   1083  CB   GLU B 404     -21.835  73.215  33.527  1.00  39.45    6
ATOM   1084  CG   GLU B 404     -20.654  72.384  34.068  1.00  47.68    6
ATOM   1085  CD   GLU B 404     -19.750  73.129  34.996  1.00  54.02    6
ATOM   1086  OE1  GLU B 404     -19.372  74.290  34.701  1.00  57.27    8
ATOM   1087  OE2  GLU B 404     -19.369  72.555  36.048  1.00  63.85    8
ATOM   1088  C    GLU B 404     -23.645  71.509  33.642  1.00  36.01    6
ATOM   1089  O    GLU B 404     -23.470  70.292  33.640  1.00  38.64    8
ATOM   1090  N    HIS B 405     -24.492  72.131  34.458  1.00  29.56    7
ATOM   1091  CA   HIS B 405     -25.306  71.387  35.405  1.00  31.69    6
ATOM   1092  CB   HIS B 405     -26.245  72.324  36.173  1.00  33.75    6
ATOM   1093  CG   HIS B 405     -25.536  73.185  37.163  1.00  34.75    6
ATOM   1094  CD2  HIS B 405     -24.234  73.286  37.524  1.00  34.58    6
ATOM   1095  ND1  HIS B 405     -26.223  74.101  37.969  1.00  32.43    7
ATOM   1096  CE1  HIS B 405     -25.334  74.703  38.769  1.00  36.15    6
ATOM   1097  NE2  HIS B 405     -24.139  74.222  38.511  1.00  39.84    7
ATOM   1098  C    HIS B 405     -26.106  70.342  34.648  1.00  34.21    6
ATOM   1099  O    HIS B 405     -26.087  69.160  35.006  1.00  37.06    8
ATOM   1100  N    TYR B 406     -26.806  70.776  33.598  1.00  30.83    7
ATOM   1101  CA   TYR B 406     -27.592  69.853  32.796  1.00  28.85    6
ATOM   1102  CB   TYR B 406     -28.192  70.537  31.579  1.00  31.48    6
ATOM   1103  CG   TYR B 406     -28.991  69.576  30.730  1.00  23.49    6
ATOM   1104  CD1  TYR B 406     -30.179  69.047  31.196  1.00  19.42    6
ATOM   1105  CE1  TYR B 406     -30.893  68.128  30.441  1.00  23.80    6
ATOM   1106  CD2  TYR B 406     -28.525  69.152  29.496  1.00  21.81    6
ATOM   1107  CE2  TYR B 406     -29.241  68.228  28.740  1.00  24.64    6
ATOM   1108  CZ   TYR B 406     -30.420  67.713  29.217  1.00  21.56    6
ATOM   1109  OH   TYR B 406     -31.120  66.802  28.480  1.00  24.96    8
ATOM   1110  C    TYR B 406     -26.697  68.725  32.304  1.00  24.24    6
ATOM   1111  O    TYR B 406     -27.155  67.609  32.110  1.00  27.08    8
ATOM   1112  N    ILE B 407     -25.422  69.056  32.084  1.00  25.76    7
ATOM   1113  CA   ILE B 407     -24.428  68.092  31.628  1.00  33.75    6
ATOM   1114  CB   ILE B 407     -23.090  68.778  31.274  1.00  34.23    6
ATOM   1115  CG2  ILE B 407     -21.959  67.774  31.230  1.00  32.46    6
ATOM   1116  CG1  ILE B 407     -23.214  69.514  29.936  1.00  43.30    6
ATOM   1117  CD1  ILE B 407     -23.655  68.612  28.804  1.00  40.40    6
ATOM   1118  C    ILE B 407     -24.191  67.004  32.658  1.00  39.03    6
ATOM   1119  O    ILE B 407     -24.178  65.806  32.343  1.00  35.18    8
ATOM   1120  N    ASN B 408     -23.990  67.425  33.894  1.00  37.25    7
ATOM   1121  CA   ASN B 408     -23.739  66.475  34.943  1.00  37.01    6
ATOM   1122  CB   ASN B 408     -23.524  67.221  36.256  1.00  32.27    6
ATOM   1123  CG   ASN B 408     -22.296  68.137  36.202  1.00  33.56    6
ATOM   1124  OD1  ASN B 408     -21.194  67.696  35.823  1.00  31.99    8
ATOM   1125  ND2  ASN B 408     -22.478  69.397  35.604  1.00  31.23    7
ATOM   1126  C    ASN B 408     -24.876  65.453  35.036  1.00  38.14    6
```

UNITED STATES PATENT AND TRADEMARK OFFICE
CERTIFICATE OF CORRECTION

PATENT NO. : 6,965,850 B2  
APPLICATION NO. : 09/281717  
DATED : November 15, 2005  
INVENTOR(S) : John D. Baxter et al.

Page 65 of 186

It is certified that error appears in the above-identified patent and that said Letters Patent is hereby corrected as shown below:

```
ATOM   1127  O    ASN B 408   -24.624  64.253  35.105  1.00  42.16  8
ATOM   1128  N    TYR B 409   -26.122  65.924  35.003  1.00  33.62  7
ATOM   1129  CA   TYR B 409   -27.273  65.024  35.073  1.00  35.91  6
ATOM   1130  CB   TYR B 409   -28.597  65.787  34.931  1.00  34.41  6
ATOM   1131  CG   TYR B 409   -29.788  64.868  34.685  1.00  38.73  6
ATOM   1132  CD1  TYR B 409   -30.064  63.819  35.549  1.00  41.34  6
ATOM   1133  CE1  TYR B 409   -31.130  62.962  35.309  1.00  47.16  6
ATOM   1134  CD2  TYR B 409   -30.613  65.037  33.579  1.00  46.20  6
ATOM   1135  CE2  TYR B 409   -31.684  64.176  33.341  1.00  50.74  6
ATOM   1136  CZ   TYR B 409   -31.942  63.143  34.206  1.00  50.88  6
ATOM   1137  OH   TYR B 409   -33.002  62.312  33.978  1.00  53.14  8
ATOM   1138  C    TYR B 409   -27.215  64.020  33.951  1.00  38.16  6
ATOM   1139  O    TYR B 409   -27.558  62.857  34.111  1.00  41.83  8
ATOM   1140  N    ARG B 410   -26.824  64.528  32.796  1.00  42.25  7
ATOM   1141  CA   ARG B 410   -26.734  63.739  31.594  1.00  42.83  6
ATOM   1142  CB   ARG B 410   -26.350  64.646  30.441  1.00  36.83  6
ATOM   1143  CG   ARG B 410   -27.440  65.585  29.945  1.00  34.32  6
ATOM   1144  CD   ARG B 410   -28.284  64.863  28.917  1.00  36.62  6
ATOM   1145  NE   ARG B 410   -27.455  64.378  27.829  1.00  38.64  7
ATOM   1146  CZ   ARG B 410   -27.926  63.656  26.824  1.00  35.73  6
ATOM   1147  NH1  ARG B 410   -29.234  63.379  26.782  1.00  33.17  7
ATOM   1148  NH2  ARG B 410   -27.095  63.227  25.868  1.00  32.70  7
ATOM   1149  C    ARG B 410   -25.688  62.664  31.733  1.00  46.67  6
ATOM   1150  O    ARG B 410   -25.859  61.547  31.257  1.00  41.78  8
ATOM   1151  N    LYS B 411   -24.602  63.028  32.413  1.00  52.99  7
ATOM   1152  CA   LYS B 411   -23.471  62.145  32.609  1.00  58.32  6
ATOM   1153  CB   LYS B 411   -23.684  61.249  33.833  1.00  64.99  6
ATOM   1154  CG   LYS B 411   -24.998  60.544  33.968  1.00  70.48  6
ATOM   1155  CD   LYS B 411   -25.070  59.887  35.349  1.00  77.18  6
ATOM   1156  CE   LYS B 411   -26.272  58.944  35.474  1.00  84.30  6
ATOM   1157  NZ   LYS B 411   -26.286  58.242  36.809  1.00  86.48  7
ATOM   1158  C    LYS B 411   -23.172  61.341  31.365  1.00  56.66  6
ATOM   1159  O    LYS B 411   -23.574  60.199  31.210  1.00  55.47  8
ATOM   1160  N    HIS B 412   -22.458  62.026  30.479  1.00  54.67  7
ATOM   1161  CA   HIS B 412   -22.019  61.474  29.214  1.00  48.67  6
ATOM   1162  CB   HIS B 412   -21.500  62.599  28.310  1.00  43.14  6
ATOM   1163  CG   HIS B 412   -22.559  63.501  27.784  1.00  41.36  6
ATOM   1164  CD2  HIS B 412   -23.159  64.603  28.299  1.00  35.44  6
ATOM   1165  ND1  HIS B 412   -23.163  63.290  26.539  1.00  38.19  7
ATOM   1166  CE1  HIS B 412   -24.076  64.238  26.353  1.00  34.75  6
ATOM   1167  NE2  HIS B 412   -24.090  65.034  27.396  1.00  35.52  7
ATOM   1168  C    HIS B 412   -20.894  60.596  29.644  1.00  46.35  6
ATOM   1169  O    HIS B 412   -20.218  60.892  30.644  1.00  42.73  8
ATOM   1170  N    HIS B 413   -20.708  59.469  28.973  1.00  48.92  7
ATOM   1171  CA   HIS B 413   -19.593  58.614  29.371  1.00  53.15  6
ATOM   1172  CB   HIS B 413   -20.022  57.147  29.421  1.00  55.27  6
ATOM   1173  CG   HIS B 413   -20.814  56.823  30.636  1.00  58.77  6
ATOM   1174  CD2  HIS B 413   -22.019  56.223  30.822  1.00  61.65  6
ATOM   1175  ND1  HIS B 413   -20.360  57.159  31.921  1.00  60.31  7
ATOM   1176  CE1  HIS B 413   -21.267  56.758  32.809  1.00  63.01  6
ATOM   1177  NE2  HIS B 413   -22.270  56.193  32.171  1.00  62.93  7
ATOM   1178  C    HIS B 413   -18.426  58.862  28.438  1.00  53.19  6
ATOM   1179  O    HIS B 413   -17.975  57.996  27.699  1.00  54.93  8
ATOM   1180  N    VAL B 414   -17.970  60.113  28.521  1.00  53.77  7
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1181  CA   VAL  B  414    -16.845  60.674  27.788  1.00  51.06   6
ATOM   1182  CB   VAL  B  414    -17.317  61.498  26.386  1.00  51.49   6
ATOM   1183  CG1  VAL  B  414    -16.133  62.122  25.891  1.00  45.22   6
ATOM   1184  CG2  VAL  B  414    -18.095  60.631  25.617  1.00  52.67   6
ATOM   1185  C    VAL  B  414    -16.096  61.557  28.775  1.00  54.28   6
ATOM   1186  O    VAL  B  414    -16.700  62.283  29.574  1.00  55.49   8
ATOM   1187  N    THR  B  415    -14.770  61.466  28.742  1.00  56.28   7
ATOM   1188  CA   THR  B  415    -13.919  62.234  29.669  1.00  57.83   6
ATOM   1189  CB   THR  B  415    -12.488  61.686  29.658  1.00  59.64   6
ATOM   1190  OG1  THR  B  415    -11.618  62.572  30.373  1.00  66.69   8
ATOM   1191  CG2  THR  B  415    -11.988  61.483  28.227  1.00  59.42   6
ATOM   1192  C    THR  B  415    -13.840  63.726  29.352  1.00  56.98   6
ATOM   1193  O    THR  B  415    -13.987  64.135  28.216  1.00  55.70   8
ATOM   1194  N    HIS  B  416    -13.598  64.522  30.387  1.00  57.44   7
ATOM   1195  CA   HIS  B  416    -13.485  65.972  30.237  1.00  57.34   6
ATOM   1196  CB   HIS  B  416    -12.114  66.326  29.653  1.00  61.35   6
ATOM   1197  CG   HIS  B  416    -10.968  65.931  30.513  1.00  69.78   6
ATOM   1198  CD2  HIS  B  416     -9.930  65.082  30.307  1.00  71.42   6
ATOM   1199  ND1  HIS  B  416    -10.756  66.480  31.787  1.00  72.49   7
ATOM   1200  CE1  HIS  B  416     -9.631  65.973  32.281  1.00  75.50   6
ATOM   1201  NE2  HIS  B  416     -9.120  65.131  31.408  1.00  73.91   7
ATOM   1202  C    HIS  B  416    -14.560  66.515  29.320  1.00  53.79   6
ATOM   1203  O    HIS  B  416    -14.334  67.477  28.591  1.00  52.81   8
ATOM   1204  N    PHE  B  417    -15.746  65.921  29.372  1.00  48.05   7
ATOM   1205  CA   PHE  B  417    -16.841  66.329  28.505  1.00  47.99   6
ATOM   1206  CB   PHE  B  417    -18.152  65.694  28.937  1.00  46.11   6
ATOM   1207  CG   PHE  B  417    -19.233  65.781  27.898  1.00  44.27   6
ATOM   1208  CD1  PHE  B  417    -19.280  64.856  26.870  1.00  41.79   6
ATOM   1209  CD2  PHE  B  417    -20.118  66.846  27.893  1.00  40.23   6
ATOM   1210  CE1  PHE  B  417    -20.233  64.959  25.869  1.00  44.30   6
ATOM   1211  CE2  PHE  B  417    -21.072  66.955  26.893  1.00  36.80   6
ATOM   1212  CZ   PHE  B  417    -21.119  66.016  25.866  1.00  40.69   6
ATOM   1213  C    PHE  B  417    -17.020  67.833  28.423  1.00  45.69   6
ATOM   1214  O    PHE  B  417    -16.799  68.423  27.380  1.00  43.35   8
ATOM   1215  N    TRP  B  418    -17.448  68.452  29.516  1.00  45.14   7
ATOM   1216  CA   TRP  B  418    -17.681  69.889  29.508  1.00  44.89   6
ATOM   1217  CB   TRP  B  418    -18.045  70.398  30.898  1.00  42.24   6
ATOM   1218  CG   TRP  B  418    -18.162  71.905  31.018  1.00  47.11   6
ATOM   1219  CD2  TRP  B  418    -19.298  72.699  30.620  1.00  46.98   6
ATOM   1220  CE2  TRP  B  418    -18.953  74.061  30.850  1.00  48.94   6
ATOM   1221  CE3  TRP  B  418    -20.560  72.401  30.086  1.00  45.23   6
ATOM   1222  CD1  TRP  B  418    -17.223  72.778  31.462  1.00  46.24   6
ATOM   1223  NE1  TRP  B  418    -17.690  74.071  31.368  1.00  50.63   7
ATOM   1224  CZ2  TRP  B  418    -19.819  75.109  30.571  1.00  45.46   6
ATOM   1225  CZ3  TRP  B  418    -21.422  73.447  29.809  1.00  44.50   6
ATOM   1226  CH2  TRP  B  418    -21.065  74.777  30.039  1.00  47.55   6
ATOM   1227  C    TRP  B  418    -16.502  70.662  28.956  1.00  43.88   6
ATOM   1228  O    TRP  B  418    -16.671  71.424  27.986  1.00  43.17   8
ATOM   1229  N    PRO  B  419    -15.292  70.490  29.519  1.00  43.55   7
ATOM   1230  CD   PRO  B  419    -14.967  69.551  30.599  1.00  41.52   6
ATOM   1231  CA   PRO  B  419    -14.120  71.223  29.011  1.00  41.48   6
ATOM   1232  CB   PRO  B  419    -12.956  70.582  29.724  1.00  39.21   6
ATOM   1233  CG   PRO  B  419    -13.521  69.703  30.774  1.00  39.25   6
ATOM   1234  C    PRO  B  419    -14.035  71.067  27.479  1.00  36.28   6
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1235  O    PRO B 419    -13.690  72.001  26.734  1.00  37.08   8
ATOM   1236  N    LYS B 420    -14.330  69.871  26.976  1.00  35.96   7
ATOM   1237  CA   LYS B 420    -14.278  69.609  25.538  1.00  40.82   6
ATOM   1238  CB   LYS B 420    -14.452  68.103  25.271  1.00  40.78   6
ATOM   1239  CG   LYS B 420    -13.349  67.214  25.830  1.00  48.62   6
ATOM   1240  CD   LYS B 420    -13.565  65.746  25.480  1.00  55.12   6
ATOM   1241  CE   LYS B 420    -12.427  64.892  26.017  1.00  53.26   6
ATOM   1242  NZ   LYS B 420    -12.582  63.457  25.608  1.00  52.69   7
ATOM   1243  C    LYS B 420    -15.414  70.374  24.875  1.00  40.29   6
ATOM   1244  O    LYS B 420    -15.225  71.015  23.851  1.00  39.66   8
ATOM   1245  N    LEU B 421    -16.591  70.300  25.499  1.00  38.33   7
ATOM   1246  CA   LEU B 421    -17.796  70.958  25.001  1.00  37.60   6
ATOM   1247  CB   LEU B 421    -18.970  70.702  25.965  1.00  43.66   6
ATOM   1248  CG   LEU B 421    -20.370  70.850  25.418  1.00  46.50   6
ATOM   1249  CD1  LEU B 421    -20.529  69.890  24.255  1.00  45.15   6
ATOM   1250  CD2  LEU B 421    -21.383  70.538  26.486  1.00  51.31   6
ATOM   1251  C    LEU B 421    -17.547  72.452  24.823  1.00  39.59   6
ATOM   1252  O    LEU B 421    -17.975  73.035  23.836  1.00  40.66   8
ATOM   1253  N    LEU B 422    -16.847  73.059  25.780  1.00  39.57   7
ATOM   1254  CA   LEU B 422    -16.534  74.478  25.715  1.00  38.63   6
ATOM   1255  CB   LEU B 422    -15.829  74.936  26.992  1.00  41.79   6
ATOM   1256  CG   LEU B 422    -16.714  75.149  28.191  1.00  42.74   6
ATOM   1257  CD1  LEU B 422    -15.911  75.685  29.360  1.00  42.89   6
ATOM   1258  CD2  LEU B 422    -17.783  76.162  27.813  1.00  39.27   6
ATOM   1259  C    LEU B 422    -15.677  74.788  24.513  1.00  40.47   6
ATOM   1260  O    LEU B 422    -15.823  75.846  23.917  1.00  47.83   8
ATOM   1261  N    MET B 423    -14.789  73.853  24.168  1.00  34.27   7
ATOM   1262  CA   MET B 423    -13.907  74.019  23.024  1.00  35.25   6
ATOM   1263  CB   MET B 423    -12.920  72.858  22.922  1.00  32.86   6
ATOM   1264  CG   MET B 423    -12.013  72.703  24.125  1.00  40.70   6
ATOM   1265  SD   MET B 423    -10.345  72.007  23.784  1.00  47.65  16
ATOM   1266  CE   MET B 423    -10.770  70.538  22.761  1.00  47.16   6
ATOM   1267  C    MET B 423    -14.709  74.100  21.738  1.00  35.13   6
ATOM   1268  O    MET B 423    -14.341  74.807  20.803  1.00  29.85   8
ATOM   1269  N    LYS B 424    -15.811  73.361  21.704  1.00  31.56   7
ATOM   1270  CA   LYS B 424    -16.676  73.354  20.544  1.00  32.29   6
ATOM   1271  CB   LYS B 424    -17.783  72.316  20.736  1.00  30.56   6
ATOM   1272  CG   LYS B 424    -17.257  70.879  20.843  1.00  30.07   6
ATOM   1273  CD   LYS B 424    -16.444  70.510  19.611  1.00  33.22   6
ATOM   1274  CE   LYS B 424    -15.795  69.136  19.706  1.00  28.75   6
ATOM   1275  NZ   LYS B 424    -14.655  69.067  20.678  1.00  31.01   7
ATOM   1276  C    LYS B 424    -17.248  74.754  20.304  1.00  29.26   6
ATOM   1277  O    LYS B 424    -17.439  75.149  19.166  1.00  30.22   8
ATOM   1278  N    VAL B 425    -17.495  75.499  21.385  1.00  23.53   7
ATOM   1279  CA   VAL B 425    -18.014  76.852  21.278  1.00  28.91   6
ATOM   1280  CB   VAL B 425    -18.278  77.458  22.663  1.00  29.44   6
ATOM   1281  CG1  VAL B 425    -18.633  78.915  22.547  1.00  28.81   6
ATOM   1282  CG2  VAL B 425    -19.401  76.733  23.354  1.00  31.22   6
ATOM   1283  C    VAL B 425    -17.001  77.682  20.498  1.00  32.03   6
ATOM   1284  O    VAL B 425    -17.368  78.465  19.629  1.00  31.95   8
ATOM   1285  N    THR B 426    -15.721  77.508  20.827  1.00  33.61   7
ATOM   1286  CA   THR B 426    -14.645  78.221  20.137  1.00  30.76   6
ATOM   1287  CB   THR B 426    -13.270  77.912  20.761  1.00  32.34   6
ATOM   1288  OG1  THR B 426    -13.073  78.697  21.941  1.00  33.07   8
```

UNITED STATES PATENT AND TRADEMARK OFFICE
CERTIFICATE OF CORRECTION

PATENT NO. : 6,965,850 B2 Page 68 of 186
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1289  CG2  THR  B  426    -12.153  78.174  19.782  1.00  25.40   6
ATOM   1290  C    THR  B  426    -14.677  77.742  18.706  1.00  32.53   6
ATOM   1291  O    THR  B  426    -14.639  78.530  17.763  1.00  35.19   8
ATOM   1292  N    ASP  B  427    -14.749  76.425  18.566  1.00  28.83   7
ATOM   1293  CA   ASP  B  427    -14.796  75.807  17.257  1.00  35.12   6
ATOM   1294  CB   ASP  B  427    -15.096  74.302  17.380  1.00  39.14   6
ATOM   1295  CG   ASP  B  427    -13.910  73.496  17.806  1.00  45.80   6
ATOM   1296  OD1  ASP  B  427    -12.786  73.774  17.348  1.00  41.97   8
ATOM   1297  OD2  ASP  B  427    -14.064  72.517  18.583  1.00  50.06   8
ATOM   1298  C    ASP  B  427    -15.883  76.502  16.429  1.00  33.94   6
ATOM   1299  O    ASP  B  427    -15.673  76.815  15.262  1.00  38.02   8
ATOM   1300  N    LEU  B  428    -17.040  76.741  17.048  1.00  27.15   7
ATOM   1301  CA   LEU  B  428    -18.154  77.388  16.367  1.00  29.99   6
ATOM   1302  CB   LEU  B  428    -19.448  77.190  17.168  1.00  22.49   6
ATOM   1303  CG   LEU  B  428    -20.086  75.818  17.089  1.00  25.54   6
ATOM   1304  CD1  LEU  B  428    -21.282  75.729  18.012  1.00  20.60   6
ATOM   1305  CD2  LEU  B  428    -20.509  75.564  15.651  1.00  17.24   6
ATOM   1306  C    LEU  B  428    -17.901  78.863  16.103  1.00  28.94   6
ATOM   1307  O    LEU  B  428    -18.328  79.388  15.076  1.00  31.26   8
ATOM   1308  N    ARG  B  429    -17.213  79.524  17.035  1.00  27.64   7
ATOM   1309  CA   ARG  B  429    -16.894  80.937  16.883  1.00  28.13   6
ATOM   1310  CB   ARG  B  429    -16.274  81.507  18.160  1.00  29.59   6
ATOM   1311  CG   ARG  B  429    -17.246  81.752  19.302  1.00  34.85   6
ATOM   1312  CD   ARG  B  429    -16.626  82.653  20.372  1.00  47.18   6
ATOM   1313  NE   ARG  B  429    -17.373  82.714  21.620  1.00  57.93   7
ATOM   1314  CZ   ARG  B  429    -18.632  83.124  21.716  1.00  63.62   6
ATOM   1315  NH1  ARG  B  429    -19.263  83.579  20.622  1.00  60.71   7
ATOM   1316  NH2  ARG  B  429    -19.238  83.130  22.916  1.00  62.38   7
ATOM   1317  C    ARG  B  429    -15.930  81.146  15.728  1.00  29.81   6
ATOM   1318  O    ARG  B  429    -16.101  82.061  14.933  1.00  30.81   8
ATOM   1319  N    MET  B  430    -14.908  80.295  15.670  1.00  29.64   7
ATOM   1320  CA   MET  B  430    -13.920  80.343  14.614  1.00  34.72   6
ATOM   1321  CB   MET  B  430    -12.939  79.192  14.763  1.00  34.97   6
ATOM   1322  CG   MET  B  430    -11.787  79.431  15.689  1.00  45.34   6
ATOM   1323  SD   MET  B  430    -10.729  80.768  15.158  1.00  52.55  16
ATOM   1324  CE   MET  B  430    -10.070  80.157  13.610  1.00  55.56   6
ATOM   1325  C    MET  B  430    -14.638  80.217  13.284  1.00  34.01   6
ATOM   1326  O    MET  B  430    -14.395  80.996  12.385  1.00  37.29   8
ATOM   1327  N    ILE  B  431    -15.516  79.217  13.176  1.00  29.99   7
ATOM   1328  CA   ILE  B  431    -16.296  78.992  11.963  1.00  28.82   6
ATOM   1329  CB   ILE  B  431    -17.391  77.929  12.177  1.00  27.39   6
ATOM   1330  CG2  ILE  B  431    -18.314  77.841  10.959  1.00  23.87   6
ATOM   1331  CG1  ILE  B  431    -16.784  76.555  12.449  1.00  25.56   6
ATOM   1332  CD1  ILE  B  431    -17.826  75.464  12.498  1.00  17.29   6
ATOM   1333  C    ILE  B  431    -16.953  80.288  11.538  1.00  29.49   6
ATOM   1334  O    ILE  B  431    -16.837  80.725  10.398  1.00  24.19   8
ATOM   1335  N    GLY  B  432    -17.657  80.904  12.474  1.00  25.25   7
ATOM   1336  CA   GLY  B  432    -18.357  82.142  12.179  1.00  30.38   6
ATOM   1337  C    GLY  B  432    -17.395  83.209  11.725  1.00  32.75   6
ATOM   1338  O    GLY  B  432    -17.531  83.740  10.637  1.00  36.38   8
ATOM   1339  N    ALA  B  433    -16.431  83.522  12.586  1.00  26.77   7
ATOM   1340  CA   ALA  B  433    -15.407  84.514  12.299  1.00  26.48   6
ATOM   1341  CB   ALA  B  433    -14.240  84.338  13.253  1.00  19.90   6
ATOM   1342  C    ALA  B  433    -14.905  84.433  10.867  1.00  30.73   6
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1343  O    ALA B 433   -14.849  85.432  10.171  1.00  31.60   8
ATOM   1344  N    CYS B 434   -14.534  83.246  10.439  1.00  33.22   7
ATOM   1345  CA   CYS B 434   -14.023  83.021   9.120  1.00  34.34   6
ATOM   1346  CB   CYS B 434   -13.553  81.661   9.226  1.00  35.20   6
ATOM   1347  SG   CYS B 434   -12.412  81.249   8.444  1.00  54.48  16
ATOM   1348  C    CYS B 434   -15.106  83.116   8.062  1.00  34.09   6
ATOM   1349  O    CYS B 434   -14.844  83.555   6.952  1.00  34.89   8
ATOM   1350  N    HIS B 435   -16.318  82.699   8.394  1.00  34.30   7
ATOM   1351  CA   HIS B 435   -17.395  82.762   7.443  1.00  35.44   6
ATOM   1352  CB   HIS B 435   -18.700  82.404   8.103  1.00  31.76   6
ATOM   1353  CG   HIS B 435   -19.845  82.425   7.149  1.00  32.03   6
ATOM   1354  CD2  HIS B 435   -20.483  81.419   6.515  1.00  28.61   6
ATOM   1355  ND1  HIS B 435   -20.345  83.600   6.607  1.00  28.48   7
ATOM   1356  CE1  HIS B 435   -21.241  83.293   5.672  1.00  33.27   6
ATOM   1357  NE2  HIS B 435   -21.341  81.977   5.605  1.00  31.57   7
ATOM   1358  C    HIS B 435   -17.528  84.152   6.878  1.00  32.74   6
ATOM   1359  O    HIS B 435   -17.842  84.326   5.715  1.00  32.87   8
ATOM   1360  N    ALA B 436   -17.315  85.121   7.758  1.00  31.01   7
ATOM   1361  CA   ALA B 436   -17.376  86.520   7.405  1.00  29.91   6
ATOM   1362  CB   ALA B 436   -17.008  87.352   8.618  1.00  21.23   6
ATOM   1363  C    ALA B 436   -16.393  86.782   6.266  1.00  33.86   6
ATOM   1364  O    ALA B 436   -16.734  87.398   5.257  1.00  36.10   8
ATOM   1365  N    SER B 437   -15.162  86.307   6.448  1.00  35.19   7
ATOM   1366  CA   SER B 437   -14.122  86.484   5.445  1.00  33.03   6
ATOM   1367  CB   SER B 437   -12.882  85.688   5.847  1.00  35.31   6
ATOM   1368  OG   SER B 437   -11.855  85.824   4.879  1.00  44.99   8
ATOM   1369  C    SER B 437   -14.642  85.993   4.108  1.00  38.39   6
ATOM   1370  O    SER B 437   -14.700  86.730   3.127  1.00  37.54   8
ATOM   1371  N    ARG B 438   -15.008  84.719   4.096  1.00  37.32   7
ATOM   1372  CA   ARG B 438   -15.526  84.068   2.908  1.00  39.30   6
ATOM   1373  CB   ARG B 438   -16.019  82.660   3.259  1.00  42.97   6
ATOM   1374  CG   ARG B 438   -14.910  81.673   3.590  1.00  41.72   6
ATOM   1375  CD   ARG B 438   -14.044  81.488   2.356  1.00  45.23   6
ATOM   1376  NE   ARG B 438   -14.781  80.936   1.235  1.00  45.66   7
ATOM   1377  CZ   ARG B 438   -14.482  81.175  -0.040  1.00  49.71   6
ATOM   1378  NH1  ARG B 438   -13.458  81.977  -0.347  1.00  50.91   7
ATOM   1379  NH2  ARG B 438   -15.219  80.619  -1.002  1.00  46.86   7
ATOM   1380  C    ARG B 438   -16.659  84.859   2.287  1.00  42.37   6
ATOM   1381  O    ARG B 438   -16.841  84.832   1.072  1.00  40.58   8
ATOM   1382  N    PHE B 439   -17.417  85.575   3.117  1.00  42.25   7
ATOM   1383  CA   PHE B 439   -18.531  86.354   2.614  1.00  42.81   6
ATOM   1384  CB   PHE B 439   -19.198  87.132   3.731  1.00  42.18   6
ATOM   1385  CG   PHE B 439   -20.487  87.769   3.323  1.00  42.48   6
ATOM   1386  CD1  PHE B 439   -21.535  86.981   2.912  1.00  47.09   6
ATOM   1387  CD2  PHE B 439   -20.638  89.141   3.334  1.00  39.76   6
ATOM   1388  CE1  PHE B 439   -22.735  87.543   2.527  1.00  49.17   6
ATOM   1389  CE2  PHE B 439   -21.851  89.717   2.944  1.00  45.10   6
ATOM   1390  CZ   PHE B 439   -22.901  88.911   2.538  1.00  46.36   6
ATOM   1391  C    PHE B 439   -18.016  87.319   1.581  1.00  44.79   6
ATOM   1392  O    PHE B 439   -18.514  87.354   0.465  1.00  40.26   8
ATOM   1393  N    LEU B 440   -17.021  88.117   1.987  1.00  42.77   7
ATOM   1394  CA   LEU B 440   -16.415  89.115   1.109  1.00  42.96   6
ATOM   1395  CB   LEU B 440   -15.169  89.718   1.768  1.00  37.19   6
ATOM   1396  CG   LEU B 440   -15.477  90.588   2.967  1.00  36.97   6
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1397  CD1  LEU B 440    -14.219  91.352   3.402  1.00  33.65   6
ATOM   1398  CD2  LEU B 440    -16.577  91.891   2.574  1.00  35.42   6
ATOM   1399  C    LEU B 440    -16.099  88.561  -0.273  1.00  45.47   6
ATOM   1400  O    LEU B 440    -16.631  89.059  -1.265  1.00  52.48   8
ATOM   1401  N    HIS B 441    -15.238  87.549  -0.345  1.00  49.15   7
ATOM   1402  CA   HIS B 441    -14.929  86.956  -1.632  1.00  54.76   6
ATOM   1403  CB   HIS B 441    -14.150  85.700  -1.448  1.00  58.68   6
ATOM   1404  CG   HIS B 441    -12.713  85.934  -1.230  1.00  62.73   6
ATOM   1405  CD2  HIS B 441    -11.602  85.418  -1.812  1.00  65.73   6
ATOM   1406  ND1  HIS B 441    -12.245  86.850  -0.273  1.00  66.01   7
ATOM   1407  CE1  HIS B 441    -10.916  86.847  -0.309  1.00  65.55   6
ATOM   1408  NE2  HIS B 441    -10.512  85.993  -1.228  1.00  60.09   7
ATOM   1409  C    HIS B 441    -16.217  86.633  -2.301  1.00  55.93   6
ATOM   1410  O    HIS B 441    -16.418  86.938  -3.465  1.00  57.33   8
ATOM   1411  N    MET B 442    -17.106  85.997  -1.553  1.00  57.81   7
ATOM   1412  CA   MET B 442    -18.399  85.652  -2.106  1.00  59.11   6
ATOM   1413  CB   MET B 442    -19.340  85.162  -1.008  1.00  55.93   6
ATOM   1414  CG   MET B 442    -18.991  83.796  -0.456  1.00  58.52   6
ATOM   1415  SD   MET B 442    -20.310  82.994   0.505  1.00  60.99  16
ATOM   1416  CE   MET B 442    -20.525  84.203   1.827  1.00  52.61   6
ATOM   1417  C    MET B 442    -18.991  86.879  -2.785  1.00  60.31   6
ATOM   1418  O    MET B 442    -19.646  86.778  -3.817  1.00  58.18   8
ATOM   1419  N    LYS B 443    -18.731  88.045  -2.213  1.00  61.45   7
ATOM   1420  CA   LYS B 443    -19.267  89.268  -2.758  1.00  64.90   6
ATOM   1421  CB   LYS B 443    -19.182  90.358  -1.704  1.00  64.40   6
ATOM   1422  CG   LYS B 443    -20.160  91.449  -1.982  1.00  69.12   6
ATOM   1423  CD   LYS B 443    -19.763  92.673  -1.306  1.00  71.14   6
ATOM   1424  CE   LYS B 443    -20.508  92.993  -0.491  1.00  73.43   6
ATOM   1425  NZ   LYS B 443    -20.174  94.242   0.151  1.00  67.97   7
ATOM   1426  C    LYS B 443    -18.528  89.704  -4.020  1.00  67.29   6
ATOM   1427  O    LYS B 443    -18.979  90.586  -4.731  1.00  67.90   8
ATOM   1428  N    VAL B 444    -17.383  89.075  -4.285  1.00  66.57   7
ATOM   1429  CA   VAL B 444    -16.589  89.418  -5.455  1.00  64.76   6
ATOM   1430  CB   VAL B 444    -15.097  89.568  -5.082  1.00  62.76   6
ATOM   1431  CG1  VAL B 444    -14.269  89.857  -6.298  1.00  64.00   6
ATOM   1432  CG2  VAL B 444    -14.905  90.678  -4.042  1.00  59.27   6
ATOM   1433  C    VAL B 444    -16.800  88.397  -6.569  1.00  68.61   6
ATOM   1434  O    VAL B 444    -16.968  88.774  -7.729  1.00  70.60   8
ATOM   1435  N    GLU B 445    -16.812  87.118  -6.219  1.00  70.71   7
ATOM   1436  CA   GLU B 445    -16.951  86.033  -7.197  1.00  71.45   6
ATOM   1437  CB   GLU B 445    -16.169  84.809  -6.712  1.00  72.36   6
ATOM   1438  CG   GLU B 445    -14.736  85.090  -6.392  1.00  40.00   6
ATOM   1439  CD   GLU B 445    -13.998  83.890  -5.851  1.00  40.00   6
ATOM   1440  OE1  GLU B 445    -14.587  82.798  -5.665  1.00  40.00   8
ATOM   1441  OE2  GLU B 445    -12.775  83.995  -5.580  1.00  40.00   8
ATOM   1442  C    GLU B 445    -18.375  85.574  -7.422  1.00  71.46   6
ATOM   1443  O    GLU B 445    -18.605  84.542  -8.064  1.00  73.02   8
ATOM   1444  N    CYS B 446    -19.328  86.333  -6.900  1.00  71.12   7
ATOM   1445  CA   CYS B 446    -20.694  85.942  -7.062  1.00  70.83   6
ATOM   1446  CB   CYS B 446    -21.196  85.230  -5.784  1.00  71.05   6
ATOM   1447  SG   CYS B 446    -20.296  83.720  -5.349  1.00  72.83  16
ATOM   1448  C    CYS B 446    -21.563  87.135  -7.386  1.00  71.91   6
ATOM   1449  O    CYS B 446    -21.307  88.244  -6.911  1.00  72.06   8
ATOM   1450  N    PRO B 447    -22.550  86.928  -8.256  1.00  73.12   7
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1451  CD   PRO B 447    -22.837  85.637   -8.886  1.00 72.88   6
ATOM   1452  CA   PRO B 447    -23.461  87.997   -8.653  1.00 74.22   6
ATOM   1453  CB   PRO B 447    -24.399  87.338   -9.659  1.00 72.98   6
ATOM   1454  CG   PRO B 447    -23.981  85.934   -9.776  1.00 74.77   6
ATOM   1455  C    PRO B 447    -24.203  88.519   -7.451  1.00 75.94   6
ATOM   1456  O    PRO B 447    -24.601  87.749   -6.611  1.00 76.67   8
ATOM   1457  N    THR B 448    -24.390  89.828   -7.373  1.00 76.91   7
ATOM   1458  CA   THR B 448    -25.134  90.436   -6.268  1.00 78.24   6
ATOM   1459  CB   THR B 448    -24.883  91.948   -6.276  1.00 81.33   6
ATOM   1460  OG1  THR B 448    -25.474  92.525   -7.451  1.00 84.46   8
ATOM   1461  CG2  THR B 448    -23.394  92.234   -6.269  1.00 83.51   6
ATOM   1462  C    THR B 448    -26.594  90.160   -6.619  1.00 77.42   6
ATOM   1463  O    THR B 448    -27.512  90.649   -5.982  1.00 77.65   8
ATOM   1464  N    GLU B 449    -26.759  89.400   -7.697  1.00 76.29   7
ATOM   1465  CA   GLU B 449    -28.051  89.017   -8.211  1.00 75.03   6
ATOM   1466  CB   GLU B 449    -27.923  88.915   -9.719  1.00 74.62   6
ATOM   1467  CG   GLU B 449    -28.823  87.966  -10.343  1.00 40.00   6
ATOM   1468  CD   GLU B 449    -28.522  87.831  -11.756  1.00 40.00   6
ATOM   1469  OE1  GLU B 449    -27.366  88.072  -12.190  1.00 40.00   8
ATOM   1470  OE2  GLU B 449    -29.449  87.438  -12.492  1.00 40.00   8
ATOM   1471  C    GLU B 449    -28.448  87.660   -7.609  1.00 73.49   6
ATOM   1472  O    GLU B 449    -29.479  87.092   -7.953  1.00 70.24   8
ATOM   1473  N    LEU B 450    -27.624  87.158   -6.695  1.00 70.80   7
ATOM   1474  CA   LEU B 450    -27.879  85.879   -6.058  1.00 68.82   6
ATOM   1475  CB   LEU B 450    -26.772  84.887   -6.447  1.00 71.91   6
ATOM   1476  CG   LEU B 450    -26.612  84.503   -7.900  1.00 76.62   6
ATOM   1477  CD1  LEU B 450    -25.396  83.637   -8.059  1.00 77.95   6
ATOM   1478  CD2  LEU B 450    -27.849  83.775   -8.351  1.00 76.46   6
ATOM   1479  C    LEU B 450    -27.941  86.012   -4.536  1.00 66.22   6
ATOM   1480  O    LEU B 450    -28.251  85.039   -3.849  1.00 66.01   8
ATOM   1481  N    PHE B 451    -27.666  87.215   -4.012  1.00 61.96   7
ATOM   1482  CA   PHE B 451    -27.635  87.494   -2.585  1.00 58.44   6
ATOM   1483  CB   PHE B 451    -26.579  88.573   -2.263  1.00 61.34   6
ATOM   1484  CG   PHE B 451    -25.153  88.078   -2.413  1.00 63.02   6
ATOM   1485  CD1  PHE B 451    -24.675  87.587   -3.626  1.00 62.92   6
ATOM   1486  CD2  PHE B 451    -24.283  88.173   -1.346  1.00 63.07   6
ATOM   1487  CE1  PHE B 451    -23.327  87.217   -3.757  1.00 65.12   6
ATOM   1488  CE2  PHE B 451    -22.939  87.806   -1.472  1.00 64.66   6
ATOM   1489  CZ   PHE B 451    -22.459  87.335   -2.686  1.00 67.12   6
ATOM   1490  C    PHE B 451    -28.931  87.994   -1.962  1.00 56.41   6
ATOM   1491  O    PHE B 451    -29.207  89.214   -1.908  1.00 56.56   8
ATOM   1492  N    PRO B 452    -29.791  87.072   -1.473  1.00 53.28   7
ATOM   1493  CD   PRO B 452    -29.767  85.611   -1.494  1.00 50.46   6
ATOM   1494  CA   PRO B 452    -31.037  87.598   -0.843  1.00 50.26   6
ATOM   1495  CB   PRO B 452    -31.746  86.375   -0.301  1.00 49.19   6
ATOM   1496  CG   PRO B 452    -31.024  85.197   -0.842  1.00 45.89   6
ATOM   1497  C    PRO B 452    -30.636  88.567    0.251  1.00 49.62   6
ATOM   1498  O    PRO B 452    -29.628  88.401    0.906  1.00 52.35   8
ATOM   1499  N    PRO B 453    -31.494  89.539    0.535  1.00 51.50   7
ATOM   1500  CD   PRO B 453    -32.853  89.644    0.022  1.00 49.66   6
ATOM   1501  CA   PRO B 453    -31.184  90.573    1.530  1.00 50.89   6
ATOM   1502  CB   PRO B 453    -32.422  91.401    1.625  1.00 51.49   6
ATOM   1503  CG   PRO B 453    -33.378  90.827    0.724  1.00 50.82   6
ATOM   1504  C    PRO B 453    -30.829  90.039    2.906  1.00 50.99   6
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1505  O    PRO  B  453   -29.700  90.206  3.345  1.00 54.17  8
ATOM   1506  N    LEU  B  454   -31.807  89.458  3.631  1.00 51.21  7
ATOM   1507  CA   LEU  B  454   -31.538  88.945  4.948  1.00 47.17  6
ATOM   1508  CB   LEU  B  454   -32.550  87.858  5.330  1.00 44.44  6
ATOM   1509  CG   LEU  B  454   -32.347  87.412  6.748  1.00 41.33  6
ATOM   1510  CD1  LEU  B  454   -31.987  88.589  7.631  1.00 35.93  6
ATOM   1511  CD2  LEU  B  454   -33.590  86.732  7.239  1.00 34.79  6
ATOM   1512  C    LEU  B  454   -30.099  88.443  4.928  1.00 42.25  6
ATOM   1513  O    LEU  B  454   -29.323  88.774  5.812  1.00 40.82  8
ATOM   1514  N    PHE  B  455   -29.716  87.707  3.885  1.00 39.29  7
ATOM   1515  CA   PHE  B  455   -28.347  87.204  3.770  1.00 41.81  6
ATOM   1516  CB   PHE  B  455   -28.132  86.536  2.418  1.00 47.22  6
ATOM   1517  CG   PHE  B  455   -26.813  85.836  2.292  1.00 56.97  6
ATOM   1518  CD1  PHE  B  455   -26.437  84.915  3.247  1.00 57.23  6
ATOM   1519  CD2  PHE  B  455   -25.949  86.094  1.236  1.00 59.40  6
ATOM   1520  CE1  PHE  B  455   -25.225  84.234  3.153  1.00 56.58  6
ATOM   1521  CE2  PHE  B  455   -24.720  85.409  1.134  1.00 61.80  6
ATOM   1522  CZ   PHE  B  455   -24.360  84.481  2.103  1.00 59.94  6
ATOM   1523  C    PHE  B  455   -27.400  88.386  3.923  1.00 45.12  6
ATOM   1524  O    PHE  B  455   -26.657  88.450  4.889  1.00 39.95  8
ATOM   1525  N    LEU  B  456   -27.439  89.303  2.949  1.00 43.92  7
ATOM   1526  CA   LEU  B  456   -26.597  90.503  2.947  1.00 44.08  6
ATOM   1527  CB   LEU  B  456   -27.001  91.440  1.802  1.00 50.20  6
ATOM   1528  CG   LEU  B  456   -26.439  91.155  0.432  1.00 55.79  6
ATOM   1529  CD1  LEU  B  456   -27.064  92.082 -0.591  1.00 54.70  6
ATOM   1530  CD2  LEU  B  456   -24.920  91.345  0.494  1.00 53.01  6
ATOM   1531  C    LEU  B  456   -26.689  91.245  4.264  1.00 44.65  6
ATOM   1532  O    LEU  B  456   -25.678  91.540  4.886  1.00 45.93  8
ATOM   1533  N    GLU  B  457   -27.990  91.268  4.265  1.00 44.56  7
ATOM   1534  CA   GLU  B  457   -28.288  92.016  5.497  1.00 46.37  6
ATOM   1535  C    GLU  B  457   -27.434  91.452  6.628  1.00 43.60  6
ATOM   1536  O    GLU  B  457   -26.754  92.223  7.339  1.00 42.69  8
ATOM   1537  CB   GLU  B  457   -29.769  91.879  5.855  1.00 50.16  6
ATOM   1538  CG   GLU  B  457   -30.208  92.849  6.954  1.00 20.00  6
ATOM   1539  CD   GLU  B  457   -31.646  93.338  6.782  1.00 20.00  6
ATOM   1540  OE1  GLU  B  457   -32.351  92.932  5.779  1.00 20.00  8
ATOM   1541  OE2  GLU  B  457   -32.157  94.156  7.638  1.00 20.00  8
ATOM   1542  N    VAL  B  458   -27.428  90.413  7.281  1.00 43.21  7
ATOM   1543  CA   VAL  B  458   -26.706  89.739  8.351  1.00 44.98  6
ATOM   1544  CB   VAL  B  458   -27.075  88.255  8.432  1.00 44.83  6
ATOM   1545  CG1  VAL  B  458   -26.440  87.623  9.646  1.00 49.72  6
ATOM   1546  CG2  VAL  B  458   -28.562  88.086  8.474  1.00 40.89  6
ATOM   1547  C    VAL  B  458   -25.190  89.822  8.311  1.00 42.72  6
ATOM   1548  O    VAL  B  458   -24.551  90.179  9.303  1.00 42.88  8
ATOM   1549  N    PHE  B  459   -24.605  89.488  7.180  1.00 44.53  7
ATOM   1550  CA   PHE  B  459   -23.165  89.480  7.077  1.00 48.18  6
ATOM   1551  CB   PHE  B  459   -22.747  88.457  6.065  1.00 43.60  6
ATOM   1552  CG   PHE  B  459   -23.167  87.116  6.441  1.00 40.79  6
ATOM   1553  CD1  PHE  B  459   -24.494  86.750  6.368  1.00 41.01  6
ATOM   1554  CD2  PHE  B  459   -22.263  86.286  7.009  1.00 39.48  6
ATOM   1555  CE1  PHE  B  459   -24.892  85.540  6.889  1.00 40.62  6
ATOM   1556  CE2  PHE  B  459   -22.649  85.091  7.527  1.00 36.87  6
ATOM   1557  CZ   PHE  B  459   -23.967  84.711  7.455  1.00 36.39  6
ATOM   1558  C    PHE  B  459   -22.627  90.758  6.623  1.00 52.71  6
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1559  O    PHE  B  459    -21.414   91.050   6.791   1.00  51.34    8
ATOM   1560  N    GLU  B  460    -23.489   91.531   5.976   1.00  62.92    7
ATOM   1561  CA   GLU  B  460    -22.953   92.741   5.533   1.00  69.33    6
ATOM   1562  CB   GLU  B  460    -23.851   93.487   4.505   1.00  72.95    6
ATOM   1563  CG   GLU  B  460    -22.917   94.002   3.412   1.00  78.35    6
ATOM   1564  CD   GLU  B  460    -22.908   95.480   3.256   1.00  82.97    6
ATOM   1565  OE1  GLU  B  460    -23.257   96.213   4.217   1.00  88.28    8
ATOM   1566  OE2  GLU  B  460    -22.524   95.977   2.167   1.00  84.80    8
ATOM   1567  C    GLU  B  460    -22.790   93.576   6.786   1.00  71.87    6
ATOM   1568  O    GLU  B  460    -23.471   93.391   7.802   1.00  74.51    8
ATOM   1569  N    ASP  B  461    -21.796   94.449   6.696   1.00  78.50    7
ATOM   1570  CA   ASP  B  461    -21.401   95.328   7.701   1.00  84.19    6
ATOM   1571  CB   ASP  B  461    -20.182   96.032   7.125   1.00  85.82    6
ATOM   1572  CG   ASP  B  461    -19.261   95.066   6.463   1.00  89.62    6
ATOM   1573  OD1  ASP  B  461    -19.670   93.929   5.982   1.00  93.00    8
ATOM   1574  OD2  ASP  B  461    -18.084   95.361   6.387   1.00  93.04    8
ATOM   1575  C    ASP  B  461    -22.540   96.291   8.012   1.00  86.80    6
ATOM   1576  O    ASP  B  461    -23.063   96.176   9.139   1.00  88.70    8
ATOM   1577  OXT  ASP  B  461    -22.962   97.048   7.098   1.00  88.70    8
TER
ATOM   4002  C1   T3   J  1       20.152   36.643  29.561   1.00  22.34    6
ATOM   4003  C2   T3   J  1       19.021   41.567  29.283   1.00  21.84    6
ATOM   4004  C3   T3   J  1       18.880   37.086  29.226   1.00  23.43    6
ATOM   4005  C4   T3   J  1       18.249   42.606  28.776   1.00  22.31    6
ATOM   4006  C5   T3   J  1       18.747   38.372  28.856   1.00  24.83    6
ATOM   4007  C6   T3   J  1       17.938   43.621  29.664   1.00  25.16    6
ATOM   4008  C7   T3   J  1       19.799   39.296  28.753   1.00  24.65    6
ATOM   4009  C8   T3   J  1       18.330   43.594  31.028   1.00  21.93    6
ATOM   4010  C9   T3   J  1       21.101   38.940  29.075   1.00  25.09    6
ATOM   4011  C10  T3   J  1       19.063   42.558  31.465   1.00  23.66    6
ATOM   4012  C11  T3   J  1       21.254   37.600  29.456   1.00  23.12    6
ATOM   4013  C12  T3   J  1       19.459   41.490  30.621   1.00  19.67    6
ATOM   4014  C13  T3   J  1       20.370   35.228  30.075   1.00  18.97    6
ATOM   4015  C15  T3   J  1       21.549   34.480  29.455   1.00  19.32    6
ATOM   4016  C17  T3   J  1       21.535   33.003  29.710   1.00  19.02    6
ATOM   4017  I1   T3   J  1       16.898   39.029  28.661   1.00  25.29   53
ATOM   4018  I2   T3   J  1       17.058   45.327  29.184   1.00  26.49   53
ATOM   4019  I3   T3   J  1       22.763   40.262  29.169   1.00  25.67   53
ATOM   4020  N1   T3   J  1       21.800   34.859  28.024   1.00  15.12    7
ATOM   4021  O1   T3   J  1       17.934   44.682  31.806   1.00  21.79    8
ATOM   4022  O2   T3   J  1       19.432   40.560  28.362   1.00  22.05    8
ATOM   4023  O3   T3   J  1       21.911   32.260  28.776   1.00  20.38    8
ATOM   4024  O4   T3   J  1       21.137   32.622  30.840   1.00  20.16    8
TER
ATOM   4025  C1   T3   K  1      -28.131   75.928   7.543   1.00  22.34    6
ATOM   4026  C2   T3   K  1      -24.676   77.673   4.318   1.00  21.84    6
ATOM   4027  C3   T3   K  1      -28.490   76.351   6.201   1.00  23.43    6
ATOM   4028  C4   T3   K  1      -24.217   77.893   2.989   1.00  22.31    6
ATOM   4029  C5   T3   K  1      -27.485   76.499   5.233   1.00  24.83    6
ATOM   4030  C6   T3   K  1      -23.545   79.124   2.700   1.00  25.16    6
ATOM   4031  C7   T3   K  1      -26.132   76.227   5.581   1.00  24.65    6
ATOM   4032  C8   T3   K  1      -23.382   80.104   3.772   1.00  21.93    6
ATOM   4033  C9   T3   K  1      -25.685   75.833   6.855   1.00  25.09    6
ATOM   4034  C10  T3   K  1      -23.867   79.823   5.042   1.00  23.66    6
```

UNITED STATES PATENT AND TRADEMARK OFFICE
CERTIFICATE OF CORRECTION

PATENT NO.       : 6,965,850 B2
APPLICATION NO.  : 09/281717
DATED            : November 15, 2005
INVENTOR(S)      : John D. Baxter et al.

It is certified that error appears in the above-identified patent and that said Letters Patent is hereby corrected as shown below:

```
ATOM   4035  C11  T3   K   1     -26.708  75.670   7.834  1.00 23.12   6
ATOM   4036  C12  T3   K   1     -24.521  78.610   5.376  1.00 19.67   6
ATOM   4037  C13  T3   K   1     -29.211  75.830   8.626  1.00 18.97   6
ATOM   4038  C15  T3   K   1     -29.181  74.567   9.488  1.00 19.32   6
ATOM   4039  C17  T3   K   1     -30.440  74.343  10.264  1.00 19.02   6
ATOM   4040  I1   T3   K   1     -27.868  77.342   3.316  1.00 25.29  53
ATOM   4041  I2   T3   K   1     -22.732  79.619   0.850  1.00 26.49  53
ATOM   4042  I3   T3   K   1     -23.602  75.792   7.334  1.00 25.67  53
ATOM   4043  N1   T3   K   1     -28.680  73.342   8.762  1.00 15.12   7
ATOM   4044  O1   T3   K   1     -22.742  81.265   3.443  1.00 21.79   8
ATOM   4045  O2   T3   K   1     -25.267  76.388   4.595  1.00 22.05   8
ATOM   4046  O3   T3   K   1     -30.816  73.159  10.382  1.00 20.38   8
ATOM   4047  O4   T3   K   1     -31.028  75.359  10.729  1.00 20.16   8
TER
ATOM      1  C    LYS  X  686     13.868  40.176  48.888  1.00 40.00   6
ATOM      2  O    LYS  X  686     13.914  40.120  47.639  1.00 40.00   8
ATOM      3  N    LYS  X  686     14.374  42.245  50.489  1.00 40.00   7
ATOM      4  CA   LYS  X  686     14.937  41.070  49.710  1.00 40.00   6
ATOM      5  N    HIS  X  687     13.038  39.527  49.705  1.00 40.00   7
ATOM      6  CA   HIS  X  687     11.891  38.518  49.521  1.00 40.00   6
ATOM      7  CB   HIS  X  687     10.639  39.000  50.212  1.00 40.00   6
ATOM      8  CG   HIS  X  687     10.981  39.526  51.563  1.00 40.00   6
ATOM      9  CD2  HIS  X  687     11.021  38.908  52.753  1.00 40.00   6
ATOM     10  ND1  HIS  X  687     11.354  40.844  51.794  1.00 40.00   7
ATOM     11  CE1  HIS  X  687     11.614  40.994  53.034  1.00 40.00   6
ATOM     12  NE2  HIS  X  687     11.422  39.847  53.646  1.00 40.00   7
ATOM     13  C    HIS  X  687     11.183  38.108  48.208  1.00 40.00   6
ATOM     14  O    HIS  X  687     11.674  38.361  47.094  1.00 40.00   8
ATOM     15  N    LYS  X  688     10.064  37.458  48.649  1.00 40.00   7
ATOM     16  CA   LYS  X  688      8.911  36.858  47.931  1.00 40.00   6
ATOM     17  CB   LYS  X  688      8.292  37.850  46.968  1.00 40.00   6
ATOM     18  C    LYS  X  688      9.246  35.573  47.161  1.00 40.00   6
ATOM     19  O    LYS  X  688      9.319  34.473  47.722  1.00 40.00   8
ATOM     20  N    ILE  X  689      9.426  35.754  45.865  1.00 40.00   7
ATOM     21  CA   ILE  X  689      9.661  34.640  44.924  1.00 40.00   6
ATOM     22  CB   ILE  X  689      9.731  35.167  43.498  1.00 40.00   6
ATOM     23  CG2  ILE  X  689      9.638  34.053  42.453  1.00 40.00   6
ATOM     24  CG1  ILE  X  689      8.597  36.141  43.176  1.00 40.00   6
ATOM     25  CD1  ILE  X  689      8.250  36.183  41.688  1.00 40.00   6
ATOM     26  C    ILE  X  689     10.954  33.869  45.228  1.00 40.00   6
ATOM     27  O    ILE  X  689     10.920  32.657  45.511  1.00 40.00   8
ATOM     28  N    LEU  X  690     12.065  34.579  45.140  1.00 40.00   7
ATOM     29  CA   LEU  X  690     13.391  33.996  45.397  1.00 40.00   6
ATOM     30  CB   LEU  X  690     14.349  35.043  45.892  1.00 40.00   6
ATOM     31  CG   LEU  X  690     14.450  36.168  44.906  1.00 40.00   6
ATOM     32  CD1  LEU  X  690     15.397  37.261  45.363  1.00 40.00   6
ATOM     33  CD2  LEU  X  690     14.940  35.695  43.540  1.00 40.00   6
ATOM     34  C    LEU  X  690     13.271  32.999  46.466  1.00 40.00   6
ATOM     35  O    LEU  X  690     13.633  31.832  46.315  1.00 40.00   8
ATOM     36  N    HIS  X  691     12.773  33.472  47.541  1.00 40.00   7
ATOM     37  CA   HIS  X  691     12.557  32.559  48.569  1.00 40.00   6
ATOM     38  CB   HIS  X  691     11.729  33.212  49.658  1.00 40.00   6
ATOM     39  CG   HIS  X  691     12.588  34.116  50.564  1.00 40.00   6
ATOM     40  CD2  HIS  X  691     13.648  33.852  51.385  1.00 40.00   6
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM     41   ND1  HIS X 691     12.359   35.484   50.669   1.00  40.00       7
ATOM     42   CE1  HIS X 691     13.242   35.991   51.513   1.00  40.00       6
ATOM     43   NE2  HIS X 691     14.016   35.031   51.949   1.00  40.00       7
ATOM     44   C    HIS X 691     11.954   31.331   47.861   1.00  40.00       6
ATOM     45   O    HIS X 691     12.505   30.240   47.882   1.00  40.00       8
ATOM     46   N    ARG X 692     10.839   31.494   47.167   1.00  40.00       7
ATOM     47   CA   ARG X 692     10.169   30.333   46.518   1.00  40.00       6
ATOM     48   CB   ARG X 692      9.118   30.800   45.517   1.00  40.00       6
ATOM     49   C    ARG X 692     11.153   29.402   45.752   1.00  40.00       6
ATOM     50   O    ARG X 692     11.030   28.168   45.779   1.00  40.00       8
ATOM     51   N    LEU X 693     12.117   30.000   45.072   1.00  40.00       7
ATOM     52   CA   LEU X 693     13.078   29.252   44.226   1.00  40.00       6
ATOM     53   CB   LEU X 693     13.784   30.210   43.274   1.00  40.00       6
ATOM     54   CG   LEU X 693     12.796   31.012   42.432   1.00  40.00       6
ATOM     55   CD1  LEU X 693     13.479   31.969   41.458   1.00  40.00       6
ATOM     56   CD2  LEU X 693     11.884   30.126   41.579   1.00  40.00       6
ATOM     57   C    LEU X 693     14.143   28.531   45.054   1.00  40.00       6
ATOM     58   O    LEU X 693     14.702   27.508   44.633   1.00  40.00       8
ATOM     59   N    LEU X 694     14.400   29.079   46.209   1.00  40.00       7
ATOM     60   CA   LEU X 694     15.407   28.538   47.115   1.00  40.00       6
ATOM     61   CB   LEU X 694     15.871   29.626   48.084   1.00  40.00       6
ATOM     62   CG   LEU X 694     16.692   30.716   47.404   1.00  40.00       6
ATOM     63   CD1  LEU X 694     17.279   31.724   48.391   1.00  40.00       6
ATOM     64   CD2  LEU X 694     17.879   30.156   46.619   1.00  40.00       6
ATOM     65   C    LEU X 694     14.837   27.404   47.957   1.00  40.00       6
ATOM     66   O    LEU X 694     15.555   26.747   48.716   1.00  40.00       8
ATOM     67   N    GLN X 695     13.554   27.157   47.809   1.00  40.00       7
ATOM     68   CA   GLN X 695     12.883   26.188   48.685   1.00  40.00       6
ATOM     69   C    GLN X 695     12.423   24.910   47.977   1.00  40.00       6
ATOM     70   O    GLN X 695     12.309   23.845   48.598   1.00  40.00       8
ATOM     71   CB   GLN X 695     11.681   26.858   49.322   1.00  40.00       6
ATOM     72   CG   GLN X 695     12.074   28.125   50.080   1.00  20.00       6
ATOM     73   CD   GLN X 695     10.899   28.768   50.801   1.00  20.00       6
ATOM     74   OE1  GLN X 695      9.772   28.296   50.671   1.00  20.00       8
ATOM     75   NE2  GLN X 695     11.092   29.828   51.560   1.00  20.00       7
ATOM     76   N    ASP X 696     12.155   25.020   46.714   1.00  40.00       7
ATOM     77   CA   ASP X 696     11.698   23.885   45.910   1.00  40.00       6
ATOM     78   CB   ASP X 696     11.450   24.400   44.494   1.00  40.00       6
ATOM     79   CG   ASP X 696     10.782   23.411   43.548   1.00  40.00       6
ATOM     80   OD1  ASP X 696     10.550   22.203   43.920   1.00  40.00       8
ATOM     81   OD2  ASP X 696     10.449   23.804   42.362   1.00  40.00       8
ATOM     82   C    ASP X 696     12.774   22.806   45.876   1.00  40.00       6
ATOM     83   O    ASP X 696     13.937   23.077   45.562   1.00  40.00       8
ATOM     84   N    SER X 697     12.370   21.610   46.213   1.00  40.00       7
ATOM     85   CA   SER X 697     13.258   20.453   46.128   1.00  40.00       6
ATOM     86   CB   SER X 697     12.685   19.371   47.049   1.00  40.00       6
ATOM     87   OG   SER X 697     12.535   19.899   48.374   1.00  40.00       8
ATOM     88   C    SER X 697     13.329   20.130   44.613   1.00  40.00       6
ATOM     89   O    SER X 697     14.247   20.573   43.914   1.00  40.00       8
ATOM     90   N    SER X 698     12.355   19.357   44.183   1.00  40.00       7
ATOM     91   CA   SER X 698     11.985   19.100   42.752   1.00  40.00       6
ATOM     92   CB   SER X 698     11.693   20.417   42.036   1.00  40.00       6
ATOM     93   OG   SER X 698     10.510   21.000   42.577   1.00  40.00       8
ATOM     94   C    SER X 698     12.887   18.340   41.758   1.00  40.00       6
```

UNITED STATES PATENT AND TRADEMARK OFFICE
CERTIFICATE OF CORRECTION

PATENT NO. : 6,965,850 B2  Page 76 of 186
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM     95  O    SER X 698     13.253  17.158  42.026  1.00 40.00   8
ATOM     96  OXT  SER X 698     13.131  18.976  40.714  1.00 40.00   8
TER
ATOM      1  CB   LYS Y 688    -33.793  96.885   6.491  1.00 40.00   6
ATOM      2  C    LYS Y 688    -35.002  95.370   8.130  1.00 40.00   6
ATOM      3  O    LYS Y 688    -36.027  95.520   8.779  1.00 40.00   8
ATOM      4  N    LYS Y 688    -32.717  96.619   8.695  1.00 40.00   7
ATOM      5  CA   LYS Y 688    -34.040  96.591   7.954  1.00 40.00   6
ATOM      6  N    ILE Y 689    -34.578  93.781   6.908  1.00 40.00   7
ATOM      7  CA   ILE Y 689    -35.862  93.106   7.268  1.00 40.00   6
ATOM      8  CB   ILE Y 689    -35.971  91.759   6.572  1.00 40.00   6
ATOM      9  CG2  ILE Y 689    -37.270  91.077   6.932  1.00 40.00   6
ATOM     10  CG1  ILE Y 689    -35.917  91.937   5.062  1.00 40.00   6
ATOM     11  CD1  ILE Y 689    -36.341  90.691   4.289  1.00 40.00   6
ATOM     12  C    ILE Y 689    -36.032  92.870   8.780  1.00 40.00   6
ATOM     13  O    ILE Y 689    -36.913  93.446   9.442  1.00 40.00   8
ATOM     14  N    LEU Y 690    -35.019  92.834   9.787  1.00 40.00   7
ATOM     15  CA   LEU Y 690    -34.956  92.320  11.163  1.00 40.00   6
ATOM     16  CB   LEU Y 690    -33.528  92.432  11.697  1.00 40.00   6
ATOM     17  CG   LEU Y 690    -32.516  91.647  10.864  1.00 40.00   6
ATOM     18  CD1  LEU Y 690    -31.087  91.764  11.397  1.00 40.00   6
ATOM     19  CD2  LEU Y 690    -32.819  90.148  10.812  1.00 40.00   6
ATOM     20  C    LEU Y 690    -35.899  93.123  12.065  1.00 40.00   6
ATOM     21  O    LEU Y 690    -36.570  92.492  12.928  1.00 40.00   8
ATOM     22  N    HIS Y 691    -36.039  94.731  11.373  1.00 40.00   7
ATOM     23  CA   HIS Y 691    -36.634  94.923  12.683  1.00 40.00   6
ATOM     24  CB   HIS Y 691    -36.854  96.383  12.935  1.00 40.00   6
ATOM     25  CG   HIS Y 691    -35.610  97.153  13.078  1.00 40.00   6
ATOM     26  CD2  HIS Y 691    -34.757  97.640  12.159  1.00 40.00   6
ATOM     27  ND1  HIS Y 691    -35.129  97.579  14.319  1.00 40.00   7
ATOM     28  CE1  HIS Y 691    -34.039  98.290  14.122  1.00 40.00   6
ATOM     29  NE2  HIS Y 691    -33.786  98.346  12.815  1.00 40.00   7
ATOM     30  C    HIS Y 691    -37.972  94.287  12.756  1.00 40.00   6
ATOM     31  O    HIS Y 691    -38.240  93.417  13.545  1.00 40.00   8
ATOM     32  N    ARG Y 692    -38.265  94.388  11.505  1.00 40.00   7
ATOM     33  CA   ARG Y 692    -39.577  93.869  11.276  1.00 40.00   6
ATOM     34  CB   ARG Y 692    -39.653  93.692   9.795  1.00 40.00   6
ATOM     35  CG   ARG Y 692    -40.759  92.764   9.329  1.00 40.00   6
ATOM     36  CD   ARG Y 692    -40.618  92.422   7.848  1.00 40.00   6
ATOM     37  NE   ARG Y 692    -41.849  92.641   7.091  1.00 40.00   7
ATOM     38  CZ   ARG Y 692    -41.898  92.758   5.763  1.00 40.00   6
ATOM     39  NH1  ARG Y 692    -40.784  92.695   5.024  1.00 40.00   7
ATOM     40  NH2  ARG Y 692    -43.034  92.940   5.080  1.00 40.00   7
ATOM     41  C    ARG Y 692    -39.941  92.547  11.995  1.00 40.00   6
ATOM     42  O    ARG Y 692    -41.001  92.440  12.649  1.00 40.00   8
ATOM     43  N    LEU Y 693    -39.095  91.576  11.816  1.00 40.00   7
ATOM     44  CA   LEU Y 693    -39.230  90.232  12.395  1.00 40.00   6
ATOM     45  CB   LEU Y 693    -38.362  89.337  11.615  1.00 40.00   6
ATOM     46  CG   LEU Y 693    -38.737  89.375  10.132  1.00 40.00   6
ATOM     47  CD1  LEU Y 693    -37.794  88.570   9.247  1.00 40.00   6
ATOM     48  CD2  LEU Y 693    -40.142  88.827   9.862  1.00 40.00   6
ATOM     49  C    LEU Y 693    -38.921  90.378  13.816  1.00 40.00   6
ATOM     50  O    LEU Y 693    -39.191  89.474  14.615  1.00 40.00   8
ATOM     51  N    LEU Y 694    -38.366  91.533  14.076  1.00 40.00   7
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    52  CA   LEU Y 694    -38.174  91.885  15.435  1.00 40.00    6
ATOM    53  CB   LEU Y 694    -37.181  93.002  15.561  1.00 40.00    6
ATOM    54  CG   LEU Y 694    -35.799  92.377  15.869  1.00 40.00    6
ATOM    55  CD1  LEU Y 694    -34.897  93.275  16.702  1.00 40.00    6
ATOM    56  CD2  LEU Y 694    -35.897  91.055  16.661  1.00 40.00    6
ATOM    57  C    LEU Y 694    -39.596  91.903  15.915  1.00 40.00    6
ATOM    58  O    LEU Y 694    -39.985  91.253  16.838  1.00 40.00    8
ATOM    59  N    GLN Y 695    -40.787  92.229  15.048  1.00 40.00    7
ATOM    60  CA   GLN Y 695    -42.034  91.457  15.543  1.00 40.00    6
ATOM    61  C    GLN Y 695    -43.054  90.901  14.240  1.00 40.00    6
ATOM    62  O    GLN Y 695    -43.102  91.557  13.189  1.00 40.00    8
ATOM    63  CB   GLN Y 695    -42.362  92.025  16.923  1.00 40.00    6
ATOM    64  CG   GLN Y 695    -41.013  92.101  17.768  1.00 40.00    6
ATOM    65  CD   GLN Y 695    -40.943  91.235  19.059  1.00 40.00    6
ATOM    66  OE1  GLN Y 695    -41.828  90.426  19.318  1.00 40.00    8
ATOM    67  NE2  GLN Y 695    -39.938  91.399  19.916  1.00 40.00    7
ATOM    68  N    ASP Y 696    -43.802  89.498  14.402  1.00 40.00    7
ATOM    69  CA   ASP Y 696    -44.784  88.354  13.428  1.00 40.00    6
ATOM    70  C    ASP Y 696    -46.034  88.934  12.759  1.00 40.00    6
ATOM    71  O    ASP Y 696    -46.266  88.655  11.529  1.00 40.00    8
ATOM    72  CB   ASP Y 696    -45.211  87.192  14.322  1.00 40.00    6
ATOM    73  CG   ASP Y 696    -44.021  86.560  15.058  1.00 40.00    6
ATOM    74  OD1  ASP Y 696    -42.823  86.994  14.844  1.00 40.00    8
ATOM    75  OD2  ASP Y 696    -44.212  85.591  15.889  1.00 40.00    8
END
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

Appendix 2

Atomic Coordinates for Human ERα Complexed with DES, and a GRIP1 NR-box 2 Peptide

```
CRYST1   54.094   82.217   58.041   90.00    111.33   90.00    P 21    2

ORIGX1    1.000000  0.000000  0.000000   0.00000
ORIGX2    0.000000  1.000000  0.000000   0.00000
ORIGX3    0.000000  0.000000  1.000000   0.00000
SCALE1    0.018486  0.000000  0.007221   0.00000
SCALE2    0.000000  0.012163  0.000000   0.00000
SCALE3    0.000000  0.000000  0.018497   0.00000

ATOM      1   CB    SER  A   305      35.230  -14.787  -1.163   1.00   73.26
ATOM      2   C     SER  A   305      35.331  -14.303   1.289   1.00   72.95
ATOM      3   O     SER  A   305      34.146  -13.984   1.186   1.00   72.46
ATOM      4   N     SER  A   305      36.797  -16.033   0.285   1.00   74.06
ATOM      5   CA    SER  A   305      36.138  -14.713   0.061   1.00   73.59
ATOM      6   N     LEU  A   306      35.982  -14.313   2.449   1.00   72.21
ATOM      7   CA    LEU  A   306      35.329  -13.950   3.702   1.00   71.05
ATOM      8   CB    LEU  A   306      36.251  -14.286   4.878   1.00   70.19
ATOM      9   C     LEU  A   306      34.929  -12.478   3.719   1.00   69.57
ATOM     10   O     LEU  A   306      35.580  -11.638   3.100   1.00   69.96
ATOM     11   N     ALA  A   307      33.857  -12.176   4.434   1.00   68.06
ATOM     12   CA    ALA  A   307      33.356  -10.810   4.541   1.00   64.88
ATOM     13   CB    ALA  A   307      31.841  -10.795   4.436   1.00   65.83
ATOM     14   C     ALA  A   307      33.792  -10.204   5.866   1.00   63.36
ATOM     15   O     ALA  A   307      33.878   -8.984   6.005   1.00   62.73
ATOM     16   N     LEU  A   308      34.064  -11.062   6.842   1.00   62.52
ATOM     17   CA    LEU  A   308      34.487  -10.598   8.156   1.00   62.57
ATOM     18   CB    LEU  A   308      34.423  -11.745   9.171   1.00   62.81
ATOM     19   CG    LEU  A   308      33.214  -12.688   9.130   1.00   64.21
ATOM     20   CD1   LEU  A   308      33.188  -13.513  10.406   1.00   65.28
ATOM     21   CD2   LEU  A   308      31.919  -11.898   8.989   1.00   63.80
ATOM     22   C     LEU  A   308      35.903  -10.037   8.100   1.00   61.61
ATOM     23   O     LEU  A   308      36.385   -9.445   9.086   1.00   62.92
ATOM     24   N     SER  A   309      36.561  -10.219   6.959   1.00   60.50
ATOM     25   CA    SER  A   309      37.928   -9.743   6.771   1.00   58.73
ATOM     26   CB    SER  A   309      38.720  -10.750   5.934   1.00   59.53
ATOM     27   OG    SER  A   309      38.889  -10.283   4.606   1.00   59.47
ATOM     28   C     SER  A   309      37.986   -8.373   6.099   1.00   57.05
ATOM     29   O     SER  A   309      38.965   -7.637   6.249   1.00   56.70
ATOM     30   N     LEU  A   310      36.940   -8.038   5.352   1.00   52.69
ATOM     31   CA    LEU  A   310      36.877   -6.759   4.658   1.00   48.20
ATOM     32   CB    LEU  A   310      35.516   -6.596   3.974   1.00   48.32
ATOM     33   CG    LEU  A   310      35.301   -7.188   2.583   1.00   44.94
ATOM     34   CD1   LEU  A   310      33.951   -6.728   2.055   1.00   46.45
ATOM     35   CD2   LEU  A   310      36.417   -6.755   1.650   1.00   43.19
ATOM     36   C     LEU  A   310      37.086   -5.589   5.609   1.00   46.44
ATOM     37   O     LEU  A   310      36.605   -5.607   6.741   1.00   46.78
ATOM     38   N     THR  A   311      37.812   -4.576   5.148   1.00   44.36
ATOM     39   CA    THR  A   311      38.034   -3.380   5.949   1.00   42.88
ATOM     40   CB    THR  A   311      39.313   -2.633   5.532   1.00   42.31
ATOM     41   OG1   THR  A   311      39.079   -1.936   4.303   1.00   42.50
ATOM     42   CG2   THR  A   311      40.464   -3.606   5.350   1.00   46.02
ATOM     43   C     THR  A   311      36.834   -2.475   5.674   1.00   43.21
ATOM     44   O     THR  A   311      36.021   -2.776   4.800   1.00   42.12
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   45   N    ALA  A  312   36.726  -1.372   5.409  1.00  42.16
ATOM   46   CA   ALA  A  312   35.616  -0.444   6.228  1.00  40.10
ATOM   47   CB   ALA  A  312   35.741   0.709   7.205  1.00  40.07
ATOM   48   C    ALA  A  312   35.561   0.090   4.799  1.00  41.80
ATOM   49   O    ALA  A  312   34.510   0.074   4.154  1.00  37.81
ATOM   50   N    ASP  A  313   36.698   0.564   4.304  1.00  42.35
ATOM   51   CA   ASP  A  313   36.752   1.104   2.953  1.00  42.27
ATOM   52   CB   ASP  A  313   38.133   1.703   2.680  1.00  43.74
ATOM   53   CG   ASP  A  313   38.323   3.054   3.348  1.00  46.62
ATOM   54   OD1  ASP  A  313   39.414   3.645   3.205  1.00  51.01
ATOM   55   OD2  ASP  A  313   37.380   3.529   4.015  1.00  48.89
ATOM   56   C    ASP  A  313   36.422   0.027   1.926  1.00  38.68
ATOM   57   O    ASP  A  313   35.704   0.281   0.959  1.00  38.75
ATOM   58   N    GLN  A  314   36.931  -1.179   2.145  1.00  34.76
ATOM   59   CA   GLN  A  314   36.666  -2.277   1.229  1.00  33.55
ATOM   60   CB   GLN  A  314   37.462  -3.512   1.643  1.00  36.90
ATOM   61   CG   GLN  A  314   38.963  -3.384   1.436  1.00  40.45
ATOM   62   CD   GLN  A  314   39.700  -4.610   1.905  1.00  43.13
ATOM   63   OE1  GLN  A  314   39.394  -5.196   2.935  1.00  43.60
ATOM   64   NE2  GLN  A  314   40.701  -5.032   1.117  1.00  44.03
ATOM   65   C    GLN  A  314   35.176  -2.595   1.201  1.00  34.95
ATOM   66   O    GLN  A  314   34.605  -2.860   0.140  1.00  32.89
ATOM   67   N    MET  A  315   34.542  -2.564   2.374  1.00  32.54
ATOM   68   CA   MET  A  315   33.115  -2.848   2.470  1.00  35.46
ATOM   69   CB   MET  A  315   32.650  -2.794   3.926  1.00  37.09
ATOM   70   CG   MET  A  315   31.137  -2.777   4.097  1.00  39.42
ATOM   71   SD   MET  A  315   30.443  -4.425   4.053  1.00  46.55
ATOM   72   CE   MET  A  315   31.351  -5.205   5.397  1.00  45.29
ATOM   73   C    MET  A  315   32.311  -1.859   1.640  1.00  31.83
ATOM   74   O    MET  A  315   31.453  -2.247   0.852  1.00  32.10
ATOM   75   N    VAL  A  316   32.587  -0.560   1.830  1.00  32.62
ATOM   76   CA   VAL  A  316   31.882   0.470   1.079  1.00  31.09
ATOM   77   CB   VAL  A  316   32.395   1.888   1.425  1.00  34.77
ATOM   78   CG1  VAL  A  316   31.786   2.899   0.461  1.00  34.10
ATOM   79   CG2  VAL  A  316   32.021   2.246   2.862  1.00  34.40
ATOM   80   C    VAL  A  316   32.092   0.232  -0.414  1.00  33.48
ATOM   81   O    VAL  A  316   31.145   0.266  -1.200  1.00  32.49
ATOM   82   N    SER  A  317   33.337  -0.027  -0.795  1.00  33.49
ATOM   83   CA   SER  A  317   33.682  -0.280  -2.187  1.00  32.88
ATOM   84   CB   SER  A  317   35.165  -0.635  -2.297  1.00  35.77
ATOM   85   OG   SER  A  317   35.825   0.277  -3.154  1.00  42.70
ATOM   86   C    SER  A  317   32.849  -1.396  -2.801  1.00  30.71
ATOM   87   O    SER  A  317   32.279  -1.238  -3.880  1.00  31.14
ATOM   88   N    ALA  A  318   32.792  -2.529  -2.111  1.00  29.51
ATOM   89   CA   ALA  A  318   32.035  -3.676  -2.580  1.00  29.93
ATOM   90   CB   ALA  A  318   32.156  -4.811  -1.579  1.00  28.56
ATOM   91   C    ALA  A  318   30.565  -3.305  -2.771  1.00  31.55
ATOM   92   O    ALA  A  318   29.961  -3.642  -3.784  1.00  30.64
ATOM   93   N    LEU  A  319   29.997  -2.614  -1.791  1.00  34.13
ATOM   94   CA   LEU  A  319   28.597  -2.212  -1.861  1.00  32.93
ATOM   95   CB   LEU  A  319   28.170  -1.576  -0.540  1.00  31.15
ATOM   96   CG   LEU  A  319   28.076  -2.555   0.632  1.00  32.27
ATOM   97   CD1  LEU  A  319   27.523  -1.840   1.852  1.00  32.14
ATOM   98   CD2  LEU  A  319   27.194  -3.733   0.243  1.00  31.82
ATOM   99   C    LEU  A  319   28.340  -1.257  -3.020  1.00  34.41
ATOM  100   O    LEU  A  319   27.430  -1.475  -3.818  1.00  35.23
ATOM  101   N    LEU  A  320   29.140  -0.195  -3.120  1.00  32.53
ATOM  102   CA   LEU  A  320   28.972   0.756  -4.212  1.00  35.33
```

UNITED STATES PATENT AND TRADEMARK OFFICE
CERTIFICATE OF CORRECTION

| | |
|---|---|
| PATENT NO. | : 6,965,850 B2 |
| APPLICATION NO. | : 09/281717 |
| DATED | : November 15, 2005 |
| INVENTOR(S) | : John D. Baxter et al. |

It is certified that error appears in the above-identified patent and that said Letters Patent is hereby corrected as shown below:

```
ATOM   103  CB   LEU  A  320   30.052   1.839  -4.155  1.00  33.52
ATOM   104  CG   LEU  A  320   29.974   2.899  -3.054  1.00  34.60
ATOM   105  CD1  LEU  A  320   31.060   3.940  -3.292  1.00  33.69
ATOM   106  CD2  LEU  A  320   28.611   3.562  -3.044  1.00  31.05
ATOM   107  C    LEU  A  320   29.052   0.040  -5.561  1.00  35.41
ATOM   108  O    LEU  A  320   28.230   0.271  -6.446  1.00  39.16
ATOM   109  N    AASP A  321   30.043  -0.833  -5.720  0.50  36.33
ATOM   110  N    BASP A  321   30.041  -0.839  -5.695  0.50  35.76
ATOM   111  CA   AASP A  321   30.214  -1.559  -6.977  0.50  37.71
ATOM   112  CA   BASP A  321   30.268  -1.595  -6.925  0.50  37.11
ATOM   113  CB   AASP A  321   31.537  -2.334  -6.973  0.50  40.01
ATOM   114  CB   BASP A  321   31.573  -2.374  -6.826  0.50  39.41
ATOM   115  CG   AASP A  321   31.694  -3.230  -8.195  0.50  41.93
ATOM   116  CG   BASP A  321   32.770  -1.562  -7.284  0.50  39.96
ATOM   117  OD1  AASP A  321   31.523  -2.733  -9.329  0.50  42.11
ATOM   118  OD1  BASP A  321   33.312  -1.868  -8.366  0.50  43.41
ATOM   119  OD2  AASP A  321   31.988  -4.432  -8.022  0.50  42.69
ATOM   120  OD2  BASP A  321   33.170  -0.622  -6.554  0.50  41.33
ATOM   121  C    AASP A  321   29.069  -2.524  -7.275  0.50  37.19
ATOM   122  C    BASP A  321   29.123  -2.565  -7.253  0.50  36.68
ATOM   123  O    AASP A  321   28.820  -2.861  -8.434  0.50  36.87
ATOM   124  O    BASP A  321   28.934  -2.942  -8.411  0.50  36.08
ATOM   125  N    ALA  A  322   28.374  -2.968  -6.235  1.00  35.35
ATOM   126  CA   ALA  A  322   27.268  -3.902  -6.417  1.00  31.59
ATOM   127  CB   ALA  A  322   27.124  -4.781  -5.175  1.00  30.73
ATOM   128  C    ALA  A  322   25.946  -3.204  -6.709  1.00  30.07
ATOM   129  O    ALA  A  322   24.955  -3.857  -7.036  1.00  26.53
ATOM   130  N    GLU  A  323   25.932  -1.880  -6.596  1.00  27.98
ATOM   131  CA   GLU  A  323   24.713  -1.117  -6.827  1.00  29.88
ATOM   132  CB   GLU  A  323   25.027   0.380  -6.855  1.00  30.98
ATOM   133  CG   GLU  A  323   24.870   1.068  -5.509  1.00  31.62
ATOM   134  CD   GLU  A  323   23.463   0.940  -4.960  1.00  31.98
ATOM   135  OE1  GLU  A  323   23.183  -0.056  -4.257  1.00  33.10
ATOM   136  OE2  GLU  A  323   22.640   1.836  -5.233  1.00  30.01
ATOM   137  C    GLU  A  323   24.010  -1.515  -8.123  1.00  30.86
ATOM   138  O    GLU  A  323   24.655  -1.705  -9.151  1.00  28.86
ATOM   139  N    PRO  A  324   22.674  -1.659  -8.083  1.00  30.66
ATOM   140  CD   PRO  A  324   21.774  -1.466  -6.935  1.00  31.01
ATOM   141  CA   PRO  A  324   21.935  -2.032  -9.290  1.00  30.29
ATOM   142  CB   PRO  A  324   20.613  -2.598  -8.760  1.00  31.42
ATOM   143  CG   PRO  A  324   20.626  -2.363  -7.258  1.00  33.66
ATOM   144  C    PRO  A  324   21.717  -0.785 -10.138  1.00  27.46
ATOM   145  O    PRO  A  324   21.893   0.332  -9.668  1.00  26.19
ATOM   146  N    PRO  A  325   21.335  -0.959 -11.403  1.00  27.80
ATOM   147  CD   PRO  A  325   21.082  -2.198 -12.161  1.00  27.35
ATOM   148  CA   PRO  A  325   21.125   0.242 -12.211  1.00  25.59
ATOM   149  CB   PRO  A  325   21.258  -0.266 -13.637  1.00  24.02
ATOM   150  CG   PRO  A  325   20.773  -1.695 -13.559  1.00  26.00
ATOM   151  C    PRO  A  325   19.749   0.830 -11.954  1.00  23.73
ATOM   152  O    PRO  A  325   18.873   0.165 -11.402  1.00  24.83
ATOM   153  N    ILE  A  326   19.571   2.081 -12.352  1.00  22.11
ATOM   154  CA   ILE  A  326   18.296   2.762 -12.212  1.00  24.01
ATOM   155  CB   ILE  A  326   18.502   4.282 -12.133  1.00  25.97
ATOM   156  CG2  ILE  A  326   17.168   4.992 -12.286  1.00  20.75
ATOM   157  CG1  ILE  A  326   19.189   4.632 -10.805  1.00  29.31
ATOM   158  CD1  ILE  A  326   19.301   6.120 -10.525  1.00  32.91
ATOM   159  C    ILE  A  326   17.506   2.408 -13.471  1.00  25.72
ATOM   160  O    ILE  A  326   17.906   2.758 -14.581  1.00  25.55
```

UNITED STATES PATENT AND TRADEMARK OFFICE
CERTIFICATE OF CORRECTION

PATENT NO.        : 6,965,850 B2
APPLICATION NO.   : 09/281717
DATED             : November 15, 2005
INVENTOR(S)       : John D. Baxter et al.

It is certified that error appears in the above-identified patent and that said Letters Patent is hereby corrected as shown below:

```
ATOM    161   N    LEU   A   327   16.392    1.703-13.301   1.00   25.67
ATOM    162   CA   LEU   A   327   15.595    1.279-14.439   1.00   23.80
ATOM    163   CB   LEU   A   327   14.872   -0.029-14.104   1.00   23.96
ATOM    164   CG   LEU   A   327   15.778   -1.210-13.728   1.00   19.89
ATOM    165   CD1  LEU   A   327   14.944   -2.462-13.583   1.00   21.19
ATOM    166   CD2  LEU   A   327   16.890   -1.415-14.805   1.00   17.53
ATOM    167   C    LEU   A   327   14.598    2.317-14.935   1.00   27.16
ATOM    168   O    LEU   A   327   14.161    3.202-14.194   1.00   25.98
ATOM    169   N    TYR   A   328   14.251    2.207-16.210   1.00   26.56
ATOM    170   CA   TYR   A   328   13.303    3.123-16.814   1.00   24.45
ATOM    171   CB   TYR   A   328   13.724    3.465-18.245   1.00   26.72
ATOM    172   CG   TYR   A   328   14.587    4.693-18.314   1.00   27.73
ATOM    173   CD1  TYR   A   328   14.021    5.949-18.518   1.00   28.56
ATOM    174   CE1  TYR   A   328   14.798    7.092-18.509   1.00   29.10
ATOM    175   CD2  TYR   A   328   15.962    4.612-18.110   1.00   26.01
ATOM    176   CE2  TYR   A   328   16.750    5.753-18.098   1.00   30.63
ATOM    177   CZ   TYR   A   328   16.157    6.988-18.297   1.00   30.07
ATOM    178   OH   TYR   A   328   16.917    8.130-18.265   1.00   37.94
ATOM    179   C    TYR   A   328   11.923    2.501-16.827   1.00   24.95
ATOM    180   O    TYR   A   328   11.774    1.274-16.846   1.00   27.02
ATOM    181   N    SER   A   329   10.912    3.358-16.800   1.00   25.60
ATOM    182   CA   SER   A   329    9.533    2.908-16.837   1.00   29.45
ATOM    183   CB   SER   A   329    8.661    3.858-16.020   1.00   30.80
ATOM    184   OG   SER   A   329    7.297    3.721-16.364   1.00   33.74
ATOM    185   C    SER   A   329    9.129    2.947-18.313   1.00   31.30
ATOM    186   O    SER   A   329    9.908    3.397-19.154   1.00   27.35
ATOM    187   N    GLU   A   330    7.930    2.469-18.629   1.00   32.98
ATOM    188   CA   GLU   A   330    7.459    2.482-20.007   1.00   35.10
ATOM    189   CB   GLU   A   330    6.031    1.968-20.074   1.00   34.67
ATOM    190   C    GLU   A   330    7.532    3.924-20.505   1.00   40.06
ATOM    191   O    GLU   A   330    7.068    4.841-19.826   1.00   42.65
ATOM    192   N    TYR   A   331    8.124    4.126-21.681   1.00   41.16
ATOM    193   CA   TYR   A   331    8.263    5.470-22.234   1.00   42.66
ATOM    194   CB   TYR   A   331    9.323    5.482-23.350   1.00   42.54
ATOM    195   CG   TYR   A   331    9.202    4.347-24.345   1.00   38.67
ATOM    196   CD1  TYR   A   331   10.105    3.284-24.334   1.00   34.66
ATOM    197   CE1  TYR   A   331    9.985    2.228-25.233   1.00   34.89
ATOM    198   CD2  TYR   A   331    8.174    4.327-25.287   1.00   37.88
ATOM    199   CE2  TYR   A   331    8.045    3.276-26.193   1.00   34.65
ATOM    200   CZ   TYR   A   331    8.950    2.233-26.159   1.00   30.73
ATOM    201   OH   TYR   A   331    8.814    1.191-27.042   1.00   30.97
ATOM    202   C    TYR   A   331    6.943    6.043-22.754   1.00   46.24
ATOM    203   O    TYR   A   331    6.018    5.301-23.096   1.00   45.38
ATOM    204   N    ASP   A   332    6.868    7.372-22.792   1.00   49.11
ATOM    205   CA   ASP   A   332    5.684    8.092-23.262   1.00   52.40
ATOM    206   CB   ASP   A   332    5.781    8.321-24.772   1.00   52.86
ATOM    207   C    ASP   A   332    4.356    7.410-22.926   1.00   52.90
ATOM    208   O    ASP   A   332    3.561    7.116-23.818   1.00   53.94
ATOM    209   N    PRO   A   333    4.103    7.144-21.632   1.00   53.63
ATOM    210   CD   PRO   A   333    4.962    7.418-20.465   1.00   53.63
ATOM    211   CA   PRO   A   333    2.840    6.497-21.253   1.00   53.55
ATOM    212   CB   PRO   A   333    3.070    6.076-19.802   1.00   53.78
ATOM    213   CG   PRO   A   333    4.101    7.028-19.290   1.00   53.42
ATOM    214   C    PRO   A   333    1.673    7.478-21.398   1.00   52.17
ATOM    215   O    PRO   A   333    1.879    8.690-21.395   1.00   51.19
ATOM    216   N    THR   A   334    0.457    6.956-21.532   1.00   52.26
ATOM    217   CA   THR   A   334   -0.724    7.802-21.687   1.00   54.21
ATOM    218   CB   THR   A   334   -1.937    6.949-21.813   1.00   53.90
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   219  OG1  THR  A  334   -1.971   6.256-23.065  1.00  53.92
ATOM   220  CG2  THR  A  334   -3.237   7.821-21.761  1.00  54.15
ATOM   221  C    THR  A  334   -0.864   8.782-20.525  1.00  56.34
ATOM   222  O    THR  A  334   -1.389   8.443-19.461  1.00  56.44
ATOM   223  N    ARG  A  335   -0.386  10.002-20.766  1.00  58.24
ATOM   224  CA   ARG  A  335   -0.377  11.099-19.801  1.00  57.96
ATOM   225  CB   ARG  A  335   -0.569  12.427-20.531  1.00  60.22
ATOM   226  C    ARG  A  335   -1.349  10.996-18.627  1.00  56.61
ATOM   227  O    ARG  A  335   -0.919  10.908-17.475  1.00  60.70
ATOM   228  N    PRO  A  336   -2.667  11.015-18.889  1.00  52.43
ATOM   229  CD   PRO  A  336   -3.389  11.117-20.165  1.00  49.06
ATOM   230  CA   PRO  A  336   -3.587  10.915-17.752  1.00  49.58
ATOM   231  CB   PRO  A  336   -4.911  11.456-18.302  1.00  48.66
ATOM   232  CG   PRO  A  336   -4.645  11.809-19.760  1.00  51.33
ATOM   233  C    PRO  A  336   -3.698   9.468-17.279  1.00  49.25
ATOM   234  O    PRO  A  336   -4.340   8.644-17.929  1.00  48.06
ATOM   235  N    PHE  A  337   -3.063   9.170-16.147  1.00  47.90
ATOM   236  CA   PHE  A  337   -3.055   7.821-15.582  1.00  46.61
ATOM   237  CB   PHE  A  337   -2.063   7.732-14.421  1.00  47.73
ATOM   238  CG   PHE  A  337   -0.649   8.011-14.805  1.00  46.27
ATOM   239  CD1  PHE  A  337   -0.017   9.168-14.368  1.00  46.55
ATOM   240  CD2  PHE  A  337    0.061   7.113-15.591  1.00  48.12
ATOM   241  CE1  PHE  A  337    1.305   9.429-14.707  1.00  48.09
ATOM   242  CE2  PHE  A  337    1.386   7.364-15.938  1.00  47.57
ATOM   243  CZ   PHE  A  337    2.009   8.525-15.495  1.00  48.40
ATOM   244  C    PHE  A  337   -4.401   7.338-15.071  1.00  46.15
ATOM   245  O    PHE  A  337   -5.250   8.127-14.671  1.00  48.34
ATOM   246  N    SER  A  338   -4.573   6.022-15.080  1.00  45.06
ATOM   247  CA   SER  A  338   -5.781   5.385-14.578  1.00  45.12
ATOM   248  CB   SER  A  338   -6.477   4.594-15.684  1.00  44.49
ATOM   249  OG   SER  A  338   -6.227   3.206-15.554  1.00  45.78
ATOM   250  C    SER  A  338   -5.292   4.439-13.488  1.00  47.04
ATOM   251  O    SER  A  338   -4.090   4.186-13.387  1.00  44.08
ATOM   252  N    GLU  A  339   -6.206   3.916-12.676  1.00  45.63
ATOM   253  CA   GLU  A  339   -5.802   3.012-11.608  1.00  45.40
ATOM   254  CB   GLU  A  339   -7.015   2.521-10.814  1.00  45.66
ATOM   255  CG   GLU  A  339   -6.637   1.680 -9.600  1.00  46.81
ATOM   256  CD   GLU  A  339   -7.717   1.652 -8.535  1.00  47.56
ATOM   257  OE1  GLU  A  339   -8.471   0.656 -8.477  1.00  47.37
ATOM   258  OE2  GLU  A  339   -7.810   2.625 -7.754  1.00  49.29
ATOM   259  C    GLU  A  339   -5.040   1.821-12.170  1.00  45.23
ATOM   260  O    GLU  A  339   -3.862   1.641-11.872  1.00  46.51
ATOM   261  N    ALA  A  340   -5.712   1.010-12.982  1.00  42.87
ATOM   262  CA   ALA  A  340   -5.078  -0.158-13.574  1.00  40.24
ATOM   263  CB   ALA  A  340   -6.055  -0.871-14.496  1.00  41.40
ATOM   264  C    ALA  A  340   -3.837   0.273-14.350  1.00  38.83
ATOM   265  O    ALA  A  340   -2.909  -0.515-14.543  1.00  35.58
ATOM   266  N    SER  A  341   -3.836   1.535-14.773  1.00  35.79
ATOM   267  CA   SER  A  341   -2.743   2.133-15.537  1.00  36.58
ATOM   268  CB   SER  A  341   -3.231   3.454-16.154  1.00  39.01
ATOM   269  OG   SER  A  341   -2.211   4.130-16.864  1.00  36.09
ATOM   270  C    SER  A  341   -1.480   2.376-14.691  1.00  35.63
ATOM   271  O    SER  A  341   -0.389   1.913-15.038  1.00  33.20
ATOM   272  N    MET  A  342   -1.626   3.115-13.595  1.00  35.92
ATOM   273  CA   MET  A  342   -0.498   3.396-12.708  1.00  35.88
ATOM   274  CB   MET  A  342   -0.912   4.396-11.623  1.00  35.96
ATOM   275  CG   MET  A  342    0.241   5.218-11.059  1.00  38.02
ATOM   276  SD   MET  A  342   -0.308   6.374 -9.780  1.00  44.73
```

UNITED STATES PATENT AND TRADEMARK OFFICE
CERTIFICATE OF CORRECTION

PATENT NO. : 6,965,850 B2  Page 83 of 186
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    277  CE   MET  A   342    0.626    7.815-10.205  1.00  43.49
ATOM    278  C    MET  A   342   -0.011    2.100-12.089  1.00  34.17
ATOM    279  O    MET  A   342    1.195    1.880-11.909  1.00  33.40
ATOM    280  N    MET  A   343   -0.957    1.243-11.687  1.00  29.95
ATOM    281  CA   MET  A   343   -0.640   -0.034-11.062  1.00  31.96
ATOM    282  CB   MET  A   343   -1.921   -0.810-10.751  1.00  31.70
ATOM    283  CG   MET  A   343   -2.667   -0.337 -9.502  1.00  37.13
ATOM    284  SD   MET  A   343   -1.749   -0.507 -7.940  1.00  36.00
ATOM    285  CE   MET  A   343   -1.468   -2.299 -7.886  1.00  32.14
ATOM    286  C    MET  A   343    0.234   -0.875-11.979  1.00  31.72
ATOM    287  O    MET  A   343    1.159   -1.558-11.527  1.00  30.26
ATOM    288  N    GLY  A   344   -0.069   -0.823-13.272  1.00  29.04
ATOM    289  CA   GLY  A   344    0.688   -1.591-14.242  1.00  24.94
ATOM    290  C    GLY  A   344    2.104   -1.085-14.396  1.00  26.01
ATOM    291  O    GLY  A   344    3.046   -1.873-14.463  1.00  28.72
ATOM    292  N    LEU  A   345    2.257    0.332-14.471  1.00  26.97
ATOM    293  CA   LEU  A   345    3.576    0.839-14.608  1.00  31.15
ATOM    294  CB   LEU  A   345    3.459    2.361-14.753  1.00  30.06
ATOM    295  CG   LEU  A   345    2.765    2.934-15.995  1.00  33.50
ATOM    296  CD1  LEU  A   345    2.901    4.439-15.999  1.00  33.52
ATOM    297  CD2  LEU  A   345    3.379    2.324-17.257  1.00  33.22
ATOM    298  C    LEU  A   345    4.433    0.534-13.383  1.00  30.31
ATOM    299  O    LEU  A   345    5.564    0.061-13.505  1.00  32.80
ATOM    300  N    LEU  A   346    3.884    0.813-12.205  1.00  27.83
ATOM    301  CA   LEU  A   346    4.595    0.596-10.947  1.00  26.19
ATOM    302  CB   LEU  A   346    3.729    1.063 -9.783  1.00  24.51
ATOM    303  CG   LEU  A   346    3.483    2.569 -9.682  1.00  26.33
ATOM    304  CD1  LEU  A   346    2.623    2.844 -8.463  1.00  27.33
ATOM    305  CD2  LEU  A   346    4.809    3.317 -9.587  1.00  24.89
ATOM    306  C    LEU  A   346    5.032   -0.848-10.707  1.00  25.72
ATOM    307  O    LEU  A   346    6.181   -1.102-10.345  1.00  29.86
ATOM    308  N    THR  A   347    4.117   -1.793-10.891  1.00  23.80
ATOM    309  CA   THR  A   347    4.436   -3.196-10.674  1.00  23.91
ATOM    310  CB   THR  A   347    3.164   -4.058-10.541  1.00  26.39
ATOM    311  OG1  THR  A   347    2.421   -3.860-11.849  1.00  24.57
ATOM    312  CG2  THR  A   347    2.301   -3.682 -9.444  1.00  23.98
ATOM    313  C    THR  A   347    5.365   -3.734-11.756  1.00  26.17
ATOM    314  O    THR  A   347    6.176   -4.622-11.496  1.00  27.44
ATOM    315  N    ASN  A   348    5.242   -3.197-12.970  1.00  25.48
ATOM    316  CA   ASN  A   348    6.092   -3.617-14.082  1.00  23.77
ATOM    317  CB   ASN  A   348    5.687   -2.926-15.385  1.00  24.59
ATOM    318  CG   ASN  A   348    6.522   -3.302-16.571  1.00  29.93
ATOM    319  OD1  ASN  A   348    7.616   -2.799-16.771  1.00  24.81
ATOM    320  ND2  ASN  A   348    6.010   -4.236-17.391  1.00  32.61
ATOM    321  C    ASN  A   348    7.532   -3.229-13.741  1.00  22.82
ATOM    322  O    ASN  A   348    8.453   -4.037-13.870  1.00  18.83
ATOM    323  N    LEU  A   349    7.711   -1.993-13.288  1.00  22.58
ATOM    324  CA   LEU  A   349    9.030   -1.507-12.914  1.00  21.85
ATOM    325  CB   LEU  A   349    8.929   -0.028-12.536  1.00  22.00
ATOM    326  CG   LEU  A   349   10.155    0.673-11.953  1.00  23.64
ATOM    327  CD1  LEU  A   349   11.224    0.826-13.017  1.00  19.35
ATOM    328  CD2  LEU  A   349    9.726    2.040-11.415  1.00  21.97
ATOM    329  C    LEU  A   349    9.564   -2.335-11.734  1.00  22.94
ATOM    330  O    LEU  A   349   10.734   -2.749-11.717  1.00  23.97
ATOM    331  N    ALA  A   350    8.705   -2.591-10.756  1.00  21.67
ATOM    332  CA   ALA  A   350    9.113   -3.356 -9.586  1.00  21.83
ATOM    333  CB   ALA  A   350    7.963   -3.441 -8.593  1.00  18.95
ATOM    334  C    ALA  A   350    9.568   -4.757 -9.985  1.00  21.90
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   335  O    ALA  A  350   10.625  -5.221  -9.554  1.00  24.15
ATOM   336  N    ASP  A  351    8.767  -5.423 -10.010  1.00  23.34
ATOM   337  CA   ASP  A  351    9.093  -6.772 -11.259  1.00  25.87
ATOM   338  CB   ASP  A  351    8.028  -7.274 -12.239  1.00  27.03
ATOM   339  CG   ASP  A  351    8.103  -8.772 -12.458  1.00  31.64
ATOM   340  OD1  ASP  A  351    8.217  -9.196 -13.628  1.00  35.06
ATOM   341  OD2  ASP  A  351    8.049  -9.525 -11.464  1.00  36.86
ATOM   342  C    ASP  A  351   10.469  -6.825 -11.912  1.00  22.36
ATOM   343  O    ASP  A  351   11.219  -7.773 -11.702  1.00  25.15
ATOM   344  N    ARG  A  352   10.810  -5.808 -12.697  1.00  23.58
ATOM   345  CA   ARG  A  352   12.115  -5.787 -13.347  1.00  21.07
ATOM   346  CB   ARG  A  352   12.120  -4.785 -14.507  1.00  21.02
ATOM   347  CG   ARG  A  352   11.539  -5.392 -15.797  1.00  20.44
ATOM   348  CD   ARG  A  352   11.554  -4.319 -16.915  1.00  20.43
ATOM   349  NE   ARG  A  352   10.592  -3.245 -16.687  1.00  19.85
ATOM   350  CZ   ARG  A  352   10.910  -1.954 -16.641  1.00  19.69
ATOM   351  NH1  ARG  A  352   12.172  -1.564 -16.813  1.00  17.36
ATOM   352  NH2  ARG  A  352    9.962  -1.049 -16.441  1.00  21.88
ATOM   353  C    ARG  A  352   13.223  -5.442 -12.350  1.00  22.11
ATOM   354  O    ARG  A  352   14.346  -5.945 -12.454  1.00  24.13
ATOM   355  N    GLU  A  353   12.909  -4.587 -11.383  1.00  18.66
ATOM   356  CA   GLU  A  353   13.888  -4.206 -10.376  1.00  19.08
ATOM   357  CB   GLU  A  353   13.317  -3.102  -9.483  1.00  21.62
ATOM   358  CG   GLU  A  353   13.295  -1.718 -10.114  1.00  20.97
ATOM   359  CD   GLU  A  353   12.832  -0.648  -9.129  1.00  23.84
ATOM   360  OE1  GLU  A  353   11.611  -0.531  -8.926  1.00  24.76
ATOM   361  OE2  GLU  A  353   13.686   0.066  -8.557  1.00  24.95
ATOM   362  C    GLU  A  353   14.246  -5.423  -9.512  1.00  20.14
ATOM   363  O    GLU  A  353   15.398  -5.600  -9.104  1.00  19.40
ATOM   364  N    LEU  A  354   13.246  -6.257  -9.235  1.00  19.54
ATOM   365  CA   LEU  A  354   13.434  -7.452  -8.415  1.00  21.77
ATOM   366  CB   LEU  A  354   12.107  -8.209  -8.270  1.00  23.09
ATOM   367  CG   LEU  A  354   11.160  -7.606  -7.223  1.00  25.00
ATOM   368  CD1  LEU  A  354    9.720  -8.013  -7.510  1.00  23.49
ATOM   369  CD2  LEU  A  354   11.584  -8.069  -5.839  1.00  23.31
ATOM   370  C    LEU  A  354   14.500  -8.386  -8.981  1.00  23.21
ATOM   371  O    LEU  A  354   15.255  -9.007  -8.234  1.00  22.44
ATOM   372  N    VAL  A  355   14.560  -8.490 -10.302  1.00  22.52
ATOM   373  CA   VAL  A  355   15.551  -9.343 -10.938  1.00  21.66
ATOM   374  CB   VAL  A  355   15.353  -9.365 -12.466  1.00  24.35
ATOM   375  CG1  VAL  A  355   16.435 -10.214 -13.119  1.00  28.16
ATOM   376  CG2  VAL  A  355   13.957  -9.886 -12.798  1.00  21.59
ATOM   377  C    VAL  A  355   16.944  -8.811 -10.606  1.00  23.74
ATOM   378  O    VAL  A  355   17.857  -9.581 -10.291  1.00  23.51
ATOM   379  N    HIS  A  356   17.105  -7.489 -10.669  1.00  21.27
ATOM   380  CA   HIS  A  356   18.392  -6.861 -10.369  1.00  21.31
ATOM   381  CB   HIS  A  356   18.384  -5.390 -10.811  1.00  19.87
ATOM   382  CG   HIS  A  356   18.494  -5.205 -12.295  1.00  21.77
ATOM   383  CD2  HIS  A  356   17.543  -5.048 -13.248  1.00  21.66
ATOM   384  ND1  HIS  A  356   19.704  -5.177 -12.955  1.00  21.11
ATOM   385  CE1  HIS  A  356   19.496  -5.011 -14.249  1.00  24.96
ATOM   386  NE2  HIS  A  356   18.192  -4.931 -14.455  1.00  18.37
ATOM   387  C    HIS  A  356   18.702  -6.947  -8.875  1.00  21.41
ATOM   388  O    HIS  A  356   19.864  -7.111  -8.465  1.00  21.88
ATOM   389  N    MET  A  357   17.660  -6.843  -8.058  1.00  21.84
ATOM   390  CA   MET  A  357   17.837  -6.906  -6.610  1.00  21.51
ATOM   391  CB   MET  A  357   16.503  -6.668  -5.898  1.00  17.60
ATOM   392  CG   MET  A  357   16.629  -6.579  -4.369  1.00  19.36
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    393  SD   MET   A  357    15.051   -6.755  -3.531  1.00  23.64
ATOM    394  CE   MET   A  357    14.189   -5.333  -4.163  1.00  25.13
ATOM    395  C    MET   A  357    18.411   -8.259  -6.192  1.00  23.69
ATOM    396  O    MET   A  357    19.337   -8.328  -5.389  1.00  24.41
ATOM    397  N    ILE   A  358    17.856   -9.331  -6.746  1.00  27.14
ATOM    398  CA   ILE   A  358    18.314  -10.672  -6.435  1.00  28.79
ATOM    399  CB   ILE   A  358    17.529  -11.725  -7.232  1.00  33.42
ATOM    400  CG2  ILE   A  358    18.267  -13.064  -7.220  1.00  32.77
ATOM    401  CG1  ILE   A  358    16.125  -11.880  -6.644  1.00  31.94
ATOM    402  CD1  ILE   A  358    15.062  -12.196  -7.680  1.00  34.85
ATOM    403  C    ILE   A  358    19.801  -10.802  -6.728  1.00  28.75
ATOM    404  O    ILE   A  358    20.569  -11.305  -5.913  1.00  31.60
ATOM    405  N    ASN   A  359    20.207  -10.325  -7.897  1.00  27.91
ATOM    406  CA   ASN   A  359    21.601  -10.401  -8.293  1.00  29.16
ATOM    407  CB   ASN   A  359    21.721  -10.172  -9.801  1.00  31.88
ATOM    408  CG   ASN   A  359    21.253  -11.381 -10.599  1.00  39.34
ATOM    409  OD1  ASN   A  359    21.916  -12.422 -10.612  1.00  41.27
ATOM    410  ND2  ASN   A  359    20.102  -11.255 -11.253  1.00  38.58
ATOM    411  C    ASN   A  359    22.476   -9.436  -7.510  1.00  30.75
ATOM    412  O    ASN   A  359    23.686   -9.629  -7.412  1.00  33.35
ATOM    413  N    TRP   A  360    21.872   -8.400  -6.940  1.00  30.07
ATOM    414  CA   TRP   A  360    22.634   -7.451  -6.132  1.00  27.87
ATOM    415  CB   TRP   A  360    21.849   -6.150  -5.948  1.00  24.80
ATOM    416  CG   TRP   A  360    22.196   -5.392  -4.691  1.00  23.04
ATOM    417  CD2  TRP   A  360    21.501   -5.443  -3.438  1.00  19.83
ATOM    418  CE2  TRP   A  360    22.147   -4.543  -2.564  1.00  22.31
ATOM    419  CE3  TRP   A  360    20.392   -6.165  -2.972  1.00  20.09
ATOM    420  CD1  TRP   A  360    23.212   -4.488  -4.529  1.00  18.99
ATOM    421  NE1  TRP   A  360    23.187   -3.974  -3.255  1.00  21.17
ATOM    422  CZ2  TRP   A  360    21.721   -4.340  -1.243  1.00  20.43
ATOM    423  CZ3  TRP   A  360    19.968   -5.965  -1.661  1.00  20.12
ATOM    424  CH2  TRP   A  360    20.635   -5.057  -0.812  1.00  18.54
ATOM    425  C    TRP   A  360    22.892   -8.099  -4.766  1.00  24.88
ATOM    426  O    TRP   A  360    23.978   -7.980  -4.198  1.00  25.00
ATOM    427  N    ALA   A  361    21.879   -8.789  -4.252  1.00  24.08
ATOM    428  CA   ALA   A  361    21.972   -9.462  -2.958  1.00  26.06
ATOM    429  CB   ALA   A  361    20.676  -10.203  -2.672  1.00  20.27
ATOM    430  C    ALA   A  361    23.161  -10.433  -2.897  1.00  28.44
ATOM    431  O    ALA   A  361    23.843  -10.531  -1.876  1.00  28.95
ATOM    432  N    LYS   A  362    23.414  -11.144  -3.992  1.00  31.41
ATOM    433  CA   LYS   A  362    24.530  -12.097  -4.047  1.00  33.33
ATOM    434  CB   LYS   A  362    24.564  -12.824  -5.390  1.00  34.81
ATOM    435  CG   LYS   A  362    23.319  -13.608  -5.756  1.00  36.27
ATOM    436  CD   LYS   A  362    23.458  -14.178  -7.167  1.00  38.30
ATOM    437  CE   LYS   A  362    22.369  -15.193  -7.472  1.00  40.94
ATOM    438  NZ   LYS   A  362    22.111  -15.322  -8.937  1.00  42.49
ATOM    439  C    LYS   A  362    25.854  -11.351  -3.893  1.00  34.17
ATOM    440  O    LYS   A  362    26.880  -11.977  -3.595  1.00  35.40
ATOM    441  N    AARG  A  363    25.826  -10.059  -4.095  0.50  34.23
ATOM    442  N    BARG  A  363    25.826  -10.059  -4.095  0.50  34.03
ATOM    443  CA   AARG  A  363    27.035   -9.254  -3.987  0.50  33.25
ATOM    444  CA   BARG  A  363    27.035   -9.254  -3.987  0.50  32.83
ATOM    445  CB   AARG  A  363    27.031   -8.153  -5.044  0.50  34.67
ATOM    446  CB   BARG  A  363    27.031   -8.153  -5.045  0.50  34.20
ATOM    447  CG   AARG  A  363    26.933   -8.654  -6.478  0.50  36.32
ATOM    448  CG   BARG  A  363    26.930   -8.654  -6.480  0.50  35.56
ATOM    449  CD   AARG  A  363    27.745   -7.775  -7.415  0.50  38.39
ATOM    450  CD   BARG  A  363    27.752   -7.781  -7.414  0.50  37.18
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    451  NE   AARG A  363    29.171   -7.793  -7.091  0.50  39.98
ATOM    452  NE   BARG A  363    27.195   -7.725  -8.762  0.50  37.39
ATOM    453  CZ   AARG A  363    30.086   -7.038  -7.692  0.50  40.54
ATOM    454  CZ   BARG A  363    27.905   -7.457  -9.855  0.50  40.02
ATOM    455  NH1  AARG A  363    29.735   -6.218  -8.675  0.50  38.13
ATOM    456  NH1  BARG A  363    29.205   -7.191  -9.761  0.50  40.42
ATOM    457  NH2  AARG A  363    31.358   -7.123  -7.326  0.50  43.19
ATOM    458  NH2  BARG A  363    27.311   -7.436 -11.041  0.50  38.91
ATOM    459  C    AARG A  363    27.207   -8.630  -2.610  0.50  33.28
ATOM    460  C    BARG A  363    27.207   -8.630  -2.610  0.50  32.81
ATOM    461  O    AARG A  363    28.223   -7.992  -3.344  0.50  34.18
ATOM    462  O    BARG A  363    28.223   -7.992  -2.365  0.50  33.43
ATOM    463  N    VAL  A  364    26.215   -8.798  -1.740  1.00  33.12
ATOM    464  CA   VAL  A  364    26.288   -8.240  -0.389  1.00  33.63
ATOM    465  CB   VAL  A  364    24.898   -8.178   0.292  1.00  34.97
ATOM    466  CG1  VAL  A  364    25.036   -7.608   1.700  1.00  35.44
ATOM    467  CG2  VAL  A  364    23.946   -7.328  -0.533  1.00  36.69
ATOM    468  C    VAL  A  364    27.184   -9.157   0.428  1.00  34.27
ATOM    469  O    VAL  A  364    26.878  -10.341   0.603  1.00  34.95
ATOM    470  N    PRO  A  365    28.306   -8.626   0.935  1.00  36.08
ATOM    471  CD   PRO  A  365    28.775   -7.235   0.793  1.00  34.84
ATOM    472  CA   PRO  A  365    29.231   -9.442   1.733  1.00  37.82
ATOM    473  CB   PRO  A  365    30.110   -8.408   2.430  1.00  34.31
ATOM    474  CG   PRO  A  365    30.127   -7.247   1.475  1.00  37.77
ATOM    475  C    PRO  A  365    28.538  -10.373   2.720  1.00  37.61
ATOM    476  O    PRO  A  365    27.692   -9.945   3.507  1.00  37.74
ATOM    477  N    GLY  A  366    28.890  -11.654   2.654  1.00  39.04
ATOM    478  CA   GLY  A  366    28.307  -12.635   3.554  1.00  38.27
ATOM    479  C    GLY  A  366    26.991  -13.264   3.138  1.00  39.32
ATOM    480  O    GLY  A  366    26.638  -14.336   3.635  1.00  39.53
ATOM    481  N    PHE  A  367    26.246  -12.615   2.236  1.00  38.60
ATOM    482  CA   PHE  A  367    24.960  -13.148   1.783  1.00  36.35
ATOM    483  CB   PHE  A  367    24.281  -12.178   0.808  1.00  32.10
ATOM    484  CG   PHE  A  367    22.827  -12.473   0.581  1.00  30.12
ATOM    485  CD1  PHE  A  367    22.401  -13.083  -0.595  1.00  28.95
ATOM    486  CD2  PHE  A  367    21.882  -12.176   1.563  1.00  26.18
ATOM    487  CE1  PHE  A  367    21.050  -13.400  -0.792  1.00  29.42
ATOM    488  CE2  PHE  A  367    20.535  -12.491   1.373  1.00  27.60
ATOM    489  CZ   PHE  A  367    20.118  -13.103   0.196  1.00  26.81
ATOM    490  C    PHE  A  367    25.072  -14.519   1.117  1.00  36.82
ATOM    491  O    PHE  A  367    24.244  -15.398   1.359  1.00  36.55
ATOM    492  N    VAL  A  368    26.088  -14.694   0.276  1.00  38.28
ATOM    493  CA   VAL  A  368    26.289  -15.965  -0.420  1.00  42.34
ATOM    494  CB   VAL  A  368    27.386  -15.850  -1.504  1.00  41.78
ATOM    495  CG1  VAL  A  368    26.972  -14.831  -2.550  1.00  44.60
ATOM    496  CG2  VAL  A  368    28.707  -15.457  -0.873  1.00  42.23
ATOM    497  C    VAL  A  368    26.664  -17.100   0.533  1.00  43.85
ATOM    498  O    VAL  A  368    26.469  -18.274   0.216  1.00  44.85
ATOM    499  N    ASP  A  369    27.199  -16.750   1.699  1.00  44.93
ATOM    500  CA   ASP  A  369    27.579  -17.755   2.688  1.00  44.96
ATOM    501  CB   ASP  A  369    28.336  -17.106   3.849  1.00  43.76
ATOM    502  CG   ASP  A  369    29.608  -16.413   3.404  1.00  43.04
ATOM    503  OD1  ASP  A  369    30.121  -15.570   4.167  1.00  44.32
ATOM    504  OD2  ASP  A  369    30.097  -16.709   2.293  1.00  46.76
ATOM    505  C    ASP  A  369    26.340  -18.465   3.228  1.00  45.89
ATOM    506  O    ASP  A  369    26.360  -19.671   3.475  1.00  48.61
ATOM    507  N    LEU  A  370    25.261  -17.714   3.407  1.00  43.59
ATOM    508  CA   LEU  A  370    24.020  -18.279   3.924  1.00  44.24
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    509  CB   LEU  A  370   22.980  -17.173   4.110  1.00  41.42
ATOM    510  CG   LEU  A  370   23.404  -16.015   5.014  1.00  41.45
ATOM    511  CD1  LEU  A  370   22.219  -15.095   5.245  1.00  42.25
ATOM    512  CD2  LEU  A  370   23.931  -16.552   6.332  1.00  38.35
ATOM    513  C    LEU  A  370   23.449  -19.360   3.013  1.00  44.03
ATOM    514  O    LEU  A  370   23.773  -19.423   1.829  1.00  43.63
ATOM    515  N    THR  A  371   22.593  -20.206   3.575  1.00  44.29
ATOM    516  CA   THR  A  371   21.968  -21.272   2.806  1.00  44.84
ATOM    517  CB   THR  A  371   21.293  -22.302   3.730  1.00  45.65
ATOM    518  OG1  THR  A  371   20.262  -21.663   4.495  1.00  46.43
ATOM    519  CG2  THR  A  371   22.314  -22.903   4.677  1.00  46.48
ATOM    520  C    THR  A  371   20.923  -20.684   1.864  1.00  44.93
ATOM    521  O    THR  A  371   20.418  -19.585   2.092  1.00  44.36
ATOM    522  N    LEU  A  372   20.607  -21.418   0.804  1.00  43.83
ATOM    523  CA   LEU  A  372   19.624  -20.971  -0.166  1.00  44.62
ATOM    524  CB   LEU  A  372   19.407  -22.043  -1.237  1.00  47.17
ATOM    525  CG   LEU  A  372   18.512  -21.690  -2.429  1.00  46.91
ATOM    526  CD1  LEU  A  372   19.005  -20.417  -3.098  1.00  48.73
ATOM    527  CD2  LEU  A  372   18.521  -22.844  -3.420  1.00  51.12
ATOM    528  C    LEU  A  372   18.307  -20.644   0.512  1.00  44.84
ATOM    529  O    LEU  A  372   17.705  -19.602   0.261  1.00  43.25
ATOM    530  N    HIS  A  373   17.849  -21.558   1.382  1.00  43.14
ATOM    531  CA   HIS  A  373   16.599  -21.353   2.100  1.00  42.23
ATOM    532  CB   HIS  A  373   16.318  -22.525   3.062  1.00  45.38
ATOM    533  CG   HIS  A  373   15.114  -22.315   3.934  1.00  51.43
ATOM    534  CD2  HIS  A  373   13.808  -22.621   3.743  1.00  54.99
ATOM    535  ND1  HIS  A  373   15.187  -21.716   5.174  1.00  54.26
ATOM    536  CE1  HIS  A  373   13.979  -21.663   5.709  1.00  53.77
ATOM    537  NE2  HIS  A  373   13.124  -22.206   4.861  1.00  55.27
ATOM    538  C    HIS  A  373   16.665  -20.047   2.885  1.00  39.78
ATOM    539  O    HIS  A  373   15.677  -19.324   2.971  1.00  37.71
ATOM    540  N    ASP  A  374   17.839  -19.738   3.440  1.00  36.38
ATOM    541  CA   ASP  A  374   18.020  -18.516   4.219  1.00  37.21
ATOM    542  CB   ASP  A  374   19.287  -18.620   5.073  1.00  38.17
ATOM    543  CG   ASP  A  374   19.064  -19.425   6.344  1.00  41.47
ATOM    544  OD1  ASP  A  374   17.896  -19.543   6.772  1.00  37.09
ATOM    545  OD2  ASP  A  374   20.052  -19.940   6.912  1.00  44.40
ATOM    546  C    ASP  A  374   18.083  -17.277   3.326  1.00  37.19
ATOM    547  O    ASP  A  374   17.598  -16.208   3.696  1.00  38.13
ATOM    548  N    GLN  A  375   18.688  -17.431   2.152  1.00  33.13
ATOM    549  CA   GLN  A  375   18.788  -16.339   1.198  1.00  31.94
ATOM    550  CB   GLN  A  375   19.634  -16.756  -0.001  1.00  28.81
ATOM    551  CG   GLN  A  375   21.125  -16.570   0.189  1.00  31.71
ATOM    552  CD   GLN  A  375   21.920  -17.222  -0.922  1.00  34.49
ATOM    553  OE1  GLN  A  375   21.478  -17.267  -2.067  1.00  36.09
ATOM    554  NE2  GLN  A  375   23.097  -17.736  -0.568  1.00  40.32
ATOM    555  C    GLN  A  375   17.379  -16.009   0.730  1.00  31.50
ATOM    556  O    GLN  A  375   16.990  -14.840   0.653  1.00  27.42
ATOM    557  N    VAL  A  376   16.617  -17.056   0.429  1.00  30.38
ATOM    558  CA   VAL  A  376   15.242  -16.907  -0.027  1.00  33.50
ATOM    559  CB   VAL  A  376   14.588  -18.286  -0.286  1.00  30.57
ATOM    560  CG1  VAL  A  376   13.093  -18.132  -0.516  1.00  33.14
ATOM    561  CG2  VAL  A  376   15.232  -18.952  -1.485  1.00  30.79
ATOM    562  C    VAL  A  376   14.393  -16.159   1.002  1.00  33.80
ATOM    563  O    VAL  A  376   13.653  -15.237   0.661  1.00  34.89
ATOM    564  N    HIS  A  377   14.500  -16.568   2.261  1.00  33.35
ATOM    565  CA   HIS  A  377   13.730  -15.941   3.329  1.00  32.81
ATOM    566  CB   HIS  A  377   13.966  -16.694   4.644  1.00  35.24
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    567  CG   HIS  A  377   13.429  -15.989   5.851  1.00  40.15
ATOM    568  CD2  HIS  A  377   14.054  -15.495   6.946  1.00  40.86
ATOM    569  ND1  HIS  A  377   12.090  -15.703   6.012  1.00  43.08
ATOM    570  CE1  HIS  A  377   11.313  -15.062   7.154  1.00  42.44
ATOM    571  NE2  HIS  A  377   13.089  -14.922   7.740  1.00  44.85
ATOM    572  C    HIS  A  377   14.058  -14.454   3.507  1.00  28.63
ATOM    573  O    HIS  A  377   13.158  -13.619   3.613  1.00  39.20
ATOM    574  N    LEU  A  378   15.343  -14.125   3.544  1.00  24.41
ATOM    575  CA   LEU  A  378   15.759  -12.738   3.721  1.00  23.21
ATOM    576  CB   LEU  A  378   17.289  -12.650   3.743  1.00  20.98
ATOM    577  CG   LEU  A  378   17.960  -13.190   5.016  1.00  24.22
ATOM    578  CD1  LEU  A  378   19.471  -13.041   4.924  1.00  21.07
ATOM    579  CD2  LEU  A  378   17.431  -12.446   6.221  1.00  20.24
ATOM    580  C    LEU  A  378   15.190  -11.827   2.630  1.00  24.78
ATOM    581  O    LEU  A  378   14.638  -10.766   2.923  1.00  22.09
ATOM    582  N    LEU  A  379   15.321  -12.242   1.374  1.00  24.13
ATOM    583  CA   LEU  A  379   14.812  -11.447   0.262  1.00  25.02
ATOM    584  CB   LEU  A  379   15.307  -12.025  -1.062  1.00  27.12
ATOM    585  CG   LEU  A  379   16.724  -11.600  -1.437  1.00  24.39
ATOM    586  CD1  LEU  A  379   17.299  -12.557  -2.470  1.00  27.58
ATOM    587  CD2  LEU  A  379   16.679  -10.178  -1.983  1.00  29.05
ATOM    588  C    LEU  A  379   13.287  -11.355   0.246  1.00  27.61
ATOM    589  O    LEU  A  379   12.726  -10.301  -0.062  1.00  26.16
ATOM    590  N    GLU  A  380   12.616  -12.454   0.576  1.00  25.65
ATOM    591  CA   GLU  A  380   11.154  -12.471   0.592  1.00  26.85
ATOM    592  CB   GLU  A  380   10.640  -13.882   0.871  1.00  29.38
ATOM    593  CG   GLU  A  380   10.718  -14.796  -0.331  1.00  35.58
ATOM    594  CD   GLU  A  380   10.228  -16.194  -0.025  1.00  39.31
ATOM    595  OE1  GLU  A  380   10.142  -17.008  -0.967  1.00  42.89
ATOM    596  OE2  GLU  A  380    9.927  -16.478   1.153  1.00  39.45
ATOM    597  C    GLU  A  380   10.604  -11.526   1.649  1.00  25.43
ATOM    598  O    GLU  A  380    9.551  -10.925   1.469  1.00  27.75
ATOM    599  N    CYS  A  381   11.324  -11.400   2.753  1.00  25.57
ATOM    600  CA   CYS  A  381   10.907  -10.530   3.843  1.00  26.46
ATOM    601  CB   CYS  A  381   11.570  -11.000   5.149  1.00  31.46
ATOM    602  SG   CYS  A  381   11.305   -9.946   6.623  1.00  45.32
ATOM    603  C    CYS  A  381   11.262   -9.059   3.589  1.00  24.77
ATOM    604  O    CYS  A  381   10.516   -8.166   3.975  1.00  25.01
ATOM    605  N    ALA  A  382   12.377   -8.815   2.903  1.00  22.23
ATOM    606  CA   ALA  A  382   12.855   -7.449   2.681  1.00  21.83
ATOM    607  CB   ALA  A  382   14.319   -7.383   3.095  1.00  21.56
ATOM    608  C    ALA  A  382   12.705   -6.778   1.311  1.00  19.78
ATOM    609  O    ALA  A  382   12.996   -5.587   1.182  1.00  17.01
ATOM    610  N    TRP  A  383   12.261   -7.507   0.294  1.00  17.61
ATOM    611  CA   TRP  A  383   12.164   -6.915  -1.036  1.00  18.06
ATOM    612  CB   TRP  A  383   11.580   -7.928  -2.035  1.00  20.28
ATOM    613  CG   TRP  A  383   10.105   -8.201  -1.919  1.00  20.50
ATOM    614  CD2  TRP  A  383    9.049   -7.509  -2.599  1.00  22.48
ATOM    615  CE2  TRP  A  383    7.836   -8.138  -2.238  1.00  20.41
ATOM    616  CE3  TRP  A  383    9.012   -6.420  -3.482  1.00  23.06
ATOM    617  CD1  TRP  A  383    9.506   -9.189  -1.190  1.00  23.38
ATOM    618  NE1  TRP  A  383    8.142   -9.159  -1.377  1.00  22.59
ATOM    619  CZ2  TRP  A  383    6.598   -7.713  -2.724  1.00  21.98
ATOM    620  CZ3  TRP  A  383    7.780   -5.998  -3.968  1.00  25.50
ATOM    621  CH2  TRP  A  383    6.589   -6.647  -3.587  1.00  23.11
ATOM    622  C    TRP  A  383   11.448   -5.564  -1.170  1.00  19.18
ATOM    623  O    TRP  A  383   11.972   -4.663  -1.824  1.00  19.27
ATOM    624  N    LEU  A  384   10.273   -5.396  -0.567  1.00  18.32
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   625  CA   LEU  A  384   9.586  -4.118  -0.719  1.00  16.38
ATOM   626  CB   LEU  A  384   8.125  -4.218  -0.258  1.00  16.79
ATOM   627  CG   LEU  A  384   7.211  -3.013  -0.577  1.00  18.39
ATOM   628  CD1  LEU  A  384   7.464  -2.485  -1.995  1.00  13.91
ATOM   629  CD2  LEU  A  384   5.750  -3.432  -0.410  1.00  16.38
ATOM   630  C    LEU  A  384  10.324  -3.027   0.051  1.00  18.80
ATOM   631  O    LEU  A  384  10.334  -1.870  -0.357  1.00  20.90
ATOM   632  N    GLU  A  385  10.949  -3.404   1.163  1.00  18.61
ATOM   633  CA   GLU  A  385  11.718  -2.482   1.970  1.00  19.58
ATOM   634  CB   GLU  A  385  12.274  -3.154   3.213  1.00  17.43
ATOM   635  CG   GLU  A  385  11.292  -3.237   4.357  1.00  22.92
ATOM   636  CD   GLU  A  385  11.963  -3.676   5.640  1.00  25.83
ATOM   637  OE1  GLU  A  385  12.431  -2.799   6.391  1.00  23.69
ATOM   638  OE2  GLU  A  385  12.027  -4.897   5.889  1.00  27.64
ATOM   639  C    GLU  A  385  12.890  -1.934   1.156  1.00  19.46
ATOM   640  O    GLU  A  385  13.206  -0.743   1.196  1.00  15.04
ATOM   641  N    ILE  A  386  13.539  -2.842   0.431  1.00  13.32
ATOM   642  CA   ILE  A  386  14.685  -2.484  -0.388  1.00  15.01
ATOM   643  CB   ILE  A  386  15.475  -3.763  -0.807  1.00  17.43
ATOM   644  CG2  ILE  A  386  16.544  -3.424  -1.849  1.00  17.99
ATOM   645  CG1  ILE  A  386  16.185  -4.338   0.432  1.00  20.31
ATOM   646  CD1  ILE  A  386  16.682  -5.766   0.284  1.00  23.97
ATOM   647  C    ILE  A  386  14.273  -1.648  -1.598  1.00  16.10
ATOM   648  O    ILE  A  386  14.993  -0.724  -2.004  1.00  17.42
ATOM   649  N    LEU  A  387  13.112  -1.944  -2.167  1.00  17.61
ATOM   650  CA   LEU  A  387  12.620  -1.173  -3.304  1.00  18.20
ATOM   651  CB   LEU  A  387  11.359  -1.814  -3.882  1.00  17.51
ATOM   652  CG   LEU  A  387  11.519  -3.064  -4.747  1.00  26.37
ATOM   653  CD1  LEU  A  387  10.173  -3.406  -5.395  1.00  24.63
ATOM   654  CD2  LEU  A  387  12.589  -2.824  -5.808  1.00  21.58
ATOM   655  C    LEU  A  387  12.283   0.249  -2.838  1.00  17.60
ATOM   656  O    LEU  A  387  12.571   1.224  -3.530  1.00  17.15
ATOM   657  N    MET  A  388  11.677   0.357  -1.660  1.00  17.65
ATOM   658  CA   MET  A  388  11.286   1.656  -1.121  1.00  18.49
ATOM   659  CB   MET  A  388  10.302   1.460   0.034  1.00  19.65
ATOM   660  CG   MET  A  388   8.893   1.105  -0.435  1.00  15.12
ATOM   661  SD   MET  A  388   7.744   0.769   0.910  1.00  18.73
ATOM   662  CE   MET  A  388   6.163   0.908   0.048  1.00  18.34
ATOM   663  C    MET  A  388  12.451   2.553  -0.691  1.00  22.62
ATOM   664  O    MET  A  388  12.417   3.767  -0.928  1.00  22.49
ATOM   665  N    ILE  A  389  13.482   1.988  -0.064  1.00  21.45
ATOM   666  CA   ILE  A  389  14.604   2.831   0.331  1.00  18.54
ATOM   667  CB   ILE  A  389  15.590   2.108   1.299  1.00  19.35
ATOM   668  CG2  ILE  A  389  16.362   0.998   0.578  1.00  15.50
ATOM   669  CG1  ILE  A  389  16.556   3.142   1.889  1.00  21.95
ATOM   670  CD1  ILE  A  389  17.373   2.658   3.080  1.00  15.86
ATOM   671  C    ILE  A  389  15.333   3.322  -0.922  1.00  18.67
ATOM   672  O    ILE  A  389  15.813   4.453  -0.970  1.00  19.75
ATOM   673  N    GLY  A  390  15.410   2.477  -1.943  1.00  20.58
ATOM   674  CA   GLY  A  390  16.049   2.895  -3.183  1.00  19.33
ATOM   675  C    GLY  A  390  15.243   4.021  -3.819  1.00  17.48
ATOM   676  O    GLY  A  390  15.801   4.994  -4.318  1.00  21.87
ATOM   677  N    LEU  A  391  13.920   3.888  -3.787  1.00  19.17
ATOM   678  CA   LEU  A  391  13.018   4.887  -4.343  1.00  21.50
ATOM   679  CB   LEU  A  391  11.561   4.420  -4.194  1.00  18.25
ATOM   680  CG   LEU  A  391  10.480   5.497  -4.342  1.00  21.98
ATOM   681  CD1  LEU  A  391  10.579   6.156  -5.725  1.00  21.39
ATOM   682  CD2  LEU  A  391   9.115   4.868  -4.148  1.00  17.15
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    683   C     LEU   A   391    13.208    6.216   -3.620   1.00   23.27
ATOM    684   O     LEU   A   391    13.440    7.255   -4.243   1.00   23.60
ATOM    685   N     VAL   A   392    13.123    6.170   -2.395   1.00   23.04
ATOM    686   CA    VAL   A   392    13.282    7.357   -1.469   1.00   24.42
ATOM    687   CB    VAL   A   392    13.186    6.993    0.042   1.00   27.38
ATOM    688   CG1   VAL   A   392    13.733    8.129    0.897   1.00   30.37
ATOM    689   CG2   VAL   A   392    11.739    6.712    0.414   1.00   23.48
ATOM    690   C     VAL   A   392    14.626    8.014   -1.784   1.00   27.55
ATOM    691   O     VAL   A   392    14.728    9.242   -1.832   1.00   27.50
ATOM    692   N     TRP   A   393    15.652    7.186   -1.924   1.00   23.65
ATOM    693   CA    TRP   A   393    16.999    7.670   -2.204   1.00   24.76
ATOM    694   CB    TRP   A   393    17.977    6.491   -2.199   1.00   22.86
ATOM    695   CG    TRP   A   393    19.287    6.784   -2.857   1.00   25.90
ATOM    696   CD2   TRP   A   393    20.341    7.605   -2.339   1.00   29.09
ATOM    697   CE2   TRP   A   393    21.375    7.612   -3.302   1.00   29.94
ATOM    698   CE3   TRP   A   393    20.512    8.335   -1.154   1.00   30.20
ATOM    699   CD1   TRP   A   393    19.710    6.339   -4.077   1.00   26.58
ATOM    700   NE1   TRP   A   393    20.963    6.833   -4.351   1.00   30.64
ATOM    701   CZ2   TRP   A   393    22.566    8.323   -3.120   1.00   32.43
ATOM    702   CZ3   TRP   A   393    21.698    9.044   -0.971   1.00   34.58
ATOM    703   CH2   TRP   A   393    22.709    9.030   -1.950   1.00   36.54
ATOM    704   C     TRP   A   393    17.082    8.414   -3.547   1.00   25.02
ATOM    705   O     TRP   A   393    17.767    9.435   -3.650   1.00   20.97
ATOM    706   N     ARG   A   394    16.399    7.897   -4.568   1.00   23.06
ATOM    707   CA    ARG   A   394    16.412    8.531   -5.890   1.00   25.97
ATOM    708   CB    ARG   A   394    15.776    7.633   -6.965   1.00   24.05
ATOM    709   CG    ARG   A   394    16.243    6.195   -7.024   1.00   26.05
ATOM    710   CD    ARG   A   394    15.830    5.551   -8.352   1.00   22.70
ATOM    711   NE    ARG   A   394    14.443    5.071   -8.363   1.00   20.71
ATOM    712   CZ    ARG   A   394    14.053    3.912   -7.841   1.00   21.26
ATOM    713   NH1   ARG   A   394    14.944    3.108   -7.267   1.00   20.09
ATOM    714   NH2   ARG   A   394    12.783    3.544   -7.907   1.00   21.26
ATOM    715   C     ARG   A   394    15.622    9.833   -5.879   1.00   23.40
ATOM    716   O     ARG   A   394    15.889   10.729   -6.677   1.00   28.61
ATOM    717   N     SER   A   395    14.638    9.924   -4.988   1.00   26.65
ATOM    718   CA    SER   A   395    13.776   11.104   -4.902   1.00   27.46
ATOM    719   CB    SER   A   395    12.395   10.696   -4.382   1.00   26.70
ATOM    720   OG    SER   A   395    11.916    9.530   -5.029   1.00   22.95
ATOM    721   C     SER   A   395    14.316   12.240   -4.033   1.00   31.45
ATOM    722   O     SER   A   395    13.726   13.324   -3.977   1.00   28.11
ATOM    723   N     MET   A   396    15.437   11.986   -3.368   1.00   33.83
ATOM    724   CA    MET   A   396    16.061   12.964   -2.475   1.00   38.83
ATOM    725   CB    MET   A   396    17.466   12.483   -2.112   1.00   39.47
ATOM    726   CG    MET   A   396    17.585   11.919   -0.715   1.00   41.37
ATOM    727   SD    MET   A   396    19.192   12.262    0.004   1.00   42.20
ATOM    728   CE    MET   A   396    20.263   11.996   -1.404   1.00   42.84
ATOM    729   C     MET   A   396    16.143   14.376   -3.018   1.00   40.69
ATOM    730   O     MET   A   396    15.637   15.316   -2.403   1.00   38.85
ATOM    731   N     GLU   A   397    16.794   14.526   -4.166   1.00   42.19
ATOM    732   CA    GLU   A   397    16.971   15.831   -4.790   1.00   44.80
ATOM    733   CB    GLU   A   397    18.184   15.785   -5.729   1.00   46.02
ATOM    734   CG    GLU   A   397    17.883   15.189   -7.096   1.00   54.42
ATOM    735   CD    GLU   A   397    19.117   14.665   -7.810   1.00   59.40
ATOM    736   OE1   GLU   A   397    19.219   13.430   -7.990   1.00   60.63
ATOM    737   OE2   GLU   A   397    19.980   15.485   -8.196   1.00   62.71
ATOM    738   C     GLU   A   397    15.735   16.322   -5.554   1.00   42.94
ATOM    739   O     GLU   A   397    15.830   17.229   -6.376   1.00   44.68
ATOM    740   N     HIS   A   398    14.579   15.728   -5.280   1.00   40.82
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    741  CA   HIS  A  398    13.342  16.118  -5.950  1.00  39.31
ATOM    742  CB   HIS  A  398    12.924  15.043  -6.956  1.00  39.85
ATOM    743  CG   HIS  A  398    13.870  14.886  -8.104  1.00  41.57
ATOM    744  CD2  HIS  A  398    13.904  15.484  -9.318  1.00  39.28
ATOM    745  ND1  HIS  A  398    14.940  14.017  -8.074  1.00  41.85
ATOM    746  CE1  HIS  A  398    15.592  14.086  -9.220  1.00  40.88
ATOM    747  NE2  HIS  A  398    14.985  14.969  -9.993  1.00  42.30
ATOM    748  C    HIS  A  398    12.216  16.332  -4.944  1.00  37.04
ATOM    749  O    HIS  A  398    11.282  15.535  -4.864  1.00  36.51
ATOM    750  N    PRO  A  399    12.283  17.427  -4.171  1.00  39.19
ATOM    751  CD   PRO  A  399    13.328  18.467  -4.198  1.00  35.36
ATOM    752  CA   PRO  A  399    11.243  17.709  -3.173  1.00  37.10
ATOM    753  CB   PRO  A  399    11.603  19.101  -2.694  1.00  37.86
ATOM    754  CG   PRO  A  399    13.050  19.267  -2.963  1.00  35.83
ATOM    755  C    PRO  A  399     9.828  17.663  -3.744  1.00  37.02
ATOM    756  O    PRO  A  399     9.554  18.249  -4.789  1.00  38.52
ATOM    757  N    GLY  A  400     8.938  16.954  -3.057  1.00  33.58
ATOM    758  CA   GLY  A  400     7.559  16.865  -3.503  1.00  32.12
ATOM    759  C    GLY  A  400     7.230  15.706  -4.428  1.00  32.43
ATOM    760  O    GLY  A  400     6.063  15.344  -4.574  1.00  33.31
ATOM    761  N    LYS  A  401     8.237  15.112  -5.055  1.00  31.35
ATOM    762  CA   LYS  A  401     7.972  14.007  -5.966  1.00  30.75
ATOM    763  CB   LYS  A  401     8.235  14.430  -7.415  1.00  35.43
ATOM    764  CG   LYS  A  401     8.130  15.927  -7.675  1.00  35.15
ATOM    765  CD   LYS  A  401     9.096  16.353  -8.774  1.00  36.88
ATOM    766  CE   LYS  A  401     8.733  17.721  -9.331  1.00  36.71
ATOM    767  NZ   LYS  A  401     7.295  18.027  -9.116  1.00  34.22
ATOM    768  C    LYS  A  401     8.768  12.746  -5.677  1.00  30.97
ATOM    769  O    LYS  A  401     9.809  12.776  -5.006  1.00  27.60
ATOM    770  N    LEU  A  402     8.256  11.635  -6.197  1.00  27.28
ATOM    771  CA   LEU  A  402     8.889  10.334  -6.050  1.00  29.07
ATOM    772  CB   LEU  A  402     7.866   9.294  -5.590  1.00  22.55
ATOM    773  CG   LEU  A  402     7.265   9.555  -4.207  1.00  24.94
ATOM    774  CD1  LEU  A  402     6.126   8.583  -3.937  1.00  19.32
ATOM    775  CD2  LEU  A  402     8.355   9.416  -3.157  1.00  21.54
ATOM    776  C    LEU  A  402     9.448   9.948  -7.414  1.00  28.78
ATOM    777  O    LEU  A  402     8.704   9.836  -8.389  1.00  29.98
ATOM    778  N    LEU  A  403    10.761   9.770  -7.487  1.00  27.57
ATOM    779  CA   LEU  A  403    11.393   9.400  -8.744  1.00  27.17
ATOM    780  CB   LEU  A  403    12.825   9.937  -8.816  1.00  26.95
ATOM    781  CG   LEU  A  403    13.401  10.027 -10.238  1.00  30.42
ATOM    782  CD1  LEU  A  403    14.519  11.046 -10.288  1.00  30.76
ATOM    783  CD2  LEU  A  403    13.915   8.665 -10.676  1.00  33.11
ATOM    784  C    LEU  A  403    11.419   7.891  -8.901  1.00  24.78
ATOM    785  O    LEU  A  403    12.428   7.257  -8.619  1.00  24.68
ATOM    786  N    PHE  A  404    10.306   7.319  -9.344  1.00  23.11
ATOM    787  CA   PHE  A  404    10.239   5.881  -9.546  1.00  26.93
ATOM    788  CB   PHE  A  404     8.826   5.470  -9.946  1.00  27.04
ATOM    789  CG   PHE  A  404     7.850   5.513  -8.816  1.00  27.89
ATOM    790  CD1  PHE  A  404     7.028   6.623  -8.631  1.00  26.20
ATOM    791  CD2  PHE  A  404     7.750   4.444  -7.925  1.00  23.10
ATOM    792  CE1  PHE  A  404     6.116   6.668  -7.573  1.00  25.29
ATOM    793  CE2  PHE  A  404     6.845   4.481  -6.870  1.00  21.01
ATOM    794  CZ   PHE  A  404     6.026   5.595  -6.693  1.00  22.91
ATOM    795  C    PHE  A  404    11.232   5.507 -10.637  1.00  26.04
ATOM    796  O    PHE  A  404    11.882   4.464 -10.578  1.00  27.27
ATOM    797  N    ALA  A  405    11.348   6.383 -11.626  1.00  28.80
ATOM    798  CA   ALA  A  405    12.271   6.195 -12.740  1.00  29.21
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   799  CB   ALA  A  405   11.650   5.287-13.806  1.00  26.89
ATOM   800  C    ALA  A  405   12.549   7.578-13.317  1.00  30.23
ATOM   801  O    ALA  A  405   11.770   8.508-13.109  1.00  27.38
ATOM   802  N    PRO  A  406   13.672   7.737-14.032  1.00  30.05
ATOM   803  CD   PRO  A  406   14.712   6.745-14.352  1.00  26.31
ATOM   804  CA   PRO  A  406   13.977   9.053-14.604  1.00  32.10
ATOM   805  CB   PRO  A  406   15.232   8.800-15.438  1.00  31.28
ATOM   806  CG   PRO  A  406   15.865   7.602-14.776  1.00  31.44
ATOM   807  C    PRO  A  406   12.820   9.589-15.436  1.00  33.58
ATOM   808  O    PRO  A  406   12.605  10.796-15.507  1.00  32.58
ATOM   809  N    ASN  A  407   12.063   8.690-16.053  1.00  32.86
ATOM   810  CA   ASN  A  407   10.935   9.119-16.865  1.00  32.78
ATOM   811  CB   ASN  A  407   10.950   8.418-18.228  1.00  34.73
ATOM   812  CG   ASN  A  407   10.884   6.907-18.121  1.00  35.37
ATOM   813  OD1  ASN  A  407   11.189   6.317-17.077  1.00  30.24
ATOM   814  ND2  ASN  A  407   10.486   6.268-19.215  1.00  34.08
ATOM   815  C    ASN  A  407    9.605   8.901-16.166  1.00  34.90
ATOM   816  O    ASN  A  407    8.549   8.897-16.798  1.00  36.09
ATOM   817  N    LEU  A  408    9.660   8.724-14.851  1.00  33.56
ATOM   818  CA   LEU  A  408    8.452   8.544-14.061  1.00  35.89
ATOM   819  CB   LEU  A  408    8.141   7.062-13.851  1.00  33.81
ATOM   820  CG   LEU  A  408    6.696   6.823-13.397  1.00  36.44
ATOM   821  CD1  LEU  A  408    5.746   7.479-14.390  1.00  34.14
ATOM   822  CD2  LEU  A  408    6.406   5.334-13.287  1.00  32.96
ATOM   823  C    LEU  A  408    8.607   9.245-12.717  1.00  38.03
ATOM   824  O    LEU  A  408    8.880   8.614-11.695  1.00  36.38
ATOM   825  N    LEU  A  409    8.441  10.563-12.741  1.00  37.87
ATOM   826  CA   LEU  A  409    8.548  11.395-11.553  1.00  37.95
ATOM   827  CB   LEU  A  409    9.373  12.636-11.877  1.00  39.52
ATOM   828  CG   LEU  A  409   10.023  13.399-10.728  1.00  42.46
ATOM   829  CD1  LEU  A  409   11.100  12.547-10.082  1.00  43.24
ATOM   830  CD2  LEU  A  409   10.614  14.691-11.266  1.00  46.05
ATOM   831  C    LEU  A  409    7.132  11.792-11.163  1.00  37.13
ATOM   832  O    LEU  A  409    6.482  12.546-11.882  1.00  35.70
ATOM   833  N    LEU  A  410    6.654  11.284-10.030  1.00  35.29
ATOM   834  CA   LEU  A  410    5.297  11.576 -9.583  1.00  33.33
ATOM   835  CB   LEU  A  410    4.503  10.277 -9.449  1.00  29.37
ATOM   836  CG   LEU  A  410    4.645   9.238-10.560  1.00  32.75
ATOM   837  CD1  LEU  A  410    4.026   7.925-10.104  1.00  29.16
ATOM   838  CD2  LEU  A  410    3.958   9.744-11.819  1.00  30.70
ATOM   839  C    LEU  A  410    5.207  12.332 -8.261  1.00  35.14
ATOM   840  O    LEU  A  410    6.078  12.214 -7.400  1.00  36.94
ATOM   841  N    ASP  A  411    4.141  13.108 -8.105  1.00  34.76
ATOM   842  CA   ASP  A  411    3.933  13.843 -6.873  1.00  35.40
ATOM   843  CB   ASP  A  411    3.733  15.341 -7.144  1.00  40.02
ATOM   844  CG   ASP  A  411    2.471  15.645 -7.928  1.00  41.32
ATOM   845  OD1  ASP  A  411    1.570  14.785 -8.001  1.00  45.03
ATOM   846  OD2  ASP  A  411    2.383  16.764 -8.474  1.00  45.01
ATOM   847  C    ASP  A  411    2.727  13.234 -6.179  1.00  36.10
ATOM   848  O    ASP  A  411    2.033  12.395 -6.762  1.00  34.08
ATOM   849  N    ARG  A  412    2.480  13.647 -4.940  1.00  35.99
ATOM   850  CA   ARG  A  412    1.375  13.099 -4.169  1.00  39.37
ATOM   851  CB   ARG  A  412    1.260  13.824 -2.825  1.00  39.75
ATOM   852  CG   ARG  A  412    0.562  15.168 -2.870  1.00  40.49
ATOM   853  CD   ARG  A  412    0.454  15.736 -1.465  1.00  40.65
ATOM   854  NE   ARG  A  412   -0.261  14.826 -0.577  1.00  37.48
ATOM   855  CZ   ARG  A  412   -1.574  14.855 -0.384  1.00  42.84
ATOM   856  NH1  ARG  A  412   -2.316  15.754 -1.024  1.00  40.82
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    857   NH2   ARG   A   412    -2.150   13.986   0.438   1.00   38.32
ATOM    858   C     ARG   A   412     0.034   13.108  -6.889   1.00   39.80
ATOM    859   O     ARG   A   412    -0.775   12.201  -4.706   1.00   39.92
ATOM    860   N     ASN   A   413    -0.198   14.119  -5.717   1.00   41.64
ATOM    861   CA    ASN   A   413    -1.458   14.215  -6.440   1.00   43.19
ATOM    862   CB    ASN   A   413    -1.518   15.533  -7.210   1.00   46.44
ATOM    863   CG    ASN   A   413    -1.739   16.718  -6.299   1.00   47.86
ATOM    864   OD1   ASN   A   413    -2.376   16.594  -5.249   1.00   48.05
ATOM    865   ND2   ASN   A   413    -1.213   17.876  -6.687   1.00   49.43
ATOM    866   C     ASN   A   413    -1.673   13.044  -7.385   1.00   41.48
ATOM    867   O     ASN   A   413    -2.792   12.567  -7.546   1.00   40.50
ATOM    868   N     GLN   A   414    -0.600   12.577  -8.010   1.00   42.82
ATOM    869   CA    GLN   A   414    -0.703   11.448  -8.925   1.00   44.73
ATOM    870   CB    GLN   A   414     0.585   11.307  -9.741   1.00   47.52
ATOM    871   CG    GLN   A   414     0.572   12.088 -11.049   1.00   50.47
ATOM    872   CD    GLN   A   414     1.914   12.713 -11.375   1.00   53.91
ATOM    873   OE1   GLN   A   414     2.591   13.257 -10.501   1.00   53.68
ATOM    874   NE2   GLN   A   414     2.309   12.637 -12.641   1.00   56.91
ATOM    875   C     GLN   A   414    -0.970   10.163  -8.141   1.00   43.21
ATOM    876   O     GLN   A   414    -1.491    9.193  -8.682   1.00   42.33
ATOM    877   N     GLY   A   415    -0.618   10.168  -6.860   1.00   41.97
ATOM    878   CA    GLY   A   415    -0.836    8.992  -6.040   1.00   40.43
ATOM    879   C     GLY   A   415    -2.306    8.720  -5.804   1.00   40.80
ATOM    880   O     GLY   A   415    -2.696    7.601  -5.472   1.00   37.83
ATOM    881   N     LYS   A   416    -3.129    9.748  -5.978   1.00   42.16
ATOM    882   CA    LYS   A   416    -4.566    9.613  -5.779   1.00   44.34
ATOM    883   CB    LYS   A   416    -5.212   10.996  -5.704   1.00   45.65
ATOM    884   CG    LYS   A   416    -4.761   11.819  -4.510   1.00   47.42
ATOM    885   CD    LYS   A   416    -4.910   13.309  -4.777   1.00   50.97
ATOM    886   CE    LYS   A   416    -5.992   13.924  -3.898   1.00   53.25
ATOM    887   NZ    LYS   A   416    -5.416   14.766  -2.809   1.00   56.95
ATOM    888   C     LYS   A   416    -5.227    8.793  -6.886   1.00   45.33
ATOM    889   O     LYS   A   416    -6.339    8.299  -6.714   1.00   46.50
ATOM    890   N     CYS   A   417    -4.540    8.648  -8.015   1.00   45.18
ATOM    891   CA    CYS   A   417    -5.066    7.890  -9.148   1.00   46.25
ATOM    892   CB    CYS   A   417    -4.062    7.902 -10.305   1.00   49.29
ATOM    893   SG    CYS   A   417    -3.916    9.493 -11.168   1.00   49.55
ATOM    894   C     CYS   A   417    -5.373    6.452  -8.752   1.00   47.18
ATOM    895   O     CYS   A   417    -6.220    5.794  -9.359   1.00   46.50
ATOM    896   N     VAL   A   418    -4.671    5.968  -7.731   1.00   45.07
ATOM    897   CA    VAL   A   418    -4.866    4.612  -7.232   1.00   42.75
ATOM    898   CB    VAL   A   418    -3.525    3.841  -7.206   1.00   42.45
ATOM    899   CG1   VAL   A   418    -3.670    2.563  -6.410   1.00   40.22
ATOM    900   CG2   VAL   A   418    -3.071    3.538  -8.634   1.00   38.03
ATOM    901   C     VAL   A   418    -5.441    4.714  -5.818   1.00   41.46
ATOM    902   O     VAL   A   418    -4.883    5.400  -4.963   1.00   42.08
ATOM    903   N     GLU   A   419    -6.559    4.036  -5.579   1.00   40.95
ATOM    904   CA    GLU   A   419    -7.223    4.073  -4.275   1.00   42.51
ATOM    905   CB    GLU   A   419    -8.536    3.282  -4.333   1.00   44.52
ATOM    906   CG    GLU   A   419    -9.010    2.751  -2.984   1.00   50.42
ATOM    907   CD    GLU   A   419   -10.413    2.168  -3.035   1.00   54.38
ATOM    908   OE1   GLU   A   419   -10.582    1.059  -3.590   1.00   54.09
ATOM    909   OE2   GLU   A   419   -11.347    2.820  -2.516   1.00   57.90
ATOM    910   C     GLU   A   419    -6.370    3.552  -3.131   1.00   41.11
ATOM    911   O     GLU   A   419    -5.955    2.393  -3.116   1.00   39.42
ATOM    912   N     GLY   A   420    -6.129    4.419  -2.140   1.00   40.53
ATOM    913   CA    GLY   A   420    -5.346    4.049  -0.973   1.00   37.61
ATOM    914   C     GLY   A   420    -3.854    4.258  -1.140   1.00   37.01
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    915  O    GLY  A  420   -3.088   4.105  -0.190  1.00  32.59
ATOM    916  N    MET  A  421   -3.444   4.623  -2.380  1.00  36.31
ATOM    917  CA   MET  A  421   -2.035   4.825  -2.656  1.00  36.02
ATOM    918  CB   MET  A  421   -1.799   4.607  -4.160  1.00  33.84
ATOM    919  CG   MET  A  421   -0.351   4.754  -4.617  1.00  35.82
ATOM    920  SD   MET  A  421    0.806   3.611  -3.812  1.00  35.57
ATOM    921  CE   MET  A  421    0.881   2.394  -5.005  1.00  32.51
ATOM    922  C    MET  A  421   -1.474   6.180  -2.226  1.00  34.93
ATOM    923  O    MET  A  421   -0.275   6.294  -1.985  1.00  35.17
ATOM    924  N    VAL  A  422   -2.319   7.205  -2.118  1.00  33.97
ATOM    925  CA   VAL  A  422   -1.823   8.520  -1.708  1.00  31.29
ATOM    926  CB   VAL  A  422   -2.927   9.607  -1.766  1.00  33.14
ATOM    927  CG1  VAL  A  422   -3.823   9.535  -0.533  1.00  30.10
ATOM    928  CG2  VAL  A  422   -2.279  10.982  -1.854  1.00  30.08
ATOM    929  C    VAL  A  422   -1.231   8.498  -0.296  1.00  32.64
ATOM    930  O    VAL  A  422   -0.274   9.220   0.002  1.00  28.41
ATOM    931  N    GLU  A  423   -1.803   7.670   0.571  1.00  31.53
ATOM    932  CA   GLU  A  423   -1.311   7.558   1.935  1.00  35.99
ATOM    933  CB   GLU  A  423   -2.190   6.594   2.737  1.00  40.37
ATOM    934  CG   GLU  A  423   -3.588   7.129   3.043  1.00  49.41
ATOM    935  CD   GLU  A  423   -4.438   7.336   1.795  1.00  52.38
ATOM    936  OE1  GLU  A  423   -5.349   8.188   1.835  1.00  56.91
ATOM    937  OE2  GLU  A  423   -4.200   6.652   0.776  1.00  54.53
ATOM    938  C    GLU  A  423    0.127   7.043   1.886  1.00  34.83
ATOM    939  O    GLU  A  423    1.007   7.552   2.581  1.00  31.85
ATOM    940  N    ILE  A  424    0.369   6.038   1.050  1.00  30.17
ATOM    941  CA   ILE  A  424    1.711   5.488   0.929  1.00  28.99
ATOM    942  CB   ILE  A  424    1.696   4.195   0.109  1.00  30.96
ATOM    943  CG2  ILE  A  424    3.108   3.588   0.068  1.00  27.20
ATOM    944  CG1  ILE  A  424    0.671   3.230   0.725  1.00  30.77
ATOM    945  CD1  ILE  A  424    0.810   1.787   0.291  1.00  34.69
ATOM    946  C    ILE  A  424    2.700   6.483   0.312  1.00  28.21
ATOM    947  O    ILE  A  424    3.856   6.551   0.735  1.00  28.48
ATOM    948  N    PHE  A  425    2.253   7.260  -0.675  1.00  27.68
ATOM    949  CA   PHE  A  425    3.119   8.253  -1.315  1.00  27.30
ATOM    950  CB   PHE  A  425    2.381   8.958  -2.458  1.00  26.36
ATOM    951  CG   PHE  A  425    2.538   8.289  -3.798  1.00  27.22
ATOM    952  CD1  PHE  A  425    2.619   9.050  -4.958  1.00  27.36
ATOM    953  CD2  PHE  A  425    2.566   6.900  -3.905  1.00  27.89
ATOM    954  CE1  PHE  A  425    2.721   8.443  -6.207  1.00  29.63
ATOM    955  CE2  PHE  A  425    2.668   6.282  -5.149  1.00  27.28
ATOM    956  CZ   PHE  A  425    2.745   7.056  -6.303  1.00  27.63
ATOM    957  C    PHE  A  425    3.591   9.306  -0.312  1.00  25.66
ATOM    958  O    PHE  A  425    4.757   9.713  -0.328  1.00  26.33
ATOM    959  N    ASP  A  426    2.680   9.746   0.552  1.00  27.92
ATOM    960  CA   ASP  A  426    2.984  10.759   1.570  1.00  28.88
ATOM    961  CB   ASP  A  426    1.721  11.102   2.369  1.00  32.58
ATOM    962  CG   ASP  A  426    0.781  12.034   1.613  1.00  37.47
ATOM    963  OD1  ASP  A  426   -0.432  12.039   1.925  1.00  37.72
ATOM    964  OD2  ASP  A  426    1.253  12.758   0.710  1.00  36.35
ATOM    965  C    ASP  A  426    4.071  10.278   2.532  1.00  26.96
ATOM    966  O    ASP  A  426    4.974  11.030   2.900  1.00  27.20
ATOM    967  N    MET  A  427    3.978   9.022   2.947  1.00  25.76
ATOM    968  CA   MET  A  427    4.981   8.468   3.856  1.00  25.89
ATOM    969  CB   MET  A  427    4.567   7.070   4.309  1.00  21.17
ATOM    970  CG   MET  A  427    3.385   7.072   5.257  1.00  24.38
ATOM    971  SD   MET  A  427    3.153   5.489   6.080  1.00  34.32
ATOM    972  CE   MET  A  427    2.173   4.637   4.910  1.00  21.03
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    973   C     MET   A   427    6.321   8.410   3.128   1.00   22.29
ATOM    974   O     MET   A   427    7.363   8.760   3.689   1.00   22.19
ATOM    975   N     LEU   A   428    6.285   7.985   1.868   1.00   21.75
ATOM    976   CA    LEU   A   428    7.506   7.892   1.075   1.00   22.91
ATOM    977   CB    LEU   A   428    7.202   7.252  -0.287   1.00   18.47
ATOM    978   CG    LEU   A   428    6.910   5.747  -0.176   1.00   19.24
ATOM    979   CD1   LEU   A   428    6.278   5.222  -1.468   1.00   16.83
ATOM    980   CD2   LEU   A   428    8.204   5.010   0.131   1.00   16.23
ATOM    981   C     LEU   A   428    8.148   9.269   0.982   1.00   23.98
ATOM    982   O     LEU   A   428    9.366   9.416   1.034   1.00   23.06
ATOM    983   N     LEU   A   429    7.328  10.281   0.628   1.00   23.91
ATOM    984   CA    LEU   A   429    7.837  11.642   0.462   1.00   26.29
ATOM    985   CB    LEU   A   429    6.714  12.571  -0.003   1.00   27.47
ATOM    986   CG    LEU   A   429    6.331  12.411  -1.476   1.00   30.78
ATOM    987   CD1   LEU   A   429    5.022  13.139  -1.751   1.00   34.75
ATOM    988   CD2   LEU   A   429    7.449  12.952  -2.350   1.00   31.96
ATOM    989   C     LEU   A   429    8.425  12.166   1.776   1.00   25.83
ATOM    990   O     LEU   A   429    9.482  12.808   1.793   1.00   26.42
ATOM    991   N     ALA   A   430    7.734  11.890   2.877   1.00   26.45
ATOM    992   CA    ALA   A   430    8.201  12.333   4.185   1.00   26.11
ATOM    993   CB    ALA   A   430    7.214  11.909   5.265   1.00   23.13
ATOM    994   C     ALA   A   430    9.577  11.742   4.462   1.00   25.01
ATOM    995   O     ALA   A   430   10.455  12.409   5.005   1.00   24.31
ATOM    996   N     THR   A   431    9.767  10.486   4.074   1.00   25.25
ATOM    997   CA    THR   A   431   11.046   9.825   4.294   1.00   22.78
ATOM    998   CB    THR   A   431   10.973   8.323   3.962   1.00   21.36
ATOM    999   OG1   THR   A   431    9.924   7.727   4.727   1.00   20.27
ATOM   1000   CG2   THR   A   431   12.291   7.633   4.299   1.00   19.99
ATOM   1001   C     THR   A   431   12.103  10.477   3.429   1.00   23.73
ATOM   1002   O     THR   A   431   13.234  10.667   3.868   1.00   19.60
ATOM   1003   N     SER   A   432   11.736  10.819   2.197   1.00   24.32
ATOM   1004   CA    SER   A   432   12.676  11.479   1.301   1.00   26.96
ATOM   1005   CB    SER   A   432   12.067  11.650  -0.093   1.00   28.70
ATOM   1006   OG    SER   A   432   13.084  11.930  -1.039   1.00   33.42
ATOM   1007   C     SER   A   432   13.033  12.850   1.876   1.00   27.92
ATOM   1008   O     SER   A   432   14.176  13.294   1.779   1.00   30.78
ATOM   1009   N     SER   A   433   12.045  13.521   2.459   1.00   28.96
ATOM   1010   CA    SER   A   433   12.269  14.824   3.076   1.00   34.21
ATOM   1011   CB    SER   A   433   10.957  15.387   3.623   1.00   35.07
ATOM   1012   OG    SER   A   433   10.175  15.961   2.591   1.00   43.38
ATOM   1013   C     SER   A   433   13.263  14.644   4.223   1.00   33.43
ATOM   1014   O     SER   A   433   14.152  15.473   4.429   1.00   31.94
ATOM   1015   N     ARG   A   434   13.105  13.545   4.989   1.00   31.32
ATOM   1016   CA    ARG   A   434   13.980  13.336   6.086   1.00   29.78
ATOM   1017   CB    ARG   A   434   13.468  11.994   6.819   1.00   29.84
ATOM   1018   CG    ARG   A   434   14.331  11.541   7.983   1.00   32.17
ATOM   1019   CD    ARG   A   434   14.626  12.672   8.958   1.00   37.00
ATOM   1020   NE    ARG   A   434   15.321  12.169  10.140   1.00   39.44
ATOM   1021   CZ    ARG   A   434   15.935  12.935  11.034   1.00   44.06
ATOM   1022   NH1   ARG   A   434   15.949  14.255  10.885   1.00   45.52
ATOM   1023   NH2   ARG   A   434   16.528  12.381  12.084   1.00   45.01
ATOM   1024   C     ARG   A   434   15.413  13.014   5.605   1.00   29.24
ATOM   1025   O     ARG   A   434   16.352  13.563   6.173   1.00   29.72
ATOM   1026   N     PHE   A   435   15.577  12.206   4.561   1.00   28.95
ATOM   1027   CA    PHE   A   435   16.901  11.935   4.000   1.00   30.59
ATOM   1028   CB    PHE   A   435   16.777  11.045   2.758   1.00   32.03
ATOM   1029   CG    PHE   A   435   16.795   9.563   3.051   1.00   31.88
ATOM   1030   CD1   PHE   A   435   16.758   9.084   4.359   1.00   35.60
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

| ATOM | 1031 | CD2 | PHE | A | 435 | 16.847 | 8.643 | 2.009 | 1.00 | 35.89 |
| ATOM | 1032 | CE1 | PHE | A | 435 | 16.771 | 7.709 | 4.632 | 1.00 | 35.36 |
| ATOM | 1033 | CE2 | PHE | A | 435 | 16.860 | 7.371 | 2.262 | 1.00 | 32.71 |
| ATOM | 1034 | CZ | PHE | A | 435 | 16.821 | 6.807 | 3.570 | 1.00 | 33.24 |
| ATOM | 1035 | C | PHE | A | 435 | 17.576 | 13.253 | 3.607 | 1.00 | 32.73 |
| ATOM | 1036 | O | PHE | A | 435 | 18.763 | 13.464 | 3.871 | 1.00 | 31.16 |
| ATOM | 1037 | N | ARG | A | 436 | 16.812 | 14.137 | 2.975 | 1.00 | 33.37 |
| ATOM | 1038 | CA | ARG | A | 436 | 17.341 | 15.439 | 2.849 | 1.00 | 39.13 |
| ATOM | 1039 | CB | ARG | A | 436 | 16.382 | 16.306 | 1.756 | 1.00 | 40.42 |
| ATOM | 1040 | CG | ARG | A | 436 | 16.846 | 17.317 | 0.877 | 1.00 | 43.09 |
| ATOM | 1041 | CD | ARG | A | 436 | 15.750 | 17.960 | 0.040 | 1.00 | 44.53 |
| ATOM | 1042 | NE | ARG | A | 436 | 14.826 | 16.955 | -0.472 | 1.00 | 48.34 |
| ATOM | 1043 | CZ | ARG | A | 436 | 13.530 | 16.913 | -0.184 | 1.00 | 48.81 |
| ATOM | 1044 | NH1 | ARG | A | 436 | 12.997 | 17.823 | 0.619 | 1.00 | 47.80 |
| ATOM | 1045 | NH2 | ARG | A | 436 | 12.769 | 15.950 | -0.687 | 1.00 | 49.53 |
| ATOM | 1046 | C | ARG | A | 436 | 17.792 | 16.250 | 3.793 | 1.00 | 38.10 |
| ATOM | 1047 | O | ARG | A | 436 | 18.896 | 15.789 | 3.764 | 1.00 | 41.00 |
| ATOM | 1048 | N | MET | A | 437 | 16.936 | 16.334 | 4.766 | 1.00 | 39.47 |
| ATOM | 1049 | CA | MET | A | 437 | 17.257 | 17.087 | 5.975 | 1.00 | 38.20 |
| ATOM | 1050 | CB | MET | A | 437 | 16.102 | 16.998 | 6.965 | 1.00 | 39.79 |
| ATOM | 1051 | C | MET | A | 437 | 18.550 | 16.594 | 6.626 | 1.00 | 41.15 |
| ATOM | 1052 | O | MET | A | 437 | 19.303 | 17.378 | 7.201 | 1.00 | 40.20 |
| ATOM | 1053 | N | MET | A | 438 | 18.804 | 15.285 | 6.538 | 1.00 | 39.65 |
| ATOM | 1054 | CA | MET | A | 438 | 20.011 | 14.693 | 7.117 | 1.00 | 39.70 |
| ATOM | 1055 | CB | MET | A | 438 | 19.787 | 13.221 | 7.463 | 1.00 | 39.90 |
| ATOM | 1056 | CG | MET | A | 438 | 18.694 | 12.938 | 8.460 | 1.00 | 41.94 |
| ATOM | 1057 | SD | MET | A | 438 | 18.747 | 11.188 | 8.880 | 1.00 | 43.12 |
| ATOM | 1058 | CE | MET | A | 438 | 20.374 | 11.064 | 9.619 | 1.00 | 43.73 |
| ATOM | 1059 | C | MET | A | 438 | 21.176 | 14.756 | 6.142 | 1.00 | 38.03 |
| ATOM | 1060 | O | MET | A | 438 | 22.321 | 14.503 | 6.522 | 1.00 | 38.39 |
| ATOM | 1061 | N | ASN | A | 439 | 20.886 | 15.070 | 4.895 | 1.00 | 37.64 |
| ATOM | 1062 | CA | ASN | A | 439 | 21.924 | 15.118 | 3.895 | 1.00 | 35.68 |
| ATOM | 1063 | CB | ASN | A | 439 | 23.019 | 16.125 | 4.243 | 1.00 | 40.98 |
| ATOM | 1064 | CG | ASN | A | 439 | 23.933 | 16.407 | 3.090 | 1.00 | 45.09 |
| ATOM | 1065 | OD1 | ASN | A | 439 | 23.528 | 16.295 | 1.934 | 1.00 | 47.16 |
| ATOM | 1066 | ND2 | ASN | A | 439 | 25.197 | 16.733 | 3.372 | 1.00 | 46.87 |
| ATOM | 1067 | C | ASN | A | 439 | 22.552 | 13.732 | 3.739 | 1.00 | 31.06 |
| ATOM | 1068 | O | ASN | A | 439 | 23.764 | 13.581 | 3.649 | 1.00 | 29.84 |
| ATOM | 1069 | N | LEU | A | 440 | 21.692 | 12.698 | 3.704 | 1.00 | 31.47 |
| ATOM | 1070 | CA | LEU | A | 440 | 22.161 | 11.326 | 3.579 | 1.00 | 31.63 |
| ATOM | 1071 | CB | LEU | A | 440 | 20.991 | 10.344 | 3.380 | 1.00 | 33.05 |
| ATOM | 1072 | CG | LEU | A | 440 | 21.451 | 8.886 | 3.209 | 1.00 | 37.07 |
| ATOM | 1073 | CD1 | LEU | A | 440 | 21.957 | 8.353 | 4.546 | 1.00 | 36.18 |
| ATOM | 1074 | CD2 | LEU | A | 440 | 20.318 | 8.032 | 2.682 | 1.00 | 32.33 |
| ATOM | 1075 | C | LEU | A | 440 | 23.146 | 11.161 | 2.435 | 1.00 | 32.10 |
| ATOM | 1076 | O | LEU | A | 440 | 22.925 | 11.671 | 1.333 | 1.00 | 32.76 |
| ATOM | 1077 | N | GLN | A | 441 | 24.225 | 10.450 | 2.702 | 1.00 | 32.54 |
| ATOM | 1078 | CA | GLN | A | 441 | 25.255 | 10.220 | 1.699 | 1.00 | 31.97 |
| ATOM | 1079 | CB | GLN | A | 441 | 26.632 | 10.320 | 2.345 | 1.00 | 31.75 |
| ATOM | 1080 | CG | GLN | A | 441 | 26.896 | 11.669 | 2.979 | 1.00 | 35.56 |
| ATOM | 1081 | CD | GLN | A | 441 | 27.040 | 12.748 | 1.939 | 1.00 | 34.97 |
| ATOM | 1082 | OE1 | GLN | A | 441 | 27.985 | 12.782 | 1.167 | 1.00 | 35.51 |
| ATOM | 1083 | NE2 | GLN | A | 441 | 26.053 | 13.659 | 1.899 | 1.00 | 35.41 |
| ATOM | 1084 | C | GLN | A | 441 | 25.100 | 8.860 | 1.038 | 1.00 | 34.08 |
| ATOM | 1085 | O | GLN | A | 441 | 24.540 | 7.931 | 1.625 | 1.00 | 30.73 |
| ATOM | 1086 | N | GLY | A | 442 | 25.608 | 8.752 | -0.187 | 1.00 | 32.78 |
| ATOM | 1087 | CA | GLY | A | 442 | 25.528 | 7.503 | -0.921 | 1.00 | 32.91 |
| ATOM | 1088 | C | GLY | A | 442 | 26.181 | 6.350 | -0.184 | 1.00 | 31.87 |

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1089  O    GLY  A  442   25.642   5.245  -0.154  1.00  33.18
ATOM   1090  N    GLU  A  443   27.340   6.603   0.415  1.00  30.60
ATOM   1091  CA   GLU  A  443   28.057   5.567   1.150  1.00  30.85
ATOM   1092  CB   GLU  A  443   29.376   6.111   1.704  1.00  32.74
ATOM   1093  CG   GLU  A  443   30.425   6.378   0.646  1.00  36.30
ATOM   1094  CD   GLU  A  443   30.310   7.770   0.066  1.00  40.92
ATOM   1095  OE1  GLU  A  443   29.677   8.630   0.716  1.00  43.27
ATOM   1096  OE2  GLU  A  443   30.853   8.003  -1.038  1.00  46.82
ATOM   1097  C    GLU  A  443   27.206   5.048   2.299  1.00  30.43
ATOM   1098  O    GLU  A  443   27.211   3.854   2.595  1.00  28.11
ATOM   1099  N    GLU  A  444   26.482   5.955   2.948  1.00  30.26
ATOM   1100  CA   GLU  A  444   25.619   5.589   4.067  1.00  28.18
ATOM   1101  CB   GLU  A  444   25.147   6.843   4.797  1.00  26.32
ATOM   1102  CG   GLU  A  444   26.250   7.633   5.463  1.00  29.27
ATOM   1103  CD   GLU  A  444   25.748   8.944   6.023  1.00  29.62
ATOM   1104  OE1  GLU  A  444   25.006   9.652   5.304  1.00  32.00
ATOM   1105  OE2  GLU  A  444   26.088   9.268   7.182  1.00  29.02
ATOM   1106  C    GLU  A  444   24.403   4.813   3.572  1.00  26.93
ATOM   1107  O    GLU  A  444   23.970   3.841   4.191  1.00  24.78
ATOM   1108  N    PHE  A  445   23.861   5.256   2.443  1.00  27.79
ATOM   1109  CA   PHE  A  445   22.688   4.633   1.853  1.00  24.50
ATOM   1110  CB   PHE  A  445   22.254   5.416   0.610  1.00  25.40
ATOM   1111  CG   PHE  A  445   21.372   4.634  -0.316  1.00  23.74
ATOM   1112  CD1  PHE  A  445   20.034   4.419  -0.004  1.00  23.00
ATOM   1113  CD2  PHE  A  445   21.885   4.094  -1.489  1.00  22.37
ATOM   1114  CE1  PHE  A  445   19.215   3.670  -0.855  1.00  22.57
ATOM   1115  CE2  PHE  A  445   21.079   3.349  -2.342  1.00  21.69
ATOM   1116  CZ   PHE  A  445   19.741   3.138  -2.023  1.00  22.25
ATOM   1117  C    PHE  A  445   22.913   3.169   1.489  1.00  22.81
ATOM   1118  O    PHE  A  445   22.083   2.316   1.796  1.00  22.92
ATOM   1119  N    VAL  A  446   24.019   2.868   0.822  1.00  22.46
ATOM   1120  CA   VAL  A  446   24.278   1.481   0.447  1.00  22.26
ATOM   1121  CB   VAL  A  446   25.522   1.360  -0.465  1.00  22.87
ATOM   1122  CG1  VAL  A  446   25.251   2.046  -1.799  1.00  22.57
ATOM   1123  CG2  VAL  A  446   26.735   1.968   0.217  1.00  22.38
ATOM   1124  C    VAL  A  446   24.467   0.614   1.694  1.00  23.68
ATOM   1125  O    VAL  A  446   24.177  -0.586   1.680  1.00  22.91
ATOM   1126  N    CYS  A  447   24.962   1.223   2.770  1.00  22.02
ATOM   1127  CA   CYS  A  447   25.155   0.503   4.025  1.00  24.17
ATOM   1128  CB   CYS  A  447   25.953   1.359   5.011  1.00  23.95
ATOM   1129  SG   CYS  A  447   27.738   1.324   4.731  1.00  28.57
ATOM   1130  C    CYS  A  447   23.781   0.178   4.618  1.00  21.14
ATOM   1131  O    CYS  A  447   23.512  -0.960   5.002  1.00  19.37
ATOM   1132  N    LEU  A  448   22.915   1.186   4.680  1.00  19.28
ATOM   1133  CA   LEU  A  448   21.568   1.002   5.219  1.00  21.31
ATOM   1134  CB   LEU  A  448   20.803   2.324   5.207  1.00  21.90
ATOM   1135  CG   LEU  A  448   21.142   3.337   6.303  1.00  26.61
ATOM   1136  CD1  LEU  A  448   20.328   4.594   6.072  1.00  27.74
ATOM   1137  CD2  LEU  A  448   20.827   2.760   7.672  1.00  24.03
ATOM   1138  C    LEU  A  448   20.765  -0.038   4.442  1.00  21.72
ATOM   1139  O    LEU  A  448   20.006  -0.803   5.030  1.00  20.87
ATOM   1140  N    LYS  A  449   20.929  -0.055   3.119  1.00  21.42
ATOM   1141  CA   LYS  A  449   20.205  -0.997   2.269  1.00  20.98
ATOM   1142  CB   LYS  A  449   20.440  -0.659   0.788  1.00  21.55
ATOM   1143  CG   LYS  A  449   19.438  -1.297  -0.173  1.00  24.82
ATOM   1144  CD   LYS  A  449   19.456  -0.613  -1.542  1.00  23.33
ATOM   1145  CE   LYS  A  449   20.816  -0.754  -2.229  1.00  23.58
ATOM   1146  NZ   LYS  A  449   20.741  -0.482  -3.698  1.00  28.77
```

UNITED STATES PATENT AND TRADEMARK OFFICE
CERTIFICATE OF CORRECTION

PATENT NO. : 6,965,850 B2  
APPLICATION NO. : 09/281717  
DATED : November 15, 2005  
INVENTOR(S) : John D. Baxter et al.

It is certified that error appears in the above-identified patent and that said Letters Patent is hereby corrected as shown below:

```
ATOM   1147  C    LYS  A   449    20.629   -2.436   2.548  1.00   20.33
ATOM   1148  O    LYS  A   449    19.800   -3.345   2.552  1.00   20.57
ATOM   1149  N    SER  A   450    21.924   -2.637   2.777  1.00   19.25
ATOM   1150  CA   SER  A   450    22.451   -3.965   3.074  1.00   21.84
ATOM   1151  CB   SER  A   450    23.982   -3.953   3.041  1.00   20.59
ATOM   1152  OG   SER  A   450    24.460   -3.975   1.702  1.00   29.78
ATOM   1153  C    SER  A   450    21.975   -4.408   4.454  1.00   21.58
ATOM   1154  O    SER  A   450    21.728   -5.590   4.683  1.00   20.06
ATOM   1155  N    ILE  A   451    21.853   -3.449   5.369  1.00   22.20
ATOM   1156  CA   ILE  A   451    21.385   -3.741   6.725  1.00   22.82
ATOM   1157  CB   ILE  A   451    21.452   -2.476   7.616  1.00   19.62
ATOM   1158  CG2  ILE  A   451    20.593   -2.658   8.886  1.00   21.11
ATOM   1159  CG1  ILE  A   451    22.909   -2.210   7.999  1.00   22.20
ATOM   1160  CD1  ILE  A   451    23.115   -0.960   8.850  1.00   24.48
ATOM   1161  C    ILE  A   451    19.952   -4.250   6.662  1.00   21.82
ATOM   1162  O    ILE  A   451    19.575   -5.184   7.369  1.00   21.72
ATOM   1163  N    ILE  A   452    19.152   -3.642   5.795  1.00   20.18
ATOM   1164  CA   ILE  A   452    17.763   -4.058   5.649  1.00   18.13
ATOM   1165  CB   ILE  A   452    17.024   -3.145   4.627  1.00   19.72
ATOM   1166  CG2  ILE  A   452    15.720   -3.792   4.169  1.00   18.99
ATOM   1167  CG1  ILE  A   452    16.725   -1.788   5.282  1.00   18.33
ATOM   1168  CD1  ILE  A   452    16.284   -0.707   4.306  1.00   23.25
ATOM   1169  C    ILE  A   452    17.725   -5.517   5.191  1.00   19.50
ATOM   1170  O    ILE  A   452    16.980   -6.340   5.737  1.00   17.60
ATOM   1171  N    LEU  A   453    18.555   -5.844   4.209  1.00   19.23
ATOM   1172  CA   LEU  A   453    18.589   -7.205   3.679  1.00   21.60
ATOM   1173  CB   LEU  A   453    19.624   -7.316   2.554  1.00   21.50
ATOM   1174  CG   LEU  A   453    19.835   -8.729   1.989  1.00   25.06
ATOM   1175  CD1  LEU  A   453    18.550   -9.250   1.364  1.00   25.27
ATOM   1176  CD2  LEU  A   453    20.948   -8.694   0.953  1.00   24.73
ATOM   1177  C    LEU  A   453    18.906   -8.245   4.746  1.00   19.41
ATOM   1178  O    LEU  A   453    18.198   -9.241   4.893  1.00   20.75
ATOM   1179  N    LEU  A   454    19.966   -7.997   5.499  1.00   21.35
ATOM   1180  CA   LEU  A   454    20.410   -8.925   6.530  1.00   23.67
ATOM   1181  CB   LEU  A   454    21.870   -8.625   6.878  1.00   20.69
ATOM   1182  CG   LEU  A   454    22.816   -8.584   5.673  1.00   24.92
ATOM   1183  CD1  LEU  A   454    24.222   -8.268   6.132  1.00   24.27
ATOM   1184  CD2  LEU  A   454    22.785   -9.913   4.952  1.00   22.84
ATOM   1185  C    LEU  A   454    19.572   -8.945   7.807  1.00   26.06
ATOM   1186  O    LEU  A   454    19.413   -9.997   8.438  1.00   27.44
ATOM   1187  N    ASN  A   455    19.011   -7.795   8.167  1.00   25.01
ATOM   1188  CA   ASN  A   455    18.240   -7.681   9.400  1.00   26.10
ATOM   1189  CB   ASN  A   455    18.439   -6.295  10.002  1.00   22.67
ATOM   1190  CG   ASN  A   455    17.627   -6.109  11.264  1.00   26.67
ATOM   1191  OD1  ASN  A   455    17.899   -6.751  12.270  1.00   25.16
ATOM   1192  ND2  ASN  A   455    16.615   -5.246  11.212  1.00   20.73
ATOM   1193  C    ASN  A   455    16.739   -7.957   9.418  1.00   25.78
ATOM   1194  O    ASN  A   455    16.230   -8.516  10.380  1.00   29.22
ATOM   1195  N    SER  A   456    16.027   -7.549   8.381  1.00   28.51
ATOM   1196  CA   SER  A   456    14.578   -7.704   8.371  1.00   32.52
ATOM   1197  CB   SER  A   456    14.019   -7.213   7.033  1.00   35.98
ATOM   1198  OG   SER  A   456    14.266   -5.818   6.897  1.00   30.88
ATOM   1199  C    SER  A   456    14.033   -9.086   8.711  1.00   33.00
ATOM   1200  O    SER  A   456    13.112   -9.202   9.523  1.00   33.07
ATOM   1201  N    GLY  A   457    14.597  -10.130   8.117  1.00   28.40
ATOM   1202  CA   GLY  A   457    14.115  -11.464   8.413  1.00   36.28
ATOM   1203  C    GLY  A   457    15.055  -12.289   9.277  1.00   40.41
ATOM   1204  O    GLY  A   457    14.831  -13.486   9.456  1.00   38.20
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1205  N    VAL  A  458    16.095  -11.657   9.820  1.00  44.13
ATOM   1206  CA   VAL  A  458    17.079  -12.356  10.647  1.00  51.09
ATOM   1207  CB   VAL  A  458    18.214  -11.399  11.095  1.00  51.06
ATOM   1208  CG1  VAL  A  458    17.688  -10.390  12.104  1.00  51.75
ATOM   1209  CG2  VAL  A  458    19.365  -12.199  11.692  1.00  50.65
ATOM   1210  C    VAL  A  458    16.513  -13.060  11.888  1.00  57.26
ATOM   1211  O    VAL  A  458    17.085  -14.045  12.358  1.00  58.77
ATOM   1212  N    TYR  A  459    15.401  -12.560  12.416  1.00  62.31
ATOM   1213  CA   TYR  A  459    14.793  -13.177  13.592  1.00  68.49
ATOM   1214  CB   TYR  A  459    14.293  -12.100  14.560  1.00  70.46
ATOM   1215  CG   TYR  A  459    15.396  -11.196  15.069  1.00  71.73
ATOM   1216  CD1  TYR  A  459    15.127   -9.888  15.462  1.00  71.93
ATOM   1217  CE1  TYR  A  459    16.147   -9.045  15.898  1.00  72.60
ATOM   1218  CD2  TYR  A  459    16.715  -11.644  15.128  1.00  72.77
ATOM   1219  CE2  TYR  A  459    17.741  -10.812  15.560  1.00  73.55
ATOM   1220  CZ   TYR  A  459    17.450   -9.514  15.941  1.00  72.93
ATOM   1221  OH   TYR  A  459    18.467   -8.687  16.351  1.00  74.56
ATOM   1222  C    TYR  A  459    13.649  -14.097  13.187  1.00  71.86
ATOM   1223  O    TYR  A  459    13.380  -15.099  13.852  1.00  73.11
ATOM   1224  N    THR  A  460    12.981  -13.756  12.090  1.00  74.84
ATOM   1225  CA   THR  A  460    11.881  -14.567  11.589  1.00  77.66
ATOM   1226  CB   THR  A  460    11.246  -13.900  10.373  1.00  76.69
ATOM   1227  C    THR  A  460    12.436  -15.938  11.212  1.00  80.26
ATOM   1228  O    THR  A  460    11.684  -16.866  10.912  1.00  80.82
ATOM   1229  N    PHE  A  461    13.762  -16.051  11.231  1.00  82.69
ATOM   1230  CA   PHE  A  461    14.440  -17.299  10.905  1.00  85.63
ATOM   1231  CB   PHE  A  461    15.920  -17.034  10.630  1.00  85.47
ATOM   1232  C    PHE  A  461    14.284  -18.288  12.059  1.00  87.52
ATOM   1233  O    PHE  A  461    14.493  -17.940  13.224  1.00  86.53
ATOM   1234  N    LEU  A  462    13.914  -19.520  11.724  1.00  89.49
ATOM   1235  CA   LEU  A  462    13.711  -20.568  12.718  1.00  91.34
ATOM   1236  CB   LEU  A  462    12.961  -21.741  12.087  1.00  91.23
ATOM   1237  C    LEU  A  462    15.016  -21.060  13.340  1.00  92.05
ATOM   1238  O    LEU  A  462    16.042  -21.165  12.664  1.00  91.91
ATOM   1239  N    SER  A  463    14.966  -21.357  14.635  1.00  92.53
ATOM   1240  CA   SER  A  463    16.131  -21.835  15.358  1.00  92.96
ATOM   1241  CB   SER  A  463    16.033  -21.483  16.833  1.00  91.67
ATOM   1242  C    SER  A  463    16.189  -23.371  15.200  1.00  93.39
ATOM   1243  O    SER  A  463    15.156  -24.034  15.102  1.00  93.44
ATOM   1244  N    SER  A  464    17.399  -23.917  15.167  1.00  93.82
ATOM   1245  CA   SER  A  464    17.577  -25.355  15.015  1.00  93.85
ATOM   1246  CB   SER  A  464    17.284  -25.769  13.577  1.00  93.74
ATOM   1247  C    SER  A  464    18.997  -25.743  15.396  1.00  93.96
ATOM   1248  O    SER  A  464    19.815  -26.074  14.535  1.00  93.65
ATOM   1249  N    THR  A  465    19.279  -25.699  16.694  1.00  93.91
ATOM   1250  CA   THR  A  465    20.600  -26.036  17.212  1.00  93.79
ATOM   1251  CB   THR  A  465    20.952  -27.483  16.863  1.00  93.38
ATOM   1252  C    THR  A  465    21.640  -25.085  16.634  1.00  93.27
ATOM   1253  O    THR  A  465    21.302  -24.017  16.121  1.00  93.03
ATOM   1254  N    LEU  A  466    22.907  -25.479  16.723  1.00  93.26
ATOM   1255  CA   LEU  A  466    23.999  -24.665  16.207  1.00  92.34
ATOM   1256  CB   LEU  A  466    25.335  -25.338  16.498  1.00  91.59
ATOM   1257  C    LEU  A  466    23.829  -24.461  14.706  1.00  92.18
ATOM   1258  O    LEU  A  466    24.411  -23.545  14.129  1.00  92.67
ATOM   1259  N    LYS  A  467    23.028  -25.323  14.086  1.00  91.28
ATOM   1260  CA   LYS  A  467    22.772  -25.238  12.653  1.00  90.02
ATOM   1261  CB   LYS  A  467    21.740  -26.287  12.240  1.00  89.93
ATOM   1262  C    LYS  A  467    22.269  -23.841  12.308  1.00  88.35
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1263  O    LYS  A  467    23.032  -22.990  11.849  1.00  88.50
ATOM   1264  N    SER  A  468    20.981  -23.610  12.536  1.00  86.02
ATOM   1265  CA   SER  A  468    20.384  -22.315  12.252  1.00  84.10
ATOM   1266  CB   SER  A  468    18.901  -22.333  12.620  1.00  84.08
ATOM   1267  OG   SER  A  468    18.239  -23.378  11.937  1.00  83.03
ATOM   1268  C    SER  A  468    21.109  -21.230  13.040  1.00  83.39
ATOM   1269  O    SER  A  468    21.264  -20.105  12.565  1.00  83.48
ATOM   1270  N    LEU  A  469    21.558  -21.579  14.242  1.00  82.04
ATOM   1271  CA   LEU  A  469    22.276  -20.640  15.098  1.00  80.28
ATOM   1272  CB   LEU  A  469    22.595  -21.294  16.436  1.00  79.81
ATOM   1273  C    LEU  A  469    23.564  -20.174  14.419  1.00  79.18
ATOM   1274  O    LEU  A  469    24.111  -19.122  14.756  1.00  78.61
ATOM   1275  N    GLU  A  470    24.044  -20.969  13.466  1.00  76.69
ATOM   1276  CA   GLU  A  470    25.256  -20.638  12.736  1.00  74.84
ATOM   1277  CB   GLU  A  470    25.803  -21.880  12.032  1.00  74.12
ATOM   1278  C    GLU  A  470    24.920  -19.565  11.697  1.00  73.77
ATOM   1279  O    GLU  A  470    25.617  -18.556  11.581  1.00  72.94
ATOM   1280  N    GLU  A  471    23.842  -19.792  10.953  1.00  72.08
ATOM   1281  CA   GLU  A  471    23.396  -18.842   9.945  1.00  70.05
ATOM   1282  CB   GLU  A  471    22.461  -19.526   8.944  1.00  71.52
ATOM   1283  CG   GLU  A  471    23.150  -19.976   7.668  1.00  72.90
ATOM   1284  CD   GLU  A  471    24.512  -20.586   7.932  1.00  74.01
ATOM   1285  OE1  GLU  A  471    25.469  -20.258   7.198  1.00  74.22
ATOM   1286  OE2  GLU  A  471    24.626  -21.395   8.878  1.00  75.18
ATOM   1287  C    GLU  A  471    22.667  -17.692  10.630  1.00  67.33
ATOM   1288  O    GLU  A  471    21.685  -17.165  10.107  1.00  67.77
ATOM   1289  N    LYS  A  472    23.152  -17.319  11.811  1.00  62.63
ATOM   1290  CA   LYS  A  472    22.564  -16.229  12.578  1.00  57.41
ATOM   1291  CB   LYS  A  472    21.697  -16.777  13.713  1.00  58.74
ATOM   1292  CG   LYS  A  472    20.683  -15.776  14.243  1.00  60.32
ATOM   1293  CD   LYS  A  472    19.271  -16.342  14.219  1.00  60.73
ATOM   1294  CE   LYS  A  472    18.485  -15.909  15.449  1.00  61.78
ATOM   1295  NZ   LYS  A  472    19.352  -15.788  16.658  1.00  60.09
ATOM   1296  C    LYS  A  472    23.662  -15.339  13.150  1.00  53.42
ATOM   1297  O    LYS  A  472    23.631  -14.120  12.978  1.00  50.87
ATOM   1298  N    ASP  A  473    24.628  -15.949  13.830  1.00  47.52
ATOM   1299  CA   ASP  A  473    25.732  -15.194  14.405  1.00  45.55
ATOM   1300  CB   ASP  A  473    26.613  -16.094  15.269  1.00  50.48
ATOM   1301  CG   ASP  A  473    26.380  -15.885  16.749  1.00  55.50
ATOM   1302  OD1  ASP  A  473    25.272  -15.436  17.118  1.00  58.06
ATOM   1303  OD2  ASP  A  473    27.304  -16.170  17.541  1.00  59.81
ATOM   1304  C    ASP  A  473    26.557  -14.811  13.269  1.00  42.62
ATOM   1305  O    ASP  A  473    27.087  -13.506  13.373  1.00  42.10
ATOM   1306  N    HIS  A  474    26.663  -15.364  12.180  1.00  38.05
ATOM   1307  CA   HIS  A  474    27.416  -14.904  11.026  1.00  37.25
ATOM   1308  CB   HIS  A  474    27.429  -15.978   9.941  1.00  35.07
ATOM   1309  CG   HIS  A  474    28.036  -15.523   8.653  1.00  37.36
ATOM   1310  CD2  HIS  A  474    29.292  -15.113   8.355  1.00  38.86
ATOM   1311  ND1  HIS  A  474    27.322  -15.452   7.476  1.00  41.31
ATOM   1312  CE1  HIS  A  474    28.110  -15.020   6.509  1.00  40.86
ATOM   1313  NE2  HIS  A  474    29.311  -14.807   7.016  1.00  44.49
ATOM   1314  C    HIS  A  474    26.749  -13.640  10.493  1.00  36.68
ATOM   1315  O    HIS  A  474    27.417  -12.676  10.132  1.00  36.48
ATOM   1316  N    ILE  A  475    25.422  -13.652  10.447  1.00  35.93
ATOM   1317  CA   ILE  A  475    24.683  -12.499   9.963  1.00  36.21
ATOM   1318  CB   ILE  A  475    23.174  -12.797   9.868  1.00  36.31
ATOM   1319  CG2  ILE  A  475    22.411  -11.527   9.513  1.00  38.19
ATOM   1320  CG1  ILE  A  475    22.922  -13.874   8.813  1.00  36.97
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

| | | | | | | | | | |
|---|---|---|---|---|---|---|---|---|---|
| ATOM | 1321 | CD1 | ILE | A | 475 | 21.528 | -14.454 | 8.859 | 1.00 | 35.89 |
| ATOM | 1322 | C | ILE | A | 475 | 24.893 | -11.332 | 10.907 | 1.00 | 35.34 |
| ATOM | 1323 | O | ILE | A | 475 | 25.092 | -10.189 | 10.471 | 1.00 | 33.20 |
| ATOM | 1324 | N | HIS | A | 476 | 24.857 | -11.895 | 12.206 | 1.00 | 35.95 |
| ATOM | 1325 | CA | HIS | A | 476 | 25.031 | -10.540 | 13.193 | 1.00 | 35.06 |
| ATOM | 1326 | CB | HIS | A | 476 | 24.681 | -11.062 | 14.585 | 1.00 | 37.30 |
| ATOM | 1327 | CG | HIS | A | 476 | 23.210 | -11.068 | 14.860 | 1.00 | 43.06 |
| ATOM | 1328 | CD2 | HIS | A | 476 | 22.329 | -10.051 | 15.017 | 1.00 | 43.93 |
| ATOM | 1329 | ND1 | HIS | A | 476 | 22.476 | -12.230 | 14.968 | 1.00 | 45.60 |
| ATOM | 1330 | CE1 | HIS | A | 476 | 21.207 | -11.928 | 15.177 | 1.00 | 47.56 |
| ATOM | 1331 | NE2 | HIS | A | 476 | 21.091 | -10.613 | 15.211 | 1.00 | 46.21 |
| ATOM | 1332 | C | HIS | A | 476 | 26.438 | -9.966 | 13.170 | 1.00 | 35.40 |
| ATOM | 1333 | O | HIS | A | 476 | 26.634 | -8.774 | 13.415 | 1.00 | 35.45 |
| ATOM | 1334 | N | ARG | A | 477 | 27.420 | -10.808 | 12.862 | 1.00 | 34.07 |
| ATOM | 1335 | CA | ARG | A | 477 | 28.796 | -10.331 | 12.795 | 1.00 | 34.18 |
| ATOM | 1336 | CB | ARG | A | 477 | 29.757 | -11.506 | 12.605 | 1.00 | 41.04 |
| ATOM | 1337 | CG | ARG | A | 477 | 29.800 | -12.459 | 13.788 | 1.00 | 47.61 |
| ATOM | 1338 | CD | ARG | A | 477 | 30.782 | -13.599 | 13.557 | 1.00 | 55.67 |
| ATOM | 1339 | NE | ARG | A | 477 | 31.780 | -13.675 | 14.622 | 1.00 | 60.17 |
| ATOM | 1340 | CZ | ARG | A | 477 | 32.780 | -12.811 | 14.770 | 1.00 | 61.98 |
| ATOM | 1341 | NH1 | ARG | A | 477 | 32.918 | -11.803 | 13.918 | 1.00 | 64.29 |
| ATOM | 1342 | NH2 | ARG | A | 477 | 33.643 | -12.985 | 15.766 | 1.00 | 62.79 |
| ATOM | 1343 | C | ARG | A | 477 | 28.906 | -9.361 | 11.621 | 1.00 | 30.77 |
| ATOM | 1344 | O | ARG | A | 477 | 29.462 | -8.268 | 11.753 | 1.00 | 33.59 |
| ATOM | 1345 | N | VAL | A | 478 | 28.369 | -9.766 | 10.475 | 1.00 | 27.65 |
| ATOM | 1346 | CA | VAL | A | 478 | 28.389 | -8.930 | 9.280 | 1.00 | 37.07 |
| ATOM | 1347 | CB | VAL | A | 478 | 27.658 | -9.605 | 8.100 | 1.00 | 28.00 |
| ATOM | 1348 | CG1 | VAL | A | 478 | 27.672 | -8.678 | 6.890 | 1.00 | 25.83 |
| ATOM | 1349 | CG2 | VAL | A | 478 | 28.319 | -10.933 | 7.761 | 1.00 | 31.66 |
| ATOM | 1350 | C | VAL | A | 478 | 27.689 | -7.610 | 9.584 | 1.00 | 26.92 |
| ATOM | 1351 | O | VAL | A | 478 | 28.216 | -6.536 | 9.294 | 1.00 | 26.97 |
| ATOM | 1352 | N | LEU | A | 479 | 26.439 | -7.702 | 10.171 | 1.00 | 25.74 |
| ATOM | 1353 | CA | LEU | A | 479 | 25.727 | -6.516 | 10.530 | 1.00 | 27.97 |
| ATOM | 1354 | CB | LEU | A | 479 | 24.474 | -6.912 | 11.324 | 1.00 | 25.55 |
| ATOM | 1355 | CG | LEU | A | 479 | 23.211 | -7.229 | 10.517 | 1.00 | 29.01 |
| ATOM | 1356 | CD1 | LEU | A | 479 | 22.056 | -7.503 | 11.481 | 1.00 | 27.05 |
| ATOM | 1357 | CD2 | LEU | A | 479 | 22.854 | -6.063 | 9.584 | 1.00 | 24.92 |
| ATOM | 1358 | C | LEU | A | 479 | 26.592 | -5.582 | 11.369 | 1.00 | 25.39 |
| ATOM | 1359 | O | LEU | A | 479 | 26.595 | -4.370 | 11.158 | 1.00 | 27.39 |
| ATOM | 1360 | N | ASP | A | 480 | 27.324 | -6.198 | 12.330 | 1.00 | 26.04 |
| ATOM | 1361 | CA | ASP | A | 480 | 28.206 | -5.388 | 13.193 | 1.00 | 27.32 |
| ATOM | 1362 | CB | ASP | A | 480 | 28.878 | -6.305 | 14.222 | 1.00 | 26.67 |
| ATOM | 1363 | CG | ASP | A | 480 | 27.990 | -6.602 | 15.417 | 1.00 | 31.02 |
| ATOM | 1364 | OD1 | ASP | A | 480 | 28.355 | -7.505 | 16.198 | 1.00 | 31.50 |
| ATOM | 1365 | OD2 | ASP | A | 480 | 26.935 | -5.944 | 15.580 | 1.00 | 32.21 |
| ATOM | 1366 | C | ASP | A | 480 | 29.283 | -4.699 | 12.361 | 1.00 | 25.99 |
| ATOM | 1367 | O | ASP | A | 480 | 29.672 | -3.562 | 12.636 | 1.00 | 27.15 |
| ATOM | 1368 | N | LYS | A | 481 | 29.767 | -5.394 | 11.340 | 1.00 | 25.17 |
| ATOM | 1369 | CA | LYS | A | 481 | 30.794 | -4.830 | 10.477 | 1.00 | 24.93 |
| ATOM | 1370 | CB | LYS | A | 481 | 31.305 | -5.890 | 9.512 | 1.00 | 28.42 |
| ATOM | 1371 | CG | LYS | A | 481 | 32.158 | -6.963 | 10.188 | 1.00 | 35.59 |
| ATOM | 1372 | CD | LYS | A | 481 | 32.894 | -7.799 | 9.157 | 1.00 | 41.21 |
| ATOM | 1373 | CE | LYS | A | 481 | 33.883 | -6.963 | 8.350 | 1.00 | 41.48 |
| ATOM | 1374 | NZ | LYS | A | 481 | 34.954 | -6.388 | 9.215 | 1.00 | 43.22 |
| ATOM | 1375 | C | LYS | A | 481 | 30.260 | -3.635 | 9.696 | 1.00 | 26.12 |
| ATOM | 1376 | O | LYS | A | 481 | 30.979 | -2.657 | 9.463 | 1.00 | 23.73 |
| ATOM | 1377 | N | ILE | A | 482 | 28.996 | -3.705 | 9.291 | 1.00 | 25.44 |
| ATOM | 1378 | CA | ILE | A | 482 | 28.421 | -2.598 | 8.545 | 1.00 | 27.89 |

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1379  CB   ILE  A  482    27.066  -2.983   7.915  1.00  27.59
ATOM   1380  CG2  ILE  A  482    26.470  -1.788   7.183  1.00  25.97
ATOM   1381  CG1  ILE  A. 482    27.274  -4.131   6.932  1.00  33.80
ATOM   1382  CD1  ILE  A  482    26.000  -4.838   6.533  1.00  31.30
ATOM   1383  C    ILE  A  482    28.253  -1.408   9.481  1.00  27.33
ATOM   1384  O    ILE  A  482    28.312  -0.256   9.045  1.00  28.55
ATOM   1385  N    THR  A  483    28.046  -1.690  10.768  1.00  25.03
ATOM   1386  CA   THR  A  483    27.905  -0.632  11.760  1.00  23.63
ATOM   1387  CB   THR  A  483    27.535  -1.192  13.134  1.00  32.18
ATOM   1388  OG1  THR  A  483    26.181  -1.658  13.133  1.00  25.39
ATOM   1389  CG2  THR  A  483    27.673  -0.111  14.236  1.00  25.84
ATOM   1390  C    THR  A  483    29.257   0.074  11.858  1.00  23.04
ATOM   1391  O    THR  A  483    29.331   1.306  11.846  1.00  23.55
ATOM   1392  N    ASP  A  484    30.324  -0.714  11.960  1.00  22.24
ATOM   1393  CA   ASP  A  484    31.674  -0.152  12.039  1.00  25.48
ATOM   1394  CB   ASP  A  484    32.718  -1.273  12.107  1.00  26.88
ATOM   1395  CG   ASP  A  484    32.629  -2.083  13.394  1.00  32.52
ATOM   1396  OD1  ASP  A  484    32.002  -1.608  14.366  1.00  33.68
ATOM   1397  OD2  ASP  A  484    33.185  -3.198  13.434  1.00  34.63
ATOM   1398  C    ASP  A  484    31.930   0.715  10.807  1.00  25.16
ATOM   1399  O    ASP  A  484    32.481   1.812  10.905  1.00  26.05
ATOM   1400  N    THR  A  485    31.505   0.226   9.645  1.00  28.98
ATOM   1401  CA   THR  A  485    31.689   0.960   8.394  1.00  26.63
ATOM   1402  CB   THR  A  485    31.124   0.166   7.197  1.00  26.12
ATOM   1403  OG1  THR  A  485    31.753  -1.123   7.132  1.00  24.30
ATOM   1404  CG2  THR  A  485    31.381   0.907   5.898  1.00  23.31
ATOM   1405  C    THR  A  485    30.994   2.318   8.468  1.00  28.90
ATOM   1406  O    THR  A  485    31.583   3.354   8.137  1.00  27.26
ATOM   1407  N    LEU  A  486    29.743   2.310   8.915  1.00  24.76
ATOM   1408  CA   LEU  A  486    28.973   3.537   9.027  1.00  26.19
ATOM   1409  CB   LEU  A  486    27.567   3.233   9.547  1.00  27.37
ATOM   1410  CG   LEU  A  486    26.508   2.921   8.486  1.00  23.50
ATOM   1411  CD1  LEU  A  486    25.210   2.550   9.183  1.00  32.03
ATOM   1412  CD2  LEU  A  486    26.309   4.128   7.577  1.00  21.35
ATOM   1413  C    LEU  A  486    29.662   4.319   9.960  1.00  27.36
ATOM   1414  O    LEU  A  486    29.745   5.710   9.669  1.00  25.87
ATOM   1415  N    ILE  A  487    30.151   4.015  11.088  1.00  27.88
ATOM   1416  CA   ILE  A  487    30.843   4.857  12.055  1.00  28.40
ATOM   1417  CB   ILE  A  487    31.203   4.054  13.332  1.00  26.74
ATOM   1418  CG2  ILE  A  487    32.255   4.803  14.154  1.00  27.54
ATOM   1419  CG1  ILE  A  487    29.937   3.813  14.163  1.00  25.93
ATOM   1420  CD1  ILE  A  487    29.237   5.098  14.624  1.00  23.42
ATOM   1421  C    ILE  A  487    32.125   5.393  11.413  1.00  28.89
ATOM   1422  O    ILE  A  487    32.497   6.554  11.602  1.00  29.85
ATOM   1423  N    HIS  A  488    32.791   4.533  10.649  1.00  29.71
ATOM   1424  CA   HIS  A  488    34.031   4.898   9.967  1.00  34.12
ATOM   1425  CB   HIS  A  488    34.585   3.691   9.207  1.00  36.61
ATOM   1426  CG   HIS  A  488    35.799   3.997   8.385  1.00  42.74
ATOM   1427  CD2  HIS  A  488    35.970   4.089   7.045  1.00  43.12
ATOM   1428  ND1  HIS  A  488    37.034   4.239   8.946  1.00  43.13
ATOM   1429  CE1  HIS  A  488    37.913   4.466   7.987  1.00  43.40
ATOM   1430  NE2  HIS  A  488    37.293   4.381   6.825  1.00  45.63
ATOM   1431  C    HIS  A  488    33.799   6.051   8.998  1.00  32.74
ATOM   1432  O    HIS  A  488    34.577   7.004   8.955  1.00  31.06
ATOM   1433  N    LEU  A  489    32.721   5.958   8.223  1.00  33.56
ATOM   1434  CA   LEU  A  489    32.384   6.992   7.258  1.00  30.78
ATOM   1435  CB   LEU  A  489    31.145   6.587   6.464  1.00  34.67
ATOM   1436  CG   LEU  A  489    31.310   5.353   5.574  1.00  34.73
```

UNITED STATES PATENT AND TRADEMARK OFFICE
CERTIFICATE OF CORRECTION

PATENT NO. : 6,965,850 B2  Page 103 of 186
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1437  CD1  LEU  A  489   29.945   4.856   5.125  1.00  33.21
ATOM   1438  CD2  LEU  A  489   32.183   5.701   4.378  1.00  35.93
ATOM   1439  C    LEU  A  489   32.124   8.320   7.954  1.00  33.97
ATOM   1440  O    LEU  A  489   32.587   9.365   7.507  1.00  33.22
ATOM   1441  N    MET  A  490   31.387   8.274   9.058  1.00  31.33
ATOM   1442  CA   MET  A  490   31.056   9.482   9.801  1.00  30.61
ATOM   1443  CB   MET  A  490   30.000   9.161  10.862  1.00  32.34
ATOM   1444  CG   MET  A  490   28.607   8.940  10.289  1.00  30.71
ATOM   1445  SD   MET  A  490   27.457   8.247  11.496  1.00  31.14
ATOM   1446  CE   MET  A  490   26.321   7.408  10.418  1.00  30.36
ATOM   1447  C    MET  A  490   32.287  10.108  10.455  1.00  32.23
ATOM   1448  O    MET  A  490   32.412  11.330  10.317  1.00  28.25
ATOM   1449  N    ALA  A  491   33.184   9.262  10.949  1.00  33.81
ATOM   1450  CA   ALA  A  491   34.407   9.730  11.585  1.00  39.92
ATOM   1451  CB   ALA  A  491   35.168   8.554  12.185  1.00  37.22
ATOM   1452  C    ALA  A  491   35.275  10.445  10.850  1.00  42.68
ATOM   1453  O    ALA  A  491   35.865  11.487  10.838  1.00  45.32
ATOM   1454  N    LYS  A  492   35.339   9.876   9.347  1.00  44.39
ATOM   1455  CA   LYS  A  492   36.122  10.440   8.248  1.00  44.80
ATOM   1456  CB   LYS  A  492   36.136   9.477   7.052  1.00  46.96
ATOM   1457  CG   LYS  A  492   37.490   8.840   6.744  1.00  47.20
ATOM   1458  CD   LYS  A  492   37.390   7.830   5.595  1.00  45.71
ATOM   1459  CE   LYS  A  492   38.631   6.937   5.518  1.00  45.55
ATOM   1460  NZ   LYS  A  492   38.357   5.577   4.948  1.00  36.28
ATOM   1461  C    LYS  A  492   35.534  11.780   7.809  1.00  45.61
ATOM   1462  O    LYS  A  492   35.227  12.604   7.215  1.00  46.18
ATOM   1463  N    ALA  A  493   34.254  11.992   8.100  1.00  43.75
ATOM   1464  CA   ALA  A  493   33.590  13.238   7.738  1.00  42.42
ATOM   1465  CB   ALA  A  493   32.097  13.001   7.528  1.00  40.92
ATOM   1466  C    ALA  A  493   33.816  14.305   8.796  1.00  41.78
ATOM   1467  O    ALA  A  493   33.277  15.410   8.707  1.00  40.76
ATOM   1468  N    GLY  A  494   34.604  13.960   9.811  1.00  41.01
ATOM   1469  CA   GLY  A  494   34.903  14.904  10.873  1.00  41.63
ATOM   1470  C    GLY  A  494   33.857  15.060  11.965  1.00  41.18
ATOM   1471  O    GLY  A  494   33.916  16.011  12.747  1.00  38.22
ATOM   1472  N    LEU  A  495   32.905  14.138  12.043  1.00  39.53
ATOM   1473  CA   LEU  A  495   31.876  14.248  13.068  1.00  38.91
ATOM   1474  CB   LEU  A  495   30.713  13.304  12.769  1.00  39.20
ATOM   1475  CG   LEU  A  495   29.540  13.901  11.988  1.00  40.73
ATOM   1476  CD1  LEU  A  495   29.976  14.170  10.553  1.00  37.80
ATOM   1477  CD2  LEU  A  495   28.349  12.943  12.026  1.00  40.94
ATOM   1478  C    LEU  A  495   32.461  13.923  14.431  1.00  36.01
ATOM   1479  O    LEU  A  495   33.347  13.074  14.544  1.00  34.85
ATOM   1480  N    THR  A  496   31.979  14.604  15.459  1.00  37.52
ATOM   1481  CA   THR  A  496   32.462  14.350  16.812  1.00  35.45
ATOM   1482  CB   THR  A  496   31.925  15.375  17.829  1.00  37.55
ATOM   1483  OG1  THR  A  496   30.498  15.263  17.908  1.00  32.93
ATOM   1484  CG2  THR  A  496   32.315  16.797  17.434  1.00  36.16
ATOM   1485  C    THR  A  496   31.933  12.987  17.210  1.00  35.57
ATOM   1486  O    THR  A  496   31.081  12.427  16.521  1.00  34.34
ATOM   1487  N    LEU  A  497   32.429  12.452  18.319  1.00  34.88
ATOM   1488  CA   LEU  A  497   31.965  11.151  18.786  1.00  35.67
ATOM   1489  CB   LEU  A  497   32.689  10.760  20.074  1.00  41.10
ATOM   1490  CG   LEU  A  497   33.714   9.640  19.896  1.00  45.27
ATOM   1491  CD1  LEU  A  497   34.755   9.692  21.008  1.00  45.09
ATOM   1492  CD2  LEU  A  497   32.988   8.305  19.884  1.00  47.77
ATOM   1493  C    LEU  A  497   30.455  11.198  19.026  1.00  33.72
ATOM   1494  O    LEU  A  497   29.712  10.350  18.534  1.00  33.20
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1495  N    GLN  A  498    30.006  12.202 19.773  1.00  30.82
ATOM   1496  CA   GLN  A  498    28.586  12.348 20.062  1.00  31.47
ATOM   1497  CB   GLN  A  498    28.344  13.566 20.951  1.00  30.51
ATOM   1498  CG   GLN  A  498    26.894  13.796 21.341  1.00  34.38
ATOM   1499  CD   GLN  A  498    26.712  15.130 22.015  1.00  38.60
ATOM   1500  OE1  GLN  A  498    27.363  16.112 21.686  1.00  42.92
ATOM   1501  NE2  GLN  A  498    25.809  15.176 23.008  1.00  40.02
ATOM   1502  C    GLN  A  498    27.776  12.476 18.773  1.00  30.47
ATOM   1503  O    GLN  A  498    26.682  11.927 18.665  1.00  30.85
ATOM   1504  N    GLN  A  499    28.311  13.196 17.793  1.00  29.52
ATOM   1505  CA   GLN  A  499    27.603  13.362 16.524  1.00  30.24
ATOM   1506  CB   GLN  A  499    28.292  14.420 15.661  1.00  30.20
ATOM   1507  CG   GLN  A  499    28.135  15.840 16.191  1.00  31.60
ATOM   1508  CD   GLN  A  499    28.930  15.849 15.389  1.00  31.61
ATOM   1509  OE1  GLN  A  499    29.956  16.518 14.795  1.00  30.66
ATOM   1510  NE2  GLN  A  499    28.457  18.089 15.364  1.00  34.17
ATOM   1511  C    GLN  A  499    27.529  12.047 15.753  1.00  29.40
ATOM   1512  O    GLN  A  499    26.567  11.793 15.032  1.00  30.04
ATOM   1513  N    GLN  A  500    28.550  11.214 15.903  1.00  25.67
ATOM   1514  CA   GLN  A  500    28.577   9.937 15.216  1.00  29.30
ATOM   1515  CB   GLN  A  500    29.933   9.276 15.406  1.00  31.52
ATOM   1516  CG   GLN  A  500    31.012   9.839 14.508  1.00  33.05
ATOM   1517  CD   GLN  A  500    32.371   9.370 14.930  1.00  34.84
ATOM   1518  OE1  GLN  A  500    32.612   8.194 15.141  1.00  36.47
ATOM   1519  NE2  GLN  A  500    33.301  10.324 15.082  1.00  38.25
ATOM   1520  C    GLN  A  500    27.459   9.017 15.711  1.00  27.98
ATOM   1521  O    GLN  A  500    26.700   8.469 14.908  1.00  24.84
ATOM   1522  N    HIS  A  501    27.357   8.864 17.029  1.00  26.20
ATOM   1523  CA   HIS  A  501    26.327   8.021 17.631  1.00  27.63
ATOM   1524  CB   HIS  A  501    26.535   7.919 19.145  1.00  27.97
ATOM   1525  CG   HIS  A  501    27.892   7.420 19.535  1.00  34.27
ATOM   1526  CD2  HIS  A  501    28.726   6.540 18.931  1.00  36.10
ATOM   1527  ND1  HIS  A  501    28.541   7.844 20.676  1.00  31.81
ATOM   1528  CE1  HIS  A  501    29.716   7.244 20.758  1.00  34.89
ATOM   1529  NE2  HIS  A  501    29.854   6.448 19.712  1.00  37.46
ATOM   1530  C    HIS  A  501    24.935   8.572 17.348  1.00  24.93
ATOM   1531  O    HIS  A  501    23.998   7.815 17.107  1.00  26.73
ATOM   1532  N    GLN  A  502    24.796   9.892 17.379  1.00  22.79
ATOM   1533  CA   GLN  A  502    23.504  10.498 17.119  1.00  26.14
ATOM   1534  CB   GLN  A  502    23.554  12.006 17.371  1.00  22.36
ATOM   1535  CG   GLN  A  502    23.460  12.378 18.848  1.00  26.19
ATOM   1536  CD   GLN  A  502    23.589  13.875 19.089  1.00  28.67
ATOM   1537  OE1  GLN  A  502    23.632  14.663 18.149  1.00  38.40
ATOM   1538  NE2  GLN  A  502    23.651  14.268 20.355  1.00  24.72
ATOM   1539  C    GLN  A  502    23.056  10.221 15.685  1.00  26.19
ATOM   1540  O    GLN  A  502    21.913   9.822 15.453  1.00  24.09
ATOM   1541  N    ARG  A  503    23.955  10.429 14.727  1.00  24.88
ATOM   1542  CA   ARG  A  503    23.630  10.196 13.326  1.00  25.25
ATOM   1543  CB   ARG  A  503    24.772  10.668 12.418  1.00  27.63
ATOM   1544  CG   ARG  A  503    24.432  10.563 10.932  1.00  28.75
ATOM   1545  CD   ARG  A  503    25.479  11.222 10.056  1.00  27.72
ATOM   1546  NE   ARG  A  503    25.072  11.214  8.654  1.00  29.35
ATOM   1547  CZ   ARG  A  503    24.279  12.126  8.105  1.00  25.84
ATOM   1548  NH1  ARG  A  503    23.804  13.130  8.840  1.00  27.35
ATOM   1549  NH2  ARG  A  503    23.962  12.044  6.820  1.00  30.63
ATOM   1550  C    ARG  A  503    23.347   8.716 13.065  1.00  24.53
ATOM   1551  O    ARG  A  503    22.425   8.375 12.321  1.00  25.90
ATOM   1552  N    LEU  A  504    24.143   7.841 13.672  1.00  23.00
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1553  CA   LEU  A  504   23.953   6.406  13.496  1.00  22.60
ATOM   1554  CB   LEU  A  504   24.971   5.621  14.329  1.00  25.43
ATOM   1555  CG   LEU  A  504   24.781   4.100  14.344  1.00  25.23
ATOM   1556  CD1  LEU  A  504   25.166   3.505  12.991  1.00  28.52
ATOM   1557  CD2  LEU  A  504   25.627   3.495  15.444  1.00  22.14
ATOM   1558  C    LEU  A  504   22.541   6.030  13.934  1.00  22.84
ATOM   1559  O    LEU  A  504   21.846   5.288  13.246  1.00  21.51
ATOM   1560  N    ALA  A  505   22.120   6.547  15.083  1.00  20.16
ATOM   1561  CA   ALA  A  505   20.784   6.262  15.585  1.00  21.08
ATOM   1562  CB   ALA  A  505   20.605   6.868  16.980  1.00  23.57
ATOM   1563  C    ALA  A  505   19.738   6.832  14.828  1.00  20.20
ATOM   1564  O    ALA  A  505   18.754   6.164  14.293  1.00  17.31
ATOM   1565  N    GLN  A  506   19.954   8.066  14.184  1.00  22.11
ATOM   1566  CA   GLN  A  506   19.013   8.711  13.277  1.00  21.70
ATOM   1567  CB   GLN  A  506   19.502  10.111  12.903  1.00  22.26
ATOM   1568  CG   GLN  A  506   19.240  11.158  13.975  1.00  25.84
ATOM   1569  CD   GLN  A  506   20.187  12.333  13.857  1.00  32.88
ATOM   1570  OE1  GLN  A  506   20.704  12.614  12.777  1.00  31.23
ATOM   1571  NE2  GLN  A  506   20.423  13.025  14.968  1.00  32.97
ATOM   1572  C    GLN  A  506   18.813   7.881  12.016  1.00  23.57
ATOM   1573  O    GLN  A  506   17.684   7.715  11.550  1.00  21.83
ATOM   1574  N    LEU  A  507   19.905   7.354  11.474  1.00  19.98
ATOM   1575  CA   LEU  A  507   19.827   6.537  10.263  1.00  22.03
ATOM   1576  CB   LEU  A  507   21.231   6.244   9.725  1.00  23.02
ATOM   1577  CG   LEU  A  507   22.026   7.457   9.225  1.00  25.80
ATOM   1578  CD1  LEU  A  507   23.371   6.994   8.713  1.00  27.67
ATOM   1579  CD2  LEU  A  507   21.264   8.176   8.130  1.00  25.62
ATOM   1580  C    LEU  A  507   19.090   5.219  10.496  1.00  22.35
ATOM   1581  O    LEU  A  507   18.242   4.825   9.695  1.00  19.33
ATOM   1582  N    LEU  A  508   19.402   4.539  11.592  1.00  21.29
ATOM   1583  CA   LEU  A  508   18.755   3.260  11.881  1.00  20.72
ATOM   1584  CB   LEU  A  508   19.501   2.535  13.001  1.00  22.29
ATOM   1585  CG   LEU  A  508   20.977   2.311  12.678  1.00  24.70
ATOM   1586  CD1  LEU  A  508   21.642   1.551  13.814  1.00  21.37
ATOM   1587  CD2  LEU  A  508   21.095   1.542  11.367  1.00  27.88
ATOM   1588  C    LEU  A  508   17.279   3.396  12.239  1.00  19.14
ATOM   1589  O    LEU  A  508   16.498   2.478  12.003  1.00  17.80
ATOM   1590  N    LEU  A  509   16.895   4.530  12.815  1.00  19.23
ATOM   1591  CA   LEU  A  509   15.495   4.747  13.173  1.00  20.14
ATOM   1592  CB   LEU  A  509   15.347   6.030  13.999  1.00  20.28
ATOM   1593  CG   LEU  A  509   15.710   5.858  15.479  1.00  21.35
ATOM   1594  CD1  LEU  A  509   15.354   7.106  16.263  1.00  19.29
ATOM   1595  CD2  LEU  A  509   14.989   4.656  16.038  1.00  20.84
ATOM   1596  C    LEU  A  509   14.681   4.841  11.885  1.00  21.69
ATOM   1597  O    LEU  A  509   13.493   4.514  11.854  1.00  22.40
ATOM   1598  N    ILE  A  510   15.343   5.270  10.815  1.00  20.22
ATOM   1599  CA   ILE  A  510   14.710   5.397   9.508  1.00  20.40
ATOM   1600  CB   ILE  A  510   15.720   5.946   8.464  1.00  28.34
ATOM   1601  CG2  ILE  A  510   15.208   5.710   7.056  1.00  32.54
ATOM   1602  CG1  ILE  A  510   15.965   7.438   8.696  1.00  28.23
ATOM   1603  CD1  ILE  A  510   14.789   8.189   9.288  1.00  33.16
ATOM   1604  C    ILE  A  510   14.210   4.025   9.049  1.00  23.21
ATOM   1605  O    ILE  A  510   13.120   3.906   8.474  1.00  21.16
ATOM   1606  N    LEU  A  511   14.998   2.989   9.323  1.00  18.38
ATOM   1607  CA   LEU  A  511   14.633   1.634   8.917  1.00  20.10
ATOM   1608  CB   LEU  A  511   15.754   0.656   9.267  1.00  21.69
ATOM   1609  CG   LEU  A  511   17.128   1.022   8.692  1.00  26.03
ATOM   1610  CD1  LEU  A  511   18.024  -0.206   8.724  1.00  22.68
```

UNITED STATES PATENT AND TRADEMARK OFFICE
CERTIFICATE OF CORRECTION

PATENT NO. : 6,965,850 B2  Page 106 of 186
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1611  CD2  LEU  A  511   16.996   1.544   7.367  1.00  26.00
ATOM   1612  C    LEU  A  511   13.326   1.181   9.543  1.00  18.81
ATOM   1613  O    LEU  A  511   12.663   0.283   9.025  1.00  17.40
ATOM   1614  N    SER  A  512   12.963   1.799  10.664  1.00  18.68
ATOM   1615  CA   SER  A  512   11.718   1.471  11.331  1.00  18.67
ATOM   1616  CB   SER  A  512   11.661   2.117  12.720  1.00  18.58
ATOM   1617  OG   SER  A  512   10.315   2.229  13.165  1.00  27.92
ATOM   1618  C    SER  A  512   10.572   1.994  10.464  1.00  18.43
ATOM   1619  O    SER  A  512    9.584   1.296  10.236  1.00  13.91
ATOM   1620  N    HIS  A  513   10.713   3.228   9.982  1.00  18.95
ATOM   1621  CA   HIS  A  513    9.698   3.831   9.124  1.00  20.82
ATOM   1622  CB   HIS  A  513   10.013   5.315   8.894  1.00  24.36
ATOM   1623  CG   HIS  A  513    9.923   6.146  10.136  1.00  32.13
ATOM   1624  CD2  HIS  A  513    8.863   6.744  10.734  1.00  35.29
ATOM   1625  ND1  HIS  A  513   11.010   6.391  10.949  1.00  35.00
ATOM   1626  CE1  HIS  A  513   10.624   7.101  11.995  1.00  34.67
ATOM   1627  NE2  HIS  A  513    9.326   7.328  11.889  1.00  35.82
ATOM   1628  C    HIS  A  513    9.650   3.079   7.790  1.00  19.08
ATOM   1629  O    HIS  A  513    8.575   2.863   7.220  1.00  21.20
ATOM   1630  N    ILE  A  514   10.809   2.662   7.297  1.00  15.58
ATOM   1631  CA   ILE  A  514   10.849   1.921   6.038  1.00  16.48
ATOM   1632  CB   ILE  A  514   12.312   1.678   5.576  1.00  20.09
ATOM   1633  CG2  ILE  A  514   12.349   0.602   4.499  1.00  19.55
ATOM   1634  CG1  ILE  A  514   12.891   2.986   5.019  1.00  22.62
ATOM   1635  CD1  ILE  A  514   14.393   2.992   4.874  1.00  27.34
ATOM   1636  C    ILE  A  514   10.112   0.590   6.210  1.00  16.40
ATOM   1637  O    ILE  A  514    9.364   0.164   5.328  1.00  17.91
ATOM   1638  N    ARG  A  515   10.301  -0.071   7.347  1.00  18.20
ATOM   1639  CA   ARG  A  515    9.585  -1.327   7.564  1.00  18.05
ATOM   1640  CB   ARG  A  515    9.984  -1.980   8.889  1.00  18.36
ATOM   1641  CG   ARG  A  515    9.173  -3.237   9.213  1.00  17.84
ATOM   1642  CD   ARG  A  515    9.823  -4.470   8.606  1.00  17.94
ATOM   1643  NE   ARG  A  515   11.038  -4.813   9.334  1.00  26.96
ATOM   1644  CZ   ARG  A  515   11.406  -6.051   9.641  1.00  25.13
ATOM   1645  NH1  ARG  A  515   10.654  -7.080   9.281  1.00  23.49
ATOM   1646  NH2  ARG  A  515   12.511  -6.254  10.340  1.00  32.16
ATOM   1647  C    ARG  A  515    8.089  -1.020   7.594  1.00  18.29
ATOM   1648  O    ARG  A  515    7.275  -1.759   7.038  1.00  16.22
ATOM   1649  N    HIS  A  516    7.726   0.085   8.237  1.00  19.33
ATOM   1650  CA   HIS  A  516    6.317   0.441   8.330  1.00  17.78
ATOM   1651  CB   HIS  A  516    6.126   1.702   9.166  1.00  16.84
ATOM   1652  CG   HIS  A  516    4.692   2.101   9.312  1.00  18.16
ATOM   1653  CD2  HIS  A  516    3.967   3.061   8.691  1.00  21.17
ATOM   1654  ND1  HIS  A  516    3.830   1.469  10.180  1.00  20.70
ATOM   1655  CE1  HIS  A  516    2.633   2.022  10.089  1.00  21.52
ATOM   1656  NE2  HIS  A  516    2.689   2.992   9.191  1.00  20.16
ATOM   1657  C    HIS  A  516    5.708   0.659   6.954  1.00  16.63
ATOM   1658  O    HIS  A  516    4.598   0.216   6.689  1.00  18.58
ATOM   1659  N    MET  A  517    6.438   1.334   6.073  1.00  15.29
ATOM   1660  CA   MET  A  517    5.925   1.589   4.730  1.00  16.58
ATOM   1661  CB   MET  A  517    6.837   2.576   4.002  1.00  18.66
ATOM   1662  CG   MET  A  517    6.805   3.978   4.631  1.00  16.88
ATOM   1663  SD   MET  A  517    7.670   5.243   3.701  1.00  24.08
ATOM   1664  CE   MET  A  517    9.390   4.777   3.962  1.00  14.30
ATOM   1665  C    MET  A  517    5.773   0.289   3.940  1.00  17.86
ATOM   1666  O    MET  A  517    4.791   0.101   3.224  1.00  18.25
ATOM   1667  N    SER  A  518    6.741  -0.610   4.086  1.00  17.43
ATOM   1668  CA   SER  A  518    6.697  -1.896   3.403  1.00  18.40
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1669  CB   SER  A  518    7.974  -2.695   3.680  1.00  16.77
ATOM   1670  OG   SER  A  518    7.834  -4.030   3.287  1.00  24.23
ATOM   1671  C    SER  A  518    5.476  -2.695   3.884  1.00  17.91
ATOM   1672  O    SER  A  518    4.788  -3.295   3.030  1.00  18.97
ATOM   1673  N    ASN  A  519    5.204  -2.697   5.159  1.00  21.82
ATOM   1674  CA   ASN  A  519    4.047  -3.418   5.696  1.00  21.99
ATOM   1675  CB   ASN  A  519    3.957  -3.357   7.216  1.00  23.34
ATOM   1676  CG   ASN  A  519    5.046  -4.011   7.957  1.00  31.14
ATOM   1677  OD1  ASN  A  519    5.585  -4.999   7.461  1.00  32.50
ATOM   1678  ND2  ASN  A  519    5.368  -3.545   9.183  1.00  29.10
ATOM   1679  C    ASN  A  519    2.761  -2.871   5.079  1.00  23.76
ATOM   1680  O    ASN  A  519    1.902  -3.632   4.631  1.00  24.48
ATOM   1681  N    LYS  A  520    2.627  -1.548   5.078  1.00  20.58
ATOM   1682  CA   LYS  A  520    1.449  -0.900   4.512  1.00  25.49
ATOM   1683  CB   LYS  A  520    1.484   0.607   4.786  1.00  24.73
ATOM   1684  CG   LYS  A  520    1.512   0.996   6.264  1.00  32.31
ATOM   1685  CD   LYS  A  520    0.656   0.080   7.133  1.00  37.11
ATOM   1686  CE   LYS  A  520   -0.787   0.547   7.181  1.00  41.56
ATOM   1687  NZ   LYS  A  520   -1.560  -0.134   8.261  1.00  42.66
ATOM   1688  C    LYS  A  520    1.380  -1.144   3.005  1.00  25.40
ATOM   1689  O    LYS  A  520    0.316  -1.436   2.487  1.00  26.44
ATOM   1690  N    GLY  A  521    2.520  -1.021   2.332  1.00  22.88
ATOM   1691  CA   GLY  A  521    2.561  -1.236   0.897  1.00  21.53
ATOM   1692  C    GLY  A  521    2.177  -2.655   0.536  1.00  24.79
ATOM   1693  O    GLY  A  521    1.426  -2.878  -0.413  1.00  25.71
ATOM   1694  N    MET  A  522    2.696  -3.619   1.290  1.00  22.75
ATOM   1695  CA   MET  A  522    2.393  -5.027   1.058  1.00  23.40
ATOM   1696  CB   MET  A  522    3.170  -5.898   2.042  1.00  25.74
ATOM   1697  CG   MET  A  522    3.396  -7.308   1.559  1.00  31.06
ATOM   1698  SD   MET  A  522    4.572  -7.352   0.202  1.00  34.06
ATOM   1699  CE   MET  A  522    6.125  -7.329   1.113  1.00  29.28
ATOM   1700  C    MET  A  522    0.893  -5.281   1.218  1.00  26.49
ATOM   1701  O    MET  A  522    0.268  -5.920   0.361  1.00  25.47
ATOM   1702  N    GLU  A  523    0.321  -4.790   2.318  1.00  24.95
ATOM   1703  CA   GLU  A  523   -1.110  -4.954   2.566  1.00  27.15
ATOM   1704  CB   GLU  A  523   -1.555  -4.206   3.835  1.00  31.08
ATOM   1705  CG   GLU  A  523   -0.830  -4.564   5.124  1.00  38.93
ATOM   1706  CD   GLU  A  523   -1.153  -3.585   6.258  1.00  46.90
ATOM   1707  OE1  GLU  A  523   -2.225  -2.938   6.200  1.00  47.40
ATOM   1708  OE2  GLU  A  523   -0.337  -3.450   7.202  1.00  47.39
ATOM   1709  C    GLU  A  523   -1.872  -4.368   1.381  1.00  26.10
ATOM   1710  O    GLU  A  523   -2.817  -4.964   0.882  1.00  24.25
ATOM   1711  N    HIS  A  524   -1.449  -3.182   0.940  1.00  24.74
ATOM   1712  CA   HIS  A  524   -2.093  -2.505  -0.173  1.00  26.17
ATOM   1713  CB   HIS  A  524   -1.481  -1.125  -0.379  1.00  24.64
ATOM   1714  CG   HIS  A  524   -2.233  -0.278  -1.355  1.00  30.59
ATOM   1715  CD2  HIS  A  524   -3.227   0.624  -1.172  1.00  32.15
ATOM   1716  ND1  HIS  A  524   -2.008  -0.332  -2.713  1.00  27.46
ATOM   1717  CE1  HIS  A  524   -2.829   0.502  -3.336  1.00  34.58
ATOM   1718  NE2  HIS  A  524   -3.580   1.094  -2.413  1.00  30.50
ATOM   1719  C    HIS  A  524   -1.996  -3.294  -1.474  1.00  28.06
ATOM   1720  O    HIS  A  524   -2.976  -3.419  -2.217  1.00  29.81
ATOM   1721  N    LEU  A  525   -0.811  -3.824  -1.746  1.00  27.07
ATOM   1722  CA   LEU  A  525   -0.594  -4.601  -2.955  1.00  29.30
ATOM   1723  CB   LEU  A  525    0.865  -5.039  -3.051  1.00  26.39
ATOM   1724  CG   LEU  A  525    1.307  -5.765  -4.321  1.00  29.34
ATOM   1725  CD1  LEU  A  525    0.734  -5.076  -5.562  1.00  29.61
ATOM   1726  CD2  LEU  A  525    2.829  -5.769  -4.370  1.00  29.22
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

Page 108 of 186

It is certified that error appears in the above-identified patent and that said Letters Patent is hereby corrected as shown below:

```
ATOM   1727  C    LEU  A  525   -1.497  -5.822  -2.950  1.00  31.67
ATOM   1728  O    LEU  A  525   -2.126  -6.133  -3.957  1.00  32.45
ATOM   1729  N    TYR  A  526   -1.559  -6.512  -1.814  1.00  36.14
ATOM   1730  CA   TYR  A  526   -2.397  -7.698  -1.696  1.00  40.36
ATOM   1731  CB   TYR  A  526   -2.221  -8.350  -0.324  1.00  45.27
ATOM   1732  CG   TYR  A  526   -2.849  -9.722  -0.229  1.00  50.62
ATOM   1733  CD1  TYR  A  526   -2.114 -10.867  -0.537  1.00  54.55
ATOM   1734  CE1  TYR  A  526   -2.698 -12.136  -0.482  1.00  57.27
ATOM   1735  CD2  TYR  A  526   -4.188  -9.876   0.142  1.00  53.48
ATOM   1736  CE2  TYR  A  526   -4.781 -11.141   0.201  1.00  55.93
ATOM   1737  CZ   TYR  A  526   -4.029 -12.364  -0.113  1.00  56.60
ATOM   1738  OH   TYR  A  526   -4.603 -13.515  -0.063  1.00  60.70
ATOM   1739  C    TYR  A  526   -3.852  -7.298  -1.893  1.00  42.83
ATOM   1740  O    TYR  A  526   -4.673  -8.094  -2.349  1.00  43.49
ATOM   1741  N    SER  A  527   -4.158  -6.055  -1.543  1.00  41.55
ATOM   1742  CA   SER  A  527   -5.503  -5.523  -1.686  1.00  44.04
ATOM   1743  CB   SER  A  527   -5.606  -4.169  -0.979  1.00  43.47
ATOM   1744  OG   SER  A  527   -6.954  -3.789  -0.786  1.00  47.51
ATOM   1745  C    SER  A  527   -5.817  -5.356  -3.172  1.00  44.18
ATOM   1746  O    SER  A  527   -6.883  -5.757  -3.642  1.00  44.88
ATOM   1747  N    MET  A  528   -4.883  -4.755  -3.901  1.00  41.79
ATOM   1748  CA   MET  A  528   -5.047  -4.536  -5.331  1.00  44.04
ATOM   1749  CB   MET  A  528   -3.898  -3.679  -5.870  1.00  44.78
ATOM   1750  CG   MET  A  528   -3.965  -2.206  -5.468  1.00  45.37
ATOM   1751  SD   MET  A  528   -5.652  -1.598  -5.273  1.00  51.63
ATOM   1752  CE   MET  A  528   -5.553  -0.004  -6.044  1.00  46.61
ATOM   1753  C    MET  A  528   -5.087  -5.871  -6.071  1.00  44.29
ATOM   1754  O    MET  A  528   -5.689  -5.979  -7.137  1.00  44.02
ATOM   1755  N    LYS  A  529   -4.443  -6.883  -5.499  1.00  46.78
ATOM   1756  CA   LYS  A  529   -4.413  -8.213  -6.099  1.00  51.28
ATOM   1757  CB   LYS  A  529   -3.580  -9.158  -5.261  1.00  50.87
ATOM   1758  CG   LYS  A  529   -2.798 -10.204  -6.071  1.00  50.55
ATOM   1759  CD   LYS  A  529   -3.548 -11.520  -6.104  1.00  51.25
ATOM   1760  CE   LYS  A  529   -2.616 -12.694  -5.856  1.00  53.22
ATOM   1761  NZ   LYS  A  529   -2.420 -12.954  -4.402  1.00  53.22
ATOM   1762  C    LYS  A  529   -5.829  -8.758  -6.182  1.00  54.27
ATOM   1763  O    LYS  A  529   -6.325  -9.069  -7.266  1.00  55.50
ATOM   1764  N    CYS  A  530   -6.472  -8.901  -5.027  1.00  56.71
ATOM   1765  CA   CYS  A  530   -7.833  -9.416  -4.961  1.00  58.35
ATOM   1766  CB   CYS  A  530   -8.333  -9.360  -3.517  1.00  59.78
ATOM   1767  SG   CYS  A  530   -7.289 -10.304  -2.358  1.00  63.19
ATOM   1768  C    CYS  A  530   -8.766  -8.609  -5.858  1.00  59.36
ATOM   1769  O    CYS  A  530   -9.644  -9.169  -6.514  1.00  59.52
ATOM   1770  N    LYS  A  531   -8.569  -7.293  -5.888  1.00  59.24
ATOM   1771  CA   LYS  A  531   -9.390  -6.411  -6.713  1.00  60.14
ATOM   1772  CB   LYS  A  531   -9.158  -4.952  -6.317  1.00  58.92
ATOM   1773  C    LYS  A  531   -9.073  -6.615  -8.195  1.00  61.48
ATOM   1774  O    LYS  A  531   -9.618  -5.928  -9.061  1.00  61.74
ATOM   1775  N    ASN  A  532   -8.179  -7.561  -8.474  1.00  61.65
ATOM   1776  CA   ASN  A  532   -7.783  -7.890  -9.840  1.00  61.60
ATOM   1777  CB   ASN  A  532   -8.966  -8.518 -10.581  1.00  62.28
ATOM   1778  CG   ASN  A  532   -8.750  -9.985 -10.878  1.00  64.66
ATOM   1779  OD1  ASN  A  532   -8.344 10.352 -11.983  1.00  67.08
ATOM   1780  ND2  ASN  A  532   -9.016 -10.836  -9.891  1.00  62.68
ATOM   1781  C    ASN  A  532   -7.247  -6.710 -10.648  1.00  59.75
ATOM   1782  O    ASN  A  532   -7.487  -6.615 -11.850  1.00  57.50
ATOM   1783  N    VAL  A  533   -6.507  -5.822  -9.992  1.00  59.39
ATOM   1784  CA   VAL  A  533   -5.954  -4.656 -10.669  1.00  58.22
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    1785  CB   VAL  A  533   -6.223   -3.371  -9.865  1.00  59.20
ATOM    1786  CG1  VAL  A  533   -6.181   -2.163 -10.785  1.00  59.21
ATOM    1787  CG2  VAL  A  533   -7.574   -3.467  -9.172  1.00  59.57
ATOM    1788  C    VAL  A  533   -4.452   -4.767 -10.907  1.00  57.86
ATOM    1789  O    VAL  A  533   -3.846   -3.874 -11.499  1.00  60.56
ATOM    1790  N    VAL  A  534   -3.852   -5.863 -10.451  1.00  56.03
ATOM    1791  CA   VAL  A  534   -2.417   -6.063 -10.621  1.00  54.11
ATOM    1792  CB   VAL  A  534   -1.767   -6.832  -9.341  1.00  54.02
ATOM    1793  CG1  VAL  A  534   -0.300   -6.950  -9.601  1.00  52.37
ATOM    1794  CG2  VAL  A  534   -1.900   -5.635  -8.200  1.00  55.70
ATOM    1795  C    VAL  A  534   -2.089   -7.008 -11.770  1.00  54.31
ATOM    1796  O    VAL  A  534   -2.519   -8.164 -11.780  1.00  51.66
ATOM    1797  N    PRO  A  535   -1.315   -6.527 -12.785  1.00  53.54
ATOM    1798  CD   PRO  A  535   -0.749   -5.172 -12.874  1.00  54.28
ATOM    1799  CA   PRO  A  535   -0.949   -7.373 -13.893  1.00  53.24
ATOM    1800  CB   PRO  A  535    0.011   -6.500 -14.697  1.00  52.71
ATOM    1801  CG   PRO  A  535   -0.353   -5.102 -14.319  1.00  53.19
ATOM    1802  C    PRO  A  535   -0.296   -8.664 -13.411  1.00  54.25
ATOM    1803  O    PRO  A  535    0.121   -8.768 -12.254  1.00  54.56
ATOM    1804  N    LEU  A  536   -0.203   -9.645 -14.299  1.00  53.63
ATOM    1805  CA   LEU  A  536    0.382  -10.926 -13.937  1.00  53.11
ATOM    1806  CB   LEU  A  536   -0.250  -12.046 -14.763  1.00  51.88
ATOM    1807  CG   LEU  A  536   -0.686  -13.256 -13.938  1.00  51.83
ATOM    1808  CD1  LEU  A  536   -1.953  -12.917 -13.173  1.00  49.51
ATOM    1809  CD2  LEU  A  536   -0.905  -14.449 -14.854  1.00  53.43
ATOM    1810  C    LEU  A  536    1.895  -10.990 -14.081  1.00  52.58
ATOM    1811  O    LEU  A  536    2.414  -11.501 -15.075  1.00  55.33
ATOM    1812  N    TYR  A  537    2.601  -10.462 -13.087  1.00  48.72
ATOM    1813  CA   TYR  A  537    4.057  -10.501 -13.093  1.00  44.22
ATOM    1814  CB   TYR  A  537    4.627   -9.134 -12.709  1.00  44.52
ATOM    1815  CG   TYR  A  537    4.331   -8.053 -13.731  1.00  45.18
ATOM    1816  CD1  TYR  A  537    3.623   -6.905 -13.376  1.00  43.77
ATOM    1817  CE1  TYR  A  537    3.334   -5.915 -14.317  1.00  45.23
ATOM    1818  CD2  TYR  A  537    4.747   -8.187 -15.058  1.00  46.91
ATOM    1819  CE2  TYR  A  537    4.462   -7.202 -16.008  1.00  43.93
ATOM    1820  CZ   TYR  A  537    3.757   -6.071 -15.180  1.00  46.70
ATOM    1821  OH   TYR  A  537    3.472   -5.097 -16.565  1.00  48.35
ATOM    1822  C    TYR  A  537    4.401  -11.562 -12.086  1.00  41.29
ATOM    1823  O    TYR  A  537    4.330  -11.319 -10.856  1.00  41.82
ATOM    1824  N    ASP  A  538    4.748  -12.748 -12.540  1.00  40.34
ATOM    1825  CA   ASP  A  538    5.055  -13.896 -11.691  1.00  38.84
ATOM    1826  CB   ASP  A  538    5.594  -15.037 -12.554  1.00  43.47
ATOM    1827  CG   ASP  A  538    4.571  -15.831 -13.566  1.00  47.67
ATOM    1828  OD1  ASP  A  538    4.931  -16.373 -14.416  1.00  49.33
ATOM    1829  OD2  ASP  A  538    3.405  -15.073 -13.511  1.00  48.07
ATOM    1830  C    ASP  A  538    5.991  -13.676 -10.508  1.00  37.28
ATOM    1831  O    ASP  A  538    5.620  -13.964  -9.371  1.00  38.55
ATOM    1832  N    LEU  A  539    7.196  -13.200 -10.766  1.00  33.83
ATOM    1833  CA   LEU  A  539    8.155  -12.959  -9.692  1.00  32.80
ATOM    1834  CB   LEU  A  539    9.419  -12.323 -10.263  1.00  32.78
ATOM    1835  CG   LEU  A  539   10.561  -12.031  -9.292  1.00  30.93
ATOM    1836  CD1  LEU  A  539   10.913  -13.280  -8.492  1.00  33.81
ATOM    1837  CD2  LEU  A  539   11.758  -11.538 -10.077  1.00  25.92
ATOM    1838  C    LEU  A  539    7.558  -12.050  -8.614  1.00  31.85
ATOM    1839  O    LEU  A  539    7.590  -12.367  -7.423  1.00  25.63
ATOM    1840  N    LEU  A  540    7.011  -10.917  -9.042  1.00  32.07
ATOM    1841  CA   LEU  A  540    6.411   -9.976  -8.111  1.00  31.03
ATOM    1842  CB   LEU  A  540    5.792   -8.800  -8.861  1.00  30.56
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

| | | | | | | | | | |
|---|---|---|---|---|---|---|---|---|---|
| ATOM | 1843 | CG  | LEU | A | 540 | 5.124  | -7.774  | -7.945 | 1.00 31.12 |
| ATOM | 1844 | CD1 | LEU | A | 540 | 6.092  | -7.357  | -6.838 | 1.00 29.76 |
| ATOM | 1845 | CD2 | LEU | A | 540 | 4.693  | -6.572  | -8.782 | 1.00 30.85 |
| ATOM | 1846 | C   | LEU | A | 540 | 5.337  | -10.660 | -7.282 | 1.00 34.55 |
| ATOM | 1847 | O   | LEU | A | 540 | 5.316  | -10.522 | -6.063 | 1.00 31.60 |
| ATOM | 1848 | N   | LEU | A | 541 | 4.446  | -11.388 | -7.941 | 1.00 35.64 |
| ATOM | 1849 | CA  | LEU | A | 541 | 3.378  | -12.101 | -7.245 | 1.00 37.84 |
| ATOM | 1850 | CB  | LEU | A | 541 | 2.452  | -12.771 | -8.255 | 1.00 38.49 |
| ATOM | 1851 | CG  | LEU | A | 541 | 1.244  | -11.932 | -8.678 | 1.00 39.80 |
| ATOM | 1852 | CD1 | LEU | A | 541 | 0.476  | -11.478 | -7.448 | 1.00 40.02 |
| ATOM | 1853 | CD2 | LEU | A | 541 | 1.713  | -10.733 | -9.485 | 1.00 40.48 |
| ATOM | 1854 | C   | LEU | A | 541 | 3.937  | -13.147 | -6.275 | 1.00 40.10 |
| ATOM | 1855 | O   | LEU | A | 541 | 3.472  | -13.254 | -5.137 | 1.00 42.72 |
| ATOM | 1856 | N   | GLU | A | 542 | 4.929  | -13.915 | -6.723 | 1.00 38.45 |
| ATOM | 1857 | CA  | GLU | A | 542 | 5.535  | -14.932 | -5.868 | 1.00 39.59 |
| ATOM | 1858 | CB  | GLU | A | 542 | 6.738  | -15.566 | -6.564 | 1.00 41.73 |
| ATOM | 1859 | CG  | GLU | A | 542 | 6.396  | -16.327 | -7.831 | 1.00 48.34 |
| ATOM | 1860 | CD  | GLU | A | 542 | 6.931  | -17.747 | -7.819 | 1.00 52.57 |
| ATOM | 1861 | OE1 | GLU | A | 542 | 8.049  | -17.961 | -7.298 | 1.00 52.70 |
| ATOM | 1862 | OE2 | GLU | A | 542 | 6.230  | -18.647 | -8.331 | 1.00 53.69 |
| ATOM | 1863 | C   | GLU | A | 542 | 5.989  | -14.299 | -4.553 | 1.00 39.94 |
| ATOM | 1864 | O   | GLU | A | 542 | 5.367  | -14.710 | -3.472 | 1.00 40.99 |
| ATOM | 1865 | N   | MET | A | 543 | 6.844  | -13.287 | -4.663 | 1.00 38.29 |
| ATOM | 1866 | CA  | MET | A | 543 | 7.380  | -12.580 | -3.503 | 1.00 38.11 |
| ATOM | 1867 | CB  | MET | A | 543 | 8.242  | -11.408 | -3.963 | 1.00 37.34 |
| ATOM | 1868 | CG  | MET | A | 543 | 9.311  | -11.797 | -4.953 | 1.00 40.59 |
| ATOM | 1869 | SD  | MET | A | 543 | 10.829 | -12.223 | -4.114 | 1.00 45.64 |
| ATOM | 1870 | CE  | MET | A | 543 | 12.014 | -11.399 | -5.151 | 1.00 42.61 |
| ATOM | 1871 | C   | MET | A | 543 | 6.287  | -12.064 | -2.581 | 1.00 37.94 |
| ATOM | 1872 | O   | MET | A | 543 | 6.413  | -12.127 | -1.358 | 1.00 39.20 |
| ATOM | 1873 | N   | LEU | A | 544 | 5.218  | -11.544 | -3.175 | 1.00 39.44 |
| ATOM | 1874 | CA  | LEU | A | 544 | 4.100  | -11.013 | -2.408 | 1.00 40.91 |
| ATOM | 1875 | CB  | LEU | A | 544 | 3.087  | -10.344 | -3.341 | 1.00 39.88 |
| ATOM | 1876 | CG  | LEU | A | 544 | 1.775  | -9.905  | -2.688 | 1.00 42.70 |
| ATOM | 1877 | CD1 | LEU | A | 544 | 2.060  | -8.886  | -1.586 | 1.00 37.35 |
| ATOM | 1878 | CD2 | LEU | A | 544 | 0.854  | -9.317  | -3.741 | 1.00 38.47 |
| ATOM | 1879 | C   | LEU | A | 544 | 3.420  | -12.120 | -1.614 | 1.00 42.83 |
| ATOM | 1880 | O   | LEU | A | 544 | 2.957  | -11.899 | -0.496 | 1.00 42.73 |
| ATOM | 1881 | N   | ASP | A | 545 | 3.367  | -13.313 | -2.197 | 1.00 46.32 |
| ATOM | 1882 | CA  | ASP | A | 545 | 2.746  | -14.456 | -1.539 | 1.00 50.65 |
| ATOM | 1883 | CB  | ASP | A | 545 | 2.606  | -15.617 | -2.524 | 1.00 53.67 |
| ATOM | 1884 | CG  | ASP | A | 545 | 1.703  | -15.278 | -3.691 | 1.00 57.35 |
| ATOM | 1885 | OD1 | ASP | A | 545 | 0.697  | -14.568 | -3.475 | 1.00 59.99 |
| ATOM | 1886 | OD2 | ASP | A | 545 | 1.999  | -15.718 | -4.824 | 1.00 59.68 |
| ATOM | 1887 | C   | ASP | A | 545 | 3.559  | -14.898 | -0.327 | 1.00 50.74 |
| ATOM | 1888 | O   | ASP | A | 545 | 3.004  | -15.388 | 0.657  | 1.00 49.39 |
| ATOM | 1889 | N   | ALA | A | 546 | 4.874  | -14.723 | -0.401 | 1.00 51.82 |
| ATOM | 1890 | CA  | ALA | A | 546 | 5.750  | -15.095 | 0.702  | 1.00 53.12 |
| ATOM | 1891 | CB  | ALA | A | 546 | 7.180  | -14.678 | 0.395  | 1.00 53.19 |
| ATOM | 1892 | C   | ALA | A | 546 | 5.269  | -14.424 | 1.987  | 1.00 54.67 |
| ATOM | 1893 | O   | ALA | A | 546 | 5.476  | -14.940 | 3.085  | 1.00 52.32 |
| ATOM | 1894 | N   | HIS | A | 547 | 4.622  | -13.270 | 1.838  | 1.00 56.66 |
| ATOM | 1895 | CA  | HIS | A | 547 | 4.102  | -12.520 | 2.978  | 1.00 59.19 |
| ATOM | 1896 | CB  | HIS | A | 547 | 4.144  | -11.017 | 2.684  | 1.00 56.70 |
| ATOM | 1897 | CG  | HIS | A | 547 | 5.489  | -10.394 | 2.896  | 1.00 54.64 |
| ATOM | 1898 | CD2 | HIS | A | 547 | 6.644  | -10.506 | 2.199  | 1.00 53.92 |
| ATOM | 1899 | ND1 | HIS | A | 547 | 5.748  | -9.514  | 3.925  | 1.00 52.17 |
| ATOM | 1900 | CE1 | HIS | A | 547 | 7.004  | -9.111  | 3.853  | 1.00 52.16 |

UNITED STATES PATENT AND TRADEMARK OFFICE
CERTIFICATE OF CORRECTION

PATENT NO. : 6,965,850 B2  
APPLICATION NO. : 09/281717  
DATED : November 15, 2005  
INVENTOR(S) : John D. Baxter et al.

Page 111 of 186

It is certified that error appears in the above-identified patent and that said Letters Patent is hereby corrected as shown below:

```
ATOM    1901  NE2  HIS  A  547    7.570   -9.698   2.814  1.00  51.90
ATOM    1902  C    HIS  A  547    2.668  -12.940   3.306  1.00  62.77
ATOM    1903  O    HIS  A  547    1.842  -12.120   3.707  1.00  63.24
ATOM    1904  N    ARG  A  548    2.381  -14.224   3.133  1.00  68.37
ATOM    1905  CA   ARG  A  548    1.053  -14.758   3.411  1.00  72.75
ATOM    1906  CB   ARG  A  548    0.243  -14.864   2.113  1.00  73.73
ATOM    1907  CG   ARG  A  548   -1.149  -14.243   2.186  1.00  74.04
ATOM    1908  CD   ARG  A  548   -1.081  -12.728   2.297  1.00  74.50
ATOM    1909  NE   ARG  A  548   -2.305  -12.167   2.863  1.00  75.04
ATOM    1910  CZ   ARG  A  548   -2.478  -10.880   3.149  1.00  75.59
ATOM    1911  NH1  ARG  A  548   -1.506  -10.006   2.919  1.00  75.79
ATOM    1912  NH2  ARG  A  548   -3.627  -10.464   3.662  1.00  76.00
ATOM    1913  C    ARG  A  548    1.179  -16.133   4.081  1.00  74.94
ATOM    1914  O    ARG  A  548    0.197  -16.697   4.549  1.00  75.15
ATOM    1915  N    LEU  A  549    2.398  -16.665   4.063  1.00  76.49
ATOM    1916  CA   LEU  A  549    2.669  -17.969   4.653  1.00  78.14
ATOM    1917  CB   LEU  A  549    2.971  -18.986   3.557  1.00  77.55
ATOM    1918  C    LEU  A  549    3.846  -17.870   5.619  1.00  79.13
ATOM    1919  O    LEU  A  549    4.892  -17.317   5.215  1.00  80.40
ATOM    1920  OXT  LEU  A  549    3.708  -18.341   6.769  1.00  79.46
HETATM  1921  CP9  DES  A  600    5.390   -3.061  -6.139  1.00  21.38
HETATM  1922  CP8  DES  A  600    5.834   -1.989  -5.134  1.00  22.41
HETATM  1923  CP7  DES  A  600    5.038   -0.714  -5.236  1.00  21.32
HETATM  1924  CP6  DES  A  600    3.587   -0.864  -5.062  1.00  25.87
HETATM  1925  CP1  DES  A  600    2.987   -0.978  -3.784  1.00  23.92
HETATM  1926  CP2  DES  A  600    1.597   -1.150  -3.694  1.00  29.77
HETATM  1927  CP3  DES  A  600    0.842   -1.214  -4.871  1.00  31.40
HETATM  1928  OP3  DES  A  600   -0.506   -1.419  -4.834  1.00  33.36
HETATM  1929  CP4  DES  A  600    1.421   -1.099  -6.143  1.00  27.01
HETATM  1930  CP5  DES  A  600    2.793   -0.929  -6.230  1.00  27.40
HETATM  1931  C7   DES  A  600    5.671    0.461  -5.482  1.00  22.39
HETATM  1932  C6   DES  A  600    7.113    0.561  -5.809  1.00  21.75
HETATM  1933  C5   DES  A  600    7.541    0.306  -7.131  1.00  19.97
HETATM  1934  C4   DES  A  600    8.889    0.429  -7.477  1.00  23.81
HETATM  1935  C3   DES  A  600    9.814    0.804  -6.488  1.00  21.88
HETATM  1936  O3   DES  A  600   11.125    0.901  -6.839  1.00  22.32
HETATM  1937  C2   DES  A  600    9.423    1.066  -5.161  1.00  19.74
HETATM  1938  C1   DES  A  600    8.066    0.937  -4.838  1.00  21.25
HETATM  1939  C8   DES  A  600    4.894    1.765  -5.443  1.00  21.47
HETATM  1940  C9   DES  A  600    4.959    2.468  -4.070  1.00  21.38
HETATM  1941  CL   CL   A  601   14.781   -3.035 -17.739  1.00  24.10
ATOM    1942  CB   SER  B  305   12.321   21.086  25.295  1.00  64.27
ATOM    1943  C    SER  B  305   12.672   22.102  27.548  1.00  64.37
ATOM    1944  O    SER  B  305   13.701   22.760  27.702  1.00  66.90
ATOM    1945  N    SER  B  305   12.045   23.521  25.606  1.00  63.72
ATOM    1946  CA   SER  B  305   11.875   22.187  26.251  1.00  64.21
ATOM    1947  N    LEU  B  306   12.193   21.293  28.484  1.00  63.09
ATOM    1948  CA   LEU  B  306   12.884   21.133  29.757  1.00  60.98
ATOM    1949  CB   LEU  B  306   11.884   21.200  30.913  1.00  61.23
ATOM    1950  CG   LEU  B  306   12.221   20.417  32.183  1.00  62.23
ATOM    1951  CD1  LEU  B  306   13.304   21.144  32.966  1.00  62.56
ATOM    1952  CD2  LEU  B  306   10.965   20.258  33.027  1.00  64.31
ATOM    1953  C    LEU  B  306   13.660   19.819  29.803  1.00  58.39
ATOM    1954  O    LEU  B  306   14.570   19.654  30.614  1.00  58.56
ATOM    1955  N    ALA  B  307   13.293   18.881  28.933  1.00  54.82
ATOM    1956  CA   ALA  B  307   13.971   17.589  28.861  1.00  50.62
ATOM    1957  CB   ALA  B  307   13.092   16.584  28.143  1.00  51.30
ATOM    1958  C    ALA  B  307   15.303   17.719  28.122  1.00  46.84
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1959  O    ALA  B  307   16.196  16.885 28.274  1.00  45.62
ATOM   1960  N    LEU  B  308   15.431  18.769 27.320  1.00  43.46
ATOM   1961  CA   LEU  B  308   16.643  18.983 26.542  1.00  43.01
ATOM   1962  CB   LEU  B  308   16.413  20.100 25.526  1.00  41.32
ATOM   1963  CG   LEU  B  308   16.315  19.708 24.051  1.00  43.10
ATOM   1964  CD1  LEU  B  308   15.942  18.239 23.903  1.00  40.51
ATOM   1965  CD2  LEU  B  308   15.287  20.602 23.375  1.00  39.80
ATOM   1966  C    LEU  B  308   17.874  19.297 27.385  1.00  42.11
ATOM   1967  O    LEU  B  308   19.000  19.102 26.932  1.00  44.34
ATOM   1968  N    SER  B  309   17.669  19.775 28.608  1.00  40.88
ATOM   1969  CA   SER  B  309   18.796  20.100 29.475  1.00  42.79
ATOM   1970  CB   SER  B  309   18.562  21.447 30.163  1.00  41.25
ATOM   1971  OG   SER  B  309   17.459  21.379 31.046  1.00  46.67
ATOM   1972  C    SER  B  309   19.072  19.028 30.529  1.00  42.60
ATOM   1973  O    SER  B  309   20.083  19.119 31.269  1.00  44.18
ATOM   1974  N    LEU  B  310   18.217  18.012 30.696  1.00  39.44
ATOM   1975  CA   LEU  B  310   18.394  16.936 31.569  1.00  37.62
ATOM   1976  CB   LEU  B  310   17.205  15.969 31.499  1.00  38.84
ATOM   1977  CG   LEU  B  310   16.216  15.873 32.668  1.00  42.43
ATOM   1978  CD1  LEU  B  310   16.040  17.219 33.355  1.00  42.55
ATOM   1979  CD2  LEU  B  310   14.881  15.380 32.138  1.00  39.69
ATOM   1980  C    LEU  B  310   19.691  16.174 31.285  1.00  34.11
ATOM   1981  O    LEU  B  310   20.111  16.070 30.139  1.00  34.41
ATOM   1982  N    THR  B  311   20.339  15.662 32.326  1.00  34.04
ATOM   1983  CA   THR  B  311   21.564  14.888 32.127  1.00  32.34
ATOM   1984  CB   THR  B  311   22.434  14.824 33.399  1.00  31.75
ATOM   1985  OG1  THR  B  311   21.724  14.116 34.420  1.00  36.20
ATOM   1986  CG2  THR  B  311   22.782  16.212 33.893  1.00  31.05
ATOM   1987  C    THR  B  311   21.145  13.460 31.790  1.00  32.37
ATOM   1988  O    THR  B  311   19.967  13.117 31.899  1.00  28.16
ATOM   1989  N    ALA  B  312   22.106  12.628 31.396  1.00  33.23
ATOM   1990  CA   ALA  B  312   21.811  11.237 31.053  1.00  35.63
ATOM   1991  CB   ALA  B  312   23.077  10.527 30.577  1.00  34.00
ATOM   1992  C    ALA  B  312   21.210  10.489 32.240  1.00  34.29
ATOM   1993  O    ALA  B  312   20.226   9.766 32.089  1.00  33.10
ATOM   1994  N    ASP  B  313   21.800  10.665 33.419  1.00  33.90
ATOM   1995  CA   ASP  B  313   21.304   9.994 34.615  1.00  34.19
ATOM   1996  CB   ASP  B  313   22.258  10.219 35.788  1.00  42.09
ATOM   1997  CG   ASP  B  313   23.494   9.358 35.700  1.00  44.87
ATOM   1998  OD1  ASP  B  313   24.586   9.858 36.040  1.00  51.57
ATOM   1999  OD2  ASP  B  313   23.377   8.184 35.290  1.00  46.79
ATOM   2000  C    ASP  B  313   19.925  10.520 34.971  1.00  31.99
ATOM   2001  O    ASP  B  313   19.056   9.768 35.426  1.00  32.03
ATOM   2002  N    GLN  B  314   19.733  11.819 34.763  1.00  29.38
ATOM   2003  CA   GLN  B  314   18.458  12.457 35.046  1.00  29.73
ATOM   2004  CB   GLN  B  314   18.562  13.966 34.832  1.00  32.88
ATOM   2005  CG   GLN  B  314   18.970  14.732 36.085  1.00  36.47
ATOM   2006  CD   GLN  B  314   19.213  16.208 35.815  1.00  36.76
ATOM   2007  OE1  GLN  B  314   19.300  16.634 34.664  1.00  38.79
ATOM   2008  NE2  GLN  B  314   19.327  16.995 36.880  1.00  39.72
ATOM   2009  C    GLN  B  314   17.409  11.873 34.116  1.00  29.11
ATOM   2010  O    GLN  B  314   16.274  11.620 34.522  1.00  28.82
ATOM   2011  N    MET  B  315   17.801  11.657 32.864  1.00  27.27
ATOM   2012  CA   MET  B  315   16.900  11.079 31.872  1.00  30.41
ATOM   2013  CB   MET  B  315   17.595  11.029 30.509  1.00  30.10
ATOM   2014  CG   MET  B  315   16.787  10.345 29.421  1.00  38.02
ATOM   2015  SD   MET  B  315   15.252  11.220 29.065  1.00  41.12
ATOM   2016  CE   MET  B  315   15.830  12.835 28.611  1.00  39.32
```

Page 112 of 186

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   2017  C    MET  B  315   16.490   9.665 32.311  1.00  27.99
ATOM   2018  O    MET  B  315   15.302   9.351 32.396  1.00  26.68
ATOM   2019  N    VAL  B  316   17.481   8.823 32.598  1.00  27.26
ATOM   2020  CA   VAL  B  316   17.229   7.447 33.027  1.00  26.54
ATOM   2021  CB   VAL  B  316   18.554   6.708 33.381  1.00  36.22
ATOM   2022  CG1  VAL  B  316   18.272   5.404 34.096  1.00  29.81
ATOM   2023  CG2  VAL  B  316   19.302   6.410 32.074  1.00  29.75
ATOM   2024  C    VAL  B  316   16.326   7.389 34.288  1.00  27.22
ATOM   2025  O    VAL  B  316   15.397   6.579 34.318  1.00  25.55
ATOM   2026  N    SER  B  317   16.601   8.243 35.242  1.00  24.40
ATOM   2027  CA   SER  B  317   15.799   8.268 36.460  1.00  27.63
ATOM   2028  CB   SER  B  317   16.358   9.294 37.451  1.00  31.68
ATOM   2029  OG   SER  B  317   17.492   8.771 38.112  1.00  39.97
ATOM   2030  C    SER  B  317   14.345   8.600 36.154  1.00  36.73
ATOM   2031  O    SER  B  317   13.434   7.932 36.648  1.00  35.65
ATOM   2032  N    ALA  B  318   14.135   9.634 35.342  1.00  24.19
ATOM   2033  CA   ALA  B  318   12.786  10.049 34.969  1.00  24.17
ATOM   2034  CB   ALA  B  318   12.850  11.250 34.022  1.00  21.44
ATOM   2035  C    ALA  B  318   12.038   8.890 34.306  1.00  21.63
ATOM   2036  O    ALA  B  318   10.902   8.598 34.648  1.00  20.25
ATOM   2037  N    LEU  B  319   12.695   8.225 33.364  1.00  23.37
ATOM   2038  CA   LEU  B  319   12.098   7.102 32.652  1.00  25.42
ATOM   2039  CB   LEU  B  319   13.050   6.535 31.548  1.00  22.03
ATOM   2040  CG   LEU  B  319   13.264   7.622 30.394  1.00  20.71
ATOM   2041  CD1  LEU  B  319   14.146   6.995 29.331  1.00  23.60
ATOM   2042  CD2  LEU  B  319   11.918   8.020 29.803  1.00  23.82
ATOM   2043  C    LEU  B  319   11.729   5.926 33.564  1.00  27.26
ATOM   2044  O    LEU  B  319   10.615   5.396 33.488  1.00  28.91
ATOM   2045  N    LEU  B  320   12.656   5.516 34.426  1.00  26.38
ATOM   2046  CA   LEU  B  320   12.399   4.405 35.334  1.00  26.73
ATOM   2047  CB   LEU  B  320   13.657   4.075 36.145  1.00  26.87
ATOM   2048  CG   LEU  B  320   14.846   3.460 35.398  1.00  26.15
ATOM   2049  CD1  LEU  B  320   16.053   3.375 36.330  1.00  28.04
ATOM   2050  CD2  LEU  B  320   14.484   2.076 34.895  1.00  26.96
ATOM   2051  C    LEU  B  320   11.249   4.722 36.290  1.00  29.19
ATOM   2052  O    LEU  B  320   10.449   3.849 36.631  1.00  26.66
ATOM   2053  N    ASP  B  321   11.160   5.976 36.719  1.00  29.72
ATOM   2054  CA   ASP  B  321   10.112   6.371 37.647  1.00  31.36
ATOM   2055  CB   ASP  B  321   10.494   7.683 38.336  1.00  36.60
ATOM   2056  CG   ASP  B  321   11.407   7.461 39.535  1.00  46.11
ATOM   2057  OD1  ASP  B  321   10.897   7.058 40.605  1.00  46.64
ATOM   2058  OD2  ASP  B  321   12.635   7.676 39.402  1.00  45.98
ATOM   2059  C    ASP  B  321    8.742   6.494 36.989  1.00  28.29
ATOM   2060  O    ASP  B  321    7.715   6.432 37.661  1.00  27.19
ATOM   2061  N    ALA  B  322    8.726   6.650 35.672  1.00  28.34
ATOM   2062  CA   ALA  B  322    7.469   6.779 34.950  1.00  25.55
ATOM   2063  CB   ALA  B  322    7.668   7.668 33.728  1.00  24.11
ATOM   2064  C    ALA  B  322    6.911   5.420 34.523  1.00  22.80
ATOM   2065  O    ALA  B  322    5.810   5.338 33.979  1.00  24.54
ATOM   2066  N    GLU  B  323    7.662   4.355 34.781  1.00  20.16
ATOM   2067  CA   GLU  B  323    7.229   3.021 34.396  1.00  21.44
ATOM   2068  CB   GLU  B  323    8.195   1.982 34.938  1.00  23.72
ATOM   2069  CG   GLU  B  323    9.393   1.746 34.024  1.00  23.58
ATOM   2070  CD   GLU  B  323    8.988   1.134 32.685  1.00  25.23
ATOM   2071  OE1  GLU  B  323    8.852   1.881 31.692  1.00  21.74
ATOM   2072  OE2  GLU  B  323    8.809  -0.095 32.634  1.00  25.49
ATOM   2073  C    GLU  B  323    5.796   2.696 34.810  1.00  22.35
ATOM   2074  O    GLU  B  323    5.409   2.926 35.951  1.00  22.34
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    2075  N    PRO  B  324   4.986   2.165 33.880  1.00  19.10
ATOM    2076  CD   PRO  B  324   5.286   1.806 32.483  1.00  19.11
ATOM    2077  CA   PRO  B  324   3.607   1.839 34.242  1.00  22.04
ATOM    2078  CB   PRO  B  324   2.919   1.658 32.893  1.00  21.96
ATOM    2079  CG   PRO  B  324   4.015   1.137 32.015  1.00  24.13
ATOM    2080  C    PRO  B  324   3.519   0.556 35.060  1.00  23.44
ATOM    2081  O    PRO  B  324   4.590  -0.300 35.028  1.00  22.20
ATOM    2082  N    PRO  B  325   2.540   0.287 35.801  1.00  24.88
ATOM    2083  CD   PRO  B  325   1.299   1.068 35.945  1.00  26.67
ATOM    2084  CA   PRO  B  325   2.520  -0.940 36.603  1.00  25.10
ATOM    2085  CB   PRO  B  325   1.394  -0.691 37.595  1.00  27.09
ATOM    2086  CG   PRO  B  325   0.448   0.305 36.854  1.00  26.87
ATOM    2087  C    PRO  B  325   2.270  -2.192 35.776  1.00  25.77
ATOM    2088  O    PRO  B  325   1.883  -2.118 34.617  1.00  21.69
ATOM    2089  N    ILE  B  326   2.538  -3.344 36.379  1.00  24.05
ATOM    2090  CA   ILE  B  326   2.301  -4.620 35.732  1.00  22.51
ATOM    2091  CB   ILE  B  326   3.303  -5.688 36.185  1.00  25.81
ATOM    2092  CG2  ILE  B  326   3.011  -7.018 35.481  1.00  23.78
ATOM    2093  CG1  ILE  B  326   4.729  -5.209 35.900  1.00  25.75
ATOM    2094  CD1  ILE  B  326   5.241  -5.585 34.533  1.00  27.78
ATOM    2095  C    ILE  B  326   0.893  -5.020 36.149  1.00  23.53
ATOM    2096  O    ILE  B  326   0.632  -5.231 37.332  1.00  24.81
ATOM    2097  N    LEU  B  327  -0.018  -5.104 35.188  1.00  19.44
ATOM    2098  CA   LEU  B  327  -1.399  -5.437 35.493  1.00  17.03
ATOM    2099  CB   LEU  B  327  -2.336  -4.747 34.493  1.00  18.39
ATOM    2100  CG   LEU  B  327  -2.201  -3.216 34.373  1.00  20.69
ATOM    2101  CD1  LEU  B  327  -3.245  -2.679 33.406  1.00  14.87
ATOM    2102  CD2  LEU  B  327  -2.384  -2.570 35.742  1.00  14.39
ATOM    2103  C    LEU  B  327  -1.662  -6.928 35.499  1.00  19.87
ATOM    2104  O    LEU  B  327  -0.854  -7.722 35.014  1.00  20.90
ATOM    2105  N    TYR  B  328  -2.803  -7.300 35.066  1.00  20.92
ATOM    2106  CA   TYR  B  328  -3.202  -8.692 36.135  1.00  21.79
ATOM    2107  CB   TYR  B  328  -3.658  -9.050 37.580  1.00  22.91
ATOM    2108  CG   TYR  B  328  -2.515  -9.376 38.468  1.00  24.50
ATOM    2109  CD1  TYR  B  328  -2.118 -10.696 38.677  1.00  25.93
ATOM    2110  CE1  TYR  B  328  -1.034 -11.000 39.498  1.00  28.10
ATOM    2111  CD2  TYR  B  328  -1.802  -8.362 39.103  1.00  29.46
ATOM    2112  CE2  TYR  B  328  -0.716  -8.654 39.926  1.00  35.30
ATOM    2113  CZ   TYR  B  328  -0.338  -9.973 40.117  1.00  33.59
ATOM    2114  OH   TYR  B  328   0.739 -10.257 40.923  1.00  37.24
ATOM    2115  C    TYR  B  328  -4.336  -8.944 35.168  1.00  22.25
ATOM    2116  O    TYR  B  328  -5.115  -8.039 34.849  1.00  19.77
ATOM    2117  N    SER  B  329  -4.420 -10.180 34.698  1.00  25.81
ATOM    2118  CA   SER  B  329  -5.480 -10.571 33.787  1.00  29.39
ATOM    2119  CB   SER  B  329  -5.002 -11.710 32.887  1.00  27.65
ATOM    2120  OG   SER  B  329  -6.091 -12.329 32.233  1.00  28.98
ATOM    2121  C    SER  B  329  -6.625 -11.042 34.673  1.00  33.17
ATOM    2122  O    SER  B  329  -6.453 -11.157 35.888  1.00  32.52
ATOM    2123  N    GLU  B  330  -7.792 -11.289 34.084  1.00  38.75
ATOM    2124  CA   GLU  B  330  -8.930 -11.776 34.859  1.00  44.91
ATOM    2125  CB   GLU  B  330 -10.134 -11.999 33.951  1.00  45.63
ATOM    2126  C    GLU  B  330  -8.493 -13.093 35.491  1.00  48.62
ATOM    2127  O    GLU  B  330  -7.739 -13.851 34.882  1.00  52.37
ATOM    2128  N    TYR  B  331  -8.952 -13.366 36.707  1.00  51.75
ATOM    2129  CA   TYR  B  331  -8.575 -14.596 37.396  1.00  55.25
ATOM    2130  CB   TYR  B  331  -8.538 -14.365 38.911  1.00  53.04
ATOM    2131  CG   TYR  B  331  -9.769 -13.668 39.440  1.00  50.70
ATOM    2132  CD1  TYR  B  331 -10.880 -14.400 39.856  1.00  47.09
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   2133  CE1   TYR  B  331   -12.035  -13.762  40.292  1.00  46.43
ATOM   2134  CD2   TYR  B  331    -9.842  -12.273  39.478  1.00  47.82
ATOM   2135  CE2   TYR  B  331   -10.993  -11.623  39.913  1.00  43.98
ATOM   2136  CZ    TYR  B  331   -12.086  -12.376  40.314  1.00  44.33
ATOM   2137  OH    TYR  B  331   -13.239  -11.747  40.715  1.00  45.31
ATOM   2138  C     TYR  B  331    -9.528  -15.743  37.075  1.00  60.11
ATOM   2139  O     TYR  B  331   -10.748  -15.569  37.066  1.00  63.13
ATOM   2140  N     ASP  B  332    -8.952  -16.913  36.809  1.00  61.60
ATOM   2141  CA    ASP  B  332    -9.704  -18.124  36.490  1.00  63.58
ATOM   2142  CB    ASP  B  332   -10.637  -17.895  35.298  1.00  65.11
ATOM   2143  CG    ASP  B  332   -11.723  -18.953  35.200  1.00  65.32
ATOM   2144  OD1   ASP  B  332   -11.420  -20.136  35.463  1.00  63.69
ATOM   2145  OD2   ASP  B  332   -12.876  -18.602  34.866  1.00  63.61
ATOM   2146  C     ASP  B  332    -8.707  -19.227  36.153  1.00  62.86
ATOM   2147  O     ASP  B  332    -7.853  -19.056  35.207  1.00  62.26
ATOM   2148  N     PRO  B  333    -8.811  -20.379  36.833  1.00  63.96
ATOM   2149  CD    PRO  B  333    -9.808  -20.690  37.875  1.00  64.24
ATOM   2150  CA    PRO  B  333    -7.901  -21.503  36.596  1.00  64.24
ATOM   2151  CB    PRO  B  333    -8.015  -22.325  37.874  1.00  64.70
ATOM   2152  CG    PRO  B  333    -9.410  -22.071  38.347  1.00  65.00
ATOM   2153  C     PRO  B  333    -8.180  -22.340  35.351  1.00  63.90
ATOM   2154  O     PRO  B  333    -7.384  -23.214  35.007  1.00  63.70
ATOM   2155  N     THR  B  334    -9.303  -22.084  34.683  1.00  63.83
ATOM   2156  CA    THR  B  334    -9.649  -22.832  33.475  1.00  63.77
ATOM   2157  CB    THR  B  334   -11.065  -22.477  32.975  1.00  64.63
ATOM   2158  OG1   THR  B  334   -11.132  -21.078  32.675  1.00  65.95
ATOM   2159  CG2   THR  B  334   -12.102  -22.817  34.036  1.00  65.09
ATOM   2160  C     THR  B  334    -8.634  -22.499  32.388  1.00  62.62
ATOM   2161  O     THR  B  334    -8.931  -21.774  31.437  1.00  60.15
ATOM   2162  N     ARG  B  335    -7.432  -23.043  32.553  1.00  63.14
ATOM   2163  CA    ARG  B  335    -6.324  -22.820  31.633  1.00  60.70
ATOM   2164  CB    ARG  B  335    -5.130  -23.867  32.050  1.00  58.73
ATOM   2165  C     ARG  B  335    -6.657  -23.086  30.174  1.00  59.71
ATOM   2166  O     ARG  B  335    -6.302  -22.298  29.298  1.00  62.33
ATOM   2167  N     PRO  B  336    -7.377  -24.194  29.884  1.00  55.25
ATOM   2168  CD    PRO  B  336    -7.938  -25.227  30.769  1.00  53.53
ATOM   2169  CA    PRO  B  336    -7.698  -24.437  28.471  1.00  50.10
ATOM   2170  CB    PRO  B  336    -8.399  -25.799  28.476  1.00  49.70
ATOM   2171  CG    PRO  B  336    -8.164  -26.372  29.844  1.00  50.71
ATOM   2172  C     PRO  B  336    -8.602  -23.324  27.954  1.00  44.54
ATOM   2173  O     PRO  B  336    -9.809  -23.342  28.179  1.00  44.14
ATOM   2174  N     PHE  B  337    -8.007  -22.350  27.274  1.00  39.18
ATOM   2175  CA    PHE  B  337    -8.764  -21.223  26.742  1.00  38.25
ATOM   2176  CB    PHE  B  337    -7.850  -20.003  26.567  1.00  36.98
ATOM   2177  CG    PHE  B  337    -7.229  -19.517  27.846  1.00  36.81
ATOM   2178  CD1   PHE  B  337    -5.846  -19.511  28.002  1.00  38.89
ATOM   2179  CD2   PHE  B  337    -8.023  -19.062  28.893  1.00  35.97
ATOM   2180  CE1   PHE  B  337    -5.262  -19.059  29.185  1.00  36.85
ATOM   2181  CE2   PHE  B  337    -7.449  -18.608  30.079  1.00  37.15
ATOM   2182  CZ    PHE  B  337    -6.064  -18.607  30.224  1.00  38.40
ATOM   2183  C     PHE  B  337    -9.420  -21.535  25.402  1.00  36.81
ATOM   2184  O     PHE  B  337    -8.962  -22.399  24.658  1.00  36.26
ATOM   2185  N     SER  B  338   -10.504  -20.828  25.107  1.00  35.85
ATOM   2186  CA    SER  B  338   -11.198  -20.981  23.836  1.00  34.76
ATOM   2187  CB    SER  B  338   -12.713  -20.948  24.035  1.00  34.85
ATOM   2188  OG    SER  B  338   -13.164  -19.621  24.235  1.00  33.53
ATOM   2189  C     SER  B  338   -10.761  -19.761  23.037  1.00  34.99
ATOM   2190  O     SER  B  338   -10.143  -18.855  23.591  1.00  34.32
```

UNITED STATES PATENT AND TRADEMARK OFFICE
CERTIFICATE OF CORRECTION

PATENT NO. : 6,965,850 B2  Page 116 of 186
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   2191  N    GLU  B  339   -11.075  -19.722  21.750  1.00  33.01
ATOM   2192  CA   GLU  B  339   -10.682  -18.579  20.980  1.00  33.94
ATOM   2193  CB   GLU  B  339   -11.146  -18.737  19.501  1.00  33.79
ATOM   2194  CG   GLU  B  339   -10.758  -17.553  18.623  1.00  39.11
ATOM   2195  CD   GLU  B  339   -10.865  -17.852  17.137  1.00  43.17
ATOM   2196  OE1  GLU  B  339   -11.990  -17.785  16.600  1.00  45.28
ATOM   2197  OE2  GLU  B  339    -9.824  -18.152  16.510  1.00  39.19
ATOM   2198  C    GLU  B  339   -11.265  -17.295  21.531  1.00  34.28
ATOM   2199  O    GLU  B  339   -10.575  -16.283  21.631  1.00  33.65
ATOM   2200  N    ALA  B  340   -12.535  -17.339  21.920  1.00  31.12
ATOM   2201  CA   ALA  B  340   -13.194  -16.164  22.459  1.00  29.10
ATOM   2202  CB   ALA  B  340   -14.696  -16.412  22.573  1.00  33.84
ATOM   2203  C    ALA  B  340   -12.639  -15.731  23.836  1.00  28.98
ATOM   2204  O    ALA  B  340   -12.431  -14.541  24.060  1.00  30.48
ATOM   2205  N    SER  B  341   -12.407  -16.691  24.719  1.00  26.66
ATOM   2206  CA   SER  B  341   -11.882  -16.386  26.044  1.00  24.26
ATOM   2207  CB   SER  B  341   -11.867  -17.643  26.923  1.00  27.04
ATOM   2208  OG   SER  B  341   -10.851  -18.541  26.515  1.00  33.84
ATOM   2209  C    SER  B  341   -10.479  -15.793  25.960  1.00  23.97
ATOM   2210  O    SER  B  341   -10.171  -14.824  26.651  1.00  21.56
ATOM   2211  N    MET  B  342    -9.631  -16.368  25.114  1.00  26.83
ATOM   2212  CA   MET  B  342    -8.271  -15.865  24.954  1.00  27.24
ATOM   2213  CB   MET  B  342    -7.477  -16.758  24.001  1.00  30.45
ATOM   2214  CG   MET  B  342    -6.038  -16.300  23.802  1.00  35.35
ATOM   2215  SD   MET  B  342    -4.866  -17.667  23.777  1.00  44.57
ATOM   2216  CE   MET  B  342    -4.034  -17.341  22.244  1.00  41.37
ATOM   2217  C    MET  B  342    -8.322  -14.448  24.385  1.00  25.31
ATOM   2218  O    MET  B  342    -7.653  -13.541  24.874  1.00  26.67
ATOM   2219  N    MET  B  343    -9.114  -14.278  23.345  1.00  25.75
ATOM   2220  CA   MET  B  343    -9.262  -12.979  22.712  1.00  26.47
ATOM   2221  CB   MET  B  343   -10.210  -13.088  21.528  1.00  23.51
ATOM   2222  CG   MET  B  343    -9.540  -13.618  20.273  1.00  28.86
ATOM   2223  SD   MET  B  343    -8.325  -12.456  19.609  1.00  29.25
ATOM   2224  CE   MET  B  343    -9.344  -11.015  19.371  1.00  28.74
ATOM   2225  C    MET  B  343    -9.798  -11.966  23.712  1.00  25.37
ATOM   2226  O    MET  B  343    -9.360  -10.810  23.728  1.00  24.98
ATOM   2227  N    GLY  B  344   -10.739  -12.403  24.536  1.00  23.91
ATOM   2228  CA   GLY  B  344   -11.320  -11.526  25.536  1.00  22.43
ATOM   2229  C    GLY  B  344   -10.313  -11.103  26.592  1.00  22.06
ATOM   2230  O    GLY  B  344   -10.262   -9.934  26.983  1.00  20.87
ATOM   2231  N    LEU  B  345    -9.511  -12.048  27.063  1.00  19.36
ATOM   2232  CA   LEU  B  345    -8.520  -11.748  28.083  1.00  25.74
ATOM   2233  CB   LEU  B  345    -7.886  -13.040  28.600  1.00  26.78
ATOM   2234  CG   LEU  B  345    -8.794  -14.010  29.362  1.00  30.04
ATOM   2235  CD1  LEU  B  345    -8.099  -15.357  29.488  1.00  28.39
ATOM   2236  CD2  LEU  B  345    -9.122  -13.443  30.736  1.00  29.93
ATOM   2237  C    LEU  B  345    -7.425  -10.822  27.550  1.00  23.24
ATOM   2238  O    LEU  B  345    -7.037   -9.865  28.212  1.00  23.43
ATOM   2239  N    LEU  B  346    -6.937  -11.108  26.350  1.00  21.92
ATOM   2240  CA   LEU  B  346    -5.874  -10.303  25.763  1.00  22.71
ATOM   2241  CB   LEU  B  346    -5.343  -10.962  24.486  1.00  23.17
ATOM   2242  CG   LEU  B  346    -4.684  -12.331  24.668  1.00  20.66
ATOM   2243  CD1  LEU  B  346    -4.303  -12.916  23.309  1.00  18.75
ATOM   2244  CD2  LEU  B  346    -3.464  -12.188  25.553  1.00  20.84
ATOM   2245  C    LEU  B  346    -6.304   -8.873  25.458  1.00  22.99
ATOM   2246  O    LEU  B  346    -5.540   -7.935  25.695  1.00  22.07
ATOM   2247  N    THR  B  347    -7.516   -8.699  24.937  1.00  20.53
ATOM   2248  CA   THR  B  347    -7.987   -7.357  24.608  1.00  21.89
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   2249  CB   THR  B  347   -9.152  -7.388 23.601  1.00  21.65
ATOM   2250  OG1  THR  B  347  -10.218  -8.190 24.123  1.00  19.65
ATOM   2251  CG2  THR  B  347   -8.676  -7.955 22.262  1.00  22.01
ATOM   2252  C    THR  B  347   -8.426  -6.590 25.853  1.00  23.60
ATOM   2253  O    THR  B  347   -8.358  -5.357 25.883  1.00  20.31
ATOM   2254  N    ASN  B  348   -8.884  -7.314 26.874  1.00  22.27
ATOM   2255  CA   ASN  B  348   -9.293  -6.667 28.114  1.00  23.99
ATOM   2256  CB   ASN  B  348  -10.008  -7.642 29.056  1.00  22.32
ATOM   2257  CG   ASN  B  348  -10.342  -7.022 30.398  1.00  28.26
ATOM   2258  OD1  ASN  B  348   -9.478  -6.746 31.218  1.00  27.14
ATOM   2259  ND2  ASN  B  348  -11.647  -6.764 30.625  1.00  27.02
ATOM   2260  C    ASN  B  348   -8.035  -6.120 28.798  1.00  19.48
ATOM   2261  O    ASN  B  348   -8.014  -4.991 29.271  1.00  18.26
ATOM   2262  N    LEU  B  349   -6.984  -6.931 28.832  1.00  19.07
ATOM   2263  CA   LEU  B  349   -5.724  -6.516 29.446  1.00  20.37
ATOM   2264  CB   LEU  B  349   -4.716  -7.674 29.434  1.00  18.21
ATOM   2265  CG   LEU  B  349   -3.297  -7.316 29.889  1.00  18.24
ATOM   2266  CD1  LEU  B  349   -3.323  -6.904 31.356  1.00  12.44
ATOM   2267  CD2  LEU  B  349   -2.370  -8.504 29.672  1.00  21.28
ATOM   2268  C    LEU  B  349   -5.131  -5.307 28.718  1.00  19.92
ATOM   2269  O    LEU  B  349   -4.738  -4.322 29.349  1.00  16.56
ATOM   2270  N    ALA  B  350   -5.067  -5.391 27.391  1.00  16.67
ATOM   2271  CA   ALA  B  350   -4.529  -4.308 26.578  1.00  17.11
ATOM   2272  CB   ALA  B  350   -4.587  -4.690 25.095  1.00  14.15
ATOM   2273  C    ALA  B  350   -5.272  -2.988 26.805  1.00  17.92
ATOM   2274  O    ALA  B  350   -4.650  -1.926 26.904  1.00  18.71
ATOM   2275  N    ASP  B  351   -6.600  -3.053 26.857  1.00  17.51
ATOM   2276  CA   ASP  B  351   -7.409  -1.856 27.074  1.00  16.57
ATOM   2277  CB   ASP  B  351   -8.902  -2.202 27.041  1.00  18.97
ATOM   2278  CG   ASP  B  351   -9.785  -0.974 26.858  1.00  21.80
ATOM   2279  OD1  ASP  B  351   -9.660  -0.293 25.824  1.00  24.62
ATOM   2280  OD2  ASP  B  351  -10.604  -0.682 27.754  1.00  22.78
ATOM   2281  C    ASP  B  351   -7.064  -1.228 28.415  1.00  16.81
ATOM   2282  O    ASP  B  351   -6.963  -0.009 28.534  1.00  15.75
ATOM   2283  N    ARG  B  352   -6.894  -2.056 29.438  1.00  13.97
ATOM   2284  CA   ARG  B  352   -6.552  -1.509 30.742  1.00  16.09
ATOM   2285  CB   ARG  B  352   -5.728  -2.571 31.833  1.00  15.78
ATOM   2286  CG   ARG  B  352   -8.189  -2.819 32.189  1.00  17.93
ATOM   2287  CD   ARG  B  352   -8.323  -3.882 33.279  1.00  19.84
ATOM   2288  NE   ARG  B  352   -8.010  -5.222 32.785  1.00  21.36
ATOM   2289  CZ   ARG  B  352   -7.187  -6.075 33.387  1.00  21.18
ATOM   2290  NH1  ARG  B  352   -6.579  -5.741 34.516  1.00  20.51
ATOM   2291  NH2  ARG  B  352   -6.980  -7.275 32.854  1.00  28.51
ATOM   2292  C    ARG  B  352   -5.123  -0.975 30.728  1.00  15.81
ATOM   2293  O    ARG  B  352   -4.835   0.057 31.339  1.00  15.61
ATOM   2294  N    GLU  B  353   -4.231  -1.665 30.019  1.00  15.45
ATOM   2295  CA   GLU  B  353   -2.838  -1.228 29.935  1.00  16.59
ATOM   2296  CB   GLU  B  353   -1.990  -2.243 29.168  1.00  14.64
ATOM   2297  CG   GLU  B  353   -1.554  -3.456 29.973  1.00  18.23
ATOM   2298  CD   GLU  B  353   -0.620  -4.355 29.176  1.00  22.72
ATOM   2299  OE1  GLU  B  353   -1.099  -5.078 28.275  1.00  21.94
ATOM   2300  OE2  GLU  B  353    0.599  -4.324 29.442  1.00  24.41
ATOM   2301  C    GLU  B  353   -2.729   0.119 29.219  1.00  15.85
ATOM   2302  O    GLU  B  353   -1.872   0.939 29.540  1.00  13.76
ATOM   2303  N    LEU  B  354   -3.594   0.335 28.235  1.00  12.93
ATOM   2304  CA   LEU  B  354   -3.556   1.575 27.472  1.00  15.33
ATOM   2305  CB   LEU  B  354   -4.616   1.534 26.360  1.00  16.44
ATOM   2306  CG   LEU  B  354   -4.174   0.750 25.112  1.00  17.03
```

UNITED STATES PATENT AND TRADEMARK OFFICE
CERTIFICATE OF CORRECTION

PATENT NO. : 6,965,850 B2  
APPLICATION NO. : 09/281717  
DATED : November 15, 2005  
INVENTOR(S) : John D. Baxter et al.

Page 118 of 186

It is certified that error appears in the above-identified patent and that said Letters Patent is hereby corrected as shown below:

```
ATOM   2307  CD1  LEU  B  354   -5.373   0.509  24.189  1.00  16.70
ATOM   2308  CD2  LEU  B  354   -3.069   1.531  24.384  1.00  14.52
ATOM   2309  C    LEU  B  354   -3.747   2.805  28.361  1.00  12.78
ATOM   2310  O    LEU  B  354   -3.123   3.850  28.141  1.00  14.28
ATOM   2311  N    VAL  B  355   -4.600   2.682  29.369  1.00  12.60
ATOM   2312  CA   VAL  B  355   -4.844   3.791  30.279  1.00  16.78
ATOM   2313  CB   VAL  B  355   -5.925   3.429  31.327  1.00  16.84
ATOM   2314  CG1  VAL  B  355   -6.070   4.561  32.344  1.00  19.88
ATOM   2315  CG2  VAL  B  355   -7.254   3.187  30.639  1.00  19.33
ATOM   2316  C    VAL  B  355   -3.533   4.161  30.986  1.00  19.17
ATOM   2317  O    VAL  B  355   -3.158   5.328  31.049  1.00  17.30
ATOM   2318  N    HIS  B  356   -2.826   3.160  31.499  1.00  19.68
ATOM   2319  CA   HIS  B  356   -1.559   3.418  32.177  1.00  20.64
ATOM   2320  CB   HIS  B  356   -1.110   2.174  32.945  1.00  21.03
ATOM   2321  CG   HIS  B  356   -2.018   1.818  34.085  1.00  22.88
ATOM   2322  CD2  HIS  B  356   -3.128   1.045  34.135  1.00  21.70
ATOM   2323  ND1  HIS  B  356   -1.838   2.312  35.358  1.00  19.24
ATOM   2324  CE1  HIS  B  356   -2.802   1.860  36.145  1.00  18.84
ATOM   2325  NE2  HIS  B  356   -3.598   1.088  35.426  1.00  17.92
ATOM   2326  C    HIS  B  356   -0.479   3.861  31.184  1.00  19.67
ATOM   2327  O    HIS  B  356    0.424   4.614  31.547  1.00  19.61
ATOM   2328  N    MET  B  357   -0.566   3.413  29.931  1.00  14.92
ATOM   2329  CA   MET  B  357    0.428   3.830  28.939  1.00  15.13
ATOM   2330  CB   MET  B  357    0.239   3.099  27.604  1.00  13.94
ATOM   2331  CG   MET  B  357    1.149   3.631  26.476  1.00  14.71
ATOM   2332  SD   MET  B  357    0.747   3.014  24.826  1.00  17.75
ATOM   2333  CE   MET  B  357    0.746   1.222  25.122  1.00  15.21
ATOM   2334  C    MET  B  357    0.316   5.334  28.699  1.00  14.94
ATOM   2335  O    MET  B  357    1.319   6.031  28.560  1.00  17.02
ATOM   2336  N    ILE  B  358   -0.909   5.839  28.659  1.00  18.01
ATOM   2337  CA   ILE  B  358   -1.122   7.263  28.423  1.00  19.77
ATOM   2338  CB   ILE  B  358   -2.634   7.577  28.287  1.00  23.11
ATOM   2339  CG2  ILE  B  358   -2.879   9.080  28.450  1.00  25.00
ATOM   2340  CG1  ILE  B  358   -3.137   7.105  26.913  1.00  24.19
ATOM   2341  CD1  ILE  B  358   -4.600   6.653  26.890  1.00  20.17
ATOM   2342  C    ILE  B  358   -0.501   8.100  29.550  1.00  22.93
ATOM   2343  O    ILE  B  358    0.080   9.153  29.299  1.00  23.33
ATOM   2344  N    ASN  B  359   -0.619   7.631  30.790  1.00  22.34
ATOM   2345  CA   ASN  B  359   -0.029   8.341  31.924  1.00  23.24
ATOM   2346  CB   ASN  B  359   -0.480   7.726  33.224  1.00  25.10
ATOM   2347  CG   ASN  B  359   -1.831   8.171  33.649  1.00  32.65
ATOM   2348  OD1  ASN  B  359   -2.421   9.069  33.042  1.00  32.98
ATOM   2349  ND2  ASN  B  359   -2.364   7.549  34.691  1.00  33.87
ATOM   2350  C    ASN  B  359    1.473   8.306  31.837  1.00  24.77
ATOM   2351  O    ASN  B  359    2.152   9.285  32.149  1.00  24.19
ATOM   2352  N    TRP  B  360    1.995   7.149  31.438  1.00  20.82
ATOM   2353  CA   TRP  B  360    3.439   6.965  31.310  1.00  19.29
ATOM   2354  CB   TRP  B  360    3.754   5.524  30.878  1.00  18.59
ATOM   2355  CG   TRP  B  360    5.085   5.363  30.176  1.00  18.21
ATOM   2356  CD2  TRP  B  360    5.310   5.308  28.756  1.00  14.38
ATOM   2357  CE2  TRP  B  360    6.698   5.129  28.561  1.00  13.42
ATOM   2358  CE3  TRP  B  360    4.475   5.392  27.633  1.00  15.52
ATOM   2359  CD1  TRP  B  360    6.306   5.221  30.762  1.00  13.34
ATOM   2360  NE1  TRP  B  360    7.283   5.078  29.800  1.00  16.05
ATOM   2361  CZ2  TRP  B  360    7.272   5.032  27.288  1.00  16.84
ATOM   2362  CZ3  TRP  B  360    5.045   5.296  26.363  1.00  15.11
ATOM   2363  CH2  TRP  B  360    6.431   5.115  26.202  1.00  16.12
ATOM   2364  C    TRP  B  360    3.979   7.939  30.273  1.00  20.13
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   2365  O    TRP  B  360   4.991   8.606  30.497  1.00  17.26
ATOM   2366  N    ALA  B  361   3.295   8.012  29.135  1.00  19.34
ATOM   2367  CA   ALA  B  361   3.708   8.900  28.051  1.00  22.01
ATOM   2368  CB   ALA  B  361   2.682   8.855  26.921  1.00  19.53
ATOM   2369  C    ALA  B  361   3.883  10.336  28.552  1.00  22.39
ATOM   2370  O    ALA  B  361   4.858  11.005  28.210  1.00  19.57
ATOM   2371  N    LYS  B  362   2.932  10.794  29.361  1.00  21.96
ATOM   2372  CA   LYS  B  362   2.966  12.139  29.923  1.00  26.45
ATOM   2373  CB   LYS  B  362   1.741  12.363  30.811  1.00  29.79
ATOM   2374  CG   LYS  B  362   0.426  12.417  30.084  1.00  33.57
ATOM   2375  CD   LYS  B  362  -0.563  13.304  30.805  1.00  36.83
ATOM   2376  CE   LYS  B  362  -1.620  12.490  31.512  1.00  36.89
ATOM   2377  NZ   LYS  B  362  -2.873  13.276  31.664  1.00  39.07
ATOM   2378  C    LYS  B  362   4.223  12.379  30.757  1.00  27.77
ATOM   2379  O    LYS  B  362   4.661  13.517  30.922  1.00  26.93
ATOM   2380  N    ARG  B  363   4.805  11.302  31.278  1.00  26.61
ATOM   2381  CA   ARG  B  363   5.996  11.414  32.109  1.00  27.74
ATOM   2382  CB   ARG  B  363   5.887  10.457  33.298  1.00  28.93
ATOM   2383  CG   ARG  B  363   4.650  10.704  34.158  1.00  36.07
ATOM   2384  CD   ARG  B  363   4.569   9.745  35.344  1.00  42.83
ATOM   2385  NE   ARG  B  363   4.477   8.344  34.928  1.00  49.79
ATOM   2386  CZ   ARG  B  363   3.395   7.582  35.080  1.00  51.48
ATOM   2387  NH1  ARG  B  363   2.300   8.081  35.648  1.00  52.17
ATOM   2388  NH2  ARG  B  363   3.405   6.316  34.668  1.00  40.24
ATOM   2389  C    ARG  B  363   7.308  11.190  31.367  1.00  25.80
ATOM   2390  O    ARG  B  363   8.374  11.183  31.975  1.00  29.36
ATOM   2391  N    VAL  B  364   7.231  11.009  30.053  1.00  24.28
ATOM   2392  CA   VAL  B  364   8.431  10.823  29.248  1.00  21.87
ATOM   2393  CB   VAL  B  364   8.116  10.048  27.947  1.00  21.84
ATOM   2394  CG1  VAL  B  364   9.267  10.184  26.968  1.00  15.85
ATOM   2395  CG2  VAL  B  364   7.860   8.560  28.268  1.00  16.24
ATOM   2396  C    VAL  B  364   8.925  12.241  28.923  1.00  28.14
ATOM   2397  O    VAL  B  364   8.219  13.023  28.285  1.00  24.24
ATOM   2398  N    PRO  B  365  10.141  12.591  29.375  1.00  28.57
ATOM   2399  CD   PRO  B  365  11.061  11.726  30.137  1.00  30.58
ATOM   2400  CA   PRO  B  365  10.719  13.919  29.136  1.00  32.16
ATOM   2401  CB   PRO  B  365  12.189  13.739  29.507  1.00  32.70
ATOM   2402  CG   PRO  B  365  12.170  12.671  30.545  1.00  33.35
ATOM   2403  C    PRO  B  365  10.546  14.464  27.726  1.00  32.22
ATOM   2404  O    PRO  B  365  11.056  13.897  26.766  1.00  37.04
ATOM   2405  N    GLY  B  366   9.821  15.570  27.609  1.00  34.09
ATOM   2406  CA   GLY  B  366   9.612  16.182  26.310  1.00  32.54
ATOM   2407  C    GLY  B  366   8.241  15.969  25.700  1.00  33.46
ATOM   2408  O    GLY  B  366   7.791  16.779  24.886  1.00  33.73
ATOM   2409  N    PHE  B  367   7.564  14.895  26.096  1.00  31.08
ATOM   2410  CA   PHE  B  367   6.250  14.593  25.542  1.00  28.60
ATOM   2411  CB   PHE  B  367   5.745  13.244  26.058  1.00  25.96
ATOM   2412  CG   PHE  B  367   4.629  12.871  25.239  1.00  22.75
ATOM   2413  CD1  PHE  B  367   3.313  12.771  25.669  1.00  22.62
ATOM   2414  CD2  PHE  B  367   4.897  12.025  24.033  1.00  22.29
ATOM   2415  CE1  PHE  B  367   2.272  12.233  24.914  1.00  25.63
ATOM   2416  CE2  PHE  B  367   3.867  11.486  23.272  1.00  20.82
ATOM   2417  CZ   PHE  B  367   2.553  11.588  23.711  1.00  25.50
ATOM   2418  C    PHE  B  367   5.178  15.646  25.781  1.00  26.79
ATOM   2419  O    PHE  B  367   4.458  16.001  24.854  1.00  23.37
ATOM   2420  N    VAL  B  368   5.049  16.143  27.009  1.00  31.26
ATOM   2421  CA   VAL  B  368   4.020  17.151  27.277  1.00  35.71
ATOM   2422  CB   VAL  B  368   3.817  17.412  28.795  1.00  35.98
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

Page 120 of 186

It is certified that error appears in the above-identified patent and that said Letters Patent is hereby corrected as shown below:

```
ATOM   2423  CG1  VAL  B  368   2.944  16.320 29.393  1.00  37.64
ATOM   2424  CG2  VAL  B  368   5.157  17.495 29.598  1.00  35.81
ATOM   2425  C    VAL  B  368   4.328  18.482 26.598  1.00  35.87
ATOM   2426  O    VAL  B  368   3.450  19.330 26.457  1.00  37.71
ATOM   2427  N    ASP  B  369   5.572  18.665 26.175  1.00  35.49
ATOM   2428  CA   ASP  B  369   5.950  19.904 25.803  1.00  36.54
ATOM   2429  CB   ASP  B  369   7.466  19.963 25.309  1.00  39.79
ATOM   2430  CG   ASP  B  369   8.213  20.169 26.615  1.00  44.33
ATOM   2431  OD1  ASP  B  369   9.409  19.807 26.684  1.00  48.45
ATOM   2432  OD2  ASP  B  369   7.604  20.693 27.573  1.00  43.37
ATOM   2433  C    ASP  B  369   5.248  19.997 24.149  1.00  34.49
ATOM   2434  O    ASP  B  369   5.131  21.074 23.571  1.00  34.51
ATOM   2435  N    LEU  B  370   4.776  18.859 23.853  1.00  30.97
ATOM   2436  CA   LEU  B  370   4.086  18.809 22.370  1.00  29.80
ATOM   2437  CB   LEU  B  370   4.145  17.389 21.799  1.00  27.27
ATOM   2438  CG   LEU  B  370   5.522  16.733 21.688  1.00  28.07
ATOM   2439  CD1  LEU  B  370   5.353  15.242 21.400  1.00  30.38
ATOM   2440  CD2  LEU  B  370   6.316  17.396 20.574  1.00  22.82
ATOM   2441  C    LEU  B  370   2.628  19.218 22.521  1.00  28.04
ATOM   2442  O    LEU  B  370   2.066  19.151 23.611  1.00  29.71
ATOM   2443  N    THR  B  371   2.011  19.645 21.425  1.00  28.70
ATOM   2444  CA   THR  B  371   0.602  20.014 21.474  1.00  30.31
ATOM   2445  CB   THR  B  371   0.150  20.690 20.163  1.00  31.96
ATOM   2446  OG1  THR  B  371   0.284  19.763 19.080  1.00  29.49
ATOM   2447  CG2  THR  B  371   0.991  21.930 19.878  1.00  29.98
ATOM   2448  C    THR  B  371  -0.208  18.726 21.666  1.00  30.59
ATOM   2449  O    THR  B  371   0.300  17.624 21.431  1.00  27.10
ATOM   2450  N    LEU  B  372  -1.461  18.863 22.087  1.00  27.65
ATOM   2451  CA   LEU  B  372  -2.323  17.702 22.303  1.00  30.86
ATOM   2452  CB   LEU  B  372  -3.722  18.147 22.737  1.00  30.11
ATOM   2453  CG   LEU  B  372  -4.715  17.006 22.960  1.00  32.80
ATOM   2454  CD1  LEU  B  372  -4.231  16.147 24.126  1.00  34.10
ATOM   2455  CD2  LEU  B  372  -6.105  17.562 23.246  1.00  31.16
ATOM   2456  C    LEU  B  372  -2.437  16.863 21.034  1.00  31.77
ATOM   2457  O    LEU  B  372  -2.417  15.629 21.078  1.00  27.06
ATOM   2458  N    HIS  B  373  -2.564  17.548 19.905  1.00  31.30
ATOM   2459  CA   HIS  B  373  -2.685  16.888 18.614  1.00  31.35
ATOM   2460  CB   HIS  B  373  -2.844  17.935 17.503  1.00  34.30
ATOM   2461  CG   HIS  B  373  -2.503  17.430 16.132  1.00  41.27
ATOM   2462  CD2  HIS  B  373  -3.293  17.105 15.079  1.00  42.50
ATOM   2463  ND1  HIS  B  373  -1.205  17.220 15.715  1.00  43.69
ATOM   2464  CE1  HIS  B  373  -1.210  16.787 14.465  1.00  48.87
ATOM   2465  NE2  HIS  B  373  -2.465  16.708 14.056  1.00  43.72
ATOM   2466  C    HIS  B  373  -1.468  16.012 18.337  1.00  28.29
ATOM   2467  O    HIS  B  373  -1.610  14.878 17.897  1.00  30.21
ATOM   2468  N    ASP  B  374  -0.275  16.541 18.589  1.00  28.85
ATOM   2469  CA   ASP  B  374   0.950  15.783 18.350  1.00  28.28
ATOM   2470  CB   ASP  B  374   2.178  16.678 18.535  1.00  31.33
ATOM   2471  CG   ASP  B  374   2.433  17.577 17.333  1.00  39.07
ATOM   2472  OD1  ASP  B  374   3.195  18.557 17.478  1.00  40.60
ATOM   2473  OD2  ASP  B  374   1.874  17.305 16.246  1.00  38.64
ATOM   2474  C    ASP  B  374   1.029  14.592 19.303  1.00  29.05
ATOM   2475  O    ASP  B  374   1.432  13.494 18.908  1.00  24.36
ATOM   2476  N    GLN  B  375   0.642  14.814 20.556  1.00  24.52
ATOM   2477  CA   GLN  B  375   0.667  13.749 21.547  1.00  27.37
ATOM   2478  CB   GLN  B  375   0.213  14.270 22.901  1.00  26.66
ATOM   2479  CG   GLN  B  375   1.164  15.236 23.563  1.00  29.74
ATOM   2480  CD   GLN  B  375   0.623  15.691 24.890  1.00  33.13
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   2481  OE1  GLN  B  375  -0.044  14.953  25.602  1.00  32.82
ATOM   2482  NE2  GLN  B  375   0.895  16.953  25.236  1.00  33.98
ATOM   2483  C    GLN  B  375  -0.259  12.630  21.104  1.00  24.52
ATOM   2484  O    GLN  B  375   0.074  11.431  21.221  1.00  23.56
ATOM   2485  N    VAL  B  376  -1.426  13.013  20.599  1.00  21.87
ATOM   2486  CA   VAL  B  376  -2.409  12.035  20.140  1.00  23.44
ATOM   2487  CB   VAL  B  376  -3.718  12.760  19.717  1.00  22.09
ATOM   2488  CG1  VAL  B  376  -4.572  11.823  18.877  1.00  24.14
ATOM   2489  CG2  VAL  B  376  -4.486  13.193  20.954  1.00  16.96
ATOM   2490  C    VAL  B  376  -1.852  11.257  18.965  1.00  24.15
ATOM   2491  O    VAL  B  376  -1.949  10.032  18.938  1.00  22.36
ATOM   2492  N    HIS  B  377  -1.251  11.953  18.007  1.00  25.85
ATOM   2493  CA   HIS  B  377  -0.689  11.284  16.843  1.00  25.68
ATOM   2494  CB   HIS  B  377  -0.078  12.306  15.886  1.00  25.27
ATOM   2495  CG   HIS  B  377   0.535  11.690  14.667  1.00  30.63
ATOM   2496  CD2  HIS  B  377   1.838  11.959  14.287  1.00  31.03
ATOM   2497  ND1  HIS  B  377  -0.217  11.086  13.683  1.00  35.05
ATOM   2498  CE1  HIS  B  377   0.588  10.607  12.750  1.00  33.12
ATOM   2499  NE2  HIS  B  377   1.833  10.882  13.093  1.00  31.06
ATOM   2500  C    HIS  B  377   0.365  10.237  17.210  1.00  24.37
ATOM   2501  O    HIS  B  377   0.321   9.109  16.719  1.00  21.47
ATOM   2502  N    LEU  B  378   1.307  10.609  18.072  1.00  19.34
ATOM   2503  CA   LEU  B  378   2.365   9.691  18.474  1.00  20.09
ATOM   2504  CB   LEU  B  378   3.363  10.402  19.388  1.00  18.64
ATOM   2505  CG   LEU  B  378   4.230  11.489  18.736  1.00  22.15
ATOM   2506  CD1  LEU  B  378   5.104  12.148  19.796  1.00  22.51
ATOM   2507  CD2  LEU  B  378   5.094  10.885  17.638  1.00  20.68
ATOM   2508  C    LEU  B  378   1.832   8.433  19.161  1.00  18.91
ATOM   2509  O    LEU  B  378   2.262   7.320  18.859  1.00  17.52
ATOM   2510  N    LEU  B  379   0.888   8.610  20.077  1.00  18.25
ATOM   2511  CA   LEU  B  379   0.317   7.486  20.795  1.00  18.60
ATOM   2512  CB   LEU  B  379  -0.526   7.989  21.968  1.00  16.77
ATOM   2513  CG   LEU  B  379   0.292   8.353  23.214  1.00  17.90
ATOM   2514  CD1  LEU  B  379  -0.578   9.092  24.211  1.00  15.84
ATOM   2515  CD2  LEU  B  379   0.851   7.075  23.842  1.00  22.09
ATOM   2516  C    LEU  B  379  -0.518   6.605  19.872  1.00  20.17
ATOM   2517  O    LEU  B  379  -0.476   5.377  19.968  1.00  18.11
ATOM   2518  N    GLU  B  380  -1.273   7.222  18.971  1.00  19.40
ATOM   2519  CA   GLU  B  380  -2.086   6.435  18.049  1.00  20.19
ATOM   2520  CB   GLU  B  380  -2.994   7.350  17.222  1.00  22.43
ATOM   2521  CG   GLU  B  380  -4.182   7.874  18.007  1.00  25.30
ATOM   2522  CD   GLU  B  380  -5.070   8.789  17.188  1.00  29.44
ATOM   2523  OE1  GLU  B  380  -6.206   9.066  17.625  1.00  31.70
ATOM   2524  OE2  GLU  B  380  -4.631   9.230  16.110  1.00  31.75
ATOM   2525  C    GLU  B  380  -1.210   5.594  17.117  1.00  18.92
ATOM   2526  O    GLU  B  380  -1.586   4.491  16.722  1.00  19.83
ATOM   2527  N    ACYS B  381  -0.039   6.113  16.772  0.75  17.41
ATOM   2528  N    BCYS B  381  -0.035   6.113  16.779  0.25  17.76
ATOM   2529  CA   ACYS B  381   0.860   5.384  15.887  0.75  20.19
ATOM   2530  CA   BCYS B  381   0.875   5.407  15.884  0.25  17.50
ATOM   2531  CB   ACYS B  381   1.870   6.342  15.248  0.75  24.20
ATOM   2532  CB   BCYS B  381   1.830   6.406  15.226  0.25  16.63
ATOM   2533  SG   ACYS B  381   1.167   7.518  14.060  0.75  33.54
ATOM   2534  SG   BCYS B  381   3.048   5.656  14.128  0.25  10.36
ATOM   2535  C    ACYS B  381   1.626   4.269  16.592  0.75  20.59
ATOM   2536  C    BCYS B  381   1.689   4.305  16.561  0.25  19.19
ATOM   2537  O    ACYS B  381   1.737   3.161  16.069  0.75  19.16
ATOM   2538  O    BCYS B  381   1.906   3.241  15.982  0.25  19.25
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   2539  N    ALA  B  382   2.134   4.560 17.785  1.00  19.04
ATOM   2540  CA   ALA  B  382   2.955   3.602 18.530  1.00  20.27
ATOM   2541  CB   ALA  B  382   4.135   4.364 19.143  1.00  18.68
ATOM   2542  C    ALA  B  382   2.356   2.702 19.607  1.00  16.82
ATOM   2543  O    ALA  B  382   3.070   1.852 20.142  1.00  13.37
ATOM   2544  N    TRP  B  383   1.074   2.855 19.916  1.00  15.30
ATOM   2545  CA   TRP  B  383   0.487   2.089 21.013  1.00  15.80
ATOM   2546  CB   TRP  B  383  -1.009   2.410 21.160  1.00  16.63
ATOM   2547  CG   TRP  B  383  -1.871   1.775 20.129  1.00  19.93
ATOM   2548  CD2  TRP  B  383  -2.493   0.483 20.198  1.00  20.80
ATOM   2549  CE2  TRP  B  383  -3.226   0.309 19.003  1.00  19.27
ATOM   2550  CE3  TRP  B  383  -2.506  -0.542 21.155  1.00  21.32
ATOM   2551  CD1  TRP  B  383  -2.236   2.312 18.933  1.00  18.59
ATOM   2552  NE1  TRP  B  383  -3.051   1.439 18.250  1.00  23.67
ATOM   2553  CZ2  TRP  B  383  -3.963  -0.853 18.733  1.00  21.55
ATOM   2554  CZ3  TRP  B  383  -3.243  -1.702 20.888  1.00  20.29
ATOM   2555  CH2  TRP  B  383  -3.960  -1.844 19.686  1.00  19.03
ATOM   2556  C    TRP  B  383   0.701   0.579 21.020  1.00  17.35
ATOM   2557  O    TRP  B  383   0.982   0.010 22.077  1.00  13.92
ATOM   2558  N    LEU  B  384   0.568  -0.087 19.879  1.00  14.07
ATOM   2559  CA   LEU  B  384   0.773  -1.532 19.903  1.00  15.98
ATOM   2560  CB   LEU  B  384   0.181  -2.200 18.656  1.00  12.19
ATOM   2561  CG   LEU  B  384   0.173  -3.735 18.720  1.00  12.97
ATOM   2562  CD1  LEU  B  384  -0.352  -4.240 20.089  1.00  10.65
ATOM   2563  CD2  LEU  B  384  -0.707  -4.259 17.586  1.00  17.84
ATOM   2564  C    LEU  B  384   2.262  -1.861 20.034  1.00  14.64
ATOM   2565  O    LEU  B  384   2.627  -2.833 20.690  1.00  13.78
ATOM   2566  N    GLU  B  385   3.116  -1.046 19.414  1.00  14.96
ATOM   2567  CA   GLU  B  385   4.565  -1.260 19.509  1.00  13.79
ATOM   2568  CB   GLU  B  385   5.336  -0.179 18.739  1.00  15.34
ATOM   2569  CG   GLU  B  385   5.297  -0.312 17.207  1.00  15.38
ATOM   2570  CD   GLU  B  385   6.162   0.738 16.520  1.00  23.97
ATOM   2571  OE1  GLU  B  385   7.381   0.500 16.358  1.00  21.03
ATOM   2572  OE2  GLU  B  385   5.622   1.808 16.149  1.00  22.19
ATOM   2573  C    GLU  B  385   4.963  -1.161 20.987  1.00  15.79
ATOM   2574  O    GLU  B  385   5.788  -1.942 21.463  1.00  15.04
ATOM   2575  N    ILE  B  386   4.389  -0.213 21.690  1.00  13.32
ATOM   2576  CA   ILE  B  386   4.723  -0.019 23.108  1.00  14.06
ATOM   2577  CB   ILE  B  386   4.173   1.326 23.614  1.00  15.36
ATOM   2578  CG2  ILE  B  386   4.374   1.451 25.130  1.00  13.97
ATOM   2579  CG1  ILE  B  386   4.910   2.476 22.907  1.00  17.95
ATOM   2580  CD1  ILE  B  386   4.118   3.768 22.874  1.00  21.12
ATOM   2581  C    ILE  B  386   4.227  -1.164 23.993  1.00  14.97
ATOM   2582  O    ILE  B  386   4.905  -1.560 24.941  1.00  19.60
ATOM   2583  N    LEU  B  387   3.038  -1.675 23.789  1.00  15.18
ATOM   2584  CA   LEU  B  387   2.516  -2.791 24.478  1.00  15.98
ATOM   2585  CB   LEU  B  387   1.070  -3.097 24.080  1.00  17.15
ATOM   2586  CG   LEU  B  387  -0.031  -2.113 24.486  1.00  19.65
ATOM   2587  CD1  LEU  B  387  -1.371  -2.628 23.972  1.00  17.77
ATOM   2588  CD2  LEU  B  387  -0.075  -1.966 26.002  1.00  15.38
ATOM   2589  C    LEU  B  387   3.391  -4.013 24.180  1.00  14.69
ATOM   2590  O    LEU  B  387   3.712  -4.792 25.076  1.00  14.03
ATOM   2591  N    MET  B  388   3.785  -4.178 22.921  1.00  16.43
ATOM   2592  CA   MET  B  388   4.602  -5.329 22.547  1.00  16.67
ATOM   2593  CB   MET  B  388   4.673  -5.460 21.026  1.00  14.83
ATOM   2594  CG   MET  B  388   3.403  -6.066 20.453  1.00  13.91
ATOM   2595  SD   MET  B  388   3.364  -6.193 18.675  1.00  17.23
ATOM   2596  CE   MET  B  388   1.906  -7.225 18.511  1.00  14.97
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   2597  C    MET  B  388    6.004   -5.332  23.133  1.00  20.19
ATOM   2598  O    MET  B  388    6.460   -6.366  23.636  1.00  21.80
ATOM   2599  N    ILE  B  389    6.707   -4.203  23.074  1.00  15.34
ATOM   2600  CA   ILE  B  389    8.044   -4.209  23.634  1.00  15.59
ATOM   2601  CB   ILE  B  389    8.836   -2.911  23.322  1.00  14.95
ATOM   2602  CG2  ILE  B  389    8.330   -1.746  24.158  1.00  12.81
ATOM   2603  CG1  ILE  B  389   10.325   -3.164  23.602  1.00  17.24
ATOM   2604  CD1  ILE  B  389   11.228   -1.972  23.357  1.00  15.65
ATOM   2605  C    ILE  B  389    7.950   -4.446  25.147  1.00  14.30
ATOM   2606  O    ILE  B  389    8.844   -5.044  25.739  1.00  18.72
ATOM   2607  N    GLY  B  390    6.855   -4.007  25.761  1.00  13.99
ATOM   2608  CA   GLY  B  390    6.681   -4.219  27.189  1.00  14.87
ATOM   2609  C    GLY  B  390    6.444   -5.702  27.463  1.00  18.54
ATOM   2610  O    GLY  B  390    6.989   -6.282  28.403  1.00  16.54
ATOM   2611  N    LEU  B  391    5.623   -6.325  26.638  1.00  16.15
ATOM   2612  CA   LEU  B  391    5.334   -7.743  26.775  1.00  18.91
ATOM   2613  CB   LEU  B  391    4.332   -8.179  25.699  1.00  19.55
ATOM   2614  CG   LEU  B  391    4.157   -9.689  25.457  1.00  20.91
ATOM   2615  CD1  LEU  B  391    3.580  -10.351  26.699  1.00  19.41
ATOM   2616  CD2  LEU  B  391    3.232   -9.913  24.268  1.00  20.70
ATOM   2617  C    LEU  B  391    6.643   -8.518  26.625  1.00  20.31
ATOM   2618  O    LEU  B  391    7.002   -9.352  27.465  1.00  18.66
ATOM   2619  N    VAL  B  392    7.378   -8.215  25.557  1.00  18.71
ATOM   2620  CA   VAL  B  392    8.649   -8.868  25.278  1.00  19.51
ATOM   2621  CB   VAL  B  392    9.288   -8.281  24.005  1.00  23.77
ATOM   2622  CG1  VAL  B  392   10.751   -8.687  23.920  1.00  24.63
ATOM   2623  CG2  VAL  B  392    8.520   -8.773  22.767  1.00  19.94
ATOM   2624  C    VAL  B  392    9.615   -8.707  26.450  1.00  22.80
ATOM   2625  O    VAL  B  392   10.336   -9.637  26.811  1.00  19.36
ATOM   2626  N    TRP  B  393    9.617   -7.522  27.046  1.00  22.10
ATOM   2627  CA   TRP  B  393   10.492   -7.241  28.171  1.00  23.20
ATOM   2628  CB   TRP  B  393   10.388   -5.773  28.578  1.00  19.22
ATOM   2629  CG   TRP  B  393   11.056   -5.479  29.895  1.00  22.53
ATOM   2630  CD2  TRP  B  393   12.453   -5.591  30.193  1.00  20.36
ATOM   2631  CE2  TRP  B  393   12.624   -5.208  31.545  1.00  25.65
ATOM   2632  CE3  TRP  B  393   13.578   -5.976  29.449  1.00  22.12
ATOM   2633  CD1  TRP  B  393   10.452   -5.046  31.044  1.00  23.02
ATOM   2634  NE1  TRP  B  393   11.387   -4.881  32.037  1.00  24.91
ATOM   2635  CZ2  TRP  B  393   13.876   -5.200  32.171  1.00  23.00
ATOM   2636  CZ3  TRP  B  393   14.829   -5.968  30.072  1.00  23.98
ATOM   2637  CH2  TRP  B  393   14.964   -5.582  31.423  1.00  23.20
ATOM   2638  C    TRP  B  393   10.208   -8.114  29.388  1.00  24.36
ATOM   2639  O    TRP  B  393   11.128   -8.717  29.944  1.00  23.04
ATOM   2640  N    ARG  B  394    8.952   -8.189  29.819  1.00  21.29
ATOM   2641  CA   ARG  B  394    8.680   -9.003  30.990  1.00  22.43
ATOM   2642  CB   ARG  B  394    7.365   -8.601  31.667  1.00  23.97
ATOM   2643  CG   ARG  B  394    6.259   -8.149  30.759  1.00  25.16
ATOM   2644  CD   ARG  B  394    5.026   -7.727  31.574  1.00  20.86
ATOM   2645  NE   ARG  B  394    3.817   -7.937  30.786  1.00  19.54
ATOM   2646  CZ   ARG  B  394    3.327   -7.059  29.915  1.00  20.58
ATOM   2647  NH1  ARG  B  394    3.944   -5.902  29.722  1.00  17.41
ATOM   2648  NH2  ARG  B  394    2.229   -7.347  29.220  1.00  15.82
ATOM   2649  C    ARG  B  394    8.695  -10.502  30.713  1.00  21.78
ATOM   2650  O    ARG  B  394    8.657  -11.294  31.648  1.00  23.44
ATOM   2651  N    SER  B  395    8.767  -10.880  29.438  1.00  17.10
ATOM   2652  CA   SER  B  395    8.805  -12.289  29.041  1.00  25.08
ATOM   2653  CB   SER  B  395    8.206  -12.473  27.638  1.00  19.47
ATOM   2654  OG   SER  B  395    6.832  -12.136  27.619  1.00  21.73
```

Page 123 of 186

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   2655  C    SER  B  395    10.239  -12.831  29.031  1.00  26.29
ATOM   2656  O    SER  B  395    10.458  -14.030  28.854  1.00  23.75
ATOM   2657  N    MET  B  396    11.206  -11.938  29.210  1.00  30.79
ATOM   2658  CA   MET  B  396    12.620  -12.307  29.205  1.00  35.07
ATOM   2659  CB   MET  B  396    13.479  -11.063  29.423  1.00  33.84
ATOM   2660  CG   MET  B  396    14.155  -10.569  28.171  1.00  36.88
ATOM   2661  SD   MET  B  396    15.149   -9.127  28.491  1.00  40.96
ATOM   2662  CE   MET  B  396    16.675   -9.849  28.998  1.00  39.67
ATOM   2663  C    MET  B  396    12.983  -13.353  30.250  1.00  35.88
ATOM   2664  O    MET  B  396    13.828  -14.215  30.011  1.00  34.52
ATOM   2665  N    GLU  B  397    12.348  -13.266  31.410  1.00  36.19
ATOM   2666  CA   GLU  B  397    12.604  -14.206  32.492  1.00  39.24
ATOM   2667  CB   GLU  B  397    12.153  -13.605  33.821  1.00  44.38
ATOM   2668  CG   GLU  B  397    12.983  -12.422  34.271  1.00  54.05
ATOM   2669  CD   GLU  B  397    13.483  -12.587  35.686  1.00  56.78
ATOM   2670  OE1  GLU  B  397    13.380  -11.621  36.470  1.00  60.90
ATOM   2671  OE2  GLU  B  397    13.975  -13.688  36.013  1.00  60.82
ATOM   2672  C    GLU  B  397    11.878  -15.528  32.273  1.00  36.65
ATOM   2673  O    GLU  B  397    12.021  -16.459  33.061  1.00  35.84
ATOM   2674  N    HIS  B  398    11.100  -15.609  31.202  1.00  32.14
ATOM   2675  CA   HIS  B  398    10.347  -16.823  30.914  1.00  29.48
ATOM   2676  CB   HIS  B  398     8.863  -16.567  31.178  1.00  29.87
ATOM   2677  CG   HIS  B  398     8.582  -16.111  32.574  1.00  31.80
ATOM   2678  CD2  HIS  B  398     8.215  -16.801  33.678  1.00  29.12
ATOM   2679  ND1  HIS  B  398     8.727  -14.799  32.972  1.00  33.27
ATOM   2680  CE1  HIS  B  398     8.462  -14.701  34.262  1.00  32.19
ATOM   2681  NE2  HIS  B  398     8.148  -15.902  34.714  1.00  33.48
ATOM   2682  C    HIS  B  398    10.556  -17.317  29.492  1.00  25.95
ATOM   2683  O    HIS  B  398     9.637  -17.291  28.672  1.00  27.47
ATOM   2684  N    PRO  B  399    11.771  -17.801  29.186  1.00  29.09
ATOM   2685  CD   PRO  B  399    12.925  -17.922  30.096  1.00  29.93
ATOM   2686  CA   PRO  B  399    12.079  -18.300  27.845  1.00  27.40
ATOM   2687  CB   PRO  B  399    13.434  -18.988  28.016  1.00  32.09
ATOM   2688  CG   PRO  B  399    14.062  -18.284  29.170  1.00  30.81
ATOM   2689  C    PRO  B  399    11.009  -19.246  27.319  1.00  29.76
ATOM   2690  O    PRO  B  399    10.552  -20.137  28.035  1.00  29.18
ATOM   2691  N    GLY  B  400    10.601  -19.035  26.071  1.00  27.45
ATOM   2692  CA   GLY  B  400     9.588  -19.884  25.466  1.00  26.93
ATOM   2693  C    GLY  B  400     8.161  -19.537  25.849  1.00  26.73
ATOM   2694  O    GLY  B  400     7.220  -20.153  25.356  1.00  28.36
ATOM   2695  N    LYS  B  401     7.996  -18.554  26.727  1.00  25.50
ATOM   2696  CA   LYS  B  401     6.668  -18.139  27.165  1.00  23.45
ATOM   2697  CB   LYS  B  401     6.435  -18.563  28.619  1.00  28.80
ATOM   2698  CG   LYS  B  401     6.476  -20.069  28.879  1.00  28.58
ATOM   2699  CD   LYS  B  401     6.181  -20.353  30.349  1.00  35.47
ATOM   2700  CE   LYS  B  401     6.073  -21.847  30.635  1.00  38.59
ATOM   2701  NZ   LYS  B  401     7.177  -22.611  29.989  1.00  42.39
ATOM   2702  C    LYS  B  401     6.493  -16.622  27.060  1.00  21.78
ATOM   2703  O    LYS  B  401     7.465  -15.872  27.035  1.00  21.45
ATOM   2704  N    LEU  B  402     5.241  -16.181  26.995  1.00  23.45
ATOM   2705  CA   LEU  B  402     4.929  -14.759  26.925  1.00  21.37
ATOM   2706  CB   LEU  B  402     4.088  -14.449  25.689  1.00  18.47
ATOM   2707  CG   LEU  B  402     4.798  -14.673  24.360  1.00  16.89
ATOM   2708  CD1  LEU  B  402     3.821  -14.395  23.211  1.00  21.23
ATOM   2709  CD2  LEU  B  402     6.011  -13.760  24.277  1.00  23.15
ATOM   2710  C    LEU  B  402     4.147  -14.399  28.179  1.00  19.66
ATOM   2711  O    LEU  B  402     3.024  -14.880  28.381  1.00  18.05
ATOM   2712  N    LEU  B  403     4.743  -13.559  29.019  1.00  19.54
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

Page 125 of 186

It is certified that error appears in the above-identified patent and that said Letters Patent is hereby corrected as shown below:

```
ATOM   2713  CA   LEU  B  403    4.099  -13.148  30.259  1.00  20.21
ATOM   2714  CB   LEU  B  403    5.155  -12.856  31.332  1.00  23.16
ATOM   2715  CG   LEU  B  403    4.639  -12.682  32.766  1.00  29.54
ATOM   2716  CD1  LEU  B  403    5.519  -13.450  33.728  1.00  32.67
ATOM   2717  CD2  LEU  B  403    4.626  -11.213  33.138  1.00  32.38
ATOM   2718  C    LEU  B  403    3.219  -11.918  30.043  1.00  20.42
ATOM   2719  O    LEU  B  403    3.638  -10.787  30.291  1.00  19.18
ATOM   2720  N    PHE  B  404    2.003  -12.145  29.365  1.00  21.44
ATOM   2721  CA   PHE  B  404    1.066  -11.053  29.340  1.00  21.69
ATOM   2722  CB   PHE  B  404   -0.199  -11.598  28.687  1.00  17.26
ATOM   2723  CG   PHE  B  404   -0.026  -11.897  27.337  1.00  19.75
ATOM   2724  CD1  PHE  B  404    0.364  -13.167  26.801  1.00  17.90
ATOM   2725  CD2  PHE  B  404   -0.210  -10.897  26.280  1.00  17.04
ATOM   2726  CE1  PHE  B  404    0.572  -13.434  25.447  1.00  19.88
ATOM   2727  CE2  PHE  B  404   -0.007  -11.148  24.924  1.00  18.47
ATOM   2728  CZ   PHE  B  404    0.386  -12.418  24.503  1.00  16.45
ATOM   2729  C    PHE  B  404    0.768  -10.403  30.685  1.00  21.95
ATOM   2730  O    PHE  B  404    0.656   -9.177  30.804  1.00  22.99
ATOM   2731  N    ALA  B  405    0.670  -11.247  31.702  1.00  21.12
ATOM   2732  CA   ALA  B  405    0.424  -10.814  33.066  1.00  22.43
ATOM   2733  CB   ALA  B  405   -1.074  -10.603  33.304  1.00  24.69
ATOM   2734  C    ALA  B  405    0.959  -11.926  33.962  1.00  22.40
ATOM   2735  O    ALA  B  405    1.133  -13.061  33.517  1.00  21.67
ATOM   2736  N    PRO  B  406    1.246  -11.612  35.230  1.00  25.60
ATOM   2737  CD   PRO  B  406    1.129  -10.294  35.878  1.00  23.65
ATOM   2738  CA   PRO  B  406    1.765  -12.632  36.148  1.00  25.91
ATOM   2739  CB   PRO  B  406    1.899  -11.882  37.475  1.00  27.04
ATOM   2740  CG   PRO  B  406    2.017  -10.431  37.068  1.00  26.56
ATOM   2741  C    PRO  B  406    0.876  -13.873  36.259  1.00  25.12
ATOM   2742  O    PRO  B  406    1.368  -14.967  36.538  1.00  28.92
ATOM   2743  N    ASN  B  407   -0.426  -13.713  36.039  1.00  23.53
ATOM   2744  CA   ASN  B  407   -1.345  -14.852  36.109  1.00  24.09
ATOM   2745  CB   ASN  B  407   -2.553  -14.526  36.986  1.00  24.08
ATOM   2746  CG   ASN  B  407   -3.327  -13.328  36.486  1.00  26.72
ATOM   2747  OD1  ASN  B  407   -2.851  -12.574  35.635  1.00  22.65
ATOM   2748  ND2  ASN  B  407   -4.528  -13.140  37.019  1.00  26.46
ATOM   2749  C    ASN  B  407   -1.820  -15.231  34.714  1.00  26.91
ATOM   2750  O    ASN  B  407   -2.859  -15.870  34.548  1.00  28.68
ATOM   2751  N    LEU  B  408   -1.059  -14.816  33.708  1.00  27.28
ATOM   2752  CA   LEU  B  408   -1.387  -15.124  32.327  1.00  27.23
ATOM   2753  CB   LEU  B  408   -2.247  -14.030  31.699  1.00  26.61
ATOM   2754  CG   LEU  B  408   -2.815  -14.464  30.341  1.00  27.51
ATOM   2755  CD1  LEU  B  408   -3.702  -15.692  30.546  1.00  28.75
ATOM   2756  CD2  LEU  B  408   -3.598  -13.330  29.694  1.00  25.48
ATOM   2757  C    LEU  B  408   -0.113  -15.316  31.514  1.00  27.56
ATOM   2758  O    LEU  B  408    0.247  -14.465  30.695  1.00  26.86
ATOM   2759  N    LEU  B  409    0.553  -16.426  31.759  1.00  27.54
ATOM   2760  CA   LEU  B  409    1.786  -16.774  31.065  1.00  31.96
ATOM   2761  CB   LEU  B  409    2.786  -17.355  32.058  1.00  31.88
ATOM   2762  CG   LEU  B  409    4.186  -17.703  31.563  1.00  37.72
ATOM   2763  CD1  LEU  B  409    4.773  -16.551  30.770  1.00  39.57
ATOM   2764  CD2  LEU  B  409    5.066  -18.018  32.758  1.00  41.72
ATOM   2765  C    LEU  B  409    1.401  -17.805  30.009  1.00  31.53
ATOM   2766  O    LEU  B  409    0.921  -18.892  30.340  1.00  32.67
ATOM   2767  N    LEU  B  410    1.604  -17.465  28.746  1.00  29.58
ATOM   2768  CA   LEU  B  410    1.228  -18.361  27.660  1.00  31.55
ATOM   2769  CB   LEU  B  410    0.192  -17.672  26.762  1.00  29.83
ATOM   2770  CG   LEU  B  410   -1.047  -17.080  27.452  1.00  28.55
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   2771  CD1  LEU  B  410   -1.770  -16.135  26.501  1.00  26.92
ATOM   2772  CD2  LEU  B  410   -1.979  -18.380  27.891  1.00  30.49
ATOM   2773  C    LEU  B  410    2.397  -18.839  26.814  1.00  33.88
ATOM   2774  O    LEU  B  410    3.427  -18.170  26.736  1.00  36.49
ATOM   2775  N    ASP  B  411    2.238  -20.013  26.206  1.00  38.80
ATOM   2776  CA   ASP  B  411    3.275  -20.562  25.336  1.00  38.39
ATOM   2777  CB   ASP  B  411    3.657  -21.990  25.752  1.00  44.53
ATOM   2778  CG   ASP  B  411    2.476  -22.943  25.749  1.00  44.90
ATOM   2779  OD1  ASP  B  411    1.773  -23.035  24.719  1.00  45.70
ATOM   2780  OD2  ASP  B  411    2.254  -23.603  26.786  1.00  50.54
ATOM   2781  C    ASP  B  411    2.745  -20.551  23.909  1.00  38.57
ATOM   2782  O    ASP  B  411    1.549  -20.341  23.686  1.00  36.48
ATOM   2783  N    ARG  B  412    3.635  -20.777  22.949  1.00  36.85
ATOM   2784  CA   ARG  B  412    3.259  -20.763  21.541  1.00  38.32
ATOM   2785  CB   ARG  B  412    4.488  -21.083  20.675  1.00  38.69
ATOM   2786  CG   ARG  B  412    4.361  -22.314  19.799  1.00  40.05
ATOM   2787  CD   ARG  B  412    5.644  -22.552  19.012  1.00  42.98
ATOM   2788  NE   ARG  B  412    5.540  -22.099  17.626  1.00  40.95
ATOM   2789  CZ   ARG  B  412    4.649  -22.559  16.753  1.00  41.11
ATOM   2790  NH1  ARG  B  412    3.777  -23.490  17.115  1.00  44.01
ATOM   2791  NH2  ARG  B  412    4.632  -22.091  15.515  1.00  41.28
ATOM   2792  C    ARG  B  412    2.107  -21.712  21.217  1.00  37.64
ATOM   2793  O    ARG  B  412    1.287  -21.427  20.343  1.00  36.51
ATOM   2794  N    ASN  B  413    2.041  -22.834  21.923  1.00  35.32
ATOM   2795  CA   ASN  B  413    0.974  -23.798  21.688  1.00  36.68
ATOM   2796  CB   ASN  B  413    1.170  -25.035  22.570  1.00  37.54
ATOM   2797  CG   ASN  B  413    2.017  -26.100  21.901  1.00  43.56
ATOM   2798  OD1  ASN  B  413    2.309  -26.022  20.704  1.00  46.11
ATOM   2799  ND2  ASN  B  413    2.418  -27.104  22.671  1.00  47.04
ATOM   2800  C    ASN  B  413   -0.383  -23.168  21.983  1.00  34.01
ATOM   2801  O    ASN  B  413   -1.349  -23.372  21.247  1.00  32.43
ATOM   2802  N    GLN  B  414   -0.447  -22.397  23.063  1.00  32.85
ATOM   2803  CA   GLN  B  414   -1.685  -21.741  23.449  1.00  31.91
ATOM   2804  CB   GLN  B  414   -1.558  -21.172  24.863  1.00  33.17
ATOM   2805  CG   GLN  B  414   -1.528  -22.242  25.948  1.00  32.31
ATOM   2806  CD   GLN  B  414   -1.293  -21.667  27.327  1.00  34.63
ATOM   2807  OE1  GLN  B  414   -0.176  -21.277  27.666  1.00  33.23
ATOM   2808  NE2  GLN  B  414   -2.349  -21.606  28.131  1.00  34.56
ATOM   2809  C    GLN  B  414   -2.052  -20.638  22.463  1.00  29.57
ATOM   2810  O    GLN  B  414   -3.195  -20.204  22.409  1.00  31.32
ATOM   2811  N    GLY  B  415   -1.077  -20.190  21.682  1.00  30.96
ATOM   2812  CA   GLY  B  415   -1.350  -19.160  20.697  1.00  34.27
ATOM   2813  C    GLY  B  415   -2.184  -19.725  19.562  1.00  35.27
ATOM   2814  O    GLY  B  415   -2.918  -19.000  18.887  1.00  33.20
ATOM   2815  N    LYS  B  416   -2.070  -21.031  19.354  1.00  35.28
ATOM   2816  CA   LYS  B  416   -2.819  -21.707  18.299  1.00  38.26
ATOM   2817  CB   LYS  B  416   -2.398  -23.177  18.201  1.00  38.00
ATOM   2818  CG   LYS  B  416   -0.973  -23.407  17.736  1.00  40.05
ATOM   2819  CD   LYS  B  416   -0.405  -24.668  18.369  1.00  44.10
ATOM   2820  CE   LYS  B  416    0.306  -25.541  17.346  1.00  41.85
ATOM   2821  NZ   LYS  B  416    1.286  -24.760  16.543  1.00  45.63
ATOM   2822  C    LYS  B  416   -4.321  -21.645  18.559  1.00  36.93
ATOM   2823  O    LYS  B  416   -5.131  -21.790  17.638  1.00  38.36
ATOM   2824  N    CYS  B  417   -4.698  -21.430  19.817  1.00  37.10
ATOM   2825  CA   CYS  B  417   -6.106  -21.371  20.196  1.00  36.46
ATOM   2826  CB   CYS  B  417   -6.218  -21.226  21.717  1.00  39.01
ATOM   2827  SG   CYS  B  417   -5.674  -22.710  22.612  1.00  43.81
ATOM   2828  C    CYS  B  417   -6.899  -20.277  19.491  1.00  35.19
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

Page 127 of 186

It is certified that error appears in the above-identified patent and that said Letters Patent is hereby corrected as shown below:

```
ATOM   2829  O    CYS B 417   -8.127 -20.296 19.485  1.00  33.92
ATOM   2830  N    VAL B 418   -6.195 -19.316 18.906  1.00  36.04
ATOM   2831  CA   VAL B 418   -6.838 -18.236 18.163  1.00  34.59
ATOM   2832  CB   VAL B 418   -6.525 -16.880 18.775  1.00  34.87
ATOM   2833  CG1  VAL B 418   -6.831 -15.763 17.785  1.00  35.33
ATOM   2834  CG2  VAL B 418   -7.350 -16.630 20.036  1.00  33.65
ATOM   2835  C    VAL B 418   -6.241 -18.317 16.764  1.00  34.17
ATOM   2836  O    VAL B 418   -5.020 -18.323 16.611  1.00  32.73
ATOM   2837  N    GLU B 419   -7.084 -18.388 15.740  1.00  33.44
ATOM   2838  CA   GLU B 419   -6.554 -18.500 14.390  1.00  34.52
ATOM   2839  CB   GLU B 419   -7.681 -18.722 13.386  1.00  36.21
ATOM   2840  CG   GLU B 419   -8.597 -17.538 13.166  1.00  44.19
ATOM   2841  CD   GLU B 419   -9.477 -17.723 11.946  1.00  48.47
ATOM   2842  OE1  GLU B 419   -9.157 -18.605 11.119  1.00  51.04
ATOM   2843  OE2  GLU B 419  -10.484 -16.993 11.813  1.00  48.91
ATOM   2844  C    GLU B 419   -5.717 -17.289 13.997  1.00  32.89
ATOM   2845  O    GLU B 419   -6.156 -16.144 14.123  1.00  31.09
ATOM   2846  N    GLY B 420   -4.501 -17.562 13.535  1.00  32.84
ATOM   2847  CA   GLY B 420   -3.594 -16.506 13.132  1.00  34.37
ATOM   2848  C    GLY B 420   -2.732 -15.955 14.240  1.00  35.30
ATOM   2849  O    GLY B 420   -1.745 -15.246 13.975  1.00  35.94
ATOM   2850  N    MET B 421   -3.052 -16.285 15.486  1.00  30.08
ATOM   2851  CA   MET B 421   -2.289 -15.780 16.625  1.00  29.22
ATOM   2852  CB   MET B 421   -3.108 -15.922 17.914  1.00  22.54
ATOM   2853  CG   MET B 421   -2.469 -15.270 19.124  1.00  23.82
ATOM   2854  SD   MET B 421   -2.124 -13.494 18.872  1.00  28.40
ATOM   2855  CE   MET B 421   -3.697 -12.800 19.233  1.00  24.67
ATOM   2856  C    MET B 421   -0.912 -16.416 16.821  1.00  29.67
ATOM   2857  O    MET B 421    0.022 -15.751 17.269  1.00  29.76
ATOM   2858  N    VAL B 422   -0.766 -17.694 16.484  1.00  30.63
ATOM   2859  CA   VAL B 422    0.524 -18.338 16.675  1.00  29.90
ATOM   2860  CB   VAL B 422    0.482 -19.835 16.273  1.00  35.74
ATOM   2861  CG1  VAL B 422    0.514 -19.992 14.753  1.00  37.64
ATOM   2862  CG2  VAL B 422    1.659 -20.555 16.897  1.00  31.68
ATOM   2863  C    VAL B 422    1.669 -17.640 15.935  1.00  28.64
ATOM   2864  O    VAL B 422    2.788 -17.571 16.441  1.00  26.15
ATOM   2865  N    GLU B 423    1.402 -17.113 14.747  1.00  28.70
ATOM   2866  CA   GLU B 423    2.454 -16.435 13.997  1.00  31.34
ATOM   2867  CB   GLU B 423    1.963 -16.050 12.596  1.00  36.21
ATOM   2868  CG   GLU B 423    0.502 -16.376 12.325  1.00  45.83
ATOM   2869  CD   GLU B 423    0.250 -17.865 12.144  1.00  46.71
ATOM   2870  OE1  GLU B 423   -0.746 -18.368 12.706  1.00  45.97
ATOM   2871  OE2  GLU B 423    1.045 -18.530 11.442  1.00  50.05
ATOM   2872  C    GLU B 423    2.928 -15.186 14.744  1.00  30.57
ATOM   2873  O    GLU B 423    4.119 -14.870 14.759  1.00  26.59
ATOM   2874  N    ILE B 424    2.001 -14.478 15.378  1.00  26.19
ATOM   2875  CA   ILE B 424    2.381 -13.279 16.111  1.00  26.23
ATOM   2876  CB   ILE B 424    1.134 -12.435 16.452  1.00  29.33
ATOM   2877  CG2  ILE B 424    1.492 -11.315 17.425  1.00  30.91
ATOM   2878  CG1  ILE B 424    0.584 -11.817 15.160  1.00  29.09
ATOM   2879  CD1  ILE B 424   -0.895 -11.514 15.187  1.00  30.51
ATOM   2880  C    ILE B 424    3.153 -13.673 17.370  1.00  24.22
ATOM   2881  O    ILE B 424    4.152 -13.037 17.725  1.00  21.05
ATOM   2882  N    PHE B 425    2.708 -14.746 18.023  1.00  21.71
ATOM   2883  CA   PHE B 425    3.370 -15.236 19.233  1.00  18.85
ATOM   2884  CB   PHE B 425    2.650 -16.479 19.768  1.00  22.98
ATOM   2885  CG   PHE B 425    1.580 -16.183 20.795  1.00  22.17
ATOM   2886  CD1  PHE B 425    1.287 -17.112 21.792  1.00  25.47
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    2887  CD2   PHE  B  425    0.843 -15.001 20.747  1.00  26.30
ATOM    2888  CE1   PHE  B  425    0.273 -16.871 22.724  1.00  24.33
ATOM    2889  CE2   PHE  B  425   -0.174 -14.749 21.676  1.00  25.03
ATOM    2890  CZ    PHE  B  425   -0.459 -15.684 22.563  1.00  26.44
ATOM    2891  C     PHE  B  425    4.817 -15.610 18.885  1.00  20.00
ATOM    2892  O     PHE  B  425    5.741 -15.292 19.636  1.00  21.15
ATOM    2893  N     ASP  B  426    5.023 -16.281 17.754  1.00  19.87
ATOM    2894  CA    ASP  B  426    6.378 -16.685 17.377  1.00  23.20
ATOM    2895  CB    ASP  B  426    6.364 -17.510 16.090  1.00  26.53
ATOM    2896  CG    ASP  B  426    5.992 -18.965 16.335  1.00  34.28
ATOM    2897  OD1   ASP  B  426    6.242 -19.467 17.455  1.00  35.24
ATOM    2898  OD2   ASP  B  426    5.448 -19.600 15.409  1.00  31.49
ATOM    2899  C     ASP  B  426    7.302 -15.489 17.198  1.00  21.84
ATOM    2900  O     ASP  B  426    8.465 -15.526 17.593  1.00  21.55
ATOM    2901  N     MET  B  427    6.788 -14.429 16.591  1.00  20.12
ATOM    2902  CA    MET  B  427    7.597 -13.234 16.382  1.00  21.02
ATOM    2903  CB    MET  B  427    6.836 -12.228 15.520  1.00  18.53
ATOM    2904  CG    MET  B  427    6.864 -12.559 14.038  1.00  27.92
ATOM    2905  SD    MET  B  427    6.011 -11.341 13.024  1.00  32.84
ATOM    2906  CE    MET  B  427    4.363 -11.532 13.581  1.00  33.63
ATOM    2907  C     MET  B  427    7.945 -12.616 17.732  1.00  17.42
ATOM    2908  O     MET  B  427    9.073 -12.180 17.950  1.00  22.09
ATOM    2909  N     LEU  B  428    6.968 -12.597 18.634  1.00  20.47
ATOM    2910  CA    LEU  B  428    7.157 -12.033 19.968  1.00  20.13
ATOM    2911  CB    LEU  B  428    5.812 -11.964 20.706  1.00  17.58
ATOM    2912  CG    LEU  B  428    4.852 -10.887 20.179  1.00  18.41
ATOM    2913  CD1   LEU  B  428    3.443 -11.155 20.687  1.00  11.95
ATOM    2914  CD2   LEU  B  428    5.324  -9.505 20.631  1.00  17.80
ATOM    2915  C     LEU  B  428    8.159 -12.856 20.767  1.00  20.68
ATOM    2916  O     LEU  B  428    9.028 -12.305 21.493  1.00  20.45
ATOM    2917  N     LEU  B  429    8.037 -14.178 20.679  1.00  20.35
ATOM    2918  CA    LEU  B  429    8.938 -15.082 21.382  1.00  19.82
ATOM    2919  CB    LEU  B  429    8.470 -16.532 21.211  1.00  23.13
ATOM    2920  CG    LEU  B  429    7.189 -16.839 21.997  1.00  21.85
ATOM    2921  CD1   LEU  B  429    6.551 -18.123 21.494  1.00  25.39
ATOM    2922  CD2   LEU  B  429    7.537 -16.944 23.475  1.00  24.91
ATOM    2923  C     LEU  B  429   10.361 -14.936 20.865  1.00  20.74
ATOM    2924  O     LEU  B  429   11.318 -14.968 21.638  1.00  21.02
ATOM    2925  N     ALA  B  430   10.495 -14.770 19.554  1.00  31.40
ATOM    2926  CA    ALA  B  430   11.808 -14.609 18.947  1.00  22.77
ATOM    2927  CB    ALA  B  430   11.677 -14.596 17.432  1.00  21.11
ATOM    2928  C     ALA  B  430   12.467 -13.315 19.440  1.00  22.40
ATOM    2929  O     ALA  B  430   13.670 -13.277 19.713  1.00  20.62
ATOM    2930  N     THR  B  431   11.670 -12.258 19.567  1.00  21.09
ATOM    2931  CA    THR  B  431   12.183 -10.974 20.021  1.00  22.67
ATOM    2932  CB    THR  B  431   11.128  -9.866 19.863  1.00  23.77
ATOM    2933  OG1   THR  B  431   10.572  -9.936 18.547  1.00  23.84
ATOM    2934  CG2   THR  B  431   11.762  -8.489 20.073  1.00  21.78
ATOM    2935  C     THR  B  431   12.603 -11.037 21.480  1.00  21.98
ATOM    2936  O     THR  B  431   13.595 -10.429 21.879  1.00  19.85
ATOM    2937  N     SER  B  432   11.844 -11.773 22.260  1.00  24.24
ATOM    2938  CA    SER  B  432   12.169 -11.906 23.693  1.00  26.96
ATOM    2939  CB    SER  B  432   11.055 -12.661 24.423  1.00  28.00
ATOM    2940  OG    SER  B  432   11.404 -12.888 25.776  1.00  30.31
ATOM    2941  C     SER  B  432   13.491 -12.660 23.820  1.00  27.67
ATOM    2942  O     SER  B  432   14.305 -12.377 24.701  1.00  23.78
ATOM    2943  N     SER  B  433   13.691 -13.628 22.932  1.00  29.27
ATOM    2944  CA    SER  B  433   14.914 -14.421 22.928  1.00  31.96
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    2945  CB   SER   B   433    14.790  -15.575  21.938  1.00  30.84
ATOM    2946  OG   SER   B   433    14.761  -16.808  22.625  1.00  38.26
ATOM    2947  C    SER   B   433    16.104  -13.550  22.548  1.00  31.47
ATOM    2948  O    SER   B   433    17.204  -13.701  23.087  1.00  28.43
ATOM    2949  N    ARG   B   434    15.878  -12.641  21.607  1.00  29.55
ATOM    2950  CA   ARG   B   434    16.926  -11.739  21.165  1.00  29.40
ATOM    2951  CB   ARG   B   434    16.437  -10.912  19.977  1.00  31.56
ATOM    2952  CG   ARG   B   434    17.428   -9.868  19.493  1.00  36.76
ATOM    2953  CD   ARG   B   434    18.694  -10.502  18.919  1.00  37.76
ATOM    2954  NE   ARG   B   434    19.654   -9.479  18.516  1.00  39.50
ATOM    2955  CZ   ARG   B   434    20.965   -9.673  18.418  1.00  44.17
ATOM    2956  NH1  ARG   B   434    21.492  -10.861  18.696  1.00  43.17
ATOM    2957  NH2  ARG   B   434    21.750   -8.671  18.048  1.00  43.05
ATOM    2958  C    ARG   B   434    17.328  -10.827  22.326  1.00  29.15
ATOM    2959  O    ARG   B   434    18.515  -10.612  22.569  1.00  28.82
ATOM    2960  N    PHE   B   435    16.337  -10.297  23.039  1.00  24.88
ATOM    2961  CA   PHE   B   435    16.600   -9.422  24.186  1.00  25.74
ATOM    2962  CB   PHE   B   435    15.278   -8.972  24.825  1.00  26.53
ATOM    2963  CG   PHE   B   435    14.656   -7.758  24.183  1.00  30.94
ATOM    2964  CD1  PHE   B   435    15.118   -7.271  22.966  1.00  32.65
ATOM    2965  CD2  PHE   B   435    13.592   -7.108  24.797  1.00  33.60
ATOM    2966  CE1  PHE   B   435    14.529   -6.155  22.372  1.00  36.84
ATOM    2967  CE2  PHE   B   435    12.997   -5.989  24.208  1.00  34.96
ATOM    2968  CZ   PHE   B   435    13.468   -5.516  22.995  1.00  31.64
ATOM    2969  C    PHE   B   435    17.426  -10.184  25.233  1.00  25.39
ATOM    2970  O    PHE   B   435    18.414   -9.675  25.764  1.00  22.59
ATOM    2971  N    ARG   B   436    16.999  -11.405  25.528  1.00  24.58
ATOM    2972  CA   ARG   B   436    17.675  -12.253  26.503  1.00  30.25
ATOM    2973  CB   ARG   B   436    16.898  -13.569  26.662  1.00  33.32
ATOM    2974  CG   ARG   B   436    17.232  -14.358  27.915  1.00  38.17
ATOM    2975  CD   ARG   B   436    16.135  -15.367  28.260  1.00  37.27
ATOM    2976  NE   ARG   B   436    15.646  -16.085  27.086  1.00  43.92
ATOM    2977  CZ   ARG   B   436    14.433  -15.923  26.557  1.00  46.68
ATOM    2978  NH1  ARG   B   436    13.578  -15.061  27.097  1.00  45.59
ATOM    2979  NH2  ARG   B   436    14.074  -16.620  25.486  1.00  46.25
ATOM    2980  C    ARG   B   436    19.110  -12.531  26.048  1.00  29.83
ATOM    2981  O    ARG   B   436    20.057  -12.397  26.823  1.00  28.76
ATOM    2982  N    AMET  B   437    19.269  -12.921  24.789  0.50  30.27
ATOM    2983  N    BMET  B   437    19.252  -12.906  24.781  0.50  31.41
ATOM    2984  CA   AMET  B   437    20.591  -13.212  24.253  0.50  31.98
ATOM    2985  CA   BMET  B   437    20.547  -13.206  24.183  0.50  33.77
ATOM    2986  CB   AMET  B   437    20.489  -13.646  22.788  0.50  31.34
ATOM    2987  CB   BMET  B   437    20.348  -13.595  22.714  0.50  35.88
ATOM    2988  CG   AMET  B   437    20.179  -15.127  22.592  0.50  33.62
ATOM    2989  CG   BMET  B   437    21.605  -13.594  21.861  0.50  40.47
ATOM    2990  SD   AMET  B   437    20.354  -16.099  24.109  0.50  35.21
ATOM    2991  SD   BMET  B   437    21.247  -13.937  20.115  0.50  46.79
ATOM    2992  CE   AMET  B   437    22.155  -16.194  24.259  0.50  33.20
ATOM    2993  CE   BMET  B   437    21.837  -15.632  19.976  0.50  43.22
ATOM    2994  C    AMET  B   437    21.498  -11.993  24.366  0.50  33.33
ATOM    2995  C    BMET  B   437    21.487  -12.005  24.289  0.50  34.45
ATOM    2996  O    AMET  B   437    22.702  -13.123  24.594  0.50  33.54
ATOM    2997  O    BMET  B   437    22.699  -12.162  24.438  0.50  34.43
ATOM    2998  N    MET   B   438    20.913  -10.809  24.215  1.00  32.07
ATOM    2999  CA   MET   B   438    21.674   -9.560  24.298  1.00  32.48
ATOM    3000  CB   MET   B   438    20.930   -8.437  23.578  1.00  29.74
ATOM    3001  CG   MET   B   438    21.161   -8.364  22.093  1.00  36.73
ATOM    3002  SD   MET   B   438    20.425   -6.849  21.462  1.00  38.21
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   3003  CE   MET  B  438   21.693  -5.657 21.943  1.00  35.91
ATOM   3004  C    MET  B  438   21.877  -9.122 25.738  1.00  28.81
ATOM   3005  O    MET  B  438   22.686  -8.240 26.013  1.00  30.13
ATOM   3006  N    ASN  B  439   21.120  -9.721 26.646  1.00  27.14
ATOM   3007  CA   ASN  B  439   21.199  -9.359 28.038  1.00  27.34
ATOM   3008  CB   ASN  B  439   22.592  -9.524 28.598  1.00  34.85
ATOM   3009  CG   ASN  B  439   22.624  -9.480 30.080  1.00  38.58
ATOM   3010  OD1  ASN  B  439   21.584  -9.620 30.724  1.00  42.99
ATOM   3011  ND2  ASN  B  439   23.801  -9.260 30.666  1.00  41.14
ATOM   3012  C    ASN  B  439   20.745  -7.903 28.212  1.00  26.24
ATOM   3013  O    ASN  B  439   21.396  -7.106 28.891  1.00  19.76
ATOM   3014  N    LEU  B  440   19.625  -7.564 27.573  1.00  24.90
ATOM   3015  CA   LEU  B  440   19.061  -6.214 27.633  1.00  25.04
ATOM   3016  CB   LEU  B  440   17.761  -6.157 26.818  1.00  22.36
ATOM   3017  CG   LEU  B  440   17.087  -4.786 26.740  1.00  26.33
ATOM   3018  CD1  LEU  B  440   17.958  -3.843 25.923  1.00  38.33
ATOM   3019  CD2  LEU  B  440   15.704  -4.914 26.111  1.00  24.81
ATOM   3020  C    LEU  B  440   18.782  -5.785 29.074  1.00  24.71
ATOM   3021  O    LEU  B  440   18.131  -6.504 29.830  1.00  26.96
ATOM   3022  N    GLN  B  441   19.268  -4.609 29.452  1.00  25.54
ATOM   3023  CA   GLN  B  441   19.060  -4.099 30.807  1.00  25.82
ATOM   3024  CB   GLN  B  441   20.250  -3.231 31.234  1.00  30.41
ATOM   3025  CG   GLN  B  441   21.572  -3.956 31.228  1.00  30.50
ATOM   3026  CD   GLN  B  441   21.610  -5.028 32.279  1.00  32.75
ATOM   3027  OE1  GLN  B  441   21.539  -4.772 33.473  1.00  36.52
ATOM   3028  NE2  GLN  B  441   21.703  -6.288 31.823  1.00  31.09
ATOM   3029  C    GLN  B  441   17.789  -3.265 30.883  1.00  26.93
ATOM   3030  O    GLN  B  441   17.303  -2.768 29.866  1.00  25.40
ATOM   3031  N    GLY  B  442   17.266  -3.105 32.096  1.00  24.56
ATOM   3032  CA   GLY  B  442   16.058  -2.327 32.293  1.00  22.82
ATOM   3033  C    GLY  B  442   16.217  -0.873 31.885  1.00  24.19
ATOM   3034  O    GLY  B  442   15.290  -0.279 31.341  1.00  20.21
ATOM   3035  N    GLU  B  443   17.387  -0.293 32.141  1.00  22.92
ATOM   3036  CA   GLU  B  443   17.635   1.102 31.778  1.00  23.33
ATOM   3037  CB   GLU  B  443   18.960   1.590 32.378  1.00  24.26
ATOM   3038  CG   GLU  B  443   19.005   1.525 33.895  1.00  32.31
ATOM   3039  CD   GLU  B  443   19.701   0.270 34.402  1.00  37.68
ATOM   3040  OE1  GLU  B  443   19.343  -0.841 33.948  1.00  35.23
ATOM   3041  OE2  GLU  B  443   20.607   0.394 35.252  1.00  42.47
ATOM   3042  C    GLU  B  443   17.662   1.278 30.262  1.00  23.08
ATOM   3043  O    GLU  B  443   17.265   2.328 29.747  1.00  21.80
ATOM   3044  N    GLU  B  444   18.128   0.253 29.552  1.00  21.16
ATOM   3045  CA   GLU  B  444   18.182   0.302 28.093  1.00  22.60
ATOM   3046  CB   GLU  B  444   19.046  -0.834 27.545  1.00  20.89
ATOM   3047  CG   GLU  B  444   20.545  -0.617 27.705  1.00  23.24
ATOM   3048  CD   GLU  B  444   21.340  -1.869 27.393  1.00  22.11
ATOM   3049  OE1  GLU  B  444   20.817  -2.978 27.629  1.00  20.89
ATOM   3050  OE2  GLU  B  444   22.488  -1.746 26.914  1.00  25.49
ATOM   3051  C    GLU  B  444   16.758   0.155 27.552  1.00  21.06
ATOM   3052  O    GLU  B  444   16.377   0.822 26.597  1.00  23.73
ATOM   3053  N    PHE  B  445   15.987  -0.730 28.176  1.00  19.01
ATOM   3054  CA   PHE  B  445   14.600  -0.969 27.792  1.00  19.44
ATOM   3055  CB   PHE  B  445   13.989  -2.067 28.675  1.00  18.12
ATOM   3056  CG   PHE  B  445   12.483  -2.055 28.709  1.00  18.13
ATOM   3057  CD1  PHE  B  445   11.746  -2.386 27.575  1.00  18.34
ATOM   3058  CD2  PHE  B  445   11.802  -1.694 29.872  1.00  16.59
ATOM   3059  CE1  PHE  B  445   10.346  -2.359 27.592  1.00  17.15
ATOM   3060  CE2  PHE  B  445   10.406  -1.662 29.903  1.00  21.99
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   3061  CZ   PHE  B   445    9.674  -1.997 28.755  1.00  16.01
ATOM   3062  C    PHE  B   445   13.758   0.304 27.888  1.00  15.87
ATOM   3063  O    PHE  B   445   13.008   0.617 26.966  1.00  20.27
ATOM   3064  N    VAL  B   446   13.872   1.044 28.986  1.00  15.90
ATOM   3065  CA   VAL  B   446   13.074   2.269 29.112  1.00  16.78
ATOM   3066  CB   VAL  B   446   13.165   2.895 30.531  1.00  18.32
ATOM   3067  CG1  VAL  B   446   12.574   1.923 31.581  1.00  21.14
ATOM   3068  CG2  VAL  B   446   14.598   3.251 30.879  1.00  21.04
ATOM   3069  C    VAL  B   446   13.450   3.295 28.051  1.00  17.91
ATOM   3070  O    VAL  B   446   12.596   4.028 27.561  1.00  19.37
ATOM   3071  N    CYS  B   447   14.723   3.335 27.674  1.00  18.81
ATOM   3072  CA   CYS  B   447   15.161   4.255 26.635  1.00  17.34
ATOM   3073  CB   CYS  B   447   16.682   4.234 26.512  1.00  19.33
ATOM   3074  SG   CYS  B   447   17.538   5.134 27.798  1.00  23.60
ATOM   3075  C    CYS  B   447   14.537   3.826 25.301  1.00  18.09
ATOM   3076  O    CYS  B   447   13.988   4.643 24.563  1.00  17.52
ATOM   3077  N    LEU  B   448   14.633   2.533 25.006  1.00  15.60
ATOM   3078  CA   LEU  B   448   14.072   1.994 23.767  1.00  16.67
ATOM   3079  CB   LEU  B   448   14.328   0.490 23.684  1.00  14.82
ATOM   3080  CG   LEU  B   448   15.730   0.009 23.301  1.00  23.57
ATOM   3081  CD1  LEU  B   448   15.722  -1.522 23.169  1.00  21.61
ATOM   3082  CD2  LEU  B   448   16.167   0.658 21.986  1.00  18.92
ATOM   3083  C    LEU  B   448   12.573   2.249 23.652  1.00  15.98
ATOM   3084  O    LEU  B   448   12.078   2.633 22.590  1.00  18.91
ATOM   3085  N    LYS  B   449   11.849   2.037 24.745  1.00  17.94
ATOM   3086  CA   LYS  B   449   10.405   2.232 24.733  1.00  16.66
ATOM   3087  CB   LYS  B   449    9.796   1.745 26.047  1.00  16.45
ATOM   3088  CG   LYS  B   449    8.285   1.861 26.115  1.00  16.12
ATOM   3089  CD   LYS  B   449    7.730   0.952 27.193  1.00  19.09
ATOM   3090  CE   LYS  B   449    8.201   1.380 28.580  1.00  17.04
ATOM   3091  NZ   LYS  B   449    7.159   1.088 29.593  1.00  17.25
ATOM   3092  C    LYS  B   449   10.058   3.696 24.486  1.00  18.78
ATOM   3093  O    LYS  B   449    9.103   3.996 23.769  1.00  14.84
ATOM   3094  N    SER  B   450   10.837   4.610 25.059  1.00  14.50
ATOM   3095  CA   SER  B   450   10.591   6.032 24.849  1.00  17.11
ATOM   3096  CB   SER  B   450   11.440   6.866 25.815  1.00  21.20
ATOM   3097  OG   SER  B   450   10.859   6.868 27.108  1.00  30.66
ATOM   3098  C    SER  B   450   10.921   6.418 23.405  1.00  17.84
ATOM   3099  O    SER  B   450   10.279   7.293 22.821  1.00  18.82
ATOM   3100  N    ILE  B   451   11.926   5.768 22.828  1.00  16.88
ATOM   3101  CA   ILE  B   451   12.305   6.063 21.450  1.00  17.11
ATOM   3102  CB   ILE  B   451   13.564   5.268 21.025  1.00  16.69
ATOM   3103  CG2  ILE  B   451   13.724   5.298 19.505  1.00  19.31
ATOM   3104  CG1  ILE  B   451   14.804   5.897 21.676  1.00  18.96
ATOM   3105  CD1  ILE  B   451   16.083   5.130 21.431  1.00  18.98
ATOM   3106  C    ILE  B   451   11.142   5.711 20.527  1.00  18.09
ATOM   3107  O    ILE  B   451   10.820   6.464 19.608  1.00  17.07
ATOM   3108  N    ILE  B   452   10.505   4.571 20.786  1.00  18.13
ATOM   3109  CA   ILE  B   452    9.373   4.137 19.976  1.00  16.77
ATOM   3110  CB   ILE  B   452    8.804   2.775 20.477  1.00  17.40
ATOM   3111  CG2  ILE  B   452    7.464   2.496 19.831  1.00  14.33
ATOM   3112  CG1  ILE  B   452    9.763   1.635 20.107  1.00  15.36
ATOM   3113  CD1  ILE  B   452    9.449   0.323 20.805  1.00  17.76
ATOM   3114  C    ILE  B   452    8.271   5.195 20.024  1.00  17.47
ATOM   3115  O    ILE  B   452    7.733   5.586 18.992  1.00  16.50
ATOM   3116  N    LEU  B   453    7.943   5.665 21.222  1.00  16.06
ATOM   3117  CA   LEU  B   453    6.903   6.680 21.374  1.00  17.17
ATOM   3118  CB   LEU  B   453    6.736   7.061 22.850  1.00  16.23
```

UNITED STATES PATENT AND TRADEMARK OFFICE
CERTIFICATE OF CORRECTION

PATENT NO.       : 6,965,850 B2
APPLICATION NO.  : 09/281717
DATED            : November 15, 2005
INVENTOR(S)      : John D. Baxter et al.

It is certified that error appears in the above-identified patent and that said Letters Patent is hereby corrected as shown below:

| | | | | | | | | | |
|---|---|---|---|---|---|---|---|---|---|
| ATOM | 3119 | CG  | LEU | B | 453 | 5.792  | 8.238  | 23.183 | 1.00 17.60 |
| ATOM | 3120 | CD1 | LEU | B | 453 | 4.388  | 7.861  | 22.704 | 1.00 16.94 |
| ATOM | 3121 | CD2 | LEU | B | 453 | 5.816  | 8.538  | 24.667 | 1.00 17.17 |
| ATOM | 3122 | C   | LEU | B | 453 | 7.198  | 7.941  | 20.368 | 1.00 19.33 |
| ATOM | 3123 | O   | LEU | B | 453 | 6.320  | 8.438  | 19.879 | 1.00 21.37 |
| ATOM | 3124 | N   | LEU | B | 454 | 8.434  | 8.428  | 20.836 | 1.00 17.68 |
| ATOM | 3125 | CA  | LEU | B | 454 | 8.789  | 9.653  | 19.933 | 1.00 20.93 |
| ATOM | 3126 | CB  | LEU | B | 454 | 9.959  | 10.347 | 20.653 | 1.00 24.33 |
| ATOM | 3127 | CG  | LEU | B | 454 | 9.735  | 10.699 | 22.130 | 1.00 26.16 |
| ATOM | 3128 | CD1 | LEU | B | 454 | 11.046 | 11.170 | 22.749 | 1.00 24.82 |
| ATOM | 3129 | CD2 | LEU | B | 454 | 8.658  | 11.777 | 22.259 | 1.00 23.79 |
| ATOM | 3130 | C   | LEU | B | 454 | 9.120  | 9.494  | 18.449 | 1.00 20.75 |
| ATOM | 3131 | O   | LEU | B | 454 | 8.941  | 10.431 | 17.673 | 1.00 21.33 |
| ATOM | 3132 | N   | ASN | B | 455 | 9.566  | 8.311  | 18.042 | 1.00 20.54 |
| ATOM | 3133 | CA  | ASN | B | 455 | 9.951  | 8.093  | 16.651 | 1.00 19.46 |
| ATOM | 3134 | CB  | ASN | B | 455 | 11.147 | 7.149  | 16.584 | 1.00 18.68 |
| ATOM | 3135 | CG  | ASN | B | 455 | 11.576 | 6.871  | 15.161 | 1.00 17.64 |
| ATOM | 3136 | OD1 | ASN | B | 455 | 12.106 | 7.749  | 14.495 | 1.00 18.40 |
| ATOM | 3137 | ND2 | ASN | B | 455 | 11.343 | 5.648  | 14.686 | 1.00 19.06 |
| ATOM | 3138 | C   | ASN | B | 455 | 8.925  | 7.580  | 15.655 | 1.00 22.77 |
| ATOM | 3139 | O   | ASN | B | 455 | 8.790  | 8.137  | 14.554 | 1.00 21.94 |
| ATOM | 3140 | N   | SER | B | 456 | 8.224  | 6.514  | 16.023 | 1.00 25.90 |
| ATOM | 3141 | CA  | SER | B | 456 | 7.260  | 5.873  | 15.135 | 1.00 24.76 |
| ATOM | 3142 | CB  | SER | B | 456 | 6.402  | 4.894  | 15.939 | 1.00 26.91 |
| ATOM | 3143 | OG  | SER | B | 456 | 7.212  | 3.818  | 16.390 | 1.00 26.24 |
| ATOM | 3144 | C   | SER | B | 456 | 6.385  | 6.774  | 14.272 | 1.00 26.52 |
| ATOM | 3145 | O   | SER | B | 456 | 6.323  | 6.588  | 13.055 | 1.00 29.22 |
| ATOM | 3146 | N   | GLY | B | 457 | 5.716  | 7.750  | 14.872 | 1.00 22.07 |
| ATOM | 3147 | CA  | GLY | B | 457 | 4.879  | 8.627  | 14.076 | 1.00 25.19 |
| ATOM | 3148 | C   | GLY | B | 457 | 5.510  | 9.973  | 13.765 | 1.00 28.59 |
| ATOM | 3149 | O   | GLY | B | 457 | 4.851  | 10.850 | 13.214 | 1.00 28.31 |
| ATOM | 3150 | N   | VAL | B | 458 | 6.789  | 10.130 | 14.092 | 1.00 31.65 |
| ATOM | 3151 | CA  | VAL | B | 458 | 7.486  | 11.396 | 13.879 | 1.00 38.50 |
| ATOM | 3152 | CB  | VAL | B | 458 | 8.950  | 11.310 | 14.373 | 1.00 36.24 |
| ATOM | 3153 | CG1 | VAL | B | 458 | 9.827  | 10.650 | 13.324 | 1.00 38.50 |
| ATOM | 3154 | CG2 | VAL | B | 458 | 9.463  | 12.699 | 14.701 | 1.00 39.84 |
| ATOM | 3155 | C   | VAL | B | 458 | 7.483  | 11.982 | 12.464 | 1.00 46.30 |
| ATOM | 3156 | O   | VAL | B | 458 | 7.567  | 13.201 | 12.302 | 1.00 47.67 |
| ATOM | 3157 | N   | TYR | B | 459 | 7.393  | 11.138 | 11.442 | 1.00 50.45 |
| ATOM | 3158 | CA  | TYR | B | 459 | 7.385  | 11.640 | 10.069 | 1.00 57.07 |
| ATOM | 3159 | CB  | TYR | B | 459 | 8.233  | 10.740 | 9.170  | 1.00 57.06 |
| ATOM | 3160 | CG  | TYR | B | 459 | 9.673  | 10.680 | 9.611  | 1.00 59.29 |
| ATOM | 3161 | CD1 | TYR | B | 459 | 10.284 | 11.786 | 10.203 | 1.00 60.93 |
| ATOM | 3162 | CE1 | TYR | B | 459 | 11.591 | 11.725 | 10.662 | 1.00 61.86 |
| ATOM | 3163 | CD2 | TYR | B | 459 | 10.414 | 9.510  | 9.486  | 1.00 59.46 |
| ATOM | 3164 | CE2 | TYR | B | 459 | 11.726 | 9.439  | 9.943  | 1.00 59.67 |
| ATOM | 3165 | CZ  | TYR | B | 459 | 12.305 | 10.548 | 10.532 | 1.00 60.84 |
| ATOM | 3166 | OH  | TYR | B | 459 | 13.593 | 10.477 | 11.009 | 1.00 61.39 |
| ATOM | 3167 | C   | TYR | B | 459 | 5.976  | 11.753 | 9.514  | 1.00 61.22 |
| ATOM | 3168 | O   | TYR | B | 459 | 5.629  | 12.750 | 8.874  | 1.00 62.89 |
| ATOM | 3169 | N   | THR | B | 460 | 5.166  | 10.730 | 9.768  | 1.00 65.15 |
| ATOM | 3170 | CA  | THR | B | 460 | 3.783  | 10.702 | 9.309  | 1.00 67.76 |
| ATOM | 3171 | CB  | THR | B | 460 | 3.178  | 9.283  | 9.464  | 1.00 68.02 |
| ATOM | 3172 | OG1 | THR | B | 460 | 1.890  | 9.235  | 8.836  | 1.00 67.03 |
| ATOM | 3173 | CG2 | THR | B | 460 | 3.040  | 8.916  | 10.938 | 1.00 67.31 |
| ATOM | 3174 | C   | THR | B | 460 | 2.945  | 11.700 | 10.107 | 1.00 70.14 |
| ATOM | 3175 | O   | THR | B | 460 | 1.715  | 11.641 | 10.099 | 1.00 72.35 |
| ATOM | 3176 | N   | PHE | B | 461 | 3.625  | 12.620 | 10.788 | 1.00 72.64 |

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   3177  CA   PHE  B  461   2.969  13.637 11.607  1.00  75.05
ATOM   3178  CB   PHE  B  461   3.977  14.726 12.012  1.00  75.47
ATOM   3179  CG   PHE  B  461   4.235  14.789 13.492  1.00  74.33
ATOM   3180  CD1  PHE  B  461   3.200  14.609 14.404  1.00  73.98
ATOM   3181  CD2  PHE  B  461   5.517  15.035 13.975  1.00  75.22
ATOM   3182  CE1  PHE  B  461   3.438  14.662 15.775  1.00  74.02
ATOM   3183  CE2  PHE  B  461   5.765  15.080 15.344  1.00  74.50
ATOM   3184  CZ   PHE  B  461   4.722  14.897 16.245  1.00  74.10
ATOM   3185  C    PHE  B  461   1.787  14.286 10.896  1.00  75.78
ATOM   3186  O    PHE  B  461   1.775  14.279  9.645  1.00  77.08
ATOM   3187  CB   GLU  B  470   7.873  23.789 14.718  1.00  80.19
ATOM   3188  C    GLU  B  470   8.958  21.731 15.650  1.00  79.30
ATOM   3189  O    GLU  B  470   9.887  21.318 16.432  1.00  78.21
ATOM   3190  N    GLU  B  470   9.096  22.235 13.227  1.00  80.22
ATOM   3191  CA   GLU  B  470   9.060  22.830 14.595  1.00  80.03
ATOM   3192  N    GLU  B  471   7.823  21.037 15.665  1.00  78.31
ATOM   3193  CA   GLU  B  471   7.596  19.956 16.617  1.00  75.83
ATOM   3194  CB   GLU  B  471   6.118  19.543 16.604  1.00  76.70
ATOM   3195  CG   GLU  B  471   5.742  18.544 15.516  1.00  78.42
ATOM   3196  CD   GLU  B  471   5.062  19.198 14.327  1.00  79.69
ATOM   3197  OE1  GLU  B  471   3.829  19.398 14.378  1.00  80.26
ATOM   3198  OE2  GLU  B  471   5.763  19.511 13.340  1.00  80.72
ATOM   3199  C    GLU  B  471   8.487  18.756 16.292  1.00  73.13
ATOM   3200  O    GLU  B  471   8.897  18.021 17.189  1.00  73.86
ATOM   3201  N    LYS  B  472   8.785  18.565 15.009  1.00  69.65
ATOM   3202  CA   LYS  B  472   9.639  17.461 14.581  1.00  64.40
ATOM   3203  CB   LYS  B  472   9.578  17.393 13.060  1.00  63.78
ATOM   3204  CG   LYS  B  472   8.343  16.552 12.566  1.00  64.49
ATOM   3205  CD   LYS  B  472   8.544  16.003 11.161  1.00  63.81
ATOM   3206  CE   LYS  B  472   7.379  15.368 10.249  1.00  64.90
ATOM   3207  NZ   LYS  B  472   6.475  15.212  9.890  1.00  63.97
ATOM   3208  C    LYS  B  472  11.071  17.749 15.014  1.00  61.03
ATOM   3209  O    LYS  B  472  11.849  16.833 15.287  1.00  60.28
ATOM   3210  N    ASP  B  473  11.413  19.033 15.076  1.00  56.84
ATOM   3211  CA   ASP  B  473  12.745  19.451 15.488  1.00  51.69
ATOM   3212  CB   ASP  B  473  12.923  20.940 15.242  1.00  50.36
ATOM   3213  C    ASP  B  473  12.923  19.138 16.970  1.00  49.18
ATOM   3214  O    ASP  B  473  13.959  18.619 17.385  1.00  46.85
ATOM   3215  N    HIS  B  474  11.898  19.449 17.758  1.00  45.35
ATOM   3216  CA   HIS  B  474  11.923  19.203 19.196  1.00  43.65
ATOM   3217  CB   HIS  B  474  10.652  19.761 19.847  1.00  43.70
ATOM   3218  CG   HIS  B  474  10.458  19.326 21.367  1.00  43.86
ATOM   3219  CD2  HIS  B  474  11.095  19.688 22.406  1.00  44.12
ATOM   3220  ND1  HIS  B  474   9.510  18.395 21.638  1.00  46.60
ATOM   3221  CE1  HIS  B  474   9.572  18.202 22.943  1.00  45.29
ATOM   3222  NE2  HIS  B  474  10.526  18.975 23.434  1.00  47.96
ATOM   3223  C    HIS  B  474  12.030  17.707 19.471  1.00  42.38
ATOM   3224  O    HIS  B  474  12.834  17.273 20.298  1.00  42.83
ATOM   3225  N    ILE  B  475  11.214  16.923 18.773  1.00  38.86
ATOM   3226  CA   ILE  B  475  11.222  15.475 18.943  1.00  36.53
ATOM   3227  CB   ILE  B  475  10.105  14.822 19.110  1.00  36.56
ATOM   3228  CG2  ILE  B  475  10.390  13.335 17.911  1.00  36.17
ATOM   3229  CG1  ILE  B  475   8.770  14.998 18.832  1.00  35.81
ATOM   3230  CD1  ILE  B  475   7.598  14.410 18.094  1.00  41.77
ATOM   3231  C    ILE  B  475  12.575  14.898 18.532  1.00  33.72
ATOM   3232  O    ILE  B  475  13.112  14.023 19.207  1.00  31.50
ATOM   3233  N    HIS  B  476  13.121  15.375 17.429  1.00  33.65
ATOM   3234  CA   HIS  B  476  14.421  14.885 16.992  1.00  33.31
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   3235  CB    HIS  B   476   14.782  15.481  15.637  1.00  37.30
ATOM   3236  CG    HIS  B   476   14.132  14.781  14.486  1.00  43.64
ATOM   3237  CD2   HIS  B   476   13.723  13.498  14.342  1.00  45.25
ATOM   3238  ND1   HIS  B   476   13.816  15.419  13.306  1.00  48.37
ATOM   3239  CE1   HIS  B   476   13.238  14.560  12.484  1.00  48.87
ATOM   3240  NE2   HIS  B   476   13.170  13.387  13.089  1.00  48.11
ATOM   3241  C     HIS  B   476   15.506  15.213  18.022  1.00  31.20
ATOM   3242  O     HIS  B   476   16.442  14.436  18.208  1.00  27.25
ATOM   3243  N     ARG  B   477   15.387  15.365  18.694  1.00  30.64
ATOM   3244  CA    ARG  B   477   16.361  16.754  19.703  1.00  30.09
ATOM   3245  CB    ARG  B   477   16.144  18.214  20.121  1.00  33.46
ATOM   3246  CG    ARG  B   477   16.322  19.212  18.982  1.00  40.74
ATOM   3247  CD    ARG  B   477   16.274  20.649  19.479  1.00  45.91
ATOM   3248  NE    ARG  B   477   17.514  21.020  20.155  1.00  51.37
ATOM   3249  CZ    ARG  B   477   18.375  21.927  19.702  1.00  53.68
ATOM   3250  NH1   ARG  B   477   18.140  22.567  18.560  1.00  53.04
ATOM   3251  NH2   ARG  B   477   19.480  22.185  20.389  1.00  51.79
ATOM   3252  C     ARG  B   477   16.232  15.835  20.925  1.00  26.97
ATOM   3253  O     ARG  B   477   17.233  15.387  21.486  1.00  27.34
ATOM   3254  N     VAL  B   478   14.999  15.558  21.338  1.00  23.70
ATOM   3255  CA    VAL  B   478   14.780  14.685  22.482  1.00  24.79
ATOM   3256  CB    VAL  B   478   13.286  14.613  22.861  1.00  24.83
ATOM   3257  CG1   VAL  B   478   13.088  13.646  24.022  1.00  26.23
ATOM   3258  CG2   VAL  B   478   12.781  15.998  23.243  1.00  28.26
ATOM   3259  C     VAL  B   478   15.284  13.294  22.112  1.00  26.10
ATOM   3260  O     VAL  B   478   15.919  12.613  22.927  1.00  24.28
ATOM   3261  N     LEU  B   479   15.021  12.889  20.870  1.00  22.92
ATOM   3262  CA    LEU  B   479   15.456  11.584  20.379  1.00  21.96
ATOM   3263  CB    LEU  B   479   14.992  11.372  18.930  1.00  22.63
ATOM   3264  CG    LEU  B   479   13.575  10.798  18.756  1.00  20.82
ATOM   3265  CD1   LEU  B   479   13.231  10.689  17.274  1.00  22.53
ATOM   3266  CD2   LEU  B   479   13.495   9.440  19.420  1.00  23.08
ATOM   3267  C     LEU  B   479   16.975  11.471  20.453  1.00  21.90
ATOM   3268  O     LEU  B   479   17.506  10.416  20.778  1.00  23.11
ATOM   3269  N     ASP  B   480   17.675  12.560  20.143  1.00  23.65
ATOM   3270  CA    ASP  B   480   19.141  12.566  20.198  1.00  24.29
ATOM   3271  CB    ASP  B   480   19.692  13.889  19.649  1.00  26.88
ATOM   3272  CG    ASP  B   480   19.773  13.914  18.129  1.00  33.32
ATOM   3273  OD1   ASP  B   480   19.857  12.836  17.499  1.00  35.44
ATOM   3274  OD2   ASP  B   480   19.757  15.022  17.563  1.00  32.44
ATOM   3275  C     ASP  B   480   19.590  12.406  21.656  1.00  24.13
ATOM   3276  O     ASP  B   480   20.551  11.697  21.956  1.00  24.88
ATOM   3277  N     LYS  B   481   18.887  13.077  22.560  1.00  25.18
ATOM   3278  CA    LYS  B   481   19.213  13.010  23.980  1.00  26.78
ATOM   3279  CB    LYS  B   481   18.262  13.898  24.785  1.00  31.37
ATOM   3280  CG    LYS  B   481   18.962  14.788  25.804  1.00  43.84
ATOM   3281  CD    LYS  B   481   18.780  14.260  27.219  1.00  46.08
ATOM   3282  CE    LYS  B   481   20.120  13.928  27.865  1.00  50.99
ATOM   3283  NZ    LYS  B   481   21.177  14.922  27.511  1.00  54.35
ATOM   3284  C     LYS  B   481   19.124  11.575  24.495  1.00  26.87
ATOM   3285  O     LYS  B   481   19.951  11.145  25.305  1.00  20.37
ATOM   3286  N     ILE  B   482   18.124  10.830  24.027  1.00  23.26
ATOM   3287  CA    ILE  B   482   17.981   9.452  24.472  1.00  21.07
ATOM   3288  CB    ILE  B   482   16.655   8.828  24.015  1.00  19.80
ATOM   3289  CG2   ILE  B   482   16.580   7.370  24.491  1.00  17.40
ATOM   3290  CG1   ILE  B   482   15.479   9.606  24.602  1.00  17.16
ATOM   3291  CD1   ILE  B   482   14.136   9.209  23.991  1.00  19.43
ATOM   3292  C     ILE  B   482   19.135   8.616  23.947  1.00  20.21
```

UNITED STATES PATENT AND TRADEMARK OFFICE
CERTIFICATE OF CORRECTION

PATENT NO. : 6,965,850 B2  Page 135 of 186
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   3293  O    ILE  B  482  19.621   7.722 24.640  1.00  25.55
ATOM   3294  N    THR  B  483  19.369   8.896 22.722  1.00  21.89
ATOM   3295  CA   THR  B  483  20.701   8.176 22.141  1.00  22.57
ATOM   3296  CB   THR  B  483  21.030   8.662 20.695  1.00  23.34
ATOM   3297  OG1  THR  B  483  19.890   8.475 19.851  1.00  27.33
ATOM   3298  CG2  THR  B  483  22.203   7.882 20.115  1.00  24.46
ATOM   3299  C    THR  B  483  21.913   8.441 23.035  1.00  23.51
ATOM   3300  O    THR  B  483  22.650   7.520 23.381  1.00  27.01
ATOM   3301  N    ASP  B  484  22.119   9.703 23.404  1.00  22.88
ATOM   3302  CA   ASP  B  484  23.237  10.058 24.276  1.00  24.93
ATOM   3303  CB   ASP  B  484  23.201  11.546 24.652  1.00  28.69
ATOM   3304  CG   ASP  B  484  23.504  12.464 23.485  1.00  29.19
ATOM   3305  OD1  ASP  B  484  23.982  11.984 22.437  1.00  29.63
ATOM   3306  OD2  ASP  B  484  23.256  13.681 23.627  1.00  32.02
ATOM   3307  C    ASP  B  484  23.125   9.249 25.567  1.00  24.40
ATOM   3308  O    ASP  B  484  24.125   8.780 26.103  1.00  25.60
ATOM   3309  N    THR  B  485  21.899   9.096 26.065  1.00  20.16
ATOM   3310  CA   THR  B  485  21.670   8.385 27.307  1.00  22.28
ATOM   3311  CB   THR  B  485  20.203   8.521 27.763  1.00  24.64
ATOM   3312  OG1  THR  B  485  19.878   9.914 27.830  1.00  24.28
ATOM   3313  CG2  THR  B  485  19.993   7.896 29.133  1.00  23.32
ATOM   3314  C    THR  B  485  22.017   6.881 27.188  1.00  22.13
ATOM   3315  O    THR  B  485  22.574   6.284 28.115  1.00  23.30
ATOM   3316  N    LEU  B  486  21.686   6.290 26.045  1.00  23.08
ATOM   3317  CA   LEU  B  486  21.969   4.881 25.792  1.00  22.26
ATOM   3318  CB   LEU  B  486  21.346   4.452 24.464  1.00  20.93
ATOM   3319  CG   LEU  B  486  19.878   4.031 24.533  1.00  24.92
ATOM   3320  CD1  LEU  B  486  19.295   4.003 23.123  1.00  21.96
ATOM   3321  CD2  LEU  B  486  19.763   2.658 25.196  1.00  23.90
ATOM   3322  C    LEU  B  486  23.477   4.634 25.742  1.00  24.12
ATOM   3323  O    LEU  B  486  23.984   3.681 26.334  1.00  24.02
ATOM   3324  N    ILE  B  487  24.191   5.490 25.032  1.00  24.53
ATOM   3325  CA   ILE  B  487  25.640   5.345 24.913  1.00  25.16
ATOM   3326  CB   ILE  B  487  26.207   6.379 23.899  1.00  25.57
ATOM   3327  CG2  ILE  B  487  27.725   6.522 24.051  1.00  24.54
ATOM   3328  CG1  ILE  B  487  25.857   5.936 22.470  1.00  25.63
ATOM   3329  CD1  ILE  B  487  26.538   4.646 22.021  1.00  25.68
ATOM   3330  C    ILE  B  487  26.275   5.518 26.307  1.00  23.60
ATOM   3331  O    ILE  B  487  27.200   4.794 26.671  1.00  23.65
ATOM   3332  N    HIS  B  488  25.755   6.456 27.081  1.00  21.75
ATOM   3333  CA   HIS  B  488  26.251   6.720 28.431  1.00  26.07
ATOM   3334  CB   HIS  B  488  25.450   7.871 29.041  1.00  26.99
ATOM   3335  CG   HIS  B  488  25.818   8.196 30.455  1.00  33.06
ATOM   3336  CD2  HIS  B  488  25.245   7.838 31.629  1.00  32.79
ATOM   3337  ND1  HIS  B  488  26.869   9.025 30.779  1.00  36.45
ATOM   3338  CE1  HIS  B  488  26.927   9.164 32.091  1.00  35.93
ATOM   3339  NE2  HIS  B  488  25.953   8.453 32.630  1.00  33.88
ATOM   3340  C    HIS  B  488  26.123   5.463 29.292  1.00  26.85
ATOM   3341  O    HIS  B  488  27.071   5.054 29.967  1.00  28.52
ATOM   3342  N    LEU  B  489  24.949   4.850 29.266  1.00  28.00
ATOM   3343  CA   LEU  B  489  24.715   3.642 30.040  1.00  25.94
ATOM   3344  CB   LEU  B  489  23.298   3.127 29.788  1.00  27.07
ATOM   3345  CG   LEU  B  489  22.158   3.909 30.445  1.00  31.71
ATOM   3346  CD1  LEU  B  489  20.827   3.516 29.799  1.00  28.08
ATOM   3347  CD2  LEU  B  489  22.143   3.816 31.949  1.00  29.30
ATOM   3348  C    LEU  B  489  25.718   2.561 29.642  1.00  26.84
ATOM   3349  O    LEU  B  489  26.241   1.832 30.486  1.00  20.86
ATOM   3350  N    MET  B  490  25.978   2.453 28.345  1.00  23.82
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   3351  CA   MET  B  490   26.900   1.438  27.857  1.00  26.38
ATOM   3352  CB   MET  B  490   26.775   1.306  26.336  1.00  27.29
ATOM   3353  CG   MET  B  490   25.418   0.776  25.895  1.00  21.68
ATOM   3354  SD   MET  B  490   25.208   0.739  24.106  1.00  25.30
ATOM   3355  CE   MET  B  490   23.461   0.412  24.022  1.00  19.66
ATOM   3356  C    MET  B  490   28.341   1.743  28.247  1.00  26.43
ATOM   3357  O    MET  B  490   29.109   0.833  28.574  1.00  24.76
ATOM   3358  N    ALA  B  491   28.713   3.018  28.207  1.00  26.67
ATOM   3359  CA   ALA  B  491   30.074   3.394  28.577  1.00  30.73
ATOM   3360  CB   ALA  B  491   30.299   4.883  28.335  1.00  26.66
ATOM   3361  C    ALA  B  491   30.250   3.053  30.056  1.00  32.08
ATOM   3362  O    ALA  B  491   31.194   2.361  30.438  1.00  34.66
ATOM   3363  N    LYS  B  492   29.316   3.523  30.878  1.00  33.17
ATOM   3364  CA   LYS  B  492   29.354   3.267  32.309  1.00  32.82
ATOM   3365  CB   LYS  B  492   28.110   3.849  32.976  1.00  36.38
ATOM   3366  CG   LYS  B  492   28.412   4.797  34.123  1.00  38.68
ATOM   3367  CD   LYS  B  492   27.242   4.887  35.084  1.00  41.41
ATOM   3368  CE   LYS  B  492   26.299   6.013  34.698  1.00  47.57
ATOM   3369  NZ   LYS  B  492   26.395   7.184  35.618  1.00  50.76
ATOM   3370  C    LYS  B  492   29.453   1.771  32.619  1.00  34.08
ATOM   3371  O    LYS  B  492   30.090   1.382  33.593  1.00  34.31
ATOM   3372  N    ALA  B  493   28.835   0.935  31.788  1.00  32.03
ATOM   3373  CA   ALA  B  493   28.867  -0.510  31.998  1.00  30.70
ATOM   3374  CB   ALA  B  493   27.719  -1.181  31.245  1.00  28.80
ATOM   3375  C    ALA  B  493   30.201  -1.156  31.606  1.00  33.75
ATOM   3376  O    ALA  B  493   30.402  -2.356  31.819  1.00  30.53
ATOM   3377  N    GLY  B  494   31.102  -0.372  31.020  1.00  33.50
ATOM   3378  CA   GLY  B  494   32.405  -0.903  30.656  1.00  33.71
ATOM   3379  C    GLY  B  494   32.639  -1.360  29.230  1.00  34.40
ATOM   3380  O    GLY  B  494   33.663  -1.989  28.950  1.00  33.13
ATOM   3381  N    LEU  B  495   31.712  -1.056  28.326  1.00  31.76
ATOM   3382  CA   LEU  B  495   31.859  -1.452  26.925  1.00  30.57
ATOM   3383  CB   LEU  B  495   30.494  -1.415  26.216  1.00  30.67
ATOM   3384  CG   LEU  B  495   29.610  -2.675  26.256  1.00  29.59
ATOM   3385  CD1  LEU  B  495   29.315  -3.058  27.700  1.00  26.60
ATOM   3386  CD2  LEU  B  495   28.307  -2.416  25.501  1.00  27.52
ATOM   3387  C    LEU  B  495   32.829  -0.515  26.202  1.00  30.53
ATOM   3388  O    LEU  B  495   32.855   0.688  26.468  1.00  28.14
ATOM   3389  N    THR  B  496   33.628  -1.064  25.291  1.00  28.03
ATOM   3390  CA   THR  B  496   34.567  -0.243  24.529  1.00  29.06
ATOM   3391  CB   THR  B  496   35.511  -1.095  23.665  1.00  29.40
ATOM   3392  OG1  THR  B  496   34.753  -1.758  22.641  1.00  30.29
ATOM   3393  CG2  THR  B  496   36.228  -2.122  24.515  1.00  28.12
ATOM   3394  C    THR  B  496   33.770   0.652  23.590  1.00  30.12
ATOM   3395  O    THR  B  496   32.580   0.433  23.380  1.00  29.74
ATOM   3396  N    LEU  B  497   34.430   1.654  23.018  1.00  30.44
ATOM   3397  CA   LEU  B  497   33.762   2.567  22.104  1.00  28.54
ATOM   3398  CB   LEU  B  497   34.768   3.564  21.529  1.00  31.14
ATOM   3399  CG   LEU  B  497   35.209   4.719  22.434  1.00  33.58
ATOM   3400  CD1  LEU  B  497   35.120   5.659  21.652  1.00  31.42
ATOM   3401  CD2  LEU  B  497   33.992   5.469  22.942  1.00  35.08
ATOM   3402  C    LEU  B  497   33.095   1.800  20.967  1.00  27.35
ATOM   3403  O    LEU  B  497   31.967   2.105  20.574  1.00  24.03
ATOM   3404  N    GLN  B  498   33.798   0.757  20.447  1.00  26.17
ATOM   3405  CA   GLN  B  498   33.289  -0.009  19.348  1.00  26.32
ATOM   3406  CB   GLN  B  498   34.411  -0.876  18.771  1.00  27.25
ATOM   3407  CG   GLN  B  498   33.967  -1.796  17.645  1.00  32.67
ATOM   3408  CD   GLN  B  498   34.965  -2.912  17.374  1.00  38.39
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   3409  OE1  GLN  B  498   35.737  -3.298  18.254  1.00  36.78
ATOM   3410  NE2  GLN  B  498   34.953  -3.437  16.153  1.00  33.18
ATOM   3411  C    GLN  B  498   32.112  -0.888  19.774  1.00  25.70
ATOM   3412  O    GLN  B  498   31.167  -1.076  19.009  1.00  25.35
ATOM   3413  N    GLN  B  499   32.173  -1.434  20.986  1.00  24.01
ATOM   3414  CA   GLN  B  499   31.093  -2.281  21.487  1.00  25.34
ATOM   3415  CB   GLN  B  499   31.501  -2.935  22.815  1.00  28.38
ATOM   3416  CG   GLN  B  499   32.537  -4.056  22.669  1.00  29.13
ATOM   3417  CD   GLN  B  499   32.913  -4.687  23.995  1.00  30.80
ATOM   3418  OE1  GLN  B  499   33.306  -3.997  24.937  1.00  33.62
ATOM   3419  NE2  GLN  B  499   32.797  -6.004  24.074  1.00  30.64
ATOM   3420  C    GLN  B  499   29.842  -1.430  21.693  1.00  25.70
ATOM   3421  O    GLN  B  499   28.715  -1.910  21.554  1.00  26.22
ATOM   3422  N    GLN  B  500   30.062  -0.160  22.020  1.00  23.09
ATOM   3423  CA   GLN  B  500   28.989   0.793  22.256  1.00  23.53
ATOM   3424  CB   GLN  B  500   29.564   2.187  22.782  1.00  26.17
ATOM   3425  CG   GLN  B  500   29.958   2.073  24.252  1.00  27.71
ATOM   3426  CD   GLN  B  500   30.812   3.262  24.641  1.00  29.32
ATOM   3427  OE1  GLN  B  500   30.559   4.386  24.207  1.00  28.48
ATOM   3428  NE2  GLN  B  500   31.831   3.021  25.463  1.00  25.07
ATOM   3429  C    GLN  B  500   28.151   1.074  21.015  1.00  24.24
ATOM   3430  O    GLN  B  500   26.923   0.949  21.053  1.00  24.40
ATOM   3431  N    HIS  B  501   28.790   1.465  19.915  1.00  23.08
ATOM   3432  CA   HIS  B  501   28.004   1.739  18.724  1.00  26.92
ATOM   3433  CB   HIS  B  501   28.791   2.577  17.697  1.00  32.00
ATOM   3434  CG   HIS  B  501   29.988   1.896  17.105  1.00  36.97
ATOM   3435  CD2  HIS  B  501   30.122   0.710  16.465  1.00  40.32
ATOM   3436  ND1  HIS  B  501   31.224   2.505  17.042  1.00  37.88
ATOM   3437  CE1  HIS  B  501   32.066   1.724  16.389  1.00  38.81
ATOM   3438  NE2  HIS  B  501   31.422   0.638  16.028  1.00  41.21
ATOM   3439  C    HIS  B  501   27.451   0.457  18.133  1.00  25.91
ATOM   3440  O    HIS  B  501   26.369   0.457  17.531  1.00  20.13
ATOM   3441  N    GLN  B  502   28.165  -0.648  18.317  1.00  24.94
ATOM   3442  CA   GLN  B  502   27.698  -1.926  17.804  1.00  21.88
ATOM   3443  CB   GLN  B  502   28.785  -2.996  17.953  1.00  24.62
ATOM   3444  CG   GLN  B  502   29.796  -3.001  16.797  1.00  26.55
ATOM   3445  CD   GLN  B  502   30.843  -4.109  16.902  1.00  27.06
ATOM   3446  OE1  GLN  B  502   30.716  -5.033  17.705  1.00  28.49
ATOM   3447  NE2  GLN  B  502   31.882  -4.018  16.078  1.00  21.90
ATOM   3448  C    GLN  B  502   26.428  -2.341  18.554  1.00  22.39
ATOM   3449  O    GLN  B  502   25.464  -2.807  17.944  1.00  22.24
ATOM   3450  N    ARG  B  503   26.421  -2.159  19.874  1.00  20.54
ATOM   3451  CA   ARG  B  503   25.259  -2.523  20.678  1.00  22.04
ATOM   3452  CB   ARG  B  503   25.602  -2.519  22.180  1.00  22.51
ATOM   3453  CG   ARG  B  503   24.451  -3.022  23.077  1.00  23.34
ATOM   3454  CD   ARG  B  503   24.853  -3.110  24.550  1.00  22.18
ATOM   3455  NE   ARG  B  503   23.743  -3.546  25.395  1.00  19.62
ATOM   3456  CZ   ARG  B  503   23.329  -4.807  25.497  1.00  19.88
ATOM   3457  NH1  ARG  B  503   23.933  -5.765  24.809  1.00  15.40
ATOM   3458  NH2  ARG  B  503   22.303  -5.110  26.280  1.00  19.71
ATOM   3459  C    ARG  B  503   24.102  -1.558  20.409  1.00  19.05
ATOM   3460  O    ARG  B  503   23.945  -1.968  20.351  1.00  18.87
ATOM   3461  N    LEU  B  504   24.414  -0.276  20.239  1.00  20.19
ATOM   3462  CA   LEU  B  504   23.375   0.714  19.969  1.00  19.33
ATOM   3463  CB   LEU  B  504   23.972   2.117  19.855  1.00  16.25
ATOM   3464  CG   LEU  B  504   22.983   3.173  19.344  1.00  20.35
ATOM   3465  CD1  LEU  B  504   21.930   3.449  20.427  1.00  17.97
ATOM   3466  CD2  LEU  B  504   23.729   4.448  18.955  1.00  20.86
```

UNITED STATES PATENT AND TRADEMARK OFFICE
CERTIFICATE OF CORRECTION

PATENT NO. : 6,965,850 B2  Page 138 of 186
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   3467  C    LEU  B  504   22.659   0.357 18.667  1.00  21.23
ATOM   3468  O    LEU  B  504   21.433   0.478 18.866  1.00  19.38
ATOM   3469  N    ALA  B  505   23.428  -0.085 17.676  1.00  18.55
ATOM   3470  CA   ALA  B  505   22.859  -0.473 16.396  1.00  18.20
ATOM   3471  CB   ALA  B  505   23.973  -0.745 15.382  1.00  18.45
ATOM   3472  C    ALA  B  505   21.986  -1.716 16.562  1.00  19.54
ATOM   3473  O    ALA  B  505   20.871  -1.774 16.041  1.00  17.63
ATOM   3474  N    GLN  B  506   22.497  -2.706 17.293  1.00  20.30
ATOM   3475  CA   GLN  B  506   21.772  -3.955 17.513  1.00  19.48
ATOM   3476  CB   GLN  B  506   22.590  -4.893 18.409  1.00  21.75
ATOM   3477  CG   GLN  B  506   23.798  -5.351 17.727  1.00  20.85
ATOM   3478  CD   GLN  B  506   24.819  -6.070 18.736  1.00  26.18
ATOM   3479  OE1  GLN  B  506   24.564  -6.084 19.943  1.00  21.83
ATOM   3480  NE2  GLN  B  506   25.977  -6.499 18.345  1.00  25.39
ATOM   3481  C    GLN  B  506   20.421  -3.672 18.166  1.00  21.39
ATOM   3482  O    GLN  B  506   19.396  -4.233 17.766  1.00  20.87
ATOM   3483  N    LEU  B  507   20.433  -2.800 19.171  1.00  19.52
ATOM   3484  CA   LEU  B  507   19.219  -2.418 19.884  1.00  23.04
ATOM   3485  CB   LEU  B  507   19.548  -1.455 21.030  1.00  22.82
ATOM   3486  CG   LEU  B  507   20.182  -2.011 22.313  1.00  26.12
ATOM   3487  CD1  LEU  B  507   20.203  -0.916 23.360  1.00  29.33
ATOM   3488  CD2  LEU  B  507   19.415  -3.213 22.816  1.00  27.80
ATOM   3489  C    LEU  B  507   18.212  -1.730 18.971  1.00  23.19
ATOM   3490  O    LEU  B  507   17.036  -2.070 18.964  1.00  23.00
ATOM   3491  N    LEU  B  508   18.678  -0.745 18.214  1.00  21.53
ATOM   3492  CA   LEU  B  508   17.797   0.006 17.332  1.00  20.60
ATOM   3493  CB   LEU  B  508   18.535   1.236 16.805  1.00  17.57
ATOM   3494  CG   LEU  B  508   18.934   2.218 17.913  1.00  17.67
ATOM   3495  CD1  LEU  B  508   19.566   3.446 17.301  1.00  20.04
ATOM   3496  CD2  LEU  B  508   17.724   2.611 18.725  1.00  18.49
ATOM   3497  C    LEU  B  508   17.235  -0.831 16.183  1.00  21.17
ATOM   3498  O    LEU  B  508   16.118  -0.597 15.728  1.00  21.88
ATOM   3499  N    LEU  B  509   18.000  -1.813 15.713  1.00  21.89
ATOM   3500  CA   LEU  B  509   17.511  -2.657 14.631  1.00  22.81
ATOM   3501  CB   LEU  B  509   18.603  -3.597 14.145  1.00  22.65
ATOM   3502  CG   LEU  B  509   19.645  -2.891 13.278  1.00  29.11
ATOM   3503  CD1  LEU  B  509   20.697  -3.888 12.829  1.00  25.69
ATOM   3504  CD2  LEU  B  509   18.965  -2.248 12.082  1.00  27.92
ATOM   3505  C    LEU  B  509   16.302  -3.462 15.095  1.00  23.32
ATOM   3506  O    LEU  B  509   15.409  -3.759 14.303  1.00  23.36
ATOM   3507  N    ILE  B  510   16.264  -3.796 16.380  1.00  23.36
ATOM   3508  CA   ILE  B  510   15.148  -4.562 16.912  1.00  28.99
ATOM   3509  CB   ILE  B  510   15.448  -5.041 18.361  1.00  28.60
ATOM   3510  CG2  ILE  B  510   14.162  -5.435 19.075  1.00  28.10
ATOM   3511  CG1  ILE  B  510   16.383  -6.260 18.308  1.00  26.57
ATOM   3512  CD1  ILE  B  510   17.429  -6.301 19.419  1.00  30.14
ATOM   3513  C    ILE  B  510   13.852  -3.746 16.846  1.00  17.65
ATOM   3514  O    ILE  B  510   12.767  -4.308 16.759  1.00  16.11
ATOM   3515  N    LEU  B  511   13.961  -2.421 16.867  1.00  18.12
ATOM   3516  CA   LEU  B  511   12.772  -1.574 16.774  1.00  16.95
ATOM   3517  CB   LEU  B  511   13.147  -0.100 16.981  1.00  22.66
ATOM   3518  CG   LEU  B  511   13.607   0.262 18.406  1.00  22.13
ATOM   3519  CD1  LEU  B  511   13.404   1.751 18.652  1.00  25.29
ATOM   3520  CD2  LEU  B  511   12.830  -0.549 19.425  1.00  25.08
ATOM   3521  C    LEU  B  511   12.112  -1.771 15.397  1.00  16.65
ATOM   3522  O    LEU  B  511   10.915  -1.578 15.242  1.00  17.09
ATOM   3523  N    SER  B  512   12.901  -2.161 14.401  1.00  15.83
ATOM   3524  CA   SER  B  512   12.355  -2.408 13.072  1.00  18.66
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   3525  CB   SER  B  512   13.484  -2.644 12.074  1.00  17.62
ATOM   3526  OG   SER  B  512   13.079  -3.880 11.062  1.00  32.77
ATOM   3527  C    SER  B  512   11.454  -3.638 13.154  1.00  18.54
ATOM   3528  O    SER  B  512   10.373  -3.683 12.545  1.00  17.01
ATOM   3529  N    HIS  B  513   11.899  -4.635 13.929  1.00  15.54
ATOM   3530  CA   HIS  B  513   11.141  -5.860 14.115  1.00  17.67
ATOM   3531  CB   HIS  B  513   12.013  -6.916 14.790  1.00  19.03
ATOM   3532  CG   HIS  B  513   13.063  -7.475 13.886  1.00  27.06
ATOM   3533  CD2  HIS  B  513   12.980  -8.364 12.868  1.00  28.40
ATOM   3534  ND1  HIS  B  513   14.378  -7.066 13.932  1.00  28.93
ATOM   3535  CE1  HIS  B  513   15.061  -7.678 12.981  1.00  30.75
ATOM   3536  NE2  HIS  B  513   14.235  -8.472 12.321  1.00  30.08
ATOM   3537  C    HIS  B  513    9.895  -5.602 14.958  1.00  15.35
ATOM   3538  O    HIS  B  513    8.846  -6.192 14.704  1.00  16.83
ATOM   3539  N    ILE  B  514   10.012  -4.744 15.942  1.00  13.35
ATOM   3540  CA   ILE  B  514    8.865  -4.417 16.776  1.00  15.48
ATOM   3541  CB   ILE  B  514    9.295  -3.534 17.967  1.00  20.02
ATOM   3542  CG2  ILE  B  514    8.067  -2.918 18.650  1.00  12.84
ATOM   3543  CG1  ILE  B  514   10.093  -4.397 18.962  1.00  22.87
ATOM   3544  CD1  ILE  B  514   10.691  -3.641 20.115  1.00  29.62
ATOM   3545  C    ILE  B  514    7.797  -3.717 15.923  1.00  15.16
ATOM   3546  O    ILE  B  514    6.606  -3.972 16.078  1.00  16.61
ATOM   3547  N    ARG  B  515    8.224  -2.823 15.030  1.00  16.33
ATOM   3548  CA   ARG  B  515    7.280  -2.138 14.150  1.00  17.54
ATOM   3549  CB   ARG  B  515    8.010  -1.173 13.214  1.00  20.15
ATOM   3550  CG   ARG  B  515    7.080  -0.454 12.234  1.00  21.47
ATOM   3551  CD   ARG  B  515    6.407   0.749 12.891  1.00  26.05
ATOM   3552  NE   ARG  B  515    7.220   1.948 12.716  1.00  24.91
ATOM   3553  CZ   ARG  B  515    6.734   3.175 12.547  1.00  24.61
ATOM   3554  NH1  ARG  B  515    5.424   3.393 12.822  1.00  22.46
ATOM   3555  NH2  ARG  B  515    7.569   4.182 12.374  1.00  23.15
ATOM   3556  C    ARG  B  515    6.545  -3.182 13.304  1.00  16.60
ATOM   3557  O    ARG  B  515    5.332  -3.093 13.087  1.00  14.51
ATOM   3558  N    HIS  B  516    7.298  -4.171 12.827  1.00  18.50
ATOM   3559  CA   HIS  B  516    6.743  -5.237 11.997  1.00  17.26
ATOM   3560  CB   HIS  B  516    7.861  -6.176 11.533  1.00  18.14
ATOM   3561  CG   HIS  B  516    7.405  -7.323 10.668  1.00  24.87
ATOM   3562  CD2  HIS  B  516    7.060  -8.521 10.754  1.00  26.64
ATOM   3563  ND1  HIS  B  516    7.258  -6.978  9.220  1.00  21.82
ATOM   3564  CE1  HIS  B  516    6.839  -8.078  8.619  1.00  28.42
ATOM   3565  NE2  HIS  B  516    6.711  -9.028  9.526  1.00  24.47
ATOM   3566  C    HIS  B  516    5.685  -6.028 12.759  1.00  16.87
ATOM   3567  O    HIS  B  516    4.596  -6.303 12.240  1.00  14.81
ATOM   3568  N    MET  B  517    5.999  -6.396 13.997  1.00  16.48
ATOM   3569  CA   MET  B  517    5.049  -7.162 14.801  1.00  15.39
ATOM   3570  CB   MET  B  517    5.701  -7.587 16.114  1.00  21.05
ATOM   3571  CG   MET  B  517    6.790  -8.638 15.917  1.00  20.76
ATOM   3572  SD   MET  B  517    7.380  -9.330 17.470  1.00  23.96
ATOM   3573  CE   MET  B  517    8.104  -7.879 18.226  1.00  20.45
ATOM   3574  C    MET  B  517    3.789  -6.368 15.080  1.00  16.23
ATOM   3575  O    MET  B  517    2.688  -6.924 15.148  1.00  16.02
ATOM   3576  N    SER  B  518    3.954  -5.060 15.247  1.00  13.32
ATOM   3577  CA   SER  B  518    2.827  -4.186 15.505  1.00  16.34
ATOM   3578  CB   SER  B  518    3.316  -2.765 15.835  1.00  17.48
ATOM   3579  OG   SER  B  518    2.234  -1.840 15.843  1.00  17.46
ATOM   3580  C    SER  B  518    1.906  -4.147 14.284  1.00  14.73
ATOM   3581  O    SER  B  518    0.688  -4.247 14.417  1.00  19.16
ATOM   3582  N    ASN  B  519    2.474  -4.006 13.091  1.00  14.52
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   3583  CA   ASN  B  519    1.622  -3.953 11.907  1.00  15.35
ATOM   3584  CB   ASN  B  519    2.432  -3.509 10.698  1.00  19.21
ATOM   3585  CG   ASN  B  519    2.700  -2.029 10.729  1.00  20.58
ATOM   3586  OD1  ASN  B  519    1.839  -1.258 11.150  1.00  26.36
ATOM   3587  ND2  ASN  B  519    3.891  -1.618 10.307  1.00  19.62
ATOM   3588  C    ASN  B  519    0.911  -5.280 11.658  1.00  16.74
ATOM   3589  O    ASN  B  519   -0.265  -5.299 11.297  1.00  20.58
ATOM   3590  N    LYS  B  520    1.508  -6.387 11.885  1.00  18.60
ATOM   3591  CA   LYS  B  520    0.992  -7.699 11.717  1.00  20.04
ATOM   3592  CB   LYS  B  520    2.038  -8.801 11.872  1.00  25.44
ATOM   3593  CG   LYS  B  520    3.037  -8.849 10.728  1.00  31.68
ATOM   3594  CD   LYS  B  520    2.507  -9.663  9.658  1.00  42.96
ATOM   3595  CE   LYS  B  520    2.186  -8.778  8.354  1.00  45.61
ATOM   3596  NZ   LYS  B  520    1.435  -9.526  7.312  1.00  46.00
ATOM   3597  C    LYS  B  520   -0.099  -7.868 12.769  1.00  18.88
ATOM   3598  O    LYS  B  520   -1.183  -8.358 12.478  1.00  21.75
ATOM   3599  N    GLY  B  521    0.191  -7.455 13.998  1.00  17.83
ATOM   3600  CA   GLY  B  521   -0.792  -7.569 15.058  1.00  16.19
ATOM   3601  C    GLY  B  521   -2.000  -6.674 14.833  1.00  16.59
ATOM   3602  O    GLY  B  521   -3.128  -7.060 15.125  1.00  16.57
ATOM   3603  N    MET  B  522   -1.766  -5.467 14.326  1.00  17.48
ATOM   3604  CA   MET  B  522   -2.852  -4.527 14.042  1.00  18.25
ATOM   3605  CB   MET  B  522   -2.276  -3.212 13.516  1.00  21.27
ATOM   3606  CG   MET  B  522   -3.190  -2.018 13.707  1.00  26.97
ATOM   3607  SD   MET  B  522   -3.199  -1.477 15.417  1.00  30.35
ATOM   3608  CE   MET  B  522   -1.659  -0.605 15.475  1.00  29.86
ATOM   3609  C    MET  B  522   -3.794  -5.119 12.989  1.00  18.68
ATOM   3610  O    MET  B  522   -5.022  -5.008 13.097  1.00  18.80
ATOM   3611  N    GLU  B  523   -3.205  -5.731 11.966  1.00  18.22
ATOM   3612  CA   GLU  B  523   -3.968  -6.357 10.889  1.00  23.41
ATOM   3613  CB   GLU  B  523   -3.031  -6.946  9.830  1.00  28.74
ATOM   3614  CG   GLU  B  523   -2.224  -5.935  9.030  1.00  34.42
ATOM   3615  CD   GLU  B  523   -1.095  -6.597  8.239  1.00  45.58
ATOM   3616  OE1  GLU  B  523   -0.131  -5.894  7.857  1.00  49.48
ATOM   3617  OE2  GLU  B  523   -1.169  -7.825  7.999  1.00  45.97
ATOM   3618  C    GLU  B  523   -4.812  -7.482 11.465  1.00  23.98
ATOM   3619  O    GLU  B  523   -5.993  -7.616 11.147  1.00  22.08
ATOM   3620  N    HIS  B  524   -4.187  -8.287 12.326  1.00  23.46
ATOM   3621  CA   HIS  B  524   -4.846  -9.438 12.952  1.00  26.20
ATOM   3622  CB   HIS  B  524   -3.824 -10.245 13.743  1.00  27.26
ATOM   3623  CG   HIS  B  524   -4.378 -11.509 14.321  1.00  30.91
ATOM   3624  CD2  HIS  B  524   -4.308 -12.792 13.892  1.00  30.90
ATOM   3625  ND1  HIS  B  524   -5.107 -11.537 15.490  1.00  28.87
ATOM   3626  CE1  HIS  B  524   -5.461 -12.780 15.757  1.00  30.45
ATOM   3627  NE2  HIS  B  524   -4.989 -13.561 14.803  1.00  29.19
ATOM   3628  C    HIS  B  524   -5.996  -9.025 13.870  1.00  27.65
ATOM   3629  O    HIS  B  524   -7.061  -9.656 13.860  1.00  25.00
ATOM   3630  N    LEU  B  525   -5.777  -7.977 14.655  1.00  23.84
ATOM   3631  CA   LEU  B  525   -6.786  -7.493 15.588  1.00  25.77
ATOM   3632  CB   LEU  B  525   -6.217  -6.358 16.444  1.00  22.22
ATOM   3633  CG   LEU  B  525   -7.164  -5.778 17.498  1.00  26.81
ATOM   3634  CD1  LEU  B  525   -7.763  -6.922 18.321  1.00  23.32
ATOM   3635  CD2  LEU  B  525   -6.414  -4.793 18.399  1.00  18.95
ATOM   3636  C    LEU  B  525   -8.013  -6.995 14.842  1.00  26.84
ATOM   3637  O    LEU  B  525   -9.154  -7.247 15.249  1.00  26.73
ATOM   3638  N    TYR  B  526   -7.764  -6.271 13.757  1.00  26.86
ATOM   3639  CA   TYR  B  526   -8.819  -5.726 12.918  1.00  30.89
ATOM   3640  CB   TYR  B  526   -8.201  -4.818 11.854  1.00  34.31
```

UNITED STATES PATENT AND TRADEMARK OFFICE
CERTIFICATE OF CORRECTION

PATENT NO. : 6,965,850 B2  Page 141 of 186
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   3641  CG   TYR  B  526   -9.183   -4.223  10.878  1.00  43.50
ATOM   3642  CD1  TYR  B  526  -10.038   -3.311  11.287  1.00  47.66
ATOM   3643  CE1  TYR  B  526  -10.943   -2.636  10.357  1.00  48.85
ATOM   3644  CD2  TYR  B  526   -9.218   -4.651   9.552  1.00  48.52
ATOM   3645  CE2  TYR  B  526  -10.098   -4.083   8.634  1.00  52.43
ATOM   3646  CZ   TYR  B  526  -10.955   -3.077   9.043  1.00  51.67
ATOM   3647  OH   TYR  B  526  -11.810   -2.504   8.139  1.00  57.01
ATOM   3648  C    TYR  B  526   -9.577   -6.880  12.265  1.00  30.90
ATOM   3649  O    TYR  B  526  -10.793   -6.829  12.113  1.00  31.48
ATOM   3650  N    SER  B  527   -8.849   -7.926  11.889  1.00  31.39
ATOM   3651  CA   SER  B  527   -9.460   -9.095  11.266  1.00  33.73
ATOM   3652  CB   SER  B  527   -8.377  -10.048  10.749  1.00  34.13
ATOM   3653  OG   SER  B  527   -8.945  -11.222  10.196  1.00  43.67
ATOM   3654  C    SER  B  527  -10.339   -9.813  12.388  1.00  34.34
ATOM   3655  O    SER  B  527  -11.446  -10.261  11.973  1.00  33.42
ATOM   3656  N    MET  B  528   -9.840   -9.916  13.517  1.00  31.66
ATOM   3657  CA   MET  B  528  -10.574  -10.572  14.589  1.00  29.77
ATOM   3658  CB   MET  B  528   -9.682  -10.743  15.820  1.00  32.96
ATOM   3659  CG   MET  B  528   -8.651  -11.859  15.699  1.00  33.47
ATOM   3660  SD   MET  B  528   -9.359  -13.427  15.134  1.00  38.28
ATOM   3661  CE   MET  B  528  -10.265  -13.915  16.579  1.00  36.01
ATOM   3662  C    MET  B  528  -11.800   -9.747  14.953  1.00  29.42
ATOM   3663  O    MET  B  528  -12.835  -10.293  15.331  1.00  28.65
ATOM   3664  N    LYS  B  529  -11.673   -8.429  14.850  1.00  30.64
ATOM   3665  CA   LYS  B  529  -12.781   -7.533  15.149  1.00  31.80
ATOM   3666  CB   LYS  B  529  -12.323   -6.079  15.027  1.00  32.86
ATOM   3667  CG   LYS  B  529  -13.436   -5.043  15.114  1.00  36.42
ATOM   3668  CD   LYS  B  529  -13.114   -3.852  14.224  1.00  41.74
ATOM   3669  CE   LYS  B  529  -13.734   -2.564  14.741  1.00  43.45
ATOM   3670  NZ   LYS  B  529  -15.221   -2.569  14.634  1.00  46.51
ATOM   3671  C    LYS  B  529  -13.857   -7.840  14.116  1.00  35.60
ATOM   3672  O    LYS  B  529  -15.049   -7.877  14.424  1.00  34.04
ATOM   3673  N    CYS  B  530  -13.407   -8.083  12.889  1.00  40.04
ATOM   3674  CA   CYS  B  530  -14.286   -8.409  11.773  1.00  44.98
ATOM   3675  CB   CYS  B  530  -13.460   -8.535  10.491  1.00  50.64
ATOM   3676  SG   CYS  B  530  -13.369   -7.034   9.504  1.00  67.65
ATOM   3677  C    CYS  B  530  -15.065   -9.692  12.016  1.00  42.88
ATOM   3678  O    CYS  B  530  -16.274   -9.741  11.807  1.00  40.15
ATOM   3679  N    LYS  B  531  -14.360  -10.733  12.447  1.00  41.92
ATOM   3680  CA   LYS  B  531  -14.980  -12.023  12.728  1.00  42.60
ATOM   3681  CB   LYS  B  531  -13.907  -13.091  12.927  1.00  44.77
ATOM   3682  C    LYS  B  531  -15.844  -11.907  13.987  1.00  44.43
ATOM   3683  O    LYS  B  531  -16.623  -12.804  14.296  1.00  44.09
ATOM   3684  N    ASN  B  532  -15.678  -10.793  14.685  1.00  44.98
ATOM   3685  CA   ASN  B  532  -16.437  -10.496  15.893  1.00  44.10
ATOM   3686  CB   ASN  B  532  -17.833  -10.003  15.506  1.00  45.14
ATOM   3687  CG   ASN  B  532  -18.526   -9.271  16.633  1.00  46.34
ATOM   3688  OD1  ASN  B  532  -19.729   -9.424  16.837  1.00  50.62
ATOM   3689  ND2  ASN  B  532  -17.771   -8.471  17.375  1.00  46.07
ATOM   3690  C    ASN  B  532  -16.557  -11.657  16.882  1.00  43.34
ATOM   3691  O    ASN  B  532  -17.655  -11.994  17.321  1.00  41.42
ATOM   3692  N    VAL  B  533  -15.434  -12.264  17.243  1.00  43.45
ATOM   3693  CA   VAL  B  533  -15.471  -13.371  18.190  1.00  44.06
ATOM   3694  CB   VAL  B  533  -14.170  -14.219  18.120  1.00  45.56
ATOM   3695  CG1  VAL  B  533  -13.661  -14.263  16.683  1.00  45.67
ATOM   3696  CG2  VAL  B  533  -13.107  -13.644  19.045  1.00  44.16
ATOM   3697  C    VAL  B  533  -15.670  -12.835  19.611  1.00  43.24
ATOM   3698  O    VAL  B  533  -15.894  -13.602  20.548  1.00  44.21
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   3699  N    VAL  B  534   -15.596  -11.511  19.755  1.00  40.44
ATOM   3700  CA   VAL  B  534   -15.765  -10.849  21.049  1.00  37.60
ATOM   3701  CB   VAL  B  534   -14.630  -11.259  22.038  1.00  36.38
ATOM   3702  CG1  VAL  B  534   -13.324  -10.575  21.658  1.00  34.35
ATOM   3703  CG2  VAL  B  534   -15.021  -10.910  23.463  1.00  39.34
ATOM   3704  C    VAL  B  534   -15.752   -9.329  20.857  1.00  37.97
ATOM   3705  O    VAL  B  534   -15.026   -8.808  20.008  1.00  39.45
ATOM   3706  N    PRO  B  535   -16.575   -8.597  21.625  1.00  37.81
ATOM   3707  CD   PRO  B  535   -17.529   -9.078  22.640  1.00  38.74
ATOM   3708  CA   PRO  B  535   -16.608   -7.135  21.492  1.00  36.79
ATOM   3709  CB   PRO  B  535   -17.846   -6.729  22.288  1.00  36.98
ATOM   3710  CG   PRO  B  535   -18.004   -7.809  23.298  1.00  39.77
ATOM   3711  C    PRO  B  535   -15.338   -6.494  22.049  1.00  33.95
ATOM   3712  O    PRO  B  535   -14.786   -5.963  23.040  1.00  34.93
ATOM   3713  N    LEU  B  536   -14.881   -5.426  21.409  1.00  33.42
ATOM   3714  CA   LEU  B  536   -13.675   -4.732  21.851  1.00  33.40
ATOM   3715  CB   LEU  B  536   -12.829   -4.314  20.647  1.00  29.31
ATOM   3716  CG   LEU  B  536   -12.219   -5.433  19.798  1.00  30.06
ATOM   3717  CD1  LEU  B  536   -11.344   -4.822  18.714  1.00  30.85
ATOM   3718  CD2  LEU  B  536   -11.398   -6.370  20.676  1.00  28.96
ATOM   3719  C    LEU  B  536   -14.036   -3.498  22.666  1.00  30.50
ATOM   3720  O    LEU  B  536   -15.024   -2.829  22.383  1.00  29.91
ATOM   3721  N    TYR  B  537   -13.231   -3.194  23.676  1.00  28.69
ATOM   3722  CA   TYR  B  537   -13.494   -2.032  24.505  1.00  29.89
ATOM   3723  CB   TYR  B  537   -12.618   -2.071  25.750  1.00  32.50
ATOM   3724  CG   TYR  B  537   -12.849   -3.327  26.543  1.00  39.46
ATOM   3725  CD1  TYR  B  537   -13.923   -3.431  27.421  1.00  41.90
ATOM   3726  CE1  TYR  B  537   -14.174   -4.609  28.118  1.00  45.72
ATOM   3727  CD2  TYR  B  537   -12.022   -4.435  26.379  1.00  47.39
ATOM   3728  CE2  TYR  B  537   -12.262   -5.620  27.072  1.00  49.93
ATOM   3729  CZ   TYR  B  537   -13.340   -5.699  27.940  1.00  48.80
ATOM   3730  OH   TYR  B  537   -13.582   -6.872  28.624  1.00  53.90
ATOM   3731  C    TYR  B  537   -13.262   -0.761  23.709  1.00  27.09
ATOM   3732  O    TYR  B  537   -12.518   -0.787  22.729  1.00  26.15
ATOM   3733  N    ASP  B  538   -13.909    0.315  24.141  1.00  26.12
ATOM   3734  CA   ASP  B  538   -13.830    1.598  23.461  1.00  25.27
ATOM   3735  CB   ASP  B  538   -14.748    2.598  24.164  1.00  28.85
ATOM   3736  CG   ASP  B  538   -16.227    2.285  23.940  1.00  33.90
ATOM   3737  OD1  ASP  B  538   -17.052    2.613  24.819  1.00  32.68
ATOM   3738  OD2  ASP  B  538   -16.562    1.707  22.882  1.00  38.26
ATOM   3739  C    ASP  B  538   -12.447    2.217  23.261  1.00  25.18
ATOM   3740  O    ASP  B  538   -12.120    2.626  22.147  1.00  26.41
ATOM   3741  N    LEU  B  539   -11.637    2.309  24.313  1.00  20.76
ATOM   3742  CA   LEU  B  539   -10.312    2.911  24.150  1.00  19.65
ATOM   3743  CB   LEU  B  539    -9.567    2.991  25.496  1.00  17.48
ATOM   3744  CG   LEU  B  539    -8.116    3.511  25.469  1.00  16.46
ATOM   3745  CD1  LEU  B  539    -8.051    4.892  24.838  1.00  16.43
ATOM   3746  CD2  LEU  B  539    -7.564    3.569  26.895  1.00  15.37
ATOM   3747  C    LEU  B  539    -9.484    2.127  23.127  1.00  16.75
ATOM   3748  O    LEU  B  539    -8.862    2.716  22.249  1.00  20.36
ATOM   3749  N    LEU  B  540    -9.487    0.803  23.239  1.00  18.23
ATOM   3750  CA   LEU  B  540    -8.743   -0.048  22.319  1.00  18.05
ATOM   3751  CB   LEU  B  540    -8.909   -1.528  22.701  1.00  16.38
ATOM   3752  CG   LEU  B  540    -8.188   -2.554  21.821  1.00  19.81
ATOM   3753  CD1  LEU  B  540    -6.679   -2.303  21.828  1.00  19.27
ATOM   3754  CD2  LEU  B  540    -8.473   -3.952  22.327  1.00  18.00
ATOM   3755  C    LEU  B  540    -9.241    0.169  20.891  1.00  21.50
ATOM   3756  O    LEU  B  540    -8.449    0.293  19.964  1.00  20.41
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    3757  N    LEU  B  541   -10.559   0.206  20.726  1.00  22.40
ATOM    3758  CA   LEU  B  541   -11.164   0.419  19.413  1.00  23.27
ATOM    3759  CB   LEU  B  541   -12.686   0.429  19.827  1.00  25.12
ATOM    3760  CG   LEU  B  541   -13.410  -0.808  18.999  1.00  36.53
ATOM    3761  CD1  LEU  B  541   -14.910  -0.671  19.273  1.00  30.98
ATOM    3762  CD2  LEU  B  541   -13.136  -0.971  17.508  1.00  31.93
ATOM    3763  C    LEU  B  541   -10.697   1.751  18.842  1.00  22.46
ATOM    3764  O    LEU  B  541   -10.359   1.845  17.666  1.00  26.29
ATOM    3765  N    GLU  B  542   -10.694   2.781  19.680  1.00  23.96
ATOM    3766  CA   GLU  B  542   -10.248   4.106  19.270  1.00  26.91
ATOM    3767  CB   GLU  B  542   -10.250   5.050  20.468  1.00  30.84
ATOM    3768  CG   GLU  B  542   -11.166   6.245  20.347  1.00  37.30
ATOM    3769  CD   GLU  B  542   -11.138   7.105  21.597  1.00  39.98
ATOM    3770  OE1  GLU  B  542   -12.223   7.385  22.144  1.00  39.92
ATOM    3771  OE2  GLU  B  542   -10.028   7.494  22.034  1.00  38.96
ATOM    3772  C    GLU  B  542    -8.826   4.010  18.724  1.00  27.90
ATOM    3773  O    GLU  B  542    -8.530   4.492  17.634  1.00  29.32
ATOM    3774  N    MET  B  543    -7.945   3.388  19.499  1.00  36.41
ATOM    3775  CA   MET  B  543    -6.552   3.237  19.107  1.00  23.53
ATOM    3776  CB   MET  B  543    -5.749   2.591  20.247  1.00  24.60
ATOM    3777  CG   MET  B  543    -5.812   3.338  21.579  1.00  26.46
ATOM    3778  SD   MET  B  543    -5.373   5.084  21.467  1.00  29.45
ATOM    3779  CE   MET  B  543    -3.585   4.971  21.349  1.00  25.43
ATOM    3780  C    MET  B  543    -6.403   2.407  17.832  1.00  25.80
ATOM    3781  O    MET  B  543    -5.535   2.686  17.004  1.00  23.59
ATOM    3782  N    LEU  B  544    -7.254   1.394  17.673  1.00  27.74
ATOM    3783  CA   LEU  B  544    -7.202   0.522  16.499  1.00  26.32
ATOM    3784  CB   LEU  B  544    -8.069  -0.721  16.719  1.00  26.75
ATOM    3785  CG   LEU  B  544    -8.274  -1.632  15.502  1.00  28.12
ATOM    3786  CD1  LEU  B  544    -6.956  -2.294  15.136  1.00  26.36
ATOM    3787  CD2  LEU  B  544    -9.330  -2.680  15.803  1.00  27.00
ATOM    3788  C    LEU  B  544    -7.672   1.252  15.250  1.00  26.97
ATOM    3789  O    LEU  B  544    -7.036   1.181  14.195  1.00  24.25
ATOM    3790  N    ASP  B  545    -8.787   1.961  15.372  1.00  30.37
ATOM    3791  CA   ASP  B  545    -9.338   2.702  14.244  1.00  32.34
ATOM    3792  CB   ASP  B  545   -10.668   3.345  14.637  1.00  36.61
ATOM    3793  CG   ASP  B  545   -11.818   2.370  14.565  1.00  42.73
ATOM    3794  OD1  ASP  B  545   -12.858   2.624  15.211  1.00  47.39
ATOM    3795  OD2  ASP  B  545   -11.676   1.342  13.863  1.00  46.96
ATOM    3796  C    ASP  B  545    -8.382   3.762  13.711  1.00  31.27
ATOM    3797  O    ASP  B  545    -8.443   4.120  12.532  1.00  30.53
ATOM    3798  N    ALA  B  546    -7.506   4.272  14.572  1.00  29.02
ATOM    3799  CA   ALA  B  546    -6.543   5.280  14.141  1.00  31.21
ATOM    3800  CB   ALA  B  546    -5.646   5.693  15.306  1.00  30.98
ATOM    3801  C    ALA  B  546    -5.697   4.731  12.996  1.00  32.14
ATOM    3802  O    ALA  B  546    -5.189   5.490  12.170  1.00  33.78
ATOM    3803  N    HIS  B  547    -5.555   3.410  12.943  1.00  32.27
ATOM    3804  CA   HIS  B  547    -4.773   2.767  11.892  1.00  37.73
ATOM    3805  CB   HIS  B  547    -3.991   1.576  12.457  1.00  35.83
ATOM    3806  CG   HIS  B  547    -2.796   1.968  13.269  1.00  34.54
ATOM    3807  CD2  HIS  B  547    -2.698   2.553  14.486  1.00  30.23
ATOM    3808  ND1  HIS  B  547    -1.502   1.755  12.840  1.00  34.23
ATOM    3809  CE1  HIS  B  547    -0.659   2.193  13.760  1.00  36.72
ATOM    3810  NE2  HIS  B  547    -1.360   2.681  14.768  1.00  31.48
ATOM    3811  C    HIS  B  547    -5.649   2.286  10.735  1.00  43.69
ATOM    3812  O    HIS  B  547    -5.178   2.152   9.606  1.00  45.04
ATOM    3813  N    ARG  B  548    -6.919   2.020  11.019  1.00  48.35
ATOM    3814  CA   ARG  B  548    -7.843   1.551   9.983  1.00  54.74
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    3815  CB   ARG  B  548   -8.522   0.267 10.452  1.00  54.66
ATOM    3816  C    ARG  B  548   -8.886   2.619  9.681  1.00  59.94
ATOM    3817  O    ARG  B  548   -8.580   3.812  9.673  1.00  62.81
ATOM    3818  N    LEU  B  549  -10.116   2.186  9.422  1.00  64.81
ATOM    3819  CA   LEU  B  549  -11.204   3.109  9.112  1.00  67.59
ATOM    3820  CB   LEU  B  549  -12.478   2.327  8.799  1.00  68.06
ATOM    3821  C    LEU  B  549  -11.449   4.069 10.275  1.00  69.12
ATOM    3822  O    LEU  B  549  -11.451   5.297 10.036  1.00  68.96
ATOM    3823  OXT  LEU  B  549  -11.634   3.579 11.412  1.00  70.70
HETATM  3824  CP9  DES  B  600   -4.547  -6.077 22.000  1.00  18.35
HETATM  3825  CP8  DES  B  600   -3.163  -6.365 21.467  1.00  17.72
HETATM  3826  CP7  DES  B  600   -2.897  -7.853 21.381  1.00  21.17
HETATM  3827  CP6  DES  B  600   -3.719  -8.551 20.374  1.00  22.05
HETATM  3828  CP1  DES  B  600   -3.405  -8.481 18.998  1.00  21.32
HETATM  3829  CP2  DES  B  600   -4.239  -9.095 18.063  1.00  21.61
HETATM  3830  CP3  DES  B  600   -5.388  -9.771 18.509  1.00  24.89
HETATM  3831  OP3  DES  B  600   -6.244 -10.339 17.600  1.00  24.94
HETATM  3832  CP4  DES  B  600   -5.718  -9.858 19.860  1.00  24.08
HETATM  3833  CP5  DES  B  600   -4.877  -9.240 20.791  1.00  24.67
HETATM  3834  C7   DES  B  600   -1.998  -8.460 22.190  1.00  16.67
HETATM  3835  C6   DES  B  600   -1.330  -7.834 23.325  1.00  15.39
HETATM  3836  C5   DES  B  600   -2.054  -7.642 24.522  1.00  17.62
HETATM  3837  C4   DES  B  600   -1.433  -7.073 25.634  1.00  16.16
HETATM  3838  C3   DES  B  600   -0.077  -6.685 25.542  1.00  20.04
HETATM  3839  O3   DES  B  600    0.509  -6.113 26.655  1.00  15.55
HETATM  3840  C2   DES  B  600    0.669  -6.866 24.353  1.00  18.94
HETATM  3841  C1   DES  B  600    0.035  -7.440 23.241  1.00  15.20
HETATM  3842  C8   DES  B  600   -1.642  -9.903 21.942  1.00  17.61
HETATM  3843  C9   DES  B  600   -0.440 -10.009 20.998  1.00  11.63
HETATM  3844  C1   CBM  B  417   -4.997 -22.994 25.273  1.00  55.80
HETATM  3845  O4   CBM  B  417   -4.789 -24.187 25.003  1.00  55.56
HETATM  3846  O3   CBM  B  417   -4.798 -22.559 26.552  1.00  56.04
HETATM  3847  C2   CBM  B  417   -5.468 -21.960 24.264  1.00  57.04
HETATM  3848  C1   CBM  B  530  -15.278  -5.124 10.243  1.00  87.39
HETATM  3849  O4   CBM  B  530  -15.852  -5.086  9.064  1.00  87.68
HETATM  3850  O3   CBM  B  530  -15.832  -4.291 11.201  1.00  86.22
HETATM  3851  C2   CBM  B  530  -14.207  -5.886 10.628  1.00  87.65
ATOM    3852  CB   HIS  C  687    9.818 -20.030 -2.211  1.00  63.34
ATOM    3853  C    HIS  C  687   10.133 -20.267 -4.689  1.00  63.49
ATOM    3854  O    HIS  C  687   11.204 -20.840 -4.472  1.00  63.87
ATOM    3855  N    HIS  C  687    7.944 -19.563 -3.758  1.00  65.42
ATOM    3856  CA   HIS  C  687    9.424 -19.484 -3.586  1.00  64.86
ATOM    3857  N    LYS  C  688    9.533 -20.281 -5.875  1.00  62.00
ATOM    3858  CA   LYS  C  688   10.101 -20.999 -7.009  1.00  60.81
ATOM    3859  CB   LYS  C  688    8.980 -21.540 -7.901  1.00  61.76
ATOM    3860  C    LYS  C  688   11.050 -20.127 -7.827  1.00  57.47
ATOM    3861  O    LYS  C  688   12.253 -20.379 -7.858  1.00  57.64
ATOM    3862  N    ILE  C  689   10.511 -19.103 -8.482  1.00  55.74
ATOM    3863  CA   ILE  C  689   11.326 -18.212 -9.306  1.00  53.09
ATOM    3864  CB   ILE  C  689   10.496 -17.057 -9.889  1.00  53.83
ATOM    3865  CG2  ILE  C  689   11.334 -16.286-10.902  1.00  54.55
ATOM    3866  CG1  ILE  C  689    9.229 -17.603-10.551  1.00  52.90
ATOM    3867  CD1  ILE  C  689    8.406 -16.550-11.258  1.00  50.45
ATOM    3868  C    ILE  C  689   12.513 -17.611 -8.550  1.00  50.82
ATOM    3869  O    ILE  C  689   13.616 -17.550 -9.097  1.00  51.28
ATOM    3870  N    LEU  C  690   12.288 -17.162 -7.329  1.00  48.01
ATOM    3871  CA   LEU  C  690   13.362 -16.570 -6.534  1.00  47.33
ATOM    3872  CB   LEU  C  690   12.812 -16.058 -5.199  1.00  42.51
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   3873  CG   LEU  C  690   13.835  -15.501  -4.206  1.00  40.67
ATOM   3874  CD1  LEU  C  690   14.575  -14.324  -4.831  1.00  39.95
ATOM   3875  CD2  LEU  C  690   13.128  -15.078  -2.926  1.00  38.77
ATOM   3876  C    LEU  C  690   14.445  -17.615  -6.282  1.00  48.87
ATOM   3877  O    LEU  C  690   15.643  -17.340  -6.393  1.00  46.71
ATOM   3878  N    HIS  C  691   14.001  -18.818  -5.939  1.00  51.36
ATOM   3879  CA   HIS  C  691   14.886  -19.946  -5.675  1.00  53.35
ATOM   3880  CB   HIS  C  691   14.042  -21.203  -5.460  1.00  58.64
ATOM   3881  CG   HIS  C  691   14.655  -22.195  -4.526  1.00  62.94
ATOM   3882  CD2  HIS  C  691   15.503  -23.227  -4.751  1.00  64.95
ATOM   3883  ND1  HIS  C  691   14.392  -22.202  -3.173  1.00  65.49
ATOM   3884  CE1  HIS  C  691   15.053  -23.195  -2.605  1.00  68.18
ATOM   3885  NE2  HIS  C  691   15.733  -23.833  -3.540  1.00  68.77
ATOM   3886  C    HIS  C  691   15.824  -20.162  -6.861  1.00  52.19
ATOM   3887  O    HIS  C  691   17.048  -20.153  -6.717  1.00  47.53
ATOM   3888  N    ARG  C  692   15.222  -20.350  -8.032  1.00  52.37
ATOM   3889  CA   ARG  C  692   15.949  -20.586  -9.271  1.00  52.90
ATOM   3890  CB   ARG  C  692   14.955  -20.832 -10.410  1.00  54.04
ATOM   3891  CG   ARG  C  692   15.575  -20.826 -11.797  1.00  57.52
ATOM   3892  CD   ARG  C  692   14.528  -21.048 -12.874  1.00  58.25
ATOM   3893  NE   ARG  C  692   14.375  -19.878 -13.732  1.00  61.43
ATOM   3894  CZ   ARG  C  692   13.218  -19.360 -13.951  1.00  64.32
ATOM   3895  NH1  ARG  C  692   12.108  -19.706 -13.378  1.00  63.22
ATOM   3896  NH2  ARG  C  692   13.171  -18.197 -14.746  1.00  65.93
ATOM   3897  C    ARG  C  692   16.873  -19.434  -9.639  1.00  53.09
ATOM   3898  O    ARG  C  692   18.047  -19.644  -9.956  1.00  53.06
ATOM   3899  N    LEU  C  693   16.338  -18.217  -9.607  1.00  50.73
ATOM   3900  CA   LEU  C  693   17.125  -17.039  -9.945  1.00  49.53
ATOM   3901  CB   LEU  C  693   16.249  -15.784  -9.881  1.00  49.56
ATOM   3902  CG   LEU  C  693   15.781  -15.245 -11.239  1.00  49.78
ATOM   3903  CD1  LEU  C  693   15.219  -16.389 -12.079  1.00  50.30
ATOM   3904  CD2  LEU  C  693   14.728  -14.170 -11.037  1.00  48.79
ATOM   3905  C    LEU  C  693   18.318  -16.904  -9.006  1.00  48.38
ATOM   3906  O    LEU  C  693   19.382  -16.426  -9.402  1.00  46.35
ATOM   3907  N    LEU  C  694   18.135  -17.329  -7.761  1.00  46.74
ATOM   3908  CA   LEU  C  694   19.204  -17.272  -6.775  1.00  49.41
ATOM   3909  CB   LEU  C  694   18.634  -17.415  -5.362  1.00  45.20
ATOM   3910  CG   LEU  C  694   18.222  -16.128  -4.643  1.00  40.19
ATOM   3911  CD1  LEU  C  694   17.456  -16.474  -3.371  1.00  41.65
ATOM   3912  CD2  LEU  C  694   19.453  -15.307  -4.317  1.00  35.91
ATOM   3913  C    LEU  C  694   20.172  -18.417  -7.058  1.00  54.15
ATOM   3914  O    LEU  C  694   21.370  -18.320  -6.776  1.00  53.55
ATOM   3915  N    GLN  C  695   19.634  -19.498  -7.619  1.00  57.44
ATOM   3916  CA   GLN  C  695   20.416  -20.685  -7.959  1.00  62.46
ATOM   3917  CB   GLN  C  695   19.477  -21.853  -8.304  1.00  61.95
ATOM   3918  CG   GLN  C  695   19.548  -23.010  -7.311  1.00  61.49
ATOM   3919  CD   GLN  C  695   18.454  -24.053  -7.490  1.00  62.78
ATOM   3920  OE1  GLN  C  695   18.262  -24.928  -6.653  1.00  63.33
ATOM   3921  NE2  GLN  C  695   17.720  -23.969  -8.808  1.00  60.37
ATOM   3922  C    GLN  C  695   21.330  -20.414  -9.149  1.00  65.13
ATOM   3923  O    GLN  C  695   22.517  -20.740  -9.116  1.00  65.87
ATOM   3924  N    ASP  C  696   20.761  -19.824 -10.197  1.00  67.67
ATOM   3925  CA   ASP  C  696   21.492  -19.500 -11.420  1.00  70.66
ATOM   3926  CB   ASP  C  696   20.801  -18.348 -12.151  1.00  71.06
ATOM   3927  CG   ASP  C  696   20.127  -18.792 -13.430  1.00  71.70
ATOM   3928  OD1  ASP  C  696   20.637  -18.455 -14.521  1.00  72.47
ATOM   3929  OD2  ASP  C  696   19.086  -19.478 -13.342  1.00  71.41
ATOM   3930  C    ASP  C  696   22.951  -19.132 -11.169  1.00  72.41
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    3931  O    ASP  C  696    23.245  -18.115 -10.541  1.00  72.56
ATOM    3932  N    SER  C  697    23.859  -19.967 -11.688  1.00  74.67
ATOM    3933  CA   SER  C  697    25.291  -19.741 -11.507  1.00  76.45
ATOM    3934  CB   SER  C  697    26.019  -21.076 -11.377  1.00  76.00
ATOM    3935  C    SER  C  697    25.841  -18.960 -12.696  1.00  78.44
ATOM    3936  O    SER  C  697    26.286  -17.809 -12.489  1.00  79.20
ATOM    3937  OXT  SER  C  697    25.818  -19.510 -13.820  1.00  80.07
ATOM    3938  CB   LYS  D  686   -14.070   13.661  16.843  1.00  50.28
ATOM    3939  C    LYS  D  686   -13.682   14.418  19.199  1.00  51.59
ATOM    3940  O    LYS  D  686   -12.629   14.738  19.759  1.00  50.42
ATOM    3941  N    LYS  D  686   -12.910   15.796  17.283  1.00  50.43
ATOM    3942  CA   LYS  D  686   -13.976   14.872  17.769  1.00  50.62
ATOM    3943  N    HIS  D  687   -14.617   13.676  19.787  1.00  49.91
ATOM    3944  CA   HIS  D  687   -14.447   13.176  21.144  1.00  51.28
ATOM    3945  CB   HIS  D  687   -15.806   12.984  21.828  1.00  54.12
ATOM    3946  CG   HIS  D  687   -15.713   12.336  23.177  1.00  60.06
ATOM    3947  CD2  HIS  D  687   -15.418   11.064  23.539  1.00  61.05
ATOM    3948  ND1  HIS  D  687   -15.911   13.030  24.352  1.00  62.39
ATOM    3949  CE1  HIS  D  687   -15.741   12.215  25.378  1.00  62.76
ATOM    3950  NE2  HIS  D  687   -15.441   11.016  24.912  1.00  63.46
ATOM    3951  C    HIS  D  687   -13.691   11.849  21.163  1.00  49.55
ATOM    3952  O    HIS  D  687   -14.099   10.878  20.524  1.00  50.84
ATOM    3953  N    LYS  D  688   -12.593   11.816  21.909  1.00  44.00
ATOM    3954  CA   LYS  D  688   -11.784   10.611  22.038  1.00  40.31
ATOM    3955  CB   LYS  D  688   -10.446   10.773  21.299  1.00  41.42
ATOM    3956  CG   LYS  D  688   -10.513   10.595  19.780  1.00  42.76
ATOM    3957  CD   LYS  D  688    -9.123   10.716  19.152  1.00  38.66
ATOM    3958  CE   LYS  D  688    -9.162   10.529  17.540  1.00  38.28
ATOM    3959  NZ   LYS  D  688    -7.894   10.970  16.986  1.00  31.58
ATOM    3960  C    LYS  D  688   -11.506   10.378  23.517  1.00  36.70
ATOM    3961  O    LYS  D  688   -11.271   11.326  24.266  1.00  33.38
ATOM    3962  N    ILE  D  689   -11.549    9.122  23.942  1.00  33.06
ATOM    3963  CA   ILE  D  689   -11.255    8.806  25.328  1.00  28.70
ATOM    3964  CB   ILE  D  689   -11.438    7.301  25.607  1.00  30.88
ATOM    3965  CG2  ILE  D  689   -10.725    6.912  26.899  1.00  31.45
ATOM    3966  CG1  ILE  D  689   -12.927    6.971  25.721  1.00  32.57
ATOM    3967  CD1  ILE  D  689   -13.308    5.679  25.031  1.00  29.79
ATOM    3968  C    ILE  D  689    -9.790    9.193  25.541  1.00  27.64
ATOM    3969  O    ILE  D  689    -9.405    9.649  26.611  1.00  25.54
ATOM    3970  N    LEU  D  690    -8.985    9.021  24.496  1.00  24.25
ATOM    3971  CA   LEU  D  690    -7.563    9.348  24.549  1.00  26.63
ATOM    3972  CB   LEU  D  690    -6.903    9.021  23.200  1.00  22.83
ATOM    3973  CG   LEU  D  690    -5.433    9.387  22.992  1.00  25.47
ATOM    3974  CD1  LEU  D  690    -4.595    8.772  24.108  1.00  24.03
ATOM    3975  CD2  LEU  D  690    -4.956    8.898  21.616  1.00  20.87
ATOM    3976  C    LEU  D  690    -7.344   10.823  24.902  1.00  26.64
ATOM    3977  O    LEU  D  690    -6.408   11.165  25.625  1.00  28.34
ATOM    3978  N    HIS  D  691    -8.206   11.694  24.383  1.00  27.77
ATOM    3979  CA   HIS  D  691    -8.107   13.125  24.665  1.00  29.16
ATOM    3980  CB   HIS  D  691    -9.156   13.907  23.861  1.00  30.89
ATOM    3981  CG   HIS  D  691    -8.903   13.935  22.386  1.00  37.09
ATOM    3982  CD2  HIS  D  691    -7.750   14.000  21.679  1.00  41.39
ATOM    3983  ND1  HIS  D  691    -9.920   13.906  21.458  1.00  41.65
ATOM    3984  CE1  HIS  D  691    -9.407   13.953  20.242  1.00  44.64
ATOM    3985  NE2  HIS  D  691    -8.091   14.010  20.347  1.00  41.94
ATOM    3986  C    HIS  D  691    -8.338   13.373  26.159  1.00  26.65
ATOM    3987  O    HIS  D  691    -7.602   14.120  26.802  1.00  24.50
ATOM    3988  N    ARG  D  692    -9.371   12.742  26.703  1.00  25.70
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    3989  CA   ARG  D  692   -9.691  12.912 28.114  1.00  29.11
ATOM    3990  CB   ARG  D  692  -10.959  12.134 28.472  1.00  30.84
ATOM    3991  CG   ARG  D  692  -11.255  13.129 29.963  1.00  41.63
ATOM    3992  CD   ARG  D  692  -12.502  11.327 30.290  1.00  48.83
ATOM    3993  NE   ARG  D  692  -13.618  12.198 30.647  1.00  54.50
ATOM    3994  CZ   ARG  D  692  -14.498  12.677 29.774  1.00  59.37
ATOM    3995  NH1  ARG  D  692  -14.392  12.371 28.486  1.00  60.97
ATOM    3996  NH2  ARG  D  692  -15.483  13.464 30.188  1.00  59.07
ATOM    3997  C    ARG  D  692   -8.548  12.451 29.011  1.00  28.30
ATOM    3998  O    ARG  D  692   -8.139  13.167 29.929  1.00  26.50
ATOM    3999  N    LEU  D  693   -8.030  11.259 28.737  1.00  24.87
ATOM    4000  CA   LEU  D  693   -6.943  10.705 29.536  1.00  27.17
ATOM    4001  CB   LEU  D  693   -6.674   9.254 29.115  1.00  28.45
ATOM    4002  CG   LEU  D  693   -7.844   8.300 29.391  1.00  30.40
ATOM    4003  CD1  LEU  D  693   -7.575   6.932 28.778  1.00  34.79
ATOM    4004  CD2  LEU  D  693   -8.043   8.171 30.894  1.00  32.02
ATOM    4005  C    LEU  D  693   -5.670  11.539 29.440  1.00  25.96
ATOM    4006  O    LEU  D  693   -4.948  11.700 30.428  1.00  27.01
ATOM    4007  N    LEU  D  694   -5.395  12.080 28.257  1.00  25.33
ATOM    4008  CA   LEU  D  694   -4.207  12.906 28.062  1.00  27.22
ATOM    4009  CB   LEU  D  694   -3.948  13.126 26.572  1.00  24.61
ATOM    4010  CG   LEU  D  694   -3.118  12.080 25.825  1.00  22.20
ATOM    4011  CD1  LEU  D  694   -3.230  12.332 24.324  1.00  21.13
ATOM    4012  CD2  LEU  D  694   -1.666  12.148 26.275  1.00  21.34
ATOM    4013  C    LEU  D  694   -4.336  14.270 28.742  1.00  32.40
ATOM    4014  O    LEU  D  694   -3.339  14.889 29.102  1.00  31.55
ATOM    4015  N    GLN  D  695   -5.570  14.733 28.915  1.00  36.93
ATOM    4016  CA   GLN  D  695   -5.820  16.032 29.528  1.00  43.18
ATOM    4017  CB   GLN  D  695   -7.022  16.694 28.862  1.00  40.48
ATOM    4018  CG   GLN  D  695   -6.772  17.071 27.422  1.00  37.99
ATOM    4019  CD   GLN  D  695   -7.943  17.764 26.795  1.00  35.86
ATOM    4020  OE1  GLN  D  695   -7.863  18.895 26.342  1.00  38.84
ATOM    4021  NE2  GLN  D  695   -9.082  17.060 26.757  1.00  31.62
ATOM    4022  C    GLN  D  695   -6.049  16.009 31.034  1.00  48.74
ATOM    4023  O    GLN  D  695   -6.119  17.065 31.660  1.00  51.25
ATOM    4024  N    ASP  D  696   -6.175  14.818 31.611  1.00  54.01
ATOM    4025  CA   ASP  D  696   -6.398  14.702 33.047  1.00  62.23
ATOM    4026  CB   ASP  D  696   -6.217  13.238 33.485  1.00  63.97
ATOM    4027  CG   ASP  D  696   -7.527  12.467 33.475  1.00  67.72
ATOM    4028  OD1  ASP  D  696   -8.528  12.996 32.941  1.00  68.11
ATOM    4029  OD2  ASP  D  696   -7.552  11.333 34.003  1.00  68.95
ATOM    4030  C    ASP  D  696   -5.456  15.622 33.840  1.00  65.60
ATOM    4031  O    ASP  D  696   -4.312  15.189 34.134  1.00  68.33
ATOM    4032  OXT  ASP  D  696   -5.874  16.755 34.140  1.00  69.20
HETATM  4033  O    HOH     1     16.153  -0.605 -4.425  1.00  17.11
HETATM  4034  O    HOH     2     16.570  -5.304-16.560  1.00  21.44
HETATM  4035  O    HOH     3     18.526   0.742 -4.495  1.00  23.43
HETATM  4036  O    HOH     4     13.647  -2.187  8.588  1.00  25.82
HETATM  4037  O    HOH     5      9.778  -5.825  2.509  1.00  20.58
HETATM  4038  O    HOH     6     17.072  -3.605 -8.015  1.00  18.38
HETATM  4039  O    HOH     7     24.920  -1.689 -2.780  1.00  25.74
HETATM  4040  O    HOH     8      7.321  -5.649  5.061  1.00  24.11
HETATM  4041  O    HOH     9     25.976  -3.535 15.158  1.00  26.78
HETATM  4042  O    HOH    10     15.088  -7.006-15.192  1.00  19.64
HETATM  4043  O    HOH    11     14.070   0.925 -5.953  1.00  20.55
HETATM  4044  O    HOH    12     18.008   3.407 -6.654  1.00  32.30
HETATM  4045  O    HOH    13     31.949  -8.393 13.487  1.00  30.64
HETATM  4046  O    HOH    14     19.525  -2.804 -4.279  1.00  24.45
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
HETATM  4047  O   HOH  15   11.741   1.079-21.140  1.00  25.87
HETATM  4048  O   HOH  16   25.067  13.951 14.153  1.00  31.07
HETATM  4049  O   HOH  17   15.501   1.323-10.393  1.00  31.01
HETATM  4050  O   HOH  18   13.880   3.349-11.482  1.00  24.28
HETATM  4051  O   HOH  19   17.591   0.979 -8.828  1.00  35.26
HETATM  4052  O   HOH  20   23.682  -2.041 -0.314  1.00  37.90
HETATM  4053  O   HOH  21   15.754   9.496 11.841  1.00  39.44
HETATM  4054  O   HOH  22   -4.943   7.574 -3.066  1.00  37.67
HETATM  4055  O   HOH  23    6.877   0.354-15.982  1.00  36.92
HETATM  4056  O   HOH  24   15.806  -4.002  8.671  1.00  30.38
HETATM  4057  O   HOH  25   17.185  -3.158 -5.321  1.00  28.89
HETATM  4058  O   HOH  26   17.572   9.249 17.009  1.00  30.15
HETATM  4059  O   HOH  27   24.096  -2.929 11.504  1.00  31.37
HETATM  4060  O   HOH  28   22.324  -5.871-11.980  1.00  32.74
HETATM  4061  O   HOH  29   27.547 -12.361 -0.801  1.00  36.61
HETATM  4062  O   HOH  30   11.173  13.442 -2.719  1.00  35.41
HETATM  4063  O   HOH  31   15.438  -9.527  5.483  1.00  29.88
HETATM  4064  O   HOH  32    9.946  -6.564  5.983  1.00  35.05
HETATM  4065  O   HOH  33    7.599  11.680-15.261  1.00  38.68
HETATM  4066  O   HOH  34   20.112  10.503 -5.109  1.00  42.56
HETATM  4067  O   HOH  35   15.972  10.343 14.897  1.00  41.73
HETATM  4068  O   HOH  36   22.401  -5.914 -9.527  1.00  28.08
HETATM  4069  O   HOH  37   16.128  -0.899 -8.109  1.00  33.13
HETATM  4070  O   HOH  38    3.581  15.655 -3.706  1.00  41.37
HETATM  4071  O   HOH  39   31.900  13.545 21.339  1.00  37.79
HETATM  4072  O   HOH  40   20.088  -7.530 14.119  1.00  47.51
HETATM  4073  O   HOH  41   34.634   6.668 15.632  1.00  29.24
HETATM  4074  O   HOH  42   17.968  10.511 -9.085  1.00  44.60
HETATM  4075  O   HOH  43   23.258 -17.325 -4.088  1.00  44.10
HETATM  4076  O   HOH  44    4.034  -1.472 27.521  1.00  15.22
HETATM  4077  O   HOH  45   -5.943  -0.018 36.088  1.00  21.11
HETATM  4078  O   HOH  46    6.084  -1.509 29.478  1.00  19.51
HETATM  4079  O   HOH  47    9.762   1.061 15.621  1.00  27.74
HETATM  4080  O   HOH  48    1.804   0.717 17.260  1.00  20.97
HETATM  4081  O   HOH  49    0.929   0.421 30.281  1.00  19.64
HETATM  4082  O   HOH  50    9.627   4.271 31.231  1.00  19.03
HETATM  4083  O   HOH  51    2.121  -0.261 13.654  1.00  26.09
HETATM  4084  O   HOH  52   20.060  10.275 17.711  1.00  25.49
HETATM  4085  O   HOH  53   -6.786   0.736 33.483  1.00  22.34
HETATM  4086  O   HOH  54    2.751  -4.135 27.760  1.00  19.93
HETATM  4087  O   HOH  55    5.994  -4.079 31.292  1.00  32.27
HETATM  4088  O   HOH  56   19.416  16.921 21.645  1.00  25.54
HETATM  4089  O   HOH  57    4.833   2.325 29.006  1.00  19.00
HETATM  4090  O   HOH  58   -7.638  -8.931 37.809  1.00  24.79
HETATM  4091  O   HOH  59   28.442  -4.673 21.875  1.00  24.32
HETATM  4092  O   HOH  60    1.094  -4.893 32.100  1.00  24.27
HETATM  4093  O   HOH  61    0.905  -7.306 32.783  1.00  21.33
HETATM  4094  O   HOH  62    3.396  -2.971 32.306  1.00  26.13
HETATM  4095  O   HOH  63   10.363   4.576 28.391  1.00  33.43
HETATM  4096  O   HOH  64   19.551  -6.473 16.597  1.00  35.38
HETATM  4097  O   HOH  65   -2.888 -19.627 15.665  1.00  27.99
HETATM  4098  O   HOH  66   -7.275  -9.745 31.077  1.00  27.00
HETATM  4099  O   HOH  67   10.189   3.580 16.510  1.00  24.19
HETATM  4100  O   HOH  68    3.741   0.716 28.382  1.00  15.48
HETATM  4101  O   HOH  69   23.522  -4.323 13.943  1.00  27.46
HETATM  4102  O   HOH  70   17.133   8.133 19.686  1.00  32.24
HETATM  4103  O   HOH  71   -0.295   4.535 35.884  1.00  33.42
HETATM  4104  O   HOH  72    9.519  10.828 34.842  1.00  29.38
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
HETATM  4105  O   HOH   73    6.291  14.878  29.070  1.00  28.21
HETATM  4106  O   HOH   74   -1.721   6.480  13.381  1.00  49.91
HETATM  4107  O   HOH   75   10.091 -15.427  26.194  1.00  24.17
HETATM  4108  O   HOH   76    5.029   7.461  17.718  1.00  18.91
HETATM  4109  O   HOH   77    3.758   2.086  14.306  1.00  28.28
HETATM  4110  O   HOH   78   -1.390 -18.739  33.183  1.00  41.11
HETATM  4111  O   HOH   79   12.703  -8.687  32.119  1.00  36.21
HETATM  4112  O   HOH   80   22.270  -6.451  14.844  1.00  33.21
HETATM  4113  O   HOH   81    1.458   4.605  34.026  1.00  23.59
HETATM  4114  O   HOH   82    1.759  -2.158  30.374  1.00  28.78
HETATM  4115  O   HOH   83    6.153 -21.372  23.188  1.00  31.14
HETATM  4116  O   HOH   84   36.525   0.463  20.792  1.00  45.26
HETATM  4117  O   HOH   85   13.832   9.696  13.792  1.00  33.12
HETATM  4118  O   HOH   86   31.166   6.535  24.924  1.00  35.19
HETATM  4119  O   HOH   87    8.844 -10.389  34.180  1.00  48.80
HETATM  4120  O   HOH   88    9.581  -6.956  34.136  1.00  42.95
HETATM  4121  O   HOH   89   -1.563  15.887  27.596  1.00  39.35
HETATM  4122  O   HOH   90   -5.286  10.345  32.757  1.00  35.20
HETATM  4123  O   HOH   91   15.035   0.607  13.339  1.00  29.53
HETATM  4124  O   HOH   92  -10.984  -1.500  30.272  1.00  29.84
HETATM  4125  O   HOH   93   -7.239  -0.271  -1.207  1.00  48.98
HETATM  4126  O   HOH   94   18.022  -4.902  34.286  1.00  35.28
HETATM  4127  O   HOH   95   29.347  -6.319  19.920  1.00  37.20
HETATM  4128  O   HOH   96  -14.309 -19.369  20.945  1.00  30.23
HETATM  4129  O   HOH   97   31.496   4.614  18.716  1.00  38.79
HETATM  4130  O   HOH   98   26.567   9.759  25.629  1.00  29.72
HETATM  4131  O   HOH   99    2.848  14.531   1.134  1.00  38.08
HETATM  4132  O   HOH  100   -9.373   5.699  -7.953  1.00  53.23
HETATM  4133  O   HOH  101  -10.137  -0.553  -6.742  1.00  47.72
HETATM  4134  O   HOH  102   10.558 -10.363  15.403  1.00  40.97
HETATM  4135  O   HOH  103   21.079  17.166  18.929  1.00  32.40
HETATM  4136  O   HOH  104   25.810  -5.921  22.506  1.00  37.69
HETATM  4137  O   HOH  105   22.493  -1.311  34.465  1.00  49.94
HETATM  4138  O   HOH  106   19.317  10.977  38.703  1.00  40.60
HETATM  4139  O   HOH  107    4.479  13.951   3.045  1.00  45.33
HETATM  4140  O   HOH  108   20.418  19.353  34.044  1.00  42.18
HETATM  4141  O   HOH  109   -3.065   8.936  14.062  1.00  38.41
HETATM  4142  O   HOH  110   26.856  -4.674 -10.940  1.00  55.67
HETATM  4143  O   HOH  111    2.032  -6.387   5.614  1.00  42.23
HETATM  4144  O   HOH  112    0.601   0.228 -17.268  1.00  40.57
HETATM  4145  O   HOH  113    4.903  13.488 -14.050  1.00  47.72
HETATM  4146  O   HOH  114    3.986  16.140  -0.960  1.00  40.66
HETATM  4147  O   HOH  115   12.968 -19.561   2.741  1.00  40.76
HETATM  4148  O   HOH  116    7.170  15.583   2.599  1.00  43.69
HETATM  4149  O   HOH  117   -1.966  10.606   3.572  1.00  52.63
HETATM  4150  O   HOH  118   29.030  10.644   6.707  1.00  42.54
HETATM  4151  O   HOH  119    0.468   4.354   8.374  1.00  38.69
HETATM  4152  O   HOH  120   29.086  17.119  19.272  1.00  45.51
HETATM  4153  O   HOH  121   24.614  17.609  20.174  1.00  53.35
HETATM  4154  O   HOH  122  -15.318   0.362  26.686  1.00  36.77
HETATM  4155  O   HOH  123   -3.857 -24.786  28.325  1.00  39.64
HETATM  4156  O   HOH  124   21.728  22.178  31.983  1.00  43.73
HETATM  4157  O   HOH  125   31.650  -7.370  21.642  1.00  40.53
HETATM  4158  O   HOH  126   25.421  10.436  21.161  1.00  32.31
HETATM  4159  O   HOH  127   10.317  -9.457  12.998  1.00  37.77
HETATM  4160  O   HOH  128   22.723  14.887  15.427  1.00  47.90
HETATM  4161  O   HOH  129    6.702   9.556  37.596  1.00  47.81
HETATM  4162  O   HOH  130   27.987  13.557   7.167  1.00  41.15
```

UNITED STATES PATENT AND TRADEMARK OFFICE
CERTIFICATE OF CORRECTION

| | |
|---|---|
| PATENT NO. | : 6,965,850 B2 |
| APPLICATION NO. | : 09/281717 |
| DATED | : November 15, 2005 |
| INVENTOR(S) | : John D. Baxter et al. |

It is certified that error appears in the above-identified patent and that said Letters Patent is hereby corrected as shown below:

```
HETATM  4163  O    HOH  131   30.798  16.499   7.588  1.00  58.47
HETATM  4164  O    HOH  132   10.071  -0.571-20.393  1.00  38.79
HETATM  4165  O    HOH  133    9.562   8.334-21.392  1.00  36.80
HETATM  4166  O    HOH  134    6.712   6.058   8.822  1.00  37.43
HETATM  4167  O    HOH  135    5.927   8.454 10.594  1.00  42.34
HETATM  4168  O    HOH  136    4.472   6.306 10.973  1.00  37.35
HETATM  4169  O    HOH  137    6.792   7.721   7.051  1.00  47.23
HETATM  4170  O    HOH  138   24.513  11.582 33.724  1.00  45.55
HETATM  4171  O    HOH  139   -2.528 -20.361 12.354  1.00  52.13
HETATM  4172  O    HOH  140   -7.864   7.706 19.248  1.00  47.82
HETATM  4173  O    HOH  141   11.577 -16.962 24.398  1.00  39.43
HETATM  4174  O    HOH  142   18.087  12.263  -5.907  1.00  33.36
HETATM  4175  O    HOH  143   -6.816 -14.190 10.674  1.00  51.32
HETATM  4176  O    HOH  144   -7.377 -16.701 33.828  1.00  57.11
HETATM  4177  O    HOH  145   -5.379 -20.107 32.689  1.00  43.01
HETATM  4178  O    HOH  146    8.766  -7.947-16.274  1.00  49.96
HETATM  4179  O    HOH  147   10.946  -7.937-18.142  1.00  55.67
END
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

Appendix 3

Atomic Coordinates for Human ERα Complexed With OHT

```
CRYST1   58.242  58.242  277.467  90.00  90.00  120.00  P 65 2 2    12

ORIGX1    1.000000  0.000000  0.000000    0.00000
ORIGX2    0.000000  1.000000  0.000000    0.00000
ORIGX3    0.000000  0.000000  1.000000    0.00000
SCALE1    0.017170  0.009913  0.000000    0.00000
SCALE2    0.000000  0.019826  0.000000    0.00000
SCALE3    0.000000  0.000000  0.003604    0.00000

ATOM    1   CB   LEU   306    6.638   11.502    3.989  1.00  61.20
ATOM    2   C    LEU   306    7.381   10.684    6.231  1.00  61.47
ATOM    3   O    LEU   306    6.407   11.020    6.905  1.00  62.09
ATOM    4   N    LEU   306    6.369    9.128    4.588  1.00  62.32
ATOM    5   CA   LEU   306    7.232   10.330    4.754  1.00  61.30
ATOM    6   N    ALA   307    8.609   10.605    6.730  1.00  60.52
ATOM    7   CA   ALA   307    8.891   10.912    8.125  1.00  58.77
ATOM    8   CB   ALA   307   10.318   10.501    8.465  1.00  59.70
ATOM    9   C    ALA   307    8.692   12.393    8.429  1.00  57.51
ATOM   10   O    ALA   307    8.451   12.770    9.574  1.00  57.64
ATOM   11   N    LEU   308    8.789   13.228    7.400  1.00  55.82
ATOM   12   CA   LEU   308    8.638   14.668    7.573  1.00  56.62
ATOM   13   CB   LEU   308    9.298   15.402    6.406  1.00  57.48
ATOM   14   CG   LEU   308   10.637   14.822    5.948  1.00  59.17
ATOM   15   CD1  LEU   308   10.474   14.189    4.569  1.00  60.38
ATOM   16   CD2  LEU   308   11.694   15.920    5.933  1.00  58.46
ATOM   17   C    LEU   308    7.190   15.130    7.710  1.00  56.51
ATOM   18   O    LEU   308    6.935   16.307    7.961  1.00  55.58
ATOM   19   N    SER   309    6.246   14.208    7.546  1.00  57.04
ATOM   20   CA   SER   309    4.828   14.544    7.657  1.00  56.46
ATOM   21   CB   SER   309    4.034   13.896    6.514  1.00  56.79
ATOM   22   OG   SER   309    4.071   12.479    6.588  1.00  57.23
ATOM   23   C    SER   309    4.261   14.095    9.003  1.00  56.13
ATOM   24   O    SER   309    3.166   14.507    9.398  1.00  55.17
ATOM   25   N    LEU   310    5.016   13.257    9.706  1.00  54.31
ATOM   26   CA   LEU   310    4.591   12.749   11.004  1.00  53.95
ATOM   27   CB   LEU   310    5.651   11.811   11.582  1.00  54.40
ATOM   28   CG   LEU   310    5.586   10.333   11.189  1.00  56.49
ATOM   29   CD1  LEU   310    5.530   10.200    9.676  1.00  57.06
ATOM   30   CD2  LEU   310    6.809    9.610   11.739  1.00  57.28
ATOM   31   C    LEU   310    4.330   13.865   12.003  1.00  53.18
ATOM   32   O    LEU   310    4.993   14.905   11.984  1.00  53.17
ATOM   33   N    THR   311    3.352   13.641   12.874  1.00  51.71
ATOM   34   CA   THR   311    3.017   14.604   13.912  1.00  49.93
ATOM   35   CB   THR   311    1.527   14.554   14.275  1.00  48.96
ATOM   36   OG1  THR   311    1.242   13.311   14.930  1.00  47.20
ATOM   37   CG2  THR   311    0.666   14.688   13.027  1.00  50.99
ATOM   38   C    THR   311    3.815   14.201   15.145  1.00  48.84
ATOM   39   O    THR   311    4.371   13.103   15.197  1.00  46.66
ATOM   40   N    ALA   312    3.857   15.078   16.141  1.00  48.76
ATOM   41   CA   ALA   312    4.590   14.798   17.369  1.00  47.75
ATOM   42   CB   ALA   312    4.359   15.910   18.378  1.00  47.06
ATOM   43   C    ALA   312    4.171   13.460   17.964  1.00  47.41
ATOM   44   O    ALA   312    5.009   12.609   18.262  1.00  45.52
```

UNITED STATES PATENT AND TRADEMARK OFFICE
CERTIFICATE OF CORRECTION

PATENT NO. : 6,965,850 B2  Page 152 of 186
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM      45    N     ASP   313    2.868    13.275    18.143    1.00    47.58
ATOM      46    CA    ASP   313    2.367    12.032    18.714    1.00    47.63
ATOM      47    CB    ASP   313    0.848    12.100    18.879    1.00    51.96
ATOM      48    CG    ASP   313    0.430    12.872    20.118    1.00    56.21
ATOM      49    OD1   ASP   313    1.314    13.234    20.929    1.00    56.38
ATOM      50    OD2   ASP   313   -0.785    13.117    20.282    1.00    59.15
ATOM      51    C     ASP   313    2.745    10.846    17.835    1.00    43.93
ATOM      52    O     ASP   313    2.959     9.741    18.330    1.00    44.77
ATOM      53    N     GLN   314    2.826    11.081    16.531    1.00    44.52
ATOM      54    CA    GLN   314    3.182    10.028    15.588    1.00    44.73
ATOM      55    CB    GLN   314    2.849    10.464    14.156    1.00    45.05
ATOM      56    CG    GLN   314    1.534     9.886    13.626    1.00    48.47
ATOM      57    CD    GLN   314    0.982    10.646    12.428    1.00    50.37
ATOM      58    OE1   GLN   314    1.649    11.515    11.855    1.00    49.38
ATOM      59    NE2   GLN   314   -0.248    10.318    12.043    1.00    51.74
ATOM      60    C     GLN   314    4.673     9.722    15.707    1.00    43.26
ATOM      61    O     GLN   314    5.100     8.580    15.555    1.00    43.93
ATOM      62    N     MET   315    5.459    10.757    15.980    1.00    42.29
ATOM      63    CA    MET   315    6.901    10.606    16.130    1.00    41.26
ATOM      64    CB    MET   315    7.565    11.985    16.224    1.00    42.43
ATOM      65    CG    MET   315    9.082    11.939    16.356    1.00    42.34
ATOM      66    SD    MET   315    9.906    11.190    14.925    1.00    46.22
ATOM      67    CE    MET   315    9.547    12.408    13.680    1.00    37.32
ATOM      68    C     MET   315    7.218     9.791    17.379    1.00    38.89
ATOM      69    O     MET   315    8.002     8.841    17.335    1.00    40.02
ATOM      70    N     VAL   316    6.599    10.165    18.491    1.00    37.65
ATOM      71    CA    VAL   316    6.819     9.476    19.756    1.00    39.56
ATOM      72    CB    VAL   316    6.023    10.136    20.897    1.00    39.22
ATOM      73    CG1   VAL   316    6.245     9.373    22.192    1.00    44.43
ATOM      74    CG2   VAL   316    6.446    11.583    21.059    1.00    41.04
ATOM      75    C     VAL   316    6.404     8.012    19.664    1.00    40.04
ATOM      76    O     VAL   316    7.141     7.117    20.077    1.00    37.86
ATOM      77    N     SER   317    5.215     7.767    19.127    1.00    41.90
ATOM      78    CA    SER   317    4.733     6.400    18.997    1.00    41.68
ATOM      79    CB    SER   317    3.311     6.402    18.415    1.00    43.85
ATOM      80    OG    SER   317    3.225     5.631    17.230    1.00    49.38
ATOM      81    C     SER   317    5.696     5.601    18.114    1.00    39.72
ATOM      82    O     SER   317    6.011     4.446    18.407    1.00    40.21
ATOM      83    N     ALA   318    6.182     6.220    17.043    1.00    38.35
ATOM      84    CA    ALA   318    7.114     5.540    16.153    1.00    36.96
ATOM      85    CB    ALA   318    7.485     6.448    14.986    1.00    37.92
ATOM      86    C     ALA   318    8.375     5.137    16.920    1.00    38.31
ATOM      87    O     ALA   318    8.820     3.992    16.844    1.00    33.94
ATOM      88    N     LEU   319    8.938     6.089    17.664    1.00    36.92
ATOM      89    CA    LEU   319   10.161     5.854    18.438    1.00    38.56
ATOM      90    CB    LEU   319   10.660     7.174    19.040    1.00    40.86
ATOM      91    CG    LEU   319   11.136     8.264    18.071    1.00    41.25
ATOM      92    CD1   LEU   319   11.714     9.440    18.857    1.00    44.30
ATOM      93    CD2   LEU   319   12.182     7.693    17.140    1.00    42.61
ATOM      94    C     LEU   319    9.965     4.826    19.549    1.00    38.33
ATOM      95    O     LEU   319   10.773     3.916    19.729    1.00    33.91
ATOM      96    N     LEU   320    8.879     4.982    20.297    1.00    37.39
ATOM      97    CA    LEU   320    8.567     4.067    21.387    1.00    41.55
ATOM      98    CB    LEU   320    7.239     4.467    22.049    1.00    38.47
ATOM      99    CG    LEU   320    7.236     5.582    23.099    1.00    44.81
ATOM     100    CD1   LEU   320    5.876     5.634    23.803    1.00    44.96
ATOM     101    CD2   LEU   320    8.334     5.332    24.112    1.00    43.36
ATOM     102    C     LEU   320    8.466     2.642    20.843    1.00    41.11
```

UNITED STATES PATENT AND TRADEMARK OFFICE
CERTIFICATE OF CORRECTION

PATENT NO. : 6,965,850 B2  Page 153 of 186
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    103  O    LEU  320   8.971   1.697  21.443  1.00  41.87
ATOM    104  N    ASP  321   7.812   2.504  19.696  1.00  43.94
ATOM    105  CA   ASP  321   7.613   1.210  19.053  1.00  44.77
ATOM    106  CB   ASP  321   6.669   1.372  17.860  1.00  48.39
ATOM    107  CG   ASP  321   5.206   1.318  18.255  1.00  52.39
ATOM    108  OD1  ASP  321   4.901   1.422  19.464  1.00  53.56
ATOM    109  OD2  ASP  321   4.357   1.172  17.346  1.00  55.81
ATOM    110  C    ASP  321   8.911   0.565  18.568  1.00  44.37
ATOM    111  O    ASP  321   9.030  -0.661  18.533  1.00  44.67
ATOM    112  N    ALA  322   9.878   1.395  18.193  1.00  40.75
ATOM    113  CA   ALA  322  11.153   0.905  17.686  1.00  37.81
ATOM    114  CB   ALA  322  11.772   1.954  16.776  1.00  38.07
ATOM    115  C    ALA  322  12.148   0.513  18.769  1.00  35.52
ATOM    116  O    ALA  322  13.219  -0.020  18.473  1.00  36.11
ATOM    117  N    GLU  323  11.799   0.768  20.022  1.00  35.61
ATOM    118  CA   GLU  323  12.704   0.460  21.117  1.00  36.39
ATOM    119  CB   GLU  323  12.042   0.768  22.459  1.00  35.09
ATOM    120  CG   GLU  323  12.209   2.210  22.899  1.00  37.93
ATOM    121  CD   GLU  323  13.657   2.569  23.200  1.00  37.29
ATOM    122  OE1  GLU  323  14.313   3.173  22.326  1.00  34.21
ATOM    123  OE2  GLU  323  14.134   2.245  24.309  1.00  38.02
ATOM    124  C    GLU  323  13.205  -0.978  21.110  1.00  38.01
ATOM    125  O    GLU  323  12.425  -1.931  20.999  1.00  38.37
ATOM    126  N    PRO  324  14.527  -1.151  21.225  1.00  36.03
ATOM    127  CD   PRO  324  15.522  -0.069  21.345  1.00  36.69
ATOM    128  CA   PRO  324  15.158  -2.474  21.240  1.00  36.42
ATOM    129  CB   PRO  324  16.633  -2.166  21.003  1.00  35.75
ATOM    130  CG   PRO  324  16.811  -0.807  21.610  1.00  35.46
ATOM    131  C    PRO  324  14.940  -3.162  22.583  1.00  35.75
ATOM    132  O    PRO  324  14.616  -2.517  23.580  1.00  34.97
ATOM    133  N    PRO  325  15.134  -4.485  22.631  1.00  35.24
ATOM    134  CD   PRO  325  15.530  -5.386  21.534  1.00  37.02
ATOM    135  CA   PRO  325  14.942  -5.208  23.889  1.00  34.65
ATOM    136  CB   PRO  325  14.753  -6.652  23.439  1.00  35.83
ATOM    137  CG   PRO  325  15.589  -6.743  22.200  1.00  34.88
ATOM    138  C    PRO  325  16.132  -5.070  24.824  1.00  34.51
ATOM    139  O    PRO  325  17.237  -4.723  24.399  1.00  29.92
ATOM    140  N    ILE  326  15.899  -5.322  26.106  1.00  33.62
ATOM    141  CA   ILE  326  16.975  -5.265  27.075  1.00  35.02
ATOM    142  CB   ILE  326  16.458  -4.891  28.473  1.00  38.11
ATOM    143  CG2  ILE  326  17.557  -5.110  29.504  1.00  38.70
ATOM    144  CG1  ILE  326  15.987  -3.431  28.466  1.00  40.48
ATOM    145  CD1  ILE  326  16.035  -2.747  29.815  1.00  42.96
ATOM    146  C    ILE  326  17.567  -6.668  27.103  1.00  34.14
ATOM    147  O    ILE  326  16.875  -7.634  27.427  1.00  34.88
ATOM    148  N    LEU  327  18.840  -6.784  26.745  1.00  29.64
ATOM    149  CA   LEU  327  19.493  -8.083  26.716  1.00  29.54
ATOM    150  CB   LEU  327  20.528  -8.135  25.587  1.00  27.76
ATOM    151  CG   LEU  327  19.978  -7.800  24.196  1.00  29.02
ATOM    152  CD1  LEU  327  21.068  -7.993  23.139  1.00  28.76
ATOM    153  CD2  LEU  327  18.775  -8.688  23.891  1.00  31.26
ATOM    154  C    LEU  327  20.156  -8.438  28.030  1.00  31.21
ATOM    155  O    LEU  327  20.393  -7.578  28.891  1.00  30.12
ATOM    156  N    TYR  328  20.445  -9.725  28.181  1.00  30.99
ATOM    157  CA   TYR  328  21.087 -10.229  29.381  1.00  30.95
ATOM    158  CB   TYR  328  20.409 -11.520  29.842  1.00  33.38
ATOM    159  CG   TYR  328  19.194 -11.272  30.686  1.00  33.05
ATOM    160  CD1  TYR  328  19.253 -11.398  32.071  1.00  31.92
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    161   CE1   TYR   328   18.152   -11.114   32.864   1.00   36.01
ATOM    162   CD2   TYR   328   17.996   -10.862   30.110   1.00   36.05
ATOM    163   CE2   TYR   328   16.880   -10.874   30.899   1.00   37.27
ATOM    164   CZ    TYR   328   16.973   -10.702   32.274   1.00   37.66
ATOM    165   OH    TYR   328   15.896   -10.397   33.071   1.00   44.65
ATOM    166   C     TYR   328   22.529   -10.520   29.067   1.00   33.66
ATOM    167   O     TYR   328   22.884   -10.744   27.910   1.00   34.78
ATOM    168   N     SER   329   23.359   -10.496   30.103   1.00   33.97
ATOM    169   CA    SER   329   24.767   -10.800   29.962   1.00   37.29
ATOM    170   CB    SER   329   25.526   -10.342   31.204   1.00   36.51
ATOM    171   OG    SER   329   26.787   -10.965   31.282   1.00   37.13
ATOM    172   C     SER   329   24.835   -12.317   29.832   1.00   40.43
ATOM    173   O     SER   329   23.980   -13.028   30.363   1.00   40.11
ATOM    174   N     GLU   330   25.845   -12.811   29.128   1.00   41.40
ATOM    175   CA    GLU   330   25.992   -14.242   28.928   1.00   47.43
ATOM    176   CB    GLU   330   26.423   -14.524   27.484   1.00   48.64
ATOM    177   CG    GLU   330   25.278   -14.870   26.542   1.00   50.20
ATOM    178   CD    GLU   330   25.765   -15.405   25.198   1.00   53.25
ATOM    179   OE1   GLU   330   25.909   -16.640   25.062   1.00   53.27
ATOM    180   OE2   GLU   330   26.004   -14.590   24.280   1.00   51.80
ATOM    181   C     GLU   330   26.999   -14.852   29.893   1.00   49.67
ATOM    182   O     GLU   330   28.207   -14.741   29.696   1.00   50.11
ATOM    183   N     TYR   331   26.498   -15.493   30.942   1.00   53.62
ATOM    184   CA    TYR   331   27.373   -16.130   31.921   1.00   58.16
ATOM    185   CB    TYR   331   28.092   -15.078   32.774   1.00   59.55
ATOM    186   CG    TYR   331   27.239   -14.460   33.860   1.00   63.08
ATOM    187   CD1   TYR   331   26.656   -13.205   33.682   1.00   64.50
ATOM    188   CE1   TYR   331   25.864   -12.630   34.676   1.00   65.99
ATOM    189   CD2   TYR   331   27.010   -15.128   35.065   1.00   63.52
ATOM    190   CE2   TYR   331   26.219   -14.563   36.066   1.00   65.60
ATOM    191   CZ    TYR   331   25.648   -13.314   35.864   1.00   67.20
ATOM    192   OH    TYR   331   24.855   -12.753   36.839   1.00   67.40
ATOM    193   C     TYR   331   26.603   -17.080   32.823   1.00   59.05
ATOM    194   O     TYR   331   25.393   -16.942   33.002   1.00   59.22
ATOM    195   N     ASP   332   27.320   -18.045   33.387   1.00   61.62
ATOM    196   CA    ASP   332   26.719   -19.026   34.281   1.00   64.20
ATOM    197   CB    ASP   332   27.681   -20.194   34.500   1.00   65.99
ATOM    198   CG    ASP   332   26.961   -21.516   34.648   1.00   68.11
ATOM    199   OD1   ASP   332   27.575   -22.564   34.351   1.00   69.54
ATOM    200   OD2   ASP   332   25.781   -21.505   35.060   1.00   67.40
ATOM    201   C     ASP   332   26.393   -18.371   35.619   1.00   63.33
ATOM    202   O     ASP   332   27.292   -18.073   36.406   1.00   63.90
ATOM    203   N     PRO   333   25.096   -18.148   35.896   1.00   63.64
ATOM    204   CD    PRO   333   23.945   -18.509   35.053   1.00   64.35
ATOM    205   CA    PRO   333   24.677   -17.521   37.154   1.00   63.52
ATOM    206   CB    PRO   333   23.165   -17.333   36.993   1.00   63.53
ATOM    207   CG    PRO   333   22.866   -17.611   35.556   1.00   64.15
ATOM    208   C     PRO   333   25.010   -18.419   38.332   1.00   63.29
ATOM    209   O     PRO   333   25.129   -17.964   39.468   1.00   63.28
ATOM    210   N     THR   334   25.160   -19.704   38.037   1.00   64.26
ATOM    211   CA    THR   334   25.475   -20.697   39.050   1.00   66.09
ATOM    212   CB    THR   334   24.929   -22.080   38.645   1.00   66.90
ATOM    213   OG1   THR   334   25.571   -22.513   37.439   1.00   68.06
ATOM    214   CG2   THR   334   23.423   -22.012   38.411   1.00   67.57
ATOM    215   C     THR   334   26.982   -20.804   39.269   1.00   65.67
ATOM    216   O     THR   334   27.432   -21.323   40.289   1.00   64.77
ATOM    217   N     ARG   335   27.759   -20.308   38.313   1.00   65.65
ATOM    218   CA    ARG   335   29.214   -20.360   38.421   1.00   66.60
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    219   CB    ARG   335   29.835   -20.500   37.030   1.00   66.74
ATOM    220   C     ARG   335   39.757   -19.113   39.123   1.00   67.09
ATOM    221   O     ARG   335   29.100   -18.071   39.148   1.00   67.31
ATOM    222   N     PRO   336   30.968   -19.207   39.702   1.00   67.62
ATOM    223   CD    PRO   336   31.820   -20.408   39.713   1.00   67.30
ATOM    224   CA    PRO   336   31.601   -18.086   40.410   1.00   67.42
ATOM    225   CB    PRO   336   32.982   -18.621   40.783   1.00   66.43
ATOM    226   CG    PRO   336   32.829   -20.097   40.779   1.00   67.52
ATOM    227   C     PRO   336   31.701   -16.828   39.561   1.00   68.26
ATOM    228   O     PRO   336   31.996   -16.895   38.371   1.00   69.04
ATOM    229   N     PHE   337   31.460   -15.681   40.183   1.00   69.49
ATOM    230   CA    PHE   337   31.529   -14.408   39.480   1.00   71.39
ATOM    231   CB    PHE   337   30.818   -13.323   40.294   1.00   72.31
ATOM    232   CG    PHE   337   31.219   -11.924   39.921   1.00   73.21
ATOM    233   CD1   PHE   337   30.632   -11.287   38.833   1.00   72.82
ATOM    234   CD2   PHE   337   32.191   -11.245   40.653   1.00   73.43
ATOM    235   CE1   PHE   337   31.006    -9.993   38.479   1.00   73.28
ATOM    236   CE2   PHE   337   32.573    -9.950   40.306   1.00   73.00
ATOM    237   CZ    PHE   337   31.980    -9.323   39.217   1.00   72.90
ATOM    238   C     PHE   337   32.985   -14.013   39.245   1.00   71.38
ATOM    239   O     PHE   337   33.336   -13.487   38.189   1.00   71.56
ATOM    240   N     SER   338   33.825   -14.273   40.241   1.00   71.53
ATOM    241   CA    SER   338   35.248   -13.947   40.172   1.00   70.98
ATOM    242   CB    SER   338   35.957   -14.487   41.414   1.00   70.43
ATOM    243   OG    SER   338   35.547   -15.818   41.679   1.00   69.59
ATOM    244   C     SER   338   35.931   -14.504   38.924   1.00   71.20
ATOM    245   O     SER   338   36.951   -13.972   38.475   1.00   71.35
ATOM    246   N     GLU   339   35.368   -15.573   38.369   1.00   70.20
ATOM    247   CA    GLU   339   35.930   -16.215   37.183   1.00   69.48
ATOM    248   CB    GLU   339   35.279   -17.585   36.971   1.00   71.07
ATOM    249   CG    GLU   339   35.996   -18.740   37.656   1.00   72.60
ATOM    250   CD    GLU   339   35.382   -20.089   37.318   1.00   74.26
ATOM    251   OE1   GLU   339   34.786   -20.220   36.227   1.00   73.51
ATOM    252   OE2   GLU   339   35.496   -21.020   38.144   1.00   76.44
ATOM    253   C     GLU   339   35.770   -15.385   35.910   1.00   68.15
ATOM    254   O     GLU   339   36.722   -15.216   35.144   1.00   68.99
ATOM    255   N     ALA   340   34.562   -14.874   35.694   1.00   64.41
ATOM    256   CA    ALA   340   34.246   -14.083   34.507   1.00   60.69
ATOM    257   CB    ALA   340   32.767   -13.709   34.523   1.00   61.17
ATOM    258   C     ALA   340   35.096   -12.824   34.326   1.00   57.00
ATOM    259   O     ALA   340   35.634   -12.270   35.287   1.00   57.46
ATOM    260   N     SER   341   35.215   -12.388   33.076   1.00   52.15
ATOM    261   CA    SER   341   35.972   -11.188   32.736   1.00   46.83
ATOM    262   CB    SER   341   36.839   -11.439   31.497   1.00   48.64
ATOM    263   OG    SER   341   37.184   -10.226   30.846   1.00   46.48
ATOM    264   C     SER   341   34.957   -10.087   32.444   1.00   43.52
ATOM    265   O     SER   341   34.090   -10.248   31.589   1.00   39.92
ATOM    266   N     MET   342   35.052    -8.978   33.166   1.00   41.24
ATOM    267   CA    MET   342   34.121    -7.875   32.960   1.00   42.46
ATOM    268   CB    MET   342   34.449    -6.723   33.912   1.00   45.61
ATOM    269   CG    MET   342   33.228    -6.089   34.560   1.00   52.39
ATOM    270   SD    MET   342   31.791    -7.201   34.631   1.00   57.92
ATOM    271   CE    MET   342   31.999    -7.881   36.239   1.00   56.18
ATOM    272   C     MET   342   34.124    -7.365   31.516   1.00   40.22
ATOM    273   O     MET   342   33.063    -7.121   30.938   1.00   39.23
ATOM    274   N     MET   343   35.307    -7.204   30.930   1.00   38.72
ATOM    275   CA    MET   343   35.395    -6.708   29.558   1.00   38.50
ATOM    276   CB    MET   343   36.838    -6.318   29.216   1.00   41.15
```

UNITED STATES PATENT AND TRADEMARK OFFICE
CERTIFICATE OF CORRECTION

PATENT NO. : 6,965,850 B2  Page 156 of 186
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    277  CG   MET  343   37.022   -5.749   27.804   1.00   40.31
ATOM    278  SD   MET  343   36.032   -4.860   27.427   1.00   45.23
ATOM    279  CE   MET  343   36.113   -3.358   28.987   1.00   40.45
ATOM    280  C    MET  343   34.880   -7.741   28.561   1.00   35.36
ATOM    281  O    MET  343   34.368   -7.384   27.501   1.00   35.51
ATOM    282  N    GLY  344   35.017   -9.020   28.902   1.00   35.53
ATOM    283  CA   GLY  344   34.533  -10.072   28.024   1.00   33.41
ATOM    284  C    GLY  344   33.015  -10.063   28.047   1.00   31.74
ATOM    285  O    GLY  344   32.359  -10.233   27.019   1.00   29.58
ATOM    286  N    LEU  345   32.459   -9.860   29.238   1.00   32.89
ATOM    287  CA   LEU  345   31.011   -9.804   29.415   1.00   34.95
ATOM    288  CB   LEU  345   30.665   -9.631   30.902   1.00   37.56
ATOM    289  CG   LEU  345   30.942  -10.774   31.883   1.00   43.03
ATOM    290  CD1  LEU  345   30.537  -10.357   33.297   1.00   41.57
ATOM    291  CD2  LEU  345   30.164  -11.998   31.449   1.00   42.80
ATOM    292  C    LEU  345   30.430   -8.614   28.633   1.00   33.71
ATOM    293  O    LEU  345   29.479   -8.757   27.868   1.00   30.29
ATOM    294  N    LEU  346   31.021   -7.443   28.843   1.00   30.20
ATOM    295  CA   LEU  346   30.569   -6.217   28.193   1.00   32.00
ATOM    296  CB   LEU  346   31.317   -5.016   28.771   1.00   28.16
ATOM    297  CG   LEU  346   31.091   -4.767   30.269   1.00   29.84
ATOM    298  CD1  LEU  346   31.815   -3.498   30.668   1.00   29.98
ATOM    299  CD2  LEU  346   29.614   -4.644   30.581   1.00   33.97
ATOM    300  C    LEU  346   30.732   -6.250   26.682   1.00   30.70
ATOM    301  O    LEU  346   29.869   -5.765   25.955   1.00   29.13
ATOM    302  N    THR  347   31.839   -6.816   26.212   1.00   30.47
ATOM    303  CA   THR  347   32.086   -6.911   24.781   1.00   30.93
ATOM    304  CB   THR  347   33.472   -7.501   24.497   1.00   29.97
ATOM    305  OG1  THR  347   34.481   -6.604   24.982   1.00   35.40
ATOM    306  CG2  THR  347   33.666   -7.707   23.004   1.00   33.58
ATOM    307  C    THR  347   31.036   -7.804   24.122   1.00   31.97
ATOM    308  O    THR  347   30.516   -7.486   23.049   1.00   30.75
ATOM    309  N    ASN  348   30.737   -8.926   24.768   1.00   29.31
ATOM    310  CA   ASN  348   29.757   -9.868   24.242   1.00   32.63
ATOM    311  CB   ASN  348   29.767  -11.161   25.065   1.00   31.64
ATOM    312  CG   ASN  348   28.646  -12.117   24.662   1.00   39.14
ATOM    313  OD1  ASN  348   27.549  -12.078   25.220   1.00   41.91
ATOM    314  ND2  ASN  348   28.920  -12.970   23.683   1.00   42.05
ATOM    315  C    ASN  348   28.361   -9.251   24.262   1.00   29.02
ATOM    316  O    ASN  348   27.558   -9.477   23.353   1.00   32.76
ATOM    317  N    LEU  349   28.078   -8.467   25.298   1.00   28.74
ATOM    318  CA   LEU  349   26.782   -7.811   25.421   1.00   28.58
ATOM    319  CB   LEU  349   26.650   -7.148   26.795   1.00   26.96
ATOM    320  CG   LEU  349   25.376   -6.328   27.050   1.00   33.67
ATOM    321  CD1  LEU  349   24.140   -7.199   26.840   1.00   28.82
ATOM    322  CD2  LEU  349   25.392   -5.779   28.471   1.00   33.13
ATOM    323  C    LEU  349   26.638   -6.762   24.319   1.00   28.07
ATOM    324  O    LEU  349   25.616   -6.703   23.629   1.00   25.22
ATOM    325  N    ALA  350   27.675   -5.941   24.157   1.00   28.50
ATOM    326  CA   ALA  350   27.668   -4.886   23.148   1.00   28.46
ATOM    327  CB   ALA  350   28.972   -4.094   23.209   1.00   28.12
ATOM    328  C    ALA  350   27.468   -5.461   21.750   1.00   28.75
ATOM    329  O    ALA  350   26.649   -4.958   20.983   1.00   30.90
ATOM    330  N    ASP  351   28.213   -6.509   21.420   1.00   27.20
ATOM    331  CA   ASP  351   28.093   -7.143   20.112   1.00   29.75
ATOM    332  CB   ASP  351   29.036   -8.345   20.010   1.00   34.16
ATOM    333  CG   ASP  351   30.498   -7.940   19.978   1.00   37.50
ATOM    334  OD1  ASP  351   31.354   -8.831   20.148   1.00   37.55
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    335   OD2   ASP   351   30.789    -6.738   19.784   1.00   35.50
ATOM    336   C     ASP   351   26.661    -7.600   19.813   1.00   30.52
ATOM    337   O     ASP   351   26.193    -7.458   18.687   1.00   27.77
ATOM    338   N     ARG   352   25.968    -8.150   20.811   1.00   27.18
ATOM    339   CA    ARG   352   24.593    -8.602   20.605   1.00   26.21
ATOM    340   CB    ARG   352   24.148    -9.534   21.752   1.00   26.52
ATOM    341   CG    ARG   352   24.567   -10.991   21.532   1.00   31.03
ATOM    342   CD    ARG   352   24.128   -11.911   22.666   1.00   29.80
ATOM    343   NE    ARG   352   24.898   -11.675   23.879   1.00   30.44
ATOM    344   CZ    ARG   352   24.364   -11.363   25.054   1.00   31.68
ATOM    345   NH1   ARG   352   23.050   -11.251   25.177   1.00   31.18
ATOM    346   NH2   ARG   352   25.144   -11.148   26.104   1.00   32.03
ATOM    347   C     ARG   352   23.642    -7.411   20.502   1.00   27.16
ATOM    348   O     ARG   352   22.702    -7.436   19.708   1.00   26.65
ATOM    349   N     GLU   353   23.896    -6.370   21.291   1.00   24.30
ATOM    350   CA    GLU   353   23.045    -5.178   21.261   1.00   26.39
ATOM    351   CB    GLU   353   23.461    -4.204   22.365   1.00   24.91
ATOM    352   CG    GLU   353   23.147    -4.669   23.771   1.00   27.93
ATOM    353   CD    GLU   353   23.425    -3.587   24.795   1.00   30.71
ATOM    354   OE1   GLU   353   24.564    -3.534   25.304   1.00   30.09
ATOM    355   OE2   GLU   353   22.506    -2.789   25.085   1.00   30.53
ATOM    356   C     GLU   353   23.131    -4.456   19.920   1.00   24.27
ATOM    357   O     GLU   353   22.169    -3.826   19.467   1.00   28.71
ATOM    358   N     LEU   354   24.296    -4.540   19.293   1.00   26.61
ATOM    359   CA    LEU   354   24.522    -3.872   18.017   1.00   26.62
ATOM    360   CB    LEU   354   25.952    -4.121   17.543   1.00   26.36
ATOM    361   CG    LEU   354   26.372    -3.287   16.351   1.00   29.24
ATOM    362   CD1   LEU   354   26.243    -1.774   16.722   1.00   26.59
ATOM    363   CD2   LEU   354   27.794    -3.607   15.962   1.00   28.88
ATOM    364   C     LEU   354   23.559    -4.300   16.926   1.00   27.72
ATOM    365   O     LEU   354   23.074    -3.475   16.152   1.00   24.00
ATOM    366   N     VAL   355   23.291    -5.598   16.854   1.00   28.82
ATOM    367   CA    VAL   355   22.386    -6.125   15.844   1.00   29.45
ATOM    368   CB    VAL   355   22.259    -7.655   15.975   1.00   31.76
ATOM    369   CG1   VAL   355   21.423    -8.205   14.834   1.00   33.55
ATOM    370   CG2   VAL   355   23.649    -8.282   15.998   1.00   31.36
ATOM    371   C     VAL   355   21.020    -5.499   16.035   1.00   27.71
ATOM    372   O     VAL   355   20.382    -5.039   15.080   1.00   29.61
ATOM    373   N     HIS   356   20.580    -5.473   17.288   1.00   27.76
ATOM    374   CA    HIS   356   19.291    -4.906   17.627   1.00   28.35
ATOM    375   CB    HIS   356   18.936    -5.231   19.079   1.00   31.12
ATOM    376   CG    HIS   356   18.602    -6.675   19.307   1.00   35.93
ATOM    377   CD2   HIS   356   19.352    -7.700   19.773   1.00   33.95
ATOM    378   ND1   HIS   356   17.363    -7.208   19.018   1.00   36.62
ATOM    379   CE1   HIS   356   17.364    -8.499   19.304   1.00   33.33
ATOM    380   NE2   HIS   356   18.559    -8.823   19.767   1.00   32.16
ATOM    381   C     HIS   356   19.300    -3.398   17.412   1.00   28.25
ATOM    382   O     HIS   356   18.272    -2.812   17.100   1.00   28.99
ATOM    383   N     MET   357   20.457    -2.765   17.574   1.00   25.31
ATOM    384   CA    MET   357   20.526    -1.322   17.369   1.00   24.83
ATOM    385   CB    MET   357   21.902    -0.789   17.766   1.00   23.61
ATOM    386   CG    MET   357   22.011     0.736   17.699   1.00   24.66
ATOM    387   SD    MET   357   23.732     1.290   17.859   1.00   27.30
ATOM    388   CE    MET   357   24.140     0.672   19.514   1.00   23.62
ATOM    389   C     MET   357   20.256    -1.011   15.898   1.00   24.83
ATOM    390   O     MET   357   19.619    -0.003   15.569   1.00   26.78
ATOM    391   N     ILE   358   20.757    -1.874   15.020   1.00   26.25
ATOM    392   CA    ILE   358   20.553    -1.721   13.576   1.00   30.33
```

UNITED STATES PATENT AND TRADEMARK OFFICE
CERTIFICATE OF CORRECTION

PATENT NO. : 6,965,850 B2 Page 158 of 186
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    393  CB   ILE  358   21.204  -2.888  12.789  1.00  33.86
ATOM    394  CG2  ILE  358   20.759  -2.860  11.334  1.00  33.68
ATOM    395  CG1  ILE  358   22.728  -2.799  12.874  1.00  36.89
ATOM    396  CD1  ILE  358   23.299  -1.469  12.451  1.00  39.10
ATOM    397  C    ILE  358   19.055  -1.721  13.310  1.00  32.20
ATOM    398  O    ILE  358   18.519  -0.817  12.662  1.00  32.02
ATOM    399  N    ASN  359   18.379  -2.748  13.814  1.00  33.12
ATOM    400  CA   ASN  359   16.945  -2.861  13.638  1.00  33.35
ATOM    401  CB   ASN  359   16.434  -4.101  14.363  1.00  37.59
ATOM    402  CG   ASN  359   16.739  -5.374  13.627  1.00  44.38
ATOM    403  OD1  ASN  359   17.045  -5.329  12.437  1.00  47.35
ATOM    404  ND2  ASN  359   16.673  -6.508  14.320  1.00  42.48
ATOM    405  C    ASN  359   16.224  -1.634  14.149  1.00  32.74
ATOM    406  O    ASN  359   15.261  -1.163  13.530  1.00  31.39
ATOM    407  N    TRP  360   16.706  -1.104  15.264  1.00  27.92
ATOM    408  CA   TRP  360   16.102   0.087  15.842  1.00  29.47
ATOM    409  CB   TRP  360   16.703   0.347  17.228  1.00  27.66
ATOM    410  CG   TRP  360   16.522   1.747  17.707  1.00  30.40
ATOM    411  CD2  TRP  360   17.493   2.801  17.657  1.00  27.54
ATOM    412  CE2  TRP  360   16.888   3.954  18.204  1.00  29.42
ATOM    413  CE3  TRP  360   18.819   2.883  17.205  1.00  28.37
ATOM    414  CD1  TRP  360   15.399   2.284  18.264  1.00  27.75
ATOM    415  NE1  TRP  360   15.609   3.611  18.566  1.00  30.84
ATOM    416  CZ2  TRP  360   17.558   5.180  18.310  1.00  27.74
ATOM    417  CZ3  TRP  360   19.488   4.106  17.309  1.00  24.49
ATOM    418  CH2  TRP  360   18.853   5.232  17.858  1.00  25.09
ATOM    419  C    TRP  360   16.312   1.296  14.926  1.00  27.90
ATOM    420  O    TRP  360   15.360   2.002  14.581  1.00  28.83
ATOM    421  N    ALA  361   17.559   1.520  14.523  1.00  28.25
ATOM    422  CA   ALA  361   17.894   2.637  13.645  1.00  29.20
ATOM    423  CB   ALA  361   19.346   2.539  13.220  1.00  28.89
ATOM    424  C    ALA  361   17.006   2.685  12.403  1.00  31.08
ATOM    425  O    ALA  361   16.531   3.746  12.011  1.00  31.30
ATOM    426  N    LYS  362   16.795   1.526  11.783  1.00  30.93
ATOM    427  CA   LYS  362   15.981   1.443  10.581  1.00  34.15
ATOM    428  CB   LYS  362   16.012   0.016  10.023  1.00  33.67
ATOM    429  CG   LYS  362   17.252  -0.281   9.198  1.00  39.40
ATOM    430  CD   LYS  362   17.547  -1.774   9.136  1.00  43.60
ATOM    431  CE   LYS  362   18.852  -2.046   8.389  1.00  47.06
ATOM    432  NZ   LYS  362   19.178  -3.507   8.288  1.00  50.34
ATOM    433  C    LYS  362   14.545   1.872  10.815  1.00  35.81
ATOM    434  O    LYS  362   13.821   2.168   9.859  1.00  37.95
ATOM    435  N    ARG  363   14.134   1.921  12.079  1.00  34.23
ATOM    436  CA   ARG  363   12.770   2.313  12.409  1.00  36.04
ATOM    437  CB   ARG  363   12.178   1.307  13.391  1.00  36.71
ATOM    438  CG   ARG  363   12.169  -0.110  12.827  1.00  40.36
ATOM    439  CD   ARG  363   11.468  -1.086  13.746  1.00  42.17
ATOM    440  NE   ARG  363   10.161  -0.586  14.158  1.00  45.19
ATOM    441  CZ   ARG  363    9.314  -1.262  14.929  1.00  49.41
ATOM    442  NH1  ARG  363    9.642  -2.467  15.374  1.00  48.02
ATOM    443  NH2  ARG  363    8.143  -0.729  15.261  1.00  51.54
ATOM    444  C    ARG  363   12.654   3.743  12.943  1.00  37.40
ATOM    445  O    ARG  363   11.567   4.199  13.303  1.00  38.22
ATOM    446  N    VAL  364   13.785   4.442  13.002  1.00  35.66
ATOM    447  CA   VAL  364   13.804   5.836  13.431  1.00  34.06
ATOM    448  CB   VAL  364   15.231   6.271  13.827  1.00  33.87
ATOM    449  CG1  VAL  364   15.293   7.779  13.995  1.00  31.08
ATOM    450  CG2  VAL  364   15.641   5.571  15.113  1.00  31.30
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    451  C    VAL  364  13.360  6.591  12.171  1.00  33.19
ATOM    452  O    VAL  364  14.028  6.531  11.146  1.00  33.04
ATOM    453  N    PRO  365  12.225  7.310  12.234  1.00  34.69
ATOM    454  CD   PRO  365  11.359  7.492  13.413  1.00  34.19
ATOM    455  CA   PRO  365  11.724  8.050  11.069  1.00  35.96
ATOM    456  CB   PRO  365  10.608  8.918  11.645  1.00  36.59
ATOM    457  CG   PRO  365  10.135  8.157  12.842  1.00  39.59
ATOM    458  C    PRO  365  12.756  8.878  10.321  1.00  37.19
ATOM    459  O    PRO  365  13.430  9.726  10.907  1.00  40.29
ATOM    460  N    GLY  366  12.878  8.624   9.023  1.00  34.78
ATOM    461  CA   GLY  366  13.816  9.371   8.212  1.00  33.84
ATOM    462  C    GLY  366  15.168  8.722   8.007  1.00  34.26
ATOM    463  O    GLY  366  15.858  9.035   7.034  1.00  37.15
ATOM    464  N    PHE  367  15.554  7.814   8.901  1.00  33.13
ATOM    465  CA   PHE  367  16.860  7.164   8.787  1.00  32.04
ATOM    466  CB   PHE  367  17.138  6.291  10.016  1.00  30.22
ATOM    467  CG   PHE  367  18.544  5.773  10.080  1.00  30.60
ATOM    468  CD1  PHE  367  18.827  4.446   9.751  1.00  31.94
ATOM    469  CD2  PHE  367  19.589  6.601  10.485  1.00  29.20
ATOM    470  CE1  PHE  367  20.133  3.950   9.838  1.00  28.30
ATOM    471  CE2  PHE  367  20.896  6.122  10.568  1.00  28.12
ATOM    472  CZ   PHE  367  21.171  4.791  10.240  1.00  25.41
ATOM    473  C    PHE  367  17.033  6.333   7.524  1.00  31.46
ATOM    474  O    PHE  367  18.073  6.405   6.883  1.00  32.30
ATOM    475  N    VAL  368  16.027  5.541   7.165  1.00  35.20
ATOM    476  CA   VAL  368  16.123  4.718   5.959  1.00  38.98
ATOM    477  CB   VAL  368  15.076  3.584   5.945  1.00  40.61
ATOM    478  CG1  VAL  368  15.543  2.447   6.843  1.00  41.48
ATOM    479  CG2  VAL  368  13.717  4.113   6.390  1.00  41.60
ATOM    480  C    VAL  368  15.965  5.523   4.673  1.00  40.06
ATOM    481  O    VAL  368  16.156  4.992   3.579  1.00  41.66
ATOM    482  N    ASP  369  15.608  6.798   4.798  1.00  38.65
ATOM    483  CA   ASP  369  15.465  7.646   3.621  1.00  37.15
ATOM    484  CB   ASP  369  14.700  8.929   3.954  1.00  39.89
ATOM    485  CG   ASP  369  13.254  8.671   4.302  1.00  45.59
ATOM    486  OD1  ASP  369  12.686  7.672   3.806  1.00  46.34
ATOM    487  OD2  ASP  369  12.681  9.472   5.074  1.00  49.13
ATOM    488  C    ASP  369  16.855  8.010   3.136  1.00  34.91
ATOM    489  O    ASP  369  17.038  8.431   1.995  1.00  34.25
ATOM    490  N    LEU  370  17.838  7.841   4.016  1.00  31.76
ATOM    491  CA   LEU  370  19.229  8.153   3.705  1.00  28.08
ATOM    492  CB   LEU  370  20.020  8.339   5.003  1.00  28.81
ATOM    493  CG   LEU  370  19.523  9.395   6.000  1.00  28.74
ATOM    494  CD1  LEU  370  20.315  9.275   7.299  1.00  30.81
ATOM    495  CD2  LEU  370  19.693 10.792   5.404  1.00  29.77
ATOM    496  C    LEU  370  19.884  7.043   2.893  1.00  31.25
ATOM    497  O    LEU  370  19.341  5.943   2.784  1.00  31.78
ATOM    498  N    THR  371  21.052  7.333   2.331  1.00  28.86
ATOM    499  CA   THR  371  21.793  6.336   1.569  1.00  32.90
ATOM    500  CB   THR  371  22.979  6.944   0.818  1.00  33.44
ATOM    501  OG1  THR  371  23.880  7.523   1.766  1.00  34.59
ATOM    502  CG2  THR  371  22.514  8.002  -0.178  1.00  32.63
ATOM    503  C    THR  371  22.373  5.315   2.539  1.00  35.31
ATOM    504  O    THR  371  23.536  5.591   3.733  1.00  31.27
ATOM    505  N    LEU  372  22.702  4.141   2.015  1.00  34.34
ATOM    506  CA   LEU  372  23.273  3.073   2.822  1.00  35.46
ATOM    507  CB   LEU  372  23.518  1.841   1.944  1.00  37.73
ATOM    508  CG   LEU  372  24.362  0.704   2.515  1.00  42.43
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    509  CD1  LEU  372   23.690   0.145   3.757  1.00  45.60
ATOM    510  CD2  LEU  372   24.534  -0.383   1.455  1.00  44.29
ATOM    511  C    LEU  372   24.587   3.548   3.444  1.00  36.95
ATOM    512  O    LEU  372   24.813   3.374   4.643  1.00  35.57
ATOM    513  N    HIS  373   25.442   4.159   2.627  1.00  35.68
ATOM    514  CA   HIS  373   26.729   4.656   3.099  1.00  36.60
ATOM    515  CB   HIS  373   27.506   5.282   1.935  1.00  44.01
ATOM    516  CG   HIS  373   28.538   6.280   2.360  1.00  50.69
ATOM    517  CD2  HIS  373   29.857   6.138   2.636  1.00  54.69
ATOM    518  ND1  HIS  373   28.246   7.613   2.561  1.00  53.77
ATOM    519  CE1  HIS  373   29.339   8.248   2.945  1.00  57.09
ATOM    520  NE2  HIS  373   30.331   7.376   2.999  1.00  57.23
ATOM    521  C    HIS  373   26.579   5.669   4.244  1.00  36.22
ATOM    522  O    HIS  373   27.350   5.650   5.201  1.00  33.05
ATOM    523  N    ASP  374   25.580   6.549   4.148  1.00  32.03
ATOM    524  CA   ASP  374   25.342   7.541   5.196  1.00  30.76
ATOM    525  CB   ASP  374   24.354   8.603   4.713  1.00  30.12
ATOM    526  CG   ASP  374   25.018   9.672   3.860  1.00  38.83
ATOM    527  OD1  ASP  374   26.264   9.744   3.842  1.00  34.39
ATOM    528  OD2  ASP  374   24.291  10.440   3.199  1.00  35.39
ATOM    529  C    ASP  374   24.805   6.876   6.472  1.00  30.33
ATOM    530  O    ASP  374   25.152   7.275   7.587  1.00  27.04
ATOM    531  N    GLN  375   23.944   5.877   6.309  1.00  25.71
ATOM    532  CA   GLN  375   23.403   5.157   7.454  1.00  26.58
ATOM    533  CB   GLN  375   22.424   4.077   6.993  1.00  29.70
ATOM    534  CG   GLN  375   21.101   4.616   6.484  1.00  29.16
ATOM    535  CD   GLN  375   20.219   3.514   5.940  1.00  35.87
ATOM    536  OE1  GLN  375   20.155   2.426   6.510  1.00  30.97
ATOM    537  NE2  GLN  375   19.541   3.785   4.827  1.00  34.51
ATOM    538  C    GLN  375   24.556   4.502   8.214  1.00  25.51
ATOM    539  O    GLN  375   24.585   4.513   9.442  1.00  28.14
ATOM    540  N    VAL  376   25.504   3.938   7.475  1.00  26.62
ATOM    541  CA   VAL  376   26.659   3.281   8.071  1.00  29.24
ATOM    542  CB   VAL  376   27.531   2.597   7.003  1.00  29.66
ATOM    543  CG1  VAL  376   28.812   2.071   7.635  1.00  28.29
ATOM    544  CG2  VAL  376   26.745   1.469   6.341  1.00  29.90
ATOM    545  C    VAL  376   27.526   4.285   8.821  1.00  30.87
ATOM    546  O    VAL  376   27.953   4.029   9.948  1.00  30.09
ATOM    547  N    HIS  377   27.785   5.428   8.191  1.00  28.05
ATOM    548  CA   HIS  377   28.602   6.457   8.814  1.00  28.68
ATOM    549  CB   HIS  377   28.792   7.639   7.864  1.00  30.26
ATOM    550  CG   HIS  377   29.508   8.791   8.488  1.00  33.89
ATOM    551  CD2  HIS  377   29.073  10.017   8.863  1.00  34.99
ATOM    552  ND1  HIS  377   30.846   8.740   8.823  1.00  37.01
ATOM    553  CE1  HIS  377   31.201   9.884   9.377  1.00  34.79
ATOM    554  NE2  HIS  377   30.144  10.677   9.413  1.00  34.95
ATOM    555  C    HIS  377   27.983   6.954  10.114  1.00  25.13
ATOM    556  O    HIS  377   28.677   7.102  11.115  1.00  25.93
ATOM    557  N    LEU  378   26.678   7.206  10.107  1.00  24.58
ATOM    558  CA   LEU  378   26.015   7.695  11.315  1.00  26.40
ATOM    559  CB   LEU  378   24.542   8.001  11.027  1.00  26.29
ATOM    560  CG   LEU  378   24.291   9.180  10.073  1.00  28.06
ATOM    561  CD1  LEU  378   22.778   9.353   9.869  1.00  27.66
ATOM    562  CD2  LEU  378   24.911  10.458  10.642  1.00  30.08
ATOM    563  C    LEU  378   26.120   6.695  12.459  1.00  28.55
ATOM    564  O    LEU  378   26.379   7.075  13.605  1.00  24.76
ATOM    565  N    LEU  379   25.919   5.414  12.153  1.00  24.29
ATOM    566  CA   LEU  379   26.000   4.388  13.182  1.00  27.03
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    567   CB    LEU   379   25.401   3.073   13.667   1.00   28.53
ATOM    568   CG    LEU   379   23.875   3.023   12.845   1.00   30.29
ATOM    569   CD1   LEU   379   23.248   1.943   11.963   1.00   33.04
ATOM    570   CD2   LEU   379   23.563   2.759   14.313   1.00   29.45
ATOM    571   C     LEU   379   27.430   4.176   13.670   1.00   27.18
ATOM    572   O     LEU   379   27.653   3.979   14.866   1.00   25.95
ATOM    573   N     GLU   380   28.402   4.236   12.762   1.00   25.86
ATOM    574   CA    GLU   380   29.786   4.054   13.173   1.00   27.58
ATOM    575   CB    GLU   380   30.730   4.036   11.968   1.00   30.36
ATOM    576   CG    GLU   380   32.172   3.785   12.380   1.00   37.98
ATOM    577   CD    GLU   380   33.080   3.471   11.210   1.00   45.23
ATOM    578   OE1   GLU   380   32.869   4.048   10.120   1.00   42.99
ATOM    579   OE2   GLU   380   34.004   2.646   11.386   1.00   45.79
ATOM    580   C     GLU   380   30.218   5.159   14.133   1.00   27.50
ATOM    581   O     GLU   380   31.056   4.937   15.010   1.00   26.67
ATOM    582   N     ACYS  381   29.637   6.339   13.965   0.75   24.89
ATOM    583   N     BCYS  381   29.645   6.352   13.980   0.25   25.79
ATOM    584   CA    ACYS  381   29.969   7.466   14.826   0.75   24.12
ATOM    585   CA    BCYS  381   29.993   7.481   14.847   0.25   24.86
ATOM    586   CB    ACYS  381   29.621   8.781   14.122   0.75   25.96
ATOM    587   CB    BCYS  381   29.756   8.814   14.115   0.25   25.62
ATOM    588   SG    ACYS  381   30.698   9.192   12.732   0.75   31.63
ATOM    589   SG    BCYS  381   30.227  10.312   15.059   0.25   25.40
ATOM    590   C     ACYS  381   29.237   7.422   16.182   0.75   22.07
ATOM    591   C     BCYS  381   29.211   7.498   16.159   0.25   23.97
ATOM    592   O     ACYS  381   29.812   7.730   17.206   0.75   21.97
ATOM    593   O     BCYS  381   29.724   7.940   17.187   0.25   23.99
ATOM    594   N     ALA   382   27.974   7.012   16.128   1.00   23.41
ATOM    595   CA    ALA   382   27.140   7.015   17.318   1.00   22.83
ATOM    596   CB    ALA   382   25.785   7.587   16.948   1.00   25.50
ATOM    597   C     ALA   382   26.913   5.755   18.131   1.00   25.39
ATOM    598   O     ALA   382   26.374   5.837   19.234   1.00   23.09
ATOM    599   N     TRP   383   27.311   4.602   17.615   1.00   25.98
ATOM    600   CA    TRP   383   27.026   3.354   18.318   1.00   23.80
ATOM    601   CB    TRP   383   27.669   2.172   17.580   1.00   22.52
ATOM    602   CG    TRP   383   29.130   2.054   17.762   1.00   24.42
ATOM    603   CD2   TRP   383   29.797   1.347   18.803   1.00   27.31
ATOM    604   CE2   TRP   383   31.183   1.484   18.579   1.00   28.24
ATOM    605   CE3   TRP   383   29.360   0.609   19.912   1.00   27.37
ATOM    606   CD1   TRP   383   30.102   2.578   16.965   1.00   24.58
ATOM    607   NE1   TRP   383   31.342   2.239   17.446   1.00   27.35
ATOM    608   CZ2   TRP   383   32.133   0.909   19.420   1.00   28.76
ATOM    609   CZ3   TRP   383   30.305   0.039   20.745   1.00   28.09
ATOM    610   CH2   TRP   383   31.574   0.191   20.496   1.00   29.77
ATOM    611   C     TRP   383   27.356   3.309   19.802   1.00   23.54
ATOM    612   O     TRP   383   26.526   2.866   20.584   1.00   22.90
ATOM    613   N     LEU   384   28.542   3.765   20.211   1.00   20.37
ATOM    614   CA    LEU   384   28.864   3.713   21.640   1.00   22.41
ATOM    615   CB    LEU   384   30.369   3.890   21.883   1.00   24.98
ATOM    616   CG    LEU   384   30.824   3.645   23.336   1.00   27.33
ATOM    617   CD1   LEU   384   30.273   2.305   23.853   1.00   29.71
ATOM    618   CD2   LEU   384   32.336   3.648   23.398   1.00   26.07
ATOM    619   C     LEU   384   28.075   4.732   22.453   1.00   19.44
ATOM    620   O     LEU   384   27.706   4.458   23.595   1.00   23.24
ATOM    621   N     GLU   385   27.807   5.909   21.885   1.00   20.80
ATOM    622   CA    GLU   385   27.011   6.895   22.612   1.00   21.32
ATOM    623   CB    GLU   385   26.861   8.177   21.797   1.00   21.91
ATOM    624   CG    GLU   385   28.115   9.020   21.705   1.00   21.61
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    625   CD    GLU   385   27.882   10.256   20.860   1.00   29.53
ATOM    626   OE1   GLU   385   27.374   11.386   21.401   1.00   30.54
ATOM    627   OE2   GLU   385   28.188   10.219   19.658   1.00   29.97
ATOM    628   C     GLU   385   25.616    6.292   22.836   1.00   22.26
ATOM    629   O     GLU   385   25.022    6.438   23.902   1.00   22.26
ATOM    630   N     ILE   386   25.101    5.617   21.812   1.00   22.03
ATOM    631   CA    ILE   386   23.779    4.995   21.896   1.00   22.74
ATOM    632   CB    ILE   386   23.328    4.455   20.498   1.00   22.88
ATOM    633   CG2   ILE   386   22.009    3.647   20.618   1.00   23.85
ATOM    634   CG1   ILE   386   23.085    5.651   19.561   1.00   25.05
ATOM    635   CD1   ILE   386   22.994    5.297   18.078   1.00   26.43
ATOM    636   C     ILE   386   23.766    3.897   22.961   1.00   22.50
ATOM    637   O     ILE   386   22.823    3.818   23.746   1.00   24.75
ATOM    638   N     LEU   387   24.810    3.071   23.020   1.00   22.25
ATOM    639   CA    LEU   387   24.868    2.030   24.051   1.00   22.95
ATOM    640   CB    LEU   387   26.096    1.132   23.864   1.00   24.61
ATOM    641   CG    LEU   387   26.070    0.194   22.654   1.00   23.21
ATOM    642   CD1   LEU   387   27.297   -0.709   22.705   1.00   25.36
ATOM    643   CD2   LEU   387   24.791   -0.631   22.652   1.00   26.29
ATOM    644   C     LEU   387   24.944    2.660   25.438   1.00   26.22
ATOM    645   O     LEU   387   24.287    2.204   26.386   1.00   23.55
ATOM    646   N     MET   388   25.751    3.713   25.554   1.00   23.92
ATOM    647   CA    MET   388   25.924    4.385   26.835   1.00   24.26
ATOM    648   CB    MET   388   27.088    5.378   26.761   1.00   23.87
ATOM    649   CG    MET   388   28.440    4.722   26.743   1.00   24.08
ATOM    650   SD    MET   388   29.726    5.992   26.736   1.00   27.70
ATOM    651   CE    MET   388   31.139    5.041   27.078   1.00   21.74
ATOM    652   C     MET   388   24.660    5.094   27.321   1.00   23.33
ATOM    653   O     MET   388   24.341    5.026   28.505   1.00   25.58
ATOM    654   N     ILE   389   23.935    5.775   26.436   1.00   24.62
ATOM    655   CA    ILE   389   22.729    6.440   26.905   1.00   24.03
ATOM    656   CB    ILE   389   22.132    7.439   25.852   1.00   27.01
ATOM    657   CG2   ILE   389   21.413    6.705   24.706   1.00   23.98
ATOM    658   CG1   ILE   389   21.185    8.402   26.584   1.00   25.49
ATOM    659   CD1   ILE   389   20.431    9.383   25.683   1.00   25.45
ATOM    660   C     ILE   389   21.694    5.401   27.349   1.00   26.54
ATOM    661   O     ILE   389   20.938    5.631   28.294   1.00   22.58
ATOM    662   N     GLY   390   21.679    4.247   26.687   1.00   27.14
ATOM    663   CA    GLY   390   20.753    3.201   27.090   1.00   28.42
ATOM    664   C     GLY   390   21.133    2.719   28.482   1.00   29.67
ATOM    665   O     GLY   390   20.275    2.521   29.348   1.00   29.21
ATOM    666   N     LEU   391   22.433    2.547   28.699   1.00   26.06
ATOM    667   CA    LEU   391   22.955    2.091   29.983   1.00   29.23
ATOM    668   CB    LEU   391   24.476    1.937   29.899   1.00   28.37
ATOM    669   CG    LEU   391   25.206    1.656   31.210   1.00   30.81
ATOM    670   CD1   LEU   391   24.717    0.332   31.793   1.00   25.73
ATOM    671   CD2   LEU   391   26.709    1.619   30.958   1.00   25.25
ATOM    672   C     LEU   391   22.603    3.070   31.104   1.00   30.84
ATOM    673   O     LEU   391   22.156    2.669   32.186   1.00   29.19
ATOM    674   N     VAL   392   22.817    4.355   30.850   1.00   28.91
ATOM    675   CA    VAL   392   22.506    5.369   31.851   1.00   28.86
ATOM    676   CB    VAL   392   22.923    6.770   31.353   1.00   30.08
ATOM    677   CG1   VAL   392   23.329    7.854   32.237   1.00   32.32
ATOM    678   CG2   VAL   392   24.442    6.870   31.372   1.00   28.52
ATOM    679   C     VAL   392   21.013    5.327   32.165   1.00   28.42
ATOM    680   O     VAL   392   20.621    5.345   33.327   1.00   30.38
ATOM    681   N     TRP   393   20.191    5.241   31.125   1.00   28.23
ATOM    682   CA    TRP   393   18.732    5.186   31.280   1.00   29.70
```

UNITED STATES PATENT AND TRADEMARK OFFICE
CERTIFICATE OF CORRECTION

PATENT NO. : 6,965,850 B2 Page 163 of 186
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    683  CB   TRP  393   18.066   5.046  29.906  1.00  30.09
ATOM    684  CG   TRP  393   16.605   4.670  29.953  1.00  33.50
ATOM    685  CD2  TRP  393   15.516   5.499  30.369  1.00  31.76
ATOM    686  CE2  TRP  393   14.336   4.725  30.264  1.00  38.11
ATOM    687  CE3  TRP  393   15.419   6.821  30.824  1.00  32.56
ATOM    688  CD1  TRP  393   16.057   3.459  29.618  1.00  34.31
ATOM    689  NE1  TRP  393   14.696   3.486  29.801  1.00  34.36
ATOM    690  CZ2  TRP  393   13.073   5.233  30.597  1.00  37.93
ATOM    691  CZ3  TRP  393   14.162   7.326  31.155  1.00  35.24
ATOM    692  CH2  TRP  393   13.007   6.531  31.039  1.00  37.77
ATOM    693  C    TRP  393   18.256   4.051  32.191  1.00  32.07
ATOM    694  O    TRP  393   17.460   4.275  33.109  1.00  32.12
ATOM    695  N    ARG  394   18.738   2.837  31.957  1.00  31.90
ATOM    696  CA   ARG  394   18.288   1.729  32.797  1.00  36.63
ATOM    697  CB   ARG  394   18.492   0.389  32.065  1.00  36.41
ATOM    698  CG   ARG  394   19.914   0.009  31.764  1.00  36.50
ATOM    699  CD   ARG  394   19.929  -1.132  30.748  1.00  36.34
ATOM    700  NE   ARG  394   21.282  -1.561  30.417  1.00  33.97
ATOM    701  CZ   ARG  394   21.864  -1.350  29.239  1.00  31.61
ATOM    702  NH1  ARG  394   21.208  -0.715  28.281  1.00  32.42
ATOM    703  NH2  ARG  394   23.098  -1.784  29.023  1.00  29.81
ATOM    704  C    ARG  394   18.911   1.697  34.180  1.00  36.69
ATOM    705  O    ARG  394   18.445   0.966  35.048  1.00  37.07
ATOM    706  N    SER  395   19.954   2.492  34.395  1.00  33.63
ATOM    707  CA   SER  395   20.603   2.564  35.701  1.00  35.69
ATOM    708  CB   SER  395   22.112   2.784  35.540  1.00  32.94
ATOM    709  OG   SER  395   22.696   1.811  34.688  1.00  32.37
ATOM    710  C    SER  395   20.010   3.713  36.531  1.00  36.44
ATOM    711  O    SER  395   20.389   3.916  37.687  1.00  38.68
ATOM    712  N    MET  396   19.076   4.449  35.937  1.00  36.46
ATOM    713  CA   MET  396   18.431   5.588  36.589  1.00  43.08
ATOM    714  CB   MET  396   17.275   6.104  35.725  1.00  43.87
ATOM    715  CG   MET  396   17.481   7.507  35.176  1.00  46.18
ATOM    716  SD   MET  396   15.962   8.278  34.581  1.00  49.58
ATOM    717  CE   MET  396   14.988   8.298  36.065  1.00  53.58
ATOM    718  C    MET  396   17.906   5.303  37.992  1.00  46.18
ATOM    719  O    MET  396   18.125   6.089  38.913  1.00  46.34
ATOM    720  N    GLU  397   17.215   4.180  38.152  1.00  49.39
ATOM    721  CA   GLU  397   16.645   3.821  39.444  1.00  52.12
ATOM    722  CB   GLU  397   15.296   3.130  39.246  1.00  55.34
ATOM    723  CG   GLU  397   14.166   4.073  38.873  1.00  58.86
ATOM    724  CD   GLU  397   13.195   3.448  37.891  1.00  63.28
ATOM    725  OE1  GLU  397   13.660   2.925  36.854  1.00  64.68
ATOM    726  OE2  GLU  397   11.972   3.475  38.155  1.00  65.39
ATOM    727  C    GLU  397   17.548   2.933  40.283  1.00  52.75
ATOM    728  O    GLU  397   17.071   2.187  41.139  1.00  53.96
ATOM    729  N    HIS  398   18.851   3.014  40.040  1.00  50.25
ATOM    730  CA   HIS  398   19.813   2.220  40.792  1.00  49.34
ATOM    731  CB   HIS  398   20.271   1.018  39.963  1.00  52.04
ATOM    732  CG   HIS  398   19.187   0.017  39.721  1.00  53.95
ATOM    733  CD2  HIS  398   18.750  -1.022  40.472  1.00  53.92
ATOM    734  ND1  HIS  398   18.374   0.054  38.608  1.00  55.91
ATOM    735  CE1  HIS  398   17.482  -0.917  38.685  1.00  55.53
ATOM    736  NE2  HIS  398   17.688  -1.585  39.806  1.00  55.81
ATOM    737  C    HIS  398   20.999   3.084  41.196  1.00  47.44
ATOM    738  O    HIS  398   22.121   2.887  40.730  1.00  44.91
ATOM    739  N    PRO  399   20.755   4.049  42.096  1.00  46.45
ATOM    740  CD   PRO  399   19.443   4.300  42.721  1.00  47.27
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    741  CA   PRO  399   21.785   4.968  42.586  1.00  45.35
ATOM    742  CB   PRO  399   21.127   5.631  43.793  1.00  47.40
ATOM    743  CG   PRO  399   19.660   5.561  43.504  1.00  47.72
ATOM    744  C    PRO  399   23.086   4.270  42.958  1.00  44.70
ATOM    745  O    PRO  399   23.078   3.333  43.627  1.00  46.46
ATOM    746  N    GLY  400   24.202   4.840  42.509  1.00  41.57
ATOM    747  CA   GLY  400   25.506   4.281  42.813  1.00  39.84
ATOM    748  C    GLY  400   25.907   3.047  42.022  1.00  37.85
ATOM    749  O    GLY  400   27.027   2.560  42.176  1.00  40.48
ATOM    750  N    LYS  401   25.012   2.537  41.180  1.00  36.39
ATOM    751  CA   LYS  401   25.315   1.344  40.390  1.00  34.47
ATOM    752  CB   LYS  401   24.562   0.130  40.947  1.00  36.12
ATOM    753  CG   LYS  401   24.633  -0.007  42.466  1.00  39.30
ATOM    754  CD   LYS  401   24.288  -1.429  42.903  1.00  44.38
ATOM    755  CE   LYS  401   24.459  -1.605  44.408  1.00  46.68
ATOM    756  NZ   LYS  401   24.968  -2.969  44.747  1.00  53.37
ATOM    757  C    LYS  401   24.969   1.485  38.911  1.00  32.34
ATOM    758  O    LYS  401   24.141   2.308  38.531  1.00  31.16
ATOM    759  N    LEU  402   25.612   0.663  38.086  1.00  28.52
ATOM    760  CA   LEU  402   25.358   0.658  36.648  1.00  29.06
ATOM    761  CB   LEU  402   26.661   0.847  35.867  1.00  29.26
ATOM    762  CG   LEU  402   27.278   2.242  36.029  1.00  24.67
ATOM    763  CD1  LEU  402   28.623   2.310  35.310  1.00  27.47
ATOM    764  CD2  LEU  402   26.312   3.277  35.482  1.00  24.93
ATOM    765  C    LEU  402   24.755  -0.686  36.292  1.00  30.43
ATOM    766  O    LEU  402   25.367  -1.727  36.535  1.00  31.36
ATOM    767  N    LEU  403   23.552  -0.658  35.735  1.00  31.07
ATOM    768  CA   LEU  403   22.873  -1.880  35.335  1.00  32.96
ATOM    769  CB   LEU  403   21.361  -1.693  35.434  1.00  33.86
ATOM    770  CG   LEU  403   20.551  -2.991  35.415  1.00  39.29
ATOM    771  CD1  LEU  403   20.584  -3.637  36.806  1.00  43.62
ATOM    772  CD2  LEU  403   19.128  -2.689  34.998  1.00  41.32
ATOM    773  C    LEU  403   23.255  -2.218  33.899  1.00  30.06
ATOM    774  O    LEU  403   22.543  -1.870  32.956  1.00  31.63
ATOM    775  N    PHE  404   24.383  -2.893  33.733  1.00  29.19
ATOM    776  CA   PHE  404   24.834  -3.256  32.403  1.00  28.93
ATOM    777  CB   PHE  404   26.201  -3.929  32.493  1.00  30.05
ATOM    778  CG   PHE  404   27.305  -2.998  32.926  1.00  30.78
ATOM    779  CD1  PHE  404   27.794  -3.033  34.228  1.00  32.91
ATOM    780  CD2  PHE  404   27.848  -2.078  32.030  1.00  32.75
ATOM    781  CE1  PHE  404   28.816  -2.160  34.638  1.00  34.73
ATOM    782  CE2  PHE  404   28.864  -1.205  32.423  1.00  30.68
ATOM    783  CZ   PHE  404   29.350  -1.242  33.727  1.00  31.43
ATOM    784  C    PHE  404   23.809  -4.181  31.756  1.00  30.80
ATOM    785  O    PHE  404   23.625  -4.175  30.538  1.00  28.09
ATOM    786  N    ALA  405   23.138  -4.967  32.594  1.00  30.25
ATOM    787  CA   ALA  405   22.104  -5.910  32.163  1.00  29.78
ATOM    788  CB   ALA  405   22.745  -7.172  31.598  1.00  29.97
ATOM    789  C    ALA  405   21.309  -6.237  33.429  1.00  31.95
ATOM    790  O    ALA  405   21.785  -5.995  34.535  1.00  32.36
ATOM    791  N    PRO  406   20.088  -6.779  33.288  1.00  34.40
ATOM    792  CD   PRO  406   19.356  -7.102  32.053  1.00  35.81
ATOM    793  CA   PRO  406   19.303  -7.101  34.490  1.00  36.41
ATOM    794  CB   PRO  406   17.985  -7.654  33.935  1.00  35.38
ATOM    795  CG   PRO  406   17.922  -7.153  32.519  1.00  36.49
ATOM    796  C    PRO  406   19.997  -8.084  35.433  1.00  37.32
ATOM    797  O    PRO  406   19.698  -8.112  36.626  1.00  38.34
ATOM    798  N    ASN  407   20.924  -8.877  34.902  1.00  36.69
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    799  CA   ASN  407   21.652   -9.847   35.713   1.00   38.85
ATOM    800  CB   ASN  407   21.582  -11.243   35.083   1.00   39.69
ATOM    801  CG   ASN  407   22.232  -11.306   33.711   1.00   44.10
ATOM    802  OD1  ASN  407   22.345  -10.296   33.009   1.00   37.78
ATOM    803  ND2  ASN  407   22.660  -12.503   33.319   1.00   45.74
ATOM    804  C    ASN  407   23.100   -9.435   35.874   1.00   38.12
ATOM    805  O    ASN  407   23.965  -10.256   36.178   1.00   39.81
ATOM    806  N    LEU  408   23.364   -8.149   35.671   1.00   37.80
ATOM    807  CA   LEU  408   24.713   -7.631   35.799   1.00   36.89
ATOM    808  CB   LEU  408   25.449   -7.720   34.459   1.00   36.09
ATOM    809  CG   LEU  408   26.972   -7.609   34.550   1.00   35.08
ATOM    810  CD1  LEU  408   27.525   -8.775   35.354   1.00   39.15
ATOM    811  CD2  LEU  408   27.578   -7.587   33.158   1.00   36.85
ATOM    812  C    LEU  408   24.670   -6.187   36.286   1.00   40.55
ATOM    813  O    LEU  408   24.646   -5.248   35.491   1.00   38.29
ATOM    814  N    LEU  409   24.644   -6.034   37.607   1.00   39.50
ATOM    815  CA   LEU  409   24.606   -4.733   38.257   1.00   41.00
ATOM    816  CB   LEU  409   23.392   -4.658   39.184   1.00   43.69
ATOM    817  CG   LEU  409   23.164   -3.382   39.993   1.00   47.35
ATOM    818  CD1  LEU  409   22.848   -2.233   39.058   1.00   47.09
ATOM    819  CD2  LEU  409   22.014   -3.603   40.976   1.00   49.38
ATOM    820  C    LEU  409   25.894   -4.566   39.060   1.00   41.80
ATOM    821  O    LEU  409   26.178   -5.358   39.960   1.00   41.00
ATOM    822  N    LEU  410   26.676   -3.544   38.727   1.00   39.23
ATOM    823  CA   LEU  410   27.931   -3.296   39.423   1.00   40.45
ATOM    824  CB   LEU  410   29.106   -3.354   38.442   1.00   41.59
ATOM    825  CG   LEU  410   29.457   -4.660   37.716   1.00   44.87
ATOM    826  CD1  LEU  410   30.972   -4.728   37.554   1.00   45.41
ATOM    827  CD2  LEU  410   28.949   -5.872   38.484   1.00   47.02
ATOM    828  C    LEU  410   27.946   -1.944   40.133   1.00   40.67
ATOM    829  O    LEU  410   27.361   -0.970   39.652   1.00   40.22
ATOM    830  N    ASP  411   28.610   -1.890   41.281   1.00   41.57
ATOM    831  CA   ASP  411   28.717   -0.640   42.025   1.00   42.69
ATOM    832  CB   ASP  411   28.490   -0.874   43.528   1.00   44.44
ATOM    833  CG   ASP  411   29.655   -1.578   44.210   1.00   46.70
ATOM    834  OD1  ASP  411   29.537   -1.849   45.426   1.00   51.44
ATOM    835  OD2  ASP  411   30.680   -1.861   43.553   1.00   48.79
ATOM    836  C    ASP  411   30.088   -0.016   41.779   1.00   43.70
ATOM    837  O    ASP  411   30.933   -0.610   41.107   1.00   38.48
ATOM    838  N    ARG  412   30.295    1.181   42.321   1.00   46.78
ATOM    839  CA   ARG  412   31.554    1.905   42.171   1.00   49.97
ATOM    840  CB   ARG  412   31.601    3.090   43.138   1.00   51.28
ATOM    841  CG   ARG  412   30.971    4.364   42.614   1.00   54.77
ATOM    842  CD   ARG  412   31.644    5.580   43.219   1.00   54.61
ATOM    843  NE   ARG  412   33.071    5.615   42.912   1.00   56.53
ATOM    844  CZ   ARG  412   33.827    6.708   42.985   1.00   61.90
ATOM    845  NH1  ARG  412   33.291    7.866   43.356   1.00   63.48
ATOM    846  NH2  ARG  412   35.120    6.645   42.682   1.00   61.21
ATOM    847  C    ARG  412   32.771    1.026   42.429   1.00   50.29
ATOM    848  O    ARG  412   33.628    0.866   41.561   1.00   51.02
ATOM    849  N    ASN  413   32.844    0.469   43.633   1.00   51.94
ATOM    850  CA   ASN  413   33.969   -0.375   44.021   1.00   53.15
ATOM    851  CB   ASN  413   33.719   -0.980   45.403   1.00   55.88
ATOM    852  CG   ASN  413   33.654    0.073   46.496   1.00   57.99
ATOM    853  OD1  ASN  413   33.697    1.276   46.223   1.00   58.27
ATOM    854  ND2  ASN  413   33.551   -0.375   47.742   1.00   57.90
ATOM    855  C    ASN  413   34.235   -1.480   43.013   1.00   53.95
ATOM    856  O    ASN  413   35.386   -1.743   42.659   1.00   53.67
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    857  N    GLN  414   33.173   -2.129   42.547   1.00   55.33
ATOM    858  CA   GLN  414   33.336   -3.198   41.873   1.00   55.42
ATOM    859  CB   GLN  414   31.991   -3.904   41.343   1.00   55.44
ATOM    860  CG   GLN  414   31.645   -4.933   42.391   1.00   56.07
ATOM    861  CD   GLN  414   30.203   -5.376   42.336   1.00   57.40
ATOM    862  OE1  GLN  414   29.296   -4.536   42.402   1.00   60.32
ATOM    863  NE2  GLN  414   29.973   -6.664   42.199   1.00   57.27
ATOM    864  C    GLN  414   33.850   -2.630   40.259   1.00   55.51
ATOM    865  O    GLN  414   34.654   -3.265   39.578   1.00   56.16
ATOM    866  N    GLY  415   33.398   -1.430   39.910   1.00   57.07
ATOM    867  CA   GLY  415   33.849   -0.806   38.680   1.00   58.51
ATOM    868  C    GLY  415   35.350   -0.582   38.689   1.00   61.10
ATOM    869  O    GLY  415   36.023   -0.748   37.671   1.00   59.47
ATOM    870  N    LYS  416   35.877   -0.211   39.851   1.00   62.77
ATOM    871  CA   LYS  416   37.305    0.041   40.011   1.00   65.49
ATOM    872  CB   LYS  416   37.634    0.262   41.491   1.00   66.04
ATOM    873  CG   LYS  416   38.121    1.663   41.823   1.00   68.71
ATOM    874  CD   LYS  416   37.078    2.439   42.613   1.00   70.98
ATOM    875  CE   LYS  416   37.404    2.448   44.100   1.00   71.84
ATOM    876  NZ   LYS  416   36.225    2.079   44.933   1.00   71.95
ATOM    877  C    LYS  416   38.159   -1.105   39.472   1.00   66.41
ATOM    878  O    LYS  416   39.361   -0.946   39.269   1.00   67.15
ATOM    879  N    CYS  417   37.538   -2.257   39.238   1.00   67.33
ATOM    880  CA   CYS  417   38.270   -3.414   38.741   1.00   68.16
ATOM    881  CB   CYS  417   37.951   -4.642   39.602   1.00   70.88
ATOM    882  SG   CYS  417   38.592   -4.549   41.301   1.00   76.09
ATOM    883  C    CYS  417   38.015   -3.736   37.270   1.00   67.54
ATOM    884  O    CYS  417   38.632   -4.653   36.720   1.00   68.48
ATOM    885  N    VAL  418   37.111   -2.994   36.631   1.00   64.67
ATOM    886  CA   VAL  418   36.817   -3.226   35.218   1.00   59.97
ATOM    887  CB   VAL  418   35.326   -2.917   34.879   1.00   59.60
ATOM    888  CG1  VAL  418   34.971   -1.503   35.284   1.00   59.13
ATOM    889  CG2  VAL  418   35.072   -3.121   33.391   1.00   54.85
ATOM    890  C    VAL  418   37.739   -2.362   34.355   1.00   58.37
ATOM    891  O    VAL  418   37.799   -1.140   34.512   1.00   55.44
ATOM    892  N    GLU  419   38.463   -3.012   33.450   1.00   56.02
ATOM    893  CA   GLU  419   39.403   -2.328   32.570   1.00   54.28
ATOM    894  CB   GLU  419   40.149   -3.351   31.710   1.00   57.57
ATOM    895  CG   GLU  419   39.385   -3.779   30.468   1.00   60.87
ATOM    896  CD   GLU  419   40.179   -4.722   29.584   1.00   63.34
ATOM    897  OE1  GLU  419   40.432   -5.870   30.011   1.00   64.90
ATOM    898  OE2  GLU  419   40.546   -4.313   28.462   1.00   63.18
ATOM    899  C    GLU  419   38.761   -1.281   31.662   1.00   52.05
ATOM    900  O    GLU  419   37.665   -1.481   31.131   1.00   49.82
ATOM    901  N    GLY  420   39.465   -0.165   31.491   1.00   49.45
ATOM    902  CA   GLY  420   38.983    0.908   30.642   1.00   46.22
ATOM    903  C    GLY  420   37.895    1.767   31.254   1.00   44.55
ATOM    904  O    GLY  420   37.417    2.705   30.619   1.00   42.08
ATOM    905  N    MET  421   37.503    1.471   32.488   1.00   43.41
ATOM    906  CA   MET  421   36.449    2.248   33.123   1.00   42.48
ATOM    907  CB   MET  421   35.306    1.327   33.554   1.00   42.34
ATOM    908  CG   MET  421   34.590    0.635   32.396   1.00   38.22
ATOM    909  SD   MET  421   32.927    0.102   32.843   1.00   38.56
ATOM    910  CE   MET  421   32.003    1.699   32.766   1.00   35.54
ATOM    911  C    MET  421   36.923    3.059   34.312   1.00   41.64
ATOM    912  O    MET  421   36.113    3.512   35.111   1.00   39.77
ATOM    913  N    VAL  422   38.232    3.256   34.430   1.00   43.42
ATOM    914  CA   VAL  422   38.757    4.019   35.557   1.00   44.79
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    915   CB    VAL   422   40.285    4.248   35.433   1.00   46.54
ATOM    916   CG1   VAL   422   40.595    5.086   34.206   1.00   48.35
ATOM    917   CG2   VAL   422   40.813    4.920   36.696   1.00   46.24
ATOM    918   C     VAL   422   38.056    5.372   35.689   1.00   44.09
ATOM    919   O     VAL   422   37.691    5.783   36.783   1.00   44.12
ATOM    920   N     GLU   423   37.846    6.055   34.570   1.00   42.07
ATOM    921   CA    GLU   423   37.192    7.356   34.616   1.00   40.24
ATOM    922   CB    GLU   423   37.909    8.338   33.684   1.00   44.02
ATOM    923   CG    GLU   423   39.411    8.467   33.893   1.00   50.04
ATOM    924   CD    GLU   423   40.096    9.158   32.719   1.00   55.64
ATOM    925   OE1   GLU   423   39.539   10.156   32.208   1.00   56.66
ATOM    926   OE2   GLU   423   41.188    8.703   32.306   1.00   58.02
ATOM    927   C     GLU   423   35.704    7.337   34.250   1.00   35.77
ATOM    928   O     GLU   423   34.881    7.955   34.919   1.00   33.20
ATOM    929   N     ILE   424   35.345    6.617   33.197   1.00   35.16
ATOM    930   CA    ILE   424   33.949    6.643   32.771   1.00   31.63
ATOM    931   CB    ILE   424   33.803    6.087   31.347   1.00   33.58
ATOM    932   CG2   ILE   424   34.639    6.936   30.395   1.00   33.48
ATOM    933   CG1   ILE   424   34.204    4.617   31.296   1.00   34.46
ATOM    934   CD1   ILE   424   33.857    3.955   29.978   1.00   34.67
ATOM    935   C     ILE   424   32.890    6.035   33.685   1.00   28.89
ATOM    936   O     ILE   424   31.729    6.443   33.632   1.00   26.49
ATOM    937   N     PHE   425   33.261    5.091   34.542   1.00   29.26
ATOM    938   CA    PHE   425   32.257    4.520   35.447   1.00   29.87
ATOM    939   CB    PHE   425   32.903    3.529   36.423   1.00   31.26
ATOM    940   CG    PHE   425   31.948    2.496   36.959   1.00   32.17
ATOM    941   CD1   PHE   425   31.124    2.783   38.048   1.00   33.70
ATOM    942   CD2   PHE   425   31.881    1.230   36.381   1.00   30.64
ATOM    943   CE1   PHE   425   30.244    1.814   38.563   1.00   32.60
ATOM    944   CE2   PHE   425   31.010    0.256   36.883   1.00   31.55
ATOM    945   CZ    PHE   425   30.189    0.549   37.973   1.00   33.34
ATOM    946   C     PHE   425   31.594    5.649   36.240   1.00   30.17
ATOM    947   O     PHE   425   30.368    5.774   36.276   1.00   26.71
ATOM    948   N     ASP   426   32.415    6.483   36.870   1.00   29.43
ATOM    949   CA    ASP   426   31.893    7.587   37.661   1.00   32.29
ATOM    950   CB    ASP   426   33.031    8.291   38.401   1.00   33.49
ATOM    951   CG    ASP   426   33.455    7.546   39.655   1.00   39.42
ATOM    952   OD1   ASP   426   32.767    6.574   40.038   1.00   38.35
ATOM    953   OD2   ASP   426   34.480    7.934   40.256   1.00   39.58
ATOM    954   C     ASP   426   31.133    8.592   36.806   1.00   39.02
ATOM    955   O     ASP   426   30.154    9.175   37.257   1.00   31.34
ATOM    956   N     MET   427   31.585    8.797   35.572   1.00   30.69
ATOM    957   CA    MET   427   30.919    9.736   34.675   1.00   28.63
ATOM    958   CB    MET   427   31.744    9.912   33.407   1.00   26.83
ATOM    959   CG    MET   427   33.032   10.680   33.608   1.00   31.41
ATOM    960   SD    MET   427   33.952   10.783   32.077   1.00   34.87
ATOM    961   CE    MET   427   35.409   11.753   32.643   1.00   44.60
ATOM    962   C     MET   427   29.526    9.202   34.324   1.00   28.70
ATOM    963   O     MET   427   28.536    9.947   34.302   1.00   25.01
ATOM    964   N     LEU   428   29.451    7.902   34.057   1.00   25.13
ATOM    965   CA    LEU   428   28.173    7.292   33.730   1.00   27.60
ATOM    966   CB    LEU   428   28.379    5.824   33.332   1.00   28.00
ATOM    967   CG    LEU   428   29.039    5.682   31.957   1.00   26.99
ATOM    968   CD1   LEU   428   29.678    4.303   31.782   1.00   27.80
ATOM    969   CD2   LEU   428   27.995    5.927   30.894   1.00   25.33
ATOM    970   C     LEU   428   27.210    7.412   34.916   1.00   29.59
ATOM    971   O     LEU   428   26.041    7.743   34.743   1.00   27.07
ATOM    972   N     LEU   429   27.701    7.147   36.126   1.00   30.40
```

UNITED STATES PATENT AND TRADEMARK OFFICE
CERTIFICATE OF CORRECTION

PATENT NO. : 6,965,850 B2  
APPLICATION NO. : 09/281717  
DATED : November 15, 2005  
INVENTOR(S) : John D. Baxter et al.

It is certified that error appears in the above-identified patent and that said Letters Patent is hereby corrected as shown below:

```
ATOM    973   CA    LEU   429    26.859    7.251   37.323   1.00   30.59
ATOM    974   CB    LEU   429    27.675    6.884   38.871   1.00   31.76
ATOM    975   CG    LEU   429    28.078    5.415   38.797   1.00   32.43
ATOM    976   CD1   LEU   429    28.961    5.264   39.995   1.00   31.80
ATOM    977   CD2   LEU   429    26.825    4.573   38.903   1.00   34.66
ATOM    978   C     LEU   429    26.319    8.681   37.466   1.00   30.46
ATOM    979   O     LEU   429    25.143    8.901   37.769   1.00   28.40
ATOM    980   N     ALA   430    27.193    9.656   37.237   1.00   31.34
ATOM    981   CA    ALA   430    26.806   11.059   37.332   1.00   29.83
ATOM    982   CB    ALA   430    28.017   11.951   37.078   1.00   31.29
ATOM    983   C     ALA   430    25.696   11.387   36.344   1.00   31.04
ATOM    984   O     ALA   430    24.753   12.107   36.674   1.00   30.79
ATOM    985   N     THR   431    25.802   10.854   35.128   1.00   30.30
ATOM    986   CA    THR   431    24.786   11.105   34.112   1.00   38.81
ATOM    987   CB    THR   431    25.207   10.533   32.737   1.00   30.95
ATOM    988   OG1   THR   431    26.569   10.893   32.465   1.00   31.88
ATOM    989   CG2   THR   431    24.321   11.087   31.634   1.00   25.63
ATOM    990   C     THR   431    23.462   10.481   34.530   1.00   29.49
ATOM    991   O     THR   431    22.402   11.099   34.397   1.00   26.18
ATOM    992   N     SER   432    23.520    9.253   35.037   1.00   28.11
ATOM    993   CA    SER   432    22.308    8.573   35.480   1.00   29.78
ATOM    994   CB    SER   432    22.639    7.177   36.008   1.00   33.11
ATOM    995   OG    SER   432    21.454    6.412   36.136   1.00   36.92
ATOM    996   C     SER   432    21.651    9.399   36.589   1.00   31.49
ATOM    997   O     SER   432    20.433    9.576   36.613   1.00   30.09
ATOM    998   N     ASER  433    22.476    9.901   37.496   0.75   32.09
ATOM    999   N     BSER  433    22.474    9.906   37.500   0.25   31.10
ATOM   1000   CA    ASER  433    22.002   10.715   38.605   0.75   35.68
ATOM   1001   CA    BSER  433    21.985   10.717   38.608   0.25   32.21
ATOM   1002   CB    ASER  433    23.185   11.097   39.502   0.75   37.18
ATOM   1003   CB    BSER  433    23.145   11.104   39.829   0.25   31.45
ATOM   1004   OG    ASER  433    22.823   12.090   40.443   0.75   44.09
ATOM   1005   OG    BSER  433    23.785    9.953   40.053   0.25   29.52
ATOM   1006   C     ASER  433    21.299   11.971   38.091   0.75   35.01
ATOM   1007   C     BSER  433    21.295   11.976   38.092   0.25   32.88
ATOM   1008   O     ASER  433    20.257   12.373   38.612   0.75   35.34
ATOM   1009   O     BSER  433    20.264   12.391   38.622   0.25   33.42
ATOM   1010   N     ARG   434    21.867   12.579   37.054   1.00   33.38
ATOM   1011   CA    ARG   434    21.300   13.788   36.470   1.00   34.19
ATOM   1012   CB    ARG   434    22.239   14.354   35.400   1.00   33.89
ATOM   1013   CG    ARG   434    21.570   15.538   34.625   1.00   38.30
ATOM   1014   CD    ARG   434    21.559   16.787   35.479   1.00   37.91
ATOM   1015   NE    ARG   434    21.158   17.944   34.680   1.00   37.78
ATOM   1016   CZ    ARG   434    20.488   18.995   35.149   1.00   41.06
ATOM   1017   NH1   ARG   434    20.132   19.049   36.428   1.00   40.70
ATOM   1018   NH2   ARG   434    20.175   19.998   34.337   1.00   38.78
ATOM   1019   C     ARG   434    19.937   13.491   35.873   1.00   33.48
ATOM   1020   O     ARG   434    18.996   14.266   36.053   1.00   30.54
ATOM   1021   N     PHE   435    19.831   12.371   35.158   1.00   34.68
ATOM   1022   CA    PHE   435    18.563   11.963   34.549   1.00   35.02
ATOM   1023   CB    PHE   435    18.727   10.634   33.796   1.00   34.96
ATOM   1024   CG    PHE   435    19.240   10.779   32.386   1.00   37.63
ATOM   1025   CD1   PHE   435    19.459   12.035   31.824   1.00   42.03
ATOM   1026   CD2   PHE   435    19.521    9.649   31.623   1.00   41.24
ATOM   1027   CE1   PHE   435    19.953   12.164   30.521   1.00   43.11
ATOM   1028   CE2   PHE   435    20.016    9.768   30.322   1.00   40.59
ATOM   1029   CZ    PHE   435    20.233   11.029   29.775   1.00   40.63
ATOM   1030   C     PHE   435    17.527   11.780   35.657   1.00   35.49
```

Page 168 of 186

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1031  O    PHE  435   16.361  12.135  35.496  1.00  34.78
ATOM   1032  N    ARG  436   17.968  11.216  36.777  1.00  38.27
ATOM   1033  CA   ARG  436   17.094  10.982  37.924  1.00  40.67
ATOM   1034  CB   ARG  436   17.844  10.215  39.012  1.00  40.70
ATOM   1035  CG   ARG  436   16.942   9.590  40.068  1.00  44.98
ATOM   1036  CD   ARG  436   17.648   8.489  40.810  1.00  48.09
ATOM   1037  NE   ARG  436   18.982   8.841  41.275  1.00  50.16
ATOM   1038  CZ   ARG  436   20.119   8.361  40.777  1.00  52.19
ATOM   1039  NH1  ARG  436   20.099   7.472  39.790  1.00  49.34
ATOM   1040  NH2  ARG  436   21.283   8.770  41.266  1.00  51.85
ATOM   1041  C    ARG  436   16.576  12.302  38.493  1.00  40.40
ATOM   1042  O    ARG  436   15.382  12.458  38.730  1.00  41.49
ATOM   1043  N    MET  437   17.477  13.252  38.706  1.00  40.02
ATOM   1044  CA   MET  437   17.090  14.546  39.245  1.00  41.02
ATOM   1045  CB   MET  437   18.329  15.427  39.440  1.00  40.29
ATOM   1046  C    MET  437   16.099  15.221  38.299  1.00  40.81
ATOM   1047  O    MET  437   15.111  15.805  38.734  1.00  42.46
ATOM   1048  N    MET  438   16.367  15.127  37.001  1.00  39.02
ATOM   1049  CA   MET  438   15.510  15.732  35.988  1.00  40.11
ATOM   1050  CB   MET  438   16.237  15.793  34.651  1.00  38.16
ATOM   1051  CG   MET  438   17.352  16.794  34.601  1.00  41.52
ATOM   1052  SD   MET  438   17.999  16.862  32.943  1.00  43.94
ATOM   1053  CE   MET  438   16.698  17.748  32.096  1.00  39.96
ATOM   1054  C    MET  438   14.221  14.964  35.783  1.00  37.72
ATOM   1055  O    MET  438   13.305  15.451  35.125  1.00  36.82
ATOM   1056  N    ASN  439   14.155  13.759  36.337  1.00  38.81
ATOM   1057  CA   ASN  439   12.981  12.919  36.174  1.00  40.77
ATOM   1058  CB   ASN  439   11.762  13.556  36.847  1.00  44.52
ATOM   1059  CG   ASN  439   10.566  12.620  36.887  1.00  48.29
ATOM   1060  OD1  ASN  439   10.721  11.400  36.964  1.00  48.48
ATOM   1061  ND2  ASN  439    9.365  13.189  36.829  1.00  50.23
ATOM   1062  C    ASN  439   12.725  12.744  34.677  1.00  39.36
ATOM   1063  O    ASN  439   11.637  13.037  34.172  1.00  37.76
ATOM   1064  N    LEU  440   13.749  12.274  33.972  1.00  37.65
ATOM   1065  CA   LEU  440   13.655  12.052  32.532  1.00  35.22
ATOM   1066  CB   LEU  440   14.999  11.576  31.987  1.00  34.70
ATOM   1067  CG   LEU  440   15.022  11.467  30.462  1.00  35.45
ATOM   1068  CD1  LEU  440   14.890  12.862  29.869  1.00  35.24
ATOM   1069  CD2  LEU  440   16.297  10.795  29.999  1.00  35.30
ATOM   1070  C    LEU  440   12.587  11.024  32.196  1.00  36.48
ATOM   1071  O    LEU  440   12.518   9.967  32.836  1.00  37.36
ATOM   1072  N    GLN  441   11.763  11.328  31.197  1.00  36.83
ATOM   1073  CA   GLN  441   10.696  10.420  30.785  1.00  38.51
ATOM   1074  CB   GLN  441    9.431  11.211  30.443  1.00  38.23
ATOM   1075  CG   GLN  441    8.912  12.063  31.592  1.00  42.46
ATOM   1076  CD   GLN  441    8.362  11.227  32.729  1.00  44.91
ATOM   1077  OE1  GLN  441    7.268  10.668  32.629  1.00  47.31
ATOM   1078  NE2  GLN  441    9.119  11.132  33.818  1.00  44.06
ATOM   1079  C    GLN  441   11.099   9.565  29.585  1.00  38.48
ATOM   1080  O    GLN  441   11.923   9.976  28.763  1.00  35.80
ATOM   1081  N    GLY  442   10.500   8.378  29.494  1.00  36.03
ATOM   1082  CA   GLY  442   10.792   7.468  28.401  1.00  37.72
ATOM   1083  C    GLY  442   10.599   8.112  27.043  1.00  36.88
ATOM   1084  O    GLY  442   11.381   7.877  26.123  1.00  33.72
ATOM   1085  N    GLU  443    9.556   8.925  26.918  1.00  36.59
ATOM   1086  CA   GLU  443    9.269   9.603  25.661  1.00  37.13
ATOM   1087  CB   GLU  443    7.956  10.379  25.764  1.00  41.57
ATOM   1088  CG   GLU  443    6.723   9.488  25.879  1.00  47.76
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1089  CD    GLU  443    6.483   9.008  27.302  1.00  53.96
ATOM   1090  OE1   GLU  443    5.619   8.123  27.498  1.00  57.66
ATOM   1091  OE2   GLU  443    7.159   9.515  28.225  1.00  56.13
ATOM   1092  C     GLU  443   10.408  10.551  25.311  1.00  35.27
ATOM   1093  O     GLU  443   10.759  10.704  24.145  1.00  33.85
ATOM   1094  N     GLU  444   10.984  11.179  26.331  1.00  32.09
ATOM   1095  CA    GLU  444   12.097  12.095  26.126  1.00  33.92
ATOM   1096  CB    GLU  444   12.332  12.924  27.388  1.00  34.97
ATOM   1097  CG    GLU  444   11.169  13.845  27.732  1.00  38.28
ATOM   1098  CD    GLU  444   11.383  14.610  29.023  1.00  38.11
ATOM   1099  OE1   GLU  444   11.800  13.993  30.026  1.00  39.53
ATOM   1100  OE2   GLU  444   11.132  15.834  29.036  1.00  40.77
ATOM   1101  C     GLU  444   13.356  11.305  25.770  1.00  33.59
ATOM   1102  O     GLU  444   14.085  11.670  24.843  1.00  33.35
ATOM   1103  N     PHE  445   13.590  10.215  26.501  1.00  30.68
ATOM   1104  CA    PHE  445   14.753   9.357  26.276  1.00  32.49
ATOM   1105  CB    PHE  445   14.703   8.139  27.203  1.00  29.35
ATOM   1106  CG    PHE  445   15.667   7.047  26.828  1.00  30.78
ATOM   1107  CD1   PHE  445   17.036   7.201  27.030  1.00  28.25
ATOM   1108  CD2   PHE  445   15.205   5.863  26.266  1.00  30.62
ATOM   1109  CE1   PHE  445   17.933   6.195  26.675  1.00  28.67
ATOM   1110  CE2   PHE  445   16.095   4.848  25.908  1.00  31.37
ATOM   1111  CZ    PHE  445   17.460   5.015  26.113  1.00  30.37
ATOM   1112  C     PHE  445   14.850   8.885  24.829  1.00  31.11
ATOM   1113  O     PHE  445   15.924   8.947  24.221  1.00  32.20
ATOM   1114  N     VAL  446   13.739   8.415  24.266  1.00  28.63
ATOM   1115  CA    VAL  446   13.787   7.943  22.889  1.00  27.94
ATOM   1116  CB    VAL  446   12.478   7.193  22.478  1.00  28.48
ATOM   1117  CG1   VAL  446   12.318   5.939  23.343  1.00  29.61
ATOM   1118  CG2   VAL  446   11.265   8.092  22.607  1.00  27.23
ATOM   1119  C     VAL  446   14.099   9.064  21.900  1.00  27.28
ATOM   1120  O     VAL  446   14.781   8.837  20.904  1.00  28.07
ATOM   1121  N     CYS  447   13.619  10.275  22.166  1.00  28.97
ATOM   1122  CA    CYS  447   13.919  11.394  21.272  1.00  29.14
ATOM   1123  CB    CYS  447   13.156  12.653  21.693  1.00  28.90
ATOM   1124  SG    CYS  447   11.389  12.591  21.309  1.00  35.68
ATOM   1125  C     CYS  447   15.420  11.677  21.328  1.00  28.03
ATOM   1126  O     CYS  447   16.063  11.885  20.302  1.00  29.34
ATOM   1127  N     LEU  448   15.969  11.686  22.538  1.00  27.28
ATOM   1128  CA    LEU  448   17.392  11.938  22.729  1.00  25.30
ATOM   1129  CB    LEU  448   17.733  11.932  24.220  1.00  27.72
ATOM   1130  CG    LEU  448   17.248  13.135  25.040  1.00  29.54
ATOM   1131  CD1   LEU  448   17.807  13.042  26.454  1.00  30.85
ATOM   1132  CD2   LEU  448   17.688  14.434  24.376  1.00  30.24
ATOM   1133  C     LEU  448   18.245  10.902  22.008  1.00  27.62
ATOM   1134  O     LEU  448   19.207  11.252  21.327  1.00  25.10
ATOM   1135  N     LYS  449   17.905   9.621  22.162  1.00  25.16
ATOM   1136  CA    LYS  449   18.673   8.570  21.506  1.00  27.55
ATOM   1137  CB    LYS  449   18.135   7.185  21.900  1.00  28.99
ATOM   1138  CG    LYS  449   19.134   6.052  21.694  1.00  34.70
ATOM   1139  CD    LYS  449   18.737   4.789  22.459  1.00  32.67
ATOM   1140  CE    LYS  449   17.267   4.419  22.220  1.00  31.87
ATOM   1141  NZ    LYS  449   17.022   2.967  22.472  1.00  29.14
ATOM   1142  C     LYS  449   18.626   8.749  19.990  1.00  25.88
ATOM   1143  O     LYS  449   19.610   8.489  19.296  1.00  25.93
ATOM   1144  N     SER  450   17.482   9.197  19.480  1.00  26.07
ATOM   1145  CA    SER  450   17.323   9.421  18.052  1.00  27.24
ATOM   1146  CB    SER  450   15.857   9.705  17.721  1.00  32.24
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1147  OG   SER  450   15.098   8.519  17.779  1.00  34.94
ATOM   1148  C    SER  450   18.176  10.607  17.618  1.00  26.78
ATOM   1149  O    SER  450   18.763  10.598  16.535  1.00  25.85
ATOM   1150  N    ILE  451   18.231  11.632  18.463  1.00  26.94
ATOM   1151  CA   ILE  451   19.032  12.810  18.155  1.00  26.13
ATOM   1152  CB   ILE  451   18.950  13.850  19.291  1.00  27.72
ATOM   1153  CG2  ILE  451   20.019  14.929  19.101  1.00  30.83
ATOM   1154  CG1  ILE  451   17.553  14.475  19.322  1.00  29.49
ATOM   1155  CD1  ILE  451   17.377  15.473  20.447  1.00  36.24
ATOM   1156  C    ILE  451   20.489  12.381  17.989  1.00  24.88
ATOM   1157  O    ILE  451   21.161  12.771  17.034  1.00  26.96
ATOM   1158  N    ILE  452   20.977  11.582  18.931  1.00  22.72
ATOM   1159  CA   ILE  452   22.359  11.120  18.880  1.00  21.95
ATOM   1160  CB   ILE  452   22.660  10.155  20.050  1.00  23.57
ATOM   1161  CG2  ILE  452   23.982   9.435  19.804  1.00  22.10
ATOM   1162  CG1  ILE  452   22.718  10.949  21.371  1.00  21.70
ATOM   1163  CD1  ILE  452   22.768  10.060  22.624  1.00  25.30
ATOM   1164  C    ILE  452   22.656  10.419  17.557  1.00  23.02
ATOM   1165  O    ILE  452   23.650  10.708  16.885  1.00  21.25
ATOM   1166  N    LEU  453   21.779   9.497  17.173  1.00  22.83
ATOM   1167  CA   LEU  453   21.984   8.768  15.935  1.00  22.05
ATOM   1168  CB   LEU  453   20.843   7.764  15.733  1.00  22.06
ATOM   1169  CG   LEU  453   20.713   7.189  14.324  1.00  22.03
ATOM   1170  CD1  LEU  453   21.815   6.165  14.107  1.00  24.81
ATOM   1171  CD2  LEU  453   19.328   6.535  14.156  1.00  24.73
ATOM   1172  C    LEU  453   22.092   9.687  14.717  1.00  23.95
ATOM   1173  O    LEU  453   22.962   9.501  13.860  1.00  24.60
ATOM   1174  N    LEU  454   21.220  10.687  14.638  1.00  26.72
ATOM   1175  CA   LEU  454   21.234  11.599  13.494  1.00  26.45
ATOM   1176  CB   LEU  454   19.852  12.242  13.330  1.00  25.51
ATOM   1177  CG   LEU  454   18.737  11.222  13.052  1.00  30.16
ATOM   1178  CD1  LEU  454   17.405  11.926  12.955  1.00  28.76
ATOM   1179  CD2  LEU  454   19.037  10.478  11.759  1.00  32.89
ATOM   1180  C    LEU  454   22.292  12.703  13.552  1.00  28.34
ATOM   1181  O    LEU  454   22.778  13.148  12.513  1.00  29.06
ATOM   1182  N    ASN  455   22.638  13.146  14.757  1.00  26.56
ATOM   1183  CA   ASN  455   23.604  14.236  14.934  1.00  26.79
ATOM   1184  CB   ASN  455   23.284  14.998  16.224  1.00  26.20
ATOM   1185  CG   ASN  455   24.174  16.217  16.419  1.00  27.26
ATOM   1186  OD1  ASN  455   24.171  17.134  15.602  1.00  30.83
ATOM   1187  ND2  ASN  455   24.931  16.230  17.506  1.00  27.16
ATOM   1188  C    ASN  455   25.062  13.782  14.954  1.00  30.63
ATOM   1189  O    ASN  455   25.965  14.517  14.525  1.00  27.69
ATOM   1190  N    SER  456   25.268  12.569  15.461  1.00  30.48
ATOM   1191  CA   SER  456   26.572  11.928  15.579  1.00  35.26
ATOM   1192  CB   SER  456   26.393  10.393  15.505  1.00  39.69
ATOM   1193  OG   SER  456   25.871   9.953  14.243  1.00  30.73
ATOM   1194  C    SER  456   27.627  13.344  14.562  1.00  35.56
ATOM   1195  O    SER  456   28.599  13.041  14.884  1.00  33.00
ATOM   1196  N    GLY  457   27.437  11.886  13.334  1.00  33.88
ATOM   1197  CA   GLY  457   28.393  12.189  12.292  1.00  36.77
ATOM   1198  C    GLY  457   27.876  13.017  11.136  1.00  37.02
ATOM   1199  O    GLY  457   28.310  12.805  10.013  1.00  38.66
ATOM   1200  N    VAL  458   26.967  13.956  11.392  1.00  39.12
ATOM   1201  CA   VAL  458   26.438  14.802  10.317  1.00  43.81
ATOM   1202  CB   VAL  458   25.231  15.648  10.755  1.00  44.25
ATOM   1203  CG1  VAL  458   24.209  15.713   9.631  1.00  44.51
ATOM   1204  CG2  VAL  458   24.638  15.098  12.013  1.00  50.53
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM    1205  C    VAL  458   27.472  15.801   9.817  1.00  46.72
ATOM    1206  O    VAL  458   27.391  16.265   8.681  1.00  47.08
ATOM    1207  N    TYR  459   28.432  16.144  10.670  1.00  50.74
ATOM    1208  CA   TYR  459   29.456  17.114  10.301  1.00  55.43
ATOM    1209  CB   TYR  459   29.647  18.129  11.433  1.00  56.62
ATOM    1210  CG   TYR  459   28.375  18.870  11.781  1.00  59.34
ATOM    1211  CD1  TYR  459   28.094  19.229  13.095  1.00  60.73
ATOM    1212  CE1  TYR  459   26.900  19.867  13.429  1.00  62.14
ATOM    1213  CD2  TYR  459   27.430  19.175  10.795  1.00  62.16
ATOM    1214  CE2  TYR  459   26.234  19.812  11.118  1.00  63.83
ATOM    1215  CZ   TYR  459   25.976  20.154  12.437  1.00  62.88
ATOM    1216  OH   TYR  459   24.790  20.764  12.767  1.00  62.56
ATOM    1217  C    TYR  459   30.791  16.489   9.928  1.00  57.21
ATOM    1218  O    TYR  459   31.793  17.189   9.798  1.00  56.86
ATOM    1219  N    THR  460   30.800  15.173   9.750  1.00  59.22
ATOM    1220  CA   THR  460   32.018  14.474   9.366  1.00  62.25
ATOM    1221  CB   THR  460   32.502  13.531  10.499  1.00  63.07
ATOM    1222  OG1  THR  460   33.474  12.613   9.983  1.00  67.80
ATOM    1223  CG2  THR  460   31.344  12.759  11.084  1.00  60.23
ATOM    1224  C    THR  460   31.759  13.678   8.086  1.00  63.54
ATOM    1225  O    THR  460   32.457  12.708   7.782  1.00  63.91
ATOM    1226  N    PHE  461   30.758  14.113   7.326  1.00  65.06
ATOM    1227  CA   PHE  461   30.395  13.446   6.080  1.00  67.00
ATOM    1228  CB   PHE  461   29.052  13.975   5.563  1.00  66.48
ATOM    1229  CG   PHE  461   27.867  13.147   5.991  1.00  66.30
ATOM    1230  CD1  PHE  461   26.657  13.754   6.312  1.00  65.58
ATOM    1231  CD2  PHE  461   27.963  11.760   6.085  1.00  66.41
ATOM    1232  CE1  PHE  461   25.562  12.996   6.723  1.00  65.45
ATOM    1233  CE2  PHE  461   26.872  10.994   6.494  1.00  66.83
ATOM    1234  CZ   PHE  461   25.670  11.616   6.814  1.00  65.12
ATOM    1235  C    PHE  461   31.463  13.604   5.004  1.00  68.38
ATOM    1236  O    PHE  461   32.181  14.606   4.962  1.00  68.98
ATOM    1237  N    LEU  462   31.542  12.601   4.132  1.00  69.57
ATOM    1238  CA   LEU  462   32.511  12.545   3.039  1.00  71.68
ATOM    1239  CB   LEU  462   32.080  11.475   2.030  1.00  71.00
ATOM    1240  C    LEU  462   32.810  13.856   2.304  1.00  72.40
ATOM    1241  O    LEU  462   33.725  14.590   2.680  1.00  73.45
ATOM    1242  N    SER  463   32.043  14.141   1.253  1.00  73.22
ATOM    1243  CA   SER  463   32.262  15.343   0.449  1.00  72.61
ATOM    1244  CB   SER  463   32.544  14.942  -1.005  1.00  73.38
ATOM    1245  C    SER  463   31.126  16.362   0.491  1.00  71.17
ATOM    1246  O    SER  463   30.455  16.528   1.511  1.00  72.05
ATOM    1247  N    SER  464   30.932  17.049  -0.633  1.00  68.86
ATOM    1248  CA   SER  464   29.892  18.063  -0.759  1.00  66.06
ATOM    1249  CB   SER  464   30.514  19.457  -0.704  1.00  66.26
ATOM    1250  C    SER  464   29.108  17.887  -2.060  1.00  63.72
ATOM    1251  O    SER  464   28.657  18.862  -2.662  1.00  62.88
ATOM    1252  N    THR  465   28.954  16.638  -2.493  1.00  60.93
ATOM    1253  CA   THR  465   28.205  16.343  -3.709  1.00  57.47
ATOM    1254  CB   THR  465   28.185  14.824  -4.004  1.00  57.80
ATOM    1255  OG1  THR  465   27.525  14.135  -2.934  1.00  54.75
ATOM    1256  CG2  THR  465   29.606  14.287  -4.149  1.00  57.49
ATOM    1257  C    THR  465   26.767  16.824  -3.523  1.00  54.93
ATOM    1258  O    THR  465   26.349  17.129  -2.407  1.00  54.26
ATOM    1259  N    LEU  466   26.013  16.892  -4.614  1.00  51.85
ATOM    1260  CA   LEU  466   24.625  17.330  -4.550  1.00  49.25
ATOM    1261  CB   LEU  466   24.013  17.349  -5.956  1.00  48.74
ATOM    1262  CG   LEU  466   22.953  18.415  -6.253  1.00  48.72
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1263  CD1  LEU  466   22.156  18.002  -7.482  1.00  48.32
ATOM   1264  CD2  LEU  466   22.033  18.594  -5.057  1.00  48.14
ATOM   1265  C    LEU  466   23.817  16.397  -3.650  1.00  48.16
ATOM   1266  O    LEU  466   22.961  16.845  -2.883  1.00  45.90
ATOM   1267  N    LYS  467   24.093  15.099  -3.750  1.00  46.47
ATOM   1268  CA   LYS  467   23.399  14.100  -2.947  1.00  47.45
ATOM   1269  CB   LYS  467   23.802  12.693  -3.395  1.00  49.38
ATOM   1270  CG   LYS  467   22.829  11.602  -2.974  1.00  32.70
ATOM   1271  CD   LYS  467   23.561  10.301  -2.682  1.00  56.48
ATOM   1272  CE   LYS  467   23.105   9.180  -3.604  1.00  59.54
ATOM   1273  NZ   LYS  467   24.150   8.117  -3.732  1.00  61.22
ATOM   1274  C    LYS  467   23.738  14.284  -1.472  1.00  46.89
ATOM   1275  O    LYS  467   22.884  14.108  -0.604  1.00  46.06
ATOM   1276  N    SER  468   24.989  14.644  -1.202  1.00  45.82
ATOM   1277  CA   SER  468   25.457  14.854   0.160  1.00  46.82
ATOM   1278  CB   SER  468   26.976  15.050   0.173  1.00  47.85
ATOM   1279  OG   SER  468   27.407  15.837   1.435  1.00  55.73
ATOM   1280  C    SER  468   24.778  16.063   0.790  1.00  44.24
ATOM   1281  O    SER  468   24.473  16.062   1.983  1.00  42.98
ATOM   1282  N    LEU  469   24.547  17.100  -0.011  1.00  42.33
ATOM   1283  CA   LEU  469   23.890  18.301   0.486  1.00  40.42
ATOM   1284  CB   LEU  469   24.002  19.427  -0.545  1.00  44.47
ATOM   1285  CG   LEU  469   25.438  19.874  -0.849  1.00  46.70
ATOM   1286  CD1  LEU  469   25.514  20.477  -2.246  1.00  46.70
ATOM   1287  CD2  LEU  469   25.890  20.883   0.199  1.00  47.32
ATOM   1288  C    LEU  469   22.423  17.996   0.786  1.00  39.06
ATOM   1289  O    LEU  469   21.856  18.505   1.760  1.00  34.97
ATOM   1290  N    GLU  470   21.814  17.151  -0.046  1.00  35.46
ATOM   1291  CA   GLU  470   20.418  16.768   0.145  1.00  34.38
ATOM   1292  CB   GLU  470   19.914  15.963  -1.052  1.00  38.02
ATOM   1293  CG   GLU  470   19.772  16.773  -2.329  1.00  42.67
ATOM   1294  CD   GLU  470   19.339  15.923  -3.509  1.00  48.30
ATOM   1295  OE1  GLU  470   19.671  14.716  -3.538  1.00  50.53
ATOM   1296  OE2  GLU  470   18.666  16.463  -4.412  1.00  51.06
ATOM   1297  C    GLU  470   20.290  15.916   1.403  1.00  34.37
ATOM   1298  O    GLU  470   19.321  16.035   2.157  1.00  32.60
ATOM   1299  N    GLU  471   21.274  15.046   1.606  1.00  34.66
ATOM   1300  CA   GLU  471   21.309  14.162   2.766  1.00  35.68
ATOM   1301  CB   GLU  471   22.515  13.222   2.671  1.00  34.57
ATOM   1302  CG   GLU  471   22.376  12.122   1.614  1.00  37.98
ATOM   1303  CD   GLU  471   21.476  10.989   2.063  1.00  39.79
ATOM   1304  OE1  GLU  471   20.268  11.027   1.743  1.00  41.12
ATOM   1305  OE2  GLU  471   21.974  10.061   2.737  1.00  32.11
ATOM   1306  C    GLU  471   21.393  14.983   4.052  1.00  34.79
ATOM   1307  O    GLU  471   20.596  14.793   4.969  1.00  32.80
ATOM   1308  N    LYS  472   22.358  15.898   4.112  1.00  33.93
ATOM   1309  CA   LYS  472   22.518  16.739   5.291  1.00  35.58
ATOM   1310  CB   LYS  472   23.683  17.710   5.097  1.00  39.11
ATOM   1311  CG   LYS  472   25.050  17.050   5.138  1.00  41.47
ATOM   1312  CD   LYS  472   26.080  17.957   5.794  1.00  46.97
ATOM   1313  CE   LYS  472   27.445  17.286   5.862  1.00  48.40
ATOM   1314  NZ   LYS  472   27.850  16.702   4.547  1.00  51.55
ATOM   1315  C    LYS  472   21.237  17.523   5.582  1.00  34.78
ATOM   1316  O    LYS  472   20.795  17.607   6.724  1.00  33.95
ATOM   1317  N    ASP  473   20.643  18.097   4.545  1.00  33.47
ATOM   1318  CA   ASP  473   19.420  18.865   4.720  1.00  34.63
ATOM   1319  CB   ASP  473   18.923  19.404   3.380  1.00  37.21
ATOM   1320  CG   ASP  473   17.654  20.221   3.522  1.00  43.24
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1321  OD1  ASP  473  16.559  19.687   3.230  1.00  45.20
ATOM   1322  OD2  ASP  473  17.750  21.396   3.932  1.00  45.69
ATOM   1323  C    ASP  473  18.339  17.998   5.338  1.00  32.93
ATOM   1324  O    ASP  473  17.642  18.416   6.264  1.00  32.87
ATOM   1325  N    HIS  474  18.199  16.784   4.827  1.00  32.74
ATOM   1326  CA   HIS  474  17.185  15.882   5.343  1.00  32.21
ATOM   1327  CB   HIS  474  17.185  14.575   4.568  1.00  32.79
ATOM   1328  CG   HIS  474  16.047  13.675   4.924  1.00  36.22
ATOM   1329  CD2  HIS  474  14.711  13.813   4.750  1.00  38.33
ATOM   1330  ND1  HIS  474  16.227  12.456   5.542  1.00  38.97
ATOM   1331  CE1  HIS  474  15.053  11.883   5.732  1.00  37.99
ATOM   1332  NE2  HIS  474  14.116  12.686   5.261  1.00  37.43
ATOM   1333  C    HIS  474  17.403  15.573   6.815  1.00  29.74
ATOM   1334  O    HIS  474  16.460  15.543   7.596  1.00  29.90
ATOM   1335  N    ILE  475  18.653  15.326   7.185  1.00  27.80
ATOM   1336  CA   ILE  475  18.971  15.014   8.571  1.00  25.61
ATOM   1337  CB   ILE  475  20.478  14.708   8.720  1.00  25.59
ATOM   1338  CG2  ILE  475  20.877  14.713  10.193  1.00  27.17
ATOM   1339  CG1  ILE  475  20.787  13.341   8.092  1.00  26.17
ATOM   1340  CD1  ILE  475  22.258  13.071   7.849  1.00  27.07
ATOM   1341  C    ILE  475  18.576  16.201   9.460  1.00  27.91
ATOM   1342  O    ILE  475  17.928  16.038  10.485  1.00  29.16
ATOM   1343  N    HIS  476  18.956  17.404   9.054  1.00  29.41
ATOM   1344  CA   HIS  476  18.621  18.575   9.846  1.00  29.73
ATOM   1345  CB   HIS  476  19.342  19.796   9.281  1.00  32.27
ATOM   1346  CG   HIS  476  20.777  19.867   9.699  1.00  39.44
ATOM   1347  CD2  HIS  476  21.355  19.707  10.915  1.00  39.81
ATOM   1348  ND1  HIS  476  21.809  20.067   8.808  1.00  39.79
ATOM   1349  CE1  HIS  476  22.959  20.027   9.456  1.00  39.98
ATOM   1350  NE2  HIS  476  22.712  19.809  10.735  1.00  40.26
ATOM   1351  C    HIS  476  17.120  18.810   9.948  1.00  31.40
ATOM   1352  O    HIS  476  16.636  19.336  10.951  1.00  29.79
ATOM   1353  N    ARG  477  16.374  18.396   8.929  1.00  31.82
ATOM   1354  CA   ARG  477  14.929  18.570   8.956  1.00  31.53
ATOM   1355  CB   ARG  477  14.343  18.376   7.557  1.00  34.95
ATOM   1356  CG   ARG  477  14.425  19.627   6.700  1.00  40.46
ATOM   1357  CD   ARG  477  13.698  19.445   5.370  1.00  45.22
ATOM   1358  NE   ARG  477  14.107  20.456   4.399  1.00  53.05
ATOM   1359  CZ   ARG  477  13.647  21.705   4.376  1.00  55.89
ATOM   1360  NH1  ARG  477  12.756  22.106   5.274  1.00  56.17
ATOM   1361  NH2  ARG  477  14.084  22.558   3.487  1.00  59.49
ATOM   1362  C    ARG  477  14.310  17.582   9.931  1.00  30.70
ATOM   1363  O    ARG  477  13.360  17.903  10.649  1.00  30.24
ATOM   1364  N    VAL  478  14.863  16.375   9.972  1.00  29.67
ATOM   1365  CA   VAL  478  14.351  15.369  10.887  1.00  29.68
ATOM   1366  CB   VAL  478  14.937  13.975  10.575  1.00  32.01
ATOM   1367  CG1  VAL  478  14.461  12.973  11.609  1.00  32.93
ATOM   1368  CG2  VAL  478  14.506  13.528   9.169  1.00  31.00
ATOM   1369  C    VAL  478  14.696  15.774  12.316  1.00  29.81
ATOM   1370  O    VAL  478  13.860  15.677  13.220  1.00  30.25
ATOM   1371  N    LEU  479  15.929  16.232  12.516  1.00  28.81
ATOM   1372  CA   LEU  479  16.360  16.674  13.836  1.00  28.74
ATOM   1373  CB   LEU  479  17.799  17.210  13.779  1.00  26.65
ATOM   1374  CG   LEU  479  18.910  16.152  13.853  1.00  26.05
ATOM   1375  CD1  LEU  479  20.231  16.772  13.395  1.00  25.81
ATOM   1376  CD2  LEU  479  19.028  15.603  15.277  1.00  25.34
ATOM   1377  C    LEU  479  15.411  17.777  14.313  1.00  29.54
ATOM   1378  O    LEU  479  14.997  17.786  15.472  1.00  29.00
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1379  N    ASP  480   15.076  18.703  13.415  1.00  31.52
ATOM   1380  CA   ASP  480   14.162  19.800  13.741  1.00  33.84
ATOM   1381  CB   ASP  480   13.943  20.712  12.528  1.00  34.37
ATOM   1382  CG   ASP  480   15.055  21.743  12.345  1.00  36.26
ATOM   1383  OD1  ASP  480   15.119  22.354  11.257  1.00  36.56
ATOM   1384  OD2  ASP  480   15.860  21.951  13.374  1.00  34.19
ATOM   1385  C    ASP  480   12.818  19.222  14.174  1.00  33.48
ATOM   1386  O    ASP  480   12.186  19.724  15.105  1.00  33.89
ATOM   1387  N    LYS  481   12.379  18.161  13.498  1.00  33.90
ATOM   1388  CA   LYS  481   11.106  17.536  13.839  1.00  32.97
ATOM   1389  CB   LYS  481   10.719  16.489  12.784  1.00  34.66
ATOM   1390  C    LYS  481   11.164  16.895  15.235  1.00  33.37
ATOM   1391  O    LYS  481   10.167  16.869  15.943  1.00  35.37
ATOM   1392  N    ILE  482   12.328  16.377  15.607  1.00  32.71
ATOM   1393  CA   ILE  482   12.487  15.764  16.922  1.00  31.60
ATOM   1394  CB   ILE  482   13.743  14.913  17.028  1.00  32.65
ATOM   1395  CG2  ILE  482   13.877  14.338  18.430  1.00  32.50
ATOM   1396  CG1  ILE  482   13.697  13.785  15.995  1.00  32.72
ATOM   1397  CD1  ILE  482   14.978  12.969  15.908  1.00  33.37
ATOM   1398  C    ILE  482   12.456  16.853  17.994  1.00  31.69
ATOM   1399  O    ILE  482   11.946  16.649  19.097  1.00  29.98
ATOM   1400  N    THR  483   13.027  18.012  17.679  1.00  31.33
ATOM   1401  CA   THR  483   13.022  19.109  18.644  1.00  31.71
ATOM   1402  CB   THR  483   13.756  20.351  18.109  1.00  32.92
ATOM   1403  OG1  THR  483   15.111  20.012  17.788  1.00  29.99
ATOM   1404  CG2  THR  483   13.756  21.452  19.160  1.00  30.47
ATOM   1405  C    THR  483   11.559  19.483  18.920  1.00  32.85
ATOM   1406  O    THR  483   11.146  19.598  20.070  1.00  31.83
ATOM   1407  N    ASP  484   10.785  19.656  17.851  1.00  31.91
ATOM   1408  CA   ASP  484    9.369  20.003  17.965  1.00  34.15
ATOM   1409  CB   ASP  484    8.708  20.013  16.591  1.00  37.41
ATOM   1410  CG   ASP  484    9.270  21.080  15.680  1.00  42.02
ATOM   1411  OD1  ASP  484    9.871  22.045  16.198  1.00  43.26
ATOM   1412  OD2  ASP  484    9.106  20.952  14.445  1.00  42.49
ATOM   1413  C    ASP  484    8.657  18.985  18.840  1.00  33.16
ATOM   1414  O    ASP  484    7.830  19.339  19.676  1.00  34.86
ATOM   1415  N    THR  485    8.996  17.715  18.646  1.00  33.91
ATOM   1416  CA   THR  485    8.396  16.635  19.414  1.00  34.41
ATOM   1417  CB   THR  485    8.875  15.268  18.885  1.00  33.58
ATOM   1418  OG1  THR  485    8.400  15.094  17.542  1.00  37.04
ATOM   1419  CG2  THR  485    8.347  14.138  19.751  1.00  30.89
ATOM   1420  C    THR  485    8.708  16.757  20.903  1.00  35.15
ATOM   1421  O    THR  485    7.818  16.600  21.744  1.00  31.99
ATOM   1422  N    LEU  486    9.966  17.046  21.229  1.00  33.77
ATOM   1423  CA   LEU  486   10.368  17.192  22.621  1.00  34.31
ATOM   1424  CB   LEU  486   11.879  17.448  22.721  1.00  32.00
ATOM   1425  CG   LEU  486   12.776  16.201  22.754  1.00  34.99
ATOM   1426  CD1  LEU  486   14.233  16.613  22.521  1.00  32.65
ATOM   1427  CD2  LEU  486   12.635  15.481  24.105  1.00  29.90
ATOM   1428  C    LEU  486    9.597  18.348  23.256  1.00  34.87
ATOM   1429  O    LEU  486    9.078  18.225  24.362  1.00  35.85
ATOM   1430  N    ILE  487    9.513  19.469  22.548  1.00  35.59
ATOM   1431  CA   ILE  487    8.787  20.625  23.064  1.00  36.79
ATOM   1432  CB   ILE  487    8.890  21.826  22.095  1.00  37.32
ATOM   1433  CG2  ILE  487    7.833  22.884  22.443  1.00  40.19
ATOM   1434  CG1  ILE  487   10.292  22.443  22.181  1.00  36.00
ATOM   1435  CD1  ILE  487   10.635  23.041  23.544  1.00  33.58
ATOM   1436  C    ILE  487    7.315  20.257  23.276  1.00  38.56
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1437  O    ILE  487   6.708  20.628  24.282  1.00  38.52
ATOM   1438  N    HIS  488   6.749  19.521  22.326  1.00  40.33
ATOM   1439  CA   HIS  488   5.357  19.096  22.427  1.00  42.29
ATOM   1440  CB   HIS  488   4.962  18.282  21.197  1.00  44.26
ATOM   1441  CG   HIS  488   3.612  17.647  21.305  1.00  47.75
ATOM   1442  CD2  HIS  488   2.369  18.175  21.214  1.00  47.46
ATOM   1443  ND1  HIS  488   3.440  16.298  21.534  1.00  51.09
ATOM   1444  CE1  HIS  488   2.148  16.023  21.577  1.00  51.15
ATOM   1445  NE2  HIS  488   1.477  17.144  21.385  1.00  50.22
ATOM   1446  C    HIS  488   5.154  18.254  23.685  1.00  42.55
ATOM   1447  O    HIS  488   4.233  18.498  24.467  1.00  43.02
ATOM   1448  N    LEU  489   6.022  17.266  23.879  1.00  39.91
ATOM   1449  CA   LEU  489   5.936  16.399  25.048  1.00  39.93
ATOM   1450  CB   LEU  489   7.087  15.396  25.048  1.00  38.83
ATOM   1451  CG   LEU  489   6.961  14.242  24.036  1.00  39.31
ATOM   1452  CD1  LEU  489   8.259  13.456  24.027  1.00  39.01
ATOM   1453  CD2  LEU  489   5.799  13.345  24.459  1.00  41.98
ATOM   1454  C    LEU  489   5.973  17.203  26.339  1.00  40.24
ATOM   1455  O    LEU  489   5.267  16.888  27.298  1.00  38.72
ATOM   1456  N    MET  490   6.798  18.246  26.353  1.00  39.94
ATOM   1457  CA   MET  490   6.939  19.102  27.522  1.00  41.50
ATOM   1458  CB   MET  490   8.208  19.953  27.394  1.00  39.15
ATOM   1459  CG   MET  490   9.495  19.169  27.608  1.00  41.69
ATOM   1460  SD   MET  490  10.978  20.106  27.161  1.00  35.76
ATOM   1461  CE   MET  490  12.178  18.775  27.056  1.00  39.22
ATOM   1462  C    MET  490   5.718  20.004  27.717  1.00  42.33
ATOM   1463  O    MET  490   5.296  20.258  28.848  1.00  41.09
ATOM   1464  N    ALA  491   5.162  20.498  26.616  1.00  43.15
ATOM   1465  CA   ALA  491   3.983  21.351  26.693  1.00  43.79
ATOM   1466  CB   ALA  491   3.622  21.879  25.311  1.00  43.93
ATOM   1467  C    ALA  491   2.841  20.510  27.251  1.00  46.16
ATOM   1468  O    ALA  491   2.073  20.967  28.095  1.00  44.69
ATOM   1469  N    LYS  492   2.752  19.268  26.783  1.00  46.29
ATOM   1470  CA   LYS  492   1.711  18.351  27.222  1.00  49.90
ATOM   1471  CB   LYS  492   1.772  17.053  26.411  1.00  50.03
ATOM   1472  CG   LYS  492   1.087  17.135  25.062  1.00  53.81
ATOM   1473  CD   LYS  492  -0.002  16.084  24.930  1.00  59.00
ATOM   1474  CE   LYS  492  -0.988  16.453  23.827  1.00  61.85
ATOM   1475  NZ   LYS  492  -1.351  15.281  22.976  1.00  62.89
ATOM   1476  C    LYS  492   1.841  18.025  28.701  1.00  51.15
ATOM   1477  O    LYS  492   0.845  17.784  29.379  1.00  53.37
ATOM   1478  N    ALA  493   3.072  18.012  29.199  1.00  50.15
ATOM   1479  CA   ALA  493   3.321  17.706  30.600  1.00  49.17
ATOM   1480  CB   ALA  493   4.777  17.314  30.794  1.00  50.39
ATOM   1481  C    ALA  493   2.971  18.885  31.501  1.00  49.36
ATOM   1482  O    ALA  493   3.089  18.799  32.723  1.00  51.57
ATOM   1483  N    GLY  494   2.554  19.989  30.893  1.00  48.61
ATOM   1484  CA   GLY  494   2.185  21.159  31.671  1.00  46.92
ATOM   1485  C    GLY  494   3.322  22.107  32.006  1.00  45.46
ATOM   1486  O    GLY  494   3.206  22.921  32.919  1.00  43.58
ATOM   1487  N    LEU  495   4.431  22.009  31.284  1.00  44.81
ATOM   1488  CA   LEU  495   5.555  22.899  31.540  1.00  42.34
ATOM   1489  CB   LEU  495   6.847  22.293  30.988  1.00  43.79
ATOM   1490  CG   LEU  495   7.712  21.459  31.936  1.00  40.99
ATOM   1491  CD1  LEU  495   7.022  20.156  32.260  1.00  44.70
ATOM   1492  CD2  LEU  495   9.072  21.189  31.270  1.00  42.12
ATOM   1493  C    LEU  495   5.278  24.227  30.847  1.00  42.13
ATOM   1494  O    LEU  495   4.664  24.258  29.778  1.00  42.49
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1495  N    THR  496    5.718   25.324   31.452  1.00  42.73
ATOM   1496  CA   THR  496    5.521   26.636   30.845  1.00  43.56
ATOM   1497  CB   THR  496    5.841   27.767   31.829  1.00  46.09
ATOM   1498  OG1  THR  496    7.222   27.688   32.208  1.00  43.92
ATOM   1499  CG2  THR  496    4.965   27.662   33.064  1.00  45.63
ATOM   1500  C    THR  496    6.471   26.764   29.660  1.00  45.54
ATOM   1501  O    THR  496    7.370   25.939   29.488  1.00  43.39
ATOM   1502  N    LEU  497    6.280   27.800   28.849  1.00  45.02
ATOM   1503  CA   LEU  497    7.135   28.020   27.688  1.00  45.12
ATOM   1504  CB   LEU  497    6.710   29.286   26.944  1.00  46.62
ATOM   1505  CG   LEU  497    5.933   29.080   25.640  1.00  50.30
ATOM   1506  CD1  LEU  497    5.886   30.397   24.875  1.00  50.95
ATOM   1507  CD2  LEU  497    6.589   27.990   24.798  1.00  50.91
ATOM   1508  C    LEU  497    8.599   28.135   28.101  1.00  44.94
ATOM   1509  O    LEU  497    9.474   27.516   27.493  1.00  45.03
ATOM   1510  N    GLN  498    8.862   28.927   29.137  1.00  41.14
ATOM   1511  CA   GLN  498   10.221   29.101   29.627  1.00  40.54
ATOM   1512  CB   GLN  498   10.246   30.140   30.743  1.00  43.82
ATOM   1513  CG   GLN  498   11.585   30.270   31.437  1.00  43.37
ATOM   1514  CD   GLN  498   11.539   31.260   32.584  1.00  47.03
ATOM   1515  OE1  GLN  498   10.565   31.308   33.332  1.00  49.18
ATOM   1516  NE2  GLN  498   12.591   32.054   32.727  1.00  45.30
ATOM   1517  C    GLN  498   10.777   27.773   30.145  1.00  39.39
ATOM   1518  O    GLN  498   11.923   27.422   29.866  1.00  35.05
ATOM   1519  N    GLN  499    9.965   27.040   30.902  1.00  36.49
ATOM   1520  CA   GLN  499   10.391   25.748   31.434  1.00  36.91
ATOM   1521  CB   GLN  499    9.314   25.155   32.344  1.00  38.84
ATOM   1522  CG   GLN  499    9.155   25.825   33.703  1.00  41.33
ATOM   1523  CD   GLN  499    8.039   25.187   34.512  1.00  42.74
ATOM   1524  OE1  GLN  499    7.027   24.760   33.955  1.00  45.44
ATOM   1525  NE2  GLN  499    8.222   25.107   35.829  1.00  43.48
ATOM   1526  C    GLN  499   10.655   24.773   30.285  1.00  35.03
ATOM   1527  O    GLN  499   11.446   23.832   30.422  1.00  36.59
ATOM   1528  N    GLN  500    9.980   24.994   29.162  1.00  34.14
ATOM   1529  CA   GLN  500   10.136   24.138   27.990  1.00  34.65
ATOM   1530  CB   GLN  500    9.042   24.436   26.958  1.00  33.90
ATOM   1531  CG   GLN  500    7.672   23.872   27.315  1.00  36.63
ATOM   1532  CD   GLN  500    6.558   24.419   26.435  1.00  40.17
ATOM   1533  OE1  GLN  500    6.660   24.417   25.207  1.00  40.22
ATOM   1534  NE2  GLN  500    5.482   24.886   27.064  1.00  41.82
ATOM   1535  C    GLN  500   11.511   24.350   27.358  1.00  34.96
ATOM   1536  O    GLN  500   12.256   23.387   27.124  1.00  30.79
ATOM   1537  N    HIS  501   11.835   25.612   27.078  1.00  34.21
ATOM   1538  CA   HIS  501   13.117   25.966   26.480  1.00  37.42
ATOM   1539  CB   HIS  501   13.195   27.476   26.246  1.00  43.08
ATOM   1540  CG   HIS  501   12.043   28.027   25.468  1.00  51.13
ATOM   1541  CD2  HIS  501   11.534   27.678   24.263  1.00  53.05
ATOM   1542  ND1  HIS  501   11.264   29.068   25.926  1.00  54.54
ATOM   1543  CE1  HIS  501   10.325   29.337   25.037  1.00  54.36
ATOM   1544  NE2  HIS  501   10.466   28.508   24.018  1.00  55.19
ATOM   1545  C    HIS  501   14.255   25.543   27.395  1.00  35.79
ATOM   1546  O    HIS  501   15.271   24.996   26.945  1.00  36.20
ATOM   1547  N    GLN  502   14.086   25.799   28.685  1.00  33.90
ATOM   1548  CA   GLN  502   15.110   25.438   29.650  1.00  32.18
ATOM   1549  CB   GLN  502   14.740   25.977   31.033  1.00  35.84
ATOM   1550  CG   GLN  502   14.787   27.498   31.113  1.00  32.66
ATOM   1551  CD   GLN  502   14.420   28.028   32.486  1.00  36.62
ATOM   1552  OE1  GLN  502   14.102   27.262   33.397  1.00  33.99
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1553  NE2  GLN  502  14.462  29.348  32.640  1.00  36.22
ATOM   1554  C    GLN  502  15.340  23.932  29.716  1.00  31.79
ATOM   1555  O    GLN  502  16.483  23.479  29.769  1.00  28.00
ATOM   1556  N    ARG  503  14.366  23.146  29.705  1.00  30.99
ATOM   1557  CA   ARG  503  14.436  21.704  29.779  1.00  29.91
ATOM   1558  CB   ARG  503  13.107  21.011  30.053  1.00  32.79
ATOM   1559  CG   ARG  503  13.258  19.541  30.400  1.00  30.84
ATOM   1560  CD   ARG  503  11.930  18.935  30.798  1.00  30.61
ATOM   1561  NE   ARG  503  12.021  17.490  30.992  1.00  28.50
ATOM   1562  CZ   ARG  503  12.489  16.908  32.093  1.00  29.00
ATOM   1563  NH1  ARG  503  12.917  17.640  33.114  1.00  29.85
ATOM   1564  NH2  ARG  503  12.512  15.583  32.180  1.00  33.73
ATOM   1565  C    ARG  503  15.051  21.152  28.496  1.00  29.89
ATOM   1566  O    ARG  503  15.895  20.259  28.548  1.00  29.69
ATOM   1567  N    LEU  504  14.624  21.675  27.351  1.00  28.99
ATOM   1568  CA   LEU  504  15.164  21.223  26.075  1.00  28.90
ATOM   1569  CB   LEU  504  14.566  22.023  24.916  1.00  27.72
ATOM   1570  CG   LEU  504  15.327  21.901  23.593  1.00  30.47
ATOM   1571  CD1  LEU  504  15.252  20.453  23.117  1.00  31.74
ATOM   1572  CD2  LEU  504  14.742  22.843  22.542  1.00  29.85
ATOM   1573  C    LEU  504  16.681  21.419  26.089  1.00  29.69
ATOM   1574  O    LEU  504  17.439  20.536  25.672  1.00  26.38
ATOM   1575  N    ALA  505  17.114  22.585  26.564  1.00  28.51
ATOM   1576  CA   ALA  505  18.535  22.899  26.632  1.00  25.98
ATOM   1577  CB   ALA  505  18.735  24.361  27.039  1.00  29.86
ATOM   1578  C    ALA  505  19.261  21.977  27.604  1.00  26.67
ATOM   1579  O    ALA  505  20.340  21.462  27.290  1.00  25.54
ATOM   1580  N    GLN  506  18.677  21.771  28.784  1.00  23.59
ATOM   1581  CA   GLN  506  19.299  20.907  29.785  1.00  27.67
ATOM   1582  CB   GLN  506  18.434  20.796  31.043  1.00  27.75
ATOM   1583  CG   GLN  506  18.414  22.027  31.945  1.00  32.48
ATOM   1584  CD   GLN  506  17.111  22.116  32.736  1.00  38.40
ATOM   1585  OE1  GLN  506  16.319  21.167  32.754  1.00  35.97
ATOM   1586  NE2  GLN  506  16.879  23.257  33.386  1.00  38.07
ATOM   1587  C    GLN  506  19.500  19.509  29.217  1.00  24.53
ATOM   1588  O    GLN  506  20.536  18.889  29.441  1.00  26.42
ATOM   1589  N    LEU  507  18.505  19.017  28.484  1.00  26.78
ATOM   1590  CA   LEU  507  18.578  17.678  27.902  1.00  26.18
ATOM   1591  CB   LEU  507  17.225  17.286  27.395  1.00  31.48
ATOM   1592  CG   LEU  507  16.052  16.961  28.231  1.00  32.59
ATOM   1593  CD1  LEU  507  14.836  16.561  27.389  1.00  33.78
ATOM   1594  CD2  LEU  507  16.431  15.838  29.174  1.00  30.18
ATOM   1595  C    LEU  507  19.652  17.583  26.819  1.00  26.03
ATOM   1596  O    LEU  507  20.421  16.621  26.771  1.00  27.28
ATOM   1597  N    LEU  508  19.713  18.583  25.950  1.00  24.31
ATOM   1598  CA   LEU  508  20.690  18.557  24.863  1.00  23.68
ATOM   1599  CB   LEU  508  20.339  19.629  23.828  1.00  23.91
ATOM   1600  CG   LEU  508  19.004  19.436  23.102  1.00  24.68
ATOM   1601  CD1  LEU  508  18.905  20.416  21.945  1.00  25.11
ATOM   1602  CD2  LEU  508  18.903  17.994  22.580  1.00  27.53
ATOM   1603  C    LEU  508  22.127  18.727  25.341  1.00  22.93
ATOM   1604  O    LEU  508  23.062  18.200  24.736  1.00  21.36
ATOM   1605  N    LEU  509  22.302  19.451  26.441  1.00  23.86
ATOM   1606  CA   LEU  509  23.637  19.661  26.991  1.00  26.28
ATOM   1607  CB   LEU  509  23.598  20.735  28.095  1.00  28.08
ATOM   1608  CG   LEU  509  23.578  22.214  27.672  1.00  33.98
ATOM   1609  CD1  LEU  509  23.529  23.114  28.921  1.00  35.23
ATOM   1610  CD2  LEU  509  24.818  22.525  26.855  1.00  30.48
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1611  C    LEU  509   24.154  18.327  27.540  1.00  26.08
ATOM   1612  O    LEU  509   25.354  18.068  27.547  1.00  23.92
ATOM   1613  N    ILE  510   23.254  17.462  27.993  1.00  24.60
ATOM   1614  CA   ILE  510   23.712  16.172  28.496  1.00  25.12
ATOM   1615  CB   ILE  510   22.568  15.368  29.161  1.00  28.51
ATOM   1616  CG2  ILE  510   23.051  13.965  29.506  1.00  31.67
ATOM   1617  CG1  ILE  510   22.141  16.060  30.459  1.00  31.19
ATOM   1618  CD1  ILE  510   20.713  15.749  30.882  1.00  37.16
ATOM   1619  C    ILE  510   24.337  15.351  27.364  1.00  23.86
ATOM   1620  O    ILE  510   25.225  14.534  27.600  1.00  24.14
ATOM   1621  N    LEU  511   23.889  15.586  26.133  1.00  25.10
ATOM   1622  CA   LEU  511   24.420  14.862  24.977  1.00  25.63
ATOM   1623  CB   LEU  511   23.628  15.225  23.714  1.00  23.85
ATOM   1624  CG   LEU  511   22.152  14.801  23.659  1.00  25.78
ATOM   1625  CD1  LEU  511   21.648  14.920  22.224  1.00  26.55
ATOM   1626  CD2  LEU  511   21.990  13.363  24.146  1.00  26.29
ATOM   1627  C    LEU  511   25.912  15.152  24.771  1.00  27.10
ATOM   1628  O    LEU  511   26.641  14.332  24.214  1.00  24.98
ATOM   1629  N    SER  512   26.372  16.319  25.213  1.00  24.75
ATOM   1630  CA   SER  512   27.787  16.637  25.076  1.00  23.68
ATOM   1631  CB   SER  512   28.023  18.129  25.358  1.00  26.12
ATOM   1632  OG   SER  512   29.271  18.327  25.986  1.00  37.17
ATOM   1633  C    SER  512   28.594  15.765  26.050  1.00  23.15
ATOM   1634  O    SER  512   29.742  15.383  25.769  1.00  22.15
ATOM   1635  N    AHIS 513   27.993  15.456  27.192  0.50  21.53
ATOM   1636  N    BHIS 513   28.008  15.453  27.202  0.50  20.99
ATOM   1637  CA   AHIS 513   28.645  14.624  28.196  0.50  21.79
ATOM   1638  CA   BHIS 513   28.696  14.607  28.174  0.50  20.94
ATOM   1639  CB   AHIS 513   27.920  14.776  29.536  0.50  23.59
ATOM   1640  CB   BHIS 513   27.991  14.636  29.536  0.50  21.59
ATOM   1641  CG   AHIS 513   28.145  16.109  30.179  0.50  27.34
ATOM   1642  CG   BHIS 513   28.800  14.032  30.642  0.50  23.94
ATOM   1643  CD2  AHIS 513   29.223  16.816  30.824  0.50  27.56
ATOM   1644  CD2  BHIS 513   30.095  14.211  31.001  0.50  24.22
ATOM   1645  ND1  AHIS 513   27.204  17.117  30.160  0.50  30.62
ATOM   1646  ND1  BHIS 513   28.285  13.105  31.523  0.50  27.00
ATOM   1647  CE1  AHIS 513   27.693  18.185  30.763  0.50  26.32
ATOM   1648  CE1  BHIS 513   29.225  12.740  32.376  0.50  24.40
ATOM   1649  NE2  AHIS 513   28.916  17.908  31.176  0.50  28.30
ATOM   1650  NE2  BHIS 513   30.334  13.396  32.081  0.50  25.54
ATOM   1651  C    AHIS 513   28.666  13.164  27.738  0.50  19.81
ATOM   1652  C    BHIS 513   28.720  13.171  27.652  0.50  19.42
ATOM   1653  O    AHIS 513   29.601  12.426  28.026  0.50  22.45
ATOM   1654  O    BHIS 513   29.707  12.457  27.809  0.50  22.62
ATOM   1655  N    ILE  514   27.633  12.753  27.015  1.00  20.76
ATOM   1656  CA   ILE  514   27.572  11.396  26.492  1.00  20.94
ATOM   1657  CB   ILE  514   26.154  11.086  25.953  1.00  27.76
ATOM   1658  CG2  ILE  514   26.169   9.800  25.123  1.00  28.26
ATOM   1659  CG1  ILE  514   25.185  10.965  27.139  1.00  27.91
ATOM   1660  CD1  ILE  514   23.752  10.649  26.753  1.00  34.31
ATOM   1661  C    ILE  514   28.641  11.256  25.398  1.00  20.66
ATOM   1662  O    ILE  514   29.298  10.226  25.285  1.00  22.21
ATOM   1663  N    ARG  515   28.825  12.294  24.589  1.00  20.48
ATOM   1664  CA   ARG  515   29.861  12.243  23.554  1.00  21.98
ATOM   1665  CB   ARG  515   29.861  13.535  22.726  1.00  23.11
ATOM   1666  CG   ARG  515   31.003  13.611  21.737  1.00  25.76
ATOM   1667  CD   ARG  515   30.664  12.818  20.491  1.00  28.55
ATOM   1668  NE   ARG  515   29.580  13.482  19.788  1.00  36.24
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1669  CZ   ARG  515   29.615  13.827  18.508  1.00  38.91
ATOM   1670  NH1  ARG  515   30.689  13.566  17.796  1.00  35.37
ATOM   1671  NH2  ARG  515   28.579  14.459  17.971  1.00  40.27
ATOM   1672  C    ARG  515   31.221  12.087  24.225  1.00  21.29
ATOM   1673  O    ARG  515   32.068  11.305  23.795  1.00  30.06
ATOM   1674  N    HIS  516   31.420  12.844  25.293  1.00  23.23
ATOM   1675  CA   HIS  516   32.675  12.812  26.034  1.00  34.78
ATOM   1676  CB   HIS  516   32.566  13.794  27.206  1.00  34.03
ATOM   1677  CG   HIS  516   33.826  13.948  27.990  1.00  31.42
ATOM   1678  CD2  HIS  516   34.138  13.587  29.257  1.00  35.87
ATOM   1679  ND1  HIS  516   34.938  14.586  27.489  1.00  33.59
ATOM   1680  CE1  HIS  516   35.882  14.613  28.411  1.00  35.70
ATOM   1681  NE2  HIS  516   35.422  14.013  29.495  1.00  33.35
ATOM   1682  C    HIS  516   32.965  11.390  26.537  1.00  24.03
ATOM   1683  O    HIS  516   34.059  10.852  26.362  1.00  23.66
ATOM   1684  N    MET  517   31.969  10.786  27.168  1.00  20.91
ATOM   1685  CA   MET  517   32.109   9.436  27.684  1.00  24.21
ATOM   1686  CB   MET  517   30.837   9.038  28.424  1.00  23.88
ATOM   1687  CG   MET  517   30.607   9.903  29.693  1.00  26.32
ATOM   1688  SD   MET  517   29.435   9.222  30.790  1.00  26.67
ATOM   1689  CE   MET  517   27.914   9.390  29.807  1.00  23.26
ATOM   1690  C    MET  517   32.399   8.448  26.584  1.00  23.26
ATOM   1691  O    MET  517   33.213   7.547  26.728  1.00  26.08
ATOM   1692  N    SER  518   31.736   8.612  25.423  1.00  21.93
ATOM   1693  CA   SER  518   31.977   7.717  24.301  1.00  23.08
ATOM   1694  CB   SER  518   30.976   8.027  23.173  1.00  22.02
ATOM   1695  OG   SER  518   31.283   7.336  21.978  1.00  24.01
ATOM   1696  C    SER  518   33.432   7.862  23.810  1.00  25.15
ATOM   1697  O    SER  518   34.111   6.866  23.532  1.00  22.94
ATOM   1698  N    ASN  519   33.923   9.097  23.713  1.00  22.42
ATOM   1699  CA   ASN  519   35.295   9.309  23.260  1.00  21.87
ATOM   1700  CB   ASN  519   35.605  10.807  23.157  1.00  24.46
ATOM   1701  CG   ASN  519   34.864  11.469  22.021  1.00  29.02
ATOM   1702  OD1  ASN  519   34.661  10.864  20.965  1.00  31.93
ATOM   1703  ND2  ASN  519   34.459  12.715  22.224  1.00  28.81
ATOM   1704  C    ASN  519   36.293   8.643  24.201  1.00  21.46
ATOM   1705  O    ASN  519   37.251   8.015  23.752  1.00  23.55
ATOM   1706  N    LYS  520   36.070   8.782  25.504  1.00  23.23
ATOM   1707  CA   LYS  520   36.964   8.171  26.488  1.00  26.35
ATOM   1708  CB   LYS  520   36.581   8.592  27.913  1.00  27.83
ATOM   1709  CG   LYS  520   36.618  10.101  28.174  1.00  33.74
ATOM   1710  CD   LYS  520   37.962  10.710  27.811  1.00  42.09
ATOM   1711  CE   LYS  520   39.047  10.307  28.802  1.00  43.97
ATOM   1712  NZ   LYS  520   39.858  11.480  29.254  1.00  48.07
ATOM   1713  C    LYS  520   36.899   6.644  26.376  1.00  27.71
ATOM   1714  O    LYS  520   37.913   5.957  26.501  1.00  27.15
ATOM   1715  N    GLY  521   35.704   6.117  26.141  1.00  25.02
ATOM   1716  CA   GLY  521   35.562   4.676  26.003  1.00  26.67
ATOM   1717  C    GLY  521   36.254   4.168  24.753  1.00  27.06
ATOM   1718  O    GLY  521   36.924   3.128  24.775  1.00  25.84
ATOM   1719  N    AMET 522   36.101   4.893  23.650  0.50  25.87
ATOM   1720  N    BMET 522   35.095   4.908  23.658  0.50  27.62
ATOM   1721  CA   AMET 522   36.727   4.491  22.401  0.50  27.27
ATOM   1722  CA   BMET 522   35.703   4.551  22.384  0.50  30.14
ATOM   1723  CB   AMET 522   36.267   5.396  21.260  0.50  26.50
ATOM   1724  CB   BMET 522   35.252   5.525  21.288  0.50  32.46
ATOM   1725  CG   AMET 522   34.827   5.162  20.866  0.50  25.05
ATOM   1726  CG   BMET 522   35.681   4.854  20.045  0.50  35.70
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1727  SD   AMET  522   34.585   3.587   20.020  0.50  27.07
ATOM   1728  SD   BMET  522   34.197   5.672   19.408  0.50  40.01
ATOM   1729  CE   AMET  522   33.142   4.017   19.031  0.50  31.29
ATOM   1730  CE   BMET  522   34.733   6.085   17.745  0.50  42.13
ATOM   1731  C    AMET  522   38.242   4.532   22.512  0.50  28.99
ATOM   1732  C    BMET  522   38.224   4.567   22.483  0.50  30.76
ATOM   1733  O    AMET  522   38.939   3.743   21.870  0.50  31.65
ATOM   1734  O    BMET  522   38.905   3.793   21.807  0.50  32.87
ATOM   1735  N    GLU   523   38.749   5.452   23.324  1.00  30.85
ATOM   1736  CA   GLU   523   40.190   5.576   23.513  1.00  34.09
ATOM   1737  CB   GLU   523   40.515   6.725   24.480  1.00  35.59
ATOM   1738  CG   GLU   523   40.658   8.079   23.784  1.00  43.35
ATOM   1739  CD   GLU   523   40.560   9.265   24.739  1.00  46.83
ATOM   1740  OE1  GLU   523   39.832  10.240   24.416  1.00  47.64
ATOM   1741  OE2  GLU   523   41.212   9.225   25.808  1.00  43.09
ATOM   1742  C    GLU   523   40.718   4.260   24.061  1.00  34.62
ATOM   1743  O    GLU   523   41.733   3.747   23.596  1.00  33.87
ATOM   1744  N    HIS   524   40.021   3.700   25.042  1.00  36.33
ATOM   1745  CA   HIS   524   40.455   2.427   25.607  1.00  39.20
ATOM   1746  CB   HIS   524   39.678   2.093   26.878  1.00  40.75
ATOM   1747  CG   HIS   524   40.061   0.774   27.473  1.00  48.10
ATOM   1748  CD2  HIS   524   41.192   0.376   28.104  1.00  48.56
ATOM   1749  ND1  HIS   524   39.247  -0.338   27.412  1.00  48.84
ATOM   1750  CE1  HIS   524   39.859  -1.362   27.978  1.00  50.19
ATOM   1751  NE2  HIS   524   41.041  -0.956   28.407  1.00  51.61
ATOM   1752  C    HIS   524   40.290   1.282   24.613  1.00  38.06
ATOM   1753  O    HIS   524   41.226   0.521   24.371  1.00  38.18
ATOM   1754  N    LEU   525   39.101   1.162   24.034  1.00  36.96
ATOM   1755  CA   LEU   525   38.831   0.093   23.084  1.00  37.40
ATOM   1756  CB   LEU   525   37.416   0.241   22.514  1.00  35.89
ATOM   1757  CG   LEU   525   36.268   0.107   23.527  1.00  33.17
ATOM   1758  CD1  LEU   525   34.936   0.246   22.811  1.00  31.77
ATOM   1759  CD2  LEU   525   36.343  -1.240   24.238  1.00  35.92
ATOM   1760  C    LEU   525   39.859   0.057   21.954  1.00  41.32
ATOM   1761  O    LEU   525   40.244  -1.015   21.487  1.00  40.76
ATOM   1762  N    TYR   526   40.314   1.227   21.522  1.00  43.68
ATOM   1763  CA   TYR   526   41.300   1.297   20.449  1.00  49.00
ATOM   1764  CB   TYR   526   41.376   2.722   19.890  1.00  51.86
ATOM   1765  CG   TYR   526   42.305   2.878   18.704  1.00  57.70
ATOM   1766  CD1  TYR   526   41.835   2.718   17.400  1.00  58.93
ATOM   1767  CE1  TYR   526   42.681   2.875   16.305  1.00  61.21
ATOM   1768  CD2  TYR   526   43.653   3.200   18.883  1.00  58.58
ATOM   1769  CE2  TYR   526   44.510   3.359   17.790  1.00  61.15
ATOM   1770  CZ   TYR   526   44.016   3.194   16.505  1.00  61.09
ATOM   1771  OH   TYR   526   44.851   3.343   15.417  1.00  63.79
ATOM   1772  C    TYR   526   42.671   0.871   20.964  1.00  50.14
ATOM   1773  O    TYR   526   43.471   0.303   20.323  1.00  50.73
ATOM   1774  N    SER   527   42.930   1.139   22.240  1.00  52.72
ATOM   1775  CA   SER   527   44.205   0.790   22.857  1.00  55.88
ATOM   1776  CB   SER   527   44.351   1.516   24.199  1.00  55.00
ATOM   1777  OG   SER   527   43.752   0.788   25.257  1.00  52.46
ATOM   1778  C    SER   527   44.365  -0.718   23.054  1.00  60.39
ATOM   1779  O    SER   527   45.398  -1.185   23.534  1.00  60.43
ATOM   1780  N    MET   528   43.335  -1.472   22.678  1.00  63.86
ATOM   1781  CA   MET   528   43.347  -2.929   22.788  1.00  67.95
ATOM   1782  CB   MET   528   42.534  -3.381   24.008  1.00  67.85
ATOM   1783  CG   MET   528   41.237  -2.606   24.322  1.00  70.10
ATOM   1784  SD   MET   528   39.895  -3.569   24.983  1.00  71.70
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

| | | | | | | | | | |
|---|---|---|---|---|---|---|---|---|---|
| ATOM | 1785 | CE  | MET | 528 | 39.231 | -4.412  | 23.554 | 1.00 | 72.57 |
| ATOM | 1786 | C   | MET | 528 | 42.726 | -3.502  | 21.513 | 1.00 | 70.33 |
| ATOM | 1787 | O   | MET | 528 | 43.170 | -4.602  | 21.513 | 1.00 | 72.43 |
| ATOM | 1788 | N   | LYS | 529 | 42.834 | -2.739  | 20.428 | 1.00 | 71.53 |
| ATOM | 1789 | CA  | LYS | 529 | 42.274 | -3.122  | 19.136 | 1.00 | 72.00 |
| ATOM | 1790 | CB  | LYS | 529 | 42.508 | -2.004  | 18.119 | 1.00 | 71.30 |
| ATOM | 1791 | C   | LYS | 529 | 42.813 | -4.439  | 18.587 | 1.00 | 72.47 |
| ATOM | 1792 | O   | LYS | 529 | 43.990 | -4.762  | 18.751 | 1.00 | 70.37 |
| ATOM | 1793 | N   | CYS | 530 | 41.932 | -5.191  | 17.930 | 1.00 | 74.48 |
| ATOM | 1794 | CA  | CYS | 530 | 42.279 | -6.474  | 17.325 | 1.00 | 76.67 |
| ATOM | 1795 | CB  | CYS | 530 | 41.004 | -7.245  | 16.952 | 1.00 | 77.23 |
| ATOM | 1796 | SG  | CYS | 530 | 40.447 | -8.491  | 18.146 | 1.00 | 79.38 |
| ATOM | 1797 | C   | CYS | 530 | 43.098 | -6.220  | 16.065 | 1.00 | 78.08 |
| ATOM | 1798 | O   | CYS | 530 | 43.241 | -5.076  | 15.623 | 1.00 | 78.81 |
| ATOM | 1799 | N   | LYS | 531 | 43.637 | -7.289  | 15.487 | 1.00 | 78.22 |
| ATOM | 1800 | CA  | LYS | 531 | 44.424 | -7.187  | 14.267 | 1.00 | 78.15 |
| ATOM | 1801 | CB  | LYS | 531 | 45.600 | -8.182  | 14.305 | 1.00 | 78.33 |
| ATOM | 1802 | C   | LYS | 531 | 43.508 | -7.467  | 13.067 | 1.00 | 77.93 |
| ATOM | 1803 | O   | LYS | 531 | 42.549 | -6.734  | 12.839 | 1.00 | 78.07 |
| ATOM | 1804 | N   | ASN | 532 | 43.784 | -8.539  | 12.328 | 1.00 | 77.80 |
| ATOM | 1805 | CA  | ASN | 532 | 42.984 | -8.902  | 11.152 | 1.00 | 77.30 |
| ATOM | 1806 | CB  | ASN | 532 | 43.550 | -10.166 | 10.521 | 1.00 | 77.55 |
| ATOM | 1807 | C   | ASN | 532 | 41.485 | -9.082  | 11.423 | 1.00 | 77.34 |
| ATOM | 1808 | O   | ASN | 532 | 40.904 | -10.123 | 11.118 | 1.00 | 78.13 |
| ATOM | 1809 | N   | VAL | 533 | 40.859 | -8.055  | 11.998 | 1.00 | 76.13 |
| ATOM | 1810 | CA  | VAL | 533 | 39.436 | -8.098  | 12.380 | 1.00 | 73.77 |
| ATOM | 1811 | CB  | VAL | 533 | 39.155 | -7.715  | 13.752 | 1.00 | 73.62 |
| ATOM | 1812 | CG1 | VAL | 533 | 39.690 | -6.327  | 14.047 | 1.00 | 73.13 |
| ATOM | 1813 | CG2 | VAL | 533 | 37.662 | -7.782  | 14.021 | 1.00 | 73.14 |
| ATOM | 1814 | C   | VAL | 533 | 38.685 | -7.143  | 11.352 | 1.00 | 72.97 |
| ATOM | 1815 | O   | VAL | 533 | 39.024 | -5.960  | 11.252 | 1.00 | 73.91 |
| ATOM | 1816 | N   | VAL | 534 | 37.671 | -7.656  | 10.666 | 1.00 | 70.02 |
| ATOM | 1817 | CA  | VAL | 534 | 36.866 | -6.867  | 9.747  | 1.00 | 66.70 |
| ATOM | 1818 | CB  | VAL | 534 | 35.619 | -7.646  | 9.328  | 1.00 | 67.32 |
| ATOM | 1819 | C   | VAL | 534 | 36.463 | -5.541  | 10.393 | 1.00 | 63.87 |
| ATOM | 1820 | O   | VAL | 534 | 35.895 | -5.519  | 11.486 | 1.00 | 63.55 |
| ATOM | 1821 | N   | PRO | 535 | 36.756 | -4.415  | 9.719  | 1.00 | 60.92 |
| ATOM | 1822 | CD  | PRO | 535 | 37.424 | -4.354  | 8.408  | 1.00 | 61.01 |
| ATOM | 1823 | CA  | PRO | 535 | 36.424 | -3.077  | 10.229 | 1.00 | 56.83 |
| ATOM | 1824 | CB  | PRO | 535 | 36.867 | -2.135  | 9.107  | 1.00 | 58.70 |
| ATOM | 1825 | CG  | PRO | 535 | 37.023 | -3.009  | 7.893  | 1.00 | 61.55 |
| ATOM | 1826 | C   | PRO | 535 | 34.944 | -2.902  | 10.371 | 1.00 | 52.90 |
| ATOM | 1827 | O   | PRO | 535 | 34.067 | -3.461  | 9.908  | 1.00 | 52.01 |
| ATOM | 1828 | N   | LEU | 536 | 34.672 | -2.120  | 11.610 | 1.00 | 48.60 |
| ATOM | 1829 | CA  | LEU | 536 | 33.303 | -1.874  | 12.042 | 1.00 | 45.08 |
| ATOM | 1830 | CB  | LEU | 536 | 33.280 | -0.796  | 13.128 | 1.00 | 44.35 |
| ATOM | 1831 | CG  | LEU | 536 | 32.267 | -0.911  | 14.273 | 1.00 | 43.48 |
| ATOM | 1832 | CD1 | LEU | 536 | 31.919 | 0.490   | 14.745 | 1.00 | 43.41 |
| ATOM | 1833 | CD2 | LEU | 536 | 31.022 | -1.654  | 13.835 | 1.00 | 39.55 |
| ATOM | 1834 | C   | LEU | 536 | 32.434 | -1.433  | 10.871 | 1.00 | 43.58 |
| ATOM | 1835 | O   | LEU | 536 | 31.287 | -1.862  | 10.734 | 1.00 | 42.14 |
| ATOM | 1836 | N   | TYR | 537 | 32.992 | -0.575  | 10.024 | 1.00 | 43.02 |
| ATOM | 1837 | CA  | TYR | 537 | 32.269 | -0.066  | 8.866  | 1.00 | 43.34 |
| ATOM | 1838 | CB  | TYR | 537 | 33.200 | 0.786   | 7.997  | 1.00 | 44.76 |
| ATOM | 1839 | CG  | TYR | 537 | 32.483 | 1.558   | 6.913  | 1.00 | 48.28 |
| ATOM | 1840 | CD1 | TYR | 537 | 32.190 | 0.954   | 5.687  | 1.00 | 48.46 |
| ATOM | 1841 | CE1 | TYR | 537 | 31.504 | 1.660   | 4.693  | 1.00 | 52.48 |
| ATOM | 1842 | CD2 | TYR | 537 | 32.073 | 2.875   | 7.123  | 1.00 | 49.99 |

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1843  CE2  TYR  537   31.383    3.584    6.135  1.00  53.73
ATOM   1844  CZ   TYR  537   31.100    2.967    4.924  1.00  54.01
ATOM   1845  OH   TYR  537   30.401    3.648    3.952  1.00  55.90
ATOM   1846  C    TYR  537   31.683   -1.199    8.032  1.00  43.15
ATOM   1847  O    TYR  537   30.500   -1.191    7.696  1.00  41.54
ATOM   1848  N    ASP  538   32.521   -2.175    7.703  1.00  44.67
ATOM   1849  CA   ASP  538   32.097   -3.309    6.893  1.00  45.49
ATOM   1850  CB   ASP  538   33.322   -4.136    6.479  1.00  51.32
ATOM   1851  CG   ASP  538   34.361   -3.284    5.748  1.00  56.17
ATOM   1852  OD1  ASP  538   35.436   -3.820    5.396  1.00  57.29
ATOM   1853  OD2  ASP  538   34.097   -2.079    5.526  1.00  59.24
ATOM   1854  C    ASP  538   31.071   -4.195    7.587  1.00  43.48
ATOM   1855  O    ASP  538   30.177   -4.738    6.940  1.00  43.95
ATOM   1856  N    LEU  539   31.193   -4.345    8.901  1.00  41.57
ATOM   1857  CA   LEU  539   30.244   -5.157    9.654  1.00  39.11
ATOM   1858  CB   LEU  539   30.734   -5.351   11.092  1.00  41.88
ATOM   1859  CG   LEU  539   29.770   -6.065   12.044  1.00  46.11
ATOM   1860  CD1  LEU  539   29.298   -7.379   11.423  1.00  46.99
ATOM   1861  CD2  LEU  539   30.474   -6.319   13.377  1.00  45.76
ATOM   1862  C    LEU  539   28.891   -4.451    9.651  1.00  36.38
ATOM   1863  O    LEU  539   27.849   -5.070    9.436  1.00  35.74
ATOM   1864  N    LEU  540   28.919   -3.146    9.894  1.00  35.50
ATOM   1865  CA   LEU  540   27.703   -2.336    9.903  1.00  35.59
ATOM   1866  CB   LEU  540   28.061   -0.877   10.219  1.00  37.63
ATOM   1867  CG   LEU  540   27.856   -0.252   11.605  1.00  40.28
ATOM   1868  CD1  LEU  540   27.526   -1.399   12.645  1.00  38.55
ATOM   1869  CD2  LEU  540   29.114    0.506   11.985  1.00  41.04
ATOM   1870  C    LEU  540   27.060   -2.415    8.510  1.00  35.50
ATOM   1871  O    LEU  540   25.846   -2.585    8.371  1.00  33.21
ATOM   1872  N    LEU  541   27.892   -2.289    7.483  1.00  37.01
ATOM   1873  CA   LEU  541   27.418   -2.340    6.101  1.00  38.51
ATOM   1874  CB   LEU  541   28.591   -2.152    5.145  1.00  39.67
ATOM   1875  CG   LEU  541   28.301   -2.112    3.643  1.00  40.92
ATOM   1876  CD1  LEU  541   27.184   -1.130    3.348  1.00  42.44
ATOM   1877  CD2  LEU  541   29.572   -1.716    2.908  1.00  44.18
ATOM   1878  C    LEU  541   26.723   -3.676    5.833  1.00  39.75
ATOM   1879  O    LEU  541   25.615   -3.713    5.297  1.00  36.48
ATOM   1880  N    GLU  542   27.366   -4.770    6.230  1.00  40.88
ATOM   1881  CA   GLU  542   26.790   -6.097    6.037  1.00  41.89
ATOM   1882  CB   GLU  542   27.719   -7.170    6.620  1.00  44.11
ATOM   1883  CG   GLU  542   27.010   -8.457    7.052  1.00  50.60
ATOM   1884  CD   GLU  542   26.434   -9.245    5.887  1.00  55.80
ATOM   1885  OE1  GLU  542   25.570  -10.117    6.130  1.00  58.81
ATOM   1886  OE2  GLU  542   26.842   -8.996    4.728  1.00  57.19
ATOM   1887  C    GLU  542   25.414   -6.195    6.691  1.00  41.58
ATOM   1888  O    GLU  542   24.472   -6.720    6.102  1.00  42.82
ATOM   1889  N    MET  543   25.298   -5.686    7.915  1.00  40.09
ATOM   1890  CA   MET  543   24.036   -5.731    8.634  1.00  36.43
ATOM   1891  CB   MET  543   24.270   -5.424   10.111  1.00  39.95
ATOM   1892  CG   MET  543   25.137   -6.459   10.808  1.00  41.95
ATOM   1893  SD   MET  543   24.918   -6.445   12.604  1.00  47.17
ATOM   1894  CE   MET  543   25.324   -4.749   12.964  1.00  40.88
ATOM   1895  C    MET  543   23.001   -4.769    8.072  1.00  35.02
ATOM   1896  O    MET  543   21.898   -5.073    8.048  1.00  35.31
ATOM   1897  N    LEU  544   23.457   -3.605    7.629  1.00  32.90
ATOM   1898  CA   LEU  544   22.559   -2.603    7.074  1.00  36.88
ATOM   1899  CB   LEU  544   23.225   -1.226    7.111  1.00  34.51
ATOM   1900  CG   LEU  544   23.268   -0.562    8.490  1.00  31.94
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
ATOM   1901  CD1  LEU  544  24.284   0.564   8.478  1.00  32.27
ATOM   1902  CD2  LEU  544  21.897  -0.029   8.846  1.00  29.02
ATOM   1903  C    LEU  544  22.148  -2.941   5.840  1.00  38.94
ATOM   1904  O    LEU  544  20.971  -2.842   5.294  1.00  39.52
ATOM   1905  N    ASP  545  23.118  -3.338   4.817  1.00  41.05
ATOM   1906  CA   ASP  545  22.850  -3.685   3.418  1.00  40.78
ATOM   1907  CB   ASP  545  24.159  -3.780   2.620  1.00  37.75
ATOM   1908  CG   ASP  545  23.922  -3.937   1.120  1.00  35.19
ATOM   1909  OD1  ASP  545  24.881  -4.265   0.380  1.00  33.48
ATOM   1910  OD2  ASP  545  22.768  -3.734   0.691  1.00  31.33
ATOM   1911  C    ASP  545  22.116  -5.015   3.349  1.00  42.87
ATOM   1912  O    ASP  545  22.681  -6.030   2.929  1.00  44.32
ATOM   1913  N    ALA  546  20.853  -5.009   3.755  1.00  43.49
ATOM   1914  CA   ALA  546  20.069  -6.229   3.746  1.00  46.96
ATOM   1915  CB   ALA  546  19.213  -6.305   5.006  1.00  47.82
ATOM   1916  C    ALA  546  19.193  -6.362   2.508  1.00  49.55
ATOM   1917  O    ALA  546  18.804  -5.368   1.883  1.00  48.75
ATOM   1918  N    HIS  547  18.895  -7.606   2.152  1.00  50.98
ATOM   1919  CA   HIS  547  18.042  -7.884   1.006  1.00  53.77
ATOM   1920  CB   HIS  547  18.431  -9.223   0.369  1.00  52.69
ATOM   1921  CG   HIS  547  18.395 -10.382   1.317  1.00  55.05
ATOM   1922  CD2  HIS  547  17.477 -10.752   2.242  1.00  53.94
ATOM   1923  ND1  HIS  547  19.395 -11.329   1.371  1.00  56.23
ATOM   1924  CE1  HIS  547  19.095 -12.232   2.286  1.00  55.36
ATOM   1925  NE2  HIS  547  17.936 -11.906   2.830  1.00  57.01
ATOM   1926  C    HIS  547  16.603  -7.936   1.518  1.00  55.69
ATOM   1927  O    HIS  547  16.362  -7.796   2.720  1.00  54.30
ATOM   1928  N    ARG  548  15.653  -8.139   0.612  1.00  57.00
ATOM   1929  CA   ARG  548  14.245  -8.212   0.987  1.00  60.65
ATOM   1930  CB   ARG  548  13.432  -7.171   0.208  1.00  62.69
ATOM   1931  CG   ARG  548  14.272  -6.222  -0.637  1.00  67.54
ATOM   1932  CD   ARG  548  13.448  -5.063  -1.171  1.00  71.92
ATOM   1933  NE   ARG  548  13.702  -3.826  -0.432  1.00  76.95
ATOM   1934  CZ   ARG  548  14.864  -3.178  -0.429  1.00  79.04
ATOM   1935  NH1  ARG  548  15.891  -3.644  -1.128  1.00  80.66
ATOM   1936  NH2  ARG  548  15.001  -2.063   0.278  1.00  80.39
ATOM   1937  C    ARG  548  13.695  -9.608   0.711  1.00  61.65
ATOM   1938  O    ARG  548  12.500  -9.781   0.466  1.00  62.05
ATOM   1939  N    LEU  549  14.576 -10.603   0.756  1.00  62.39
ATOM   1940  CA   LEU  549  14.188 -11.985   0.507  1.00  64.02
ATOM   1941  CB   LEU  549  15.433 -12.828   0.195  1.00  62.14
ATOM   1942  CG   LEU  549  16.461 -12.191  -0.753  1.00  60.76
ATOM   1943  CD1  LEU  549  17.699 -13.074  -0.878  1.00  57.77
ATOM   1944  CD2  LEU  549  15.823 -11.972  -2.108  1.00  58.38
ATOM   1945  C    LEU  549  13.431 -12.574   1.702  1.00  66.65
ATOM   1946  O    LEU  549  12.759 -13.600   1.577  1.00  67.15
ATOM   1947  N    HIS  550  13.541 -11.920   2.856  1.00  67.72
ATOM   1948  CA   HIS  550  12.858 -12.378   4.065  1.00  69.93
ATOM   1949  CB   HIS  550  13.753 -12.190   5.298  1.00  70.76
ATOM   1950  CG   HIS  550  14.977 -13.054   5.306  1.00  71.50
ATOM   1951  CD2  HIS  550  15.539 -13.821   4.341  1.00  71.63
ATOM   1952  ND1  HIS  550  15.793 -13.172   6.411  1.00  71.98
ATOM   1953  CE1  HIS  550  16.805 -13.972   6.126  1.00  72.04
ATOM   1954  NE2  HIS  550  16.674 -14.379   4.876  1.00  71.39
ATOM   1955  C    HIS  550  11.556 -11.603   4.275  1.00  71.15
ATOM   1956  O    HIS  550  10.940 -11.684   5.340  1.00  70.66
ATOM   1957  N    ALA  551  11.143 -10.851   3.258  1.00  72.22
ATOM   1958  CA   ALA  551   9.919 -10.057   3.338  1.00  73.58
```

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

| | | | | | | | | | |
|---|---|---|---|---|---|---|---|---|---|
| ATOM | 1959 | CB | ALA | 551 | 9.904 | -9.014 | 2.221 | 1.00 | 73.21 |
| ATOM | 1960 | C | ALA | 551 | 8.658 | -10.920 | 3.286 | 1.00 | 74.69 |
| ATOM | 1961 | O | ALA | 551 | 7.684 | -10.474 | 2.621 | 1.00 | 76.13 |
| ATOM | 1962 | OXT | ALA | 551 | 8.631 | -12.025 | 3.852 | 1.00 | 73.79 |
| HETATM | 1963 | C10 | OHT | 600 | 30.581 | 1.481 | 29.471 | 1.00 | 26.84 |
| HETATM | 1964 | C9 | OHT | 600 | 30.713 | -0.043 | 29.358 | 1.00 | 32.85 |
| HETATM | 1965 | C8 | OHT | 600 | 31.366 | -0.385 | 28.037 | 1.00 | 25.56 |
| HETATM | 1966 | C11 | OHT | 600 | 32.761 | 0.051 | 27.916 | 1.00 | 27.51 |
| HETATM | 1967 | C16 | OHT | 600 | 33.218 | 0.797 | 26.797 | 1.00 | 28.35 |
| HETATM | 1968 | C15 | OHT | 600 | 34.551 | 1.237 | 26.747 | 1.00 | 30.39 |
| HETATM | 1969 | C14 | OHT | 600 | 35.443 | 0.923 | 27.792 | 1.00 | 30.23 |
| HETATM | 1970 | C13 | OHT | 600 | 35.004 | 0.185 | 28.890 | 1.00 | 31.45 |
| HETATM | 1971 | C12 | OHT | 600 | 33.666 | -0.241 | 28.955 | 1.00 | 27.93 |
| HETATM | 1972 | C7 | OHT | 600 | 30.682 | -1.089 | 27.077 | 1.00 | 24.41 |
| HETATM | 1973 | C1 | OHT | 600 | 29.211 | -1.258 | 27.032 | 1.00 | 24.25 |
| HETATM | 1974 | C2 | OHT | 600 | 28.644 | -2.526 | 26.706 | 1.00 | 25.92 |
| HETATM | 1975 | C3 | OHT | 600 | 27.254 | -2.868 | 26.580 | 1.00 | 26.32 |
| HETATM | 1976 | C4 | OHT | 600 | 26.438 | -1.553 | 26.813 | 1.00 | 29.02 |
| HETATM | 1977 | O4 | OHT | 600 | 25.072 | -1.605 | 26.716 | 1.00 | 28.42 |
| HETATM | 1978 | C5 | OHT | 600 | 26.980 | -0.286 | 27.130 | 1.00 | 26.98 |
| HETATM | 1979 | C6 | OHT | 600 | 28.362 | -0.147 | 27.231 | 1.00 | 25.23 |
| HETATM | 1980 | C17 | OHT | 600 | 31.370 | -1.693 | 25.942 | 1.00 | 26.61 |
| HETATM | 1981 | C18 | OHT | 600 | 32.508 | -2.498 | 26.151 | 1.00 | 26.77 |
| HETATM | 1982 | C19 | OHT | 600 | 33.166 | -3.052 | 25.072 | 1.00 | 27.50 |
| HETATM | 1983 | C20 | OHT | 600 | 32.676 | -2.794 | 23.786 | 1.00 | 27.50 |
| HETATM | 1984 | O20 | OHT | 600 | 33.206 | -3.566 | 22.795 | 1.00 | 31.35 |
| HETATM | 1985 | C23 | OHT | 600 | 33.009 | -3.135 | 21.448 | 1.00 | 40.09 |
| HETATM | 1986 | C24 | OHT | 600 | 34.226 | -3.490 | 20.575 | 1.00 | 44.80 |
| HETATM | 1987 | N24 | OHT | 600 | 34.141 | -4.901 | 20.203 | 1.00 | 49.00 |
| HETATM | 1988 | C25 | OHT | 600 | 33.375 | -5.040 | 18.933 | 1.00 | 51.64 |
| HETATM | 1989 | C26 | OHT | 600 | 35.495 | -5.459 | 20.004 | 1.00 | 52.06 |
| HETATM | 1990 | C21 | OHT | 600 | 31.540 | -2.005 | 23.558 | 1.00 | 27.19 |
| HETATM | 1991 | C22 | OHT | 600 | 30.892 | -1.450 | 24.645 | 1.00 | 27.93 |
| HETATM | 1992 | O1 | HOH | 1 | 20.714 | -12.010 | 23.057 | 1.00 | 27.20 |
| HETATM | 1993 | O1 | HOH | 2 | 22.563 | -0.070 | 25.819 | 1.00 | 25.77 |
| HETATM | 1994 | O1 | HOH | 3 | 25.183 | 19.202 | 23.149 | 1.00 | 42.52 |
| HETATM | 1995 | O1 | HOH | 4 | 35.158 | 5.823 | 37.390 | 1.00 | 33.92 |
| HETATM | 1996 | O1 | HOH | 5 | 22.116 | -9.922 | 18.914 | 1.00 | 30.18 |
| HETATM | 1997 | O1 | HOH | 6 | 29.812 | 6.536 | 19.652 | 1.00 | 26.11 |
| HETATM | 1998 | O1 | HOH | 7 | 13.362 | 4.463 | 20.376 | 1.00 | 29.40 |
| HETATM | 1999 | O1 | HOH | 8 | 19.799 | -11.295 | 20.187 | 1.00 | 28.70 |
| HETATM | 2000 | O1 | HOH | 9 | 21.205 | 1.466 | 23.794 | 1.00 | 22.47 |
| HETATM | 2001 | O1 | HOH | 10 | 21.177 | -4.961 | 29.066 | 1.00 | 33.00 |
| HETATM | 2002 | O1 | HOH | 11 | 18.591 | 1.863 | 20.518 | 1.00 | 32.59 |
| HETATM | 2003 | O1 | HOH | 12 | 16.298 | 21.566 | 15.992 | 1.00 | 33.62 |
| HETATM | 2004 | O1 | HOH | 13 | 18.611 | 1.975 | 24.494 | 1.00 | 29.70 |
| HETATM | 2005 | O1 | HOH | 14 | 38.009 | 8.910 | 21.156 | 1.00 | 39.92 |
| HETATM | 2006 | O1 | HOH | 15 | 26.549 | 11.664 | 18.080 | 1.00 | 30.25 |
| HETATM | 2007 | O1 | HOH | 16 | 20.282 | -4.239 | 26.512 | 1.00 | 32.70 |
| HETATM | 2008 | O1 | HOH | 17 | 32.858 | 8.754 | 20.237 | 1.00 | 29.88 |
| HETATM | 2009 | O1 | HOH | 18 | 8.497 | 16.136 | 29.934 | 1.00 | 46.80 |
| HETATM | 2010 | O1 | HOH | 19 | 21.940 | 19.301 | 31.632 | 1.00 | 35.73 |
| HETATM | 2011 | O1 | HOH | 20 | 35.153 | 2.682 | 14.122 | 1.00 | 41.02 |
| HETATM | 2012 | O1 | HOH | 21 | 20.358 | -2.268 | 21.013 | 1.00 | 29.43 |
| HETATM | 2013 | O1 | HOH | 22 | 35.562 | 10.036 | 36.334 | 1.00 | 41.37 |
| HETATM | 2014 | O1 | HOH | 23 | 17.248 | 18.187 | 17.571 | 1.00 | 33.96 |
| HETATM | 2015 | O1 | HOH | 24 | 18.445 | 20.973 | 12.346 | 1.00 | 43.44 |
| HETATM | 2016 | O1 | HOH | 25 | 12.152 | 23.054 | 33.132 | 1.00 | 36.04 |

UNITED STATES PATENT AND TRADEMARK OFFICE
CERTIFICATE OF CORRECTION

PATENT NO. : 6,965,850 B2
APPLICATION NO. : 09/281717
DATED : November 15, 2005
INVENTOR(S) : John D. Baxter et al.

It is certified that error appears in the above-identified patent and that said Letters Patent is hereby corrected as shown below:

```
HETATM  2017  O1  HOH  26  13.181  22.222   9.699  1.00  37.03
HETATM  2018  O1  HOH  27  19.399  -6.090  12.808  1.00  44.86
HETATM  2019  O1  HOH  28  37.895  13.599  31.395  1.00  47.26
HETATM  2020  O1  HOH  29  11.570   6.212   7.982  1.00  51.10
HETATM  2021  O1  HOH  30  20.172  -2.568  23.445  1.00  51.70
HETATM  2022  O1  HOH  31  36.402  -5.369  23.739  1.00  58.20
HETATM  2023  O1  HOH  32  25.127  13.802  19.187  1.00  35.29
HETATM  2024  O1  HOH  33  23.181   4.937  38.538  1.00  33.77
HETATM  2025  O1  HOH  34  20.550   0.421  21.276  1.00  29.12
HETATM  2026  O1  HOH  35  39.599  13.954  27.312  1.00  44.08
HETATM  2027  O1  HOH  36  26.445  13.863  21.285  1.00  34.97
HETATM  2028  O1  HOH  37  13.759   5.079   9.108  1.00  38.54
HETATM  2029  O1  HOH  38  14.150  24.731  34.529  1.00  49.72
HETATM  2030  O1  HOH  39  21.060  13.886  -6.319  1.00  59.79
HETATM  2031  O1  HOH  40  32.215   6.217   8.726  1.00  60.22
HETATM  2032  O1  HOH  41  35.105  15.704   9.069  1.00  45.15
HETATM  2033  O1  HOH  42  11.427  19.451   9.903  1.00  39.56
HETATM  2034  O1  HOH  43  19.662  23.472  10.333  1.00  47.71
HETATM  2035  O1  HOH  44   9.231   3.690  12.337  1.00  45.98
HETATM  2036  O1  HOH  45  15.313  -6.036  17.192  1.00  39.07
HETATM  2037  O1  HOH  46  15.517  -3.266  17.907  1.00  37.67
HETATM  2038  O1  HOH  47  28.784 -16.713  25.163  1.00  55.44
HETATM  2039  O1  HOH  48  27.868 -10.898  28.271  1.00  31.27
HETATM  2040  O1  HOH  49   6.955  13.568  28.233  1.00  48.83
HETATM  2041  O1  HOH  50  22.051 -15.030  28.603  1.00  36.91
HETATM  2042  O1  HOH  51   7.026  31.002  30.284  1.00  46.73
HETATM  2043  O1  HOH  52  -1.489  12.385  15.184  1.00  51.17
HETATM  2044  O1  HOH  53   3.499   6.444  14.452  1.00  50.38
HETATM  2045  O1  HOH  54  18.665  -2.048  25.518  1.00  52.29
HETATM  2046  O1  HOH  55  28.188 -15.195  38.996  1.00  55.22
HETATM  2047  O1  HOH  56  35.275 -10.556  38.061  1.00  57.39
HETATM  2048  O1  HOH  57  37.771  -9.103  34.605  1.00  54.17
HETATM  2049  O1  HOH  58  31.403  -3.039  17.983  1.00  46.80
HETATM  2050  O1  HOH  59  30.455  -6.352  17.005  1.00  47.05
HETATM  2051  O1  HOH  60  25.985   8.255   0.416  1.00  43.32
HETATM  2052  O1  HOH  61  35.679   0.749  10.462  1.00  42.99
HETATM  2053  O1  HOH  62  14.741   4.029  33.936  1.00  49.59
HETATM  2054  O1  HOH  63  16.333   2.592  35.952  1.00  45.13
HETATM  2055  O1  HOH  64  23.809   7.186  39.798  1.00  45.36
HETATM  2056  O1  HOH  65  27.012  -1.948  46.995  1.00  63.39
HETATM  2057  O1  HOH  66  25.956  -6.422  42.144  1.00  44.94
HETATM  2058  O1  HOH  67  23.510  -8.414  39.036  1.00  39.06
HETATM  2059  O1  HOH  68  41.475   0.971  33.110  1.00  55.50
HETATM  2060  O1  HOH  69  36.519   8.863  38.836  1.00  41.56
HETATM  2061  O1  HOH  70  30.111  14.823  12.793  1.00  44.58
HETATM  2062  O1  HOH  71  26.850  -6.092   1.594  1.00  40.15
HETATM  2063  O1  HOH  72  20.448  -3.169   1.055  1.00  42.50
HETATM  2064  O1  HOH  73  33.896   3.047  16.172  1.00  46.39
HETATM  2065  O1  HOH  74  16.884   0.446  26.043  1.00  61.50
HETATM  2066  O1  HOH  75  18.595   0.296  27.866  1.00  47.33
HETATM  2067  O1  HOH  76   6.166  21.439  19.124  1.00  47.94
HETATM  2068  O1  HOH  77  18.484  20.060  16.232  1.00  35.52
HETATM  2069  O1  HOH  78   1.985  23.265  29.187  1.00  45.42
HETATM  2070  O1  HOH  79  12.729  30.461  27.530  1.00  62.79
END
```

SEQUENCE LISTING

```
<160> NUMBER OF SEQ ID NOS: 60

<210> SEQ ID NO 1
<211> LENGTH: 5
<212> TYPE: PRT
<213> ORGANISM: Homo sapiens
<220> FEATURE:
<221> NAME/KEY: Variant
<222> LOCATION: (2)..(3)
<223> OTHER INFORMATION: Xaa is any amino acid

<400> SEQUENCE: 1

Leu Xaa Xaa Leu Leu
1               5

<210> SEQ ID NO 2
<211> LENGTH: 6
<212> TYPE: PRT
<213> ORGANISM: Homo sapiens
<220> FEATURE:
<221> NAME/KEY: Variant
<222> LOCATION: (3)..(4)
<223> OTHER INFORMATION: Xaa is any amino acid

<400> SEQUENCE: 2

Ile Leu Xaa Xaa Leu Leu
1               5

<210> SEQ ID NO 3
<211> LENGTH: 5
<212> TYPE: PRT
<213> ORGANISM: Homo sapiens
<220> FEATURE:
<221> NAME/KEY: Variant
<222> LOCATION: (2)..(3)
<223> OTHER INFORMATION: Xaa is any amino acid

<400> SEQUENCE: 3
```

```
Phe Xaa Xaa Leu Trp
1               5

<210> SEQ ID NO 4
<211> LENGTH: 5
<212> TYPE: PRT
<213> ORGANISM: Homo sapiens
<220> FEATURE:
<221> NAME/KEY: Variant
<222> LOCATION: (2)..(3)
<223> OTHER INFORMATION: Xaa is any amino acid

<400> SEQUENCE: 4

Phe Xaa Xaa Ala Leu
1               5

<210> SEQ ID NO 5
<211> LENGTH: 34
<212> TYPE: PRT
<213> ORGANISM: Homo sapiens

<400> SEQUENCE: 5

Ala Glu Gly His Ser Arg Leu His Asp Ser Lys Gly Gln Thr Lys Leu
1               5                  10                  15

Leu Gln Leu Leu Thr Thr Lys Ser Glu Gln Met Glu Pro Ser Pro Leu
            20                  25                  30

Ala Ser

<210> SEQ ID NO 6
<211> LENGTH: 34
<212> TYPE: PRT
<213> ORGANISM: Homo sapiens
<220> FEATURE:
<221> NAME/KEY: MUTAGEN
<222> LOCATION: (15)..(15)
<223> OTHER INFORMATION: Ile --> Ala
<220> FEATURE:
<221> NAME/KEY: MUTAGEN
<222> LOCATION: (16)..(16)
<223> OTHER INFORMATION: Leu --> Ala
<220> FEATURE:
<221> NAME/KEY: MUTAGEN
<222> LOCATION: (19)..(20)
<223> OTHER INFORMATION: Leu --> Ala
<220> FEATURE:
<221> NAME/KEY: MUTAGEN
<222> LOCATION: (16)..(20)
<223> OTHER INFORMATION: Leu(16) --> Ala; Leu (20) -->Ala
<220> FEATURE:
<221> NAME/KEY: MUTAGEN
<222> LOCATION: (15)..(16)
<223> OTHER INFORMATION: IleLeu --> AlaAla
<220> FEATURE:
<221> NAME/KEY: MUTAGEN
<222> LOCATION: (17)..(18)
<223> OTHER INFORMATION: HisArg -->AlaAla
<220> FEATURE:
<221> NAME/KEY: MUTAGEN
<222> LOCATION: (15)..(15)
<223> OTHER INFORMATION: Ile -->Phe
<220> FEATURE:
<221> NAME/KEY: MUTAGEN
<222> LOCATION: (16)..(16)
<223> OTHER INFORMATION: Leu -->Phe
<220> FEATURE:
<221> NAME/KEY: MUTAGEN
<222> LOCATION: (19)..(19)
<223> OTHER INFORMATION: Leu -->Phe
<220> FEATURE:
<221> NAME/KEY: MUTAGEN
<222> LOCATION: (20)..(20)
```

<223> OTHER INFORMATION: Leu -->Phe

<400> SEQUENCE: 6

Pro Gly Ser Thr His Gly Thr Ser Leu Lys Glu Lys His Lys Ile Leu
1               5                   10                  15

His Arg Leu Leu Gln Asp Ser Ser Pro Val Asp Leu Ala Lys Leu
            20                  25                  30

Thr Ala

<210> SEQ ID NO 7
<211> LENGTH: 31
<212> TYPE: PRT
<213> ORGANISM: Homo sapiens

<400> SEQUENCE: 7

Glu Pro Ala Ser Pro Lys Lys Lys Glu Asn Ala Leu Leu Arg Tyr Leu
1               5                   10                  15

Leu Asp Lys Asp Asp Thr Lys Asp Ile Gly Leu Pro Glu Ile Thr
            20                  25                  30

<210> SEQ ID NO 8
<211> LENGTH: 34
<212> TYPE: PRT
<213> ORGANISM: Homo sapiens

<400> SEQUENCE: 8

Ala Asp Gly Gln Ser Arg Leu His Asp Ser Lys Gly Gln Thr Lys Leu
1               5                   10                  15

Leu Gln Leu Leu Thr Thr Lys Ser Glu Gln Met Glu Pro Ser Pro Leu
            20                  25                  30

Ala Ser

<210> SEQ ID NO 9
<211> LENGTH: 34
<212> TYPE: PRT
<213> ORGANISM: Homo sapiens

<400> SEQUENCE: 9

Ser Gly Ser Thr His Gly Thr Ser Leu Lys Glu Lys His Lys Ile Leu
1               5                   10                  15

His Arg Leu Leu Gln Asp Ser Ser Pro Val Asp Leu Ala Lys Leu
            20                  25                  30

Thr Ala

<210> SEQ ID NO 10
<211> LENGTH: 31
<212> TYPE: PRT
<213> ORGANISM: Homo sapiens

<400> SEQUENCE: 10

Glu Pro Val Ser Pro Lys Lys Lys Glu Asn Ala Leu Leu Arg Tyr Leu
1               5                   10                  15

Leu Asp Lys Asp Asp Thr Lys Asp Ile Gly Leu Pro Glu Ile Thr
            20                  25                  30

<210> SEQ ID NO 11
<211> LENGTH: 34
<212> TYPE: PRT
<213> ORGANISM: Homo sapiens

<400> SEQUENCE: 11

-continued

```
Ala Glu Gly His Ser Arg Leu His Asp Ser Lys Gly Gln Thr Lys Leu
1               5                   10                  15

Leu Gln Leu Leu Thr Thr Lys Ser Glu Gln Met Glu Pro Ser Pro Leu
            20                  25                  30

Pro Ser

<210> SEQ ID NO 12
<211> LENGTH: 34
<212> TYPE: PRT
<213> ORGANISM: Homo sapiens

<400> SEQUENCE: 12

Pro Gly Ser Thr His Gly Thr Ser Leu Lys Glu Lys His Lys Ile Leu
1               5                   10                  15

His Arg Leu Leu Gln Asp Ser Ser Ser Pro Val Asp Leu Ala Lys Leu
            20                  25                  30

Thr Ala

<210> SEQ ID NO 13
<211> LENGTH: 31
<212> TYPE: PRT
<213> ORGANISM: Homo sapiens

<400> SEQUENCE: 13

Glu Pro Ala Ser Pro Lys Lys Lys Glu Asn Ala Leu Leu Arg Tyr Leu
1               5                   10                  15

Leu Asp Lys Asp Asp Thr Lys Asp Ile Gly Leu Pro Ser Ile Thr
            20                  25                  30

<210> SEQ ID NO 14
<211> LENGTH: 34
<212> TYPE: PRT
<213> ORGANISM: Homo sapiens

<400> SEQUENCE: 14

Ala Glu Asn Gln Arg Gly Pro Leu Glu Ser Lys Gly His Lys Lys Leu
1               5                   10                  15

Leu Gln Leu Leu Thr Cys Ser Ser Glu Asp Arg Gly His Ser Ser Leu
            20                  25                  30

Thr Asn

<210> SEQ ID NO 15
<211> LENGTH: 34
<212> TYPE: PRT
<213> ORGANISM: Homo sapiens

<400> SEQUENCE: 15

Thr Ser Asn Met His Gly Ser Leu Leu Gln Glu Lys His Arg Ile Leu
1               5                   10                  15

His Lys Leu Leu Gln Asn Gly Asn Ser Pro Ala Glu Val Ala Lys Ile
            20                  25                  30

Thr Ala

<210> SEQ ID NO 16
<211> LENGTH: 32
<212> TYPE: PRT
<213> ORGANISM: Homo sapiens

<400> SEQUENCE: 16
```

-continued

Glu Gln Leu Ser Pro Lys Lys Lys Glu Asn Asn Ala Leu Leu Arg Tyr
1               5                   10                  15

Leu Leu Asp Arg Asp Asp Pro Ser Asp Val Leu Ala Lys Lys Leu Gln
            20                  25                  30

<210> SEQ ID NO 17
<211> LENGTH: 34
<212> TYPE: PRT
<213> ORGANISM: Homo sapiens

<400> SEQUENCE: 17

Ala Glu Asn Gln Arg Gly Pro Leu Glu Ser Lys Gly His Lys Lys Leu
1               5                   10                  15

Leu Gln Leu Leu Thr Cys Ser Ser Asp Asp Arg Gly His Ser Ser Leu
            20                  25                  30

Thr Asn

<210> SEQ ID NO 18
<211> LENGTH: 34
<212> TYPE: PRT
<213> ORGANISM: Homo sapiens

<400> SEQUENCE: 18

Thr Ser Asn Met His Gly Ser Leu Leu Gln Glu Lys His Arg Ile Leu
1               5                   10                  15

His Lys Leu Leu Gln Asn Gly Asn Ser Pro Ala Glu Val Ala Lys Ile
            20                  25                  30

Thr Ala

<210> SEQ ID NO 19
<211> LENGTH: 32
<212> TYPE: PRT
<213> ORGANISM: Homo sapiens

<400> SEQUENCE: 19

Glu Gln Leu Ser Pro Lys Lys Lys Glu Asn Asn Ala Leu Leu Arg Tyr
1               5                   10                  15

Leu Leu Asp Arg Asp Asp Pro Ser Asp Ala Leu Ser Lys Glu Leu Gln
            20                  25                  30

<210> SEQ ID NO 20
<211> LENGTH: 34
<212> TYPE: PRT
<213> ORGANISM: Homo sapiens

<400> SEQUENCE: 20

Ser Glu Thr Pro Arg Gly Pro Leu Glu Ser Lys Gly His Lys Lys Leu
1               5                   10                  15

Leu Gln Leu Leu Thr Cys Ser Ser Glu Asp Arg Gly His Ser Ser Leu
            20                  25                  30

Thr Asn

<210> SEQ ID NO 21
<211> LENGTH: 34
<212> TYPE: PRT
<213> ORGANISM: Homo sapiens

<400> SEQUENCE: 21

Thr Ser Asn Val His Gly Ser Leu Leu Gln Glu Lys His Arg Ile Leu
1               5                   10                  15

His Lys Leu Leu Gln Asn Gly Asn Ser Pro Ala Glu Val Ala Lys Ile
            20                  25                  30
Thr Ala

<210> SEQ ID NO 22
<211> LENGTH: 32
<212> TYPE: PRT
<213> ORGANISM: Homo sapiens

<400> SEQUENCE: 22

Glu Gln Leu Ser Pro Lys Lys Glu Asn Asn Ala Leu Leu Arg Tyr
1               5                   10                  15

Leu Leu Asp Arg Asp Asp Pro Ser Asp Ala Leu Ser Lys Glu Leu Gln
            20                  25                  30

<210> SEQ ID NO 23
<211> LENGTH: 32
<212> TYPE: PRT
<213> ORGANISM: Homo sapiens

<400> SEQUENCE: 23

Ser Glu Gly Asp Ser Lys Tyr Ser Gln Thr Ser His Lys Leu Val Gln
1               5                   10                  15

Leu Leu Thr Thr Thr Ala Glu Gln Gln Leu Arg His Ala Asp Ile Asp
            20                  25                  30

<210> SEQ ID NO 24
<211> LENGTH: 33
<212> TYPE: PRT
<213> ORGANISM: Homo sapiens

<400> SEQUENCE: 24

Thr Cys Pro Ser Ser His Ser Ser Leu Thr Glu Arg His Lys Ile Leu
1               5                   10                  15

His Arg Leu Leu Gln Glu Gly Ser Pro Ser Asp Ile Thr Thr Leu Ser
            20                  25                  30

Val

<210> SEQ ID NO 25
<211> LENGTH: 34
<212> TYPE: PRT
<213> ORGANISM: Homo sapiens

<400> SEQUENCE: 25

Glu Leu Asp Ala Ala Lys Lys Lys Glu Ser Lys Asp His Gln Leu Leu
1               5                   10                  15

Arg Tyr Leu Leu Asp Lys Asp Glu Lys Asp Leu Arg Ser Thr Pro Asn
            20                  25                  30

Leu Cys

<210> SEQ ID NO 26
<211> LENGTH: 34
<212> TYPE: PRT
<213> ORGANISM: Homo sapiens
<220> FEATURE:
<221> NAME/KEY: SITE
<222> LOCATION: (2)..(2)
<223> OTHER INFORMATION: Xaa is a negatively charged amino acid
<220> FEATURE:
<221> NAME/KEY: SITE
<222> LOCATION: (17)..(17)
<223> OTHER INFORMATION: Xaa is a hydrophobic amino acid
<220> FEATURE:

```
<221> NAME/KEY: SITE
<222> LOCATION: (25)..(25)
<223> OTHER INFORMATION: Xaa is a negatively charged amino acid
<220> FEATURE:
<221> NAME/KEY: Variant
<222> LOCATION: (1)..(1)
<223> OTHER INFORMATION: Xaa is any amino acid
<220> FEATURE:
<221> NAME/KEY: Variant
<222> LOCATION: (3)..(9)
<223> OTHER INFORMATION: Xaa is any amino acid
<220> FEATURE:
<221> NAME/KEY: Variant
<222> LOCATION: (11)..(14)
<223> OTHER INFORMATION: Xaa is any amino acid
<220> FEATURE:
<221> NAME/KEY: Variant
<222> LOCATION: (22)..(24)
<223> OTHER INFORMATION: Xaa is any amino acid
<220> FEATURE:
<221> NAME/KEY: Variant
<222> LOCATION: (26)..(34)
<223> OTHER INFORMATION: Xaa is any amino acid

<400> SEQUENCE: 26

Xaa Xaa Xaa Xaa Xaa Xaa Xaa Xaa Xaa Ser Xaa Xaa Xaa Xaa Lys Leu
 1               5                  10                  15

Xaa Gln Leu Leu Thr Xaa Xaa Xaa Xaa Xaa Xaa Xaa Xaa Xaa Xaa
             20                  25                  30

Xaa Xaa

<210> SEQ ID NO 27
<211> LENGTH: 34
<212> TYPE: PRT
<213> ORGANISM: Homo sapiens
<220> FEATURE:
<221> NAME/KEY: SITE
<222> LOCATION: (12)..(12)
<223> OTHER INFORMATION: Xaa is a positively charged amino acid
<220> FEATURE:
<221> NAME/KEY: SITE
<222> LOCATION: (14)..(14)
<223> OTHER INFORMATION: Xaa is a positively charged amino acid
<220> FEATURE:
<221> NAME/KEY: SITE
<222> LOCATION: (18)..(18)
<223> OTHER INFORMATION: Xaa is a positively charged amino acid
<220> FEATURE:
<221> NAME/KEY: SITE
<222> LOCATION: (28)..(28)
<223> OTHER INFORMATION: Xaa is a negatively charged amino acid
<220> FEATURE:
<221> NAME/KEY: SITE
<222> LOCATION: (29)..(29)
<223> OTHER INFORMATION: Xaa is a hydrophobic amino acid
<220> FEATURE:
<221> NAME/KEY: SITE
<222> LOCATION: (32)..(32)
<223> OTHER INFORMATION: Xaa is a hydrophobic amino acid

<400> SEQUENCE: 27

Xaa Xaa Xaa Xaa Xaa Xaa Xaa Xaa Leu Xaa Glu Xaa His Xaa Ile Leu
 1               5                  10                  15

His Xaa Leu Leu Gln Xaa Xaa Xaa Ser Pro Xaa Xaa Xaa Xaa Xaa
             20                  25                  30

Xaa Xaa

<210> SEQ ID NO 28
<211> LENGTH: 34
<212> TYPE: PRT
<213> ORGANISM: Homo sapiens
```

```
<220> FEATURE:
<221> NAME/KEY: SITE
<222> LOCATION: (22)..(22)
<223> OTHER INFORMATION: Xaa is a positively charged amino acid
<220> FEATURE:
<221> NAME/KEY: SITE
<222> LOCATION: (24)..(24)
<223> OTHER INFORMATION: Xaa is a negatively charged amino acid
<220> FEATURE:
<221> NAME/KEY: SITE
<222> LOCATION: (33)..(33)
<223> OTHER INFORMATION: Xaa is a hydrophobic amino acid
<220> FEATURE:
<221> NAME/KEY: Variant
<222> LOCATION: (2)..(5)
<223> OTHER INFORMATION: Xaa is any amino acid
<220> FEATURE:
<221> NAME/KEY: Variant
<222> LOCATION: (10)..(14)
<223> OTHER INFORMATION: Xaa is any amino acid
<220> FEATURE:
<221> NAME/KEY: Variant
<222> LOCATION: (25)..(32)
<223> OTHER INFORMATION: Xaa is any amino acid
<220> FEATURE:
<221> NAME/KEY: Variant
<222> LOCATION: (34)..(34)
<223> OTHER INFORMATION: Xaa is any amino acid

<400> SEQUENCE: 28

Glu Xaa Xaa Xaa Xaa Lys Lys Lys Glu Xaa Xaa Xaa Xaa Xaa Leu Leu
1               5                   10                  15

Arg Tyr Leu Leu Asp Xaa Asp Xaa Xaa Xaa Xaa Xaa Xaa Xaa Xaa
            20                  25                  30

Xaa Xaa

<210> SEQ ID NO 29
<211> LENGTH: 18
<212> TYPE: PRT
<213> ORGANISM: Homo sapiens

<400> SEQUENCE: 29

Thr Ser Leu Lys Glu Lys His Lys Leu Leu Arg Tyr Leu Leu Gln Asp
1               5                   10                  15

Ser Ser

<210> SEQ ID NO 30
<211> LENGTH: 33
<212> TYPE: PRT
<213> ORGANISM: Homo sapiens
<220> FEATURE:
<221> NAME/KEY: MUTAGEN
<222> LOCATION: (5)..(5)
<223> OTHER INFORMATION: Thr --> Arg (T281R)
<220> FEATURE:
<221> NAME/KEY: MUTAGEN
<222> LOCATION: (8)..(8)
<223> OTHER INFORMATION: Val  --> Arg (V284R)
<220> FEATURE:
<221> NAME/KEY: MUTAGEN
<222> LOCATION: (9)..(9)
<223> OTHER INFORMATION: Asp  --> Ala (D285A)
<220> FEATURE:
<221> NAME/KEY: MUTAGEN
<222> LOCATION: (12)..(12)
<223> OTHER INFORMATION: Lys  --> Ala (K288A)
<220> FEATURE:
<221> NAME/KEY: MUTAGEN
<222> LOCATION: (22)..(22)
<223> OTHER INFORMATION: Cys  --> Arg (C298R)
<220> FEATURE:
<221> NAME/KEY: MUTAGEN
```

```
<222> LOCATION: (26)..(26)
<223> OTHER INFORMATION: Ile --> Arg (I302R)
<220> FEATURE:
<221> NAME/KEY: MUTAGEN
<222> LOCATION: (30)..(30)
<223> OTHER INFORMATION: Lys --> Ala (K306A)

<400> SEQUENCE: 30

Thr Pro Ala Ile Thr Arg Val Val Asp Phe Ala Lys Lys Leu Pro Met
1               5                   10                  15

Phe Cys Glu Leu Pro Cys Glu Asp Gln Ile Ile Leu Leu Lys Gly Cys
            20                  25                  30

Cys

<210> SEQ ID NO 31
<211> LENGTH: 12
<212> TYPE: PRT
<213> ORGANISM: Homo sapiens
<220> FEATURE:
<221> NAME/KEY: MUTAGEN
<222> LOCATION: (5)..(5)
<223> OTHER INFORMATION: Leu --> Arg (L454R)
<220> FEATURE:
<221> NAME/KEY: MUTAGEN
<222> LOCATION: (7)..(7)
<223> OTHER INFORMATION: Leu --> Arg (L456R)
<220> FEATURE:
<221> NAME/KEY: MUTAGEN
<222> LOCATION: (8)..(8)
<223> OTHER INFORMATION: Glu -->Lys (E457K)

<400> SEQUENCE: 31

Leu Phe Pro Pro Leu Phe Leu Glu Val Phe Glu Asp
1               5                   10

<210> SEQ ID NO 32
<211> LENGTH: 33
<212> TYPE: PRT
<213> ORGANISM: Homo sapiens

<400> SEQUENCE: 32

Thr Pro Ala Ile Thr Arg Val Val Asp Phe Ala Lys Lys Leu Pro Met
1               5                   10                  15

Phe Ser Glu Leu Pro Cys Glu Asp Gln Ile Ile Leu Leu Lys Gly Cys
            20                  25                  30

Cys

<210> SEQ ID NO 33
<211> LENGTH: 12
<212> TYPE: PRT
<213> ORGANISM: Homo sapiens

<400> SEQUENCE: 33

Leu Phe Pro Pro Leu Phe Leu Glu Val Phe Glu Asp
1               5                   10

<210> SEQ ID NO 34
<211> LENGTH: 33
<212> TYPE: PRT
<213> ORGANISM: Homo sapiens

<400> SEQUENCE: 34

Thr Lys Cys Ile Ile Lys Ile Val Glu Phe Ala Lys Arg Leu Pro Gly
1               5                   10                  15

Phe Thr Gly Leu Ser Ile Ala Asp Gln Ile Thr Leu Leu Lys Ala Ala
```

```
                    20                  25                  30
Cys

<210> SEQ ID NO 35
<211> LENGTH: 12
<212> TYPE: PRT
<213> ORGANISM: Homo sapiens

<400> SEQUENCE: 35

Leu Phe Pro Pro Leu Phe Leu Glu Val Phe Glu Asp
1               5                   10

<210> SEQ ID NO 36
<211> LENGTH: 33
<212> TYPE: PRT
<213> ORGANISM: Homo sapiens

<400> SEQUENCE: 36

Asp Lys Gln Leu Phe Thr Leu Val Glu Trp Ala Lys Arg Ile Pro His
1               5                   10                  15

Phe Ser Glu Leu Pro Leu Asp Asp Gln Val Ile Leu Leu Lys Ala Gly
                20                  25                  30

Trp

<210> SEQ ID NO 37
<211> LENGTH: 12
<212> TYPE: PRT
<213> ORGANISM: Homo sapiens

<400> SEQUENCE: 37

Pro Ile Asp Thr Phe Leu Met Glu Met Leu Glu Ala
1               5                   10

<210> SEQ ID NO 38
<211> LENGTH: 33
<212> TYPE: PRT
<213> ORGANISM: Homo sapiens

<400> SEQUENCE: 38

Val Glu Ala Val Gln Glu Ile Thr Glu Tyr Ala Lys Asn Ile Pro Gly
1               5                   10                  15

Phe Ile Asn Leu Asp Leu Asn Asp Gln Val Thr Leu Leu Lys Tyr Gly
                20                  25                  30

Val

<210> SEQ ID NO 39
<211> LENGTH: 12
<212> TYPE: PRT
<213> ORGANISM: Homo sapiens

<400> SEQUENCE: 39

Ser Leu His Pro Leu Leu Gln Glu Ile Tyr Lys Asp
1               5                   10

<210> SEQ ID NO 40
<211> LENGTH: 33
<212> TYPE: PRT
<213> ORGANISM: Homo sapiens

<400> SEQUENCE: 40

Ser Tyr Ser Ile Gln Lys Val Ile Gly Phe Ala Lys Met Ile Pro Gly
1               5                   10                  15
```

```
Phe Arg Asp Leu Thr Ser Glu Asp Gln Ile Val Leu Leu Lys Ser Ser
            20                  25                  30
Ala
```

<210> SEQ ID NO 41
<211> LENGTH: 12
<212> TYPE: PRT
<213> ORGANISM: Homo sapiens

<400> SEQUENCE: 41

```
Lys Leu Thr Pro Leu Val Leu Glu Val Phe Gly Asn
1               5                   10
```

<210> SEQ ID NO 42
<211> LENGTH: 33
<212> TYPE: PRT
<213> ORGANISM: Homo sapiens
<220> FEATURE:
<221> NAME/KEY: MUTAGEN
<222> LOCATION: (12)..(12)
<223> OTHER INFORMATION: Lys --> Ala (K362A)
<220> FEATURE:
<221> NAME/KEY: MUTAGEN
<222> LOCATION: (26)..(26)
<223> OTHER INFORMATION: Val -->Arg (V376R)

<400> SEQUENCE: 42

```
Asp Arg Glu Leu Val His Met Ile Asn Trp Ala Lys Arg Val Pro Gly
1               5                   10                  15
Phe Val Asp Leu Thr Leu His Asp Gln Val His Leu Leu Glu Cys Ala
            20                  25                  30
Trp
```

<210> SEQ ID NO 43
<211> LENGTH: 12
<212> TYPE: PRT
<213> ORGANISM: Homo sapiens
<220> FEATURE:
<221> NAME/KEY: MUTAGEN
<222> LOCATION: (8)..(8)
<223> OTHER INFORMATION: Glu -->Lys (E542K)

<400> SEQUENCE: 43

```
Pro Leu Tyr Asp Leu Leu Leu Glu Met Leu Asp Ala
1               5                   10
```

<210> SEQ ID NO 44
<211> LENGTH: 33
<212> TYPE: PRT
<213> ORGANISM: Homo sapiens

<400> SEQUENCE: 44

```
Gly Arg Gln Val Ile Ala Ala Val Lys Trp Ala Lys Ala Ile Pro Gly
1               5                   10                  15
Phe Arg Asn Leu His Leu Asp Asp Gln Met Thr Leu Leu Gln Tyr Ser
            20                  25                  30
Trp
```

<210> SEQ ID NO 45
<211> LENGTH: 12
<212> TYPE: PRT
<213> ORGANISM: Homo sapiens

<400> SEQUENCE: 45

```
Glu Phe Pro Glu Met Leu Ala Glu Ile Ile Thr Asn
1               5                   10
```

<210> SEQ ID NO 46
<211> LENGTH: 33
<212> TYPE: PRT
<213> ORGANISM: Homo sapiens

<400> SEQUENCE: 46

```
Glu Arg Gln Leu Leu Ser Val Val Lys Trp Ser Lys Ser Leu Pro Gly
1               5                   10                  15

Phe Arg Asn Leu His Ile Asp Asp Gln Ile Thr Leu Ile Gln Tyr Ser
            20                  25                  30

Trp
```

<210> SEQ ID NO 47
<211> LENGTH: 12
<212> TYPE: PRT
<213> ORGANISM: Homo sapiens

<400> SEQUENCE: 47

```
Glu Phe Pro Glu Met Met Ser Glu Val Ile Ala Ala
1               5                   10
```

<210> SEQ ID NO 48
<211> LENGTH: 33
<212> TYPE: PRT
<213> ORGANISM: Homo sapiens

<400> SEQUENCE: 48

```
Gly Lys Gln Met Ile Gln Val Val Lys Trp Ala Lys Val Leu Pro Gly
1               5                   10                  15

Phe Lys Asn Leu Pro Leu Glu Asp Gln Ile Thr Leu Ile Gln Tyr Ser
            20                  25                  30

Trp
```

<210> SEQ ID NO 49
<211> LENGTH: 12
<212> TYPE: PRT
<213> ORGANISM: Homo sapiens

<400> SEQUENCE: 49

```
Glu Phe Pro Ala Met Leu Val Glu Ile Ile Ser Asp
1               5                   10
```

<210> SEQ ID NO 50
<211> LENGTH: 33
<212> TYPE: PRT
<213> ORGANISM: Homo sapiens

<400> SEQUENCE: 50

```
Glu Arg Gln Leu Val His Val Val Lys Trp Ala Lys Ala Leu Pro Gly
1               5                   10                  15

Phe Arg Asn Leu His Val Asp Asp Gln Met Ala Val Ile Gln Tyr Ser
            20                  25                  30

Trp
```

<210> SEQ ID NO 51
<211> LENGTH: 12
<212> TYPE: PRT
<213> ORGANISM: Homo sapiens

```
<400> SEQUENCE: 51

Asp Phe Pro Glu Met Met Ala Glu Ile Ile Ser Val
1               5                   10

<210> SEQ ID NO 52
<211> LENGTH: 251
<212> TYPE: PRT
<213> ORGANISM: Homo sapiens
<220> FEATURE:
<221> NAME/KEY: VARIANT
<222> LOCATION: (45)..(52)
<223> OTHER INFORMATION: Xaa is any amino acid
<220> FEATURE:
<223> OTHER INFORMATION: Position 1 corresponds to position 211 of
      mature peptide

<400> SEQUENCE: 52

Lys Pro Glu Pro Thr Asp Glu Glu Trp Glu Leu Ile Lys Thr Val Thr
1               5                   10                  15

Ala Ala His Val Ala Thr Asn Ala Gln Gly Ser His Trp Lys Asn Lys
                20                  25                  30

Arg Lys Phe Leu Pro Glu Asp Ile Gly Gln Ala Pro Xaa Xaa Xaa Xaa
            35                  40                  45

Xaa Xaa Xaa Xaa Lys Val Asp Leu Glu Ala Phe Ser His Phe Thr Lys
    50                  55                  60

Ile Ile Thr Pro Ala Ile Thr Arg Val Val Asp Phe Ala Lys Lys Leu
65                  70                  75                  80

Pro Met Phe Cys Glu Leu Pro Cys Glu Asp Gln Ile Ile Leu Leu Lys
                85                  90                  95

Gly Cys Cys Met Glu Ile Met Ser Leu Arg Ala Ala Val Arg Tyr Asp
            100                 105                 110

Pro Glu Ser Glu Thr Leu Thr Leu Asn Gly Glu Met Ala Val Thr Arg
        115                 120                 125

Gly Gln Leu Lys Asn Gly Gly Leu Gly Val Val Ser Asp Ala Ile Phe
    130                 135                 140

Asp Leu Gly Met Ser Leu Ser Ser Phe Asn Leu Asp Asp Thr Glu Val
145                 150                 155                 160

Ala Leu Leu Gln Ala Val Leu Leu Met Ser Ser Asp Arg Pro Gly Leu
                165                 170                 175

Ala Cys Val Ala Arg Ile Glu Lys Tyr Gln Asp Ser Phe Leu Leu Ala
            180                 185                 190

Phe Glu His Tyr Ile Asn Tyr Arg Lys His His Val Thr His Phe Trp
        195                 200                 205

Pro Lys Leu Leu Met Lys Val Thr Asp Leu Arg Met Ile Gly Ala Cys
    210                 215                 220

His Ala Ser Arg Phe Leu His Met Lys Val Glu Cys Pro Thr Glu Leu
225                 230                 235                 240

Phe Pro Pro Leu Phe Leu Glu Val Phe Glu Asp
                245                 250

<210> SEQ ID NO 53
<211> LENGTH: 251
<212> TYPE: PRT
<213> ORGANISM: Homo sapiens
<220> FEATURE:
<221> NAME/KEY: VARIANT
<222> LOCATION: (45)..(50)
<223> OTHER INFORMATION: Xaa is any amino acid
<220> FEATURE:
```

<223> OTHER INFORMATION: Position 1 corresponds to position 211 of
      mature peptide

<400> SEQUENCE: 53

Lys Pro Glu Pro Thr Asp Glu Trp Glu Leu Ile Lys Thr Val Thr
1               5                  10                  15

Ala Ala His Val Ala Thr Asn Ala Gln Gly Ser His Trp Lys Asn Lys
            20                  25                  30

Arg Lys Phe Leu Pro Glu Asp Ile Gly Gln Ala Pro Xaa Xaa Xaa
        35                  40                  45

Xaa Xaa Gly Gly Lys Val Asp Leu Glu Ala Phe Ser His Phe Thr Lys
    50                  55                  60

Ile Ile Thr Pro Ala Ile Thr Arg Val Val Asp Phe Ala Lys Lys Leu
65                  70                  75                  80

Pro Met Phe Cys Glu Leu Pro Cys Glu Asp Gln Ile Ile Leu Leu Lys
                85                  90                  95

Gly Cys Cys Met Glu Ile Met Ser Leu Arg Ala Ala Val Arg Tyr Asp
            100                 105                 110

Pro Glu Ser Glu Thr Leu Thr Leu Asn Gly Glu Met Ala Val Thr Arg
        115                 120                 125

Gly Gln Leu Lys Asn Gly Gly Leu Gly Val Val Ser Asp Ala Ile Phe
    130                 135                 140

Asp Leu Gly Met Ser Leu Ser Ser Phe Asn Leu Asp Asp Thr Glu Val
145                 150                 155                 160

Ala Leu Leu Gln Ala Val Leu Leu Met Ser Ser Asp Arg Pro Gly Leu
                165                 170                 175

Ala Cys Val Ala Arg Ile Glu Lys Tyr Gln Asp Ser Phe Leu Leu Ala
            180                 185                 190

Phe Glu His Tyr Ile Asn Tyr Arg Lys His His Val Thr His Phe Trp
        195                 200                 205

Pro Lys Leu Leu Met Lys Val Thr Asp Leu Arg Met Ile Gly Ala Cys
    210                 215                 220

His Ala Ser Arg Phe Leu His Met Lys Val Glu Cys Pro Thr Glu Leu
225                 230                 235                 240

Phe Pro Pro Leu Phe Leu Glu Val Phe Glu Asp
                245                 250

<210> SEQ ID NO 54
<211> LENGTH: 13
<212> TYPE: PRT
<213> ORGANISM: Homo sapiens
<220> FEATURE:
<223> OTHER INFORMATION: Position 1 corresponds to position 686 of
      mature peptide

<400> SEQUENCE: 54

Lys His Lys Ile Leu His Arg Leu Leu Gln Asp Ser Ser
1               5                  10

<210> SEQ ID NO 55
<211> LENGTH: 9
<212> TYPE: PRT
<213> ORGANISM: Homo sapiens
<220> FEATURE:
<223> OTHER INFORMATION: Position 1 corresponds to position 688 of
      mature peptide

<400> SEQUENCE: 55

Lys Ile Leu His Arg Leu Leu Gln Asp

-continued

<210> SEQ ID NO 56
<211> LENGTH: 245
<212> TYPE: PRT
<213> ORGANISM: Homo sapiens
<220> FEATURE:
<223> OTHER INFORMATION: Position 1 corresponds to position 305 of
      mature peptide

<400> SEQUENCE: 56

Ser Leu Ala Leu Ser Leu Thr Ala Asp Gln Met Val Ser Ala Leu Leu
1               5                   10                  15

Asp Ala Glu Pro Pro Ile Leu Tyr Ser Glu Tyr Asp Pro Thr Arg Pro
            20                  25                  30

Phe Ser Glu Ala Ser Met Met Gly Leu Leu Thr Asn Leu Ala Asp Arg
        35                  40                  45

Glu Leu Val His Met Ile Asn Trp Ala Lys Arg Val Pro Gly Phe Val
    50                  55                  60

Asp Leu Thr Leu His Asp Gln Val His Leu Leu Glu Cys Ala Trp Leu
65                  70                  75                  80

Glu Ile Leu Met Ile Gly Leu Val Trp Arg Ser Met Glu His Pro Gly
                85                  90                  95

Lys Leu Leu Phe Ala Pro Asn Leu Leu Leu Asp Arg Asn Gln Gly Lys
            100                 105                 110

Cys Val Glu Gly Met Val Glu Ile Phe Asp Met Leu Leu Ala Thr Ser
        115                 120                 125

Ser Arg Phe Arg Met Met Asn Leu Gln Gly Glu Glu Phe Val Cys Leu
    130                 135                 140

Lys Ser Ile Ile Leu Leu Asn Ser Gly Val Tyr Thr Phe Leu Ser Ser
145                 150                 155                 160

Thr Leu Lys Ser Leu Glu Glu Lys Asp His Ile His Arg Val Leu Asp
                165                 170                 175

Lys Ile Thr Asp Thr Leu Ile His Leu Met Ala Lys Ala Gly Leu Thr
            180                 185                 190

Leu Gln Gln Gln His Gln Arg Leu Ala Gln Leu Leu Leu Ile Leu Ser
        195                 200                 205

His Ile Arg His Met Ser Asn Lys Gly Met Glu His Leu Tyr Ser Met
    210                 215                 220

Lys Cys Lys Asn Val Val Pro Leu Tyr Asp Leu Leu Leu Glu Met Leu
225                 230                 235                 240

Asp Ala His Arg Leu
                245

<210> SEQ ID NO 57
<211> LENGTH: 237
<212> TYPE: PRT
<213> ORGANISM: Homo sapiens
<220> FEATURE:
<223> OTHER INFORMATION: Position 1 corresponds to position 305 of
      mature peptide

<400> SEQUENCE: 57

Ser Leu Ala Leu Ser Leu Thr Ala Asp Gln Met Val Ser Ala Leu Leu
1               5                   10                  15

Asp Ala Glu Pro Pro Ile Leu Tyr Ser Glu Tyr Asp Pro Thr Arg Pro
            20                  25                  30

Phe Ser Glu Ala Ser Met Met Gly Leu Leu Thr Asn Leu Ala Asp Arg

```
                35                  40                  45
Glu Leu Val His Met Ile Asn Trp Ala Lys Lys Arg Val Pro Gly Phe
 50                  55                  60
Val Asp Leu Thr Leu His Asp Gln Val His Leu Leu Glu Cys Ala Trp
 65                  70                  75                  80
Leu Glu Ile Leu Met Ile Gly Leu Val Trp Arg Ser Met Glu His Pro
                 85                  90                  95
Gly Lys Leu Leu Phe Ala Pro Asn Leu Leu Asp Arg Asn Gln Gly
            100                 105                 110
Lys Cys Val Gly Gly Met Val Glu Ile Phe Asp Met Leu Leu Ala Thr
            115                 120                 125
Ser Ser Arg Phe Arg Met Met Asn Leu Gln Gly Glu Glu Phe Val Cys
130                 135                 140
Leu Lys Ser Ile Ile Leu Leu Asn Ser Gly Val Tyr Thr Phe Glu Lys
145                 150                 155                 160
Asp His Ile His Arg Val Leu Asp Lys Ile Thr Asp Thr Leu Ile His
                165                 170                 175
Leu Met Ala Lys Ala Gly Leu Thr Leu Gln Gln Gln His Gln Arg Leu
            180                 185                 190
Ala Gln Leu Leu Leu Ile Leu Ser His Ile Arg His Met Ser Asn Lys
            195                 200                 205
Gly Met Glu His Leu Tyr Ser Met Lys Cys Lys Asn Val Val Pro Leu
        210                 215                 220
Tyr Asp Leu Leu Leu Glu Met Leu Asp Ala His Arg Leu
225                 230                 235

<210> SEQ ID NO 58
<211> LENGTH: 11
<212> TYPE: PRT
<213> ORGANISM: Homo sapiens
<220> FEATURE:
<223> OTHER INFORMATION: Position 1 corresponds to position 687 of
      mature peptide

<400> SEQUENCE: 58

His Lys Ile Leu His Arg Leu Leu Gln Asp Ser
 1               5                  10

<210> SEQ ID NO 59
<211> LENGTH: 246
<212> TYPE: PRT
<213> ORGANISM: Homo sapiens
<220> FEATURE:
<223> OTHER INFORMATION: Position 1 corresponds to position 306 of
      mature peptide

<400> SEQUENCE: 59

Leu Ala Leu Ser Leu Thr Ala Asp Gln Met Val Ser Ala Leu Leu Asp
 1               5                  10                  15
Ala Glu Pro Pro Ile Leu Tyr Ser Glu Tyr Asp Pro Thr Arg Pro Phe
                20                  25                  30
Ser Glu Ala Ser Met Met Gly Leu Leu Thr Asn Leu Ala Asp Arg Glu
            35                  40                  45
Leu Val His Met Ile Asn Trp Ala Lys Arg Val Pro Gly Phe Val Asp
 50                  55                  60
Leu Thr Leu His Asp Gln Val His Leu Leu Glu Cys Ala Trp Leu Glu
 65                  70                  75                  80
Ile Leu Met Ile Gly Leu Val Trp Arg Ser Met Glu His Pro Gly Lys
```

```
                        85                  90                  95
Leu Leu Phe Ala Pro Asn Leu Leu Asp Arg Asn Gln Gly Lys Cys
                100                 105                 110

Val Glu Gly Met Val Glu Ile Phe Asp Met Leu Leu Ala Thr Ser Ser
                115                 120                 125

Arg Phe Arg Met Met Asn Leu Gln Gly Glu Glu Phe Val Cys Leu Lys
                130                 135                 140

Ser Ile Ile Leu Leu Asn Ser Gly Val Tyr Thr Phe Leu Ser Ser Thr
145                 150                 155                 160

Leu Lys Ser Leu Glu Glu Lys Asp His Ile His Arg Val Leu Asp Lys
                165                 170                 175

Ile Thr Asp Thr Leu Ile His Leu Met Ala Lys Ala Gly Leu Thr Leu
                180                 185                 190

Gln Gln Gln His Gln Arg Leu Ala Gln Leu Leu Leu Ile Leu Ser His
                195                 200                 205

Ile Arg His Met Ser Asn Lys Gly Met Glu His Leu Tyr Ser Met Lys
                210                 215                 220

Cys Lys Asn Val Val Pro Leu Tyr Asp Leu Leu Leu Glu Met Leu Asp
225                 230                 235                 240

Ala His Arg Leu His Ala
                245

<210> SEQ ID NO 60
<211> LENGTH: 11
<212> TYPE: PRT
<213> ORGANISM: Homo sapiens
<220> FEATURE:
<223> OTHER INFORMATION: Position 1 corresponds to position 686 of
      mature peptide

<400> SEQUENCE: 60

Lys His Lys Ile Leu His Arg Leu Leu Gln Asp
1               5                   10
```